US010548953B2

(12) United States Patent
Liu et al.

(10) Patent No.: US 10,548,953 B2
(45) Date of Patent: Feb. 4, 2020

(54) FACTOR VIII-XTEN FUSIONS AND USES THEREOF

(71) Applicant: Bioverativ Therapeutics Inc., Waltham, MA (US)

(72) Inventors: Tongyao Liu, Lexington, MA (US); Pei-Yun Chang, Menlo Park, CA (US); John Kulman, Belmont, MA (US); Volker Schellenberger, Palo Alto, CA (US); Haiyan Jiang, Belmont, MI (US); Robert T. Peters, Needham, MA (US); Ekta Seth Chhabra, Framingham, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 624 days.

(21) Appl. No.: 14/912,047

(22) PCT Filed: Aug. 14, 2014

(86) PCT No.: PCT/US2014/051144
§ 371 (c)(1),
(2) Date: Feb. 12, 2016

(87) PCT Pub. No.: WO2015/023891
PCT Pub. Date: Feb. 19, 2015

(65) Prior Publication Data

US 2016/0199454 A1 Jul. 14, 2016

Related U.S. Application Data

(60) Provisional application No. 61/866,016, filed on Aug. 14, 2013.

(51) Int. Cl.

| | |
|---|---|
| ***A61K 38/37*** | (2006.01) |
| ***A61K 9/00*** | (2006.01) |
| ***C07K 14/00*** | (2006.01) |
| ***C07K 14/755*** | (2006.01) |
| ***C12N 15/85*** | (2006.01) |
| ***A61K 48/00*** | (2006.01) |

(52) U.S. Cl.
CPC ............ *A61K 38/37* (2013.01); *A61K 9/0019* (2013.01); *A61K 48/00* (2013.01); *C07K 14/00* (2013.01); *C07K 14/755* (2013.01); *C12N 15/85* (2013.01); *C07K 2319/31* (2013.01)

(58) Field of Classification Search
CPC ...... A61K 38/37; A61K 48/00; A61K 9/0019; C07K 14/755; C07K 14/00; C07K 2319/31; C12N 15/85
USPC ............ 514/14.1, 44 R; 530/383; 435/320.1, 435/325
See application file for complete search history.

(56) References Cited

U.S. PATENT DOCUMENTS

| | | | |
|---|---|---|---|
| 3,992,518 | A | 11/1976 | Chien et al. |
| 4,088,864 | A | 5/1978 | Theeuwes et al. |
| 4,179,337 | A | 12/1979 | Davis et al. |
| 4,200,098 | A | 4/1980 | Ayer et al. |
| 4,200,984 | A | 5/1980 | Fink |
| 4,215,051 | A | 7/1980 | Palmer et al. |
| 4,284,444 | A | 8/1981 | Bernstein et al. |
| 4,398,908 | A | 8/1983 | Siposs |
| 4,435,173 | A | 3/1984 | Siposs et al. |
| 4,456,591 | A | 6/1984 | Thomas |
| 4,542,025 | A | 9/1985 | Tice et al. |
| 4,599,311 | A | 7/1986 | Kawasaki |
| 4,683,195 | A | 7/1987 | Mullis et al. |
| 4,683,202 | A | 7/1987 | Mullis |
| 4,684,479 | A | 8/1987 | D'Arrigo |
| 4,713,339 | A | 12/1987 | Levinson et al. |
| 4,757,006 | A | 7/1988 | Toole, Jr. et al. |
| 4,770,999 | A | 9/1988 | Kaufman et al. |
| 4,784,950 | A | 11/1988 | Hagen et al. |
| 4,800,159 | A | 1/1989 | Mullis et al. |
| 4,845,075 | A | 7/1989 | Murray et al. |
| 4,861,800 | A | 8/1989 | Buyske |
| 4,868,112 | A | 9/1989 | Toole, Jr. |
| 4,870,008 | A | 9/1989 | Brake |
| 4,882,279 | A | 11/1989 | Cregg |
| 4,897,268 | A | 1/1990 | Tice et al. |
| 4,931,373 | A | 6/1990 | Kawasaki et al. |
| 4,933,185 | A | 6/1990 | Wheatley et al. |

(Continued)

FOREIGN PATENT DOCUMENTS

| | | | |
|---|---|---|---|
| AU | 609829 | B2 | 5/1991 |
| CN | 1761684 | A | 4/2006 |

(Continued)

OTHER PUBLICATIONS

Saenko et al. (1997) J. Biol. Chem., vol. 272 (29),18007-18014.*

(Continued)

*Primary Examiner* — Ann Marie S Wehbe

(74) *Attorney, Agent, or Firm* — Lathrop Gage LLP; James H. Velema, Esq.; James V. DeGiulio, Esq.

(57) ABSTRACT

The present invention provides chimeric proteins comprising a Factor VIII (FVIII) polypeptide and XTEN polypeptides. The FVIII polypeptide can have a reduced affinity for von Willebrand Factor (VWF). XTEN polypeptides of appropriate sizes are inserted into the FVIII polypeptide at particular locations in order to extend the half-life of the FVIII polypeptide. The invention also includes nucleotides, vectors, host cells, and methods of using the chimeric proteins, e.g., to treat bleeding diseases and disorders.

17 Claims, 5 Drawing Sheets

Figure 4:
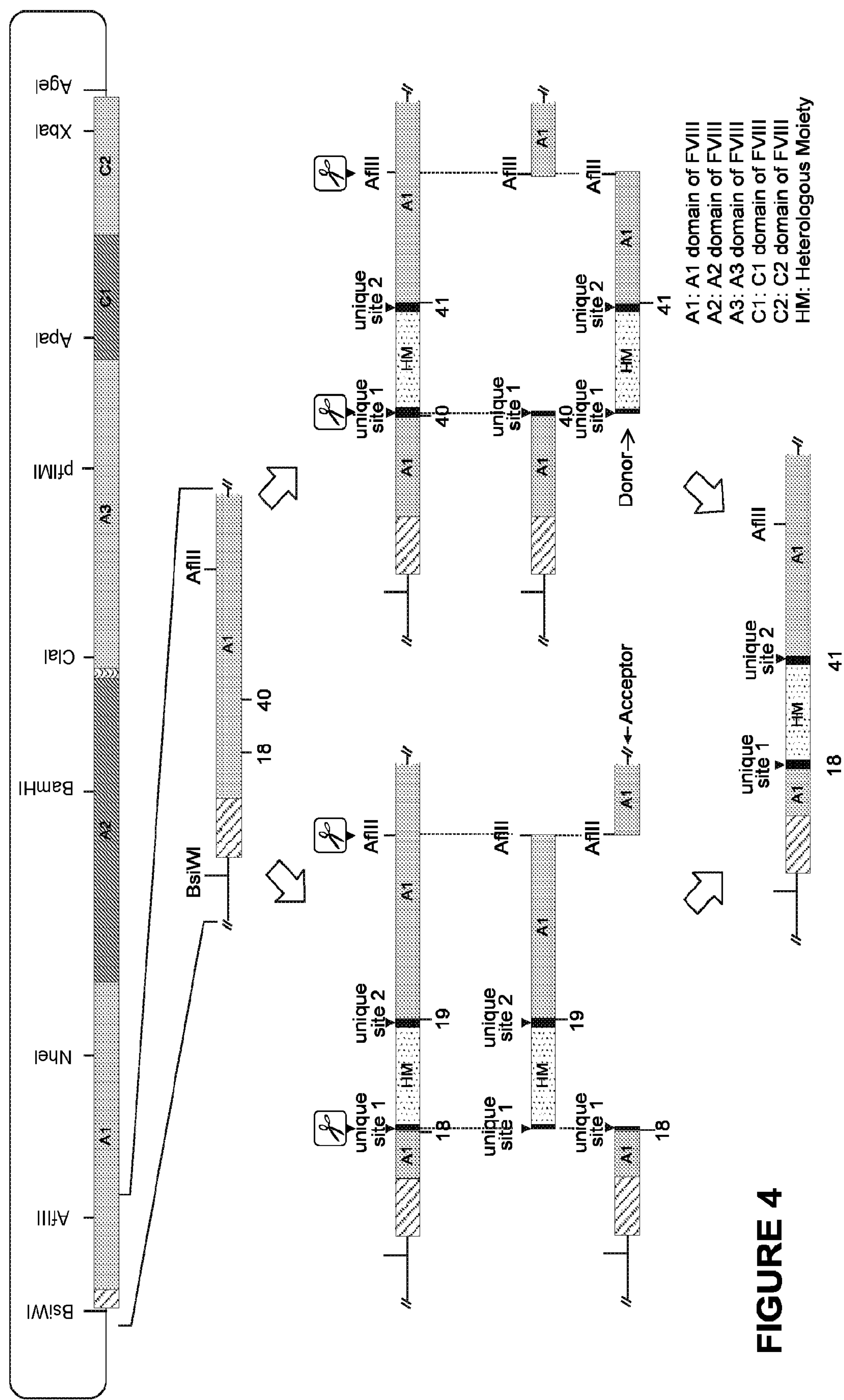

Specification includes a Sequence Listing.

(56) References Cited

U.S. PATENT DOCUMENTS 4,965,188 A 10/1990 Mullis et al.
4,965,199 A 10/1990 Capon et al.
4,976,696 A 12/1990 Sanderson et al.
4,988,337 A 1/1991 Ito
4,994,371 A 2/1991 Davie et al.
5,004,803 A 4/1991 Kaufman et al.
5,004,804 A 4/1991 Kuo et al.
5,017,378 A 5/1991 Turner et al.
5,037,743 A 8/1991 Welch et al.
5,089,474 A 2/1992 Castro et al.
5,112,950 A 5/1992 Meulien et al.
5,171,844 A 12/1992 Van Ooyen et al.
5,176,502 A 1/1993 Sanderson et al.
5,186,938 A 2/1993 Sablotsky et al.
5,198,349 A 3/1993 Kaufman
5,215,680 A 6/1993 D'Arrigo
5,223,409 A 6/1993 Ladner et al.
5,250,421 A 10/1993 Kaufman et al.
5,270,176 A 12/1993 Dorschug et al.
5,298,022 A 3/1994 Bernardi
5,318,540 A 6/1994 Athayde et al.
5,364,771 A 11/1994 Lollar et al.
5,364,934 A 11/1994 Drayna et al.
5,407,609 A 4/1995 Tice et al.
5,424,199 A 6/1995 Goeddel et al.
5,492,534 A 2/1996 Athayde et al.
5,534,617 A 7/1996 Cunningham et al.
5,543,502 A 8/1996 Nordfang et al.
5,554,730 A 9/1996 Woiszwillo et al.
5,573,776 A 11/1996 Harrison et al.
5,576,291 A 11/1996 Curtis et al.
5,578,709 A 11/1996 Woiszwillo
5,595,886 A 1/1997 Chapman et al.
5,599,907 A 2/1997 Anderson et al.
5,610,278 A 3/1997 Nordfang et al.
5,643,575 A 7/1997 Martinez et al.
5,648,260 A 7/1997 Winter et al.
5,658,570 A 8/1997 Newman et al.
5,660,848 A 8/1997 Moo-Young
5,712,122 A 1/1998 Boime et al.
5,739,277 A 4/1998 Presta et al.
5,756,115 A 5/1998 Moo-Young et al.
5,789,203 A 8/1998 Chapman et al.
5,833,982 A 11/1998 Berkner et al.
5,834,250 A 11/1998 Wells et al.
5,837,679 A 11/1998 Wolf et al.
5,846,951 A 12/1998 Gregoriadis
5,859,204 A 1/1999 Lollar
5,869,046 A 2/1999 Presta et al.
5,874,104 A 2/1999 Adler-Moore et al.
5,916,588 A 6/1999 Popescu et al.
5,919,766 A 7/1999 Osterberg et al.
5,942,252 A 8/1999 Tice et al.
5,965,156 A 10/1999 Proffitt et al.
5,972,885 A 10/1999 Spira et al.
5,981,216 A 11/1999 Kenten et al.
5,981,719 A 11/1999 Woiszwillo et al.
6,005,082 A 12/1999 Smeds
6,024,983 A 2/2000 Tice et al.
6,030,613 A 2/2000 Blumberg et al.
6,037,452 A 3/2000 Minamino et al.
6,043,094 A 3/2000 Martin et al.
6,048,720 A 4/2000 Dalborg et al.
6,056,973 A 5/2000 Allen et al.
6,060,447 A 5/2000 Chapman et al.
6,086,875 A 7/2000 Blumberg et al.
6,090,925 A 7/2000 Woiszwillo et al.
6,096,871 A 8/2000 Presta et al.
6,110,498 A 8/2000 Rudnic et al.
6,121,022 A 9/2000 Presta et al.
6,126,966 A 10/2000 Abra et al.
6,183,770 B1 2/2001 Muchin et al.
6,194,551 B1 2/2001 Idusogie et al.
6,228,620 B1 5/2001 Chapman et al.
6,242,195 B1 6/2001 Idusogie et al.
6,251,632 B1 6/2001 Lillicrap et al.
6,254,573 B1 7/2001 Haim et al.
6,268,053 B1 7/2001 Woiszwillo et al.
6,277,375 B1 8/2001 Ward
6,284,276 B1 9/2001 Rudnic et al.
6,294,170 B1 9/2001 Boone et al.
6,294,191 B1 9/2001 Meers et al.
6,294,201 B1 9/2001 Kettelhoit et al.
6,303,148 B1 10/2001 Hennink et al.
6,309,370 B1 10/2001 Haim et al.
6,310,183 B1 10/2001 Johannessen et al.
6,316,024 B1 11/2001 Allen et al.
6,316,226 B1 11/2001 Van Ooyen et al.
6,329,186 B1 12/2001 Nielsen et al.
6,346,513 B1 2/2002 Van Ooyen et al.
6,352,716 B1 3/2002 Janoff et al.
6,352,721 B1 3/2002 Faour
6,358,703 B1 3/2002 Cho et al.
6,361,796 B1 3/2002 Rudnic et al.
6,376,463 B1 4/2002 Lollar
6,395,302 B1 5/2002 Hennink et al.
6,406,632 B1 6/2002 Safir et al.
6,406,713 B1 6/2002 Janoff et al.
6,458,387 B1 10/2002 Scott et al.
6,458,563 B1 10/2002 Lollar
6,485,726 B1 11/2002 Blumberg et al.
6,514,532 B2 2/2003 Rudnic et al.
6,517,859 B1 2/2003 Tice et al.
6,528,624 B1 3/2003 Idusogie et al.
6,534,090 B2 3/2003 Puthli et al.
6,538,124 B1 3/2003 Idusogie et al.
6,572,585 B2 6/2003 Choi
6,669,961 B2 12/2003 Kim et al.
6,696,245 B2 2/2004 Winter et al.
6,713,086 B2 3/2004 Qiu et al.
6,715,485 B1 4/2004 Djupesland
6,733,753 B2 5/2004 Boone et al.
6,737,056 B1 5/2004 Presta
6,743,211 B1 6/2004 Prausnitz et al.
6,759,057 B1 7/2004 Weiner et al.
6,770,744 B2 8/2004 Lollar
6,814,979 B2 11/2004 Rudnic et al.
6,818,439 B1 11/2004 Jolly et al.
6,821,505 B2 11/2004 Ward
6,833,352 B2 12/2004 Johannessen et al.
6,838,093 B2 1/2005 Burnside et al.
6,890,918 B2 5/2005 Burnside et al.
6,905,688 B2 6/2005 Rosen et al.
6,911,323 B2 6/2005 Persson et al.
6,919,311 B2 7/2005 Lenting et al.
6,945,952 B2 9/2005 Kwon
6,960,657 B2 11/2005 Persson et al.
6,998,253 B1 2/2006 Presta et al.
7,026,524 B2 4/2006 Persson et al.
7,041,635 B2 5/2006 Kim et al.
7,045,318 B2 5/2006 Ballance
7,083,784 B2 8/2006 Dall'Acqua et al.
7,091,321 B2 8/2006 Gillies et al.
7,125,841 B2 10/2006 Sheehan
7,138,505 B1 11/2006 Kuo et al.
7,176,288 B2 2/2007 Persson et al.
7,199,223 B2 4/2007 Bossard et al.
7,211,559 B2 5/2007 Saenko et
7,276,475 B2 10/2007 Defrees et al.
7,276,593 B2 10/2007 Vernet
7,294,513 B2 11/2007 Wyatt
7,317,091 B2 1/2008 Lazar et al.
7,329,640 B2 2/2008 Vlasuk
7,348,004 B2 3/2008 Peters et al.
7,404,956 B2 7/2008 Peters et al.
7,413,537 B2 8/2008 Ladner et al.
7,414,022 B2 8/2008 Pedersen et al.
7,442,778 B2 10/2008 Gegg et al.
7,452,967 B2 11/2008 Bertin
7,507,406 B2 3/2009 Gillies et al.
7,511,024 B2 3/2009 Pedersen et al.
7,514,257 B2 4/2009 Lee et al.
7,528,242 B2 5/2009 Anderson et al.
7,560,107 B2 7/2009 Lollar

(56) References Cited

U.S. PATENT DOCUMENTS 7,566,701 B2 7/2009 Diener et al.
7,632,921 B2 12/2009 Pan et al.
7,645,860 B2 1/2010 Turecek et al.
7,700,733 B2 4/2010 Haaning et al.
7,700,734 B2 4/2010 Lin et al.
7,786,070 B2 8/2010 Johannessen et al.
7,790,415 B2 9/2010 Gillies et al.
7,846,445 B2 12/2010 Schellenberger et al.
7,846,455 B2 12/2010 Collins et al.
7,855,279 B2 12/2010 Schellenberger et al.
7,862,820 B2 1/2011 Peters et al.
7,884,075 B2 2/2011 Scheiflinger et al.
7,939,632 B2 5/2011 Metzner et al.
8,357,779 B2 1/2013 Scheiflinger et al.
8,492,530 B2 7/2013 Schellenberger et al.
8,563,521 B2 10/2013 Skerra et al.
8,575,104 B2 11/2013 Weimer et al.
8,673,860 B2 3/2014 Schellenberger et al.
8,680,050 B2 3/2014 Schellenberger et al.
8,703,717 B2 4/2014 Schellenberger et al.
8,716,448 B2 5/2014 Schellenberger et al.
8,754,194 B2 6/2014 Schulte et al.
8,835,388 B2 9/2014 Scheiflinger et al.
8,933,197 B2 1/2015 Stemmer et al.
9,168,312 B2 10/2015 Schellenberger et al.
9,376,672 B2 6/2016 Schellenberger et al.
2002/0042079 A1 4/2002 Simon et al.
2002/0150881 A1 10/2002 Ladner et al.
2003/0049689 A1 3/2003 Edwards et al.
2003/0069395 A1 4/2003 Sato et al.
2003/0181381 A1 9/2003 Himmelspach et al.
2003/0190740 A1 10/2003 Altman
2003/0228309 A1 12/2003 Salcedo et al.
2003/0235536 A1 12/2003 Richard et al.
2004/0043446 A1 3/2004 Defrees et al.
2004/0101740 A1 5/2004 Sanders
2004/0106118 A1 6/2004 Kolmar et al.
2004/0192599 A1 9/2004 Schuh et al.
2004/0203107 A1 10/2004 Murray
2004/0259780 A1 12/2004 Glasebrook et al.
2005/0042721 A1 2/2005 Fang et al.
2005/0048512 A1 3/2005 Kolkman et al.
2005/0100990 A1 5/2005 Saenko et al.
2005/0118136 A1 6/2005 Leung et al.
2005/0123997 A1 6/2005 Lollar
2005/0260605 A1 11/2005 Punnonen et al.
2005/0287153 A1 12/2005 Dennis
2006/0026719 A1 2/2006 Kieliszewski et al.
2006/0040856 A1 2/2006 Defrees et al.
2006/0074199 A1 4/2006 Hirata et al.
2006/0084113 A1 4/2006 Ladner et al.
2006/0115876 A1 6/2006 Pan et al.
2006/0122376 A1 6/2006 Chapman et al.
2006/0205036 A1 9/2006 Ostergaard et al.
2006/0211621 A1 9/2006 Knudsen et al.
2006/0287220 A1 12/2006 Li et al.
2006/0293232 A1 12/2006 Levy et al.
2006/0293238 A1 12/2006 Kaufman et al.
2007/0021494 A1 1/2007 Taveras et al.
2007/0048282 A1 3/2007 Rosen et al.
2007/0161087 A1 7/2007 Glaesner et al.
2007/0191272 A1 8/2007 Stemmer et al.
2007/0191597 A1 8/2007 Jain et al.
2007/0203058 A1 8/2007 Lau et al.
2007/0212703 A1 9/2007 Stemmer et al.
2007/0231329 A1 10/2007 Lazar et al.
2007/0237765 A1 10/2007 Lazar et al.
2007/0237766 A1 10/2007 Lazar et al.
2007/0237767 A1 10/2007 Lazar et al.
2007/0243188 A1 10/2007 Lazar et al.
2007/0244301 A1 10/2007 Siekmann et al.
2007/0248603 A1 10/2007 Lazar et al.
2007/0286859 A1 12/2007 Lazar et al.
2008/0004206 A1 1/2008 Rosen et al.
2008/0033413 A1 2/2008 Inochkin et al.
2008/0039341 A1 2/2008 Schellenberger et al.
2008/0057056 A1 3/2008 Lazar et al.
2008/0146782 A1 6/2008 DeFrees et al.
2008/0153751 A1 6/2008 Rosen et al.
2008/0161243 A1 7/2008 Rosen et al.
2008/0167219 A1 7/2008 Lin et al.
2008/0167238 A1 7/2008 Rosen et al.
2008/0176288 A1 7/2008 Leung et al.
2008/0193441 A1 8/2008 Trown et al.
2008/0194481 A1 8/2008 Rosen et al.
2008/0214462 A1 9/2008 Dockal et al.
2008/0227691 A1 9/2008 Ostergaard et al.
2008/0233100 A1 9/2008 Chen et al.
2008/0234193 A1 9/2008 Bossard et al.
2008/0255040 A1 10/2008 DeFrees
2008/0260755 A1 10/2008 Metzner et al.
2008/0261877 A1 10/2008 Ballance et al.
2008/0269125 A1 10/2008 Ballance et al.
2008/0286808 A1 11/2008 Schellenberger et al.
2008/0312157 A1 12/2008 Levy et al.
2009/0011992 A1 1/2009 Olsen et al.
2009/0042787 A1 2/2009 Metzner et al.
2009/0058322 A1 3/2009 Toma et al.
2009/0060862 A1 3/2009 Chang et al.
2009/0087411 A1 4/2009 Fares et al.
2009/0092582 A1 4/2009 Stemmer et al.
2009/0099031 A1 4/2009 Stemmer et al.
2009/0117104 A1 5/2009 Baker et al.
2009/0118185 A1 5/2009 Fay et al.
2009/0169553 A1 7/2009 Day
2009/0192076 A1 7/2009 Matthiessen et al.
2009/0250598 A1 10/2009 Hamada et al.
2009/0263380 A1 10/2009 Gilles et al.
2010/0022445 A1 1/2010 Scheiflinger et al.
2010/0081187 A1 4/2010 Griffith et al.
2010/0081615 A1 4/2010 Pan et al.
2010/0120664 A1 5/2010 Schulte et al.
2010/0130427 A1 5/2010 Bossard et al.
2010/0143326 A1 6/2010 Rischel et al.
2010/0189682 A1 7/2010 Schellenberger et al.
2010/0239554 A1 9/2010 Schellenberger et al.
2010/0260706 A1 10/2010 Bogin et al.
2010/0285021 A1 11/2010 Jacquemin et al.
2010/0292130 A1 11/2010 Skerra et al.
2010/0323956 A1 12/2010 Schellenberger et al.
2011/0046060 A1 2/2011 Schellenberger et al.
2011/0046061 A1 2/2011 Schellenberger et al.
2011/0077199 A1 3/2011 Schellenberger et al.
2011/0124565 A1 5/2011 Hauser et al.
2011/0151433 A1 6/2011 Schellenberger et al.
2011/0172146 A1 7/2011 Schellenberger et al.
2011/0183907 A1 7/2011 Weimer et al.
2011/0286988 A1 11/2011 Jiang et al.
2011/0287041 A1 11/2011 Carrico et al.
2011/0287517 A1 11/2011 Steward et al.
2011/0288005 A1 11/2011 Silverman et al.
2011/0312881 A1 12/2011 Silverman et al.
2012/0065077 A1 3/2012 Astermark et al.
2012/0121706 A1 5/2012 Kuliopulos et al.
2012/0142593 A1 6/2012 Zhao et al.
2012/0178691 A1* 7/2012 Schellenberger .... C07K 14/755 514/14.1
2012/0220011 A1 8/2012 Schellenberger et al.
2012/0230947 A1 9/2012 Schellenberger et al.
2012/0263701 A1 10/2012 Schellenberger et al.
2012/0263703 A1 10/2012 Schellenberger et al.
2012/0289468 A1 11/2012 Barnett
2013/0017997 A1* 1/2013 Schellenberger .... C07K 14/755 514/14.1
2013/0039884 A1 2/2013 Bogin et al.
2013/0108629 A1 5/2013 Dumont et al.
2013/0165389 A1 6/2013 Schellenberger et al.
2013/0172274 A1 7/2013 Chilkoti
2013/0183280 A1 7/2013 Oestergaard et al.
2014/0018297 A1 1/2014 Bolt et al.
2014/0050693 A1 2/2014 Skerra et al.
2014/0072561 A1 3/2014 Weimer et al.
2014/0186327 A1 7/2014 Schellenberger et al.
2014/0273096 A1 9/2014 Schulte et al.

(56) References Cited

U.S. PATENT DOCUMENTS

| | | | |
|---|---|---|---|
| 2014/0301974 | A1 | 10/2014 | Schellenberger et al. |
| 2014/0328819 | A1 | 11/2014 | Schellenberger et al. |
| 2014/0356326 | A1 | 12/2014 | Schellenberger et al. |
| 2014/0371136 | A1 | 12/2014 | Schellenberger et al. |
| 2015/0023959 | A1 | 1/2015 | Chhabra et al. |
| 2015/0038421 | A1 | 2/2015 | Schellenberger et al. |
| 2015/0158929 | A1 | 6/2015 | Schellenberger et al. |
| 2015/0175503 | A1 | 6/2015 | Marks et al. |
| 2015/0259431 | A1 | 9/2015 | Stemmer et al. |
| 2015/0266943 | A1 | 9/2015 | Chhabra et al. |
| 2015/0328819 | A1 | 11/2015 | Schellenberger et al. |
| 2015/0344862 | A1 | 12/2015 | Schellenberger et al. |
| 2016/0115467 | A1 | 4/2016 | Salas |
| 2016/0229903 | A1 | 8/2016 | Chhabra et al. |
| 2016/0251408 | A1 | 9/2016 | Chhabra et al. |
| 2016/0376344 | A1 | 12/2016 | Schellenberger et al. |
| 2017/0073393 | A1 | 3/2017 | Chhabra et al. |

FOREIGN PATENT DOCUMENTS

| | | | |
|---|---|---|---|
| CN | 101190945 | A | 6/2008 |
| EP | 0036776 | A2 | 9/1981 |
| EP | 0154316 | A2 | 9/1985 |
| EP | 0184438 | A2 | 6/1986 |
| EP | 0238023 | A2 | 9/1987 |
| EP | 0244234 | A2 | 11/1987 |
| EP | 0272277 | A1 | 6/1988 |
| EP | 0295597 | A2 | 12/1988 |
| EP | 0401384 | A1 | 12/1990 |
| EP | 0272277 | B1 | 9/1993 |
| EP | 1203014 | B1 | 10/2004 |
| EP | 0506757 | B2 | 10/2005 |
| EP | 1252192 | B1 | 8/2006 |
| EP | 1935430 | A1 | 6/2008 |
| EP | 2256135 | A1 | 12/2010 |
| EP | 2173890 | B1 | 3/2011 |
| EP | 2371856 | A2 | 10/2011 |
| EP | 2032607 | B1 | 1/2014 |
| EP | 2796145 | A1 | 10/2014 |
| WO | WO-8704187 | A1 | 7/1987 |
| WO | WO-8800831 | A1 | 2/1988 |
| WO | WO-8803558 | A1 | 5/1988 |
| WO | WO-8807089 | A1 | 9/1988 |
| WO | WO-8807220 | A1 | 9/1988 |
| WO | WO-8808035 | A1 | 10/1988 |
| WO | WO-8909051 | A1 | 10/1989 |
| WO | WO-9109122 | A1 | 6/1991 |
| WO | WO-9210576 | A1 | 6/1992 |
| WO | WO-9216221 | A1 | 10/1992 |
| WO | WO-9320093 | A1 | 10/1993 |
| WO | WO-9411503 | A2 | 5/1994 |
| WO | WO-9534326 | A1 | 12/1995 |
| WO | WO-9614339 | A1 | 5/1996 |
| WO | WO-9733552 | A1 | 9/1997 |
| WO | WO-9805787 | A1 | 2/1998 |
| WO | WO-9822577 | A1 | 5/1998 |
| WO | WO-9823289 | A1 | 6/1998 |
| WO | WO-9852976 | A1 | 11/1998 |
| WO | WO-9941383 | A1 | 8/1999 |
| WO | WO-9949901 | A1 | 10/1999 |
| WO | WO-9951642 | A1 | 10/1999 |
| WO | WO-9958572 | A1 | 11/1999 |
| WO | WO-0003317 | A1 | 1/2000 |
| WO | WO-0009560 | A2 | 2/2000 |
| WO | WO-0032767 | A1 | 6/2000 |
| WO | WO-0042072 | A2 | 7/2000 |
| WO | WO-0187922 | A2 | 11/2001 |
| WO | WO-0244215 | A2 | 6/2002 |
| WO | WO-02060919 | A2 | 8/2002 |
| WO | WO-02077036 | A2 | 10/2002 |
| WO | WO-02079232 | A2 | 10/2002 |
| WO | WO-03074569 | A2 | 9/2003 |
| WO | WO-03077834 | A2 | 9/2003 |
| WO | WO-2004016750 | A2 | 2/2004 |
| WO | WO-2004029207 | A2 | 4/2004 |
| WO | WO-2004035752 | A2 | 4/2004 |
| WO | WO-2004044859 | A1 | 5/2004 |
| WO | WO-2004063351 | A2 | 7/2004 |
| WO | WO-2004074455 | A2 | 9/2004 |
| WO | WO-2004099249 | A2 | 11/2004 |
| WO | WO-2005016455 | A2 | 2/2005 |
| WO | WO-2005025499 | A2 | 3/2005 |
| WO | WO-2005040217 | A2 | 5/2005 |
| WO | WO-2005047327 | A2 | 5/2005 |
| WO | WO-2005069845 | A2 | 8/2005 |
| WO | WO-2005070963 | A1 | 8/2005 |
| WO | WO-2005077981 | A2 | 8/2005 |
| WO | WO-2005092925 | A2 | 10/2005 |
| WO | WO-2005123780 | A2 | 12/2005 |
| WO | WO-2006019447 | A1 | 2/2006 |
| WO | WO-2006047350 | A2 | 5/2006 |
| WO | WO-2006053299 | A2 | 5/2006 |
| WO | WO-2006081249 | A2 | 8/2006 |
| WO | WO-2006085967 | A2 | 8/2006 |
| WO | WO-2006081249 | A3 | 2/2007 |
| WO | WO-2007021494 | A2 | 2/2007 |
| WO | WO-2007073486 | A2 | 6/2007 |
| WO | WO-2007090584 | A1 | 8/2007 |
| WO | WO-2007103455 | A2 | 9/2007 |
| WO | WO-2007103515 | A2 | 9/2007 |
| WO | WO-2007103455 | A3 | 11/2007 |
| WO | WO-2007/144173 | A1 | 12/2007 |
| WO | WO-2008033413 | A2 | 3/2008 |
| WO | WO-2008049931 | A1 | 5/2008 |
| WO | WO-2008057683 | A2 | 5/2008 |
| WO | WO-2008077616 | A1 | 7/2008 |
| WO | WO-2008155134 | A1 | 12/2008 |
| WO | WO-2009023270 | A2 | 2/2009 |
| WO | WO-2009023270 | A3 | 2/2009 |
| WO | WO-2009058322 | A1 | 5/2009 |
| WO | WO-2009062100 | A1 | 5/2009 |
| WO | WO-2009149303 | A1 | 12/2009 |
| WO | WO-2009156137 | A1 | 12/2009 |
| WO | WO-2010060081 | A1 | 5/2010 |
| WO | WO-2010062768 | A1 | 6/2010 |
| WO | WO-2010091122 | A1 | 8/2010 |
| WO | WO-2010111414 | A1 | 9/2010 |
| WO | WO-2010144502 | A2 | 12/2010 |
| WO | WO-2010144508 | A1 | 12/2010 |
| WO | WO-2011020866 | A2 | 2/2011 |
| WO | WO-2011028228 | A1 | 3/2011 |
| WO | WO-2011028229 | A1 | 3/2011 |
| WO | WO-2011028344 | A2 | 3/2011 |
| WO | WO-2011060242 | A2 | 5/2011 |
| WO | WO-2011069164 | A2 | 6/2011 |
| WO | WO-2011084808 | A2 | 7/2011 |
| WO | WO 2011/101242 | * | 8/2011 |
| WO | WO-2011101242 | A1 | 8/2011 |
| WO | WO-2011101284 | A1 | 8/2011 |
| WO | WO-2011123813 | A2 | 10/2011 |
| WO | WO-2012006623 | A1 | 1/2012 |
| WO | WO-2012006624 | A2 | 1/2012 |
| WO | WO-2012006633 | A1 | 1/2012 |
| WO | WO-2012006635 | A1 | 1/2012 |
| WO | WO-2012007324 | A2 | 1/2012 |
| WO | WO-2012170969 | A2 | 12/2012 |
| WO | WO-2013106787 | A1 | 7/2013 |
| WO | WO-2013122617 | A1 | 8/2013 |
| WO | WO-2013123457 | A1 | 8/2013 |
| WO | WO-2013160005 | A1 | 10/2013 |
| WO | WO-2014011819 | A2 | 1/2014 |
| WO | WO-2014101287 | A1 | 7/2014 |
| WO | WO-2014173873 | A1 | 10/2014 |
| WO | WO-2014194282 | A2 | 12/2014 |
| WO | WO-2014198699 | A2 | 12/2014 |
| WO | WO-2014210547 | A1 | 12/2014 |
| WO | WO-2014210558 | A1 | 12/2014 |
| WO | WO-2015023891 | A2 | 2/2015 |
| WO | WO-2015106052 | A1 | 7/2015 |

(56) References Cited

OTHER PUBLICATIONS

Ackerman, M.J. and Clapham, D.E., "Ion Channels—Basic Science and Clinical Disease," The New England Journal of Medicine 336(22):1575-1586, Boston, Mass. Med. Soc., United States (1997).
Adams, G.P., et, al., "High Affinity Restricts the Localization and Tumor Penetration of Single-Chain Fv Antibody Molecules," Cancer Res. 61(12):4750-55, Am. Assoc. Cancer Res., United States (2001).
Adams, GP., et al., "Increased Affinity Leads to Improved Selective Tumor Delivery of Single-Chain Fv Antibodies," Cancer research 58(3):485-490, Am. Assoc. Cancer Res., United States (1998).
Agersoe, H., et al., "Prolonged effect of N8-Gp in haemophilia A dogs supports less frequent dosing," Journal of Thrombosis and Haemostasis 9(Suppl. 2): P-MO-181, ISTH Meeting, International Society on Thrombosis and Haemostasis, United States (2011).
Ahmad, S., et al., "ASAView: Database and tool for solvent accessibility representation in proteins," BMC Bioinformatics 5:51:1-5, BioMed Central, England (2004).
Alam, K.S., et al., "Expression and Purification of a Mutant Human Growth Hormone That is Resistant to Proteolytic Cleavage by Thrombin, Plasmin and Human Plasma in Vitro," Journal of Biotechnology 65(2-3):183-190, Elsevier Science Publishers, Netherlands (1998).
Alber, T. and Kawasaki, G., "Nucleotide Sequence of the Triose Phosphate Isomerase Gene of *Saccharomyces cerevisiae,*" Journal of Molecular and Applied Genetics 1(5):419-434, Raven Press, United States (1982).
Algiman, M., et al., "Natural antibodies to factor VIII (anti-hemophilic factor) in healthy individuals," Proceedings of the National Academy of Sciences 89(9):3795-3799, National Academy of Sciences, United States (1992).
Altschul, S.F., et al., "Basic Local Alignment Search Tool," Journal of Molecular Biology 215(3):403-410, Academic Press Limited, England (1990).
Alvarez, P., et al., "Improving Protein Pharmacokinetics by Genetic Fusion to Simple Amino Acid Sequences," Journal of Biological Chemistry 279(5):3375-3381, The American Society for Biochemistry and Molecular Biology, Inc., United States (2004).
Amin, N., et al., "Construction of Stabilized Proteins by Combinatorial Consensus Mutagenesis," Protein Engineering, Design & Selection : PEDS 17(11):787-793, Oxford University Press, England (2004).
Ansong, C., et al., "Epitope mapping factor VIII A2 domain by affinity-directed mass spectrometry: residues 497-510 and 584-593 comprise a discontinuous epitope for the monoclonal antibody R8B12," Journal of Thrombosis and Haemostasis 4(4):842-847. Blackwell Publishing Ltd., England (2006).
Antcheva, N., et al., "Proteins of Circularly Permuted Sequence Present Within the Same Organism: the Major Serine Proteinase inhibitor from Capsicum Annuum Seeds," Protein Science : a Publication of the Protein Society 10(11):2280-2290, Cold Spring Harbor Laboratory Press, United States (2001).
Appa, R., et al., "Investigating clearance mechanisms for recombinant activated factor VII in a perfused liver model," Journal of Thrombosis and Haemostasis 104(2):243-251, Stuttgart, Schattauer, Germany (Aug. 2010).
"Approval Letter—NovoSeven," U.S. Food and Drug Administration, Department of Health and Human Services, FDA Reference No. 96-0597, accessed at http://www.fda.gov/BiologicsBloodVaccines/BloodBloodProducts/ApprovedProducts/LicensedProductsBLAs/FractionatedPlasmaProducts/ucm056916.htm#, accessed on Dec. 12, 2014, 2 pages.
Araki, K., et al., "Four Disulfide Bonds' Allocation of Na+, K(+)-Atpase inhibitor (Spai)," Biochemical and Biophysical Research Communications 172(1):42-46, Academic Press, United States (1990).
Arap, W., et al., "Steps Toward Mapping the Human Vasculature by Phage Display," Nature medicine 8(2):121-127, Nature Publishing Company, United States (2002).
Armour, K.L., et al., "Recombinant Human IgG Molecules Lacking Fcγ Receptor I Binding and Monocyte Triggering Activities," European Journal of Immunology 29(8):2613-2624, Wiley-VCH, Germany (1999).
Arnau, J., et al., "Current strategies for the use of affinity tags and tag removal for the purification of recombinant proteins," Protein Expression and Purification 48(1):1-13, Elsevier Inc., United States (2006).
Arndt, K.M., et al., "Factors Influencing the Dimer to Monomer Transition of an Antibody Single-Chain Fv Fragment," Biochemistry 37:12918-12926, American Chemical Society, United States (1998).
Arruda, V.R., et al., "Posttranslational modifications of recombinant myotube-synthesized human factor IX," Blood 97(1):130-38, The American Society of Hematology, United States (2001).
Assadi-Porter, F.M., et al., "Sweetness Determinant Sites of Brazzein, a Small, Heat-Stable, Sweet-Tasting Protein," Archives of Biochemistry and Biophysics 376(2):259-265, Academic Press, United States (2000).
Aster, J.C., et al., "the Folding and Structure integrity of the First Lin-12 Module of Human Notch1 are Calcium-Dependent," Biochemistry 38(15):473-4742, Washington American Chemical Society., United States (1999).
Peters, R.T., et al., "Biochemical and fuctional characterization of a recombinant monomeric factor VIII-Fc fusion protein," Journal of Thrombosis and Haemostasis 11:132-141, International Society on Thrombosis and Haemostasis, England (2012).
Bachmann, M.F., et al., "T helper cell-independent neutralizing B cell response against vesicular stomatitis virus: role of antigen patterns in B cell induction?," European Journal of Immunology 25(12):3445-3451, Wiley-VCH Verlag GmbH, Germany (1995).
Bailon, P., et al., "Rational design of a potent, long-lasting form of interferon: a 40 kDa branched polyethylene glycol-conjugated interferon alpha-2a for the treatment of hepatitis C," Bioconjugate Chemistry 12(2):195-202, American Chemical Society, United States (2001).
Bajaj, S.P. and Birktoft, J.J., "Human factor IX and Factor IXa," Methods in Enzymology 222:96-128, Academic Press, Inc., England (1993).
Baneyx, F. and Mujacic, M., "Recombinant Protein Folding and Misfolding in *Escherichia coli*," Nature Biotechnology 22(11):1399-1408, Nature America Publishing, United States (2004).
Baron, E., "From cloning to a commercial realization. human alpha interferon," Critical Reviews in Biotechnology 10(3):79-190, CRC Press, Ltd, United States (1990).
Barrowcliffe, T.W., et al., "Coagulation and Chromogenic Assays of Factor VIII Activity: General Aspects, Standardization, and Recommendations," Seminars in Thrombosis and Hemostasis 28():247-256, Thieme Medical Publishers, Inc., United States (2002).
Barta, E., et al., "Repeats With Variations: Accelerated Evolution of the Pin2 Family of Proteinase inhibitors," Trends in Genetics 18(12):600-603, Elsevier Trends Journals, England (2002).
Bateman, A. and Bennett, H.P., "Granulins : the Structure and Function of an Emerging Family of Growth Factors," The Journal of Endocrinolgy 158(2):145-151, BioScientifica, England (1998).
Beissinger, M. and Buchner, J., "How Chaperones Fold Proteins," Biological Chemistry 379(3):245-259, Walter De Gruyter, Germany (1998).
Belaaouaj, A.A., et al., "Matrix Metalloproteinases Cleave Tissue Factor Pathway Inhibitor: Effects on coagulation," The Journal of Biological Chemistry 275(35):27123-27128, The American Society for Biochemistry and Molecular Biology, Inc., United States (2000).
Belew, M., et al., "Purification of recombinant human granulocyte-macrophage colony-stimulating factor from the inclusion bodies produced by transformed *Escherichia coli* cells," Journal of Chromtography 679(1):67-83, Elsevier, Netherlands (1994).
Benhar, I. and Pastan, I., "Cloning, Expression and Characterization of the Fv Fragments of the Anti-Carbohydrate mAbs B1 and B5 as Single-Chain Immunotoxins," Protein Engineering Design and Selection 7(11):1509-1515, Oxford University Press, England (1994).
Bensch, K,W., et al., "Hbd-1: A Novel Beta-Defensin from Human Plasma," FEBS Letters 368(2):331-335, Elsevier Science B.V, Netherlands (1995).

(56) References Cited

OTHER PUBLICATIONS

Berger, S.L., et al., "Phoenix Mutagenesis: One-Step Reassembly of Multiply Cleaved Plasmids With Mixtures of Mutant and Wild-Type Fragments," Analytical Biochemistry 214(2):571-579, Academic Press, United States (1993).
Beste, G., et al., "Small Antibody-like Proteins with Prescribed Ligand Specificities Derived from the Lipocalin Fold," Proceedings of the National Academy of Sciences 96(5):1898-1903, National Academy of Sciences, United States (1999).
Binz, H.K., et al., "Engineering Novel Binding Proteins from Nonimmunoglobulin Domains," Nature biotechnology 23(10):1257-1268, Nature America Publishing, United States (2005).
Bird, R.E., et al., "Single-Chain Antigen-Binding Proteins," Science 242(4877):423-426, Association for the Advancement of Science, United States (1988).
Bittner, B., et al., "Recombinant Human Erythropoietin (Rhepo) Loaded Poly(Lactide-Co-Glycolide) Microspheres: influence of the Encapsulation Technique and Polymer Purity on Microsphere Characteristics," European Journal of Pharmaceutics and Biopharmaceutics 45(3):295-305, Elsevier Science, Netherlands (1998).
Bjoern., S. and Thim, L., "Activation of Coagulation Factor VII to VIIa," Research Disclosure 26960:564-565, Questel Ireland Ltd., Ireland (1986).
Bjorkman, S. and Berntorp, E., "Pharmacokinetics of Coagulation Factors: Clinical Relevance for Patients with Haemophilia," Clinical Pharmacokinetics 40(11):815-832, Adis International Ltd., New Zealand (2001).
Blanchette, J., et al., "Principles of Transmucosal Delivery of therapeutic Agents," Biomedicine & Pharmacotherapy 58(3):142-151, Editions Scientifiques Elsevier, France (2004).
Bloch, C, J.R., et al., "1H Nmr Structure of an Antifungal Gamma-Thionin Protein Sialpha1: Similarity to Scorpion Toxins," Proteins 32(3):334-349, Wiley-Liss, United States (1998).
Bobrow, R.S., "Excess Factor VIII: a Common Cause of Hypercoagulability," J Am Board Fam Pract 18(2):147-149, American Board of Family Medicine, United States (2005).
Bodenmuller, et al., "the Neuropeptide Head Activator Loses Its Biological Acitivity by Dimerization," The EMBO Journal 5(8):1825-1829, Wiley Blackwell, England (1986).
Boder, E.T., et al., "Directed Evolution of Antibody Fragments With Monovalent Femtomolar Antigen-Binding Affinity," Proceedings of the National Academy of Sciences of the United States of America 97(20):10701-10705, National Academy of Sciences, United States (2000).
Boshart, M., et al., "A Very Strong Enhancer is Located Upstream of an Immediate Early Gene of Human Cytomegalovirus," Cell 41(2):521-530, Cell Press, United States (1985).
Briët, E., et al., "High Titer Inhibitors in Severe Haemophilia A: A Meta-analysis Based on Eight Long-term Follow-up Studies concerning Inhibitors Associated with Crude or Intermediate Purity Factor VIII Products," Journal of Thrombosis and Haemostastis 72(1):162-164, International Society on Thrombosis and Haemostasis, England (1994).
Brooks, D.J., et al., "Evolution of Amino Acid Frequencies in Proteins Over Deep Time: inferred Order of introduction of Amino Acids into the Genetic Code," Molecular Biology and Evolution 19(10):1645-1655, Oxford University Press, United States (2002).
Buchner, J., "Supervising the Fold: Functional Principles of Molecular Chaperones," FASEB Journal 10(1):10-19, The Federation, United States (1996).
Bulaj, G., et al., "Efficient Oxidative Folding of Conotoxins and the Radiation of Venomous Cone Snails," Proceedings of the National Academy of Sciences of the United States of America 100(Suppl 2):14562-14568, National Academy of Sciences, United States (2003).
Burmeister, W.P., et al., "Crystal structure of the complex of rat neonatal Fc receptor with Fc," Nature 372(6504):379-383, Nature Publishing Group, England (1994).
Buscaglia, C.A., et al., "Tandem amino acid repeats from Trypanosoma cruzi shed antigens increase the half-life of proteins in blood," Blood 93(6):2025-2032, American Society of Hematology, United States (1999).
Calabrese, J.C., et al., "Crystal Structure of Phenylalanine Ammonia Lyase: Multiple Helix Dipoles Implicated in Catalysis," Biochemistry 43(36):11403-11416, Washington American Chemical Society, United States (2004).
Caliceti, P. and Veronese, F.M., "Pharmacokinetic and biodistribution properties of poly(ethylene glycol)-protein conjugates," Advanced Drug Delivery Reviews 55(10):1261-1277, Elsevier B.V., Netherlands (2003).
Caliceti, P., et al., "Biopharmaceutical Properties of Uricase Conjugated to Neutral and Amphiphilic Polymers," Bioconjugate Chemistry 10(4):638-646, American Chemical Society, United States (1999).
Calvete, J.J., et al., "Disulphide-Bond Pattern and Molecular Modelling of the Dimeric Disintegrin Emf-10 , A Potent and Selective integrin Alpha5Beta1 Antagonist from Eristocophis Macmahoni Venom," The Biochemical Journal 345(Pt 3):573-581, Published by Portland Press on behalf of the Biochemical Society, England (2000).
Calvete, J.J., et al., "Snake Venom Disintegrins: Evolution of Structure and Function," Toxicon 45(8):1063-1074, Pergamon Press, England (2005).
Calvete, J.J., et al., "Snake Venom Disintegrins: Novel Dimeric Disintegrins and Structural Diversification by Disulphide Bond Engineering," The Biochemical Journal 372(Pt 3):725-734, Published by Portland Press on behalf of the Biochemical Society, London (2003).
Cameron, C., et al., "The Canine Factor VIII cDNA and 5' Flanking Sequence," Thrombosis and Haemostasis 79(2):317-322, Schattauer Verlag, Germany (1998).
Cao, P., et al., "Development of a Compact Anti-Baff Antibody in *Escherichia coli*," Applied Microbiology and Biotechnology 73(1):151-157, Springer International, Germany (2006).
Capon, D.J., et al., "Designing CD4 Immunoadhesins for AIDS Therapy," Nature 337(6207):525-531, Nature Publishing Group, England (1989).
Carr, M.D., et al., "Solution Structure of a Trefoil-Motif-Containing Cell Growth Factor, Porcine Spasmolytic Protein," Proceedings of the National Academy of Sciences of the United States of America 91(6):2206-2210, National Academy of Sciences, United States (1994).
Castor, B., et al., "Septic Cutaneous Lesions Caused by *Mycobacterium malmoense* in a Patient With Hairy Cell Leukemia," European Journal of Clinical Microbiology & Infectious Diseases 13(2):145-148, Springer, Germany (1994).
Chang, A.C.Y., et al., "Phenotypic expression in *E. coli* of a DNA sequence coding for mouse dihydrofolate reductase," Nature 275(5681):617-624, MacMillan Journals Ltd, United States (1978).
Chen, L.H., et al., "Expression, Purification, and in Vitro Refolding of a Humanized Single-Chain Fv Antibody Against Human Ctla4 (Cd152)," Protein Expression and Purification 46(2):495-502, Academic Press, United States (2006).
Chen, L.Q., et al., "Crystal Structure of a Bovine Neurophysin Ii Dipeptide Complex At 2," Proceedings of the National Academy of Sciences of the United States of America 88(10):4240-4244, National Academy of Sciences, United States (1991).
Chen, X.J., et al., "Site-Directed Mutations in a Highly Conserved Region of Bacillus Thuringiensis Delta-Endotoxin Affect inhibition of Short Circuit Current Across Bombyx Mori Midguts," Proceedings of the National Academy of Sciences of the Unites States of America 90(19):9041-9045, National Academy of Sciences, United States (1993).
Chirino, A.J., et al., "Minimizing the Immunogenicity of Protein therapeutics," Drug Discovery Today 9(2):82-90, Elsevier Science Ltd., England (2004).
Cho, J.W. and Troy, F.A. II, "Polysialic Acid Engineering: Synthesis of Polysialylated Neoglycosphingolipids by using the Polysialyltransferase from Neuroinvasive *Escherichia coli* K1," Proceedings of the National Academy of Sciences USA 91(24):11427-11431, National Academy of Sciences, United States (1994).

(56) References Cited

OTHER PUBLICATIONS

Chong, J.M. and Speicher, D.W., "Determination of Disulfide Bond assignments and N-Glycosylation Sites of the Human Gastrointestinal Carcinoma Antigen Ga733-2 (Co17-1A, Egp, Ks1-4, Ksa, and Ep-Cam)." The Journal of Biological Chemistry 276(8):804-5813, American Society for Biochemistry and Molecular Biology, United States (2001).

Chong, J.M., et al., "Disulfide Bond assignments of Secreted Frizzled-Related Protein-1 Provide insights About Frizzled Homology and Netrin Modules," The Journal of Biological Chemistry 277(7):5134-5144, American Society for Biochemistry and Molecular Biology, United States (2002).

Choo, K.H., et al., "Molecular Cloning of the Gene for Human Anti-haemophilic Factor IX," Nature 299(5879):178-180, Macmillan Journals Ltd., England (1982).

Chou, P.Y., "Prediction of protein conformation," Biochemistry 13(2):222-245, The American Chemical Society, United States (1974).

Chowdhury, P.S. and Pastan, I., "Improving antibody affinity by mimicking somatic hypermutation in vitro," Nature Biotechnology 17(6):568-572, Nature Publishing Group, United States (1999).

Christmann, A., et al., "the Cystine Knot of a Squash-Type Protease inhibitor as a Structural Scaffold for *Escherichia coli* Cell Surface Display of Comformationally Constrained Peptides," Protein Engineering 12(9):797-806, Oxford University Press, England (1999).

Clark, R., et al., "Long-acting growth hormones produced by conjugation with polyethylene glycol," Journal of Biological Chemistry 271(36):21969-21977, The American Society for Biochemistry and Molecular Biology, Inc., United States (1996).

Clark, R.G., et al., "Recombinant Human Growth Hormone (Gh )-Binding Protein Enhances the Growth-Promoting Activity of Human Gh in the Rat," Endocrinology 137(10):4308-4315, Endocrine Society, United States (1996).

Cleland, J.L., et al., "An Extended Half-life Exenatide Construct for Weekly Administration in the Treatment of Diabetes Mellitus," Diabetes 58:A511-A512, American Diabetes Association, United States (2009).

Cleland, J.L., et al., "Emerging Protein Delivery Methods," Current Opinion in Biotechnology 12(2):212-219, Elsevier, England (2001).

Coia, G., et al., "Use of Mutator Cells as a Means for increasing Production Levels of a Recombinant Antibody Directed Against Hepatitis B," Gene 201(1-2):203-209, Elsevier/North-Holland, Netherlands (1997).

Collen, D., et al., "Polyethylene Glycol-Derivatized Cysteine-Substitution Variants of Recombinant Staphylokinase for Single-Bolus Treatment of Acute Myocardial Infarction," Circulation 102(15):1766-1772, American Heart Association, United States (2000).

Conticello, S.G., et al., "Mechanisms for Evolving Hypervariability: the Case of Conopeptides," Molecular Biology and Evolution 18(2):120-131, Oxford University Press, United States (2001).

Saenko, E.L., et al., "A Role for the C2 Domain of Factor VIII in Bniding to von Willebrand Factor," The Journal of Biological Chemistry 269(15):11601-11605, The American Society for Biochemistry and Molecular Biology, Inc., United States (1994).

Meloun, B., et al., "Complete Amino Acid Sequence of Human Serum Albumin," FEBS Letters 58(1): 134-137, North-Holland Publishing Company, Netherlands (1975).

Zaveckas, M., et al., "Effect of Surface Histidine Mutations and their Number on the Partitioning and Refolding of Recombinant Human Granulocyte-Colony Stimulating Factor (Cys17Ser) in Aqueous Two-Phase Systems Containing Chelated Metal Ions," Journal Chromatography B 852(1-2):409-419, Elsevier, Netherlands (2007).

Wasley, L.C., et al., "PACE/furin can process the vitamin K-dependent pro-factor IX precursor within the secretory pathway," J. Biol. Chem. 268(12):8458-65, Am. Soc. Biol. Chem., United States (1993).

Zhang, A.H., et al., "Factor VIII inhibitors: risk factors and methods for prevention and immune modulation," Clinical Reviews in Allergy & Immunology 37(2):114-124, Humana Press, United States (Feb. 6, 2009).

Co-pending U.S. Appl. No. 14/517,680, inventors Schellenberger, et al., filed on Oct. 17, 2014 (Not Published).

Zhou Y.F., et al., "Sequence and Structure Relationships within Von Willebrand Factor," Blood 120(2):449-458, American Society of Hematology, United States (2012).

Corisdeo, S. and Wang, B., "Functional Expression and Display of an Antibody Fab Fragment in *Escherichia coli*: Study of Vector Designs and Culture Conditions," Protein Expression and Purification 34(2):270-279, Academic Press, United States (2004).

Corsaro, C.M. and Pearson M.L., "Enhancing the efficiency of DNA-mediated gene transfer in mammalian cells," Somatic Cell Genetics 7(5):603-616, Plenum Publishing Corporation, United States (1981).

Craik, D.J., et al., "Plant Cyclotides: A Unique Family of Cyclic and Knotted Proteins That Defines the Cyclic Cystine Knot Structural Motif," Journal of Molecular Biology 294(5):1327-1336, Elsevier, England (1999).

Crameri, A., et al., "Improved Green Fluorescent Protein by Molecular Evolution Using Dna Shuffling," Nature Biotechnology 14(3):315-319, Nature America Publishing, United States (1996).

Cull, M.G., et al., "Screening for receptor ligands using large libraries of peptides linked to the C terminus of the lac repressor," Proceedings of the National Academy of Sciences 89(5):1865-1869, National Academy of Sciences, United States (1992).

Cutler, J.A., et al., "The Identification and Classification of 41 novel Mutations in the Factor VIII Gene (F8C)," Human Mutation 19(3):274-278, Wiley-Liss, Inc., England (2002).

Daley, M.E., et al., "Structure and Dynamics of a Beta-Helical Antifreeze Protein," Biochemistry 41(17):5515-5525, American Chemical Society., United States (2002).

Daniel, S., et al., "Screening for Potassium Channel Modulators by a High Through-Put 86-Rubidium Efflux assay in a 96-Well Microtiter Plate," Journal of Pharmacological Methods 25(3):185-193, Elsevier/north-Holland, United States (1991).

Danner, S. and Belasco, J.G., "T7 Phage Display: A Novel Genetic Selection System for Cloning RNA-Binding Proteins from Cdna Libraries," Proceedings of the National Academy of Sciences of the United States of America 98(23):12954-12959, National Academy of Sciences, United States (2001).

D'Aquino, J.A., et al., "The magnitude of the backbone conformational entropy change in protein folding," Proteins 25(2):143-156, Wiley-Liss, Inc., England (1996).

Dattani, M.T., et al., "An investigation into the Lability of the Bioactivity of Human Growth Hormone Using the Esta Biassay," Hormone Research 46(2):64-73, Karger, Switzerland (1996).

Dauplais, M., et al., "On the Convergent Evolution of Animal Toxins," The Journal of Biological Chemistry 272(7):4302-4309, American Society for Biochemistry and Molecular Biology, United States (1997).

De A., et al., "Crystal Structure of a Disulfide-Linked "Trefoil" Motif Found in a Large Family of Putative Growth Factors," Proceedings of the National Academy of Sciences of the United States of America 91(3):1084-1088, National Academy of Sciences, United States (1994).

De Boer, H.A., et al., "The tac promoter: a functional hybrid derived from the trp and lac promoters," Proceedings of the National Academy of Sciences 80(1):21-25, National Academy of Sciences, United States (1983).

De, Kruif, J., et al., "Selection and Application of Human Single Chain Fv Antibody Fragments from a Semi-Synthetic Phage Antibody Display Library With Designes Cdr3 Regions," Journal of Molecular Biology 241(1):97-105, Elsevier, England (1995).

Deckert, P.M., et al., "Pharmacokinetics and microdistribution of polyethylene glycol-modified humanized A33 antibody targeting colon cancer xenografts," International Journal of Cancer 8(3):382-390, Wiley-Liss, Inc., United States (2000).

Delgado, C., et al., "The Uses and Properties of PEG-Linked Proteins," Critical Reviews in Therapeutic Drug Carrier Systems 9(3-4):249-304, CRC Press, Inc., United States (1992).

(56) References Cited

OTHER PUBLICATIONS

Dennis, M.S., et al., "Albumin Binding as a General Strategy for Improving the Pharmacokinetics of Proteins," The Journal of Biological Chemistry 277(38):35035-35043, The American Society for Biochemistry and Molecular Biology, Inc., United States (2002).
Denoto, F.M., et al., "Human growth hormone DNA sequence and mRNA structure: possible alternative splicing," Nucleic Acids Research 9(15):3719-3730, IRL Press Limited, England (1981).
Der Maur, A.A., et al., "Direct in Vivo Screening of intrabody Libraries Constructed on a Highly Stable Single-Chain Framework," The Journal of Biological Chemistry 277(47):45075-45085, American Society for Biochemistry and Molecular Biology, United States (2002).
Desplancq, D., et al., "Multimerization Behaviour of Single Chain Fv Variants for the Tumour-Binding Antibody B72.3," Protein Engineering 7(8):1027-1033, Oxford University Press, England (1994).
Dhalluin, C., et al., "Structural and biophysical characterization of the 40 kDa PEG-interferon-$\alpha$2a and its individual positional isomers," Bioconjugate Chemistry 16(3):504-517, American Chemical Society, United States (2005).
Di Lullo, G.A., et al., "Mapping the Ligand-Binding Sites and Disease-associated Mutations on the Most Abundant Protein in the Human, Type I Collagen," The Journal of Biological Chemistry 277(6):4223-4231, American Society for Biochemistry and Molecular Biology, United States (2002).
Diaz-Collier, J.A., et al., "Refold and characterization of recombinant tissue factor pathway inhibitor expressed in *Escherichia coli*," Thrombosis and Haemostasis 71(3):339-346, Schattauer GmbH, Germany (1994).
Dietrich, C.G., et al., "Abc or Oral Bioavailability: Transporters as Gatekeepers in the Gut," Gut 52(12):1788-1795, Stuttgart, Schattauer., Germany (2003).
Dolezal, O., et al., "Scfv Multimers of the Anti-Neuraminidase Antibody Nc10: Shortening of the Linker in Single-Chain Fv Fragment assembled in V(L) to V(H) Orientation Drives the formation of Dimers, Trimers, Tetramers and Higher Molecular Mass Multimer," Protein Engineering 13(8):565-574, Oxford University Press, England (2000).
Dooley, H., et al., "Stabilzation of Antibody Fragments in Adverse Environments," Biotechnology and Applied Biochemistry 28 (Pt I):77-83, Wiley-Blackwell, United States (1998)
Doyle, D.A., et al., "Crystal Structures of a Complexed and Peptide-Free Membrane Protein-Binding Domain: Molecular Basis of Peptide Recognition by Pdz" Cell 85(7):1067-1076, Cell Press United States (1996).
Dufton, M.J., "Classification of Elapid Snake Neurotoxins and Cytotoxins According to Chain Length: Evolutionary Implications," Journal of Molecular Evolution 20(2):128-134, Springer-Verlag., Germany (1984).
Dumont, J.A., et al., "Prolonged Activity of a Recombinant Factor VIII-Fc Fusion Protein in Hemophilia A Mice and Dogs," Blood 119(13):3024-3030, The American Society of Hematology, United States (2012).
Dumoulin, M., et al., "Single-Domain Antibody Fragments with High Conformational Stability," Protein Science 11(3):500-515, Cold Spring Harbor Laboratory Press, United States (2002).
Dutton, J.L., et al., "A New Level of Conotoxin Diversity, A Non-Native Disulfide Bond Connectivity in Alpha-Conotoxin Auib Reduces Structural Definition But increases Biological Activity," The Journal of Biological Chemistry 277(50):48849-48857, American Society for Biochemistry and Molecular Biology, United States (2002).
Dyson, M.R., et al., "Production of Soluble Mammalian Proteins in *Escherichia coli*: Identification of Protein Features That Correlate With Successful Expression," BMC Biotechnology 4:32, American Society for Biochemistry and Molecular Biology, United States (2004).
Eaton, D.L., et al., "Construction and Characterization of an Active Factor VIII Variant Lacking the Central One-Third of the Molecule," Biochemistry 25(26):8343-8347, American Chemical Society, United States (1986).
Ellis, L.B and Milius, R.P., "Valid and invalid implementations of GOR secondary structure predictions," Computer Applications in Biosciences 10(3):341-348, Oxford University Press, United Kingdom (1994).
Engels, et al., "Gene Synthesis," Angewandte Chemie International Edition, 28(6):716-734, VCH Verlagsgesellschaft mbH, Germany (1989).
European Search Report and opinion for EP Application No. 08795371, dated Jan. 27, 2011.
European search report dated Feb. 4, 2010 for Application No. 6804210.
European search report dated Mar. 26, 2009 for Application No. 7752636.6.
European search report dated Mar. 5, 2009 for Application No. 7752549.1.
Fair, D.S. and Bahnak, B.R., et al., "Human hepatoma cells secrete single chain factor X, prothrombin, and antithrombin III," Blood 64(1):194-204, Grune & Stratton, Inc., United States (1984).
Fajloun, Z., et al., "Maurotoxin Versus Pi1/Hstx1 Scorpion Toxins," The Journal of Biological Chemistry 275(50):39394-39402, American Society for Biochemistry and Molecular Biology, United States (2000).
Felici, F., et al., "Selection of antibody ligands from a large library of oligopeptides expressed on a multivalent exposition vector," Journal of Molecular Biology 222(2):301-310, Elsevier Science, United States (1991).
Fisher, et al. "Genetic selection for protein solubility enabled by the folding quatliy control feature of the twin-arginin translocation pathway," Protein Science (2006) (online).
Fitzgerald, K. and Greenwald, I., "interchangeability of Caenorhabditis Elegans Dsl Proteins and intrinsic Signalling Activity of their Extracellular Domains in Vivo," Development 121(12):4275-4282, Company of Biologists Limited, England (1995).
Franz., T.J., "Percutaneous Absorption on the Relevance of in Vitro Data," Journal of Investigative Dermatology 64(3):190-195, Williams & Wilkins Co., United States (1975).
Frenal, et al.,, "Exploring Structural Features of the interaction Between the Scorpion Toxincnergl and Erg K+ Channels," Proteins 56(2):367-375, Wiley-Liss, United States (2004).
Freshney, R.I., "Quantitation and Experimental Design," in Culture of Animal Cells, pp. 227-296, Alan R. Liss, Inc. United States (1987).
Friend, P.J., et al., "Phase I Study of an Engineered Aglycosylated Humanized CD3 Antibody in Renal Transplant Rejection," Transplantation 68(11):1632-1637, Lippincott Williams & Wilkins, Inc., United States (1999).
Fulcher, C.A., et al., "Localization of human factor FVIII inhibitor epitopes to two polypeptide fragments," Proceedings of the National Academy of Sciences 82(22):7728-7732, National Academy of Sciences, United States (1985).
Gamez, et al., "Development of Pegylated forms of Recombinant Rhodosporidium Toruloides Phenylalanine Ammonia-Lyase for the Treatment of Classical Phenylketonuria," The Journal of the American Society of Gene Therapy 11(6):986-989, Academic Press, United States (2005).
Garnier, J., et al., "GOR method for predicting protein secondary structure from amino acid sequence," Methods in Enzymology 266:540-553, Academic Press, Inc., United States (1996).
Geething, N.C., et al., "Gcg-XTEN: an improved glucagon capable of preventing hypoglycemia without increasing baseline blood glucose," PLoS ONE 5(4):e10175, PLoS ONE, United States (Apr. 2010).
George, R.A. and Heringa, J., "An analysis of protein domain linkers: their classification and role in protein folding," Protein Engineering Design 15(11):871-879, Oxford University Press, England (2003).

(56) References Cited

OTHER PUBLICATIONS

Gilkes, N.R., et al., "Domains in Microbial Beta-1, 4-Glycanases: Sequence Conservation, Function, and Enzyme Families," Microbiological reviews 55(2):303-315, American Society for Microbiology, United States (1991).
Gilles, J.G., et al., "Anti-factor VIII antibodies of hemophiliac patients are frequently directed towards nonfunctional determinants and do not exhibit isotypic restriction," Blood 82(8):2452-2461, The American Society of Hematology, United States (1993).
Gitschier, J., et al., "Characterization of the Human Factor VIII Gene," Nature 312(5992):326-330, Nature Publishing Group, England (1984).
Gleeson, M.A., et al., "Transformation of the Methylotrophic Yeast *Hansenula polymorpha,*" Journal of General Microbiology 132:3459-3465, Society for General Microbiology, England (1986).
Goeddel, D.V., et al., "Direct expression in *Escherichia coli* of a DNA sequence coding for human growth hormone," Nature 281(5732):544-548, MacMillan Journals Ltd., United States (1979).
Goeddel, D.V., et al., "Synthesis of human fibroblast interferon by *E. coli,*" Nucleic Acids Research 8(18):4057-4074, IRL Press Limited, England (1980).
Gomez-Duarte., et al., "Expression of Fragment C of Tetanus Toxin Fused to a Carboxyl-Terminal Fragment of Diphtheria Toxin in *Salmonella typhi* Cvd 908 Vaccine Strain," Vaccine 13(16):1596-1602, Elsevier Science, Netherlands (1995).
Gouw, S.C., et al., "The multifactorial etiology of inhibitor development in hemophilia. genetics and environment," Seminars in Thrombosis and Hemostasis 35(8):723-734, Thieme Medical Publishers, Inc., United States (Nov. 2009).
Graff, C.P. and Wittrup, K.D., "Theoretical Analysis of Antibody Targeting of Tumor Spheroids: Importance of Dosage for Penetration, and Affinity for Retention," Cancer Research 63(6):1288-1296, American Association for Cancer Research, United States (2003).
Graham, F.L. and Smiley, J., "Characteristics of a Human Cell Line Transformed by DNA from Human Adenovirus Type 5," Journal of General Virology 36(1):59-72, Society for General Microbiology , England (1977).
Graham, F.L. and Van Der Eb, J., "A new technique for the assay of infectivity of human adenovirus 5 DNA," Virology 52(2):456-467, Academic Press, Inc., United States (1973).
Graw, J., et al., "Haemophilia A: From Mutation Analysis to New Therapies," Nature Reviews. Genetics 6(6):488-501, Nature Publishing Group, England (2005).
Gray, W.R., et al., "Peptide Toxins from Venomous Conus Snails," Annual Review of Biochemistry 57:665-700, Annual Reviews, United States (1988).
Greenwald, R.B., et al., "Effective Drug Delivery by PEGylated Drug Conjugates," Advanced Drug Delivery Reviews 55(2):217-250, Elsevier Science Publishers, B.V., Netherlands (2003).
Guncar, G., et al., "Crystal Structure of Mhc Class Ii-associated P41 Ii Fragment Bound to Cathepsin L Reveals the Structural Basis for Differentiation Between Cathepsins L and S," The EMBO Journal 18(4):793-803, Wiley Blackwell, England (1999).
Guo, M., et al., "Crystal Structure of the Cysteine-Rich Secretory Protein Stecrisp Reveals That the Cysteine-Rich Domain Has a K+ Channel inhibitor-Like Fold," The Journal of Biological Chemistry 280(13):12405-12412, American Society for Biochemistry and Molecular Biology, United States (2005).
Gupta, A., et al., "A Classification of Disulfide Patterns and Its Relationship to Protein Structure and Function," Protein Science : a Publication of the Protein Society 13(8):2045-2058, Cold Spring Harbor Laboratory Press, United States (2004).
Gustafsson, C., et al., "Codon Bias and Heterologous Protein Expression," Trends in Biotechnology 22(7):346-353, Elsevier Science Publishers, England (2004).
Hamers-Casterman, C., et al., "Naturally Occurring Antibodies Devoid of Light Chains," Nature 363(6428):446-448, Nature Publishing Group, England (1993).
Hammer, J., "New Methods to Predict Mhc-Binding Sequences Within Protein Antigens," Current Opinion in Immunology 7(2):263-269, Elsevier, England (1995).
Harlow, E. and Lane, D., "Cell Staining," Cold Spring Harbor Laboratory: 359-420 (1988).
Harris, J.L., et al., "Rapid and general profiling of protease specificity by using combinatorial fluorogenic substrate libraries," Proceedings of the National Academy of Sciences 97(14):7754-7759, National Academy of Sciences, United States (2000).
Harris, J.M. and Chess, R.B., "Effect of pegylation on pharmaceuticals," Nature Reviews Drug Discovery 2(3):214-221, Nature Publishing Group, England (2003).
Healey, J.F., et al., "The cDNA and Derived Amino Acid Sequence of Porcine Factor VIII," Blood 88(11):4209-4214, The American Society of Hematology, United States (1996).
Hedner, U. and Kisiel, W., "Use of human factor VIIa in the treatment of two hemophilia A patients with higher-titer inhibitors," The Journal of Clinical Investigation 71 (6):1836-1841, The American Society for Clinical Investigation, United States (1983).
Hedner, U., "NovoSeven® as a Universal Haemostatic Agent," Blood Coagulation & Fibrinolysis 11(Suppl 1):S107-S111, Lippincott Williams & Wilkins, England (2000).
Hennighausen, L.G. and Sippel, A.E., "Mouse Whey Acidic Protein is a Novel Member of the Family of 'Four-Disulfide Core' Proteins," Nucleic Acids Research 10(8):2677-2684, Oxford University Press, England (1982).
Hermeling, S., et al., "Structure-Immunogenicity Relationships of therapeutic Proteins," Pharmaceutical Research 21(6):897-903, Kluwer Academic/Plenum Publishers, United States (2004).
Higgins, J.A., et al., "Polyclonal and Clonal Analysis of Human Cd4+ T-Lymphocyte Responses to Nut Extracts," Immunology 84(1):91-97, Blackwell Scientific Publications, England (1995).
Higgins, J.M., et al., "Characterization of Mutant forms of Recombinant Human Properdin Lacking Single Thromospindin Type I Repeats," Journal of Immunology 155(12):5777-5785, American Association of Imunologists, United States (1995).
Hill, J.M., et al., "Conotoxin TVIIA, A Novel Peptide from the Venom of Conus Tulipa 1," European Journal of Biochemistry / FEBS 267(15):4642-4648, Blackwell Science Ltd. on behalf of the Federation of European Biochemical Societies, England (2000).
Hinds, K.D., et al., "PEGylated insulin in PLGA microparticles. In vivo and in vitro analysis," Journal of Controlled Release 104(3):447-460, Elsevier B.V., Netherlands (2005).
Hirel, P.H., et al., "Extent of N-Terminal Methionine Excision from *Escherichia coli* Proteins is Governed by the Side-Chain Length of the Penultimate Amino Acid," Proceedings of the National Academy of Sciences of the United States of America 86(21):8247-8251, National Academy of Sciences, United States (1989).
Ho, S.N., et al., "Site-Directed Mutagenesis by Overlap Extension Using the Polymerase Chain Reaction," Gene 77(1):51-59, Elsevier Science Publishers B.V., Netherlands (1989).
Hoeben, R.C., et al., "Expression of Functional Factor VIII in Primary Human Skin Fibroblasts after Retrovirus-mediated Gene Transfel," The Journal of Biological Chemistry 265(13):7318-7323, The American society for Biochemistry and Molecular Biology, United States (1990).
Hogg, P.J., "Disulfide Bonds as Switches for Protein Function," Trends in Biochemical Sciences 28(4):210-214, Elsevier Trends Journals, England (2003).
Holevinsky, K.O., et al., "Atp-Sensitive K+ Channel Opener Acts as a Potent Cl-Channel inhibitor in Vascular Smooth Muscle Cells," The Journal of Membrane Biology 137(1):59-70, Springer., United States (1994).
Hopp, T.P. and Woods, K.R., "Prediction of protein antigenic determinants from amino acid sequences," Proceedings of the National Academy of Sciences 78(6):3824-3828, National Academy of Sciences, United States (1981).
Horton, R.M., et al., "Gene Splicing by Overlap Extension," Methods in Enzymology 217:270-279, Academic Press, United States (1993).
Hsu, C.T., et al., "Vaccination against gonadotropin-releasing hormone (GnRH) using toxin receptor-binding domain-conjugated

(56) References Cited

OTHER PUBLICATIONS

GnRH repeats," Cancer Research 60(14):3701-3705, American Association for Cancer Research, United States (2000).
Hudson, P.J. and Kortt, A.A., "High Avidity Scfv Multimers; Diabodies and Triabodies," Journal of Immunological Methods 231(1-2):177-189, Elsevier, Netherlands (1999).
Hugli, T.E., "Structure and Function of C3A Anaphylatoxin," Current topics in Microbiology and Immunology 153:181-208, Springer Verlag, Germany (1990).
Huston, J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences USA 85(16):5879-5883, National Academy of Sciences, United States (1988).
International Search Report and Written Opinion for Application No. PCT/US2011/043568, ISA/US, United States, dated Nov. 25, 2011, 10 pages.
International Search Report and Written Opinion for International Application No. PCT/US2010/002148, dated Dec. 1, 2010.
International Search Report and Written Opinion for International Application No. PCT/US2010/02147, dated Dec. 20, 2010.
International Search Report and Written Opinion for International Application No. PCT/US2010/061590, dated Jul. 12, 2011.
International Search Report and Written Opinion for International Application No. PCT/US2011/48517, ISA United States, dated Mar. 14, 2012.
International search report dated Jan. 17, 2008 for PCT Application No. US2006/37713.
International search report dated Sep. 26, 2007 for PCT Application No. US2007/05857.
International Search Report for International Application No. PCT/US2007/05952, dated Dec. 26, 2007.
International Search Report for International Application No. PCT/US2008/09787, dated Mar. 16, 2009.
International Search Report for International Application No. PCT/US2010/23106, dated Apr. 20, 2010.
International Search Report for International Application No. PCT/US2010/37855, dated Oct. 29, 2010.
International Search Report for International Application No. PCT/US2012/46326, dated Jan. 25, 2013.
Israel, E.J., et al., "Expression of the neonatal Fc receptor, FcRn, on human intestinal epithelial cells," Immunology 92(1):69-74, Blackwell Sciences, England (1997).
Iwasaki, W., et al., "Solution Structure of Midkine, A New Heparin-Binding Growth Factor," The EMBO Journal 16(23):6936-6946, Wiley Blackwell, England (1997).
Jackson, J.K., et al., "the Characterization of Paclitaxel-Loaded Microspheres Manufactured from Blends of Poly(Lactic-Co-Glycolic Acid) (Plga) and Low Molecular Weight Diblock Copolymers," International Journal of Pharmaceutics 342(1-2):6-17, Elsevier/North-Holland Biomedical Press., Netherlands (2007) .
Jacquemin, M., et al., "A human antibody directed to the factor VIII Cl domain inhibits factor VIII cofactor activity and binding to von Willebrand factor," Blood 95(1):156-163, The American Society of Hematology, United States (2000).
Johansson, J. and Hellman, L., "Modifications increasing the efficacy of recombinant vaccines; marked increase in antibody titers with moderately repetitive variants of a therapeutic allergy vaccine," Vaccine 25(9):1676-1682, Elsevier Ltd., United States (2007).
Jonassen, I., et, al., "Finding Flexible Patterns in Unaligned Protein Sequences", Protein Science 4(8):1587-1595, Cold Spring Harbor Laboratory Press, United States (1995).
Jones, M.D., et, al., "Determination of Tumor Necrosis Factor Binding Protein Disulfide Structure : Deviation of the Fourth Domain Structure from the Tnfr/Ngfr Family Cysteine-Rich Region Signature," Biochemistry 36(48):14914-14923, American Chemical Society., United States (1997).
Jones, P.T., et al., "Replacing the Complementarity-Determining Regions in a Human Antibody with those from a Mouse," Nature 321(6069):522-525, Nature Publishing Group, England (1986).
Jonsson, J., et, al., "Quantitative Sequence-Activity Models (Qsam )—Tools for Sequence Design", Nucleic Acids Research 21(3):733-739, Oxford University Press, England (1993).
Joosten, R.P., et al., "A series of PDB related databases for everyday needs," Nucleic Acids Research 39:D411-D419, Oxford University Press, England (2011).
Jung, S. and Honegger, A., "Improving In Vivo Folding and Stability of a Single-Chain Fv Antibody Fragment by Loop Grafting", Protein Engineering 10(8):959-966, Oxford University Press, England (1997).
Kabsch, W., "Dictionary of protein secondary structure: pattern recognition of hydrogen-bonded and geometrical features," Biopolymers 22(12):2577-2637, John Wiley & Sons, Inc., United States (1983).
Kamikubo, Y., et, al., "Disulfide Bonding Arrangements in Active forms of the Somatomedin B Domain of Human Vitronectin ", Biochemistry 43(21):6519-6534, American Chemical Society., United States (2004).
Kasper, C.K., et al., "A More Uniform Measurement of Factor VIII Inhibitors," Thrombosis ET Diathesis Haemorhagica 34(1):612, F.K. Schattauer Verlag, New York (1975) (Abstract).
Kasuda, S., et al., "Establishment of embryonic stem cells secreting human factor VIII for cell-based treatment of hemophilia A," Journal of Thrombosis and Haemostasis 6(8):1352-1359, International Society of Thrombosis and Haemostasis, England (May 2008).
Kaufman, R.J. and Sharp, P.A., "Amplification and expression of sequences contransfected with a modular dihydrofolate reductase complementary DNA gene," Journal of Molecular Biology 159(4):601-621, Academic Press, Inc. Ltd., England (1982).
Kaufman, R.J. and Sharp, P.A., "Construction of a modular dihydrofolate reductase cDNA gene: analysis of signals utilized for efficient expression," Molecular and Cellular Biology 2(11):1304-1319, American Society for Microbiology, United States (1982).
Kay, B.K., et, al., "An M13 Phage Library Displaying Random 38-Amino-Acid Peptides as a Source of Novel Sequences With Affinity to Selected Targets", Gene 128(1):59-65, Elsevier/North-Holland, Netherlands (1993).
Kazatchkine, M.D., et al., "Circulating immune complexes containing anti-VIII antibodies in multi-transfused patients with haemophilia A," American Journal of Clinical and Experimental Immunology 39(2):315-320, Blackwell Scientific Publications, United States (1980).
Kelly, K.A. and Jones, D.A., "isolation of a Colon Tumor Specific Binding Peptide Using Phage Display Selection", Neoplasia 5(5):437-444, BC Decker, Canada (2003).
Kemball-Cook, G., et al., "The factor VIII Structure and Mutation Resource Site: HAMSTeRS version 4," Nucleic Acids Research 26(1):216-219, Oxford University Press, England (1998).
Khan, R.H., et, al., "Solubilization of Recombinant Ovine Growth Hormone With Retention of Native-Like Secondary Structure and Its Refolding from the Inclusion Bodies of *Escherichia coli*", Biotechnology Progress 14(5):722-728, Wiley-Blackwell, United States (1998).
Kim, J.I., et al., "Three-Dimensional Solution Structure of the Calcium Channel Antagonist Omega-Agatoxin Iva: Consensus Molecular Folding of Calcium Channel Blockers," Journal of Molecular Biology 250(5):659-671, Elsevier, England (1995).
Kimble, J. and Simpson, P., "the Lin-12/Notch Signaling Pathway and Its Regulation," Annual Review of Cell and Developmental Biology 13:333-361, Annual Reviews, United States (1997).
Kisiel, W. and Fujikawa, K., "Enzymological aspects of blood coagulation," Behring Institute Mitteilungen 73:29-42, (1983).
Kissel, T., et al., "Aba-Triblock Copolymers from Biodegradable Polyester A-Blocks and Hydrophilic Poly (Ethylene Oxide ) B-Blocks as a Candidate for in Situ forming Hydrogel Delivery Systems for Proteins," Advanced Drug Delivery Reviews 54(1):99-134, Elsevier Science Publishers, Netherlands (2002).
Klitgaard, T. and Nielsen, T.G., "Overview of the human pharmacokinetics of recombinant activated factor VII," British Journal of Clinical Pharmacology 65(1):3-11, Blackwell Publishing Ltd., England (2007).
Kobayashi, N., et al., "FcRn-Mediated Transcytosis of Immunoglobulin G in Human Renal Proximal Tubular Epithelial Cells,"

(56) References Cited

OTHER PUBLICATIONS

American Journal of Physiology 282(2):F358-F365, American Physiological Society, United States (2002).
Kochendoerfer, G., "Chemical and biological properties of polymer-modified proteins," Expert Opinion on Biological Therapy 3(8):1253-1261, Ashley Publications Ltd., England (2003).
Kohn, J.E., et al., "Random-coil behavior and the dimensions of chemically unfolded proteins," Proc Natl Acad Sci USA 101(34):12491-14296, National Academy of Sciences, United States (2004).
Koide, A., et al., The Fibronectin type III Domain as a Scaffold for Koide, A., et al., "The Fibronectin type III Domain as a Scaffold for Novel Binding Proteins," Journal of Molecular Biology 284(4):1141-1151, Academic Press, United States (1998).
Konig, T. and Skerra, A., "Use of an Albumin-Binding Domain for the Selective Immobilisation of Recombinant Capture Antibody Fragments on ELISA Plates," Journal of Immunological Methods 218(1-2):73-83, Elsevier Science B.V., Netherlands (1998).
Kornblatt, J.A. and Lake, D.F., "Cross-linking of cytochrome oxidase subunits with difluorodinitrobenzene," Canadian Journal of Biochemistry 58(3):219-224, National Research Council of Canada, Canada (1980).
Kortt, A.A., et al., "Single-Chain Fv Fragments of Anti-Neuraminidase Antibody Nc10 Containing Five- and Ten-Residue Linkers form Dimers and with Zero-Residue Linker A Trimer," Protein Engineering 10(4):423-433, Oxford University Press, England (1997).
Kou, G., et al., "Preparation and Characterization of Recombinant Protein Scfv(Cd11C)-Trp2 for Tumor therapy from inclusion Bodies in *Escherichia coli*," Protein Expression and Purification 52(1):131-138, Academic Press, United States (2007).
Kratzner, R., et, al., "Structure of Ecballium Elaterium Trypsin Inhibitor Ii (Eeti-Ii ): A Rigid Molecular Scaffold", Acta Crystallographica 61(Pt 9):1255-1262, Wiley-Blackwell, United States (2005).
Kristensen, P. and Winter, G., "Proteolytic Selection for Protein Folding Using Filamentous Bacteriophages," Folding & Design 3(5):321-328, Current Biology, England (1998).
Kubetzko, S., et al., "Protein PEGylation decreases observed target association rates via a dual blocking mechanism," Molecular Pharmacology 68(5):1439-1454, The American Society for Pharmacology and Experimental Therapeutics, United States (2005).
Kurachi, K. and Davie, E.W., "Isolation and characterization of a cDNA coding for human factor IX," Proceedings of the National Academy of Sciences 79(21):6461-6464, National Academy of Sciences, United States (1982).
Kwon, Y.M. and Kim, S.W., "Biodegradable Triblock Copolymer Microspheres Based on thermosensitive Sol-Gel Transition," Pharmaceutical Research 21(2):339-343, Kluwer Academic/Plenum Publishers, United States (2004).
Kyngas, J. and Valjakka, J., "Unreliability of the Chou-Fasman parameters in predicting protein secondary structure," Protein Engineering 11(5):345-348, Oxford University Press, England (1998).
Lane, M.E., et, al., "Influence of Post-Emulsification Drying Processes on the Microencapsulation of Human Serum Albumin", International Journal of Pharmaceutics 307(1):16-22, Amsterdam, Elsevier/North-Holland Biomedical Press., Netherlands (2006).
Langner, K-D., et al., "Synthesis of Biologically Active Deletion Mutants of Human Factor VIII:C," Behring Institute Mitteilungen 82:16-25, Behringwerke AG, Germany (1988).
Lapatto, R., et al., "X-Ray Structure of Antistasin At 1," The EMBO Journal 16(17):5151-5161, Wiley Blackwell, England (1997).
Larrick, J.W., et al., "Rapid Cloning of Rearranged Immunoglobulin Genes from Human Hybridoma Cells using Mixed Primers and the Polymerase Chain Reaction,"Biochemical and Biophysical Research Communications 160(3):1250-1256, Academic Press, United States (1989).
Lauber, T., et al., "Homologous Proteins With Different Folds: the Three-Dimensional Structures of Domains 1 and 6 of the Multiple Kazal-Type inhibitor Lekti," Journal of Molecular Biology 328(1):205-219, Elsevier, England (2003).
Lavigne-Lissalde, G., et al., "Characteristics, mechanisms of action, and epitope mapping of anti-factor VIII antibodies," Clinical Reviews in Allergy Immunology 37(2):67-79, Humana Press, United States (Oct. 2009).
Le Gall, F., et al., "Di-, Tri- and Tetrameric Single Chain Fv Antibody Fragments Against Human Cd19: Effect of Valency on Cell Binding," FEBS Letters 453(1-2):164-168, Elsevier Science B.V, Netherlands (1999).
Lee, A.Y., et al., "A recombinant human G-CSF/GM-CSF fusion protein from *E. coli* showing colony stimulating activity on human bone marrow cells," Biotechnology Letters 25(3):205-211, Kluwer Academic Publishers, Netherlands (2003).
Lee V.H., "Mucosal Drug Delivery," Journal of the National Cancer Institute Monographs 29:41-44, Oxford University Press, United States (2001).
Lenting, P.J., et al., "Clearance mechanisms of von Willebrand factor and factor VIII," Journal of Thrombosis and Haemostasis 5(7):1353-1360, International Society on Thrombosis and Haemostasis, England (2007).
Lenting, P.J., et al., "The Life Cycle of Coagulation Factor VIII in View of its Structure and Function," Blood 92(11):3983-3996, American Society of Hematology, United States (1998).
Lenting, P.J., et al., "The light chain of factor VIII comprises a binding site for low density lipoprotein receptor-related protein," The Journal of Biological Chemistry 274(34):23734-23739, The American Society for Biochemistry and Molecular Biology, Inc., United States (1999).
Leong, S.R., et, al., "Adapting Pharmacokinetic Properties of a Humanized Anti-Interleukin-8 Antibody for therapeutic Applications Using Site-Specific Pegylation", Cytokine 16(3):106-119, Elsevier Science Ltd., England (2001).
Leong, S.R., et, al., "Optimized Expression and Specific Activity of Il-12 by Directed Molecular Evolution", Proceedings of the National Academy of Sciences of the United States of America 100(3):1163-1168, National Academy of Sciences, United States (2003).
Lethagen, S., et al., "Clinical application of the chromogenic assay of factor VIII in haemophilia A, and different variants of von Willebrand's disease," Scandinavian Journal of Haematology 37(5):448-453, Munksgaard and International Publishers Ltd, United States (1986).
Leung, et al., "A method for random mutagenesis of a defined DNA segment using a modified polymerase chain reaction" Technique 1: 11-15, (1989).
Leung-Hagesteijn, C., et al., "Unc-5, A Transmembrane Protein With Immunoglobulin and Thrombospondin Type 1 Domains, Guides Cell and Prioneer Axon Migrations in C," Cell 7(2):289-299, Cell Press, United States (1992).
Levitt, M., "A simplified representation of protein conformations for rapid simulation of protein folding," Journal of Molecular Biology 104(1):59-107, Elsevier Ltd., United States (1976).
Levy, R., et al., "Isolation of Trans-Acting Genes That Enhance Soluble Expression of Scfv Antibodies in the E," Journal of Immunological Methods 321(1-2):164-173, Elsevier, Netherlands (2007).
Leyte, A., et al., "The interaction between human blood-coagulation factor VIII and von Willebrand factor:Characterization of high-affinity binding site on Factor VIII," Biochemical Journal 257(3):679-683, Biochemical Society, England (1989).
Leyte, A.,et al., "Sulfation of Tyrl680 of human blood coagulation factor VIII is essential for the interaction of factor VIII with von Willebrand factor," The Journal of Biological Chemistry 266(2):740-746, The American Society for Biochemistry and Molecular Biology,Inc., United State (1991).
Lillicrap, D., "Extending Half-life in Coagulation Factors: Where do We Stand?," Thrombosis Research, 122(Suppl 4):S2-S8, Pergamon Press, United States (Oct. 2008).
Lin, C.C. and Metters, A.T., "Metal-Chelating Affinity Hydrogels for Sustained Protein Release", Journal of Biomedical Materials Research Part A 83(4):954-964, John Wiley & Sons, United States (2007).
Lirazan, M.B., et, al., "The Spasmodic Peptide Defines a New Conotoxin Superfamily", Biochemistry 39(7):1583-1588, Washington, American Chemical Society., United States (2000).

(56) References Cited

OTHER PUBLICATIONS

Liu, L., et, al., "The Human Beta-Defensin-1 and Alpha-Defensins are Encoded by Adjacent Genes: Two Peptide Families With Differing Disulfide Topology Share a Common Ancestry", Genomics 43(3):316-320, Academic Press, United States (1997).
Liu, T., et al., "Evaluation of PEG-FVIII Molecules with Prolonged Half-lives in a Murine FVIII-Dependent Bleeding Model," Journal of Thrombosis and Haemostasis 9(Suppl. 2): P-M-035, ISTH Meeting, Poster: Factor VIII, Factor V, Exhibition Area, International Society on Thrombosis and Haemostasis, United States (2007).
Liu, T., et al., "Recombinant FVIII Fc fusion protein is fully active in treating acute injury and demonstrates prolonged prophylactic efficacy in hemophilia a mice," Journal of Thrombosis and Haemostasis 9(Suppl. 2): P-WE-131, ISTH Meeting, International Society on Thrombosis and Haemostasis, United States (2011).
Logan, J., et al., "Adenovirus Tripartite Leader Sequence Enhances Translation of mRNAs Late After Infection," Proceedings of the National Academy of Sciences USA 81(12):3655-3659, National Academy of Sciences, United States (1984).
Lollar, P., et al., "Inhibition of human factor VIIIa by anti-A2 subunit antibodies," The Journal of Clinical Investigation 93(6):2497-2504, The American Society for Biochemistry and Molecular Biology,Inc., United States (1994).
London, F.S. and Walsh, P.N., "Zymogen factor IX potentiates factor IXa-catalyzed factor X activation," Biochemistry 39(32):9850-9858, American Chemical Society, United States (2000).
Lowman, H.B., et al., "Selecting High-Affinity Binding Proteins by Monovalent Phage Display", Biochemistry 30(45):10832-10838, Washington, American Chemical Society., United States (1991).
Loyter, A., et al., "Mechanisms of DNA uptake by mammalian cells: fate of exogenously added DNA monitored by the use of fluorescent dyes," Proceedings of the National Academy of Sciences 79(2):422-426, National Academy of Sciences, United States (1982).
Mackett, M., et al., "General Method for Production and Selection of Infectious Vaccinia Virus Recombinants Expressing Foreign Genes," Journal of Virology 49(3):857-864, American Society for Microbiology, United States (1984).
Mackett, M., et al., "Vaccinia Virus: A Selectable Eukaryotic Cloning and Expression Vector," Proceedings of the National Academy of Sciences USA 79(23):7415-7419, National Academy of Sciences, United States (1982).
Maggio, "A Renaissance in Peptide Therapeutics in Underway" Drug Delivery Reports 23-26, (2006).
Maggio, E.T., "Intravail: Highly Effective Intranasal Delivery of Peptide and Protein Drugs", Expert Opinion on Drug Delivery 3(4):529-539, Informa Healthcare, England (2006).
Maillere, B., et, al., "Immunogenicity of a Disulphide-Containing Neurotoxin : Presentation to T-Cells Requires a Reduction Step", Toxicon 33(4):475-482, Pergamon Press, England (1995).
Maillere, B., et, al., "Role of Thiols in the Presentation of a Snake Toxin to Murine T Cells", Journal of Immunology 150(12):5270-5280, American Association of Immunologists, United States (1993).
Malardier, L., et al., "Cloning of the nitrate reductase gene (niaD) of Aspergillus nidulans and its use for transformation of Fusarium oxysporum," Gene 78(1):147-156, Elsevier Science Publishers B.V., Netherlands (1989).
Marshall, C.B., et, al., "Enhancing the Activity of a Beta-Helical Antifreeze Protein by the Engineered Addition of Coils", Biochemistry 43(37):11637-11646, Washington, American Chemical Society., United States (2004).
Martin, L., et al., "Rational Design of a Cd4 Mimic That inhibits Hiv-1 Entry and Exposes Cryptic Neutralization Epitopes," Nature Biotechnology 21(1):71-76, Nature America Publishing, United States (2003).
Martin, P.G., et al., "Evaluation of a novel ELISA screening test for detection of factor VIII inhibitory antibodies in haemophiliacs," Clinical & Laboratory Haematology 21(2):125-128, Blackwell Publishing, England (1999).
Martineau, P., et, al., "Expression of an Antibody Fragment at High Levels in the Bacterial Cytoplasm", Journal of Molecular Biology 280(1):117-127, Elsevier, England (1998).
Matthews, D.J. and Wells, J.A., "Substrate phage: selection of protease substrates by monovalent phage display," Science 260(5111):1113-1117, American Association for the Advancement of Science, United States (1993).
McCue, J.T., et al., "Application of a Novel Affinity Adsorbent for the Capture and Purification of Recombinant Factor VIII Compounds," Journal of Chromatography A 1216(45):7824-7830, Elsevier, Netherlands (Nov. 6, 2009).
McDonald, D.M. and Baluk, P., "Significance of Blood Vessel Leakiness in Cancer," Cancer research 62(18):5381-5385, American Association for Cancer Research, United States (2002).
McKnight, G.L., et al., "Identification and molecular analysis of a third Aspergillus nidulans alcohol dehydrogenase gene," The EMBO Journal 4(8):2093-2099, IRL Press Limited, England (1985).
McNulty, J.C., et, al., "High-Resolution Nmr Structure of the Chemically-Synthesized Melanocortin Receptor Binding Domain Agrp (87-132 ) of the Agouti-Related Protein ", Biochemistry 40(51):15520-15527, American Chemical Society., United States (2001).
Zhu, S., et al., "Molecular Cloning and Sequencing of Two 'Short Chain' and Two 'Long Chain' K(+) Channel-blocking Peptides from the Chinese Scorpion Butkus Martensii Karsch," FEBS Letters 457(3):509-514, Elsevier Science, Netherlands (1999).
Meeks, S.L., et al., "Antihuman factor VIII C2 domain antibodies in hemophilia A mice recognize a functionally complex continuous spectrum of epitopes dominated by inhibitors or factor VIII activation," Blood 110(13):4234-4242, The American Society of Hematology, United States (2007).
Meeks, S.L., et al., "Non-classical anti-factor VIII C2 domain antibodies are pathogenic in a murine in vivo bleeding model," Journal of Thrombosis and Haemostasis 7(4):658-664, International Society on Thrombosis and Haemostasis, England (Apr. 2009).
Mei, B., et al., "Expression of Human Coagulation Factor VIII in a Human Hybrid Cell Line, HKB11," Molecular Biotechnology 34(2):165-178, Humana Press Inc., United States (2006).
Meier, S., et, al., "Determination of a High-Precision Nmr Structure of the Minicollagen Cysteine Rich Domain from Hydra and Characterization of Its Disulfide Bond", FEBS Letters 569(1-3):112-116, Elsevier Science B.V. Netherlands (2004).
International Search Report for International Patent Application No. PCT/US2015/010738, United States Patent Office, Alexandria, Virginia, dated May 15, 2015.
Meulien, P., et al., "A new Recombinant Procoagulant Protein Derived from the cDNA Encoding Human Factor VIII," Protein Engineering 2(4):301-306, IRL Press Ltd., England (1988).
Miao, H.Z., et al., "Bioengineering of coagulation factor VIII for improved secretion," Blood 103(9):3412-3419, The American Society of Hematology, United States (2004).
Miljanich, G.P., "Ziconotide: Neuronal Calcium Channel Blocker for Treating Severe Chronic Pain", Current Medicinal Chemistry 11(23):3029-3040, Bentham Science Publishers, Netherlands (2004).
Misenheimer, T.M. and Mosher, D.F., "Biophysical Characterization of the Signature Domains of Thrombospondin-4 and Thrombospondin-2", The Journal of Biological Chemistry 280(50):41229-41235, American Society for Biochemistry and Molecular Biology, United States (2005).
Misenheimer, T.M., et, al., "Disulfide Connectivity of Recombinant C-Terminal Region of Human Thrombospondin2", The Journal of Biological Chemistry 276(49):45882-45887, American Society for Biochemistry and Molecular Biology, United States (2001).
Mitraki, A. and Jonathan, K.,, "Protein Folding Intermediates and Inclusion Body Formation," Nature Biotechnology 7:690-697, Nature Publishing Group, England (1989).
Mogk, A., et, al., "Mechanisms of Protein Folding: Molecular Chaperones and their Application in Biotechnology", a European journal of Chemical Biology 3(9):807-814, Wiley-VCH Verlag, Germany (2002).
Morfini, M. "Secondary prophylaxis with factor IX concentrates: continuous infusion," Blood Transfusion 6(Suppl 2):521-S25, Italy (Sep. 2008).

(56) References Cited

OTHER PUBLICATIONS

Morpurgo, M., et al., "Covalent modification of mushroom tyrosinase with different amphiphic polymers for pharmaceutical and biocatalysis applications," Applied Biochemistry and Biotechnology 56(1):59-72, Humana Press, Inc., United States (1996).
Mount, J.D., et al., "Sustained Phenotypic Correction of Hemophilia B dogs with a Factor IX Null Mutation by Liver-Directed Gene Therapy," Blood 99(8):2670-2676, The American Society of Hematology, United States (2002).
Mrsny, R.J., et al., "Bacterial Toxins as Tools for Mucosal Vaccination," Drug Discovery Today 7(4):247-258, Elsevier Science Ltd., England (2002).
Murtuza, B., et al., "Transplantation of Skeletal Myoblasts Secreting an II-1 Inhibitor Modulates Adverse Remodeling in Infarcted Murine Myocardium", Proceedings of the National Academy of Sciences of the United States of America 101(12):4216-4221, National Academy of Sciences, United States (2004).
Narita, M., et al., "The Low-Density Lipoprotein Receptor-Related Protein (LRP) Mediates Clearance of Coagulation Factor Xa in Vivo," Blood 91(2):555-560, The American Society of Hematology, United States (1998).
Narmoneva, D.A., et, al., "Self-Assembling Short Oligopeptides and the Promotion of Angiogenesis," Biomaterials 26(23):4837-4846, Elsevier Science, Netherlands (2005).
Needleman, S.B. and Wunsch, C.D., "A General Method Applicable to the Search for Similarities in the Amino Acid Sequence of Two Proteins," Journal of Molecular Biology 48(3):443-453, Academic Press, England (1970).
Neumann, E., et al., "Gene Transfer into Mouse Lyoma Cells by Electroporation in High Electric Fields," The EMBO Journal 1(7):841-845, IRL Press Limited, England (1982).
Ngo, J.C., et al., "Crystal structure of human factor VIII: implications for the formation of the factor IXa-factor VIIIa complex," Structure 16(4):597-606, Elsevier Ltd., United States (Apr. 2008).
Nielsen, C.U. and Brodin, B., "Di/Tri-Peptide Transporters as Drug Delivery Targets: Regulation of Transport Under Physiological and Patho-Physiological Conditions", Current Drug Targets 4(5):373-388, Bentham Science Publishers, Netherlands (2003).
Nielsen, K.J., et, al., "Solution Structure of Mu-Conotoxin Piiia, A Preferential Inhibitor of Persistent Tetrodotoxin-Sensitive Sodium Channel", The Journal of biological chemistry 277(30):27247-27255, American Society for Biochemistry and Molecular Biology, United States (2002).
Noe, D.A., "A mathematical model of coagulation factor VIII kinetics," Haemostasis 26(6):289-303, S. Karger AG, Basel, Germany (1996).
Nord, K., et al., "Binding Proteins Selected from Combinatorial Libraries of an Alpha-Helical Bacterial Receptor Domain," Nature Biotechnology 15(8):772-777, Nature America Publishing, United States (1997).
O'Brien, D.P., et al., "Purification and Characterization of Factor VIII 372-Cys: A Hypofunctional Cofactor From a Patient With Moderately Severe Hemophilia A," Blood 75(8):1664-1672, American Society of Hematology, United States (1990).
O'Connell, D., et, al., "Phage Versus Phagemid Libraries for Generation of Human Monoclonal Antibodies", Journal of Molecular Biology 321(1):49-56, Elsevier, England (2002).
Office Action dated Apr. 16, 2013, in U.S. Appl. No. 12/806,005, Schellenberger, et al., filed Aug. 2, 2010.
Office Action dated Aug. 23, 2012, in U.S. Appl. No. 12/848,984, Schellenberger, et al., filed Aug. 2, 2010.
Office Action dated Feb. 25, 2014, in U.S. Appl. No. 13/392,509, Schellenberger, et al., filed Feb. 24, 2012.
Office Action dated Jan. 14, 2014, in U.S. Appl. No. 12/796,650, Schellenberger, et al., filed Jun. 8, 2010.
Office Action dated Jul. 2, 2013 in U.S. Appl. No. 13/392,511, Schellenberger, V. et al., filed Jun. 27, 2012.
Office Action dated Jun. 21, 2013, in U.S. Appl. No. 12/806,004, Schellenberger, et al., filed Aug. 2, 2010.
Office Action dated Mar. 22, 2013, in U.S. Appl. No. 12/796,650, Schellenberger, et al., filed Jun. 8, 2010.
Office Action dated May 7, 2013, in U.S. Appl. No. 12/699,761, Schellenberger, et al., filed Feb. 3, 2010.
Office Action dated May 20, 2014 in U.S. Appl. No. 13/392,511, Schellenberger, V. et al., filed Jun. 27, 2012.
Office Action dated Oct. 5, 2012, in U.S. Appl. No. 12/806,004, Schellenberger, et al., filed Aug. 2, 2010.
Office Action dated Oct. 20, 2014 in U.S. Appl. No. 13/392,511, Schellenberger, V. et al., filed Jun. 27, 2012.
Office Action dated Sep. 11, 2013, in U.S. Appl. No. 12/848,984, Schellenberger, et al., filed Aug. 2, 2010.
Ofir, K., et, al., "Versatile Protein Microarray Based on Carbohydrate-Binding Modules", Proteomics 5(7):1806-1814, Wiley-VCH, Germany (2005).
Okten, Z., et, al., "Myosin VI Walks Hand-Over-Hand Along Actin", Nature structural molecular biology 11(9):884-887, Nature Pub. Group, United States (2004).
O'Leary, JM., et, al., "Solution Structure and Dynamics of a Prototypical Chordin-Like Cysteine-Rich Repeat (Von Willebrand Factor Type C Module) from Collagen Iia", The Journal of Biological Chemistry 279(51):53857-53866, American Society for Biochemistry and Molecular Biology, United States (2004).
Zhuo, R., et al., "Procoagulant stimulus processing by the intrinsic pathway of blood plasma coagulation," Biomaterials 26(16):2965-2973, Elsevier Ltd., United States (2005).
Osterud, B., et al., "Activation of the coagulation factor VII by tissue thromboplastin and calcium," Biochemistry 11(15):2853-2857, American Chemical Society, United States (1972).
Padiolleau-Lefevre, S., et, al., "Expression and Detection Strategies for an Scfv Fragment Retaining the Same High Affinity Than Fab and Whole Antibody: Implications for therapeutic Use in Prion Diseases", Molecular immunology 44(8):1888-1896, Pergamon Press, England (2007).
Pallaghy, P.K., et, al., "A Common Structural Motif Incorporating a Cystine Knot and a Triple-Stranded Beta-Sheet in Toxic and Inhibitory Polypeptides", Protein Science 3(10):1833-1839, Cold Spring Harbor Laboratory Press, United States (1994).
Pallaghy, P.K., et, al., "Three-Dimensional Structure in Solution of the Calcium Channel Blocker Omega-Conotoxin", Journal of Molecular Biology 234(2):405-420, Elsevier, England (1993).
Palmiter, R.D., et al., "Metallothionein-human GH fusion genes stimulate growth of mice," Science 222(4625):809-814, American Association for the Advancement of Science, United States (1983).
Pan, T.C., et, al., "Structure and Expression of Fibulin-2, A Novel Extracellular Matrix Protein With Multiple Egf-Like Repeats and Consensus Motifs for Calcium Binding", The Journal of Cell Biology 123(5):1269-1277, Rockefeller University Press, United States (1993).
Panda, A.K., "Bioprocessing of therapeutic Proteins from the Inclusion Bodies of *Escherichia coli*", Advances in Biochemical Engineering/Biotechnology 85:43-93, Springer Verlag, Germany (2003).
Panicali, D., et al., "Construction of Poxviruses as Cloning Vectors: Insertion of the Thymidine Kinase Gene from Herpes Simplex Virus into the DNA of Infectious Vaccinia Virus," Proceedings of the National Academy of Sciences of the United States of America 79(16):4927-4931, The National Academy of Sciences of the United States (1982).
Park, C.H., et al., "A diagnostic challenge: mild hemophilia B with normal activated partial thromboplastin time," Blood Coagulation and Fibrinolysis 21(4):368-371, Lippincott Williams & Wilkins, England (Jun. 2010).
Patra, A.K., et, al., "Optimization of Inclusion Body Solubilization and Renaturation of Recombinant Human Growth Hormone from *Escherichia coli*", Protein Expression and Purification 18(2):182-192, Academic Press, United States (2000).
Pelegrini, P.B. and Franco, O.L., "Plant Gamma-Thionins: Novel Insights on the Mechanism of Action of a Multi-Functional Class of Defense Proteins", The International Journal of Biochemistry Cell Biology 37(11):2239-2253, Elsevier, Netherlands (2005).
Pepinsky, R.B., et al., "Improved pharmacokinetic properties of a polyethylene glycol-modified form of interferon-β-1a with preserved in vitro bioactivity," The Journal of Pharmacology and

(56) References Cited

OTHER PUBLICATIONS

Experimental Therapeutics 297(3):1059-1066, The American Society for Pharmacology and Experimental Therapeutics, United States (2001).
Petersen, SV., et, al., "the Dual Nature of Human Extracellular Superoxide Dismutase: One Sequence and Two Structures", Proceedings of the National Academy of Sciences of the United States of America 100(24):13875-13880, National Academy of Sciences, United States (2003).
Pi, C., et al., "Analysis of Expressed Sequence Tags from the Venom Ducts of Conus Striatus: Focusing on the Expression Profile of Conotoxins," Biochimie 88(2):131-140, Editions Scientifiques Elsevier, France (2006).
Pimanda, J.E.. et. al., "The Von Willebrand Factor-Reducing Activity of Thrombospondin-1 is Located in the Calcium-Binding/C-Terminal Sequence and Requires a Free Thiol at Position 974", Blood 100(8):2832-2838, American Society of Hematology, United States (2002).
Pipe, S.W., et al., "Functional factor VIII made with von Willebrand factor at high levels in transgenic milk," Journal of Thrombosis and Haemostasis 9(11):2235-2242, International Society on Thrombosis and Haemostasis, England (Nov. 2011).
Pipe, S.W., et al., "Functional roles of the factor VIII B domain," Haemophilia 15(6):1187-1196, Blackwell Publishing Ltd., England (Nov. 2009).
Pipe, S.W. "The promise and challenges of bioengineered recombinant clotting factors," Journal of Thrombosis and Haemostasis 3(8):1692-1701, International Society on Thrombosis and Haemostasis, United States (2005).
Pokidysheva, E., et, al., "The Structure of the Cys-Rich Terminal Domain of Hydra Minicollagen, Which is Involved in Disulfide Networks of the Nematocyst Wall", The Journal of Biological Chemistry 279(29):30395-30401, American Society for Biochemistry and Molecular Biology, United States (2004).
Pool, J.G., et al., "Ineffectiveness of intramuscularly injected Factor 8 concentrate in two hemophilic patients," The New England Journal of Medicine 275(10):547-548, Massachusetts Medical Society, United States (1966).
Popkov, M., et, al., "Isolation of Human Prostate Cancer Cell Reactive Antibodies Using Phage Display Technology", Journal of Immunological Methods 291(1-2):137-151, Elsevier, Netherlands (2004).
Prilusky, J., et al., "Foldlndex: a simple tool to predict whether a given protein sequence is intrinsically unfolded," Bioinformatics 21(16):3435-3438, Oxford University Press, England (2005).
Prinz, W.A., et al., "The Role of the Thioredoxin and Glutaredoxin Pathways in Reducing Protein Disulfide Bonds in the *Escherichia coli* Cytoplasm," the Journal of Biological Chemistry 272(25):15661-15667, American Society for Biochemistry and Molecular Biology, United States (1997).
Qi, R.F., et al., "Structural Features and Molecular Evolution of Bowman-Birk Protease inhibitors and their Potential Application," Acta biochimica et biophysica Sinica 37(5):283-292, American Society for Biochemistry and Molecular Biology, United States (2005).
Rao, L.V.M., et al., "Activation of human factor VII during clotting in vitro," Blood 65(1):218-226, Grune & Stratton, Inc., United States (1985).
Rao, M.B., et al., "Molecular and Biotechnological aspects of Microbial Proteases," Microbiology and Molecular Biology Reviews : MMBR 62(3):597-635, American Society for Microbiology, United States (1998).
Rasmussen, U.B., et al., "Tumor Cell-Targeting by Phage-Displayed Peptides," Cancer gene therapy 9(7):606-612, Nature Publishing Group, England (2002).
Rawlings, N.D., et al., "Evolutionary Families of Peptidase inhibitors," The Biochemical Journal 378(Pt 3):705-716, Published by Portland Press on behalf of the Biochemical Society, England (2004).
Rawlings, N.D., et al., "MEROPS: the peptidase database," Nucleic Acids Research 36:D320-D325, Oxford University Press, England (Nov. 2007).
Rebay, I., et al., "Specific EGF Repeats of Notch Mediate Interactions with Delta and Serrate: Implications for Notch as a Multifunctional Receptor," Cell 67(4):687-699, Cell Press, United States (1991).
Roberge, M., et al., "Construction and Optimization of a Cc49-Based Scfv-Beta-Lactamase Fusion Protein for Adept," Protein engineering, design & selection : PEDS 19(4):141-145, Oxford University Press, England (2006).
Rosa, G.D., et al., "Influence of the Co-Encapsulation of Different Non-Ionic Surfactants on the Properties of Plga insulin-Loaded Microspheres," Journal of Controlled Release 69(2):283-295, Elsevier Science Publishers, Netherlands (2000).
Rosenfeld, R.D., et al., "Biochemical, Biophysical, and Pharmacological Characterization of Bacterially Expressed Human Agouti-Related Protein," Biochemistry 37(46):16041-16052, Washington, American Chemical Society., United States (1998).
Rosén, S., "Assay of Factor VIII:C with a Chromogenic Substrate," New Frontiers in Hemophilia Research, the XVth World Federation of Hemophilia Congress, Stockholm, Sweden, Jun. 27-Jul. 1, 1983, published in Scandinavian Journal of Rheumatology Supplement 33(S40):139-145, Munksgaard, Denmark (1984).
Roth, J. et al., "From Microbes to Man" in Polysialic Acid, Roth J., Rutishauser U., Troy F.A., eds., pp. 335-348, BirkhauserVerlag, Basel, Switzerland (1993).
Roussel, A., et al., "Complexation of Two Proteic insect inhibitors to the Active Site of Chymotrypsin Suggests Decoupled Roles for Binding and Selectivity," The Journal of biological chemistry 276(42):38893-38898, American Society for Biochemistry and Molecular Biology, United States (2001).
Routledge, E.G., et al., "The Effect of Aglycosylation on the Immunogenicity of a Humanized Therapeutic CD3 Monoclonal Antibody," Transplantation 60(8):847-853, Williams & Wilkins, United States (1995).
Ruberti, F., et al., "The Use of the RACE Method to Clone Hybridoma cDNA When V Region Primers Fail," Journal of Immunological Methods 173(1):33-39, Elsevier, United States (1994).
Ruther, U. and Muller-Hill, B., "Easy Identification of cDNA Clones," EMBO J 2(10):1791-1794, IRL Press Ltd, England (1983).
Rychkov, G. And Petukhov, M., "Joint neighbors approximation of macromolecular solvent accessible surface area," Journal of Computational Chemistry 28(12):1974-1989, Wiley Periodicals, Inc., United States (2007).
Saenko, E.L., et al., "Role of the low density lipoprotein-related protein receptor in mediation of factor VIII catabolism," The Journal of Biological Chemistry 274(53):37685-37692, The American Society for Biochemistry and Molecular Biology, Inc., United States (1999).
Saenko, E.L., et al., "The future of recombinant coagulation factors," Journal of Thrombosis and Haemostasis 1:922-930, International Society on Thrombosis and Haemostasis, England (2005).
Saenko, E.L. and Pipe, S.W., "Strategies Towards a Longer Acting Factor VIII," Haemophilia 12 (Suppl 3):42-51, Blackwell Publishing Ltd, England (2006).
Sahdev, S., et al., "Production of Active Eukaryotic Proteins Through Bacterial Expression Systems: A Review of the Existing Biotechnology Strategies," Molecular and Cellular Biochemistry 307(1-2):249-264, Kluwer Academic, Netherlands (Jan. 2008).
Salloum, F.N., et al., "Anakinra in Experimental Acute Myocardial Infarction—Does Dosage or Duration of Treatment Matter," Cardiovascular drugs and therapy sponsored by the International Society of Cardiovascular Pharmacotherapy 23(2):129-135, Kluwer Academic for the International Society for Cardiovascular Pharmacotherapy, United States (Apr. 2009).
GenBank: EIW63862.1. hypothetical protein TRAVEDRAFT_138159 (Trametes versicolor FP-101664 SS 1]. Available at http://www.ncbi.nlm.nih.gov/protein/392570690?report=genbank&log$=protalign&blast_rank=1&RID=3ERS0M7501R. Accessed on Jun. 11, 2015, 3 pages.
NCBI Reference Sequence: WP_005158338.1. Serine phosphatase RsbU, regulator of sigma subunit [Amycolatopsis azure]]. Available

(56) References Cited

OTHER PUBLICATIONS at http://www.ncbi.nlm.nih.gov/protein/491300334?report=genbank &log$=protalign&blast_rank=1&RID=3ERS0M7501R. Accessed on Jun. 11, 2015, 2 pages.
Sarver, N., et al., "Stable Expression of Recombinant Factor VIII Molecules Using a Bovine Papillomavirus Vector," DNA 6(6):553-564, Mary Ann Liebert, Inc., United States (1987).
Scandella, D., et al., "Epitope mapping of human factor VIII inhibitor antibodies by deletion analysis of factor VIII fragments expressed in *Escherichia coli*," Proceedings of the National Academy of Sciences 85(16):6152-6156, Natinal Academy of Sciences, United States (1988).
Scandella, D., et al., "Localization of epitopes for human factor VIII inhibitor antibodies by immunoblotting and antibody neutralization," Blood 74(5):1618-1626, Grune & Stratton, Inc., United States (1989).
Schellenberger, V., et al., "A Recombinant Polypeptide Extends the in Vivo Half-Life of Peptides and Proteins in a Tunable Manner," Nature Biotechnology 27(12):1186-1190, Nature America, Inc., United States (Dec. 2009).
Schellenberger, V., et al., "Analysis of enzyme specificity by multiple substrate kinetics," Biochemistry 32(16):4344-4348, The American Chemical Society, United States (1993).
Schlapschy, M., et al., "Fusion of a recombinant antibody fragment with a homo-amino-acid polymer: effects on biophysical properties and prolonged plasma half-life," Protein Engineering Design & Selection 20(6):273-284, Oxford University Press, England (2007).
Schmidt, A.E. and Bajaj, S.P., "Structure-function relationships in factor IX and factor Ixa," Trends in Cardiovascular Medicine 13(1):39-45, Elsevier Science, United States (2003).
Scholle, M.D., et, al., "Efficient Construction of a Large Collection of Phage-Displayed Combinatorial Peptide Libraries", Combinatorial Chemistry High Throughput Screening 8(6):545-551, Bentham Science Publishers, Netherlands (2005).
Schulte, S., et al., "Prolonged in-vivo half-life of factor VIIa by fusion to albumin," Blood (ASH Annual Meeting) 110:Abstract 3142, American Society of Hematology, United States (2007).
Schulte, S., "Use of Albumin Fusion Technology to Prolong the Half-Life of Recombinant Factor VIIa," Thrombosis Research 122(Suppl 4):S14-S19, Elsevier Ltd. United States (Dec. 2008).
Schultz-Cherry, S., et, al., "Regulation of Transforming Growth Factor-Beta Activation by Discrete Sequences of Thrombospondin 1", The Journal of Biological Chemistry 270(13):7304-7310, American Society for Biochemistry and Molecular Biology, United States (1995).
Schultz-Cherry, S., et, al., "The Type 1 Repeats of Thrombospondin 1 Activate Latent Transforming Growth Factor-Beta", The Journal of Biological Chemistry 269(43):26783-26788, American Society for Biochemistry and Molecular Biology, United States (1994).
Schulz, H., et, al., "Potential of Nir-Ft-Raman Spectroscopy in Natural Carotenoid Analysis", Biopolymers 77(4):212-221, Wiley Interscience, United States (2005).
NCBI Reference Sequence: XP_003746909.1. Predicted: electron transfer flavoprotein subunit alpha, mitochondrial-like [Metaseiulus occidentalis]. Available at http://www.ncbi.nlm.nih.gov/protein/391345263?report=genbank&log$=protalign&blast_rank=1&RID=3ERS0M7501R. Accessed on Jun. 11, 2015, 3 pages.
Sheffield, W.P., et al., "Effects of genetic fusion of factor IX to albumin on in vivo clearance in mice and rabbits," British Journal of Haematology 126(4):565-573, Blackwell Publishing Ltd., England (2004).
Shen, B.W., et al., "The tertiary structure and domain organization of coagulation factor VIII," Blood 111(3):1240-1247, The American Society of Hematology, United States (Feb. 2008).
Shen, Z. and Jacob S-Lorena, M., "A Type I Peritrophic Matrix Protein from the Malaria Vector Anopheles Gambiae Binds to Chitin Cloning, Expression, and Characterization", The Journal of Biological Chemistry 273(28):17665-17670, American Society for Biochemistry and Molecular Biology, United States (1998).
Shields, R.L., et al., "High Resolution Mapping of the Binding Site on Human IgG1 for FcγRI, FcγRII, FcγRIII, and FcRn and Design of IgG1 Variants with Improved Binding to the FcγR*," The Journal of Biological Chemistry 276(9):6591-6604, The American Society for Biochemistry and Molecular Biology, Inc. United States (2001).
Shima, M., et al., "A factor VIII neutralizing monoclonal antibody and a human inhibitor alloantibody recognizing epitopes in the C2 domain inhibit factor VIII binding to von Willebrand factor and to phosphatidylserine," Journal of Thrombosis and Haemostasis 69(3):240-246, Schattauer GmbH, Germany (1993).
Sidhu, S.S., et, al., "Phage Display for Selection of Novel Binding Peptides", Methods in Enzymology 328:333-363, New York, Academic Press., United States (2000).
Silverman, J., et, al., "Multivalent Avimer Proteins Evolved by Exon Shuffling of a Family of Human Receptor Domains", Nature Biotechnology 23(12):1556-1561, Nature America Publishing, United States (2005).
Simonet, G., et al., "Structural and Functional Properties of a Novel Serine Protease inhibiting Peptide Family in Arthropods," Comparative Biochemistry and Physiology. Part B, Biochemistry & molecular biology 132(1):247-255, Pergamon, England (2002).
Simonsen, C.C., et al., "Isolation and Expression of an Altered Mouse Dihydrofolate Reductase cDNA," Proceedings of the National Academy of Sciences 80(9):2495-2499, National Academy of Sciences, United States (1983).
Singh, H. and Raghava, G.P.S., "ProPred: Prediction of HLA-DR binding sites," Bioinformatics 17(12):1236-1237, Oxford University Press, England (2001).
Skinner, W.S., et, al., "Purification and Characterization of Two Classes of Neurotoxins from the Funnel Web Spider, *Agelenopsis aperta*", The Journal of Biological Chemistry 264(4):2150-2155, American Society for Biochemistry and Molecular Biology, United States (1989).
Smith, D.B. and Johnson, K.S., "Single-step purification of polypeptides expressed in *Escherichia coli* as fusions with glutathione S-transferase," Gene 67(1):31-40, Elsevier Science B.V., Netherlands (1988).
Smith, G.E., et al., "Molecular Engineering of the Autographa californica Nuclear Polyhedrosis Virus Genome: Deletion Mutations Within the Polyhedrin Gene," Journal of Virology 46(2):584-593, American Society for Microbiology, United States (1983).
Smith, G.P. and Petrenko, V.A., "Phage Display," Chemical Reviews 97(2):391-410, American Chemical Society, United States (1997).
Smith, T.F. and Waterman, M.S., "Comparison of Biosequences," Advances in Applied Mathematics 2(4):482-489, Academic Press, Inc., United States (1981).
So, T., et, al., "Contribution of Conformational Stability of Hen Lysozyme to Induction of Type 2 T-Helper Immune Responses," Immunology 104(3):259-268, Blackwell Scientific Publications, England (2001).
Sommermeyer, V.K., et al., "Klinisch Verwendete Hydroxyethylstarke: Physikalisch-Chemische Charakterisierung," Krankenhauspharmazie 8(8):271-278, Deutscher Apotheker Verlag, Birkenwalstr, Germany (1987).
Southern, P.J. and Berg, P., "Transformation of mammalian cells to antibiotic resistance with a bacterial gene under control of the SV40 early region promoter," Journal of Molecular and Applied Genetics 1(4):327-341, Raven Press, United States (1982).
Srivastava, R. and McShane, M.J., "Application of Self-Assembled Ultra-Thin Film Coatings to Stabilize Macromolecule Encapsulation in Alginate Microspheres", Journal of Microencapsulation 22(4):397-411, Informa Healthcare, England (2005).
Stamos, J., et, al., "Crystal Structure of the Hgf Beta-Chain in Complex With the Sema Domain of the Met Receptor", The EMBO Journal 23(12):2325-2335, Wiley Blackwell, England (2004).
Steipe, B., et, al., "Sequence Statistics Reliably Predict Stabilizing Mutations in a Protein Domain," Journal of Molecular Biology 240(3):188-192, Elsevier, England (1994).
Stemmer, W.P., et, al., "Single-Step Assembly of a Gene and Entire Plasmid from Large Numbers of Oligodeoxyribonucleotides," Gene 164(1):49-53, Amsterdam, Elsevier/North-Holland, Netherlands (1995).

(56) References Cited

OTHER PUBLICATIONS

Stemmer, W.P., "Rapid Evolution of a Protein in Vitro by Dna Shuffling," Nature 370(6488):389-391, Nature Publishing Group, England (1994).
Stickler, M., et al., "Human population-based identification of CD4+ T-cell peptide epitope determinants," Journal of Immunological Methods 281(1-2)95-108, Elsevier B.V., Netherlands (2003).
Stites, W.E. and Pranata, J., "Empirical Evaluation of the Influence of Side Chains on the Conformational Entropy of the Polypeptide Backbone," PROTEINS: Structure, Function and Genetics 22(2):132-140, Wiley-Liss, Inc., United States (1995).
Stoll, B.R., et al., "A Mechanistic Analysis of Carrier-Mediated Oral Delivery of Protein therapeutics," Journal of controlled release 64(1-3):217-228, Elsevier Science Publishers, Netherlands (2000).
Story, C.M., et al., "A Major Histocompatibility Complex Class I-like Fc Receptor Cloned from Human Placenta: Possible Role in Transfer of Immunoglobulin G from Mother to Fetus," The Journal of Experimental Medicine 180(6):2377-2381, The Rockefeller University Press, United States (1994).
Sturniolo, T., et al., "Generation of tissue-specific and promiscuous HLA ligand databases using DNA microarrays and virtual HLA class II matrices," Nature Biotechnology 17(6):555-561, Nature America Inc., United States (1999).
Subramani, S., et al., "Expression of the mouse dihydrofolate reductase complementary deoxyribonucleic acid in simian virus 40 vectors," Molecular and Cellular Biology 1(9):854-864, American Society for Microbiology, United States (1981).
Suetake, T., et al., "Chitin-Binding Proteins in Invertebrates and Plants Comprise a Common Chitin-Binding Structural Motif", The Journal of Biological Chemistry 275(24):17929-17932, American Society for Biochemistry and Molecular Biology, United States (2000).
Suetake, T., et al., "Production and Characterization of Recombinant Tachycitin, the Cys-Rich Chitin-Binding Protein", Protein Engineering 15(9):763-769, Oxford University Press, England (2002).
Summers, M.D. and Smith, G.E., "Baculovirus structural polypeptides," Virology 84(2):390-402, Academic Press, Inc., United States (1978).
Takahashi, H., et al., "Solution Structure of Hanatoxinl, A Gating Modifier of Voltage-Dependent K(+) Channels: Common Surface Features of Gating Modifier Toxins," Journal of Molecular Biology 297(3):771-780, Elsevier, England (2000).
Takenobu, T., et al., "Development of P53 Protein Transduction therapy Using Membrane-Permeable Peptides and the Application to Oral Cancer Cells", Molecular Cancer Therapeutics 1(12):1043-1049, American Association for Cancer Research, Inc., United States (2002).
Tam, J.P. and Lu, Y.A., "A Biomimetic Strategy in the Synthesis and Fragmentation of Cyclic Protein", Protein science 7(7):1583-1592, Cold Spring Harbor Laboratory Press, United States (1998).
Tavladoraki, P., et al., "A Single-Chain Antibody Fragment is Functionally Expressed in the Cytoplasm of Both *Escherichia coli* and Transgenic Plants," European Journal of Biochemistry / FEBS 262(2):617-624, Blackwell Science Ltd. on behalf of the Federation of European Biochemical Societies, England (1999).
Tax, F.E., et al., "Sequence of C. elegans lag-2 reveals a cell-signalling domain shared with Delta and Serrate of *Drosophila*," Nature 368(6467):150-154, The National Academy of Sciences, United States (1994).
Terpe, K., "Overview of Tag Protein Fusions: from Molecular and Biochemical Fundamentals to Commercial Systems", Applied Microbiology and Biotechnology 60(5):523-533, Springer International, Germany (2003).
Thai, R., et al., "Antigen Stability Controls Antigen Presentation", The Journal of Biological Chemistry 279(48):50257-50266, American Society for Biochemistry and Molecular Biology, United States (2004).
Thomas, P.S., "Hybridization of denatured RNA and small DNA fragments transferred to nitrocellulose," Proceedings of the National Academy of Sciences 77(9):5201-5205, National Academy of Sciences, United States (1980).
Tolkatchev, D., et al., "Design and Solution Structure of a Well-Folded Stack of Two Beta-Hairpins Based on the Amino-Terminal Fragment of Human Granulin A," Biochemistry 39(11):2878-2886 Washington, Americal Chemical Society., United States (2000).
Toole, J.J., et al., "A large region (95 kDa) of human factor VIII is dispensable for in vitro procoagulant activity," Proceedings of the National Academy of Sciences USA 83(16):5939-5942, National Academy of Sciences, United States (1986).
Toole, J.J., et al., "Molecular Cloning of a cDNA Encoding Human Antihaemophilic Factor," Nature 312(5992):342-347, Nature Publishing Group, England (1984).
Torres, a.M., et al., "Solution Structure of a Defensin-Like Peptide from Platypus Venom", the Biochemical Journal 341( Pt 3):785-794, Published by Portland Press on behalf of the Biochemical Society, England (1999).
Towfighi, F., et al., "Comparative measurement of anti-factor VIII antibody by Bethesda assay and ELISA reveals restricted isotype profile and epitope specificity," Acta Haematol 114(2):84-90, S. Karger AG, Basel, Germany(2005).
Tuddenham, E.G.D., et al., "Response to infusions of polyelectrolyte fractionated human factor VIII concentrate in human haemophilia A and von Willebrand's disease," British Journal of Haematology 52(2):259-267, Wiley-Blackwell, England (1982).
Tur, M.K., et al., "A Novel Approach for Immunization, Screening and Characterization of Selected Scfv Libraries Using Membrane Fractions of Tumor Cells", International Journal of Molecular Medicine 11(4):523-527, D.A. Spandidos, Greece (2003).
UniProtKB/Swiss-Prot, "ELNE_HUMAN," accession No. P08246, accessed at http://www.uniprot.org/uniprot/P08246, accessed on Dec. 16, 2014, 19 pages.
UniProtKB/Swiss-Prot, "FA10_HUMAN," accession No. P00742, accessed at http://www.uniprot.org/uniprot/P00742, accessed on Dec. 16, 2014, 25 pages.
UniProtKB/Swiss-Prot, "FA11_HUMAN," accession No. P03951, accessed at http://www.uniprot.org/uniprot/P03951, accessed on Dec. 16, 2014, 22 pages.
UniProtKB/Swiss-Prot, "FA12_HUMAN," accession No. P00748, accessed at http://www.uniprot.org/uniprot/P00748, accessed on Dec. 16, 2014, 14 pages.
UniProtKB/Swiss-Prot, "FA7_HUMAN," accession No. P08709, accessed at http://www.uniprot.org/uniprot/P08709, accessed on Dec. 16, 2014, 27 pages.
UniProtKB/Swiss-Prot, "FA9_HUMAN," accession No. P00734, accessed at http://www.uniprot.org/uniprot/P00740, accessed on Dec. 16, 2014, 26 pages.
UniProtKB/Swiss-Prot, "KLKB1_HUMAN," accession No. P03952, accessed at http://www.uniprot.org/uniprot/P03952, accessed on Dec. 16, 2014, 11 pages.
UniProtKB/Swiss-Prot, "MMP12_HUMAN," accession No. P39900, accessed at http://www.uniprot.org/uniprot/P39900, accessed on Dec. 16, 2014, 12 pages.
UniProtKB/Swiss-Prot, "MMP13_HUMAN," accession No. P45452, accessed at http://www.uniprot.org/uniprot/P45452, accessed on Dec. 16, 2014, 15 pages.
UniProtKB/Swiss-Prot, "MMP17_HUMAN," accession No. Q9ULZ9, accessed at http://www.uniprot.org/uniprot/Q9ULZ9, accessed on Dec. 16, 2014, 11 pages.
UniProtKB/Swiss-Prot, "MMP20_HUMAN," accession No. O60882, accessed at http://www.uniprot.org/uniprot/O60882, accessed on Dec. 16, 2014, 10 pages.
UniProtKB/Swiss-Prot, "THRB_HUMAN," accession No. P00734, accessed at http://www.uniprot.org/uniprot/P00734, accessed on Dec. 16, 2014, 42 pages.
Urlaub, G. and Chasin, L.A., "Isolation of Chinese hamster cell mutants deficient in dihydrofolate reductase activity," Proceedings of the National Academy of Sciences 77(7):4216-4220, National Academy of Sciences, United States (1980).

(56) References Cited

OTHER PUBLICATIONS

Uversky, V.N., et al., "Why are "natively unfolded" proteins unstructured under physiologic conditions?," PROTEINS: Structure, Function and Genetics 41(3):415-427, Wiley-Liss, Inc., United States (2000).
Valente, C.A., et al., "Optimization of the Primary Recovery of Human Interferon Alpha2B from *Escherichia coli* Inclusion Bodies", Protein Expression and Purification 45(1):226-234, Academic Press, United States (2006).
Van Den Hooven H.W., et, al., "Disulfide Bond Structure of the Avr9 Elicitor of the Fungal Tomato Pathogen Cladosporium Fulvum : Evidence for a Cystine Knot", Biochemistry 40(12):3458-3466, Washington, American Chemical Society., United States (2001).
Van Vlijmen, H.W., et, al., "A Novel Database of Disulfide Patterns and Its Application to the Discovery of Distantly Related Homologs", Journal of Molecular Biology 335(4):1083-1092, Elsevier, England (2004).
Vanhercke, T., et, al., "Reducing Mutational Bias in Random Protein Libraries", Analytical Biochemistry 339(1): 9-14, Academic Press, United States (2005).
Vardar, D., et al., "Nuclear Magnetic Resonance Structure of a Prototype Lin12-Notch Repeat Module from Human Notch1," Biochemistry 42(23):7061-7067, American Chemical Society, United States (2003).
Vehar, G.A., et al., "Structure of Human Factor VIII" Nature 312(5992):337-342, Nature Publishing Group, England (1984).
Venkatachalam, C.M. and Ramachandran, G.N., "Conformation of polypeptide chains," Annual Review of Biochemistry 38:45-82, Annual Reviews, United States (1969).
Venkateswarlu, D., "Structural investigation of zymogenic and activated forms of human blood coagulation factor VIII: a computational molecular dynamics study," BMC Structural Biology 10:7, BioMed Central, England (Feb. 2010).
Ventura, S., "Sequence Determinants of Protein Aggregation: Tools to Increase Protein Solubility", Microbial Cell Factories 4(1):11, Academic Press, United States (2005).
Verbruggen, B., et al., "Improvements in factor VIII inhibitor detection: From Bethesda to Nijmegen," Seminard in Thrombosis and Hemostasis 35(8):752-759, Thieme Medical Publishers, Inc., United States (Nov. 2009).
Verbruggen, B., et al., "The Nijmegen modification of the Bethesda assay for factor VIII:C inhibitors: improved specificity and reliability," Journal of Thrombosis and Haemostasis 73(2):247-251, Schattauer GmbH, Germany (1995).
Vestergaard-Bogind, B., et, al., "Single-File Diffusion Through the Ca2+-Activated K+ Channel of Human Red Cells", The Journal of Membrane Biology 88(1):67-75, New York, Springer., United States (1985).
Voisey, J. and Van, Daal, A., "Agouti: from Mouse to Man, from Skin to Fat", Pigment cell research sponsored by the European Society for Pigment Cell Research and the International Pigment Cell Society 15(1):10-18, Munksgaard International Publishers, Denmark (2002).
Vorobjev, P.E., et al., "Oligonucleotide Conjugated to Linear and Branched High Molecular Weight Polyethylene Glycol as Substrates for RNase H," Nucleosides & Nucleotides 18(11-12):2745-2750, Marcel Dekker, Inc., United States (1999).
Vranken, W.F., et al., "A 30-Residue Fragment of the Carp Granulin-1 Protein Folds into a Stack of Two Beta-Hairpins Similar to That Found in the Native Protein," The Journal of Peptide Research : official journal of the American Peptide Society 53(5):590-597, Munksgaard, Denmark (1999).
Wagenvoord, R.J., et al., "Development of a Simple Chromogenic Factor VIII Assay for Clinical Use," Haemostasis 19(4):196-204, Karger Publishers, Switzerland (1989).
Walker, J.R., et al., "Using protein-based motifs to stabilize peptides," The Journal of Peptide Research 62(5):214-226, Blackwell Munksgaard, Denmark (2003).
Wang., "Parenteral Formulations of Proteins and Peptides: Stability and Stabilizers," Journal of Parenteral Science and Technology 42:2S, Parenteral Drug Association, Bethesda (1988).
Wang, X., et, al., "Structure-Function Studies of Omega-Atracotoxin, a Potent Antagonist of Insect Voltage-Gated Calcium Channels", European journal of biochemistry / FEBS 264(2):488-494, Blackwell Science Ltd. on behalf of the Federation of European Biochemical Societies, England (1999).
Ward, E.S. and Ghetie, V., "The Effector Functions of Immunoglobulins: Implications for Therapy," Therapeutic Immunology 2(2):77-94, Blackwell Science Ltd., England (1995).
Ward, E.S., et al., "Binding Activities of a Repertoire of Single Immunoglobulin Variable Domains Secreted from *Escherichia coli*," Nature 331:544-546, Nature Publishing Group, England (1989).
Watters, J.M., et, al., "An Optimized Method for Cell-Based Phage Display Panning", Immunotechnology 3(1):21-29, Elsevier, Netherlands (1997).
Weidler, B., et al., "Pharmakokinetische Merkmale als Kriterien fur den klinischen Einsatz von Hydrozyethylstarke," Arzneimittel-Forschung 41(5):494-498, Editio Cantor, Germany (1991).
Weimer, T., et al., "Prolonged in-vivo half-life of factor VIIa by fusion to albumin," Thrombosis and Haemostasis 99(4):659-667, Schattauer GmbH, Germany (Apr. 2008).
Weiss, H.J., et al., "Stabilization of factor VIII in plasma by the von Willebrand factor. Studies on posttransfusion and dissociated factor VIII and in patients with von Willebrand's disease," The Journal of Clinical Investigation 60(2):390-404, The American Society for Biochemistry and Molecular Biology,Inc., United States (1977).
Weiss, M.S., et, al., "A Cooperative Model for Receptor Recognition and Cell Adhesion : Evidence from the Molecular Packing in the 16-A Crystal Structure of the Pheromone Er-1 from the Ciliated Protozoan Euplotes Raikovi ", Proceedings of the National Academy of Sciences of the United States of America 92(22):10172-10176, National Academy of Sciences, United States (1995).
Wentzel, A., et, al., "Sequence Requirements of the Gpng Beta-Turn of the Ecballium Elaterium Trypsin Inhibitor Ii Explored by Combinatorial Library Screening", The Journal of Biological Chemistry 274(30):21037-21043, American Society for Biochemistry and Molecular Biology, United States (1999).
Werle, M., et, al., "The Potential of Cystine-Knot Microproteins as Novel Pharmacophoric Scaffolds in Oral Peptide Drug Delivery", Journal of Drug Targeting 14(3):137-146, Informa Healthcare, England (2006).
Werther, W.A., et al., "Humanization of an Anti-Lymphocyte Function-associated Antigen (Lfa)-1 Monoclonal Antibody and Reengineering of the Humanized Antibody for Binding to Rhesus Lfa-1," Journal of Immunology 157(11):4986-4995, American Association of Immunologists, United States (1996).
White, G.C., II. and Shoemaker, C.B., "Factor VIII Gene and Hemophilia A," Blood 73(1):1-12, Grune & Stratton, Inc., United States (1989).
Whitlow, M., et, al., "Multivalent Fvs: Characterization of Single-Chain Fv Oligomers and Preparation of a Bispecific Fv", Protein Engineering 7(8):1017-1026, Oxford University Press, England (1994).
Wigler, M., et al., "Biochemical Transfer of Single-Copy Eucaryotic Genes Using Total Cellular DNA as Donor," Cell 14(3):725-731, Cell Press, United States (1978).
Winter, G. and Harris, W.J., "Humanized Antibodies", Trends in pharmacological sciences 14(5):139-143, Published by Elsevier in Association with the International Union of Pharmacology, England (1993).
Wittrup, K.D., "Protein Engineering by Cell-Surface Display", Current Opinion in Biotechnology 12(4):395-399, Elsevier, England (2001).
Wood, W.I., et al., "Expression of Active Human Factor VIII from Recombinant DNA Clones," Nature 312(5992):330-337, Nature Publishing Group, England (1984).
Worn, A. and Pluckthun, A., "Stability Engineering of Antibody Single-Chain Fv Fragments ," Journal of Molecular Biology 305(5):989-1010, Elsevier, England (2001).
Worn, A., et, al., "Correlation Between In Vitro Stability and In Vivo Performance of Anti-Gcn4 Intrabodies as Cytoplasmic Inhibitors",

(56) References Cited

OTHER PUBLICATIONS

The Journal of Biological Chemistry 275(4):2795-2803, American Society for Biochemistry and Molecular Biology, United States (2000).
Wrammert, J., et, al., "Rapid Cloning of High-Affinity Human Monoclonal Antibodies Against Influenza Virus," Nature 453(7195):667-671, Nature Publishing Group, England (May 2008).
Wright, P.E. and Dyson, H.J., "Intrinsically unstructured proteins: re-assessing the protein structure-function paradigm," Journal of Molecular Biology 293(2):321-331, Academic Press, England (1999).
Xiong, J.P., et, al., "A Novel Adaptation of the Integrin Psi Domain Revealed from Its Crystal Structure", The Journal of Biological Chemistry 279(39):40252-40254, American Society for Biochemistry and Molecular Biology, United States (2004).
Xu, Y., et, al., "Solution Structure of Bmp02 , A New Potassium Channel Blocker from the Venom of the Chinese Scorpion Buthus Martensi Karsch ", Biochemistry 39(45):13669-13675, American Chemical Society., United States (2000).
Yamazaki, T., et, al., "A Possible Physiological Function and the Tertiary Structure of a 4-Kda Peptide in Legumes", European Journal of Biochemistry / FEBS 270(6):1269-1276, Blackwell Science Ltd. on behalf of the Federation of European Biochemical Societies, England (2003).
Yang, C.Y., et al., "Intestinal Peptide Transport Systems and Oral Drug Availability," Pharmaceutical Research 16(9):1331-1343, Kluwer Academic/Plenum Publishers, United States (1999).
Yang, K., et al., "Tailoring structure-function and pharmacokinetic properties of single-chain Fv proteins by site-specific PEGylation," Protein Engineering 16(10):761-770, Oxford University Press, England (2003).
Yang, W.P., et al., "CDR Walking Mutagenesis for the Affinity Maturation of a Potent Human Anti-Hiv-1 Antibody into the Picomolar Range," Journal of Molecular Biology 254(3):392-403, Elsevier, England (1995).
Yang, Z.R., et al., "RONN: the bio-basis function neural network technique applied to the detection of natively disordered regions in proteins," Bioinformatics 21(16):3369-3376, Oxford University Press, England (2005).
Yankai, Z., et al., "Ten tandem repeats of β-hCG 109-118 enhance immunogenicity and anti-tumor effects of β-hCG C-terminal peptide carried by mycobacterial heat-shock protein HSP65," Biochemical and Biophysical Research Communications 345(4):1365-1371, Elsevier Inc., United States (2006).
Yuan, X., et, al., "Solution Structure of the Transforming Growth Factor Beta-Binding Protein-Like Module, A Domain Associated With Matrix Fibrils", The EMBO Journal 16(22):6659-6666, Wiley Blackwell, England (1997).
International Search Report for International Patent Application No. PCT/US2013/021330, United States Patent Office, Alexandria, Virginia, dated Apr. 29, 2013.
International Search Report for International Patent Application No. PCT/US2013/026521, United States Patent Office, Alexandria, Virginia, dated Apr. 24, 2013.
International Search Report for International Patent Application No. PCT/US2013/049989, United States Patent Office, Alexandria, Virginia, dated Dec. 16, 2013.
International Search Report for International Patent Application No. PCT/US2014/044731, United States Patent Office, Alexandria, Virginia, dated Nov. 4, 2014.
International Search Report for International Patent Application No. PCT/US2014/051144, United States Patent Office, Alexandria, Virginia, dated Feb. 10, 2015.
International Search Report for International Patent Application No. PCT/US2014/040370, United States Patent Office, Alexandria, Virginia, dated Jan. 9, 2015.
Office action dated Nov. 1, 2016, in United States Patent Application No. 14/379,192, inventor Schellenberger, et al., filed Feb. 20, 2015.
Co-pending U.S. Appl. No. 14/521,397, inventors Stemmer, W., et al., filed Oct. 22, 2014 (Not Published).
Bai, Y., et al., "Recombinant granulocyte colony-stimulating factor-transferrin fusion protein as an oral myelopoietic agent," Proceedings of the National Academy of Sciences USA 102(20):7292-7296, National Academy of Sciences, United States (2005).
Bovenschen, N., et al., "LDL Receptor Cooperates with LDL Receptor-Related Protein in Regulating Plasma Levels of Coagulation Factor VIII in Vivo," Blood 106(3):906-912, The American Society of Hematology, United States (2005).
Bovenschen, N., "LDL Receptor Polymorphisms Revisited," Blood 116(25):5439-5440, The American Society of Hematology, United States (Dec. 2010).
Brandsma, M.E., et al., "Recombinant human transferrin: Beyond iron binding and transport," Biotechnology Advances 29(2):230-238, Elsevier, United States (2011).
Co-pending U.S. Appl. No. 14/466,567, inventors Schellenberger, et al., filed Aug. 22, 2014 (Not Published).
Office Action dated Jun. 17, 2015, in United States Patent Application No. 14/317,888, Schellenberger, et al., filed Jun. 27, 2014.
Davidson, M.W., "Engineered fluorescent proteins: innovations and applications," Nature Methods 6(10):713-717, Nature Publishing Group, England (2009).
Fang, H., et al., "The protein structure and effect of factor VIII," Thrombosis Research 119(1):1-13, Elsevier, United States (2007).
Fares, F.A., "Design of a long-acting follitropin agonist by fusing the C-terminal sequence of the chorionic gonadotropin beta subunit to the follitropin beta subunit," Proceedings of the National Academy of Sciences 89(10):4304-4308, The National Academy of Sciences of the United States (1992).
Fraczkiewicz, R., et al., "Exact and Efficient Analytical Calculation of the Accessible Surface Areas and Their Gradients for Macromolecules ," Journal of Computational Chemistry 19:319-333, John Wiley & Sons, United States (1998).
Francis, G.E., "Protein Modification and Fusion Proteins," Focus on Growth Factors 3(2):4-10, Mediscript, England (1992).
GenBank, "*Homo sapiens* coagulation factor VIII, procoagulant component (F8), transcript variant 1, mRNA," Accession No. NM_000132.3, accessed at http://www.ncbi.nlm.nih.gov/nuccore/NM_000132.3, accessed on May 11, 2014, 12 pages.
GenBank, "*Homo sapiens* Transferrin (TF), mRNA," Accession No. NM001063.3 published on May 25, 2014, accessed at http://www.ncbi.nlm.nih.gov/nuccore/NM_001063, accessed on Sep. 24, 2014, 5 pages.
GenBank, "*Homo sapiens* Transferrin (TF), mRNA," Accession No. XM002793 published on May 13, 2002, accessed at https://www.ncbi.nlm.nih.gov/nuccore/XM_002793.7?report=genbank, accessed on Sep. 24, 2014, 2 pages.
GenBank, "*Homo sapiens* Transferrin (TF), mRNA," Accession No. XM039845 published Jul. 16, 2001, accessed at https://www.ncbi.nlm.nih.gov/nuccore/XM_039845.1?report=genbank, accessed on Sep. 24, 2014, 2 pages.
GenBank, "*Homo sapiens* Transferrin (TF), mRNA," Accession No. XM039847 published on Jul. 16, 2001, accessed at http://www.ncbi.nlm.nih.gov/nuccore/XM_039847.1?report=genbank, accessed on Sep. 24, 2014, 2 pages.
GenBank, "Human Transferrin mRNA, Complete cds," Accession No. M12530.1, published on Jan. 14, 1995, accessed at http://www.ncbi.nlm.nih.gov/nuccore/M1253014, accessed on Jan. 15, 2015, 2 pages.
GenBank, "Transferrin [human, liver, mRNA, 2347 nt]," Accession No. S95936.1, published on May 7, 1993, accessed at http://www.ncbi.nlm.nih.gov/nuccore/S95936, accessed on Sep. 24, 2014, 2 pages.
Wang, Y., et al., "Receptor-Mediated Activation of a Proinsulin-Transferrin Fusion Protein in Hepatoma Cells," Journal of Controlled Release 155(3):386-392, Elsevier B.V., Netherlands (2011).
Holt, L.J., et al., "Anti-Serum Albumin Domain Antibodies for Extending the Half-Lives of Short Lived Drugs," Protein Engineering, Design and Selection 21(5):283-288, Oxford University Press, England (2008).
Gruppo, R.A., et al., "Comparative Effectiveness of Full-length and B-domain Deleted Factor VIII for Prophylaxis—A Meta-analysis," Haemophilia 9(3):251-260, Blackwell Science, England (2003).

(56) References Cited

OTHER PUBLICATIONS

Kim, B.J., et al., "Transferrin Fusion Technology: a Novel Approach to Prolonging Biological Half-Life of Insulinotropic Peptides," The Journal of Pharmacology and Experimental Therapeutics 334(3):682-692, American Society for Pharmacology and Experimental Therapeutics, United States (Sep. 2010).
Kraulis, P.J., et al., "The Serum Albumin-Binding Domain of Streptococcal Protein G is a Three-Helical Bundle: a Heteronuclear NMR study," FEBS Letters 378(2):190-194, Elsevier Science B.V,Netherlands (1996).
Kulman, J.D., et al., "A versatile system for site-specific enzymatic biotinylation and regulated expression of proteins in cultured mammalian cells," Protein Expression and Purification 52(2):320-328, Elsevier, United States (2007).
Lee, C.A., et al., "Pharmacokinetics of Recombinant Factor VIII (Recombinate) Using One-Stage Clotting and Chromogenic Factor VIII Assay," Thrombosis and Haemostasis 82(6):1644-1647, Schattauer Verlag, Germany (1999).
Lenting, P.J., et al., "Biochemistry of FVIII and Inhibitors: The Disappearing Act of Factor VIII," Haemophilia 16(102):6-15, Blackwell Publishing Ltd, England (May 2010).
Li, H., et al., "The role of the transferrin-transferrin-receptor system in drug delivery and targeting," TRENDS in Pharmacological Sciences 23(5):206-209, Elsevier Science Ltd., England (2002).
Linhult, M., et al., "Mutational Analysis of the Interaction Between Albumin-Binding Domain from Streptococcal Protein G and Human Serum Albumin," Protein Science 11(2):206-213, Cold Spring Harbor Laboratory Press, United States (2002).
Lippi, G., et al., "Diagnostic approach to inherited bleeding disorders," Clinical Chemistry and Laboratory Medicine 45(1):2-12, Walter de Gruyter, Germany (2007).
Malik, F., et al., "Polyethylene Glycol (PEG)-modified Granulocyte-Macrophage Colony-stimulating Factor (GM-CSF) with Conserved Biological Activity," Experimental Hematology 20(8):1028-1035, International Society for Experimental Hematology, United States (1992).
Mannucci, P.M. and Tuddenham, E.G.D., "The Hemophilias—from Royal Genes to Gene Therapy," New England Journal of Medicine 344(23):1773-1779, Massachusetts Medical Society, United States (2001).
Martinelli, N., et al., "Polymorphisms at LDLR Locus may be Associated with Coronary Artery Disease through Modulation of Coagulation Factor VIII Activity and Independently from Lipid Profile," Blood 116(25):5688-5697, The American Society of Hematology, United States (Dec. 2010).
Matsumoto, T., et al., "The measurement of low levels of factor VIII or factor IX in hemophilia A and hemophilia B plasma by clot waveform analysis and thrombin generation assay," Journal of Thrombosis and Haemostasis 4(2):377-384, International Society on Thrombosis and Haemostasis, England (2006).
Mei, B., et al., "Rational Design of a Fully active, Long-Acting PEGylated Factor VIII for Hemophilia A Treatment," Blood 116(2):270-279, The American Society of Hematology, United States (Jul. 2010).
Mize, G.J., et al., "Regulated expression of active biotinylated G-protein coupled receptors in mammalian cells," Protein Expression and Purification 57(2):280-289, Elsevier, United States (2008).
Muller, D. and Kontermann, R.E., "Recombinant Bispecific Antibodies for Cellular Cancer Immunotherapy," Current Opinion in Molecular Therapeutics 9(4):319-326, The Thomson Corporation, United States (2007).
Ormo, M., et al., "Crystal structure of the Aequorea victoria green fluorescent protein," Science 273(5280):1392-1395, Association for the Advancement of Science, United States (1996).
Peters, R.T., et al., "Prolonged Activity of Factor IX as a Monomeric Fc Fusion Protein," Blood, Thrombosis and Hemostasis, 115 (10):2057-2064, Blood 115(10):2057-2064, The American Society of Hematology, United States (Mar. 11, 2010).
Puthenveetil, S., et al., "Yeast display evolution of a kinetically efficient 13-amino acid substrate for lipoic acid ligase," Journal of the American Chemical Society 131(45):16430-16438, American Chemical Society, United States (Nov. 2009).
Rizzo., et al., "Fluorescent protein tracking and detection," In Live Cell Imaging:A Laboratory Manual, pp. 3-34, Cold Spring Harbor Laboratory Press (2010).
Rodriguez-Merchan, E.C. "Management of Musculoskeletal Complications of Hemophilia," Seminars in Thrombosis and Hemostasis 29(1):87-95, Thieme, United States (2003).
Roovers, R.C., et al., "Efficient Inhibition of EGFR Signaling and of Tumour Growth by Antagonistic Anti-EGFR Nanobodies," Cancer Immunology, Immunotherapy 56(3):303-317, Springer Verlag, Germany (2007).
Rosen, S., et al., "Clinical application of a chromogenic substrate method for determination of factor VIII activity," Thrombosis and Haemostasis 54(4):818-823, Stuttgart, Schattauer, Germany (1985).
Schatz, P.J., "Use of peptide libraries to map the substrate specificity of a peptide-modifying enzyme: a 13 residue consensus peptide specifies biotinylation in *Escherichia coli*," Biotechnology 11(10):1138-1143, Nature Publishing Group, New York (1993).
Schulte, S., "Pioneering designs for recombinant coagulation factors," Thrombosis Research 128(1):S9-S12, Elsevier, United States (2011).
Shapiro, A.D., "Recombinant factor IX-Fc fusion protein (rFIXFc) demonstrates safety and prolonged activity in a phase 1/2a study in hemophilia B patients," Blood 119(3):666-672, The American Society of Hematology, United States (2012).
Shimomura, O., et al., "Extraction, purification and properties of aequorin, a bioluminescent protein from the luminous hydromedusan, Aequorea," Journal of Cellular and Comparative Physiology 59:223-239, Wiley-Liss, United States (1962).
Spencer., et al., "Lentiviral Vector Platform for Production of Bioengineered RecombinantCoagulation Factor VIII," Molecular Therapy 19(2):302-309, Nature Publishing Group, England (2011).
Supplementary Partial European Search Report for EP Application No. 12868427, European Patent Office, The Hague, dated Sep. 18, 2015, 8 pages.
Trussel, S., et al., "New Strategy for the Extension of the Serum Half-Life of Antibody Fragments," Bioconjugate Chemistry 20(12):2286-2292, American Chemical Society, United States (2009).
Uttamapinant, C., et al., "A fluorophore ligase for site-specific protein labeling inside living cells," Proceedings of the National Academy of Sciences 107(24):10914-10919, The National Academy of Sciences of the United States (Jun. 2010).
Lozier, J.N., et al., "The Chapel Hill Hemophilia A Dog Colony Exhibits a Factor VIII Gene Inversion," Proceedings of the National Academy of Sciences USA 99(20):12991-12996, National Academy of Sciences, United States (2002).
Powell, J.S., et al., "Safety and Prolonged Activity of Recombinant Factor VIII Fc Fusion Protein in Hemophilia a Patients," Blood 119(13):3031-3037, The American Society of Hematology, United States (2012).
Office Action dated Mar. 9, 2016 in U.S. Appl. No. 14/218,524, filed Mar. 18, 2014.
Office Action dated Nov. 24, 2015 in U.S. Appl. No. 14/317,888, filed Jun. 27, 2014.
International Search Report and Written Opinion for International Patent Application No. PCT/US2014/044718, United States Patent Office, Alexandria, Virginia, dated Nov. 4, 2014, 10 pages.
Database Geneseq [Online] Jan. 12, 2012, "Human B-domain Deleted Factor VIII Protein (S743/Q1638) SEQ:2.". XP002743820, Retrieved from EBI accession No. GSP:AZS50750 Database accession No. AZS5075.
National Heart Lung and Blood Institute, "The Diagnosis, Evaluation and Management of von Willebrand Disease Scientific Overview," accessed at http://www.nhlbi.nih.gov/guidelines/vwd/2scientificoverview.htm, accessed on Oct. 22, 2011.
Genbank, "*Homo sapiens* von Willebrand factor (VWF), mRNA" NCBI Reference Sequence: NM_000552.3, accessed at http://www.ncbinlm.nih.gov/nuccore/NM_000552.3, accessed on Mar. 29, 2016, 10 pages.
Genbank, "transferrin precursor [*Homo sapiens*]" Accession AAA61140.1, accessed at http://www.ncbi.nlm.nih.gov/protein/AAA61140, accessed on Mar. 29, 2016, 3 pages.

(56) References Cited

OTHER PUBLICATIONS

Genbank, "Von Willebrand factor preproprotein [*Homo sapiens*]," NCBI Reference Sequence: NP_000543.2, accessed at http://www.ncbi.nlm.nih.gov/protein/NP_000543.2, accessed on Mar. 29, 2016, 6 pages.
Goudemand, J., et al., "Pharmacokinetic Studies on Wilfactin, a Von Willebrand Factor Concentrate with a Low Factor VIII Content Treated with Three Virus-inactivation/removal Methods," Journal of Thrombosis and Haemostasis 3(10):2219-2227, Blackwell Publishers, England (2005).
Lee, M.T, "Ch. 12: Disorders of Coagulation" in Pediatric Hematology Secrets, Weiner M.A. and Cario, M.S. eds., pp. 47-52, Hanley & Belfus, United States (2001).
Proft, T., "Sortase-mediated protein ligation: an emerging biotechnology tool for protein modification and immobilization," Biotechnology Letters 32:1-10, Springer Science+Business Media B.V., Netherlands (Sep. 2009).
Counts, R. B., et al., "Disulfide Bonds and the Quaternary Structure of Factor VIII/von Willebrand Factor," *J. Clin. Invest.* 62(3):702-09, The American Society for Clinical Investigation, Inc. (1978).
Thermo Scientific, "Instructions: Imidoester Crosslinkers: DMA, DMP, DMS, DTBP," available at https://tools.thermofisher.com/content/sfs/manuals/MAN0011314_ImidoesterCrsLnk_DMA_DMP_DMS_DTBP_UG.pdf, 2 pages (2012).
Nogami, K., et al., "A novel mechanism of factor VIII protection by von Willebrand factor from activated protein C—catalyzed inactivation," *Blood 99*(11):3993-98, American Society of Hematology (2002).
Nogami, K., et al., "Relationship between the binding sites for von Willebrand factor, phospholipid, and human factor VIII C2 inhibitor alloantibodies within the factor VIII C2 domain," *Int. J. Hematol. 85*(4):317-22, Springer (2007).
Office Action dated Mar. 29, 2017, in U.S. Appl. No. 14/413,765, inventor Ekta Seth Chhabra, filed Jul. 10, 2013.
Office Action dated Jul. 21, 2017, in U.S. Appl. No. 14/413,765, inventor Ekta Seth Chhabra, filed Jul. 10, 2013.
Office Action dated May 17, 2017, in U.S. Appl. No. 14/371,948, inventor Ekta Seth Chhabra, filed Jul. 11, 2014.
Office action dated May 23, 2017, in U.S. Appl. No. 14/894,108, inventor Ekta Seth Chhabra, filed May 3, 2016.
Office Action dated Sep. 25, 2017, in United States Application No. 14/379,196, Kulman, filed Feb. 15, 2013.
Office Action dated Dec. 12, 2017, in U.S. Appl. No. 14/371,948, Chhabra et al., filed Jan. 12, 2013.
Heinz et al., Factor VIII-eGFP fusion proteins with preserved functional activity for the analysis of the early secretory pathway of factor VIII, Thromb. Haemost. 102:925-35 (2009).
D'Oiron, R., et al., "Mild/moderate Haemophilia A: New Insights into Molecular Mechanisms and Inhibitor Development," Haemophilia 14(Suppl 3):138-146, Blackwell Science, England (Jul. 2008).
Office action dated Dec. 15, 2017, in U.S. Appl. No. 14/894,108, inventor Ekta Seth Chhabra, filed May 3, 2016.
Office action dated Mar. 16, 2018, in U.S. Appl. No. 14/379,192, inventor Schellenberger, filed Feb. 20, 2015.
Office action dated Sep. 27, 2017, in U.S. Appl. No. 14/379,192, inventor Schellenberger, filed Feb. 20, 2015.
Office action dated May 30, 2017, in U.S. Appl. No. 14/379,192, inventor Schellenberger, et al., filed Feb. 20, 2015.

* cited by examiner

Figure 1: Half-life of chimeric proteins comprising FVIII polypeptides and XTEN insertions

| FVIII-XTEN construct ID | No. of XTEN insertions | Insertion sites (no.= aa residue; B=B-domain; CT= C-term) | XTEN size | Half-life in FVIII/VWF DKO (hr.) | Half-life in Hem A (hr.) | Deletion 745-1685aa |
|---|---|---|---|---|---|---|
| LSD0049.002 | 3 | 18/B/CT | 144AG/144AE/288AE | 12.6 | - | No |
| PBC276.003 | 3 | 18/B/CT | 288AG/144AE/288AE | 9.97 | - | No |
| PBC278.004 | 3 | 1720/B/CT | 288AG/144AE/288AE | 10.4 | - | No |
| LSD0055.021 | 3 | 1900/B/CT | 144AE/144AE/288AE | 16 | - | No |
| PNL044 | 3 | 1900/B/CT | 144AE/144AE/288AE | - | 15.4 | No |
| **PNL049** | **4** | **18/1900/B/CT** | **42AE/144AE/144AE/288AE** | - | **22** | **Yes** |
| **PNL050** | **4** | **1720/1900/B/CT** | **42AE/144AE/144AE/288AE** | - | **23** | **Yes** |
| LSD62.001 | 4 | 18/1720/B/CT | 144AG/144AG/144AE/288AE | 14.07 | - | No |
| **PNL051** | **4** | **18/1720/B/CT** | **42AE/42AE/144AE/288AE** | - | **22** | **Yes** |

Figure 2: Half-life of chimeric proteins comprising FVIII polypeptides with reduced binding to VWF and 4 XTEN insertions
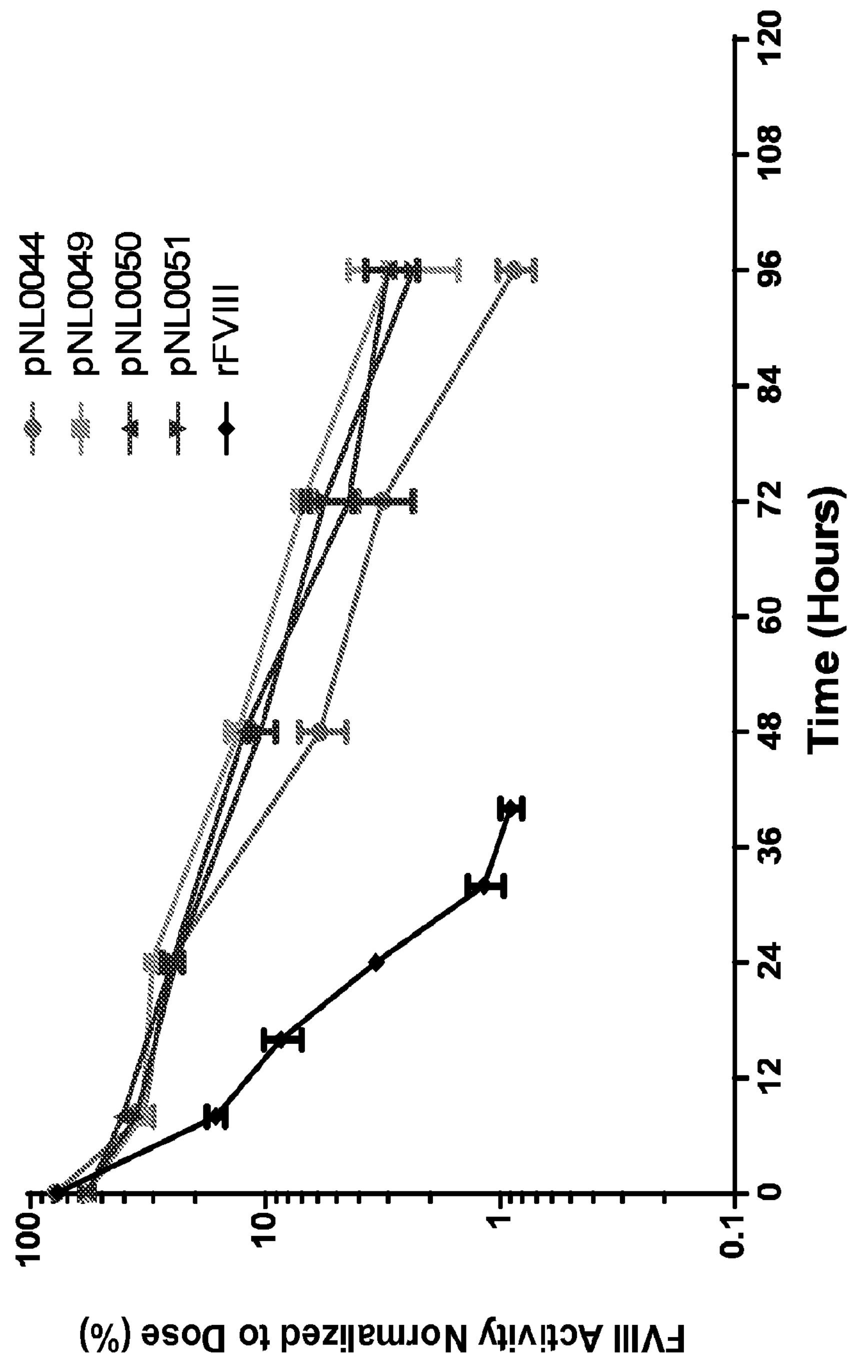

Figure 3: Effect of XTEN size and insertion site on half-life
| Base Construct | 3rd XTEN Insertion site | Length of 3rd XTEN | Cell culture activity | $t_{1/2}$ in DKO Mice |
|---|---|---|---|---|
| A1 A2 A3 C1 C2 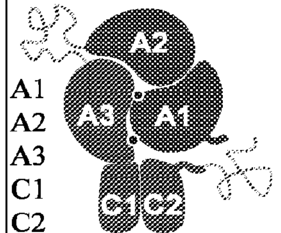 | A1-18 | 42 | 14.8 | 15.1 |
| | | 72 | 13 | 14.8 |
| | | 144 | 5.7 | 12.6 |
| | | 288 | 2.2 | 9.8 |
| | A2-403 | 42 | 4.7 | 12.1 |
| | | 144 | 1.8 | 11.1 |
| | | 288 | 1.0 | 10.9 |
| | A3-1720 | 42 | 6.1 | 16.3 |
| | | 72 | 3.0 | 15.1 |
| | | 144 | 1.5 | 13.8 |
| | | 288 | 0.8 | 10.3 |
| | A3-1900 | 42 | 6.6 | 13 |
| | | 72 | 3.0 | 16.1 |
| | | 144 | 2.6 | 16/17.3 |
| | | 288 | 2.0 | 9.5 |

Figure 5: Half-life effect of a fifth 42aa XTEN insertion in each insertion loop
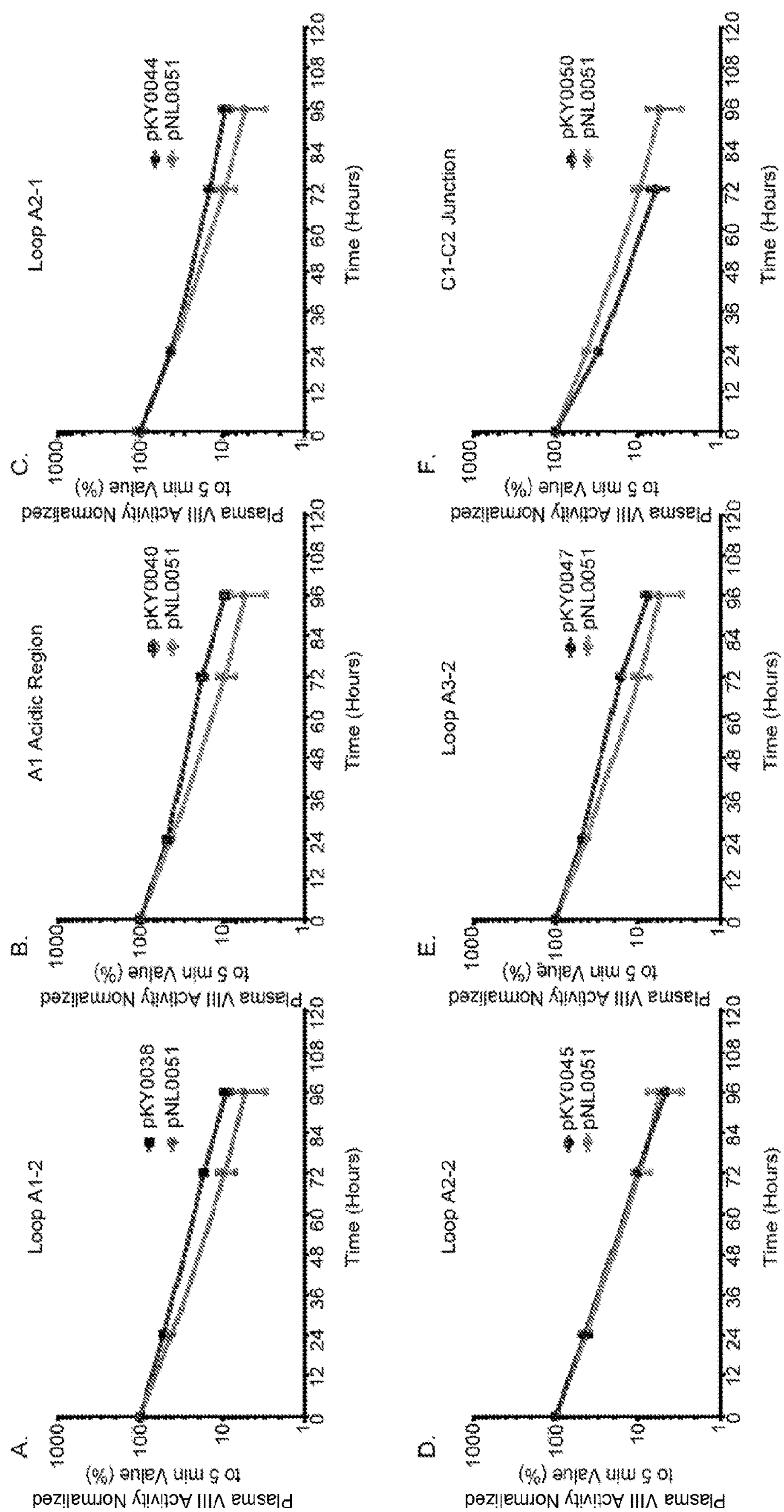

SEQUENCE LISTING

```
<160> NUMBER OF SEQ ID NOS: 108

<210> SEQ ID NO 1
<211> LENGTH: 1421
<212> TYPE: PRT
<213> ORGANISM: Artificial Sequence
<220> FEATURE:
<223> OTHER INFORMATION: Mature FVIII Del 745-1656

<400> SEQUENCE: 1

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
```

```
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480
```

```
Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Asp Gln Glu Glu Ile Asp
            740                 745                 750

Tyr Asp Asp Thr Ile Ser Val Glu Met Lys Lys Glu Asp Phe Asp Ile
        755                 760                 765

Tyr Asp Glu Asp Glu Asn Gln Ser Pro Arg Ser Phe Gln Lys Lys Thr
    770                 775                 780

Arg His Tyr Phe Ile Ala Ala Val Glu Arg Leu Trp Asp Tyr Gly Met
785                 790                 795                 800

Ser Ser Ser Pro His Val Leu Arg Asn Arg Ala Gln Ser Gly Ser Val
                805                 810                 815

Pro Gln Phe Lys Lys Val Val Phe Gln Glu Phe Thr Asp Gly Ser Phe
            820                 825                 830

Thr Gln Pro Leu Tyr Arg Gly Glu Leu Asn Glu His Leu Gly Leu Leu
        835                 840                 845

Gly Pro Tyr Ile Arg Ala Glu Val Glu Asp Asn Ile Met Val Thr Phe
    850                 855                 860

Arg Asn Gln Ala Ser Arg Pro Tyr Ser Phe Tyr Ser Ser Leu Ile Ser
865                 870                 875                 880

Tyr Glu Glu Asp Gln Arg Gln Gly Ala Glu Pro Arg Lys Asn Phe Val
                885                 890                 895
```

```
Lys Pro Asn Glu Thr Lys Thr Tyr Phe Trp Lys Val Gln His His Met
            900                 905                 910

Ala Pro Thr Lys Asp Glu Phe Asp Cys Lys Ala Trp Ala Tyr Phe Ser
        915                 920                 925

Asp Val Asp Leu Glu Lys Asp Val His Ser Gly Leu Ile Gly Pro Leu
    930                 935                 940

Leu Val Cys His Thr Asn Thr Leu Asn Pro Ala His Gly Arg Gln Val
945                 950                 955                 960

Thr Val Gln Glu Phe Ala Leu Phe Phe Thr Ile Phe Asp Glu Thr Lys
                965                 970                 975

Ser Trp Tyr Phe Thr Glu Asn Met Glu Arg Asn Cys Arg Ala Pro Cys
            980                 985                 990

Asn Ile Gln Met Glu Asp Pro Thr  Phe Lys Glu Asn Tyr  Arg Phe His
        995                 1000                1005

Ala Ile  Asn Gly Tyr Ile Met  Asp Thr Leu Pro Gly  Leu Val Met
    1010                 1015                1020

Ala Gln  Asp Gln Arg Ile Arg  Trp Tyr Leu Leu Ser  Met Gly Ser
    1025                 1030                1035

Asn Glu  Asn Ile His Ser Ile  His Phe Ser Gly His  Val Phe Thr
    1040                 1045                1050

Val Arg  Lys Lys Glu Glu Tyr  Lys Met Ala Leu Tyr  Asn Leu Tyr
    1055                 1060                1065

Pro Gly  Val Phe Glu Thr Val  Glu Met Leu Pro Ser  Lys Ala Gly
    1070                 1075                1080

Ile Trp  Arg Val Glu Cys Leu  Ile Gly Glu His Leu  His Ala Gly
    1085                 1090                1095

Met Ser  Thr Leu Phe Leu Val  Tyr Ser Asn Lys Cys  Gln Thr Pro
    1100                 1105                1110

Leu Gly  Met Ala Ser Gly His  Ile Arg Asp Phe Gln  Ile Thr Ala
    1115                 1120                1125

Ser Gly  Gln Tyr Gly Gln Trp  Ala Pro Lys Leu Ala  Arg Leu His
    1130                 1135                1140

Tyr Ser  Gly Ser Ile Asn Ala  Trp Ser Thr Lys Glu  Pro Phe Ser
    1145                 1150                1155

Trp Ile  Lys Val Asp Leu Leu  Ala Pro Met Ile Ile  His Gly Ile
    1160                 1165                1170

Lys Thr  Gln Gly Ala Arg Gln  Lys Phe Ser Ser Leu  Tyr Ile Ser
    1175                 1180                1185

Gln Phe  Ile Ile Met Tyr Ser  Leu Asp Gly Lys Lys  Trp Gln Thr
    1190                 1195                1200

Tyr Arg  Gly Asn Ser Thr Gly  Thr Leu Met Val Phe  Phe Gly Asn
    1205                 1210                1215

Val Asp  Ser Ser Gly Ile Lys  His Asn Ile Phe Asn  Pro Pro Ile
    1220                 1225                1230

Ile Ala  Arg Tyr Ile Arg Leu  His Pro Thr His Tyr  Ser Ile Arg
    1235                 1240                1245

Ser Thr  Leu Arg Met Glu Leu  Met Gly Cys Asp Leu  Asn Ser Cys
    1250                 1255                1260

Ser Met  Pro Leu Gly Met Glu  Ser Lys Ala Ile Ser  Asp Ala Gln
    1265                 1270                1275

Ile Thr  Ala Ser Ser Tyr Phe  Thr Asn Met Phe Ala  Thr Trp Ser
    1280                 1285                1290

Pro Ser  Lys Ala Arg Leu His  Leu Gln Gly Arg Ser  Asn Ala Trp
```

```
    1295                1300                1305

Arg Pro  Gln Val Asn Asn Pro  Lys Glu Trp Leu Gln  Val Asp Phe
    1310                1315                1320

Gln Lys  Thr Met Lys Val Thr  Gly Val Thr Thr Gln  Gly Val Lys
    1325                1330                1335

Ser Leu  Leu Thr Ser Met Tyr  Val Lys Glu Phe Leu  Ile Ser Ser
    1340                1345                1350

Ser Gln  Asp Gly His Gln Trp  Thr Leu Phe Phe Gln  Asn Gly Lys
    1355                1360                1365

Val Lys  Val Phe Gln Gly Asn  Gln Asp Ser Phe Thr  Pro Val Val
    1370                1375                1380

Asn Ser  Leu Asp Pro Pro Leu  Leu Thr Arg Tyr Leu  Arg Ile His
    1385                1390                1395

Pro Gln  Ser Trp Val His Gln  Ile Ala Leu Arg Met  Glu Val Leu
    1400                1405                1410

Gly Cys  Glu Ala Gln Asp Leu  Tyr
    1415                1420


<210> SEQ ID NO 2
<211> LENGTH: 1392
<212> TYPE: PRT
<213> ORGANISM: Artificial Sequence
<220> FEATURE:
<223> OTHER INFORMATION: Mature FVIII Del745-1685

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
```

-continued

```
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655
```

```
Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Gln Ser Pro Arg Ser Phe Gln
            740                 745                 750

Lys Lys Thr Arg His Tyr Phe Ile Ala Ala Val Glu Arg Leu Trp Asp
        755                 760                 765

Tyr Gly Met Ser Ser Ser Pro His Val Leu Arg Asn Arg Ala Gln Ser
    770                 775                 780

Gly Ser Val Pro Gln Phe Lys Lys Val Val Phe Gln Glu Phe Thr Asp
785                 790                 795                 800

Gly Ser Phe Thr Gln Pro Leu Tyr Arg Gly Glu Leu Asn Glu His Leu
                805                 810                 815

Gly Leu Leu Gly Pro Tyr Ile Arg Ala Glu Val Glu Asp Asn Ile Met
            820                 825                 830

Val Thr Phe Arg Asn Gln Ala Ser Arg Pro Tyr Ser Phe Tyr Ser Ser
        835                 840                 845

Leu Ile Ser Tyr Glu Glu Asp Gln Arg Gln Gly Ala Glu Pro Arg Lys
    850                 855                 860

Asn Phe Val Lys Pro Asn Glu Thr Lys Thr Tyr Phe Trp Lys Val Gln
865                 870                 875                 880

His His Met Ala Pro Thr Lys Asp Glu Phe Asp Cys Lys Ala Trp Ala
                885                 890                 895

Tyr Phe Ser Asp Val Asp Leu Glu Lys Asp Val His Ser Gly Leu Ile
            900                 905                 910

Gly Pro Leu Leu Val Cys His Thr Asn Thr Leu Asn Pro Ala His Gly
        915                 920                 925

Arg Gln Val Thr Val Gln Glu Phe Ala Leu Phe Phe Thr Ile Phe Asp
    930                 935                 940

Glu Thr Lys Ser Trp Tyr Phe Thr Glu Asn Met Glu Arg Asn Cys Arg
945                 950                 955                 960

Ala Pro Cys Asn Ile Gln Met Glu Asp Pro Thr Phe Lys Glu Asn Tyr
                965                 970                 975

Arg Phe His Ala Ile Asn Gly Tyr Ile Met Asp Thr Leu Pro Gly Leu
            980                 985                 990

Val Met Ala Gln Asp Gln Arg Ile  Arg Trp Tyr Leu Leu  Ser Met Gly
        995                 1000                1005

Ser Asn  Glu Asn Ile His Ser  Ile His Phe Ser Gly  His Val Phe
    1010                1015                1020

Thr Val  Arg Lys Lys Glu Glu  Tyr Lys Met Ala Leu  Tyr Asn Leu
    1025                1030                1035

Tyr Pro  Gly Val Phe Glu Thr  Val Glu Met Leu Pro  Ser Lys Ala
    1040                1045                1050

Gly Ile  Trp Arg Val Glu Cys  Leu Ile Gly Glu His  Leu His Ala
    1055                1060                1065
```

```
Gly Met  Ser Thr Leu Phe Leu  Val Tyr Ser Asn Lys  Cys Gln Thr
    1070                 1075                 1080

Pro Leu  Gly Met Ala Ser Gly  His Ile Arg Asp Phe  Gln Ile Thr
    1085                 1090                 1095

Ala Ser  Gly Gln Tyr Gly Gln  Trp Ala Pro Lys Leu  Ala Arg Leu
    1100                 1105                 1110

His Tyr  Ser Gly Ser Ile Asn  Ala Trp Ser Thr Lys  Glu Pro Phe
    1115                 1120                 1125

Ser Trp  Ile Lys Val Asp Leu  Leu Ala Pro Met Ile  Ile His Gly
    1130                 1135                 1140

Ile Lys  Thr Gln Gly Ala Arg  Gln Lys Phe Ser Ser  Leu Tyr Ile
    1145                 1150                 1155

Ser Gln  Phe Ile Ile Met Tyr  Ser Leu Asp Gly Lys  Lys Trp Gln
    1160                 1165                 1170

Thr Tyr  Arg Gly Asn Ser Thr  Gly Thr Leu Met Val  Phe Phe Gly
    1175                 1180                 1185

Asn Val  Asp Ser Ser Gly Ile  Lys His Asn Ile Phe  Asn Pro Pro
    1190                 1195                 1200

Ile Ile  Ala Arg Tyr Ile Arg  Leu His Pro Thr His  Tyr Ser Ile
    1205                 1210                 1215

Arg Ser  Thr Leu Arg Met Glu  Leu Met Gly Cys Asp  Leu Asn Ser
    1220                 1225                 1230

Cys Ser  Met Pro Leu Gly Met  Glu Ser Lys Ala Ile  Ser Asp Ala
    1235                 1240                 1245

Gln Ile  Thr Ala Ser Ser Tyr  Phe Thr Asn Met Phe  Ala Thr Trp
    1250                 1255                 1260

Ser Pro  Ser Lys Ala Arg Leu  His Leu Gln Gly Arg  Ser Asn Ala
    1265                 1270                 1275

Trp Arg  Pro Gln Val Asn Asn  Pro Lys Glu Trp Leu  Gln Val Asp
    1280                 1285                 1290

Phe Gln  Lys Thr Met Lys Val  Thr Gly Val Thr Thr  Gln Gly Val
    1295                 1300                 1305

Lys Ser  Leu Leu Thr Ser Met  Tyr Val Lys Glu Phe  Leu Ile Ser
    1310                 1315                 1320

Ser Ser  Gln Asp Gly His Gln  Trp Thr Leu Phe Phe  Gln Asn Gly
    1325                 1330                 1335

Lys Val  Lys Val Phe Gln Gly  Asn Gln Asp Ser Phe  Thr Pro Val
    1340                 1345                 1350

Val Asn  Ser Leu Asp Pro Pro  Leu Leu Thr Arg Tyr  Leu Arg Ile
    1355                 1360                 1365

His Pro  Gln Ser Trp Val His  Gln Ile Ala Leu Arg  Met Glu Val
    1370                 1375                 1380

Leu Gly  Cys Glu Ala Gln Asp  Leu Tyr
    1385                 1390
```

```
<210> SEQ ID NO 3
<211> LENGTH: 19
<212> TYPE: PRT
<213> ORGANISM: Artificial Sequence
<220> FEATURE:
<223> OTHER INFORMATION: Signal Peptide

<400> SEQUENCE: 3

Met Gln Ile Glu Leu Ser Thr Cys Phe Phe Leu Cys Leu Leu Arg Phe
1               5                   10                  15
```

Cys Phe Ser

<210> SEQ ID NO 4
<211> LENGTH: 2332
<212> TYPE: PRT
<213> ORGANISM: Homo sapiens

<400> SEQUENCE: 4

Ala Thr Arg Arg Tyr Tyr Leu Gly Ala Val Glu Leu Ser Trp Asp Tyr
1 5 10 15

Met Gln Ser Asp Leu Gly Glu Leu Pro Val Asp Ala Arg Phe Pro Pro
20 25 30

Arg Val Pro Lys Ser Phe Pro Phe Asn Thr Ser Val Val Tyr Lys Lys
35 40 45

Thr Leu Phe Val Glu Phe Thr Asp His Leu Phe Asn Ile Ala Lys Pro
50 55 60

Arg Pro Pro Trp Met Gly Leu Leu Gly Pro Thr Ile Gln Ala Glu Val
65 70 75 80

Tyr Asp Thr Val Val Ile Thr Leu Lys Asn Met Ala Ser His Pro Val
85 90 95

Ser Leu His Ala Val Gly Val Ser Tyr Trp Lys Ala Ser Glu Gly Ala
100 105 110

Glu Tyr Asp Asp Gln Thr Ser Gln Arg Glu Lys Glu Asp Asp Lys Val
115 120 125

Phe Pro Gly Gly Ser His Thr Tyr Val Trp Gln Val Leu Lys Glu Asn
130 135 140

Gly Pro Met Ala Ser Asp Pro Leu Cys Leu Thr Tyr Ser Tyr Leu Ser
145 150 155 160

His Val Asp Leu Val Lys Asp Leu Asn Ser Gly Leu Ile Gly Ala Leu
165 170 175

Leu Val Cys Arg Glu Gly Ser Leu Ala Lys Glu Lys Thr Gln Thr Leu
180 185 190

His Lys Phe Ile Leu Leu Phe Ala Val Phe Asp Glu Gly Lys Ser Trp
195 200 205

His Ser Glu Thr Lys Asn Ser Leu Met Gln Asp Arg Asp Ala Ala Ser
210 215 220

Ala Arg Ala Trp Pro Lys Met His Thr Val Asn Gly Tyr Val Asn Arg
225 230 235 240

Ser Leu Pro Gly Leu Ile Gly Cys His Arg Lys Ser Val Tyr Trp His
245 250 255

Val Ile Gly Met Gly Thr Thr Pro Glu Val His Ser Ile Phe Leu Glu
260 265 270

Gly His Thr Phe Leu Val Arg Asn His Arg Gln Ala Ser Leu Glu Ile
275 280 285

Ser Pro Ile Thr Phe Leu Thr Ala Gln Thr Leu Leu Met Asp Leu Gly
290 295 300

Gln Phe Leu Leu Phe Cys His Ile Ser Ser His Gln His Asp Gly Met
305 310 315 320

Glu Ala Tyr Val Lys Val Asp Ser Cys Pro Glu Glu Pro Gln Leu Arg
325 330 335

Met Lys Asn Asn Glu Glu Ala Glu Asp Tyr Asp Asp Asp Leu Thr Asp
340 345 350

Ser Glu Met Asp Val Val Arg Phe Asp Asp Asp Asn Ser Pro Ser Phe
355 360 365

```
Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
```

```
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr  Asn Lys Thr Ser Asn  Asn Ser Ala
        995                 1000                1005

Thr Asn  Arg Lys Thr His Ile  Asp Gly Pro Ser Leu  Leu Ile Glu
    1010                1015                1020

Asn Ser  Pro Ser Val Trp Gln  Asn Ile Leu Glu Ser  Asp Thr Glu
    1025                1030                1035

Phe Lys  Lys Val Thr Pro Leu  Ile His Asp Arg Met  Leu Met Asp
    1040                1045                1050

Lys Asn  Ala Thr Ala Leu Arg  Leu Asn His Met Ser  Asn Lys Thr
    1055                1060                1065

Thr Ser  Ser Lys Asn Met Glu  Met Val Gln Gln Lys  Lys Glu Gly
    1070                1075                1080

Pro Ile  Pro Pro Asp Ala Gln  Asn Pro Asp Met Ser  Phe Phe Lys
    1085                1090                1095

Met Leu  Phe Leu Pro Glu Ser  Ala Arg Trp Ile Gln  Arg Thr His
    1100                1105                1110

Gly Lys  Asn Ser Leu Asn Ser  Gly Gln Gly Pro Ser  Pro Lys Gln
    1115                1120                1125

Leu Val  Ser Leu Gly Pro Glu  Lys Ser Val Glu Gly  Gln Asn Phe
    1130                1135                1140

Leu Ser  Glu Lys Asn Lys Val  Val Val Gly Lys Gly  Glu Phe Thr
    1145                1150                1155

Lys Asp  Val Gly Leu Lys Glu  Met Val Phe Pro Ser  Ser Arg Asn
    1160                1165                1170

Leu Phe  Leu Thr Asn Leu Asp  Asn Leu His Glu Asn  Asn Thr His
    1175                1180                1185

Asn Gln  Glu Lys Lys Ile Gln  Glu Glu Ile Glu Lys  Lys Glu Thr
    1190                1195                1200
```

```
Leu Ile  Gln Glu Asn Val Val  Leu Pro Gln Ile His  Thr Val Thr
    1205                 1210                 1215

Gly Thr  Lys Asn Phe Met Lys  Asn Leu Phe Leu Leu  Ser Thr Arg
    1220                 1225                 1230

Gln Asn  Val Glu Gly Ser Tyr  Asp Gly Ala Tyr Ala  Pro Val Leu
    1235                 1240                 1245

Gln Asp  Phe Arg Ser Leu Asn  Asp Ser Thr Asn Arg  Thr Lys Lys
    1250                 1255                 1260

His Thr  Ala His Phe Ser Lys  Lys Gly Glu Glu Glu  Asn Leu Glu
    1265                 1270                 1275

Gly Leu  Gly Asn Gln Thr Lys  Gln Ile Val Glu Lys  Tyr Ala Cys
    1280                 1285                 1290

Thr Thr  Arg Ile Ser Pro Asn  Thr Ser Gln Gln Asn  Phe Val Thr
    1295                 1300                 1305

Gln Arg  Ser Lys Arg Ala Leu  Lys Gln Phe Arg Leu  Pro Leu Glu
    1310                 1315                 1320

Glu Thr  Glu Leu Glu Lys Arg  Ile Ile Val Asp Asp  Thr Ser Thr
    1325                 1330                 1335

Gln Trp  Ser Lys Asn Met Lys  His Leu Thr Pro Ser  Thr Leu Thr
    1340                 1345                 1350

Gln Ile  Asp Tyr Asn Glu Lys  Glu Lys Gly Ala Ile  Thr Gln Ser
    1355                 1360                 1365

Pro Leu  Ser Asp Cys Leu Thr  Arg Ser His Ser Ile  Pro Gln Ala
    1370                 1375                 1380

Asn Arg  Ser Pro Leu Pro Ile  Ala Lys Val Ser Ser  Phe Pro Ser
    1385                 1390                 1395

Ile Arg  Pro Ile Tyr Leu Thr  Arg Val Leu Phe Gln  Asp Asn Ser
    1400                 1405                 1410

Ser His  Leu Pro Ala Ala Ser  Tyr Arg Lys Lys Asp  Ser Gly Val
    1415                 1420                 1425

Gln Glu  Ser Ser His Phe Leu  Gln Gly Ala Lys Lys  Asn Asn Leu
    1430                 1435                 1440

Ser Leu  Ala Ile Leu Thr Leu  Glu Met Thr Gly Asp  Gln Arg Glu
    1445                 1450                 1455

Val Gly  Ser Leu Gly Thr Ser  Ala Thr Asn Ser Val  Thr Tyr Lys
    1460                 1465                 1470

Lys Val  Glu Asn Thr Val Leu  Pro Lys Pro Asp Leu  Pro Lys Thr
    1475                 1480                 1485

Ser Gly  Lys Val Glu Leu Leu  Pro Lys Val His Ile  Tyr Gln Lys
    1490                 1495                 1500

Asp Leu  Phe Pro Thr Glu Thr  Ser Asn Gly Ser Pro  Gly His Leu
    1505                 1510                 1515

Asp Leu  Val Glu Gly Ser Leu  Leu Gln Gly Thr Glu  Gly Ala Ile
    1520                 1525                 1530

Lys Trp  Asn Glu Ala Asn Arg  Pro Gly Lys Val Pro  Phe Leu Arg
    1535                 1540                 1545

Val Ala  Thr Glu Ser Ser Ala  Lys Thr Pro Ser Lys  Leu Leu Asp
    1550                 1555                 1560

Pro Leu  Ala Trp Asp Asn His  Tyr Gly Thr Gln Ile  Pro Lys Glu
    1565                 1570                 1575

Glu Trp  Lys Ser Gln Glu Lys  Ser Pro Glu Lys Thr  Ala Phe Lys
    1580                 1585                 1590
```

```
Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980

Glu Thr Val Glu Met Leu Pro Ser Lys Ala Gly Ile Trp Arg Val
```

```
    1985                1990                1995

Glu Cys  Leu Ile Gly Glu His  Leu His Ala Gly Met  Ser Thr Leu
    2000                2005                2010

Phe Leu  Val Tyr Ser Asn Lys  Cys Gln Thr Pro Leu  Gly Met Ala
    2015                2020                2025

Ser Gly  His Ile Arg Asp Phe  Gln Ile Thr Ala Ser  Gly Gln Tyr
    2030                2035                2040

Gly Gln  Trp Ala Pro Lys Leu  Ala Arg Leu His Tyr  Ser Gly Ser
    2045                2050                2055

Ile Asn  Ala Trp Ser Thr Lys  Glu Pro Phe Ser Trp  Ile Lys Val
    2060                2065                2070

Asp Leu  Leu Ala Pro Met Ile  Ile His Gly Ile Lys  Thr Gln Gly
    2075                2080                2085

Ala Arg  Gln Lys Phe Ser Ser  Leu Tyr Ile Ser Gln  Phe Ile Ile
    2090                2095                2100

Met Tyr  Ser Leu Asp Gly Lys  Lys Trp Gln Thr Tyr  Arg Gly Asn
    2105                2110                2115

Ser Thr  Gly Thr Leu Met Val  Phe Phe Gly Asn Val  Asp Ser Ser
    2120                2125                2130

Gly Ile  Lys His Asn Ile Phe  Asn Pro Pro Ile Ile  Ala Arg Tyr
    2135                2140                2145

Ile Arg  Leu His Pro Thr His  Tyr Ser Ile Arg Ser  Thr Leu Arg
    2150                2155                2160

Met Glu  Leu Met Gly Cys Asp  Leu Asn Ser Cys Ser  Met Pro Leu
    2165                2170                2175

Gly Met  Glu Ser Lys Ala Ile  Ser Asp Ala Gln Ile  Thr Ala Ser
    2180                2185                2190

Ser Tyr  Phe Thr Asn Met Phe  Ala Thr Trp Ser Pro  Ser Lys Ala
    2195                2200                2205

Arg Leu  His Leu Gln Gly Arg  Ser Asn Ala Trp Arg  Pro Gln Val
    2210                2215                2220

Asn Asn  Pro Lys Glu Trp Leu  Gln Val Asp Phe Gln  Lys Thr Met
    2225                2230                2235

Lys Val  Thr Gly Val Thr Thr  Gln Gly Val Lys Ser  Leu Leu Thr
    2240                2245                2250

Ser Met  Tyr Val Lys Glu Phe  Leu Ile Ser Ser Ser  Gln Asp Gly
    2255                2260                2265

His Gln  Trp Thr Leu Phe Phe  Gln Asn Gly Lys Val  Lys Val Phe
    2270                2275                2280

Gln Gly  Asn Gln Asp Ser Phe  Thr Pro Val Val Asn  Ser Leu Asp
    2285                2290                2295

Pro Pro  Leu Leu Thr Arg Tyr  Leu Arg Ile His Pro  Gln Ser Trp
    2300                2305                2310

Val His  Gln Ile Ala Leu Arg  Met Glu Val Leu Gly  Cys Glu Ala
    2315                2320                2325

Gln Asp  Leu Tyr
    2330


<210> SEQ ID NO 5
<211> LENGTH: 7053
<212> TYPE: DNA
<213> ORGANISM: Homo sapiens

<400> SEQUENCE: 5
```

```
atgcaaatag agctctccac ctgcttcttt ctgtgccttt tgcgattctg ctttagtgcc     60
accagaagat actacctggg tgcagtggaa ctgtcatggg actatatgca aagtgatctc    120
ggtgagctgc ctgtggacgc aagatttcct cctagagtgc caaaatcttt tccattcaac    180
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact tttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaga attcaagaca ccctagcact aggcaaaagc aatttaatgc caccacaatt   2340
ccagaaaatg acatagagaa gactgaccct tggtttgcac acagaacacc tatgcctaaa   2400
```

```
atacaaaatg tctcctctag tgatttgttg atgctcttgc gacagagtcc tactccacat   2460
gggctatcct tatctgatct ccaagaagcc aaatatgaga ctttttctga tgatccatca   2520
cctggagcaa tagacagtaa taacagcctg tctgaaatga cacacttcag gccacagctc   2580
catcacagtg gggacatggt atttacccct gagtcaggcc tccaattaag attaaatgag   2640
aaactgggga caactgcagc aacagagttg aagaaacttg atttcaaagt ttctagtaca   2700
tcaaataatc tgatttcaac aattccatca gacaatttgg cagcaggtac tgataataca   2760
agttccttag gacccccaag tatgccagtt cattatgata gtcaattaga taccactcta   2820
tttggcaaaa agtcatctcc ccttactgag tctggtggac ctctgagctt gagtgaagaa   2880
aataatgatt caaagttgtt agaatcaggt ttaatgaata gccaagaaag ttcatgggga   2940
aaaaatgtat cgtcaacaga gagtggtagg ttatttaaag ggaaaagagc tcatggacct   3000
gctttgttga ctaaagataa tgccttattc aaagttagca tctctttgtt aaagacaaac   3060
aaaacttcca ataattcagc aactaataga aagactcaca ttgatggccc atcattatta   3120
attgagaata gtccatcagt ctggcaaaat atattagaaa gtgacactga gtttaaaaaa   3180
gtgacacctt tgattcatga cagaatgctt atggacaaaa atgctacagc tttgaggcta   3240
aatcatatgt caaataaaac tacttcatca aaaaacatgg aaatggtcca acagaaaaaa   3300
gagggcccca ttccaccaga tgcacaaaat ccagatatgt cgttctttaa gatgctattc   3360
ttgccagaat cagcaaggtg gatacaaagg actcatggaa agaactctct gaactctggg   3420
caaggcccca gtccaaagca attagtatcc ttaggaccag aaaaatctgt ggaaggtcag   3480
aatttcttgt ctgagaaaaa caaagtggta gtaggaaagg gtgaatttac aaaggacgta   3540
ggactcaaag agatggtttt tccaagcagc agaaacctat ttcttactaa cttggataat   3600
ttacatgaaa ataatacaca caatcaagaa aaaaaaattc aggaagaaat agaaaagaag   3660
gaaacattaa tccaagagaa tgtagttttg cctcagatac atacagtgac tggcactaag   3720
aatttcatga agaacctttt cttactgagc actaggcaaa atgtagaagg ttcatatgac   3780
ggggcatatg ctccagtact tcaagatttt aggtcattaa atgattcaac aaatagaaca   3840
aagaaacaca cagctcattt ctcaaaaaaa ggggaggaag aaaacttgga aggcttggga   3900
aatcaaacca agcaaattgt agagaaatat gcatgcacca caaggatatc tcctaataca   3960
agccagcaga attttgtcac gcaacgtagt aagagagctt tgaaacaatt cagactccca   4020
ctagaagaaa cagaacttga aaaaaggata attgtggatg acacctcaac ccagtggtcc   4080
aaaaacatga aacatttgac cccgagcacc ctcacacaga tagactacaa tgagaaggag   4140
aaaggggcca ttactcagtc tcccttatca gattgcctta cgaggagtca tagcatccct   4200
caagcaaata gatctccatt acccattgca aaggtatcat catttccatc tattagacct   4260
atatatctga ccagggtcct attccaagac aactcttctc atcttccagc agcatcttat   4320
agaaagaaag attctggggt ccaagaaagc agtcatttct tacaaggagc caaaaaaaat   4380
aacctttctt tagccattct aaccttggag atgactggtg atcaaagaga ggttggctcc   4440
ctggggacaa gtgccacaaa ttcagtcaca tacaagaaag ttgagaacac tgttctcccg   4500
aaaccagact tgcccaaaac atctggcaaa gttgaattgc ttccaaaagt tcacatttat   4560
cagaaggacc tattccctac ggaaactagc aatgggtctc ctggccatct ggatctcgtg   4620
gaagggagcc ttcttcaggg aacagaggga gcgattaagt ggaatgaagc aaacagacct   4680
ggaaaagttc cctttctgag agtagcaaca gaaagctctg caaagactcc ctccaagcta   4740
```

-continued

```
ttggatcctc ttgcttggga taaccactat ggtactcaga taccaaaaga agagtggaaa   4800
tcccaagaga agtcaccaga aaaaacagct tttaagaaaa aggataccat tttgtccctg   4860
aacgcttgtg aaagcaatca tgcaatagca gcaataaatg agggacaaaa taagcccgaa   4920
atagaagtca cctgggcaaa gcaaggtagg actgaaaggc tgtgctctca aaacccacca   4980
gtcttgaaac gccatcaacg ggaaataact cgtactactc ttcagtcaga tcaagaggaa   5040
attgactatg atgataccat atcagttgaa atgaagaagg aagattttga catttatgat   5100
gaggatgaaa atcagagccc ccgcagcttt caaaagaaaa cacgacacta ttttattgct   5160
gcagtggaga ggctctggga ttatgggatg agtagctccc cacatgttct aagaaacagg   5220
gctcagagtg gcagtgtccc tcagttcaag aaagttgttt tccaggaatt tactgatggc   5280
tcctttactc agcccttata ccgtggagaa ctaaatgaac atttgggact cctggggcca   5340
tatataagag cagaagttga agataatatc atggtaactt tcagaaatca ggcctctcgt   5400
ccctattcct tctattctag ccttatttct tatgaggaag atcagaggca aggagcagaa   5460
cctagaaaaa actttgtcaa gcctaatgaa accaaaactt acttttggaa agtgcaacat   5520
catatggcac ccactaaaga tgagtttgac tgcaaagcct gggcttattt ctctgatgtt   5580
gacctggaaa aagatgtgca ctcaggcctg attggacccc ttctggtctg ccacactaac   5640
acactgaacc ctgctcatgg gagacaagtg acagtacagg aatttgctct gtttttcacc   5700
atctttgatg agaccaaaag ctggtacttc actgaaaata tggaaagaaa ctgcagggct   5760
ccctgcaata tccagatgga agatcccact tttaaagaga attatcgctt ccatgcaatc   5820
aatggctaca taatggatac actacctggc ttagtaatgg ctcaggatca aaggattcga   5880
tggtatctgc tcagcatggg cagcaatgaa aacatccatt ctattcattt cagtggacat   5940
gtgttcactg tacgaaaaaa agaggagtat aaaatggcac tgtacaatct ctatccaggt   6000
gtttttgaga cagtggaaat gttaccatcc aaagctggaa tttggcgggt ggaatgcctt   6060
attggcgagc atctacatgc tgggatgagc acactttttc tggtgtacag caataagtgt   6120
cagactcccc tgggaatggc ttctggacac attagagatt ttcagattac agcttcagga   6180
caatatggac agtgggcccc aaagctggcc agacttcatt attccggatc aatcaatgcc   6240
tggagcacca aggagccctt ttcttggatc aaggtggatc tgttggcacc aatgattatt   6300
cacggcatca agacccaggg tgcccgtcag aagttctcca gcctctacat ctctcagttt   6360
atcatcatgt atagtcttga tgggaagaag tggcagactt atcgaggaaa ttccactgga   6420
accttaatgg tcttctttgg caatgtggat tcatctggga taaaacacaa tatttttaac   6480
cctccaatta ttgctcgata catccgtttg cacccaactc attatagcat tcgcagcact   6540
cttcgcatgg agttgatggg ctgtgattta aatagttgca gcatgccatt gggaatggag   6600
agtaaagcaa tatcagatgc acagattact gcttcatcct actttaccaa tatgtttgcc   6660
acctggtctc cttcaaaagc tcgacttcac ctccaaggga ggagtaatgc ctggagacct   6720
caggtgaata atccaaaaga gtggctgcaa gtggacttcc agaagacaat gaaagtcaca   6780
ggagtaacta ctcagggagt aaaatctctg cttaccagca tgtatgtgaa ggagttcctc   6840
atctccagca gtcaagatgg ccatcagtgg actctctttt ttcagaatgg caaagtaaag   6900
gtttttcagg gaaatcaaga ctccttcaca cctgtggtga actctctaga cccaccgtta   6960
ctgactcgct accttcgaat tcacccccag agttgggtgc accagattgc cctgaggatg   7020
gaggttctgg gctgcgaggc acaggacctc tac                                7053
```

```
<210> SEQ ID NO 6
<211> LENGTH: 1438
<212> TYPE: PRT
<213> ORGANISM: Artificial Sequence
<220> FEATURE:
<223> OTHER INFORMATION: BDD FVIII

<400> SEQUENCE: 6

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
```

```
370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800
```

```
Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn  Met Glu Arg Asn Cys  Arg Ala Pro
        995                 1000                1005

Cys Asn  Ile Gln Met Glu Asp  Pro Thr Phe Lys Glu  Asn Tyr Arg
    1010                1015                1020

Phe His  Ala Ile Asn Gly Tyr  Ile Met Asp Thr Leu  Pro Gly Leu
    1025                1030                1035

Val Met  Ala Gln Asp Gln Arg  Ile Arg Trp Tyr Leu  Leu Ser Met
    1040                1045                1050

Gly Ser  Asn Glu Asn Ile His  Ser Ile His Phe Ser  Gly His Val
    1055                1060                1065

Phe Thr  Val Arg Lys Lys Glu  Glu Tyr Lys Met Ala  Leu Tyr Asn
    1070                1075                1080

Leu Tyr  Pro Gly Val Phe Glu  Thr Val Glu Met Leu  Pro Ser Lys
    1085                1090                1095

Ala Gly  Ile Trp Arg Val Glu  Cys Leu Ile Gly Glu  His Leu His
    1100                1105                1110

Ala Gly  Met Ser Thr Leu Phe  Leu Val Tyr Ser Asn  Lys Cys Gln
    1115                1120                1125

Thr Pro  Leu Gly Met Ala Ser  Gly His Ile Arg Asp  Phe Gln Ile
    1130                1135                1140

Thr Ala  Ser Gly Gln Tyr Gly  Gln Trp Ala Pro Lys  Leu Ala Arg
    1145                1150                1155

Leu His  Tyr Ser Gly Ser Ile  Asn Ala Trp Ser Thr  Lys Glu Pro
    1160                1165                1170

Phe Ser  Trp Ile Lys Val Asp  Leu Leu Ala Pro Met  Ile Ile His
    1175                1180                1185

Gly Ile  Lys Thr Gln Gly Ala  Arg Gln Lys Phe Ser  Ser Leu Tyr
    1190                1195                1200
```

```
Ile Ser  Gln Phe Ile Ile Met  Tyr Ser Leu Asp Gly  Lys Lys Trp
    1205                 1210                 1215

Gln Thr  Tyr Arg Gly Asn Ser  Thr Gly Thr Leu Met  Val Phe Phe
    1220                 1225                 1230

Gly Asn  Val Asp Ser Ser Gly  Ile Lys His Asn Ile  Phe Asn Pro
    1235                 1240                 1245

Pro Ile  Ile Ala Arg Tyr Ile  Arg Leu His Pro Thr  His Tyr Ser
    1250                 1255                 1260

Ile Arg  Ser Thr Leu Arg Met  Glu Leu Met Gly Cys  Asp Leu Asn
    1265                 1270                 1275

Ser Cys  Ser Met Pro Leu Gly  Met Glu Ser Lys Ala  Ile Ser Asp
    1280                 1285                 1290

Ala Gln  Ile Thr Ala Ser Ser  Tyr Phe Thr Asn Met  Phe Ala Thr
    1295                 1300                 1305

Trp Ser  Pro Ser Lys Ala Arg  Leu His Leu Gln Gly  Arg Ser Asn
    1310                 1315                 1320

Ala Trp  Arg Pro Gln Val Asn  Asn Pro Lys Glu Trp  Leu Gln Val
    1325                 1330                 1335

Asp Phe  Gln Lys Thr Met Lys  Val Thr Gly Val Thr  Thr Gln Gly
    1340                 1345                 1350

Val Lys  Ser Leu Leu Thr Ser  Met Tyr Val Lys Glu  Phe Leu Ile
    1355                 1360                 1365

Ser Ser  Ser Gln Asp Gly His  Gln Trp Thr Leu Phe  Phe Gln Asn
    1370                 1375                 1380

Gly Lys  Val Lys Val Phe Gln  Gly Asn Gln Asp Ser  Phe Thr Pro
    1385                 1390                 1395

Val Val  Asn Ser Leu Asp Pro  Pro Leu Leu Thr Arg  Tyr Leu Arg
    1400                 1405                 1410

Ile His  Pro Gln Ser Trp Val  His Gln Ile Ala Leu  Arg Met Glu
    1415                 1420                 1425

Val Leu  Gly Cys Glu Ala Gln  Asp Leu Tyr
    1430                 1435
```

<210> SEQ ID NO 7
<211> LENGTH: 4371
<212> TYPE: DNA
<213> ORGANISM: Artificial Sequence
<220> FEATURE:
<223> OTHER INFORMATION: BDD FVIII

<400> SEQUENCE: 7

```
atgcaaatag agctctccac ctgcttcttt ctgtgccttt tgcgattctg ctttagtgcc     60

accagaagat actacctggg tgcagtggaa ctgtcatggg actatatgca aagtgatctc    120

ggtgagctgc ctgtggacgc aagatttcct cctagagtgc caaaatcttt tccattcaac    180

acctcagtcg tgtacaaaaa gactctgttt gtagaattca cggatcacct tttcaacatc    240

gctaagccaa ggccaccctg gatgggtctg ctaggtccta ccatccaggc tgaggtttat    300

gatacagtgg tcattacact taagaacatg gcttcccatc ctgtcagtct tcatgctgtt    360

ggtgtatcct actggaaagc ttctgaggga gctgaatatg atgatcagac cagtcaaagg    420

gagaaagaag atgataaagt cttccctggt ggaagccata catatgtctg gcaggtcctg    480

aaagagaatg gtccaatggc ctctgaccca ctgtgcctta cctactcata tctttctcat    540

gtggacctgg taaaagactt gaattcaggc ctcattggag ccctactagt atgtagagaa    600

gggagtctgg ccaaggaaaa gacacagacc ttgcacaaat ttatactact ttttgctgta    660
```

```
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
```

```
tttgctctgt ttttcaccat ctttgatgag accaaaagct ggtacttcac tgaaaatatg   3060

gaaagaaact gcagggctcc ctgcaatatc cagatggaag atcccacttt taaagagaat   3120

tatcgcttcc atgcaatcaa tggctacata atggatacac tacctggctt agtaatggct   3180

caggatcaaa ggattcgatg gtatctgctc agcatgggca gcaatgaaaa catccattct   3240

attcatttca gtggacatgt gttcactgta cgaaaaaaag aggagtataa aatggcactg   3300

tacaatctct atccaggtgt ttttgagaca gtggaaatgt taccatccaa agctggaatt   3360

tggcgggtgg aatgccttat tggcgagcat ctacatgctg ggatgagcac actttttctg   3420

gtgtacagca ataagtgtca gactcccctg ggaatggctt ctggacacat tagagatttt   3480

cagattacag cttcaggaca atatggacag tgggccccaa agctggccag acttcattat   3540

tccggatcaa tcaatgcctg gagcaccaag gagccctttt cttggatcaa ggtggatctg   3600

ttggcaccaa tgattattca cggcatcaag acccagggtg cccgtcagaa gttctccagc   3660

ctctacatct ctcagtttat catcatgtat agtcttgatg ggaagaagtg gcagacttat   3720

cgaggaaatt ccactggaac cttaatggtc ttctttggca atgtggattc atctgggata   3780

aaacacaata tttttaaccc tccaattatt gctcgataca tccgtttgca cccaactcat   3840

tatagcattc gcagcactct tcgcatggag ttgatgggct gtgatttaaa tagttgcagc   3900

atgccattgg gaatggagag taaagcaata tcagatgcac agattactgc ttcatcctac   3960

tttaccaata tgtttgccac ctggtctcct tcaaaagctc gacttcacct ccaagggagg   4020

agtaatgcct ggagacctca ggtgaataat ccaaaagagt ggctgcaagt ggacttccag   4080

aagacaatga aagtcacagg agtaactact cagggagtaa aatctctgct taccagcatg   4140

tatgtgaagg agttcctcat ctccagcagt caagatggcc atcagtggac tctctttttt   4200

cagaatggca aagtaaaggt ttttcaggga aatcaagact ccttcacacc tgtggtgaac   4260

tctctagacc caccgttact gactcgctac cttcgaattc acccccagag ttgggtgcac   4320

cagattgccc tgaggatgga ggttctgggc tgcgaggcac aggacctcta c            4371
```

<210> SEQ ID NO 8
<211> LENGTH: 25
<212> TYPE: PRT
<213> ORGANISM: Artificial Sequence
<220> FEATURE:
<223> OTHER INFORMATION: Cleavage site

<400> SEQUENCE: 8

```
Thr Leu Asp Pro Arg Ser Phe Leu Leu Arg Asn Pro Asn Asp Lys Tyr
1               5                   10                  15

Glu Pro Phe Trp Glu Asp Glu Glu Lys
            20                  25
```

<210> SEQ ID NO 9
<211> LENGTH: 4
<212> TYPE: PRT
<213> ORGANISM: Artificial Sequence
<220> FEATURE:
<223> OTHER INFORMATION: Cleavage site

<400> SEQUENCE: 9

```
Arg Arg Arg Arg
1
```

<210> SEQ ID NO 10
<211> LENGTH: 6
<212> TYPE: PRT

<213> ORGANISM: Artificial Sequence
<220> FEATURE:
<223> OTHER INFORMATION: Cleavage site

<400> SEQUENCE: 10

Arg Lys Arg Arg Lys Arg
1               5

<210> SEQ ID NO 11
<211> LENGTH: 5
<212> TYPE: PRT
<213> ORGANISM: Artificial Sequence
<220> FEATURE:
<223> OTHER INFORMATION: Cleavage site

<400> SEQUENCE: 11

Arg Arg Arg Arg Ser
1               5

<210> SEQ ID NO 12
<211> LENGTH: 1438
<212> TYPE: PRT
<213> ORGANISM: Artificial Sequence
<220> FEATURE:
<223> OTHER INFORMATION: Mature FVIII Y1680F

<400> SEQUENCE: 12

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

```
Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670
```

```
Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Phe Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn  Met Glu Arg Asn Cys  Arg Ala Pro
        995                 1000                1005

Cys Asn  Ile Gln Met Glu Asp  Pro Thr Phe Lys Glu  Asn Tyr Arg
    1010                1015                1020

Phe His  Ala Ile Asn Gly Tyr  Ile Met Asp Thr Leu  Pro Gly Leu
    1025                1030                1035

Val Met  Ala Gln Asp Gln Arg  Ile Arg Trp Tyr Leu  Leu Ser Met
    1040                1045                1050

Gly Ser  Asn Glu Asn Ile His  Ser Ile His Phe Ser  Gly His Val
    1055                1060                1065

Phe Thr  Val Arg Lys Lys Glu  Glu Tyr Lys Met Ala  Leu Tyr Asn
    1070                1075                1080

Leu Tyr  Pro Gly Val Phe Glu  Thr Val Glu Met Leu  Pro Ser Lys
```

```
    1085                1090                1095

Ala Gly  Ile Trp Arg Val Glu  Cys Leu Ile Gly Glu  His Leu His
    1100                1105                1110

Ala Gly  Met Ser Thr Leu Phe  Leu Val Tyr Ser Asn  Lys Cys Gln
    1115                1120                1125

Thr Pro  Leu Gly Met Ala Ser  Gly His Ile Arg Asp  Phe Gln Ile
    1130                1135                1140

Thr Ala  Ser Gly Gln Tyr Gly  Gln Trp Ala Pro Lys  Leu Ala Arg
    1145                1150                1155

Leu His  Tyr Ser Gly Ser Ile  Asn Ala Trp Ser Thr  Lys Glu Pro
    1160                1165                1170

Phe Ser  Trp Ile Lys Val Asp  Leu Leu Ala Pro Met  Ile Ile His
    1175                1180                1185

Gly Ile  Lys Thr Gln Gly Ala  Arg Gln Lys Phe Ser  Ser Leu Tyr
    1190                1195                1200

Ile Ser  Gln Phe Ile Ile Met  Tyr Ser Leu Asp Gly  Lys Lys Trp
    1205                1210                1215

Gln Thr  Tyr Arg Gly Asn Ser  Thr Gly Thr Leu Met  Val Phe Phe
    1220                1225                1230

Gly Asn  Val Asp Ser Ser Gly  Ile Lys His Asn Ile  Phe Asn Pro
    1235                1240                1245

Pro Ile  Ile Ala Arg Tyr Ile  Arg Leu His Pro Thr  His Tyr Ser
    1250                1255                1260

Ile Arg  Ser Thr Leu Arg Met  Glu Leu Met Gly Cys  Asp Leu Asn
    1265                1270                1275

Ser Cys  Ser Met Pro Leu Gly  Met Glu Ser Lys Ala  Ile Ser Asp
    1280                1285                1290

Ala Gln  Ile Thr Ala Ser Ser  Tyr Phe Thr Asn Met  Phe Ala Thr
    1295                1300                1305

Trp Ser  Pro Ser Lys Ala Arg  Leu His Leu Gln Gly  Arg Ser Asn
    1310                1315                1320

Ala Trp  Arg Pro Gln Val Asn  Asn Pro Lys Glu Trp  Leu Gln Val
    1325                1330                1335

Asp Phe  Gln Lys Thr Met Lys  Val Thr Gly Val Thr  Thr Gln Gly
    1340                1345                1350

Val Lys  Ser Leu Leu Thr Ser  Met Tyr Val Lys Glu  Phe Leu Ile
    1355                1360                1365

Ser Ser  Ser Gln Asp Gly His  Gln Trp Thr Leu Phe  Phe Gln Asn
    1370                1375                1380

Gly Lys  Val Lys Val Phe Gln  Gly Asn Gln Asp Ser  Phe Thr Pro
    1385                1390                1395

Val Val  Asn Ser Leu Asp Pro  Pro Leu Leu Thr Arg  Tyr Leu Arg
    1400                1405                1410

Ile His  Pro Gln Ser Trp Val  His Gln Ile Ala Leu  Arg Met Glu
    1415                1420                1425

Val Leu  Gly Cys Glu Ala Gln  Asp Leu Tyr
    1430                1435
```

<210> SEQ ID NO 13
<211> LENGTH: 1438
<212> TYPE: PRT
<213> ORGANISM: Artificial Sequence
<220> FEATURE:
<223> OTHER INFORMATION: Mature FVIII R1648A

<400> SEQUENCE: 13

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415
```

```
Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Ala Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830
```

-continued

```
Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn  Met Glu Arg Asn Cys  Arg Ala Pro
        995                 1000                1005

Cys Asn  Ile Gln Met Glu Asp  Pro Thr Phe Lys Glu  Asn Tyr Arg
    1010                1015                1020

Phe His  Ala Ile Asn Gly Tyr  Ile Met Asp Thr Leu  Pro Gly Leu
    1025                1030                1035

Val Met  Ala Gln Asp Gln Arg  Ile Arg Trp Tyr Leu  Leu Ser Met
    1040                1045                1050

Gly Ser  Asn Glu Asn Ile His  Ser Ile His Phe Ser  Gly His Val
    1055                1060                1065

Phe Thr  Val Arg Lys Lys Glu  Glu Tyr Lys Met Ala  Leu Tyr Asn
    1070                1075                1080

Leu Tyr  Pro Gly Val Phe Glu  Thr Val Glu Met Leu  Pro Ser Lys
    1085                1090                1095

Ala Gly  Ile Trp Arg Val Glu  Cys Leu Ile Gly Glu  His Leu His
    1100                1105                1110

Ala Gly  Met Ser Thr Leu Phe  Leu Val Tyr Ser Asn  Lys Cys Gln
    1115                1120                1125

Thr Pro  Leu Gly Met Ala Ser  Gly His Ile Arg Asp  Phe Gln Ile
    1130                1135                1140

Thr Ala  Ser Gly Gln Tyr Gly  Gln Trp Ala Pro Lys  Leu Ala Arg
    1145                1150                1155

Leu His  Tyr Ser Gly Ser Ile  Asn Ala Trp Ser Thr  Lys Glu Pro
    1160                1165                1170

Phe Ser  Trp Ile Lys Val Asp  Leu Leu Ala Pro Met  Ile Ile His
    1175                1180                1185

Gly Ile  Lys Thr Gln Gly Ala  Arg Gln Lys Phe Ser  Ser Leu Tyr
    1190                1195                1200

Ile Ser  Gln Phe Ile Ile Met  Tyr Ser Leu Asp Gly  Lys Lys Trp
    1205                1210                1215

Gln Thr  Tyr Arg Gly Asn Ser  Thr Gly Thr Leu Met  Val Phe Phe
    1220                1225                1230

Gly Asn  Val Asp Ser Ser Gly  Ile Lys His Asn Ile  Phe Asn Pro
```

```
    1235                1240                1245

Pro Ile  Ile Ala Arg Tyr Ile  Arg Leu His Pro Thr  His Tyr Ser
    1250                1255                1260

Ile Arg  Ser Thr Leu Arg Met  Glu Leu Met Gly Cys  Asp Leu Asn
    1265                1270                1275

Ser Cys  Ser Met Pro Leu Gly  Met Glu Ser Lys Ala  Ile Ser Asp
    1280                1285                1290

Ala Gln  Ile Thr Ala Ser Ser  Tyr Phe Thr Asn Met  Phe Ala Thr
    1295                1300                1305

Trp Ser  Pro Ser Lys Ala Arg  Leu His Leu Gln Gly  Arg Ser Asn
    1310                1315                1320

Ala Trp  Arg Pro Gln Val Asn  Asn Pro Lys Glu Trp  Leu Gln Val
    1325                1330                1335

Asp Phe  Gln Lys Thr Met Lys  Val Thr Gly Val Thr  Thr Gln Gly
    1340                1345                1350

Val Lys  Ser Leu Leu Thr Ser  Met Tyr Val Lys Glu  Phe Leu Ile
    1355                1360                1365

Ser Ser  Ser Gln Asp Gly His  Gln Trp Thr Leu Phe  Phe Gln Asn
    1370                1375                1380

Gly Lys  Val Lys Val Phe Gln  Gly Asn Gln Asp Ser  Phe Thr Pro
    1385                1390                1395

Val Val  Asn Ser Leu Asp Pro  Pro Leu Leu Thr Arg  Tyr Leu Arg
    1400                1405                1410

Ile His  Pro Gln Ser Trp Val  His Gln Ile Ala Leu  Arg Met Glu
    1415                1420                1425

Val Leu  Gly Cys Glu Ala Gln  Asp Leu Tyr
    1430                1435


<210> SEQ ID NO 14
<211> LENGTH: 1438
<212> TYPE: PRT
<213> ORGANISM: Artificial Sequence
<220> FEATURE:
<223> OTHER INFORMATION: Mature FVIII R1648A Y1680F

<400> SEQUENCE: 14

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
```

```
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575
```

```
Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Ala Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Phe Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990
```

```
Lys Ser Trp Tyr Phe Thr Glu Asn  Met Glu Arg Asn Cys  Arg Ala Pro
        995                 1000                 1005

Cys Asn  Ile Gln Met Glu Asp  Pro Thr Phe Lys Glu  Asn Tyr Arg
    1010                 1015                 1020

Phe His  Ala Ile Asn Gly Tyr  Ile Met Asp Thr Leu  Pro Gly Leu
    1025                 1030                 1035

Val Met  Ala Gln Asp Gln Arg  Ile Arg Trp Tyr Leu  Leu Ser Met
    1040                 1045                 1050

Gly Ser  Asn Glu Asn Ile His  Ser Ile His Phe Ser  Gly His Val
    1055                 1060                 1065

Phe Thr  Val Arg Lys Lys Glu  Glu Tyr Lys Met Ala  Leu Tyr Asn
    1070                 1075                 1080

Leu Tyr  Pro Gly Val Phe Glu  Thr Val Glu Met Leu  Pro Ser Lys
    1085                 1090                 1095

Ala Gly  Ile Trp Arg Val Glu  Cys Leu Ile Gly Glu  His Leu His
    1100                 1105                 1110

Ala Gly  Met Ser Thr Leu Phe  Leu Val Tyr Ser Asn  Lys Cys Gln
    1115                 1120                 1125

Thr Pro  Leu Gly Met Ala Ser  Gly His Ile Arg Asp  Phe Gln Ile
    1130                 1135                 1140

Thr Ala  Ser Gly Gln Tyr Gly  Gln Trp Ala Pro Lys  Leu Ala Arg
    1145                 1150                 1155

Leu His  Tyr Ser Gly Ser Ile  Asn Ala Trp Ser Thr  Lys Glu Pro
    1160                 1165                 1170

Phe Ser  Trp Ile Lys Val Asp  Leu Leu Ala Pro Met  Ile Ile His
    1175                 1180                 1185

Gly Ile  Lys Thr Gln Gly Ala  Arg Gln Lys Phe Ser  Ser Leu Tyr
    1190                 1195                 1200

Ile Ser  Gln Phe Ile Ile Met  Tyr Ser Leu Asp Gly  Lys Lys Trp
    1205                 1210                 1215

Gln Thr  Tyr Arg Gly Asn Ser  Thr Gly Thr Leu Met  Val Phe Phe
    1220                 1225                 1230

Gly Asn  Val Asp Ser Ser Gly  Ile Lys His Asn Ile  Phe Asn Pro
    1235                 1240                 1245

Pro Ile  Ile Ala Arg Tyr Ile  Arg Leu His Pro Thr  His Tyr Ser
    1250                 1255                 1260

Ile Arg  Ser Thr Leu Arg Met  Glu Leu Met Gly Cys  Asp Leu Asn
    1265                 1270                 1275

Ser Cys  Ser Met Pro Leu Gly  Met Glu Ser Lys Ala  Ile Ser Asp
    1280                 1285                 1290

Ala Gln  Ile Thr Ala Ser Ser  Tyr Phe Thr Asn Met  Phe Ala Thr
    1295                 1300                 1305

Trp Ser  Pro Ser Lys Ala Arg  Leu His Leu Gln Gly  Arg Ser Asn
    1310                 1315                 1320

Ala Trp  Arg Pro Gln Val Asn  Asn Pro Lys Glu Trp  Leu Gln Val
    1325                 1330                 1335

Asp Phe  Gln Lys Thr Met Lys  Val Thr Gly Val Thr  Thr Gln Gly
    1340                 1345                 1350

Val Lys  Ser Leu Leu Thr Ser  Met Tyr Val Lys Glu  Phe Leu Ile
    1355                 1360                 1365

Ser Ser  Ser Gln Asp Gly His  Gln Trp Thr Leu Phe  Phe Gln Asn
    1370                 1375                 1380

Gly Lys  Val Lys Val Phe Gln  Gly Asn Gln Asp Ser  Phe Thr Pro
```

```
    1385                1390                1395

Val Val  Asn Ser Leu Asp Pro  Pro Leu Leu Thr Arg  Tyr Leu Arg
    1400                1405                1410

Ile His  Pro Gln Ser Trp Val  His Gln Ile Ala Leu  Arg Met Glu
    1415                1420                1425

Val Leu  Gly Cys Glu Ala Gln  Asp Leu Tyr
    1430                1435


<210> SEQ ID NO 15
<211> LENGTH: 1447
<212> TYPE: PRT
<213> ORGANISM: Artificial Sequence
<220> FEATURE:
<223> OTHER INFORMATION: Mature FVIII SVA IQIRSV Insertion

<400> SEQUENCE: 15

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
```

```
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Ser Val Ala Ile Gln Ile Arg Ser Val
    370                 375                 380

Lys Lys His Pro Lys Thr Trp Val His Tyr Ile Ala Ala Glu Glu Glu
385                 390                 395                 400

Asp Trp Asp Tyr Ala Pro Leu Val Leu Ala Pro Asp Asp Arg Ser Tyr
                405                 410                 415

Lys Ser Gln Tyr Leu Asn Asn Gly Pro Gln Arg Ile Gly Arg Lys Tyr
            420                 425                 430

Lys Lys Val Arg Phe Met Ala Tyr Thr Asp Glu Thr Phe Lys Thr Arg
        435                 440                 445

Glu Ala Ile Gln His Glu Ser Gly Ile Leu Gly Pro Leu Leu Tyr Gly
    450                 455                 460

Glu Val Gly Asp Thr Leu Leu Ile Ile Phe Lys Asn Gln Ala Ser Arg
465                 470                 475                 480

Pro Tyr Asn Ile Tyr Pro His Gly Ile Thr Asp Val Arg Pro Leu Tyr
                485                 490                 495

Ser Arg Arg Leu Pro Lys Gly Val Lys His Leu Lys Asp Phe Pro Ile
            500                 505                 510

Leu Pro Gly Glu Ile Phe Lys Tyr Lys Trp Thr Val Thr Val Glu Asp
        515                 520                 525

Gly Pro Thr Lys Ser Asp Pro Arg Cys Leu Thr Arg Tyr Tyr Ser Ser
    530                 535                 540

Phe Val Asn Met Glu Arg Asp Leu Ala Ser Gly Leu Ile Gly Pro Leu
545                 550                 555                 560

Leu Ile Cys Tyr Lys Glu Ser Val Asp Gln Arg Gly Asn Gln Ile Met
                565                 570                 575

Ser Asp Lys Arg Asn Val Ile Leu Phe Ser Val Phe Asp Glu Asn Arg
            580                 585                 590

Ser Trp Tyr Leu Thr Glu Asn Ile Gln Arg Phe Leu Pro Asn Pro Ala
        595                 600                 605

Gly Val Gln Leu Glu Asp Pro Glu Phe Gln Ala Ser Asn Ile Met His
    610                 615                 620

Ser Ile Asn Gly Tyr Val Phe Asp Ser Leu Gln Leu Ser Val Cys Leu
625                 630                 635                 640

His Glu Val Ala Tyr Trp Tyr Ile Leu Ser Ile Gly Ala Gln Thr Asp
                645                 650                 655

Phe Leu Ser Val Phe Phe Ser Gly Tyr Thr Phe Lys His Lys Met Val
            660                 665                 670

Tyr Glu Asp Thr Leu Thr Leu Phe Pro Phe Ser Gly Glu Thr Val Phe
        675                 680                 685

Met Ser Met Glu Asn Pro Gly Leu Trp Ile Leu Gly Cys His Asn Ser
    690                 695                 700

Asp Phe Arg Asn Arg Gly Met Thr Ala Leu Leu Lys Val Ser Ser Cys
705                 710                 715                 720

Asp Lys Asn Thr Gly Asp Tyr Tyr Glu Asp Ser Tyr Glu Asp Ile Ser
                725                 730                 735
```

```
Ala Tyr Leu Leu Ser Lys Asn Asn Ala Ile Glu Pro Arg Ser Phe Ser
            740                 745                 750

Gln Asn Pro Pro Val Leu Lys Arg His Gln Arg Glu Ile Thr Arg Thr
        755                 760                 765

Thr Leu Gln Ser Asp Gln Glu Glu Ile Asp Tyr Asp Asp Thr Ile Ser
    770                 775                 780

Val Glu Met Lys Lys Glu Asp Phe Asp Ile Tyr Asp Glu Asp Glu Asn
785                 790                 795                 800

Gln Ser Pro Arg Ser Phe Gln Lys Lys Thr Arg His Tyr Phe Ile Ala
                805                 810                 815

Ala Val Glu Arg Leu Trp Asp Tyr Gly Met Ser Ser Ser Pro His Val
            820                 825                 830

Leu Arg Asn Arg Ala Gln Ser Gly Ser Val Pro Gln Phe Lys Lys Val
        835                 840                 845

Val Phe Gln Glu Phe Thr Asp Gly Ser Phe Thr Gln Pro Leu Tyr Arg
    850                 855                 860

Gly Glu Leu Asn Glu His Leu Gly Leu Leu Gly Pro Tyr Ile Arg Ala
865                 870                 875                 880

Glu Val Glu Asp Asn Ile Met Val Thr Phe Arg Asn Gln Ala Ser Arg
                885                 890                 895

Pro Tyr Ser Phe Tyr Ser Ser Leu Ile Ser Tyr Glu Glu Asp Gln Arg
            900                 905                 910

Gln Gly Ala Glu Pro Arg Lys Asn Phe Val Lys Pro Asn Glu Thr Lys
        915                 920                 925

Thr Tyr Phe Trp Lys Val Gln His His Met Ala Pro Thr Lys Asp Glu
    930                 935                 940

Phe Asp Cys Lys Ala Trp Ala Tyr Phe Ser Asp Val Asp Leu Glu Lys
945                 950                 955                 960

Asp Val His Ser Gly Leu Ile Gly Pro Leu Leu Val Cys His Thr Asn
                965                 970                 975

Thr Leu Asn Pro Ala His Gly Arg Gln Val Thr Val Gln Glu Phe Ala
            980                 985                 990

Leu Phe Phe Thr Ile Phe Asp Glu  Thr Lys Ser Trp Tyr  Phe Thr Glu
        995                 1000                1005

Asn Met  Glu Arg Asn Cys Arg  Ala Pro Cys Asn Ile  Gln Met Glu
    1010                1015                1020

Asp Pro  Thr Phe Lys Glu Asn  Tyr Arg Phe His Ala  Ile Asn Gly
    1025                1030                1035

Tyr Ile  Met Asp Thr Leu Pro  Gly Leu Val Met Ala  Gln Asp Gln
    1040                1045                1050

Arg Ile  Arg Trp Tyr Leu Leu  Ser Met Gly Ser Asn  Glu Asn Ile
    1055                1060                1065

His Ser  Ile His Phe Ser Gly  His Val Phe Thr Val  Arg Lys Lys
    1070                1075                1080

Glu Glu  Tyr Lys Met Ala Leu  Tyr Asn Leu Tyr Pro  Gly Val Phe
    1085                1090                1095

Glu Thr  Val Glu Met Leu Pro  Ser Lys Ala Gly Ile  Trp Arg Val
    1100                1105                1110

Glu Cys  Leu Ile Gly Glu His  Leu His Ala Gly Met  Ser Thr Leu
    1115                1120                1125

Phe Leu  Val Tyr Ser Asn Lys  Cys Gln Thr Pro Leu  Gly Met Ala
    1130                1135                1140
```

```
Ser Gly  His Ile Arg Asp Phe  Gln Ile Thr Ala Ser  Gly Gln Tyr
    1145                 1150                 1155

Gly Gln  Trp Ala Pro Lys Leu  Ala Arg Leu His Tyr  Ser Gly Ser
    1160                 1165                 1170

Ile Asn  Ala Trp Ser Thr Lys  Glu Pro Phe Ser Trp  Ile Lys Val
    1175                 1180                 1185

Asp Leu  Leu Ala Pro Met Ile  Ile His Gly Ile Lys  Thr Gln Gly
    1190                 1195                 1200

Ala Arg  Gln Lys Phe Ser Ser  Leu Tyr Ile Ser Gln  Phe Ile Ile
    1205                 1210                 1215

Met Tyr  Ser Leu Asp Gly Lys  Lys Trp Gln Thr Tyr  Arg Gly Asn
    1220                 1225                 1230

Ser Thr  Gly Thr Leu Met Val  Phe Phe Gly Asn Val  Asp Ser Ser
    1235                 1240                 1245

Gly Ile  Lys His Asn Ile Phe  Asn Pro Pro Ile Ile  Ala Arg Tyr
    1250                 1255                 1260

Ile Arg  Leu His Pro Thr His  Tyr Ser Ile Arg Ser  Thr Leu Arg
    1265                 1270                 1275

Met Glu  Leu Met Gly Cys Asp  Leu Asn Ser Cys Ser  Met Pro Leu
    1280                 1285                 1290

Gly Met  Glu Ser Lys Ala Ile  Ser Asp Ala Gln Ile  Thr Ala Ser
    1295                 1300                 1305

Ser Tyr  Phe Thr Asn Met Phe  Ala Thr Trp Ser Pro  Ser Lys Ala
    1310                 1315                 1320

Arg Leu  His Leu Gln Gly Arg  Ser Asn Ala Trp Arg  Pro Gln Val
    1325                 1330                 1335

Asn Asn  Pro Lys Glu Trp Leu  Gln Val Asp Phe Gln  Lys Thr Met
    1340                 1345                 1350

Lys Val  Thr Gly Val Thr Thr  Gln Gly Val Lys Ser  Leu Leu Thr
    1355                 1360                 1365

Ser Met  Tyr Val Lys Glu Phe  Leu Ile Ser Ser Ser  Gln Asp Gly
    1370                 1375                 1380

His Gln  Trp Thr Leu Phe Phe  Gln Asn Gly Lys Val  Lys Val Phe
    1385                 1390                 1395

Gln Gly  Asn Gln Asp Ser Phe  Thr Pro Val Val Asn  Ser Leu Asp
    1400                 1405                 1410

Pro Pro  Leu Leu Thr Arg Tyr  Leu Arg Ile His Pro  Gln Ser Trp
    1415                 1420                 1425

Val His  Gln Ile Ala Leu Arg  Met Glu Val Leu Gly  Cys Glu Ala
    1430                 1435                 1440

Gln Asp  Leu Tyr
    1445


<210> SEQ ID NO 16
<211> LENGTH: 1441
<212> TYPE: PRT
<213> ORGANISM: Artificial Sequence
<220> FEATURE:
<223> OTHER INFORMATION: Mature FVIII ATR Insertion

<400> SEQUENCE: 16

Ala Thr Arg Ala Thr Arg Arg Tyr Tyr Leu Gly Ala Val Glu Leu Ser
1               5                   10                  15

Trp Asp Tyr Met Gln Ser Asp Leu Gly Glu Leu Pro Val Asp Ala Arg
            20                  25                  30
```

```
Phe Pro Pro Arg Val Pro Lys Ser Phe Pro Phe Asn Thr Ser Val Val
        35                  40                  45

Tyr Lys Lys Thr Leu Phe Val Glu Phe Thr Asp His Leu Phe Asn Ile
    50                  55                  60

Ala Lys Pro Arg Pro Pro Trp Met Gly Leu Leu Gly Pro Thr Ile Gln
65                  70                  75                  80

Ala Glu Val Tyr Asp Thr Val Val Ile Thr Leu Lys Asn Met Ala Ser
                85                  90                  95

His Pro Val Ser Leu His Ala Val Gly Val Ser Tyr Trp Lys Ala Ser
            100                 105                 110

Glu Gly Ala Glu Tyr Asp Asp Gln Thr Ser Gln Arg Glu Lys Glu Asp
        115                 120                 125

Asp Lys Val Phe Pro Gly Gly Ser His Thr Tyr Val Trp Gln Val Leu
    130                 135                 140

Lys Glu Asn Gly Pro Met Ala Ser Asp Pro Leu Cys Leu Thr Tyr Ser
145                 150                 155                 160

Tyr Leu Ser His Val Asp Leu Val Lys Asp Leu Asn Ser Gly Leu Ile
                165                 170                 175

Gly Ala Leu Leu Val Cys Arg Glu Gly Ser Leu Ala Lys Glu Lys Thr
            180                 185                 190

Gln Thr Leu His Lys Phe Ile Leu Leu Phe Ala Val Phe Asp Glu Gly
        195                 200                 205

Lys Ser Trp His Ser Glu Thr Lys Asn Ser Leu Met Gln Asp Arg Asp
    210                 215                 220

Ala Ala Ser Ala Arg Ala Trp Pro Lys Met His Thr Val Asn Gly Tyr
225                 230                 235                 240

Val Asn Arg Ser Leu Pro Gly Leu Ile Gly Cys His Arg Lys Ser Val
                245                 250                 255

Tyr Trp His Val Ile Gly Met Gly Thr Thr Pro Glu Val His Ser Ile
            260                 265                 270

Phe Leu Glu Gly His Thr Phe Leu Val Arg Asn His Arg Gln Ala Ser
        275                 280                 285

Leu Glu Ile Ser Pro Ile Thr Phe Leu Thr Ala Gln Thr Leu Leu Met
    290                 295                 300

Asp Leu Gly Gln Phe Leu Leu Phe Cys His Ile Ser Ser His Gln His
305                 310                 315                 320

Asp Gly Met Glu Ala Tyr Val Lys Val Asp Ser Cys Pro Glu Glu Pro
                325                 330                 335

Gln Leu Arg Met Lys Asn Asn Glu Glu Ala Glu Asp Tyr Asp Asp Asp
            340                 345                 350

Leu Thr Asp Ser Glu Met Asp Val Val Arg Phe Asp Asp Asp Asn Ser
        355                 360                 365

Pro Ser Phe Ile Gln Ile Arg Ser Val Ala Lys Lys His Pro Lys Thr
    370                 375                 380

Trp Val His Tyr Ile Ala Ala Glu Glu Glu Asp Trp Asp Tyr Ala Pro
385                 390                 395                 400

Leu Val Leu Ala Pro Asp Asp Arg Ser Tyr Lys Ser Gln Tyr Leu Asn
                405                 410                 415

Asn Gly Pro Gln Arg Ile Gly Arg Lys Tyr Lys Lys Val Arg Phe Met
            420                 425                 430

Ala Tyr Thr Asp Glu Thr Phe Lys Thr Arg Glu Ala Ile Gln His Glu
        435                 440                 445

Ser Gly Ile Leu Gly Pro Leu Leu Tyr Gly Glu Val Gly Asp Thr Leu
```

```
    450                 455                 460

Leu Ile Ile Phe Lys Asn Gln Ala Ser Arg Pro Tyr Asn Ile Tyr Pro
465                 470                 475                 480

His Gly Ile Thr Asp Val Arg Pro Leu Tyr Ser Arg Arg Leu Pro Lys
                485                 490                 495

Gly Val Lys His Leu Lys Asp Phe Pro Ile Leu Pro Gly Glu Ile Phe
            500                 505                 510

Lys Tyr Lys Trp Thr Val Thr Val Glu Asp Gly Pro Thr Lys Ser Asp
        515                 520                 525

Pro Arg Cys Leu Thr Arg Tyr Tyr Ser Ser Phe Val Asn Met Glu Arg
    530                 535                 540

Asp Leu Ala Ser Gly Leu Ile Gly Pro Leu Leu Ile Cys Tyr Lys Glu
545                 550                 555                 560

Ser Val Asp Gln Arg Gly Asn Gln Ile Met Ser Asp Lys Arg Asn Val
                565                 570                 575

Ile Leu Phe Ser Val Phe Asp Glu Asn Arg Ser Trp Tyr Leu Thr Glu
            580                 585                 590

Asn Ile Gln Arg Phe Leu Pro Asn Pro Ala Gly Val Gln Leu Glu Asp
        595                 600                 605

Pro Glu Phe Gln Ala Ser Asn Ile Met His Ser Ile Asn Gly Tyr Val
    610                 615                 620

Phe Asp Ser Leu Gln Leu Ser Val Cys Leu His Glu Val Ala Tyr Trp
625                 630                 635                 640

Tyr Ile Leu Ser Ile Gly Ala Gln Thr Asp Phe Leu Ser Val Phe Phe
                645                 650                 655

Ser Gly Tyr Thr Phe Lys His Lys Met Val Tyr Glu Asp Thr Leu Thr
            660                 665                 670

Leu Phe Pro Phe Ser Gly Glu Thr Val Phe Met Ser Met Glu Asn Pro
        675                 680                 685

Gly Leu Trp Ile Leu Gly Cys His Asn Ser Asp Phe Arg Asn Arg Gly
    690                 695                 700

Met Thr Ala Leu Leu Lys Val Ser Ser Cys Asp Lys Asn Thr Gly Asp
705                 710                 715                 720

Tyr Tyr Glu Asp Ser Tyr Glu Asp Ile Ser Ala Tyr Leu Leu Ser Lys
                725                 730                 735

Asn Asn Ala Ile Glu Pro Arg Ser Phe Ser Gln Asn Pro Pro Val Leu
            740                 745                 750

Lys Arg His Gln Arg Glu Ile Thr Arg Thr Thr Leu Gln Ser Asp Gln
        755                 760                 765

Glu Glu Ile Asp Tyr Asp Asp Thr Ile Ser Val Glu Met Lys Lys Glu
    770                 775                 780

Asp Phe Asp Ile Tyr Asp Glu Asp Glu Asn Gln Ser Pro Arg Ser Phe
785                 790                 795                 800

Gln Lys Lys Thr Arg His Tyr Phe Ile Ala Ala Val Glu Arg Leu Trp
                805                 810                 815

Asp Tyr Gly Met Ser Ser Ser Pro His Val Leu Arg Asn Arg Ala Gln
            820                 825                 830

Ser Gly Ser Val Pro Gln Phe Lys Lys Val Val Phe Gln Glu Phe Thr
        835                 840                 845

Asp Gly Ser Phe Thr Gln Pro Leu Tyr Arg Gly Glu Leu Asn Glu His
    850                 855                 860

Leu Gly Leu Leu Gly Pro Tyr Ile Arg Ala Glu Val Glu Asp Asn Ile
865                 870                 875                 880
```

```
Met Val Thr Phe Arg Asn Gln Ala Ser Arg Pro Tyr Ser Phe Tyr Ser
                885                 890                 895

Ser Leu Ile Ser Tyr Glu Glu Asp Gln Arg Gln Gly Ala Glu Pro Arg
            900                 905                 910

Lys Asn Phe Val Lys Pro Asn Glu Thr Lys Thr Tyr Phe Trp Lys Val
        915                 920                 925

Gln His His Met Ala Pro Thr Lys Asp Glu Phe Asp Cys Lys Ala Trp
    930                 935                 940

Ala Tyr Phe Ser Asp Val Asp Leu Glu Lys Asp Val His Ser Gly Leu
945                 950                 955                 960

Ile Gly Pro Leu Leu Val Cys His Thr Asn Thr Leu Asn Pro Ala His
                965                 970                 975

Gly Arg Gln Val Thr Val Gln Glu Phe Ala Leu Phe Phe Thr Ile Phe
            980                 985                 990

Asp Glu Thr Lys Ser Trp Tyr Phe  Thr Glu Asn Met Glu  Arg Asn Cys
        995                 1000                1005

Arg Ala  Pro Cys Asn Ile Gln  Met Glu Asp Pro Thr  Phe Lys Glu
    1010                1015                1020

Asn Tyr  Arg Phe His Ala Ile  Asn Gly Tyr Ile Met  Asp Thr Leu
    1025                1030                1035

Pro Gly  Leu Val Met Ala Gln  Asp Gln Arg Ile Arg  Trp Tyr Leu
    1040                1045                1050

Leu Ser  Met Gly Ser Asn Glu  Asn Ile His Ser Ile  His Phe Ser
    1055                1060                1065

Gly His  Val Phe Thr Val Arg  Lys Lys Glu Glu Tyr  Lys Met Ala
    1070                1075                1080

Leu Tyr  Asn Leu Tyr Pro Gly  Val Phe Glu Thr Val  Glu Met Leu
    1085                1090                1095

Pro Ser  Lys Ala Gly Ile Trp  Arg Val Glu Cys Leu  Ile Gly Glu
    1100                1105                1110

His Leu  His Ala Gly Met Ser  Thr Leu Phe Leu Val  Tyr Ser Asn
    1115                1120                1125

Lys Cys  Gln Thr Pro Leu Gly  Met Ala Ser Gly His  Ile Arg Asp
    1130                1135                1140

Phe Gln  Ile Thr Ala Ser Gly  Gln Tyr Gly Gln Trp  Ala Pro Lys
    1145                1150                1155

Leu Ala  Arg Leu His Tyr Ser  Gly Ser Ile Asn Ala  Trp Ser Thr
    1160                1165                1170

Lys Glu  Pro Phe Ser Trp Ile  Lys Val Asp Leu Leu  Ala Pro Met
    1175                1180                1185

Ile Ile  His Gly Ile Lys Thr  Gln Gly Ala Arg Gln  Lys Phe Ser
    1190                1195                1200

Ser Leu  Tyr Ile Ser Gln Phe  Ile Ile Met Tyr Ser  Leu Asp Gly
    1205                1210                1215

Lys Lys  Trp Gln Thr Tyr Arg  Gly Asn Ser Thr Gly  Thr Leu Met
    1220                1225                1230

Val Phe  Phe Gly Asn Val Asp  Ser Ser Gly Ile Lys  His Asn Ile
    1235                1240                1245

Phe Asn  Pro Pro Ile Ile Ala  Arg Tyr Ile Arg Leu  His Pro Thr
    1250                1255                1260

His Tyr  Ser Ile Arg Ser Thr  Leu Arg Met Glu Leu  Met Gly Cys
    1265                1270                1275
```

```
Asp Leu  Asn Ser Cys Ser Met  Pro Leu Gly Met Glu  Ser Lys Ala
    1280                 1285                 1290

Ile Ser  Asp Ala Gln Ile Thr  Ala Ser Ser Tyr Phe  Thr Asn Met
    1295                 1300                 1305

Phe Ala  Thr Trp Ser Pro Ser  Lys Ala Arg Leu His  Leu Gln Gly
    1310                 1315                 1320

Arg Ser  Asn Ala Trp Arg Pro  Gln Val Asn Asn Pro  Lys Glu Trp
    1325                 1330                 1335

Leu Gln  Val Asp Phe Gln Lys  Thr Met Lys Val Thr  Gly Val Thr
    1340                 1345                 1350

Thr Gln  Gly Val Lys Ser Leu  Leu Thr Ser Met Tyr  Val Lys Glu
    1355                 1360                 1365

Phe Leu  Ile Ser Ser Ser Gln  Asp Gly His Gln Trp  Thr Leu Phe
    1370                 1375                 1380

Phe Gln  Asn Gly Lys Val Lys  Val Phe Gln Gly Asn  Gln Asp Ser
    1385                 1390                 1395

Phe Thr  Pro Val Val Asn Ser  Leu Asp Pro Pro Leu  Leu Thr Arg
    1400                 1405                 1410

Tyr Leu  Arg Ile His Pro Gln  Ser Trp Val His Gln  Ile Ala Leu
    1415                 1420                 1425

Arg Met  Glu Val Leu Gly Cys  Glu Ala Gln Asp Leu  Tyr
    1430                 1435                 1440


<210> SEQ ID NO 17
<211> LENGTH: 1441
<212> TYPE: PRT
<213> ORGANISM: Artificial Sequence
<220> FEATURE:
<223> OTHER INFORMATION: Mature FVIII VQL Insertion

<400> SEQUENCE: 17

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190
```

```
His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Val Gln Leu
                325                 330                 335

Gln Leu Arg Met Lys Asn Asn Glu Glu Ala Glu Asp Tyr Asp Asp Asp
            340                 345                 350

Leu Thr Asp Ser Glu Met Asp Val Val Arg Phe Asp Asp Asp Asn Ser
        355                 360                 365

Pro Ser Phe Ile Gln Ile Arg Ser Val Ala Lys Lys His Pro Lys Thr
    370                 375                 380

Trp Val His Tyr Ile Ala Ala Glu Glu Glu Asp Trp Asp Tyr Ala Pro
385                 390                 395                 400

Leu Val Leu Ala Pro Asp Asp Arg Ser Tyr Lys Ser Gln Tyr Leu Asn
                405                 410                 415

Asn Gly Pro Gln Arg Ile Gly Arg Lys Tyr Lys Lys Val Arg Phe Met
            420                 425                 430

Ala Tyr Thr Asp Glu Thr Phe Lys Thr Arg Glu Ala Ile Gln His Glu
        435                 440                 445

Ser Gly Ile Leu Gly Pro Leu Leu Tyr Gly Glu Val Gly Asp Thr Leu
    450                 455                 460

Leu Ile Ile Phe Lys Asn Gln Ala Ser Arg Pro Tyr Asn Ile Tyr Pro
465                 470                 475                 480

His Gly Ile Thr Asp Val Arg Pro Leu Tyr Ser Arg Arg Leu Pro Lys
                485                 490                 495

Gly Val Lys His Leu Lys Asp Phe Pro Ile Leu Pro Gly Glu Ile Phe
            500                 505                 510

Lys Tyr Lys Trp Thr Val Thr Val Glu Asp Gly Pro Thr Lys Ser Asp
        515                 520                 525

Pro Arg Cys Leu Thr Arg Tyr Tyr Ser Ser Phe Val Asn Met Glu Arg
    530                 535                 540

Asp Leu Ala Ser Gly Leu Ile Gly Pro Leu Leu Ile Cys Tyr Lys Glu
545                 550                 555                 560

Ser Val Asp Gln Arg Gly Asn Gln Ile Met Ser Asp Lys Arg Asn Val
                565                 570                 575

Ile Leu Phe Ser Val Phe Asp Glu Asn Arg Ser Trp Tyr Leu Thr Glu
            580                 585                 590

Asn Ile Gln Arg Phe Leu Pro Asn Pro Ala Gly Val Gln Leu Glu Asp
        595                 600                 605

Pro Glu Phe Gln Ala Ser Asn Ile Met His Ser Ile Asn Gly Tyr Val
```

```
    610                 615                 620

Phe Asp Ser Leu Gln Leu Ser Val Cys Leu His Glu Val Ala Tyr Trp
625                 630                 635                 640

Tyr Ile Leu Ser Ile Gly Ala Gln Thr Asp Phe Leu Ser Val Phe Phe
                645                 650                 655

Ser Gly Tyr Thr Phe Lys His Lys Met Val Tyr Glu Asp Thr Leu Thr
            660                 665                 670

Leu Phe Pro Phe Ser Gly Glu Thr Val Phe Met Ser Met Glu Asn Pro
        675                 680                 685

Gly Leu Trp Ile Leu Gly Cys His Asn Ser Asp Phe Arg Asn Arg Gly
    690                 695                 700

Met Thr Ala Leu Leu Lys Val Ser Ser Cys Asp Lys Asn Thr Gly Asp
705                 710                 715                 720

Tyr Tyr Glu Asp Ser Tyr Glu Asp Ile Ser Ala Tyr Leu Leu Ser Lys
                725                 730                 735

Asn Asn Ala Ile Glu Pro Arg Ser Phe Ser Gln Asn Pro Pro Val Leu
            740                 745                 750

Lys Arg His Gln Arg Glu Ile Thr Arg Thr Thr Leu Gln Ser Asp Gln
        755                 760                 765

Glu Glu Ile Asp Tyr Asp Asp Thr Ile Ser Val Glu Met Lys Lys Glu
    770                 775                 780

Asp Phe Asp Ile Tyr Asp Glu Asp Glu Asn Gln Ser Pro Arg Ser Phe
785                 790                 795                 800

Gln Lys Lys Thr Arg His Tyr Phe Ile Ala Ala Val Glu Arg Leu Trp
                805                 810                 815

Asp Tyr Gly Met Ser Ser Ser Pro His Val Leu Arg Asn Arg Ala Gln
            820                 825                 830

Ser Gly Ser Val Pro Gln Phe Lys Lys Val Val Phe Gln Glu Phe Thr
        835                 840                 845

Asp Gly Ser Phe Thr Gln Pro Leu Tyr Arg Gly Glu Leu Asn Glu His
    850                 855                 860

Leu Gly Leu Leu Gly Pro Tyr Ile Arg Ala Glu Val Glu Asp Asn Ile
865                 870                 875                 880

Met Val Thr Phe Arg Asn Gln Ala Ser Arg Pro Tyr Ser Phe Tyr Ser
                885                 890                 895

Ser Leu Ile Ser Tyr Glu Glu Asp Gln Arg Gln Gly Ala Glu Pro Arg
            900                 905                 910

Lys Asn Phe Val Lys Pro Asn Glu Thr Lys Thr Tyr Phe Trp Lys Val
        915                 920                 925

Gln His His Met Ala Pro Thr Lys Asp Glu Phe Asp Cys Lys Ala Trp
    930                 935                 940

Ala Tyr Phe Ser Asp Val Asp Leu Glu Lys Asp Val His Ser Gly Leu
945                 950                 955                 960

Ile Gly Pro Leu Leu Val Cys His Thr Asn Thr Leu Asn Pro Ala His
                965                 970                 975

Gly Arg Gln Val Thr Val Gln Glu Phe Ala Leu Phe Phe Thr Ile Phe
            980                 985                 990

Asp Glu Thr Lys Ser Trp Tyr Phe  Thr Glu Asn Met Glu  Arg Asn Cys
        995                 1000                1005

Arg Ala  Pro Cys Asn Ile Gln  Met Glu Asp Pro Thr  Phe Lys Glu
    1010                1015                1020

Asn Tyr  Arg Phe His Ala Ile  Asn Gly Tyr Ile Met  Asp Thr Leu
    1025                1030                1035
```

```
Pro Gly  Leu Val Met Ala Gln  Asp Gln Arg Ile Arg  Trp Tyr Leu
    1040                 1045                 1050

Leu Ser  Met Gly Ser Asn Glu  Asn Ile His Ser Ile  His Phe Ser
    1055                 1060                 1065

Gly His  Val Phe Thr Val Arg  Lys Lys Glu Glu Tyr  Lys Met Ala
    1070                 1075                 1080

Leu Tyr  Asn Leu Tyr Pro Gly  Val Phe Glu Thr Val  Glu Met Leu
    1085                 1090                 1095

Pro Ser  Lys Ala Gly Ile Trp  Arg Val Glu Cys Leu  Ile Gly Glu
    1100                 1105                 1110

His Leu  His Ala Gly Met Ser  Thr Leu Phe Leu Val  Tyr Ser Asn
    1115                 1120                 1125

Lys Cys  Gln Thr Pro Leu Gly  Met Ala Ser Gly His  Ile Arg Asp
    1130                 1135                 1140

Phe Gln  Ile Thr Ala Ser Gly  Gln Tyr Gly Gln Trp  Ala Pro Lys
    1145                 1150                 1155

Leu Ala  Arg Leu His Tyr Ser  Gly Ser Ile Asn Ala  Trp Ser Thr
    1160                 1165                 1170

Lys Glu  Pro Phe Ser Trp Ile  Lys Val Asp Leu Leu  Ala Pro Met
    1175                 1180                 1185

Ile Ile  His Gly Ile Lys Thr  Gln Gly Ala Arg Gln  Lys Phe Ser
    1190                 1195                 1200

Ser Leu  Tyr Ile Ser Gln Phe  Ile Ile Met Tyr Ser  Leu Asp Gly
    1205                 1210                 1215

Lys Lys  Trp Gln Thr Tyr Arg  Gly Asn Ser Thr Gly  Thr Leu Met
    1220                 1225                 1230

Val Phe  Phe Gly Asn Val Asp  Ser Ser Gly Ile Lys  His Asn Ile
    1235                 1240                 1245

Phe Asn  Pro Pro Ile Ile Ala  Arg Tyr Ile Arg Leu  His Pro Thr
    1250                 1255                 1260

His Tyr  Ser Ile Arg Ser Thr  Leu Arg Met Glu Leu  Met Gly Cys
    1265                 1270                 1275

Asp Leu  Asn Ser Cys Ser Met  Pro Leu Gly Met Glu  Ser Lys Ala
    1280                 1285                 1290

Ile Ser  Asp Ala Gln Ile Thr  Ala Ser Ser Tyr Phe  Thr Asn Met
    1295                 1300                 1305

Phe Ala  Thr Trp Ser Pro Ser  Lys Ala Arg Leu His  Leu Gln Gly
    1310                 1315                 1320

Arg Ser  Asn Ala Trp Arg Pro  Gln Val Asn Asn Pro  Lys Glu Trp
    1325                 1330                 1335

Leu Gln  Val Asp Phe Gln Lys  Thr Met Lys Val Thr  Gly Val Thr
    1340                 1345                 1350

Thr Gln  Gly Val Lys Ser Leu  Leu Thr Ser Met Tyr  Val Lys Glu
    1355                 1360                 1365

Phe Leu  Ile Ser Ser Ser Gln  Asp Gly His Gln Trp  Thr Leu Phe
    1370                 1375                 1380

Phe Gln  Asn Gly Lys Val Lys  Val Phe Gln Gly Asn  Gln Asp Ser
    1385                 1390                 1395

Phe Thr  Pro Val Val Asn Ser  Leu Asp Pro Pro Leu  Leu Thr Arg
    1400                 1405                 1410

Tyr Leu  Arg Ile His Pro Gln  Ser Trp Val His Gln  Ile Ala Leu
    1415                 1420                 1425
```

```
Arg Met  Glu Val Leu Gly Cys  Glu Ala Gln Asp Leu  Tyr
    1430                 1435                 1440


<210> SEQ ID NO 18
<211> LENGTH: 1441
<212> TYPE: PRT
<213> ORGANISM: Artificial Sequence
<220> FEATURE:
<223> OTHER INFORMATION: Mature FVIII SVA Insertion

<400> SEQUENCE: 18

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350
```

```
Ser Glu Met Asp Val Val Arg Phe Asp Asp Asp Asn Ser Pro Ser Phe
        355                 360                 365

Ile Gln Ile Arg Ser Val Ala Ser Val Ala Lys Lys His Pro Lys Thr
    370                 375                 380

Trp Val His Tyr Ile Ala Ala Glu Glu Glu Asp Trp Asp Tyr Ala Pro
385                 390                 395                 400

Leu Val Leu Ala Pro Asp Asp Arg Ser Tyr Lys Ser Gln Tyr Leu Asn
                405                 410                 415

Asn Gly Pro Gln Arg Ile Gly Arg Lys Tyr Lys Lys Val Arg Phe Met
            420                 425                 430

Ala Tyr Thr Asp Glu Thr Phe Lys Thr Arg Glu Ala Ile Gln His Glu
        435                 440                 445

Ser Gly Ile Leu Gly Pro Leu Leu Tyr Gly Glu Val Gly Asp Thr Leu
    450                 455                 460

Leu Ile Ile Phe Lys Asn Gln Ala Ser Arg Pro Tyr Asn Ile Tyr Pro
465                 470                 475                 480

His Gly Ile Thr Asp Val Arg Pro Leu Tyr Ser Arg Arg Leu Pro Lys
                485                 490                 495

Gly Val Lys His Leu Lys Asp Phe Pro Ile Leu Pro Gly Glu Ile Phe
            500                 505                 510

Lys Tyr Lys Trp Thr Val Thr Val Glu Asp Gly Pro Thr Lys Ser Asp
        515                 520                 525

Pro Arg Cys Leu Thr Arg Tyr Tyr Ser Ser Phe Val Asn Met Glu Arg
    530                 535                 540

Asp Leu Ala Ser Gly Leu Ile Gly Pro Leu Leu Ile Cys Tyr Lys Glu
545                 550                 555                 560

Ser Val Asp Gln Arg Gly Asn Gln Ile Met Ser Asp Lys Arg Asn Val
                565                 570                 575

Ile Leu Phe Ser Val Phe Asp Glu Asn Arg Ser Trp Tyr Leu Thr Glu
            580                 585                 590

Asn Ile Gln Arg Phe Leu Pro Asn Pro Ala Gly Val Gln Leu Glu Asp
        595                 600                 605

Pro Glu Phe Gln Ala Ser Asn Ile Met His Ser Ile Asn Gly Tyr Val
    610                 615                 620

Phe Asp Ser Leu Gln Leu Ser Val Cys Leu His Glu Val Ala Tyr Trp
625                 630                 635                 640

Tyr Ile Leu Ser Ile Gly Ala Gln Thr Asp Phe Leu Ser Val Phe Phe
                645                 650                 655

Ser Gly Tyr Thr Phe Lys His Lys Met Val Tyr Glu Asp Thr Leu Thr
            660                 665                 670

Leu Phe Pro Phe Ser Gly Glu Thr Val Phe Met Ser Met Glu Asn Pro
        675                 680                 685

Gly Leu Trp Ile Leu Gly Cys His Asn Ser Asp Phe Arg Asn Arg Gly
    690                 695                 700

Met Thr Ala Leu Leu Lys Val Ser Ser Cys Asp Lys Asn Thr Gly Asp
705                 710                 715                 720

Tyr Tyr Glu Asp Ser Tyr Glu Asp Ile Ser Ala Tyr Leu Leu Ser Lys
                725                 730                 735

Asn Asn Ala Ile Glu Pro Arg Ser Phe Ser Gln Asn Pro Pro Val Leu
            740                 745                 750

Lys Arg His Gln Arg Glu Ile Thr Arg Thr Thr Leu Gln Ser Asp Gln
        755                 760                 765

Glu Glu Ile Asp Tyr Asp Asp Thr Ile Ser Val Glu Met Lys Lys Glu
```

```
    770                 775                 780

Asp Phe Asp Ile Tyr Asp Glu Asp Glu Asn Gln Ser Pro Arg Ser Phe
785                 790                 795                 800

Gln Lys Lys Thr Arg His Tyr Phe Ile Ala Ala Val Glu Arg Leu Trp
                805                 810                 815

Asp Tyr Gly Met Ser Ser Ser Pro His Val Leu Arg Asn Arg Ala Gln
            820                 825                 830

Ser Gly Ser Val Pro Gln Phe Lys Lys Val Val Phe Gln Glu Phe Thr
        835                 840                 845

Asp Gly Ser Phe Thr Gln Pro Leu Tyr Arg Gly Glu Leu Asn Glu His
    850                 855                 860

Leu Gly Leu Leu Gly Pro Tyr Ile Arg Ala Glu Val Glu Asp Asn Ile
865                 870                 875                 880

Met Val Thr Phe Arg Asn Gln Ala Ser Arg Pro Tyr Ser Phe Tyr Ser
                885                 890                 895

Ser Leu Ile Ser Tyr Glu Glu Asp Gln Arg Gln Gly Ala Glu Pro Arg
            900                 905                 910

Lys Asn Phe Val Lys Pro Asn Glu Thr Lys Thr Tyr Phe Trp Lys Val
        915                 920                 925

Gln His His Met Ala Pro Thr Lys Asp Glu Phe Asp Cys Lys Ala Trp
    930                 935                 940

Ala Tyr Phe Ser Asp Val Asp Leu Glu Lys Asp Val His Ser Gly Leu
945                 950                 955                 960

Ile Gly Pro Leu Leu Val Cys His Thr Asn Thr Leu Asn Pro Ala His
                965                 970                 975

Gly Arg Gln Val Thr Val Gln Glu Phe Ala Leu Phe Phe Thr Ile Phe
            980                 985                 990

Asp Glu Thr Lys Ser Trp Tyr Phe  Thr Glu Asn Met Glu  Arg Asn Cys
        995                 1000                1005

Arg Ala  Pro Cys Asn Ile Gln  Met Glu Asp Pro Thr  Phe Lys Glu
    1010                1015                1020

Asn Tyr  Arg Phe His Ala Ile  Asn Gly Tyr Ile Met  Asp Thr Leu
    1025                1030                1035

Pro Gly  Leu Val Met Ala Gln  Asp Gln Arg Ile Arg  Trp Tyr Leu
    1040                1045                1050

Leu Ser  Met Gly Ser Asn Glu  Asn Ile His Ser Ile  His Phe Ser
    1055                1060                1065

Gly His  Val Phe Thr Val Arg  Lys Lys Glu Glu Tyr  Lys Met Ala
    1070                1075                1080

Leu Tyr  Asn Leu Tyr Pro Gly  Val Phe Glu Thr Val  Glu Met Leu
    1085                1090                1095

Pro Ser  Lys Ala Gly Ile Trp  Arg Val Glu Cys Leu  Ile Gly Glu
    1100                1105                1110

His Leu  His Ala Gly Met Ser  Thr Leu Phe Leu Val  Tyr Ser Asn
    1115                1120                1125

Lys Cys  Gln Thr Pro Leu Gly  Met Ala Ser Gly His  Ile Arg Asp
    1130                1135                1140

Phe Gln  Ile Thr Ala Ser Gly  Gln Tyr Gly Gln Trp  Ala Pro Lys
    1145                1150                1155

Leu Ala  Arg Leu His Tyr Ser  Gly Ser Ile Asn Ala  Trp Ser Thr
    1160                1165                1170

Lys Glu  Pro Phe Ser Trp Ile  Lys Val Asp Leu Leu  Ala Pro Met
    1175                1180                1185
```

```
Ile Ile  His Gly Ile Lys Thr  Gln Gly Ala Arg Gln  Lys Phe Ser
    1190                 1195                 1200

Ser Leu  Tyr Ile Ser Gln Phe  Ile Ile Met Tyr Ser  Leu Asp Gly
    1205                 1210                 1215

Lys Lys  Trp Gln Thr Tyr Arg  Gly Asn Ser Thr Gly  Thr Leu Met
    1220                 1225                 1230

Val Phe  Phe Gly Asn Val Asp  Ser Ser Gly Ile Lys  His Asn Ile
    1235                 1240                 1245

Phe Asn  Pro Pro Ile Ile Ala  Arg Tyr Ile Arg Leu  His Pro Thr
    1250                 1255                 1260

His Tyr  Ser Ile Arg Ser Thr  Leu Arg Met Glu Leu  Met Gly Cys
    1265                 1270                 1275

Asp Leu  Asn Ser Cys Ser Met  Pro Leu Gly Met Glu  Ser Lys Ala
    1280                 1285                 1290

Ile Ser  Asp Ala Gln Ile Thr  Ala Ser Ser Tyr Phe  Thr Asn Met
    1295                 1300                 1305

Phe Ala  Thr Trp Ser Pro Ser  Lys Ala Arg Leu His  Leu Gln Gly
    1310                 1315                 1320

Arg Ser  Asn Ala Trp Arg Pro  Gln Val Asn Asn Pro  Lys Glu Trp
    1325                 1330                 1335

Leu Gln  Val Asp Phe Gln Lys  Thr Met Lys Val Thr  Gly Val Thr
    1340                 1345                 1350

Thr Gln  Gly Val Lys Ser Leu  Leu Thr Ser Met Tyr  Val Lys Glu
    1355                 1360                 1365

Phe Leu  Ile Ser Ser Ser Gln  Asp Gly His Gln Trp  Thr Leu Phe
    1370                 1375                 1380

Phe Gln  Asn Gly Lys Val Lys  Val Phe Gln Gly Asn  Gln Asp Ser
    1385                 1390                 1395

Phe Thr  Pro Val Val Asn Ser  Leu Asp Pro Pro Leu  Leu Thr Arg
    1400                 1405                 1410

Tyr Leu  Arg Ile His Pro Gln  Ser Trp Val His Gln  Ile Ala Leu
    1415                 1420                 1425

Arg Met  Glu Val Leu Gly Cys  Glu Ala Gln Asp Leu  Tyr
    1430                 1435                 1440
```

<210> SEQ ID NO 19
<211> LENGTH: 1441
<212> TYPE: PRT
<213> ORGANISM: Artificial Sequence
<220> FEATURE:
<223> OTHER INFORMATION: Mature FVIII LPK Insertion

<400> SEQUENCE: 19

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95
```

```
Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Leu Pro Lys
                485                 490                 495

Gly Val Lys His Leu Lys Asp Phe Pro Ile Leu Pro Gly Glu Ile Phe
            500                 505                 510
```

```
Lys Tyr Lys Trp Thr Val Thr Val Glu Asp Gly Pro Thr Lys Ser Asp
        515                 520                 525

Pro Arg Cys Leu Thr Arg Tyr Tyr Ser Ser Phe Val Asn Met Glu Arg
    530                 535                 540

Asp Leu Ala Ser Gly Leu Ile Gly Pro Leu Leu Ile Cys Tyr Lys Glu
545                 550                 555                 560

Ser Val Asp Gln Arg Gly Asn Gln Ile Met Ser Asp Lys Arg Asn Val
                565                 570                 575

Ile Leu Phe Ser Val Phe Asp Glu Asn Arg Ser Trp Tyr Leu Thr Glu
            580                 585                 590

Asn Ile Gln Arg Phe Leu Pro Asn Pro Ala Gly Val Gln Leu Glu Asp
        595                 600                 605

Pro Glu Phe Gln Ala Ser Asn Ile Met His Ser Ile Asn Gly Tyr Val
    610                 615                 620

Phe Asp Ser Leu Gln Leu Ser Val Cys Leu His Glu Val Ala Tyr Trp
625                 630                 635                 640

Tyr Ile Leu Ser Ile Gly Ala Gln Thr Asp Phe Leu Ser Val Phe Phe
                645                 650                 655

Ser Gly Tyr Thr Phe Lys His Lys Met Val Tyr Glu Asp Thr Leu Thr
            660                 665                 670

Leu Phe Pro Phe Ser Gly Glu Thr Val Phe Met Ser Met Glu Asn Pro
        675                 680                 685

Gly Leu Trp Ile Leu Gly Cys His Asn Ser Asp Phe Arg Asn Arg Gly
    690                 695                 700

Met Thr Ala Leu Leu Lys Val Ser Ser Cys Asp Lys Asn Thr Gly Asp
705                 710                 715                 720

Tyr Tyr Glu Asp Ser Tyr Glu Asp Ile Ser Ala Tyr Leu Leu Ser Lys
                725                 730                 735

Asn Asn Ala Ile Glu Pro Arg Ser Phe Ser Gln Asn Pro Pro Val Leu
            740                 745                 750

Lys Arg His Gln Arg Glu Ile Thr Arg Thr Thr Leu Gln Ser Asp Gln
        755                 760                 765

Glu Glu Ile Asp Tyr Asp Asp Thr Ile Ser Val Glu Met Lys Lys Glu
    770                 775                 780

Asp Phe Asp Ile Tyr Asp Glu Asp Glu Asn Gln Ser Pro Arg Ser Phe
785                 790                 795                 800

Gln Lys Lys Thr Arg His Tyr Phe Ile Ala Ala Val Glu Arg Leu Trp
                805                 810                 815

Asp Tyr Gly Met Ser Ser Ser Pro His Val Leu Arg Asn Arg Ala Gln
            820                 825                 830

Ser Gly Ser Val Pro Gln Phe Lys Lys Val Val Phe Gln Glu Phe Thr
        835                 840                 845

Asp Gly Ser Phe Thr Gln Pro Leu Tyr Arg Gly Glu Leu Asn Glu His
    850                 855                 860

Leu Gly Leu Leu Gly Pro Tyr Ile Arg Ala Glu Val Glu Asp Asn Ile
865                 870                 875                 880

Met Val Thr Phe Arg Asn Gln Ala Ser Arg Pro Tyr Ser Phe Tyr Ser
                885                 890                 895

Ser Leu Ile Ser Tyr Glu Glu Asp Gln Arg Gln Gly Ala Glu Pro Arg
            900                 905                 910

Lys Asn Phe Val Lys Pro Asn Glu Thr Lys Thr Tyr Phe Trp Lys Val
        915                 920                 925

Gln His His Met Ala Pro Thr Lys Asp Glu Phe Asp Cys Lys Ala Trp
```

```
    930                 935                 940

Ala Tyr Phe Ser Asp Val Asp Leu Glu Lys Asp Val His Ser Gly Leu
945                 950                 955                 960

Ile Gly Pro Leu Leu Val Cys His Thr Asn Thr Leu Asn Pro Ala His
                965                 970                 975

Gly Arg Gln Val Thr Val Gln Glu Phe Ala Leu Phe Phe Thr Ile Phe
            980                 985                 990

Asp Glu Thr Lys Ser Trp Tyr Phe  Thr Glu Asn Met Glu  Arg Asn Cys
        995                 1000                1005

Arg Ala  Pro Cys Asn Ile Gln  Met Glu Asp Pro Thr  Phe Lys Glu
    1010                 1015                1020

Asn Tyr  Arg Phe His Ala Ile  Asn Gly Tyr Ile Met  Asp Thr Leu
    1025                 1030                1035

Pro Gly  Leu Val Met Ala Gln  Asp Gln Arg Ile Arg  Trp Tyr Leu
    1040                 1045                1050

Leu Ser  Met Gly Ser Asn Glu  Asn Ile His Ser Ile  His Phe Ser
    1055                 1060                1065

Gly His  Val Phe Thr Val Arg  Lys Lys Glu Glu Tyr  Lys Met Ala
    1070                 1075                1080

Leu Tyr  Asn Leu Tyr Pro Gly  Val Phe Glu Thr Val  Glu Met Leu
    1085                 1090                1095

Pro Ser  Lys Ala Gly Ile Trp  Arg Val Glu Cys Leu  Ile Gly Glu
    1100                 1105                1110

His Leu  His Ala Gly Met Ser  Thr Leu Phe Leu Val  Tyr Ser Asn
    1115                 1120                1125

Lys Cys  Gln Thr Pro Leu Gly  Met Ala Ser Gly His  Ile Arg Asp
    1130                 1135                1140

Phe Gln  Ile Thr Ala Ser Gly  Gln Tyr Gly Gln Trp  Ala Pro Lys
    1145                 1150                1155

Leu Ala  Arg Leu His Tyr Ser  Gly Ser Ile Asn Ala  Trp Ser Thr
    1160                 1165                1170

Lys Glu  Pro Phe Ser Trp Ile  Lys Val Asp Leu Leu  Ala Pro Met
    1175                 1180                1185

Ile Ile  His Gly Ile Lys Thr  Gln Gly Ala Arg Gln  Lys Phe Ser
    1190                 1195                1200

Ser Leu  Tyr Ile Ser Gln Phe  Ile Ile Met Tyr Ser  Leu Asp Gly
    1205                 1210                1215

Lys Lys  Trp Gln Thr Tyr Arg  Gly Asn Ser Thr Gly  Thr Leu Met
    1220                 1225                1230

Val Phe  Phe Gly Asn Val Asp  Ser Ser Gly Ile Lys  His Asn Ile
    1235                 1240                1245

Phe Asn  Pro Pro Ile Ile Ala  Arg Tyr Ile Arg Leu  His Pro Thr
    1250                 1255                1260

His Tyr  Ser Ile Arg Ser Thr  Leu Arg Met Glu Leu  Met Gly Cys
    1265                 1270                1275

Asp Leu  Asn Ser Cys Ser Met  Pro Leu Gly Met Glu  Ser Lys Ala
    1280                 1285                1290

Ile Ser  Asp Ala Gln Ile Thr  Ala Ser Ser Tyr Phe  Thr Asn Met
    1295                 1300                1305

Phe Ala  Thr Trp Ser Pro Ser  Lys Ala Arg Leu His  Leu Gln Gly
    1310                 1315                1320

Arg Ser  Asn Ala Trp Arg Pro  Gln Val Asn Asn Pro  Lys Glu Trp
    1325                 1330                1335
```

```
Leu Gln  Val Asp Phe Gln Lys  Thr Met Lys Val Thr  Gly Val Thr
    1340                 1345                 1350

Thr Gln  Gly Val Lys Ser Leu  Leu Thr Ser Met Tyr  Val Lys Glu
    1355                 1360                 1365

Phe Leu  Ile Ser Ser Ser Gln  Asp Gly His Gln Trp  Thr Leu Phe
    1370                 1375                 1380

Phe Gln  Asn Gly Lys Val Lys  Val Phe Gln Gly Asn  Gln Asp Ser
    1385                 1390                 1395

Phe Thr  Pro Val Val Asn Ser  Leu Asp Pro Pro Leu  Leu Thr Arg
    1400                 1405                 1410

Tyr Leu  Arg Ile His Pro Gln  Ser Trp Val His Gln  Ile Ala Leu
    1415                 1420                 1425

Arg Met  Glu Val Leu Gly Cys  Glu Ala Gln Asp Leu  Tyr
    1430                 1435                 1440


<210> SEQ ID NO 20
<211> LENGTH: 1441
<212> TYPE: PRT
<213> ORGANISM: Artificial Sequence
<220> FEATURE:
<223> OTHER INFORMATION: Mature FVIII RAQ Insertion

<400> SEQUENCE: 20

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255
```

```
Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670
```

```
Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Arg Ala Gln
            820                 825                 830

Ser Gly Ser Val Pro Gln Phe Lys Lys Val Val Phe Gln Glu Phe Thr
        835                 840                 845

Asp Gly Ser Phe Thr Gln Pro Leu Tyr Arg Gly Glu Leu Asn Glu His
    850                 855                 860

Leu Gly Leu Leu Gly Pro Tyr Ile Arg Ala Glu Val Glu Asp Asn Ile
865                 870                 875                 880

Met Val Thr Phe Arg Asn Gln Ala Ser Arg Pro Tyr Ser Phe Tyr Ser
                885                 890                 895

Ser Leu Ile Ser Tyr Glu Glu Asp Gln Arg Gln Gly Ala Glu Pro Arg
            900                 905                 910

Lys Asn Phe Val Lys Pro Asn Glu Thr Lys Thr Tyr Phe Trp Lys Val
        915                 920                 925

Gln His His Met Ala Pro Thr Lys Asp Glu Phe Asp Cys Lys Ala Trp
    930                 935                 940

Ala Tyr Phe Ser Asp Val Asp Leu Glu Lys Asp Val His Ser Gly Leu
945                 950                 955                 960

Ile Gly Pro Leu Leu Val Cys His Thr Asn Thr Leu Asn Pro Ala His
                965                 970                 975

Gly Arg Gln Val Thr Val Gln Glu Phe Ala Leu Phe Phe Thr Ile Phe
            980                 985                 990

Asp Glu Thr Lys Ser Trp Tyr Phe  Thr Glu Asn Met Glu  Arg Asn Cys
        995                 1000                1005

Arg Ala  Pro Cys Asn Ile Gln  Met Glu Asp Pro Thr  Phe Lys Glu
    1010                1015                1020

Asn Tyr  Arg Phe His Ala Ile  Asn Gly Tyr Ile Met  Asp Thr Leu
    1025                1030                1035

Pro Gly  Leu Val Met Ala Gln  Asp Gln Arg Ile Arg  Trp Tyr Leu
    1040                1045                1050

Leu Ser  Met Gly Ser Asn Glu  Asn Ile His Ser Ile  His Phe Ser
    1055                1060                1065

Gly His  Val Phe Thr Val Arg  Lys Lys Glu Glu Tyr  Lys Met Ala
    1070                1075                1080

Leu Tyr  Asn Leu Tyr Pro Gly  Val Phe Glu Thr Val  Glu Met Leu
```

```
    1085                1090                1095

Pro Ser  Lys Ala Gly Ile Trp  Arg Val Glu Cys Leu  Ile Gly Glu
    1100                1105                1110

His Leu  His Ala Gly Met Ser  Thr Leu Phe Leu Val  Tyr Ser Asn
    1115                1120                1125

Lys Cys  Gln Thr Pro Leu Gly  Met Ala Ser Gly His  Ile Arg Asp
    1130                1135                1140

Phe Gln  Ile Thr Ala Ser Gly  Gln Tyr Gly Gln Trp  Ala Pro Lys
    1145                1150                1155

Leu Ala  Arg Leu His Tyr Ser  Gly Ser Ile Asn Ala  Trp Ser Thr
    1160                1165                1170

Lys Glu  Pro Phe Ser Trp Ile  Lys Val Asp Leu Leu  Ala Pro Met
    1175                1180                1185

Ile Ile  His Gly Ile Lys Thr  Gln Gly Ala Arg Gln  Lys Phe Ser
    1190                1195                1200

Ser Leu  Tyr Ile Ser Gln Phe  Ile Ile Met Tyr Ser  Leu Asp Gly
    1205                1210                1215

Lys Lys  Trp Gln Thr Tyr Arg  Gly Asn Ser Thr Gly  Thr Leu Met
    1220                1225                1230

Val Phe  Phe Gly Asn Val Asp  Ser Ser Gly Ile Lys  His Asn Ile
    1235                1240                1245

Phe Asn  Pro Pro Ile Ile Ala  Arg Tyr Ile Arg Leu  His Pro Thr
    1250                1255                1260

His Tyr  Ser Ile Arg Ser Thr  Leu Arg Met Glu Leu  Met Gly Cys
    1265                1270                1275

Asp Leu  Asn Ser Cys Ser Met  Pro Leu Gly Met Glu  Ser Lys Ala
    1280                1285                1290

Ile Ser  Asp Ala Gln Ile Thr  Ala Ser Ser Tyr Phe  Thr Asn Met
    1295                1300                1305

Phe Ala  Thr Trp Ser Pro Ser  Lys Ala Arg Leu His  Leu Gln Gly
    1310                1315                1320

Arg Ser  Asn Ala Trp Arg Pro  Gln Val Asn Asn Pro  Lys Glu Trp
    1325                1330                1335

Leu Gln  Val Asp Phe Gln Lys  Thr Met Lys Val Thr  Gly Val Thr
    1340                1345                1350

Thr Gln  Gly Val Lys Ser Leu  Leu Thr Ser Met Tyr  Val Lys Glu
    1355                1360                1365

Phe Leu  Ile Ser Ser Ser Gln  Asp Gly His Gln Trp  Thr Leu Phe
    1370                1375                1380

Phe Gln  Asn Gly Lys Val Lys  Val Phe Gln Gly Asn  Gln Asp Ser
    1385                1390                1395

Phe Thr  Pro Val Val Asn Ser  Leu Asp Pro Pro Leu  Leu Thr Arg
    1400                1405                1410

Tyr Leu  Arg Ile His Pro Gln  Ser Trp Val His Gln  Ile Ala Leu
    1415                1420                1425

Arg Met  Glu Val Leu Gly Cys  Glu Ala Gln Asp Leu  Tyr
    1430                1435                1440
```

<210> SEQ ID NO 21
<211> LENGTH: 1441
<212> TYPE: PRT
<213> ORGANISM: Artificial Sequence
<220> FEATURE:
<223> OTHER INFORMATION: Mature FVIII RAQ Insertion R1648A

<400> SEQUENCE: 21

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415
```

```
Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Ala Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Arg Ala Gln
            820                 825                 830
```

```
Ser Gly Ser Val Pro Gln Phe Lys Lys Val Val Phe Gln Glu Phe Thr
        835                 840                 845

Asp Gly Ser Phe Thr Gln Pro Leu Tyr Arg Gly Glu Leu Asn Glu His
    850                 855                 860

Leu Gly Leu Leu Gly Pro Tyr Ile Arg Ala Glu Val Glu Asp Asn Ile
865                 870                 875                 880

Met Val Thr Phe Arg Asn Gln Ala Ser Arg Pro Tyr Ser Phe Tyr Ser
                885                 890                 895

Ser Leu Ile Ser Tyr Glu Glu Asp Gln Arg Gln Gly Ala Glu Pro Arg
            900                 905                 910

Lys Asn Phe Val Lys Pro Asn Glu Thr Lys Thr Tyr Phe Trp Lys Val
        915                 920                 925

Gln His His Met Ala Pro Thr Lys Asp Glu Phe Asp Cys Lys Ala Trp
    930                 935                 940

Ala Tyr Phe Ser Asp Val Asp Leu Glu Lys Asp Val His Ser Gly Leu
945                 950                 955                 960

Ile Gly Pro Leu Leu Val Cys His Thr Asn Thr Leu Asn Pro Ala His
                965                 970                 975

Gly Arg Gln Val Thr Val Gln Glu Phe Ala Leu Phe Phe Thr Ile Phe
            980                 985                 990

Asp Glu Thr Lys Ser Trp Tyr Phe  Thr Glu Asn Met Glu  Arg Asn Cys
        995                 1000                1005

Arg Ala  Pro Cys Asn Ile Gln  Met Glu Asp Pro Thr  Phe Lys Glu
    1010                1015                1020

Asn Tyr  Arg Phe His Ala Ile  Asn Gly Tyr Ile Met  Asp Thr Leu
    1025                1030                1035

Pro Gly  Leu Val Met Ala Gln  Asp Gln Arg Ile Arg  Trp Tyr Leu
    1040                1045                1050

Leu Ser  Met Gly Ser Asn Glu  Asn Ile His Ser Ile  His Phe Ser
    1055                1060                1065

Gly His  Val Phe Thr Val Arg  Lys Lys Glu Glu Tyr  Lys Met Ala
    1070                1075                1080

Leu Tyr  Asn Leu Tyr Pro Gly  Val Phe Glu Thr Val  Glu Met Leu
    1085                1090                1095

Pro Ser  Lys Ala Gly Ile Trp  Arg Val Glu Cys Leu  Ile Gly Glu
    1100                1105                1110

His Leu  His Ala Gly Met Ser  Thr Leu Phe Leu Val  Tyr Ser Asn
    1115                1120                1125

Lys Cys  Gln Thr Pro Leu Gly  Met Ala Ser Gly His  Ile Arg Asp
    1130                1135                1140

Phe Gln  Ile Thr Ala Ser Gly  Gln Tyr Gly Gln Trp  Ala Pro Lys
    1145                1150                1155

Leu Ala  Arg Leu His Tyr Ser  Gly Ser Ile Asn Ala  Trp Ser Thr
    1160                1165                1170

Lys Glu  Pro Phe Ser Trp Ile  Lys Val Asp Leu Leu  Ala Pro Met
    1175                1180                1185

Ile Ile  His Gly Ile Lys Thr  Gln Gly Ala Arg Gln  Lys Phe Ser
    1190                1195                1200

Ser Leu  Tyr Ile Ser Gln Phe  Ile Ile Met Tyr Ser  Leu Asp Gly
    1205                1210                1215

Lys Lys  Trp Gln Thr Tyr Arg  Gly Asn Ser Thr Gly  Thr Leu Met
    1220                1225                1230

Val Phe  Phe Gly Asn Val Asp  Ser Ser Gly Ile Lys  His Asn Ile
```

```
    1235                1240                1245

Phe Asn  Pro Pro Ile Ile Ala  Arg Tyr Ile Arg Leu  His Pro Thr
    1250                1255                1260

His Tyr  Ser Ile Arg Ser Thr  Leu Arg Met Glu Leu  Met Gly Cys
    1265                1270                1275

Asp Leu  Asn Ser Cys Ser Met  Pro Leu Gly Met Glu  Ser Lys Ala
    1280                1285                1290

Ile Ser  Asp Ala Gln Ile Thr  Ala Ser Ser Tyr Phe  Thr Asn Met
    1295                1300                1305

Phe Ala  Thr Trp Ser Pro Ser  Lys Ala Arg Leu His  Leu Gln Gly
    1310                1315                1320

Arg Ser  Asn Ala Trp Arg Pro  Gln Val Asn Asn Pro  Lys Glu Trp
    1325                1330                1335

Leu Gln  Val Asp Phe Gln Lys  Thr Met Lys Val Thr  Gly Val Thr
    1340                1345                1350

Thr Gln  Gly Val Lys Ser Leu  Leu Thr Ser Met Tyr  Val Lys Glu
    1355                1360                1365

Phe Leu  Ile Ser Ser Ser Gln  Asp Gly His Gln Trp  Thr Leu Phe
    1370                1375                1380

Phe Gln  Asn Gly Lys Val Lys  Val Phe Gln Gly Asn  Gln Asp Ser
    1385                1390                1395

Phe Thr  Pro Val Val Asn Ser  Leu Asp Pro Pro Leu  Leu Thr Arg
    1400                1405                1410

Tyr Leu  Arg Ile His Pro Gln  Ser Trp Val His Gln  Ile Ala Leu
    1415                1420                1425

Arg Met  Glu Val Leu Gly Cys  Glu Ala Gln Asp Leu  Tyr
    1430                1435                1440


<210> SEQ ID NO 22
<211> LENGTH: 36
<212> TYPE: PRT
<213> ORGANISM: Artificial Sequence
<220> FEATURE:
<223> OTHER INFORMATION: XTEN AE36

<400> SEQUENCE: 22

Gly Ser Pro Ala Gly Ser Pro Thr Ser Thr Glu Glu Gly Thr Ser Glu
1               5                   10                  15

Ser Ala Thr Pro Glu Ser Gly Pro Gly Ser Glu Pro Ala Thr Ser Gly
            20                  25                  30

Ser Glu Thr Pro
        35


<210> SEQ ID NO 23
<211> LENGTH: 72
<212> TYPE: PRT
<213> ORGANISM: Artificial Sequence
<220> FEATURE:
<223> OTHER INFORMATION: XTEN AE72

<400> SEQUENCE: 23

Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Glu Ser Ala Thr Pro Glu
            20                  25                  30

Ser Gly Pro Gly Ser Glu Pro Ala Thr Ser Gly Ser Glu Thr Pro Gly
        35                  40                  45
```

```
Thr Ser Glu Ser Ala Thr Pro Glu Ser Gly Pro Gly Thr Ser Thr Glu
    50                  55                  60

Pro Ser Glu Gly Ser Ala Pro Gly
65                  70


<210> SEQ ID NO 24
<211> LENGTH: 78
<212> TYPE: PRT
<213> ORGANISM: Artificial Sequence
<220> FEATURE:
<223> OTHER INFORMATION: XTEN AE78

<400> SEQUENCE: 24

Gly Ala Pro Thr Ser Glu Ser Ala Thr Pro Glu Ser Gly Pro Gly Ser
1               5                   10                  15

Glu Pro Ala Thr Ser Gly Ser Glu Thr Pro Gly Thr Ser Glu Ser Ala
            20                  25                  30

Thr Pro Glu Ser Gly Pro Gly Ser Glu Pro Ala Thr Ser Gly Ser Glu
        35                  40                  45

Thr Pro Gly Thr Ser Glu Ser Ala Thr Pro Glu Ser Gly Pro Gly Thr
    50                  55                  60

Ser Thr Glu Pro Ser Glu Gly Ser Ala Pro Gly Ala Ser Ser
65                  70                  75


<210> SEQ ID NO 25
<211> LENGTH: 144
<212> TYPE: PRT
<213> ORGANISM: Artificial Sequence
<220> FEATURE:
<223> OTHER INFORMATION: XTEN AE144_2A

<400> SEQUENCE: 25

Thr Ser Thr Glu Pro Ser Glu Gly Ser Ala Pro Gly Ser Pro Ala Gly
1               5                   10                  15

Ser Pro Thr Ser Thr Glu Glu Gly Thr Ser Thr Glu Pro Ser Glu Gly
            20                  25                  30

Ser Ala Pro Gly Thr Ser Thr Glu Pro Ser Glu Gly Ser Ala Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly Thr Ser Glu Ser Ala Thr Pro Glu
65                  70                  75                  80

Ser Gly Pro Gly Ser Glu Pro Ala Thr Ser Gly Ser Glu Thr Pro Gly
                85                  90                  95

Thr Ser Thr Glu Pro Ser Glu Gly Ser Ala Pro Gly Thr Ser Thr Glu
            100                 105                 110

Pro Ser Glu Gly Ser Ala Pro Gly Thr Ser Glu Ser Ala Thr Pro Glu
        115                 120                 125

Ser Gly Pro Gly Thr Ser Glu Ser Ala Thr Pro Glu Ser Gly Pro Gly
    130                 135                 140


<210> SEQ ID NO 26
<211> LENGTH: 144
<212> TYPE: PRT
<213> ORGANISM: Artificial Sequence
<220> FEATURE:
<223> OTHER INFORMATION: XTEN AE144_3B

<400> SEQUENCE: 26

Ser Pro Ala Gly Ser Pro Thr Ser Thr Glu Glu Gly Thr Ser Glu Ser
```

```
1               5                   10                  15

Ala Thr Pro Glu Ser Gly Pro Gly Ser Glu Pro Ala Thr Ser Gly Ser
            20                  25                  30

Glu Thr Pro Gly Thr Ser Glu Ser Ala Thr Pro Glu Ser Gly Pro Gly
        35                  40                  45

Thr Ser Thr Glu Pro Ser Glu Gly Ser Ala Pro Gly Thr Ser Thr Glu
    50                  55                  60

Pro Ser Glu Gly Ser Ala Pro Gly Thr Ser Thr Glu Pro Ser Glu Gly
65                  70                  75                  80

Ser Ala Pro Gly Thr Ser Thr Glu Pro Ser Glu Gly Ser Ala Pro Gly
                85                  90                  95

Thr Ser Thr Glu Pro Ser Glu Gly Ser Ala Pro Gly Thr Ser Thr Glu
            100                 105                 110

Pro Ser Glu Gly Ser Ala Pro Gly Ser Pro Ala Gly Ser Pro Thr Ser
        115                 120                 125

Thr Glu Glu Gly Thr Ser Thr Glu Pro Ser Glu Gly Ser Ala Pro Gly
    130                 135                 140


<210> SEQ ID NO 27
<211> LENGTH: 144
<212> TYPE: PRT
<213> ORGANISM: Artificial Sequence
<220> FEATURE:
<223> OTHER INFORMATION: XTEN AE144_4A

<400> SEQUENCE: 27

Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Glu Ser Ala Thr Pro Glu
            20                  25                  30

Ser Gly Pro Gly Ser Glu Pro Ala Thr Ser Gly Ser Glu Thr Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly Thr Ser Glu Ser Ala Thr Pro Glu
65                  70                  75                  80

Ser Gly Pro Gly Ser Pro Ala Gly Ser Pro Thr Ser Thr Glu Glu Gly
                85                  90                  95

Ser Pro Ala Gly Ser Pro Thr Ser Thr Glu Glu Gly Ser Pro Ala Gly
            100                 105                 110

Ser Pro Thr Ser Thr Glu Glu Gly Thr Ser Glu Ser Ala Thr Pro Glu
        115                 120                 125

Ser Gly Pro Gly Thr Ser Thr Glu Pro Ser Glu Gly Ser Ala Pro Gly
    130                 135                 140


<210> SEQ ID NO 28
<211> LENGTH: 144
<212> TYPE: PRT
<213> ORGANISM: Artificial Sequence
<220> FEATURE:
<223> OTHER INFORMATION: XTEN AE144_5A

<400> SEQUENCE: 28

Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Glu Ser Ala Thr Pro Glu
            20                  25                  30
```

```
Ser Gly Pro Gly Ser Glu Pro Ala Thr Ser Gly Ser Glu Thr Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly Ser Pro Ala Gly Ser Pro Thr Ser
65                  70                  75                  80

Thr Glu Glu Gly Thr Ser Glu Ser Ala Thr Pro Glu Ser Gly Pro Gly
                85                  90                  95

Ser Glu Pro Ala Thr Ser Gly Ser Glu Thr Pro Gly Thr Ser Glu Ser
            100                 105                 110

Ala Thr Pro Glu Ser Gly Pro Gly Ser Pro Ala Gly Ser Pro Thr Ser
        115                 120                 125

Thr Glu Glu Gly Ser Pro Ala Gly Ser Pro Thr Ser Thr Glu Glu Gly
    130                 135                 140
```

<210> SEQ ID NO 29
<211> LENGTH: 144
<212> TYPE: PRT
<213> ORGANISM: Artificial Sequence
<220> FEATURE:
<223> OTHER INFORMATION: XTEN AE144_6B

<400> SEQUENCE: 29

```
Thr Ser Thr Glu Pro Ser Glu Gly Ser Ala Pro Gly Thr Ser Glu Ser
1               5                   10                  15

Ala Thr Pro Glu Ser Gly Pro Gly Thr Ser Glu Ser Ala Thr Pro Glu
            20                  25                  30

Ser Gly Pro Gly Thr Ser Glu Ser Ala Thr Pro Glu Ser Gly Pro Gly
        35                  40                  45

Ser Glu Pro Ala Thr Ser Gly Ser Glu Thr Pro Gly Ser Glu Pro Ala
    50                  55                  60

Thr Ser Gly Ser Glu Thr Pro Gly Ser Pro Ala Gly Ser Pro Thr Ser
65                  70                  75                  80

Thr Glu Glu Gly Thr Ser Thr Glu Pro Ser Glu Gly Ser Ala Pro Gly
                85                  90                  95

Thr Ser Thr Glu Pro Ser Glu Gly Ser Ala Pro Gly Ser Glu Pro Ala
            100                 105                 110

Thr Ser Gly Ser Glu Thr Pro Gly Thr Ser Glu Ser Ala Thr Pro Glu
        115                 120                 125

Ser Gly Pro Gly Thr Ser Thr Glu Pro Ser Glu Gly Ser Ala Pro Gly
    130                 135                 140
```

<210> SEQ ID NO 30
<211> LENGTH: 144
<212> TYPE: PRT
<213> ORGANISM: Artificial Sequence
<220> FEATURE:
<223> OTHER INFORMATION: XTEN AG144_A

<400> SEQUENCE: 30

```
Gly Ala Ser Pro Gly Thr Ser Ser Thr Gly Ser Pro Gly Ser Ser Pro
1               5                   10                  15

Ser Ala Ser Thr Gly Thr Gly Pro Gly Ser Ser Pro Ser Ala Ser Thr
            20                  25                  30

Gly Thr Gly Pro Gly Thr Pro Gly Ser Gly Thr Ala Ser Ser Ser Pro
        35                  40                  45

Gly Ser Ser Thr Pro Ser Gly Ala Thr Gly Ser Pro Gly Ser Ser Pro
    50                  55                  60
```

```
Ser Ala Ser Thr Gly Thr Gly Pro Gly Ala Ser Pro Gly Thr Ser Ser
65                  70                  75                  80

Thr Gly Ser Pro Gly Thr Pro Gly Ser Gly Thr Ala Ser Ser Ser Pro
                85                  90                  95

Gly Ser Ser Thr Pro Ser Gly Ala Thr Gly Ser Pro Gly Thr Pro Gly
            100                 105                 110

Ser Gly Thr Ala Ser Ser Ser Pro Gly Ala Ser Pro Gly Thr Ser Ser
        115                 120                 125

Thr Gly Ser Pro Gly Ala Ser Pro Gly Thr Ser Ser Thr Gly Ser Pro
    130                 135                 140


<210> SEQ ID NO 31
<211> LENGTH: 144
<212> TYPE: PRT
<213> ORGANISM: Artificial Sequence
<220> FEATURE:
<223> OTHER INFORMATION: XTEN AG144_B

<400> SEQUENCE: 31

Gly Thr Pro Gly Ser Gly Thr Ala Ser Ser Ser Pro Gly Ser Ser Thr
1               5                   10                  15

Pro Ser Gly Ala Thr Gly Ser Pro Gly Ala Ser Pro Gly Thr Ser Ser
            20                  25                  30

Thr Gly Ser Pro Gly Thr Pro Gly Ser Gly Thr Ala Ser Ser Ser Pro
        35                  40                  45

Gly Ser Ser Thr Pro Ser Gly Ala Thr Gly Ser Pro Gly Ser Ser Pro
    50                  55                  60

Ser Ala Ser Thr Gly Thr Gly Pro Gly Ser Ser Pro Ser Ala Ser Thr
65                  70                  75                  80

Gly Thr Gly Pro Gly Ser Ser Thr Pro Ser Gly Ala Thr Gly Ser Pro
                85                  90                  95

Gly Ser Ser Thr Pro Ser Gly Ala Thr Gly Ser Pro Gly Ala Ser Pro
            100                 105                 110

Gly Thr Ser Ser Thr Gly Ser Pro Gly Ala Ser Pro Gly Thr Ser Ser
        115                 120                 125

Thr Gly Ser Pro Gly Ala Ser Pro Gly Thr Ser Ser Thr Gly Ser Pro
    130                 135                 140


<210> SEQ ID NO 32
<211> LENGTH: 144
<212> TYPE: PRT
<213> ORGANISM: Artificial Sequence
<220> FEATURE:
<223> OTHER INFORMATION: XTEN AG144_C

<400> SEQUENCE: 32

Gly Thr Pro Gly Ser Gly Thr Ala Ser Ser Ser Pro Gly Ala Ser Pro
1               5                   10                  15

Gly Thr Ser Ser Thr Gly Ser Pro Gly Ala Ser Pro Gly Thr Ser Ser
            20                  25                  30

Thr Gly Ser Pro Gly Ala Ser Pro Gly Thr Ser Ser Thr Gly Ser Pro
        35                  40                  45

Gly Ser Ser Pro Ser Ala Ser Thr Gly Thr Gly Pro Gly Thr Pro Gly
    50                  55                  60

Ser Gly Thr Ala Ser Ser Ser Pro Gly Ala Ser Pro Gly Thr Ser Ser
65                  70                  75                  80

Thr Gly Ser Pro Gly Ala Ser Pro Gly Thr Ser Ser Thr Gly Ser Pro
```

```
                85                  90                  95

Gly Ala Ser Pro Gly Thr Ser Ser Thr Gly Ser Pro Gly Ser Ser Thr
            100                 105                 110

Pro Ser Gly Ala Thr Gly Ser Pro Gly Ser Ser Thr Pro Ser Gly Ala
        115                 120                 125

Thr Gly Ser Pro Gly Ala Ser Pro Gly Thr Ser Ser Thr Gly Ser Pro
    130                 135                 140


<210> SEQ ID NO 33
<211> LENGTH: 144
<212> TYPE: PRT
<213> ORGANISM: Artificial Sequence
<220> FEATURE:
<223> OTHER INFORMATION: XTEN AG144_F

<400> SEQUENCE: 33

Gly Ser Ser Pro Ser Ala Ser Thr Gly Thr Gly Pro Gly Ser Ser Pro
1               5                   10                  15

Ser Ala Ser Thr Gly Thr Gly Pro Gly Ala Ser Pro Gly Thr Ser Ser
            20                  25                  30

Thr Gly Ser Pro Gly Ala Ser Pro Gly Thr Ser Ser Thr Gly Ser Pro
        35                  40                  45

Gly Ser Ser Thr Pro Ser Gly Ala Thr Gly Ser Pro Gly Ser Ser Pro
    50                  55                  60

Ser Ala Ser Thr Gly Thr Gly Pro Gly Ala Ser Pro Gly Thr Ser Ser
65                  70                  75                  80

Thr Gly Ser Pro Gly Ser Ser Pro Ser Ala Ser Thr Gly Thr Gly Pro
                85                  90                  95

Gly Thr Pro Gly Ser Gly Thr Ala Ser Ser Ser Pro Gly Ser Ser Thr
            100                 105                 110

Pro Ser Gly Ala Thr Gly Ser Pro Gly Ser Ser Thr Pro Ser Gly Ala
        115                 120                 125

Thr Gly Ser Pro Gly Ala Ser Pro Gly Thr Ser Ser Thr Gly Ser Pro
    130                 135                 140


<210> SEQ ID NO 34
<211> LENGTH: 288
<212> TYPE: PRT
<213> ORGANISM: Artificial Sequence
<220> FEATURE:
<223> OTHER INFORMATION: XTEN AE288_2

<400> SEQUENCE: 34

Gly Ser Pro Ala Gly Ser Pro Thr Ser Thr Glu Glu Gly Thr Ser Glu
1               5                   10                  15

Ser Ala Thr Pro Glu Ser Gly Pro Gly Ser Glu Pro Ala Thr Ser Gly
            20                  25                  30

Ser Glu Thr Pro Gly Thr Ser Glu Ser Ala Thr Pro Glu Ser Gly Pro
        35                  40                  45

Gly Thr Ser Thr Glu Pro Ser Glu Gly Ser Ala Pro Gly Thr Ser Thr
    50                  55                  60

Glu Pro Ser Glu Gly Ser Ala Pro Gly Thr Ser Thr Glu Pro Ser Glu
65                  70                  75                  80

Gly Ser Ala Pro Gly Thr Ser Thr Glu Pro Ser Glu Gly Ser Ala Pro
                85                  90                  95

Gly Thr Ser Thr Glu Pro Ser Glu Gly Ser Ala Pro Gly Thr Ser Thr
            100                 105                 110
```

```
Glu Pro Ser Glu Gly Ser Ala Pro Gly Ser Pro Ala Gly Ser Pro Thr
        115                 120                 125

Ser Thr Glu Glu Gly Thr Ser Thr Glu Pro Ser Glu Gly Ser Ala Pro
    130                 135                 140

Gly Thr Ser Glu Ser Ala Thr Pro Glu Ser Gly Pro Gly Ser Glu Pro
145                 150                 155                 160

Ala Thr Ser Gly Ser Glu Thr Pro Gly Thr Ser Glu Ser Ala Thr Pro
                165                 170                 175

Glu Ser Gly Pro Gly Ser Glu Pro Ala Thr Ser Gly Ser Glu Thr Pro
            180                 185                 190

Gly Thr Ser Glu Ser Ala Thr Pro Glu Ser Gly Pro Gly Thr Ser Thr
        195                 200                 205

Glu Pro Ser Glu Gly Ser Ala Pro Gly Thr Ser Glu Ser Ala Thr Pro
    210                 215                 220

Glu Ser Gly Pro Gly Ser Pro Ala Gly Ser Pro Thr Ser Thr Glu Glu
225                 230                 235                 240

Gly Ser Pro Ala Gly Ser Pro Thr Ser Thr Glu Glu Gly Ser Pro Ala
                245                 250                 255

Gly Ser Pro Thr Ser Thr Glu Glu Gly Thr Ser Glu Ser Ala Thr Pro
            260                 265                 270

Glu Ser Gly Pro Gly Thr Ser Thr Glu Pro Ser Glu Gly Ser Ala Pro
        275                 280                 285
```

<210> SEQ ID NO 35
<211> LENGTH: 1896
<212> TYPE: PRT
<213> ORGANISM: Artificial Sequence
<220> FEATURE:
<223> OTHER INFORMATION: FVIII198

<400> SEQUENCE: 35

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190
```

```
Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
```

```
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Glu Ile Thr Arg Thr Thr Leu
            980                 985                 990

Gln Ser Asp Gln Glu Glu Ile Asp  Tyr Asp Asp Thr Ile  Ser Val Glu
        995                 1000                1005

Met Lys  Lys Glu Asp Phe Asp  Ile Tyr Asp Glu Asp  Glu Asn Gln
    1010                1015                1020

Ser Pro  Arg Ser Phe Gln Lys  Lys Thr Arg His Tyr  Phe Ile Ala
    1025                1030                1035
```

```
Ala Val  Glu Arg Leu Trp Asp  Tyr Gly Met Ser Ser  Ser Pro His
    1040                 1045                 1050

Val Leu  Arg Asn Arg Ala Gln  Ser Gly Ser Val Pro  Gln Phe Lys
    1055                 1060                 1065

Lys Val  Val Phe Gln Glu Phe  Thr Asp Gly Ser Phe  Thr Gln Pro
    1070                 1075                 1080

Leu Tyr  Arg Gly Glu Leu Asn  Glu His Leu Gly Leu  Leu Gly Pro
    1085                 1090                 1095

Tyr Ile  Arg Ala Glu Val Glu  Asp Asn Ile Met Val  Thr Phe Arg
    1100                 1105                 1110

Asn Gln  Ala Ser Arg Pro Tyr  Ser Phe Tyr Ser Ser  Leu Ile Ser
    1115                 1120                 1125

Tyr Glu  Glu Asp Gln Arg Gln  Gly Ala Glu Pro Arg  Lys Asn Phe
    1130                 1135                 1140

Val Lys  Pro Asn Glu Thr Lys  Thr Tyr Phe Trp Lys  Val Gln His
    1145                 1150                 1155

His Met  Ala Pro Thr Lys Asp  Glu Phe Asp Cys Lys  Ala Trp Ala
    1160                 1165                 1170

Tyr Phe  Ser Asp Val Asp Leu  Glu Lys Asp Val His  Ser Gly Leu
    1175                 1180                 1185

Ile Gly  Pro Leu Leu Val Cys  His Thr Asn Thr Leu  Asn Pro Ala
    1190                 1195                 1200

His Gly  Arg Gln Val Thr Val  Gln Glu Phe Ala Leu  Phe Phe Thr
    1205                 1210                 1215

Ile Phe  Asp Glu Thr Lys Ser  Trp Tyr Phe Thr Glu  Asn Met Glu
    1220                 1225                 1230

Arg Asn  Cys Arg Ala Pro Cys  Asn Ile Gln Met Glu  Asp Pro Thr
    1235                 1240                 1245

Phe Lys  Glu Asn Tyr Arg Phe  His Ala Ile Asn Gly  Tyr Ile Met
    1250                 1255                 1260

Asp Thr  Leu Pro Gly Leu Val  Met Ala Gln Asp Gln  Arg Ile Arg
    1265                 1270                 1275

Trp Tyr  Leu Leu Ser Met Gly  Ser Asn Glu Asn Ile  His Ser Ile
    1280                 1285                 1290

His Phe  Ser Gly His Val Phe  Thr Val Arg Lys Lys  Glu Glu Tyr
    1295                 1300                 1305

Lys Met  Ala Leu Tyr Asn Leu  Tyr Pro Gly Val Phe  Glu Thr Val
    1310                 1315                 1320

Glu Met  Leu Pro Ser Lys Ala  Gly Ile Trp Arg Val  Glu Cys Leu
    1325                 1330                 1335

Ile Gly  Glu His Leu His Ala  Gly Met Ser Thr Leu  Phe Leu Val
    1340                 1345                 1350

Tyr Ser  Asn Lys Cys Gln Thr  Pro Leu Gly Met Ala  Ser Gly His
    1355                 1360                 1365

Ile Arg  Asp Phe Gln Ile Thr  Ala Ser Gly Gln Tyr  Gly Gln Trp
    1370                 1375                 1380

Ala Pro  Lys Leu Ala Arg Leu  His Tyr Ser Gly Ser  Ile Asn Ala
    1385                 1390                 1395

Trp Ser  Thr Lys Glu Pro Phe  Ser Trp Ile Lys Val  Asp Leu Leu
    1400                 1405                 1410

Ala Pro  Met Ile Ile His Gly  Ile Lys Thr Gln Gly  Ala Arg Gln
    1415                 1420                 1425
```

```
Lys Phe Ser Ser Leu Tyr Ile Ser Gln Phe Ile Ile Met Tyr Ser
    1430                1435                1440

Leu Asp Gly Lys Lys Trp Gln Thr Tyr Arg Gly Asn Ser Thr Gly
    1445                1450                1455

Thr Leu Met Val Phe Phe Gly Asn Val Asp Ser Ser Gly Ile Lys
    1460                1465                1470

His Asn Ile Phe Asn Pro Pro Ile Ile Ala Arg Tyr Ile Arg Leu
    1475                1480                1485

His Pro Thr His Tyr Ser Ile Arg Ser Thr Leu Arg Met Glu Leu
    1490                1495                1500

Met Gly Cys Asp Leu Asn Ser Cys Ser Met Pro Leu Gly Met Glu
    1505                1510                1515

Ser Lys Ala Ile Ser Asp Ala Gln Ile Thr Ala Ser Ser Tyr Phe
    1520                1525                1530

Thr Asn Met Phe Ala Thr Trp Ser Pro Ser Lys Ala Arg Leu His
    1535                1540                1545

Leu Gln Gly Arg Ser Asn Ala Trp Arg Pro Gln Val Asn Asn Pro
    1550                1555                1560

Lys Glu Trp Leu Gln Val Asp Phe Gln Lys Thr Met Lys Val Thr
    1565                1570                1575

Gly Val Thr Thr Gln Gly Val Lys Ser Leu Leu Thr Ser Met Tyr
    1580                1585                1590

Val Lys Glu Phe Leu Ile Ser Ser Ser Gln Asp Gly His Gln Trp
    1595                1600                1605

Thr Leu Phe Phe Gln Asn Gly Lys Val Lys Val Phe Gln Gly Asn
    1610                1615                1620

Gln Asp Ser Phe Thr Pro Val Val Asn Ser Leu Asp Pro Pro Leu
    1625                1630                1635

Leu Thr Arg Tyr Leu Arg Ile His Pro Gln Ser Trp Val His Gln
    1640                1645                1650

Ile Ala Leu Arg Met Glu Val Leu Gly Cys Glu Ala Gln Asp Leu
    1655                1660                1665

Tyr Asp Lys Thr His Thr Cys Pro Pro Cys Pro Ala Pro Glu Leu
    1670                1675                1680

Leu Gly Gly Pro Ser Val Phe Leu Phe Pro Pro Lys Pro Lys Asp
    1685                1690                1695

Thr Leu Met Ile Ser Arg Thr Pro Glu Val Thr Cys Val Val Val
    1700                1705                1710

Asp Val Ser His Glu Asp Pro Glu Val Lys Phe Asn Trp Tyr Val
    1715                1720                1725

Asp Gly Val Glu Val His Asn Ala Lys Thr Lys Pro Arg Glu Glu
    1730                1735                1740

Gln Tyr Asn Ser Thr Tyr Arg Val Val Ser Val Leu Thr Val Leu
    1745                1750                1755

His Gln Asp Trp Leu Asn Gly Lys Glu Tyr Lys Cys Lys Val Ser
    1760                1765                1770

Asn Lys Ala Leu Pro Ala Pro Ile Glu Lys Thr Ile Ser Lys Ala
    1775                1780                1785

Lys Gly Gln Pro Arg Glu Pro Gln Val Tyr Thr Leu Pro Pro Ser
    1790                1795                1800

Arg Asp Glu Leu Thr Lys Asn Gln Val Ser Leu Thr Cys Leu Val
    1805                1810                1815

Lys Gly Phe Tyr Pro Ser Asp Ile Ala Val Glu Trp Glu Ser Asn
```

```
    1820                1825                1830

Gly Gln  Pro Glu Asn Asn Tyr  Lys Thr Thr Pro Pro  Val Leu Asp
    1835                1840                1845

Ser Asp  Gly Ser Phe Phe Leu  Tyr Ser Lys Leu Thr  Val Asp Lys
    1850                1855                1860

Ser Arg  Trp Gln Gln Gly Asn  Val Phe Ser Cys Ser  Val Met His
    1865                1870                1875

Glu Ala  Leu His Asn His Tyr  Thr Gln Lys Ser Leu  Ser Leu Ser
    1880                1885                1890

Pro Gly  Lys
    1895


<210> SEQ ID NO 36
<211> LENGTH: 42
<212> TYPE: PRT
<213> ORGANISM: Artificial Sequence
<220> FEATURE:
<223> OTHER INFORMATION: XTEN AE42

<400> SEQUENCE: 36

Gly Ala Pro Gly Ser Pro Ala Gly Ser Pro Thr Ser Thr Glu Glu Gly
1               5                   10                  15

Thr Ser Glu Ser Ala Thr Pro Glu Ser Gly Pro Gly Ser Glu Pro Ala
            20                  25                  30

Thr Ser Gly Ser Glu Thr Pro Ala Ser Ser
        35                  40


<210> SEQ ID NO 37
<211> LENGTH: 144
<212> TYPE: PRT
<213> ORGANISM: Artificial Sequence
<220> FEATURE:
<223> OTHER INFORMATION: XTEN AE144

<400> SEQUENCE: 37

Gly Ser Glu Pro Ala Thr Ser Gly Ser Glu Thr Pro Gly Thr Ser Glu
1               5                   10                  15

Ser Ala Thr Pro Glu Ser Gly Pro Gly Ser Glu Pro Ala Thr Ser Gly
            20                  25                  30

Ser Glu Thr Pro Gly Ser Pro Ala Gly Ser Pro Thr Ser Thr Glu Glu
        35                  40                  45

Gly Thr Ser Thr Glu Pro Ser Glu Gly Ser Ala Pro Gly Ser Glu Pro
    50                  55                  60

Ala Thr Ser Gly Ser Glu Thr Pro Gly Ser Glu Pro Ala Thr Ser Gly
65                  70                  75                  80

Ser Glu Thr Pro Gly Ser Glu Pro Ala Thr Ser Gly Ser Glu Thr Pro
                85                  90                  95

Gly Thr Ser Thr Glu Pro Ser Glu Gly Ser Ala Pro Gly Thr Ser Glu
            100                 105                 110

Ser Ala Thr Pro Glu Ser Gly Pro Gly Ser Glu Pro Ala Thr Ser Gly
        115                 120                 125

Ser Glu Thr Pro Gly Thr Ser Thr Glu Pro Ser Glu Gly Ser Ala Pro
    130                 135                 140


<210> SEQ ID NO 38
<211> LENGTH: 144
<212> TYPE: PRT
<213> ORGANISM: Artificial Sequence
<220> FEATURE:
```

<223> OTHER INFORMATION: XTEN AG144

<400> SEQUENCE: 38

```
Gly Thr Pro Gly Ser Gly Thr Ala Ser Ser Ser Pro Gly Ser Ser Thr
1               5                   10                  15

Pro Ser Gly Ala Thr Gly Ser Pro Gly Ser Ser Pro Ser Ala Ser Thr
            20                  25                  30

Gly Thr Gly Pro Gly Ser Ser Pro Ser Ala Ser Thr Gly Thr Gly Pro
        35                  40                  45

Gly Ala Ser Pro Gly Thr Ser Ser Thr Gly Ser Pro Gly Ala Ser Pro
    50                  55                  60

Gly Thr Ser Ser Thr Gly Ser Pro Gly Ser Ser Thr Pro Ser Gly Ala
65                  70                  75                  80

Thr Gly Ser Pro Gly Ser Ser Pro Ser Ala Ser Thr Gly Thr Gly Pro
                85                  90                  95

Gly Ala Ser Pro Gly Thr Ser Ser Thr Gly Ser Pro Gly Ser Ser Pro
            100                 105                 110

Ser Ala Ser Thr Gly Thr Gly Pro Gly Thr Pro Gly Ser Gly Thr Ala
        115                 120                 125

Ser Ser Ser Pro Gly Ser Ser Thr Pro Ser Gly Ala Thr Gly Ser Pro
    130                 135                 140
```

<210> SEQ ID NO 39
<211> LENGTH: 288
<212> TYPE: PRT
<213> ORGANISM: Artificial Sequence
<220> FEATURE:
<223> OTHER INFORMATION: XTEN AE288

<400> SEQUENCE: 39

```
Gly Thr Ser Glu Ser Ala Thr Pro Glu Ser Gly Pro Gly Ser Glu Pro
1               5                   10                  15

Ala Thr Ser Gly Ser Glu Thr Pro Gly Thr Ser Glu Ser Ala Thr Pro
            20                  25                  30

Glu Ser Gly Pro Gly Ser Glu Pro Ala Thr Ser Gly Ser Glu Thr Pro
        35                  40                  45

Gly Thr Ser Glu Ser Ala Thr Pro Glu Ser Gly Pro Gly Thr Ser Thr
    50                  55                  60

Glu Pro Ser Glu Gly Ser Ala Pro Gly Ser Pro Ala Gly Ser Pro Thr
65                  70                  75                  80

Ser Thr Glu Glu Gly Thr Ser Glu Ser Ala Thr Pro Glu Ser Gly Pro
                85                  90                  95

Gly Ser Glu Pro Ala Thr Ser Gly Ser Glu Thr Pro Gly Thr Ser Glu
            100                 105                 110

Ser Ala Thr Pro Glu Ser Gly Pro Gly Ser Pro Ala Gly Ser Pro Thr
        115                 120                 125

Ser Thr Glu Glu Gly Ser Pro Ala Gly Ser Pro Thr Ser Thr Glu Glu
    130                 135                 140

Gly Thr Ser Thr Glu Pro Ser Glu Gly Ser Ala Pro Gly Thr Ser Glu
145                 150                 155                 160

Ser Ala Thr Pro Glu Ser Gly Pro Gly Thr Ser Glu Ser Ala Thr Pro
                165                 170                 175

Glu Ser Gly Pro Gly Thr Ser Glu Ser Ala Thr Pro Glu Ser Gly Pro
            180                 185                 190

Gly Ser Glu Pro Ala Thr Ser Gly Ser Glu Thr Pro Gly Ser Glu Pro
        195                 200                 205
```

```
Ala Thr Ser Gly Ser Glu Thr Pro Gly Ser Pro Ala Gly Ser Pro Thr
    210                 215                 220

Ser Thr Glu Glu Gly Thr Ser Thr Glu Pro Ser Glu Gly Ser Ala Pro
225                 230                 235                 240

Gly Thr Ser Thr Glu Pro Ser Glu Gly Ser Ala Pro Gly Ser Glu Pro
                245                 250                 255

Ala Thr Ser Gly Ser Glu Thr Pro Gly Thr Ser Glu Ser Ala Thr Pro
            260                 265                 270

Glu Ser Gly Pro Gly Thr Ser Thr Glu Pro Ser Glu Gly Ser Ala Pro
        275                 280                 285


<210> SEQ ID NO 40
<211> LENGTH: 288
<212> TYPE: PRT
<213> ORGANISM: Artificial Sequence
<220> FEATURE:
<223> OTHER INFORMATION: XTEN AG288

<400> SEQUENCE: 40

Pro Gly Ala Ser Pro Gly Thr Ser Ser Thr Gly Ser Pro Gly Ala Ser
1               5                   10                  15

Pro Gly Thr Ser Ser Thr Gly Ser Pro Gly Thr Pro Gly Ser Gly Thr
            20                  25                  30

Ala Ser Ser Ser Pro Gly Ser Ser Thr Pro Ser Gly Ala Thr Gly Ser
        35                  40                  45

Pro Gly Thr Pro Gly Ser Gly Thr Ala Ser Ser Ser Pro Gly Ser Ser
    50                  55                  60

Thr Pro Ser Gly Ala Thr Gly Ser Pro Gly Thr Pro Gly Ser Gly Thr
65                  70                  75                  80

Ala Ser Ser Ser Pro Gly Ser Ser Thr Pro Ser Gly Ala Thr Gly Ser
                85                  90                  95

Pro Gly Ser Ser Thr Pro Ser Gly Ala Thr Gly Ser Pro Gly Ser Ser
            100                 105                 110

Pro Ser Ala Ser Thr Gly Thr Gly Pro Gly Ser Ser Pro Ser Ala Ser
        115                 120                 125

Thr Gly Thr Gly Pro Gly Ala Ser Pro Gly Thr Ser Ser Thr Gly Ser
    130                 135                 140

Pro Gly Thr Pro Gly Ser Gly Thr Ala Ser Ser Ser Pro Gly Ser Ser
145                 150                 155                 160

Thr Pro Ser Gly Ala Thr Gly Ser Pro Gly Ser Ser Pro Ser Ala Ser
                165                 170                 175

Thr Gly Thr Gly Pro Gly Ser Ser Pro Ser Ala Ser Thr Gly Thr Gly
            180                 185                 190

Pro Gly Ala Ser Pro Gly Thr Ser Ser Thr Gly Ser Pro Gly Ala Ser
        195                 200                 205

Pro Gly Thr Ser Ser Thr Gly Ser Pro Gly Ser Ser Thr Pro Ser Gly
    210                 215                 220

Ala Thr Gly Ser Pro Gly Ser Ser Pro Ser Ala Ser Thr Gly Thr Gly
225                 230                 235                 240

Pro Gly Ala Ser Pro Gly Thr Ser Ser Thr Gly Ser Pro Gly Ser Ser
                245                 250                 255

Pro Ser Ala Ser Thr Gly Thr Gly Pro Gly Thr Pro Gly Ser Gly Thr
            260                 265                 270

Ala Ser Ser Ser Pro Gly Ser Ser Thr Pro Ser Gly Ala Thr Gly Ser
        275                 280                 285
```

<210> SEQ ID NO 41
<211> LENGTH: 576
<212> TYPE: PRT
<213> ORGANISM: Artificial Sequence
<220> FEATURE:
<223> OTHER INFORMATION: XTEN AE576

<400> SEQUENCE: 41

```
Gly Ser Pro Ala Gly Ser Pro Thr Ser Thr Glu Glu Gly Thr Ser Glu
1               5                   10                  15

Ser Ala Thr Pro Glu Ser Gly Pro Gly Thr Ser Thr Glu Pro Ser Glu
            20                  25                  30

Gly Ser Ala Pro Gly Ser Pro Ala Gly Ser Pro Thr Ser Thr Glu Glu
        35                  40                  45

Gly Thr Ser Thr Glu Pro Ser Glu Gly Ser Ala Pro Gly Thr Ser Thr
    50                  55                  60

Glu Pro Ser Glu Gly Ser Ala Pro Gly Thr Ser Glu Ser Ala Thr Pro
65                  70                  75                  80

Glu Ser Gly Pro Gly Ser Glu Pro Ala Thr Ser Gly Ser Glu Thr Pro
                85                  90                  95

Gly Ser Glu Pro Ala Thr Ser Gly Ser Glu Thr Pro Gly Ser Pro Ala
            100                 105                 110

Gly Ser Pro Thr Ser Thr Glu Glu Gly Thr Ser Glu Ser Ala Thr Pro
        115                 120                 125

Glu Ser Gly Pro Gly Thr Ser Thr Glu Pro Ser Glu Gly Ser Ala Pro
    130                 135                 140

Gly Thr Ser Thr Glu Pro Ser Glu Gly Ser Ala Pro Gly Ser Pro Ala
145                 150                 155                 160

Gly Ser Pro Thr Ser Thr Glu Glu Gly Thr Ser Thr Glu Pro Ser Glu
                165                 170                 175

Gly Ser Ala Pro Gly Thr Ser Thr Glu Pro Ser Glu Gly Ser Ala Pro
            180                 185                 190

Gly Thr Ser Glu Ser Ala Thr Pro Glu Ser Gly Pro Gly Thr Ser Thr
        195                 200                 205

Glu Pro Ser Glu Gly Ser Ala Pro Gly Thr Ser Glu Ser Ala Thr Pro
    210                 215                 220

Glu Ser Gly Pro Gly Ser Glu Pro Ala Thr Ser Gly Ser Glu Thr Pro
225                 230                 235                 240

Gly Thr Ser Thr Glu Pro Ser Glu Gly Ser Ala Pro Gly Thr Ser Thr
                245                 250                 255

Glu Pro Ser Glu Gly Ser Ala Pro Gly Thr Ser Glu Ser Ala Thr Pro
            260                 265                 270

Glu Ser Gly Pro Gly Thr Ser Glu Ser Ala Thr Pro Glu Ser Gly Pro
        275                 280                 285

Gly Ser Pro Ala Gly Ser Pro Thr Ser Thr Glu Glu Gly Thr Ser Glu
    290                 295                 300

Ser Ala Thr Pro Glu Ser Gly Pro Gly Ser Glu Pro Ala Thr Ser Gly
305                 310                 315                 320

Ser Glu Thr Pro Gly Thr Ser Glu Ser Ala Thr Pro Glu Ser Gly Pro
                325                 330                 335

Gly Thr Ser Thr Glu Pro Ser Glu Gly Ser Ala Pro Gly Thr Ser Thr
            340                 345                 350

Glu Pro Ser Glu Gly Ser Ala Pro Gly Thr Ser Thr Glu Pro Ser Glu
        355                 360                 365
```

```
Gly Ser Ala Pro Gly Thr Ser Thr Glu Pro Ser Glu Gly Ser Ala Pro
    370                 375                 380

Gly Thr Ser Thr Glu Pro Ser Glu Gly Ser Ala Pro Gly Thr Ser Thr
385                 390                 395                 400

Glu Pro Ser Glu Gly Ser Ala Pro Gly Ser Pro Ala Gly Ser Pro Thr
                405                 410                 415

Ser Thr Glu Glu Gly Thr Ser Thr Glu Pro Ser Glu Gly Ser Ala Pro
            420                 425                 430

Gly Thr Ser Glu Ser Ala Thr Pro Glu Ser Gly Pro Gly Ser Glu Pro
        435                 440                 445

Ala Thr Ser Gly Ser Glu Thr Pro Gly Thr Ser Glu Ser Ala Thr Pro
    450                 455                 460

Glu Ser Gly Pro Gly Ser Glu Pro Ala Thr Ser Gly Ser Glu Thr Pro
465                 470                 475                 480

Gly Thr Ser Glu Ser Ala Thr Pro Glu Ser Gly Pro Gly Thr Ser Thr
                485                 490                 495

Glu Pro Ser Glu Gly Ser Ala Pro Gly Thr Ser Glu Ser Ala Thr Pro
            500                 505                 510

Glu Ser Gly Pro Gly Ser Pro Ala Gly Ser Pro Thr Ser Thr Glu Glu
        515                 520                 525

Gly Ser Pro Ala Gly Ser Pro Thr Ser Thr Glu Glu Gly Ser Pro Ala
    530                 535                 540

Gly Ser Pro Thr Ser Thr Glu Glu Gly Thr Ser Glu Ser Ala Thr Pro
545                 550                 555                 560

Glu Ser Gly Pro Gly Thr Ser Thr Glu Pro Ser Glu Gly Ser Ala Pro
                565                 570                 575


<210> SEQ ID NO 42
<211> LENGTH: 576
<212> TYPE: PRT
<213> ORGANISM: Artificial Sequence
<220> FEATURE:
<223> OTHER INFORMATION: XTEN AG576

<400> SEQUENCE: 42

Pro Gly Thr Pro Gly Ser Gly Thr Ala Ser Ser Ser Pro Gly Ser Ser
1               5                   10                  15

Thr Pro Ser Gly Ala Thr Gly Ser Pro Gly Ser Ser Pro Ser Ala Ser
            20                  25                  30

Thr Gly Thr Gly Pro Gly Ser Ser Pro Ser Ala Ser Thr Gly Thr Gly
        35                  40                  45

Pro Gly Ser Ser Thr Pro Ser Gly Ala Thr Gly Ser Pro Gly Ser Ser
    50                  55                  60

Thr Pro Ser Gly Ala Thr Gly Ser Pro Gly Ala Ser Pro Gly Thr Ser
65                  70                  75                  80

Ser Thr Gly Ser Pro Gly Ala Ser Pro Gly Thr Ser Ser Thr Gly Ser
                85                  90                  95

Pro Gly Ala Ser Pro Gly Thr Ser Ser Thr Gly Ser Pro Gly Thr Pro
            100                 105                 110

Gly Ser Gly Thr Ala Ser Ser Ser Pro Gly Ala Ser Pro Gly Thr Ser
        115                 120                 125

Ser Thr Gly Ser Pro Gly Ala Ser Pro Gly Thr Ser Ser Thr Gly Ser
    130                 135                 140

Pro Gly Ala Ser Pro Gly Thr Ser Ser Thr Gly Ser Pro Gly Ser Ser
145                 150                 155                 160
```

```
Pro Ser Ala Ser Thr Gly Thr Gly Pro Gly Thr Pro Gly Ser Gly Thr
                165                 170                 175

Ala Ser Ser Ser Pro Gly Ala Ser Pro Gly Thr Ser Ser Thr Gly Ser
            180                 185                 190

Pro Gly Ala Ser Pro Gly Thr Ser Ser Thr Gly Ser Pro Gly Ala Ser
        195                 200                 205

Pro Gly Thr Ser Ser Thr Gly Ser Pro Gly Ser Ser Thr Pro Ser Gly
    210                 215                 220

Ala Thr Gly Ser Pro Gly Ser Ser Thr Pro Ser Gly Ala Thr Gly Ser
225                 230                 235                 240

Pro Gly Ala Ser Pro Gly Thr Ser Ser Thr Gly Ser Pro Gly Thr Pro
                245                 250                 255

Gly Ser Gly Thr Ala Ser Ser Ser Pro Gly Ser Ser Thr Pro Ser Gly
            260                 265                 270

Ala Thr Gly Ser Pro Gly Ser Ser Thr Pro Ser Gly Ala Thr Gly Ser
        275                 280                 285

Pro Gly Ser Ser Thr Pro Ser Gly Ala Thr Gly Ser Pro Gly Ser Ser
    290                 295                 300

Pro Ser Ala Ser Thr Gly Thr Gly Pro Gly Ala Ser Pro Gly Thr Ser
305                 310                 315                 320

Ser Thr Gly Ser Pro Gly Ala Ser Pro Gly Thr Ser Ser Thr Gly Ser
                325                 330                 335

Pro Gly Thr Pro Gly Ser Gly Thr Ala Ser Ser Ser Pro Gly Ala Ser
            340                 345                 350

Pro Gly Thr Ser Ser Thr Gly Ser Pro Gly Ala Ser Pro Gly Thr Ser
        355                 360                 365

Ser Thr Gly Ser Pro Gly Ala Ser Pro Gly Thr Ser Ser Thr Gly Ser
    370                 375                 380

Pro Gly Ala Ser Pro Gly Thr Ser Ser Thr Gly Ser Pro Gly Thr Pro
385                 390                 395                 400

Gly Ser Gly Thr Ala Ser Ser Ser Pro Gly Ser Ser Thr Pro Ser Gly
                405                 410                 415

Ala Thr Gly Ser Pro Gly Thr Pro Gly Ser Gly Thr Ala Ser Ser Ser
            420                 425                 430

Pro Gly Ser Ser Thr Pro Ser Gly Ala Thr Gly Ser Pro Gly Thr Pro
        435                 440                 445

Gly Ser Gly Thr Ala Ser Ser Ser Pro Gly Ser Ser Thr Pro Ser Gly
    450                 455                 460

Ala Thr Gly Ser Pro Gly Ser Ser Thr Pro Ser Gly Ala Thr Gly Ser
465                 470                 475                 480

Pro Gly Ser Ser Pro Ser Ala Ser Thr Gly Thr Gly Pro Gly Ser Ser
                485                 490                 495

Pro Ser Ala Ser Thr Gly Thr Gly Pro Gly Ala Ser Pro Gly Thr Ser
            500                 505                 510

Ser Thr Gly Ser Pro Gly Thr Pro Gly Ser Gly Thr Ala Ser Ser Ser
        515                 520                 525

Pro Gly Ser Ser Thr Pro Ser Gly Ala Thr Gly Ser Pro Gly Ser Ser
    530                 535                 540

Pro Ser Ala Ser Thr Gly Thr Gly Pro Gly Ser Ser Pro Ser Ala Ser
545                 550                 555                 560

Thr Gly Thr Gly Pro Gly Ala Ser Pro Gly Thr Ser Ser Thr Gly Ser
                565                 570                 575
```

```
<210> SEQ ID NO 43
<211> LENGTH: 864
<212> TYPE: PRT
<213> ORGANISM: Artificial Sequence
<220> FEATURE:
<223> OTHER INFORMATION: XTEN AE864

<400> SEQUENCE: 43

Gly Ser Pro Ala Gly Ser Pro Thr Ser Thr Glu Glu Gly Thr Ser Glu
1               5                   10                  15

Ser Ala Thr Pro Glu Ser Gly Pro Gly Thr Ser Thr Glu Pro Ser Glu
            20                  25                  30

Gly Ser Ala Pro Gly Ser Pro Ala Gly Ser Pro Thr Ser Thr Glu Glu
        35                  40                  45

Gly Thr Ser Thr Glu Pro Ser Glu Gly Ser Ala Pro Gly Thr Ser Thr
    50                  55                  60

Glu Pro Ser Glu Gly Ser Ala Pro Gly Thr Ser Glu Ser Ala Thr Pro
65                  70                  75                  80

Glu Ser Gly Pro Gly Ser Glu Pro Ala Thr Ser Gly Ser Glu Thr Pro
                85                  90                  95

Gly Ser Glu Pro Ala Thr Ser Gly Ser Glu Thr Pro Gly Ser Pro Ala
            100                 105                 110

Gly Ser Pro Thr Ser Thr Glu Glu Gly Thr Ser Glu Ser Ala Thr Pro
        115                 120                 125

Glu Ser Gly Pro Gly Thr Ser Thr Glu Pro Ser Glu Gly Ser Ala Pro
    130                 135                 140

Gly Thr Ser Thr Glu Pro Ser Glu Gly Ser Ala Pro Gly Ser Pro Ala
145                 150                 155                 160

Gly Ser Pro Thr Ser Thr Glu Glu Gly Thr Ser Thr Glu Pro Ser Glu
                165                 170                 175

Gly Ser Ala Pro Gly Thr Ser Thr Glu Pro Ser Glu Gly Ser Ala Pro
            180                 185                 190

Gly Thr Ser Glu Ser Ala Thr Pro Glu Ser Gly Pro Gly Thr Ser Thr
        195                 200                 205

Glu Pro Ser Glu Gly Ser Ala Pro Gly Thr Ser Glu Ser Ala Thr Pro
    210                 215                 220

Glu Ser Gly Pro Gly Ser Glu Pro Ala Thr Ser Gly Ser Glu Thr Pro
225                 230                 235                 240

Gly Thr Ser Thr Glu Pro Ser Glu Gly Ser Ala Pro Gly Thr Ser Thr
                245                 250                 255

Glu Pro Ser Glu Gly Ser Ala Pro Gly Thr Ser Glu Ser Ala Thr Pro
            260                 265                 270

Glu Ser Gly Pro Gly Thr Ser Glu Ser Ala Thr Pro Glu Ser Gly Pro
        275                 280                 285

Gly Ser Pro Ala Gly Ser Pro Thr Ser Thr Glu Glu Gly Thr Ser Glu
    290                 295                 300

Ser Ala Thr Pro Glu Ser Gly Pro Gly Ser Glu Pro Ala Thr Ser Gly
305                 310                 315                 320

Ser Glu Thr Pro Gly Thr Ser Glu Ser Ala Thr Pro Glu Ser Gly Pro
                325                 330                 335

Gly Thr Ser Thr Glu Pro Ser Glu Gly Ser Ala Pro Gly Thr Ser Thr
            340                 345                 350

Glu Pro Ser Glu Gly Ser Ala Pro Gly Thr Ser Thr Glu Pro Ser Glu
        355                 360                 365
```

```
Gly Ser Ala Pro Gly Thr Ser Thr Glu Pro Ser Glu Gly Ser Ala Pro
    370                 375                 380

Gly Thr Ser Thr Glu Pro Ser Glu Gly Ser Ala Pro Gly Thr Ser Thr
385                 390                 395                 400

Glu Pro Ser Glu Gly Ser Ala Pro Gly Ser Pro Ala Gly Ser Pro Thr
                405                 410                 415

Ser Thr Glu Glu Gly Thr Ser Thr Glu Pro Ser Glu Gly Ser Ala Pro
            420                 425                 430

Gly Thr Ser Glu Ser Ala Thr Pro Glu Ser Gly Pro Gly Ser Glu Pro
        435                 440                 445

Ala Thr Ser Gly Ser Glu Thr Pro Gly Thr Ser Glu Ser Ala Thr Pro
    450                 455                 460

Glu Ser Gly Pro Gly Ser Glu Pro Ala Thr Ser Gly Ser Glu Thr Pro
465                 470                 475                 480

Gly Thr Ser Glu Ser Ala Thr Pro Glu Ser Gly Pro Gly Thr Ser Thr
                485                 490                 495

Glu Pro Ser Glu Gly Ser Ala Pro Gly Thr Ser Glu Ser Ala Thr Pro
            500                 505                 510

Glu Ser Gly Pro Gly Ser Pro Ala Gly Ser Pro Thr Ser Thr Glu Glu
        515                 520                 525

Gly Ser Pro Ala Gly Ser Pro Thr Ser Thr Glu Glu Gly Ser Pro Ala
    530                 535                 540

Gly Ser Pro Thr Ser Thr Glu Glu Gly Thr Ser Glu Ser Ala Thr Pro
545                 550                 555                 560

Glu Ser Gly Pro Gly Thr Ser Thr Glu Pro Ser Glu Gly Ser Ala Pro
                565                 570                 575

Gly Thr Ser Glu Ser Ala Thr Pro Glu Ser Gly Pro Gly Ser Glu Pro
            580                 585                 590

Ala Thr Ser Gly Ser Glu Thr Pro Gly Thr Ser Glu Ser Ala Thr Pro
        595                 600                 605

Glu Ser Gly Pro Gly Ser Glu Pro Ala Thr Ser Gly Ser Glu Thr Pro
    610                 615                 620

Gly Thr Ser Glu Ser Ala Thr Pro Glu Ser Gly Pro Gly Thr Ser Thr
625                 630                 635                 640

Glu Pro Ser Glu Gly Ser Ala Pro Gly Ser Pro Ala Gly Ser Pro Thr
                645                 650                 655

Ser Thr Glu Glu Gly Thr Ser Glu Ser Ala Thr Pro Glu Ser Gly Pro
            660                 665                 670

Gly Ser Glu Pro Ala Thr Ser Gly Ser Glu Thr Pro Gly Thr Ser Glu
        675                 680                 685

Ser Ala Thr Pro Glu Ser Gly Pro Gly Ser Pro Ala Gly Ser Pro Thr
    690                 695                 700

Ser Thr Glu Glu Gly Ser Pro Ala Gly Ser Pro Thr Ser Thr Glu Glu
705                 710                 715                 720

Gly Thr Ser Thr Glu Pro Ser Glu Gly Ser Ala Pro Gly Thr Ser Glu
                725                 730                 735

Ser Ala Thr Pro Glu Ser Gly Pro Gly Thr Ser Glu Ser Ala Thr Pro
            740                 745                 750

Glu Ser Gly Pro Gly Thr Ser Glu Ser Ala Thr Pro Glu Ser Gly Pro
        755                 760                 765

Gly Ser Glu Pro Ala Thr Ser Gly Ser Glu Thr Pro Gly Ser Glu Pro
    770                 775                 780

Ala Thr Ser Gly Ser Glu Thr Pro Gly Ser Pro Ala Gly Ser Pro Thr
```

```
785                 790                 795                 800

Ser Thr Glu Glu Gly Thr Ser Thr Glu Pro Ser Glu Gly Ser Ala Pro
                805                 810                 815

Gly Thr Ser Thr Glu Pro Ser Glu Gly Ser Ala Pro Gly Ser Glu Pro
            820                 825                 830

Ala Thr Ser Gly Ser Glu Thr Pro Gly Thr Ser Glu Ser Ala Thr Pro
        835                 840                 845

Glu Ser Gly Pro Gly Thr Ser Thr Glu Pro Ser Glu Gly Ser Ala Pro
    850                 855                 860


<210> SEQ ID NO 44
<211> LENGTH: 864
<212> TYPE: PRT
<213> ORGANISM: Artificial Sequence
<220> FEATURE:
<223> OTHER INFORMATION: XTEN AG864

<400> SEQUENCE: 44

Gly Ala Ser Pro Gly Thr Ser Ser Thr Gly Ser Pro Gly Ser Ser Pro
1               5                   10                  15

Ser Ala Ser Thr Gly Thr Gly Pro Gly Ser Ser Pro Ser Ala Ser Thr
            20                  25                  30

Gly Thr Gly Pro Gly Thr Pro Gly Ser Gly Thr Ala Ser Ser Ser Pro
        35                  40                  45

Gly Ser Ser Thr Pro Ser Gly Ala Thr Gly Ser Pro Gly Ser Ser Pro
    50                  55                  60

Ser Ala Ser Thr Gly Thr Gly Pro Gly Ala Ser Pro Gly Thr Ser Ser
65                  70                  75                  80

Thr Gly Ser Pro Gly Thr Pro Gly Ser Gly Thr Ala Ser Ser Ser Pro
                85                  90                  95

Gly Ser Ser Thr Pro Ser Gly Ala Thr Gly Ser Pro Gly Thr Pro Gly
            100                 105                 110

Ser Gly Thr Ala Ser Ser Ser Pro Gly Ala Ser Pro Gly Thr Ser Ser
        115                 120                 125

Thr Gly Ser Pro Gly Ala Ser Pro Gly Thr Ser Ser Thr Gly Ser Pro
    130                 135                 140

Gly Thr Pro Gly Ser Gly Thr Ala Ser Ser Ser Pro Gly Ser Ser Thr
145                 150                 155                 160

Pro Ser Gly Ala Thr Gly Ser Pro Gly Ala Ser Pro Gly Thr Ser Ser
                165                 170                 175

Thr Gly Ser Pro Gly Thr Pro Gly Ser Gly Thr Ala Ser Ser Ser Pro
            180                 185                 190

Gly Ser Ser Thr Pro Ser Gly Ala Thr Gly Ser Pro Gly Ser Ser Pro
        195                 200                 205

Ser Ala Ser Thr Gly Thr Gly Pro Gly Ser Ser Pro Ser Ala Ser Thr
    210                 215                 220

Gly Thr Gly Pro Gly Ser Ser Thr Pro Ser Gly Ala Thr Gly Ser Pro
225                 230                 235                 240

Gly Ser Ser Thr Pro Ser Gly Ala Thr Gly Ser Pro Gly Ala Ser Pro
                245                 250                 255

Gly Thr Ser Ser Thr Gly Ser Pro Gly Ala Ser Pro Gly Thr Ser Ser
            260                 265                 270

Thr Gly Ser Pro Gly Ala Ser Pro Gly Thr Ser Ser Thr Gly Ser Pro
        275                 280                 285

Gly Thr Pro Gly Ser Gly Thr Ala Ser Ser Ser Pro Gly Ala Ser Pro
```

```
    290                 295                 300

Gly Thr Ser Ser Thr Gly Ser Pro Gly Ala Ser Pro Gly Thr Ser Ser
305                 310                 315                 320

Thr Gly Ser Pro Gly Ala Ser Pro Gly Thr Ser Ser Thr Gly Ser Pro
                325                 330                 335

Gly Ser Ser Pro Ser Ala Ser Thr Gly Thr Gly Pro Gly Thr Pro Gly
            340                 345                 350

Ser Gly Thr Ala Ser Ser Ser Pro Gly Ala Ser Pro Gly Thr Ser Ser
        355                 360                 365

Thr Gly Ser Pro Gly Ala Ser Pro Gly Thr Ser Ser Thr Gly Ser Pro
    370                 375                 380

Gly Ala Ser Pro Gly Thr Ser Ser Thr Gly Ser Pro Gly Ser Ser Thr
385                 390                 395                 400

Pro Ser Gly Ala Thr Gly Ser Pro Gly Ser Ser Thr Pro Ser Gly Ala
                405                 410                 415

Thr Gly Ser Pro Gly Ala Ser Pro Gly Thr Ser Ser Thr Gly Ser Pro
            420                 425                 430

Gly Thr Pro Gly Ser Gly Thr Ala Ser Ser Ser Pro Gly Ser Ser Thr
        435                 440                 445

Pro Ser Gly Ala Thr Gly Ser Pro Gly Ser Ser Thr Pro Ser Gly Ala
    450                 455                 460

Thr Gly Ser Pro Gly Ser Ser Thr Pro Ser Gly Ala Thr Gly Ser Pro
465                 470                 475                 480

Gly Ser Ser Pro Ser Ala Ser Thr Gly Thr Gly Pro Gly Ala Ser Pro
                485                 490                 495

Gly Thr Ser Ser Thr Gly Ser Pro Gly Ala Ser Pro Gly Thr Ser Ser
            500                 505                 510

Thr Gly Ser Pro Gly Thr Pro Gly Ser Gly Thr Ala Ser Ser Ser Pro
        515                 520                 525

Gly Ala Ser Pro Gly Thr Ser Ser Thr Gly Ser Pro Gly Ala Ser Pro
    530                 535                 540

Gly Thr Ser Ser Thr Gly Ser Pro Gly Ala Ser Pro Gly Thr Ser Ser
545                 550                 555                 560

Thr Gly Ser Pro Gly Ala Ser Pro Gly Thr Ser Ser Thr Gly Ser Pro
                565                 570                 575

Gly Thr Pro Gly Ser Gly Thr Ala Ser Ser Ser Pro Gly Ser Ser Thr
            580                 585                 590

Pro Ser Gly Ala Thr Gly Ser Pro Gly Thr Pro Gly Ser Gly Thr Ala
        595                 600                 605

Ser Ser Ser Pro Gly Ser Ser Thr Pro Ser Gly Ala Thr Gly Ser Pro
    610                 615                 620

Gly Thr Pro Gly Ser Gly Thr Ala Ser Ser Ser Pro Gly Ser Ser Thr
625                 630                 635                 640

Pro Ser Gly Ala Thr Gly Ser Pro Gly Ser Ser Thr Pro Ser Gly Ala
                645                 650                 655

Thr Gly Ser Pro Gly Ser Ser Pro Ser Ala Ser Thr Gly Thr Gly Pro
            660                 665                 670

Gly Ser Ser Pro Ser Ala Ser Thr Gly Thr Gly Pro Gly Ala Ser Pro
        675                 680                 685

Gly Thr Ser Ser Thr Gly Ser Pro Gly Thr Pro Gly Ser Gly Thr Ala
    690                 695                 700

Ser Ser Ser Pro Gly Ser Ser Thr Pro Ser Gly Ala Thr Gly Ser Pro
705                 710                 715                 720
```

```
Gly Ser Ser Pro Ser Ala Ser Thr Gly Thr Gly Pro Gly Ser Ser Pro
                725                 730                 735

Ser Ala Ser Thr Gly Thr Gly Pro Gly Ala Ser Pro Gly Thr Ser Ser
            740                 745                 750

Thr Gly Ser Pro Gly Ala Ser Pro Gly Thr Ser Ser Thr Gly Ser Pro
        755                 760                 765

Gly Ser Ser Thr Pro Ser Gly Ala Thr Gly Ser Pro Gly Ser Ser Pro
    770                 775                 780

Ser Ala Ser Thr Gly Thr Gly Pro Gly Ala Ser Pro Gly Thr Ser Ser
785                 790                 795                 800

Thr Gly Ser Pro Gly Ser Ser Pro Ser Ala Ser Thr Gly Thr Gly Pro
                805                 810                 815

Gly Thr Pro Gly Ser Gly Thr Ala Ser Ser Ser Pro Gly Ser Ser Thr
            820                 825                 830

Pro Ser Gly Ala Thr Gly Ser Pro Gly Ser Ser Thr Pro Ser Gly Ala
        835                 840                 845

Thr Gly Ser Pro Gly Ala Ser Pro Gly Thr Ser Ser Thr Gly Ser Pro
    850                 855                 860


<210> SEQ ID NO 45
<211> LENGTH: 9
<212> TYPE: PRT
<213> ORGANISM: Artificial Sequence
<220> FEATURE:
<223> OTHER INFORMATION: FXIa cleavage site

<400> SEQUENCE: 45

Thr Gln Ser Phe Asn Asp Phe Thr Arg
1               5


<210> SEQ ID NO 46
<211> LENGTH: 10
<212> TYPE: PRT
<213> ORGANISM: Artificial Sequence
<220> FEATURE:
<223> OTHER INFORMATION: FXIa cleavage site

<400> SEQUENCE: 46

Ser Val Ser Gln Thr Ser Lys Leu Thr Arg
1               5                   10


<210> SEQ ID NO 47
<211> LENGTH: 10
<212> TYPE: PRT
<213> ORGANISM: Artificial Sequence
<220> FEATURE:
<223> OTHER INFORMATION: Thrombin cleavage site

<400> SEQUENCE: 47

Asp Phe Leu Ala Glu Gly Gly Gly Val Arg
1               5                   10


<210> SEQ ID NO 48
<211> LENGTH: 7
<212> TYPE: PRT
<213> ORGANISM: Artificial Sequence
<220> FEATURE:
<223> OTHER INFORMATION: Thrombin cleavage site

<400> SEQUENCE: 48

Thr Thr Lys Ile Lys Pro Arg
1               5
```

<210> SEQ ID NO 49
<211> LENGTH: 5
<212> TYPE: PRT
<213> ORGANISM: Artificial Sequence
<220> FEATURE:
<223> OTHER INFORMATION: Thrombin cleavage site

<400> SEQUENCE: 49

Leu Val Pro Arg Gly
1               5

<210> SEQ ID NO 50

<400> SEQUENCE: 50

000

<210> SEQ ID NO 51
<211> LENGTH: 5
<212> TYPE: PRT
<213> ORGANISM: Artificial Sequence
<220> FEATURE:
<223> OTHER INFORMATION: Thrombin cleavage site

<400> SEQUENCE: 51

Ala Leu Arg Pro Arg
1               5

<210> SEQ ID NO 52
<211> LENGTH: 11
<212> TYPE: PRT
<213> ORGANISM: Artificial Sequence
<220> FEATURE:
<223> OTHER INFORMATION: Ig constant region

<400> SEQUENCE: 52

Pro Lys Asn Ser Ser Met Ile Ser Asn Thr Pro
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Ig constant region

<400> SEQUENCE: 53

His Gln Ser Leu Gly Thr Gln
1               5

<210> SEQ ID NO 54
<211> LENGTH: 8
<212> TYPE: PRT
<213> ORGANISM: Artificial Sequence
<220> FEATURE:
<223> OTHER INFORMATION: Ig constant region

<400> SEQUENCE: 54

His Gln Asn Leu Ser Asp Gly Lys
1               5

<210> SEQ ID NO 55
<211> LENGTH: 8
<212> TYPE: PRT
<213> ORGANISM: Artificial Sequence
<220> FEATURE:

<223> OTHER INFORMATION: Ig constant region

<400> SEQUENCE: 55

His Gln Asn Ile Ser Asp Gly Lys
1               5

<210> SEQ ID NO 56
<211> LENGTH: 8
<212> TYPE: PRT
<213> ORGANISM: Artificial Sequence
<220> FEATURE:
<223> OTHER INFORMATION: Ig constant region

<400> SEQUENCE: 56

Val Ile Ser Ser His Leu Gly Gln
1               5

<210> SEQ ID NO 57
<211> LENGTH: 4
<212> TYPE: PRT
<213> ORGANISM: Artificial Sequence
<220> FEATURE:
<223> OTHER INFORMATION: Gly/Ser linker, where the sequence can be repeated between 1-100 times

<400> SEQUENCE: 57

Gly Gly Gly Ser
1

<210> SEQ ID NO 58
<211> LENGTH: 800
<212> TYPE: PRT
<213> ORGANISM: Artificial Sequence
<220> FEATURE:
<223> OTHER INFORMATION: Gly/Ser linker
<220> FEATURE:
<221> NAME/KEY: MISC_FEATURE
<222> LOCATION: (1)..(800)
<223> OTHER INFORMATION: some of the amino acids may be absent

<400> SEQUENCE: 58

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser Gly Gly Ser Gly
    50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Gly Gly Ser Gly Gly Ser
                85                  90                  95

Gly Gly Ser Gly Gly Ser Gly Gly Ser Gly Gly Ser Gly Gly Ser Gly
            100                 105                 110

Gly Ser Gly Gly Ser Gly Gly Ser Gly Gly Ser Gly Gly Ser Gly Gly
        115                 120                 125

Ser Gly Gly Ser Gly Gly Ser Gly Gly Ser Gly Gly Ser Gly Gly Ser
    130                 135                 140

Gly Gly Ser Gly Gly Ser Gly Gly Ser Gly Gly Ser Gly Gly Ser Gly
145                 150                 155                 160

Gly Ser Gly Gly Ser Gly Gly Ser Gly Gly Ser Gly Gly Ser Gly Gly

```
                165                 170                 175

Ser Gly Gly Ser Gly Gly Ser Gly Gly Ser Gly Gly Ser Gly Gly Ser
            180                 185                 190

Gly Gly Ser Gly Gly Ser Gly Gly Ser Gly Gly Ser Gly Gly Ser Gly
        195                 200                 205

Gly Ser Gly Gly Ser Gly Gly Ser Gly Gly Ser Gly Gly Ser Gly Gly
    210                 215                 220

Ser Gly Gly Ser Gly Gly Ser Gly Gly Ser Gly Gly Ser Gly Gly Ser
225                 230                 235                 240

Gly Gly Ser Gly Gly Ser Gly Gly Ser Gly Gly Ser Gly Gly Ser Gly
                245                 250                 255

Gly Ser Gly Gly Ser Gly Gly Ser Gly Gly Ser Gly Gly Ser Gly Gly
            260                 265                 270

Ser Gly Gly Ser Gly Gly Ser Gly Gly Ser Gly Gly Ser Gly Gly Ser
        275                 280                 285

Gly Gly Ser Gly Gly Ser Gly Gly Ser Gly Gly Ser Gly Gly Gly Gly
    290                 295                 300

Ser Gly Gly Gly Gly Ser Gly Gly Gly Gly Ser Gly Gly Gly Gly Ser
305                 310                 315                 320

Gly Gly Gly Gly Ser Gly Gly Gly Gly Ser Gly Gly Gly Gly Ser Gly
                325                 330                 335

Gly Gly Gly Ser Gly Gly Gly Gly Ser Gly Gly Gly Gly Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gly Gly Gly Ser Gly Gly Gly Gly
    370                 375                 380

Ser Gly Gly Gly Gly Ser Gly Gly Gly Gly Ser Gly Gly Gly Gly Ser
385                 390                 395                 400

Gly Gly Gly Gly Ser Gly Gly Gly Gly Ser Gly Gly Gly Gly Ser Gly
                405                 410                 415

Gly Gly Gly Ser Gly Gly Gly Gly Ser Gly Gly Gly Gly Ser Gly Gly
            420                 425                 430

Gly Gly Ser Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Gly Gly Gly Gly Ser Gly Gly Gly Gly Ser Gly Gly Gly Gly Ser Gly
                485                 490                 495

Gly Gly Gly Ser Gly Gly Gly Gly Ser Gly Gly Gly Gly Ser Gly Gly
            500                 505                 510

Gly Gly Ser Gly Gly Gly Gly Ser Gly Gly Gly Gly Ser Gly Gly Gly
        515                 520                 525

Gly Ser Gly Gly Gly Gly Ser Gly Gly Gly Gly Ser Gly Gly Gly Gly
    530                 535                 540

Ser Gly Gly Gly Gly Ser Gly Gly Gly Gly Ser Gly Gly Gly Gly Ser
545                 550                 555                 560

Gly Gly Gly Gly Ser Gly Gly Gly Gly Ser Gly Gly Gly Gly Ser Gly
                565                 570                 575

Gly Gly Gly Ser Gly Gly Gly Gly Ser Gly Gly Gly Gly Ser Gly Gly
            580                 585                 590
```

```
Gly Gly Ser Gly Gly Gly Gly Ser Gly Gly Gly Gly Ser Gly Gly Gly
        595                 600                 605

Gly Ser Gly Gly Gly Gly Ser Gly Gly Gly Gly Ser Gly Gly Gly Gly
    610                 615                 620

Ser Gly Gly Gly Gly Ser Gly Gly Gly Gly Ser Gly Gly Gly Gly Ser
625                 630                 635                 640

Gly Gly Gly Gly Ser Gly Gly Gly Gly Ser Gly Gly Gly Gly Ser Gly
                645                 650                 655

Gly Gly Gly Ser Gly Gly Gly Gly Ser Gly Gly Gly Gly Ser Gly Gly
            660                 665                 670

Gly Gly Ser Gly Gly Gly Gly Ser Gly Gly Gly Gly Ser Gly Gly Gly
        675                 680                 685

Gly Ser Gly Gly Gly Gly Ser Gly Gly Gly Gly Ser Gly Gly Gly Gly
    690                 695                 700

Ser Gly Gly Gly Gly Ser Gly Gly Gly Gly Ser Gly Gly Gly Gly Ser
705                 710                 715                 720

Gly Gly Gly Gly Ser Gly Gly Gly Gly Ser Gly Gly Gly Gly Ser Gly
                725                 730                 735

Gly Gly Gly Ser Gly Gly Gly Gly Ser Gly Gly Gly Gly Ser Gly Gly
            740                 745                 750

Gly Gly Ser Gly Gly Gly Gly Ser Gly Gly Gly Gly Ser Gly Gly Gly
        755                 760                 765

Gly Ser Gly Gly Gly Gly Ser Gly Gly Gly Gly Ser Gly Gly Gly Gly
    770                 775                 780

Ser Gly Gly Gly Gly Ser Gly Gly Gly Gly Ser Gly Gly Gly Gly Ser
785                 790                 795                 800
```

<210> SEQ ID NO 59
<211> LENGTH: 7
<212> TYPE: PRT
<213> ORGANISM: Artificial Sequence
<220> FEATURE:
<223> OTHER INFORMATION: Gly/Ser linker

<400> SEQUENCE: 59

```
Ser Gly Gly Ser Gly Gly Ser
1               5
```

<210> SEQ ID NO 60
<211> LENGTH: 15
<212> TYPE: PRT
<213> ORGANISM: Artificial Sequence
<220> FEATURE:
<223> OTHER INFORMATION: Gly/Ser linker

<400> SEQUENCE: 60

```
Gly Gly Ser Gly Gly Ser Gly Gly Ser Gly Gly Ser Gly Gly Gly
1               5                   10                  15
```

<210> SEQ ID NO 61
<211> LENGTH: 16
<212> TYPE: PRT
<213> ORGANISM: Artificial Sequence
<220> FEATURE:
<223> OTHER INFORMATION: Gly/Ser linker

<400> SEQUENCE: 61

```
Gly Gly Ser Gly Gly Ser Gly Gly Gly Gly Ser Gly Gly Gly Gly Ser
1               5                   10                  15
```

<210> SEQ ID NO 62
<211> LENGTH: 18
<212> TYPE: PRT
<213> ORGANISM: Artificial Sequence
<220> FEATURE:
<223> OTHER INFORMATION: Gly/Ser linker

<400> SEQUENCE: 62

```
Gly Gly Ser Gly Gly Ser Gly Gly Ser Gly Gly Ser Gly Gly Ser Gly
1               5                   10                  15

Gly Ser
```

<210> SEQ ID NO 63
<211> LENGTH: 15
<212> TYPE: PRT
<213> ORGANISM: Artificial Sequence
<220> FEATURE:
<223> OTHER INFORMATION: Gly/Ser linker

<400> SEQUENCE: 63

```
Gly Gly Gly Gly Ser Gly Gly Gly Gly Ser Gly Gly Gly Gly Ser
1               5                   10                  15
```

<210> SEQ ID NO 64
<211> LENGTH: 5
<212> TYPE: PRT
<213> ORGANISM: Artificial Sequence
<220> FEATURE:
<223> OTHER INFORMATION: Gly/Ser linker, where the sequence can be repeated between 1-20 times

<400> SEQUENCE: 64

```
Gly Gly Gly Gly Ser
1               5
```

<210> SEQ ID NO 65
<211> LENGTH: 7
<212> TYPE: PRT
<213> ORGANISM: Artificial Sequence
<220> FEATURE:
<223> OTHER INFORMATION: FXIa cleavage site

<400> SEQUENCE: 65

```
Lys Leu Thr Arg Ala Glu Thr
1               5
```

<210> SEQ ID NO 66
<211> LENGTH: 7
<212> TYPE: PRT
<213> ORGANISM: Artificial Sequence
<220> FEATURE:
<223> OTHER INFORMATION: FXIa cleavage site

<400> SEQUENCE: 66

```
Asp Phe Thr Arg Val Val Gly
1               5
```

<210> SEQ ID NO 67
<211> LENGTH: 8
<212> TYPE: PRT
<213> ORGANISM: Artificial Sequence
<220> FEATURE:
<223> OTHER INFORMATION: FXIIa cleavage site

<400> SEQUENCE: 67

```
Thr Met Thr Arg Ile Val Gly Gly
```

1 5

<210> SEQ ID NO 68
<211> LENGTH: 8
<212> TYPE: PRT
<213> ORGANISM: Artificial Sequence
<220> FEATURE:
<223> OTHER INFORMATION: Kallikrein cleavage site

<400> SEQUENCE: 68

Ser Pro Phe Arg Ser Thr Gly Gly
1 5

<210> SEQ ID NO 69
<211> LENGTH: 8
<212> TYPE: PRT
<213> ORGANISM: Artificial Sequence
<220> FEATURE:
<223> OTHER INFORMATION: FVIIa cleavage site

<400> SEQUENCE: 69

Leu Gln Val Arg Ile Val Gly Gly
1 5

<210> SEQ ID NO 70
<211> LENGTH: 8
<212> TYPE: PRT
<213> ORGANISM: Artificial Sequence
<220> FEATURE:
<223> OTHER INFORMATION: FIXa cleavage site

<400> SEQUENCE: 70

Pro Leu Gly Arg Ile Val Gly Gly
1 5

<210> SEQ ID NO 71
<211> LENGTH: 8
<212> TYPE: PRT
<213> ORGANISM: Artificial Sequence
<220> FEATURE:
<223> OTHER INFORMATION: FXa cleavage site

<400> SEQUENCE: 71

Ile Glu Gly Arg Thr Val Gly Gly
1 5

<210> SEQ ID NO 72
<211> LENGTH: 8
<212> TYPE: PRT
<213> ORGANISM: Artificial Sequence
<220> FEATURE:
<223> OTHER INFORMATION: FIIa (thrombin) cleavage site

<400> SEQUENCE: 72

Leu Thr Pro Arg Ser Leu Leu Val
1 5

<210> SEQ ID NO 73
<211> LENGTH: 8
<212> TYPE: PRT
<213> ORGANISM: Artificial Sequence
<220> FEATURE:
<223> OTHER INFORMATION: Elastase-2 cleavage site

<400> SEQUENCE: 73

Leu Gly Pro Val Ser Gly Val Pro
1 5

<210> SEQ ID NO 74
<211> LENGTH: 8
<212> TYPE: PRT
<213> ORGANISM: Artificial Sequence
<220> FEATURE:
<223> OTHER INFORMATION: Granzyme-B cleavage site

<400> SEQUENCE: 74

Val Ala Gly Asp Ser Leu Glu Glu
1               5

<210> SEQ ID NO 75
<211> LENGTH: 8
<212> TYPE: PRT
<213> ORGANISM: Artificial Sequence
<220> FEATURE:
<223> OTHER INFORMATION: MMP-12 cleavage site

<400> SEQUENCE: 75

Gly Pro Ala Gly Leu Gly Gly Ala
1               5

<210> SEQ ID NO 76
<211> LENGTH: 8
<212> TYPE: PRT
<213> ORGANISM: Artificial Sequence
<220> FEATURE:
<223> OTHER INFORMATION: MMP-13 cleavage site

<400> SEQUENCE: 76

Gly Pro Ala Gly Leu Arg Gly Ala
1               5

<210> SEQ ID NO 77
<211> LENGTH: 8
<212> TYPE: PRT
<213> ORGANISM: Artificial Sequence
<220> FEATURE:
<223> OTHER INFORMATION: MMP-17 cleavage site

<400> SEQUENCE: 77

Ala Pro Leu Gly Leu Arg Leu Arg
1               5

<210> SEQ ID NO 78
<211> LENGTH: 8
<212> TYPE: PRT
<213> ORGANISM: Artificial Sequence
<220> FEATURE:
<223> OTHER INFORMATION: MMP-20 cleavage site

<400> SEQUENCE: 78

Pro Ala Leu Pro Leu Val Ala Gln
1               5

<210> SEQ ID NO 79
<211> LENGTH: 7
<212> TYPE: PRT
<213> ORGANISM: Artificial Sequence
<220> FEATURE:
<223> OTHER INFORMATION: TEV cleavage site

<400> SEQUENCE: 79

Glu Asn Leu Tyr Phe Gln Gly
1               5

```
<210> SEQ ID NO 80
<211> LENGTH: 8
<212> TYPE: PRT
<213> ORGANISM: Artificial Sequence
<220> FEATURE:
<223> OTHER INFORMATION: Enterokinase cleavage site

<400> SEQUENCE: 80

Asp Asp Asp Lys Ile Val Gly Gly
1               5


<210> SEQ ID NO 81
<211> LENGTH: 8
<212> TYPE: PRT
<213> ORGANISM: Artificial Sequence
<220> FEATURE:
<223> OTHER INFORMATION: Protease 3C (PRESCISSION) cleavage site

<400> SEQUENCE: 81

Leu Glu Val Leu Phe Gln Gly Pro
1               5


<210> SEQ ID NO 82
<211> LENGTH: 8
<212> TYPE: PRT
<213> ORGANISM: Artificial Sequence
<220> FEATURE:
<223> OTHER INFORMATION: Sortase A cleavage site

<400> SEQUENCE: 82

Leu Pro Lys Thr Gly Ser Glu Ser
1               5


<210> SEQ ID NO 83
<211> LENGTH: 9
<212> TYPE: PRT
<213> ORGANISM: Artificial Sequence
<220> FEATURE:
<223> OTHER INFORMATION: FXIa cleavage site

<400> SEQUENCE: 83

Thr Gln Ser Phe Asn Asp Phe Thr Arg
1               5


<210> SEQ ID NO 84
<211> LENGTH: 10
<212> TYPE: PRT
<213> ORGANISM: Artificial Sequence
<220> FEATURE:
<223> OTHER INFORMATION: FXIa cleavage site

<400> SEQUENCE: 84

Ser Val Ser Gln Thr Ser Lys Leu Thr Arg
1               5                   10


<210> SEQ ID NO 85
<211> LENGTH: 10
<212> TYPE: PRT
<213> ORGANISM: Artificial Sequence
<220> FEATURE:
<223> OTHER INFORMATION: Thrombin cleavage site

<400> SEQUENCE: 85

Asp Phe Leu Ala Glu Gly Gly Gly Val Arg
1               5                   10
```

<210> SEQ ID NO 86
<211> LENGTH: 7
<212> TYPE: PRT
<213> ORGANISM: Artificial Sequence
<220> FEATURE:
<223> OTHER INFORMATION: Thrombin cleavage site

<400> SEQUENCE: 86

Thr Thr Lys Ile Lys Pro Arg
1               5

<210> SEQ ID NO 87
<211> LENGTH: 5
<212> TYPE: PRT
<213> ORGANISM: Artificial Sequence
<220> FEATURE:
<223> OTHER INFORMATION: Thrombin cleavage site

<400> SEQUENCE: 87

Leu Val Pro Arg Gly
1               5

<210> SEQ ID NO 88
<211> LENGTH: 10
<212> TYPE: PRT
<213> ORGANISM: Artificial Sequence
<220> FEATURE:
<223> OTHER INFORMATION: Thrombin cleavage site

<400> SEQUENCE: 88

Ala Leu Arg Pro Arg Val Val Gly Gly Ala
1               5                   10

<210> SEQ ID NO 89
<211> LENGTH: 4
<212> TYPE: PRT
<213> ORGANISM: Artificial Sequence
<220> FEATURE:
<223> OTHER INFORMATION: Spacer Sequence

<400> SEQUENCE: 89

Gly Ser Pro Gly
1

<210> SEQ ID NO 90
<211> LENGTH: 4
<212> TYPE: PRT
<213> ORGANISM: Artificial Sequence
<220> FEATURE:
<223> OTHER INFORMATION: Spacer Sequence

<400> SEQUENCE: 90

Glu Thr Glu Thr
1

<210> SEQ ID NO 91
<211> LENGTH: 5
<212> TYPE: PRT
<213> ORGANISM: Artificial Sequence
<220> FEATURE:
<223> OTHER INFORMATION: Spacer Sequence

<400> SEQUENCE: 91

Pro Gly Ser Ser Ser
1               5

<210> SEQ ID NO 92

<211> LENGTH: 5
<212> TYPE: PRT
<213> ORGANISM: Artificial Sequence
<220> FEATURE:
<223> OTHER INFORMATION: Spacer Sequence

<400> SEQUENCE: 92

```
Gly Pro Ser Gly Pro
1               5
```

<210> SEQ ID NO 93
<211> LENGTH: 10
<212> TYPE: PRT
<213> ORGANISM: Artificial Sequence
<220> FEATURE:
<223> OTHER INFORMATION: Spacer Sequence

<400> SEQUENCE: 93

```
Gly Ala Gly Ser Pro Gly Ala Glu Thr Ala
1               5                   10
```

<210> SEQ ID NO 94
<211> LENGTH: 144
<212> TYPE: PRT
<213> ORGANISM: Artificial Sequence
<220> FEATURE:
<223> OTHER INFORMATION: XTEN_AE144_1A

<400> SEQUENCE: 94

```
Ser Pro Ala Gly Ser Pro Thr Ser Thr Glu Glu Gly Thr Ser Glu Ser
1               5                   10                  15

Ala Thr Pro Glu Ser Gly Pro Gly Thr Ser Thr Glu Pro Ser Glu Gly
            20                  25                  30

Ser Ala Pro Gly Ser Pro Ala Gly Ser Pro Thr Ser Thr Glu Glu Gly
        35                  40                  45

Thr Ser Thr Glu Pro Ser Glu Gly Ser Ala Pro Gly Thr Ser Thr Glu
    50                  55                  60

Pro Ser Glu Gly Ser Ala Pro Gly Thr Ser Glu Ser Ala Thr Pro Glu
65                  70                  75                  80

Ser Gly Pro Gly Ser Glu Pro Ala Thr Ser Gly Ser Glu Thr Pro Gly
                85                  90                  95

Ser Glu Pro Ala Thr Ser Gly Ser Glu Thr Pro Gly Ser Pro Ala Gly
            100                 105                 110

Ser Pro Thr Ser Thr Glu Glu Gly Thr Ser Glu Ser Ala Thr Pro Glu
        115                 120                 125

Ser Gly Pro Gly Thr Ser Thr Glu Pro Ser Glu Gly Ser Ala Pro Gly
    130                 135                 140
```

<210> SEQ ID NO 95
<211> LENGTH: 72
<212> TYPE: PRT
<213> ORGANISM: Artificial Sequence
<220> FEATURE:
<223> OTHER INFORMATION: XTEN_AE72_1A_2

<400> SEQUENCE: 95

```
Thr Ser Glu Ser Ala Thr Pro Glu Ser Gly Pro Gly Ser Glu Pro Ala
1               5                   10                  15

Thr Ser Gly Ser Glu Thr Pro Gly Ser Glu Pro Ala Thr Ser Gly Ser
            20                  25                  30

Glu Thr Pro Gly Ser Pro Ala Gly Ser Pro Thr Ser Thr Glu Glu Gly
        35                  40                  45
```

```
Thr Ser Glu Ser Ala Thr Pro Glu Ser Gly Pro Gly Thr Ser Thr Glu
    50                  55                  60

Pro Ser Glu Gly Ser Ala Pro Gly
65                  70


<210> SEQ ID NO 96
<211> LENGTH: 72
<212> TYPE: PRT
<213> ORGANISM: Artificial Sequence
<220> FEATURE:
<223> OTHER INFORMATION: XTEN_AE72_1A_1

<400> SEQUENCE: 96

Ser Pro Ala Gly Ser Pro Thr Ser Thr Glu Glu Gly Thr Ser Glu Ser
1               5                   10                  15

Ala Thr Pro Glu Ser Gly Pro Gly Thr Ser Thr Glu Pro Ser Glu Gly
            20                  25                  30

Ser Ala Pro Gly Ser Pro Ala Gly Ser Pro Thr Ser Thr Glu Glu Gly
        35                  40                  45

Thr Ser Thr Glu Pro Ser Glu Gly Ser Ala Pro Gly Thr Ser Thr Glu
    50                  55                  60

Pro Ser Glu Gly Ser Ala Pro Gly
65                  70


<210> SEQ ID NO 97
<211> LENGTH: 72
<212> TYPE: PRT
<213> ORGANISM: Artificial Sequence
<220> FEATURE:
<223> OTHER INFORMATION: XTEN_AE72_6B_2

<400> SEQUENCE: 97

Ser Pro Ala Gly Ser Pro Thr Ser Thr Glu Glu Gly Thr Ser Thr Glu
1               5                   10                  15

Pro Ser Glu Gly Ser Ala Pro Gly Thr Ser Thr Glu Pro Ser Glu Gly
            20                  25                  30

Ser Ala Pro Gly Ser Glu Pro Ala Thr Ser Gly Ser Glu Thr Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly
65                  70


<210> SEQ ID NO 98
<211> LENGTH: 150
<212> TYPE: PRT
<213> ORGANISM: Artificial Sequence
<220> FEATURE:
<223> OTHER INFORMATION: XTEN AE150

<400> SEQUENCE: 98

Gly Ala Pro Gly Ser Glu Pro Ala Thr Ser Gly Ser Glu Thr Pro Gly
1               5                   10                  15

Thr Ser Glu Ser Ala Thr Pro Glu Ser Gly Pro Gly Ser Glu Pro Ala
            20                  25                  30

Thr Ser Gly Ser Glu Thr Pro Gly Ser Pro Ala Gly Ser Pro Thr Ser
        35                  40                  45

Thr Glu Glu Gly Thr Ser Thr Glu Pro Ser Glu Gly Ser Ala Pro Gly
    50                  55                  60
```

```
Ser Glu Pro Ala Thr Ser Gly Ser Glu Thr Pro Gly Ser Glu Pro Ala
65                  70                  75                  80

Thr Ser Gly Ser Glu Thr Pro Gly Ser Glu Pro Ala Thr Ser Gly Ser
                85                  90                  95

Glu Thr Pro Gly Thr Ser Thr Glu Pro Ser Glu Gly Ser Ala Pro Gly
            100                 105                 110

Thr Ser Glu Ser Ala Thr Pro Glu Ser Gly Pro Gly Ser Glu Pro Ala
        115                 120                 125

Thr Ser Gly Ser Glu Thr Pro Gly Thr Ser Thr Glu Pro Ser Glu Gly
    130                 135                 140

Ser Ala Pro Ala Ser Ser
145                 150


<210> SEQ ID NO 99
<211> LENGTH: 150
<212> TYPE: PRT
<213> ORGANISM: Artificial Sequence
<220> FEATURE:
<223> OTHER INFORMATION: XTEN AG150

<400> SEQUENCE: 99

Gly Ala Pro Gly Thr Pro Gly Ser Gly Thr Ala Ser Ser Ser Pro Gly
1               5                   10                  15

Ser Ser Thr Pro Ser Gly Ala Thr Gly Ser Pro Gly Ser Ser Pro Ser
            20                  25                  30

Ala Ser Thr Gly Thr Gly Pro Gly Ser Ser Pro Ser Ala Ser Thr Gly
        35                  40                  45

Thr Gly Pro Gly Ala Ser Pro Gly Thr Ser Ser Thr Gly Ser Pro Gly
    50                  55                  60

Ala Ser Pro Gly Thr Ser Ser Thr Gly Ser Pro Gly Ser Ser Thr Pro
65                  70                  75                  80

Ser Gly Ala Thr Gly Ser Pro Gly Ser Ser Pro Ser Ala Ser Thr Gly
                85                  90                  95

Thr Gly Pro Gly Ala Ser Pro Gly Thr Ser Ser Thr Gly Ser Pro Gly
            100                 105                 110

Ser Ser Pro Ser Ala Ser Thr Gly Thr Gly Pro Gly Thr Pro Gly Ser
        115                 120                 125

Gly Thr Ala Ser Ser Ser Pro Gly Ser Ser Thr Pro Ser Gly Ala Thr
    130                 135                 140

Gly Ser Pro Ala Ser Ser
145                 150


<210> SEQ ID NO 100
<211> LENGTH: 294
<212> TYPE: PRT
<213> ORGANISM: Artificial Sequence
<220> FEATURE:
<223> OTHER INFORMATION: XTEN AE294

<400> SEQUENCE: 100

Gly Ala Pro Gly Thr Ser Glu Ser Ala Thr Pro Glu Ser Gly Pro Gly
1               5                   10                  15

Ser Glu Pro Ala Thr Ser Gly Ser Glu Thr Pro Gly Thr Ser Glu Ser
            20                  25                  30

Ala Thr Pro Glu Ser Gly Pro Gly Ser Glu Pro Ala Thr Ser Gly Ser
        35                  40                  45

Glu Thr Pro Gly Thr Ser Glu Ser Ala Thr Pro Glu Ser Gly Pro Gly
    50                  55                  60
```

```
Thr Ser Thr Glu Pro Ser Glu Gly Ser Ala Pro Gly Ser Pro Ala Gly
65                  70                  75                  80

Ser Pro Thr Ser Thr Glu Glu Gly Thr Ser Glu Ser Ala Thr Pro Glu
                85                  90                  95

Ser Gly Pro Gly Ser Glu Pro Ala Thr Ser Gly Ser Glu Thr Pro Gly
            100                 105                 110

Thr Ser Glu Ser Ala Thr Pro Glu Ser Gly Pro Gly Ser Pro Ala Gly
        115                 120                 125

Ser Pro Thr Ser Thr Glu Glu Gly Ser Pro Ala Gly Ser Pro Thr Ser
    130                 135                 140

Thr Glu Glu Gly Thr Ser Thr Glu Pro Ser Glu Gly Ser Ala Pro Gly
145                 150                 155                 160

Thr Ser Glu Ser Ala Thr Pro Glu Ser Gly Pro Gly Thr Ser Glu Ser
                165                 170                 175

Ala Thr Pro Glu Ser Gly Pro Gly Thr Ser Glu Ser Ala Thr Pro Glu
            180                 185                 190

Ser Gly Pro Gly Ser Glu Pro Ala Thr Ser Gly Ser Glu Thr Pro Gly
        195                 200                 205

Ser Glu Pro Ala Thr Ser Gly Ser Glu Thr Pro Gly Ser Pro Ala Gly
    210                 215                 220

Ser Pro Thr Ser Thr Glu Glu Gly Thr Ser Thr Glu Pro Ser Glu Gly
225                 230                 235                 240

Ser Ala Pro Gly Thr Ser Thr Glu Pro Ser Glu Gly Ser Ala Pro Gly
                245                 250                 255

Ser Glu Pro Ala Thr Ser Gly Ser Glu Thr Pro Gly Thr Ser Glu Ser
            260                 265                 270

Ala Thr Pro Glu Ser Gly Pro Gly Thr Ser Thr Glu Pro Ser Glu Gly
        275                 280                 285

Ser Ala Pro Ala Ser Ser
    290


<210> SEQ ID NO 101
<211> LENGTH: 72
<212> TYPE: PRT
<213> ORGANISM: Artificial Sequence
<220> FEATURE:
<223> OTHER INFORMATION: XTEN_AE72_2A_1

<400> SEQUENCE: 101

Thr Ser Thr Glu Pro Ser Glu Gly Ser Ala Pro Gly Ser Pro Ala Gly
1               5                   10                  15

Ser Pro Thr Ser Thr Glu Glu Gly Thr Ser Thr Glu Pro Ser Glu Gly
            20                  25                  30

Ser Ala Pro Gly Thr Ser Thr Glu Pro Ser Glu Gly Ser Ala Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly
65                  70


<210> SEQ ID NO 102
<211> LENGTH: 72
<212> TYPE: PRT
<213> ORGANISM: Artificial Sequence
<220> FEATURE:
<223> OTHER INFORMATION: XTEN_AE72_2A_2
```

<400> SEQUENCE: 102

```
Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Thr Glu Pro Ser Glu Gly
            20                  25                  30

Ser Ala Pro Gly Thr Ser Thr Glu Pro Ser Glu Gly Ser Ala Pro Gly
        35                  40                  45

Thr Ser Glu Ser Ala Thr Pro Glu Ser Gly Pro Gly Thr Ser Glu Ser
    50                  55                  60

Ala Thr Pro Glu Ser Gly Pro Gly
65                  70
```

<210> SEQ ID NO 103
<211> LENGTH: 72
<212> TYPE: PRT
<213> ORGANISM: Artificial Sequence
<220> FEATURE:
<223> OTHER INFORMATION: XTEN_AE72_3B_1

<400> SEQUENCE: 103

```
Ser Pro Ala Gly Ser Pro Thr Ser Thr Glu Glu Gly Thr Ser Glu Ser
1               5                   10                  15

Ala Thr Pro Glu Ser Gly Pro Gly Ser Glu Pro Ala Thr Ser Gly Ser
            20                  25                  30

Glu Thr Pro Gly Thr Ser Glu Ser Ala Thr Pro Glu Ser Gly Pro Gly
        35                  40                  45

Thr Ser Thr Glu Pro Ser Glu Gly Ser Ala Pro Gly Thr Ser Thr Glu
    50                  55                  60

Pro Ser Glu Gly Ser Ala Pro Gly
65                  70
```

<210> SEQ ID NO 104
<211> LENGTH: 72
<212> TYPE: PRT
<213> ORGANISM: Artificial Sequence
<220> FEATURE:
<223> OTHER INFORMATION: XTEN_AE72_3B_2

<400> SEQUENCE: 104

```
Thr Ser Thr Glu Pro Ser Glu Gly Ser Ala Pro Gly Thr Ser Thr Glu
1               5                   10                  15

Pro Ser Glu Gly Ser Ala Pro Gly Thr Ser Thr Glu Pro Ser Glu Gly
            20                  25                  30

Ser Ala Pro Gly Thr Ser Thr Glu Pro Ser Glu Gly Ser Ala Pro Gly
        35                  40                  45

Ser Pro Ala Gly Ser Pro Thr Ser Thr Glu Glu Gly Thr Ser Thr Glu
    50                  55                  60

Pro Ser Glu Gly Ser Ala Pro Gly
65                  70
```

<210> SEQ ID NO 105
<211> LENGTH: 72
<212> TYPE: PRT
<213> ORGANISM: Artificial Sequence
<220> FEATURE:
<223> OTHER INFORMATION: XTEN_AE72_4A_2

<400> SEQUENCE: 105

```
Thr Ser Glu Ser Ala Thr Pro Glu Ser Gly Pro Gly Ser Pro Ala Gly
1               5                   10                  15
```

```
Ser Pro Thr Ser Thr Glu Glu Gly Ser Pro Ala Gly Ser Pro Thr Ser
            20                  25                  30

Thr Glu Glu Gly Ser Pro Ala Gly Ser Pro Thr Ser Thr Glu Glu Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly
65                  70
```

<210> SEQ ID NO 106
<211> LENGTH: 72
<212> TYPE: PRT
<213> ORGANISM: Artificial Sequence
<220> FEATURE:
<223> OTHER INFORMATION: XTEN_AE72_5A_2

<400> SEQUENCE: 106

```
Ser Pro Ala Gly Ser Pro Thr Ser Thr Glu Glu Gly Thr Ser Glu Ser
1               5                   10                  15

Ala Thr Pro Glu Ser Gly Pro Gly Ser Glu Pro Ala Thr Ser Gly Ser
            20                  25                  30

Glu Thr Pro Gly Thr Ser Glu Ser Ala Thr Pro Glu Ser Gly Pro Gly
        35                  40                  45

Ser Pro Ala Gly Ser Pro Thr Ser Thr Glu Glu Gly Ser Pro Ala Gly
    50                  55                  60

Ser Pro Thr Ser Thr Glu Glu Gly
65                  70
```

<210> SEQ ID NO 107
<211> LENGTH: 72
<212> TYPE: PRT
<213> ORGANISM: Artificial Sequence
<220> FEATURE:
<223> OTHER INFORMATION: XTEN_AE72_6B_1

<400> SEQUENCE: 107

```
Thr Ser Thr Glu Pro Ser Glu Gly Ser Ala Pro Gly Thr Ser Glu Ser
1               5                   10                  15

Ala Thr Pro Glu Ser Gly Pro Gly Thr Ser Glu Ser Ala Thr Pro Glu
            20                  25                  30

Ser Gly Pro Gly Thr Ser Glu Ser Ala Thr Pro Glu Ser Gly Pro Gly
        35                  40                  45

Ser Glu Pro Ala Thr Ser Gly Ser Glu Thr Pro Gly Ser Glu Pro Ala
    50                  55                  60

Thr Ser Gly Ser Glu Thr Pro Gly
65                  70
```

<210> SEQ ID NO 108
<211> LENGTH: 294
<212> TYPE: PRT
<213> ORGANISM: Artificial Sequence
<220> FEATURE:
<223> OTHER INFORMATION: XTEN AG294

<400> SEQUENCE: 108

```
Gly Ala Pro Pro Gly Ala Ser Pro Gly Thr Ser Ser Thr Gly Ser Pro
1               5                   10                  15

Gly Ala Ser Pro Gly Thr Ser Ser Thr Gly Ser Pro Gly Thr Pro Gly
            20                  25                  30
```

-continued

```
Ser Gly Thr Ala Ser Ser Ser Pro Gly Ser Ser Thr Pro Ser Gly Ala
        35                  40                  45

Thr Gly Ser Pro Gly Thr Pro Gly Ser Gly Thr Ala Ser Ser Ser Pro
    50                  55                  60

Gly Ser Ser Thr Pro Ser Gly Ala Thr Gly Ser Pro Gly Thr Pro Gly
65                  70                  75                  80

Ser Gly Thr Ala Ser Ser Ser Pro Gly Ser Ser Thr Pro Ser Gly Ala
                85                  90                  95

Thr Gly Ser Pro Gly Ser Ser Thr Pro Ser Gly Ala Thr Gly Ser Pro
            100                 105                 110

Gly Ser Ser Pro Ser Ala Ser Thr Gly Thr Gly Pro Gly Ser Ser Pro
        115                 120                 125

Ser Ala Ser Thr Gly Thr Gly Pro Gly Ala Ser Pro Gly Thr Ser Ser
    130                 135                 140

Thr Gly Ser Pro Gly Thr Pro Gly Ser Gly Thr Ala Ser Ser Ser Pro
145                 150                 155                 160

Gly Ser Ser Thr Pro Ser Gly Ala Thr Gly Ser Pro Gly Ser Ser Pro
                165                 170                 175

Ser Ala Ser Thr Gly Thr Gly Pro Gly Ser Ser Pro Ser Ala Ser Thr
            180                 185                 190

Gly Thr Gly Pro Gly Ala Ser Pro Gly Thr Ser Ser Thr Gly Ser Pro
        195                 200                 205

Gly Ala Ser Pro Gly Thr Ser Ser Thr Gly Ser Pro Gly Ser Ser Thr
    210                 215                 220

Pro Ser Gly Ala Thr Gly Ser Pro Gly Ser Ser Pro Ser Ala Ser Thr
225                 230                 235                 240

Gly Thr Gly Pro Gly Ala Ser Pro Gly Thr Ser Ser Thr Gly Ser Pro
                245                 250                 255

Gly Ser Ser Pro Ser Ala Ser Thr Gly Thr Gly Pro Gly Thr Pro Gly
            260                 265                 270

Ser Gly Thr Ala Ser Ser Ser Pro Gly Ser Ser Thr Pro Ser Gly Ala
        275                 280                 285

Thr Gly Ser Ala Ser Ser
    290
```

FACTOR VIII-XTEN FUSIONS AND USES THEREOF

REFERENCE TO SEQUENCE LISTING SUBMITTED ELECTRONICALLY VIA EFS-WEB

The content of the electronically submitted sequence listing (Name: 2159_4260002_SeqListing_ST25.txt; 298,548 bytes; and Date of Creation: Feb. 3, 2016) was originally submitted in the International Application No. PCT/US2014/051144 and is incorporated herein by reference in its entirety.

BACKGROUND OF THE INVENTION

Haemophilia A is a bleeding disorder caused by defects in the gene encoding coagulation factor VIII (FVIII) and affects 1-2 in 10,000 male births. Graw et al., *Nat. Rev. Genet.* 6(6): 488-501 (2005). Patients affected with hemophilia A can be treated with infusion of purified or recombinantly produced FVIII. All commercially available FVIII products, however, are known to have a half-life of about 8-12 hours, requiring frequent intravenous administration to the patients. See Weiner M. A. and Cairo, M. S., Pediatric Hematology Secrets, Lee, M. T., 12. Disorders of Coagulation, Elsevier Health Sciences, 2001; Lillicrap, D. Thromb. Res. 122 Suppl 4:S2-8 (2008). In addition, a number of approaches have been tried in order to extend the FVIII half-life. For example, the approaches in development to extend the half-life of clotting factors include pegylation, glycopegylation, and conjugation with albumin. See Dumont et al., Blood. 119(13): 3024-3030 (Published online Jan. 13, 2012). Regardless of the protein engineering used, however, the long acting FVIII products currently under development are reported to have limited half-lives—only to about 1.5 to 2 hours in preclinical animal models. See id. Consistent results have been demonstrated in humans, for example, rFVIIIFc was reported to improve half-life up to ~1.7 fold compared with ADVATE® in hemophilia A patients. See id. Therefore, the half-life increases, despite minor improvements, may indicate the presence of other T1/2 limiting factors. See Liu, T. et al., 2007 ISTH meeting, abstract #P-M-035; Henrik, A. et al., 2011 ISTH meeting, abstract #P=MO-181; Liu, T. et al., 2011 ISTH meeting abstract #P-WE-131.

Plasma von Willebrand Factor (VWF) has a half-life of approximately 12 hours (ranging from 9 to 15 hours). The VWF half-life may be affected by a number of factors: glycosylation pattern, ADAMTS-13 (a disintegrin and metalloprotease with thrombospondin motif-13), and various mutations in VWF.

In plasma, 95-98% of FVIII circulates in a tight non-covalent complex with full-length VWF. The formation of this complex is important for the maintenance of appropriate plasma levels of FVIII in vivo. Lenting et al., *Blood.* 92(11): 3983-96 (1998); Lenting et al., *J. Thromb. Haemost.* 5(7): 1353-60 (2007). The full-length wild-type FVIII is mostly present as a heterodimer having a heavy chain (MW 200kD) and a light chain (MW 73kD). When FVIII is activated due to proteolysis at positions 372 and 740 in the heavy chain and at position 1689 in the light chain, the VWF bound to FVIII is removed from the activated FVIII. The activated FVIII, together with activated factor IX, calcium, and phospholipid ("tenase complex"), induces the activation of factor X, generating large amounts of thrombin. Thrombin, in turn, then cleaves fibrinogen to form soluble fibrin monomers, which then spontaneously polymerize to form the soluble fibrin polymer. Thrombin also activates factor XIII, which, together with calcium, serves to crosslink and stabilize the soluble fibrin polymer, forming crosslinked (insoluble) fibrin. The activated FVIII is cleared quickly from the circulation by proteolysis.

Due to the frequent dosing and inconvenience caused by the dosing schedule, there is still a need to develop FVIII products requiring less frequent administration, i.e., a FVIII product that has a half-life longer than the 1.5- to 2-fold half-life limitation of products currently under clinical evaluation.

BRIEF SUMMARY OF THE INVENTION

Chimeric proteins comprising a FVIII polypeptide and an XTEN sequence are provided herein. It has been discovered that chimeric proteins containing (i) FVIII polypeptides with reduced affinity for von Willebrand Factor (VWF) and (ii) an XTEN sequence are particularly advantageous. Surprisingly, the selective introduction of shorter XTEN sequences at particular locations in the FVIII polypeptide have been shown to further increase the half-life of such chimeric proteins.

Accordingly, in one embodiment, the chimeric protein comprises (i) a Factor VIII (FVIII) polypeptide and (ii) an XTEN sequence wherein the FVIII polypeptide has reduced affinity for von Willebrand Factor (VWF). The chimeric protein can also comprise at least four XTEN sequences.

In another embodiment, the chimeric protein comprises (i) a FVIII polypeptide and (ii) at least four XTEN sequences.

In one embodiment, an XTEN sequence is inserted in the A1 domain of the FVIII polypeptide, between the A2 and A3 domains of the FVIII polypeptide, in the A3 domain of the FVIII polypeptide, and at the C terminus of the VIII polypeptide.

In one embodiment, at least one of the at least four XTEN sequences is no more than 72 amino acids in length. In one embodiment, at least one of the at least four XTEN sequences is 36 or 42 amino acids in length.

In one embodiment, the chimeric protein comprises a spacer between an amino acid in the FVIII polypeptide an amino acid in the XTEN. In one embodiment, the spacer comprises a cleavage sequence or amino acids encoded by polynucleotides with a restriction site.

In one embodiment, the FVIII polypeptide in the chimeric protein lacks amino acids 745-1685 of full-length mature FVIII polypeptide (SEQ ID NO: 4).

In one embodiment, the FVIII polypeptide in the chimeric protein lacks amino acids 741-1689 of full-length mature FVIII polypeptide (SEQ ID NO: 4).

In one embodiment, the FVIII polypeptide in the chimeric protein lacks amino acid 1680 of full-length mature FVIII polypeptide (SEQ ID NO: 4).

In one embodiment, the FVIII polypeptide in the chimeric protein contains a mutation in amino acid 1680 of full-length mature FVIII polypeptide (SEQ ID NO: 4).

In one embodiment, the FVIII polypeptide in the chimeric protein contains the mutation Y1680F. In one embodiment the FVIII polypeptide contains the mutation Y1680C.

In one embodiment, the FVIII polypeptide in the chimeric protein lacks amino acids corresponding to amino acid numbers 1669-1689 of full-length mature FVIII polypeptide (SEQ ID NO: 4).

In one embodiment, the FVIII polypeptide is linked to at least two XTEN sequences, at least three XTEN sequences, at least four XTEN sequences, at least five XTEN sequences, or at least six XTEN sequences. In one embodiment, the FVIII polypeptide is linked to at least four XTEN sequences.

In one embodiment, an XTEN is inserted immediately downstream of residue 18 corresponding to the mature FVIII polypeptide (SEQ ID NO: 4).

In one embodiment, an XTEN is inserted immediately downstream of residue 403 corresponding to the mature FVIII polypeptide (SEQ ID NO: 4).

In one embodiment, an XTEN is inserted immediately downstream of residue 1720 corresponding to the mature FVIII polypeptide (SEQ ID NO: 4).

In one embodiment, an XTEN is inserted immediately downstream of residue 1900 corresponding to the mature FVIII polypeptide (SEQ ID NO: 4).

In one embodiment, an XTEN is inserted immediately downstream of residue 745 corresponding to the mature FVIII polypeptide (SEQ ID NO: 4).

In one embodiment, an XTEN is inserted immediately downstream of residue 2332 corresponding to the mature FVIII polypeptide (SEQ ID NO: 4).

In one embodiment, XTEN are inserted immediately downstream of residues 18, 745, and 2332 corresponding to the mature FVIII polypeptide (SEQ ID NO: 4).

In one embodiment, XTEN are inserted immediately downstream of residues 745, 1720 and 2332 corresponding to the mature FVIII polypeptide (SEQ ID NO: 4).

In one embodiment, XTEN are inserted immediately downstream of residues 745, 1900, and 2332 corresponding to the mature FVIII polypeptide (SEQ ID NO: 4).

In one embodiment, XTEN are inserted immediately downstream of residues 18, 745, 1900, and 2332 corresponding to the mature FVIII polypeptide (SEQ ID NO: 4)

In one embodiment, XTEN are inserted immediately downstream of residues 745, 1720, 1900, and 2332 corresponding to the mature FVIII polypeptide (SEQ ID NO: 4).

In one embodiment, XTEN are inserted immediately downstream of residues 18, 745, 1720, and 2332 corresponding to the mature FVIII polypeptide (SEQ ID NO: 4).

In one embodiment, XTEN are inserted immediately downstream of residues 745 and 2332 corresponding to the mature FVIII polypeptide (SEQ ID NO: 4)

In one embodiment, an XTEN sequence is 36-72 amino acids in length or 42 to 78 amino acids in length. In one embodiment, the XTEN sequence is SEQ ID NO:22 (36AE). In one embodiment, the chimeric protein comprises a spacer between the XTEN sequence and the Factor VIII polypeptide. In one embodiment, the XTEN sequence is SEQ ID NO:36 (42AE). In one embodiment, the XTEN insertion site is immediately downstream of a residue selected from the group consisting of residues 18, 403, or 1720 corresponding to the mature FVIII polypeptide (SEQ ID NO: 4), or any combination thereof.

In one embodiment, at least two of the XTEN sequences are selected from the group consisting of SEQ ID NO: 22 (36AE) and SEQ ID NO: 36 (42AE). In one embodiment, the at least two XTEN insertion sites are immediately downstream of a residue selected from the group consisting of residues 18, 403, or 1720 corresponding to the mature FVIII polypeptide (SEQ ID NO: 4), or any combination thereof. In one embodiment, the chimeric proteins comprise XTEN insertions immediately downstream of residues 745 and 2332 corresponding to the mature FVIII polypeptide (SEQ ID NO: 4). In one embodiment, the XTEN sequence is SEQ ID NO: 23 (72AE). In one embodiment, the chimeric protein comprises a spacer between the XTEN sequence and the Factor VIII polypeptide. In one embodiment, the XTEN sequence is SEQ ID NO: 24 (78AE). In one embodiment, the XTEN is inserted immediately downstream of residue 403 or 1900 corresponding to the mature FVIII polypeptide (SEQ ID NO: 4), or any combination thereof.

In one embodiment, at least two of the XTEN sequences are selected from the group consisting of SEQ ID NO: 23 (72AE) and SEQ ID NO: 24 (78AE). In one embodiment, the at least two XTEN are inserted immediately downstream of residue 403 or 1900 corresponding to the mature FVIII polypeptide (SEQ ID NO: 4), or any combination thereof. In one embodiment, the chimeric protein further comprises XTEN insertions immediately downstream of residues 745 and 2332 corresponding to the mature FVIII polypeptide (SEQ ID NO: 4).

In one embodiment, the XTEN sequence is SEQ ID NO: 37 (144AE) or SEQ ID NO: 38 (144AG). In one embodiment, the chimeric protein comprises a spacer between the XTEN sequence and the Factor VIII polypeptide. In one embodiment, the XTEN sequence is SEQ ID NO: 98 (150AE) or SEQ ID NO: 99 (150 AG). In one embodiment, the XTEN insertion site is immediately downstream of residue 403 or 1900 corresponding to the mature FVIII polypeptide (SEQ ID NO: 4).

In one embodiment, at least two of the XTEN sequences are selected from the group consisting of SEQ ID NO: 37 (144AE), SEQ ID NO: 38 (144AG), SEQ ID NO: 98 (150AE), and SEQ ID NO: 99 (150AG). In one embodiment, the at least two XTEN insertions are immediately downstream of residue 403 or 1900 corresponding to the mature FVIII polypeptide (SEQ ID NO: 4). In one embodiment, the chimeric protein further comprises XTEN insertions immediately downstream of residues 745 and 2332 corresponding to the mature FVIII polypeptide (SEQ ID NO: 4).

In one embodiment, the at least 4 XTEN sequences comprise an XTEN sequence of SEQ ID NO: 22 (36AE) inserted immediately downstream of residue 18, an XTEN sequence of SEQ ID NO: 37 (144AE) inserted immediately downstream of residue 745, an XTEN sequence of SEQ ID NO: 37 (144 AE) inserted immediately downstream of residue 1900, and an XTEN sequence of SEQ ID NO: 39 (288 AE) inserted immediately downstream of residue 2332. In one embodiment, the chimeric protein further comprises a spacer between each XTEN sequence and the FVIII polypeptide.

In one embodiment, the at least 4 XTEN sequences comprise an XTEN sequence of SEQ ID NO: 36 (42AE) inserted immediately downstream of residue 18, an XTEN sequence of SEQ ID NO: 98 (150AE) inserted immediately downstream of residue 745, an XTEN sequence of SEQ ID NO: 98 (150 AE) inserted immediately downstream of residue 1900, and an XTEN sequence of SEQ ID NO: 100 (294 AE) inserted immediately downstream of residue 2332.

In one embodiment, the FVIII polypeptide in the chimeric protein lacks amino acids 745-1685 corresponding to the mature FVIII polypeptide (SEQ ID NO:4). In one embodiment, the FVIII polypeptide comprises amino acids 1-744 and 1686-2332 corresponding to the mature FVIII polypeptide (SEQ ID NO:4).

In one embodiment, the at least 4 XTEN sequences comprise an XTEN sequence of SEQ ID NO: 37 (144AE) or SEQ ID NO: 39 (288 AE) inserted immediately downstream of residue 745, an XTEN sequence of SEQ ID NO: 22 (36AE) inserted immediately downstream of residue 1720, an XTEN sequence of SEQ ID NO: 37 (144 AE) inserted immediately downstream of residue 1900, and an XTEN sequence of SEQ ID NO: 39 (288 AE) inserted immediately downstream of residue 2332. In one embodiment, the chimeric protein further comprises a spacer between each XTEN sequence and the FVIII polypeptide.

In one embodiment, the at least 4 XTEN sequences comprise an XTEN sequence of SEQ ID NO: 98 (150AE) inserted immediately downstream of residue 745, an XTEN sequence of SEQ ID NO: 36 (42AE) inserted immediately downstream of residue 1720, an XTEN sequence of SEQ ID NO: 98 (150 AE) inserted immediately downstream of residue 1900, and an XTEN sequence of SEQ ID NO: 100 (294AE) inserted immediately downstream of residue 2332.

In one embodiment, the FVIII polypeptide in the chimeric protein lacks amino acids 745-1685 corresponding to the mature FVIII polypeptide (SEQ ID NO:4). In one embodiment, the FVIII polypeptide comprises amino acids 1-744 and 1686-2332 corresponding to the mature FVIII polypeptide (SEQ ID NO:4).

In one embodiment, the at least 4 XTEN sequences comprise an XTEN sequence of SEQ ID NO: 22 (36AE) inserted immediately downstream of residue 18, an XTEN sequence of SEQ ID NO: 37 (144AE) inserted immediately downstream of residue 745, an XTEN sequence of SEQ ID NO: 22 (36 AE) inserted immediately downstream of residue 1720, and an XTEN sequence of SEQ ID NO: 39 (288 AE) inserted immediately downstream of residue 2332. In one embodiment, the chimeric protein further comprises a spacer between each XTEN sequence and the FVIII polypeptide.

In one embodiment, the at least 4 XTEN sequences comprise an XTEN sequence of SEQ ID NO: 36 (42AE) inserted immediately downstream of residue 18, an XTEN sequence of SEQ ID NO: 98 (150AE) inserted immediately downstream of residue 745, an XTEN sequence of SEQ ID NO: 36 (42 AE) inserted immediately downstream of residue 1720, and an XTEN sequence of SEQ ID NO: 100 (294 AE) inserted immediately downstream of residue 2332.

In one embodiment, the FVIII polypeptide in the chimeric protein lacks amino acids 745-1685 corresponding to the mature FVIII polypeptide (SEQ ID NO:4). In one embodiment, the FVIII polypeptide comprises amino acids 1-744 and 1686-2332 corresponding to the mature FVIII polypeptide (SEQ ID NO:4).

In one embodiment, the XTEN sequence extends the half-life of the FVIII polypeptide. In one embodiment, the half-life of the FVIII polypeptide, when administered to a subject, is at extended at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than that of the wild-type FVIII protein. In one embodiment, the subject is selected from the group consisting of mouse, dog, and human.

In one embodiment, the half-life of the FVIII polypeptide is at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

Polynucleotides encoding the chimeric proteins are also provided herein. In one embodiment, a polynucleotide or a set of polynucleotides encodes the chimeric protein. In one embodiment, the polynucleotide further comprises a polynucleotide chain that encodes PC5 or PC7.

Vectors are also provided herein. In one embodiment, a vector comprises the polynucleotide that encodes the chimeric protein and one or more promoter operably linked to the polynucleotide or the set of polynucleotides. Compositions comprising the vectors are also provided. In one embodiment, the composition further comprises an additional vector that comprises a polynucleotide chain encoding PC5 or PC7.

Host cells are also provided herein. In one embodiment, the host cell comprises the polynucleotide or set of polynucleotides encoding the chimeric protein, or the vector, or the composition comprising the vector. In one embodiment, the host cell is a mammalian cell. In one embodiment, the mammalian cell is selected from the group consisting of HEK293 cell, CHO cell, and BHK cell.

Pharmaceutical compositions comprising the chimeric proteins, vectors, compositions, or host cells and a pharmaceutically acceptable carrier are also provided. In one embodiment, the pharmaceutical composition is administered by a route selected from the group consisting of topical administration, intraocular administration, parenteral administration, intrathecal administration, subdural administration and oral administration. In one embodiment, the parenteral administration is intravenous or subcutaneous administration. In one embodiment, the pharmaceutical composition is used to treat a bleeding disease or condition in a subject in need thereof. In one embodiment, the bleeding disease or condition is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath and any combinations thereof. In one embodiment, the subject is scheduled to undergo a surgery. In one embodiment, the treatment is prophylactic or on-demand.

Methods of treating are also provided herein. In one embodiment, a method of treating a bleeding disease or disorder in a subject in need thereof comprises administering an effective amount of the chimeric protein, the polynucleotide, the vector, the composition, or the host cell. In one embodiment, the bleeding disease or disorder is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath. In one embodiment, the bleeding disorder is hemophilia A. In one embodiment, the treatment is prophylactic or on-demand. In one embodiment, the effective amount is 0.1 μg/kg to 500 mg/kg. In one embodiment, the chimeric protein, the polynucleotide, the vector, the composition, or the host cell is administered by a route selected from the group consisting of topical administration, intraocular administration, parenteral administration, intrathecal administration, subdural administration and oral administration. In one embodiment, the parenteral administration is selected from the group consisting of intravenous administration, subcutaneous administration, intramuscular administration, and intradermal administration.

Methods of making chimeric proteins are also provided herein. In one embodiment, the method comprises transfecting one or more host cell with the polynucleotide, the vector, or the composition and expressing the chimeric protein in the host cell.

Methods of extending or increasing half-life of the FVIII protein are also provided herein. In one embodiment, the method comprises adding an effective amount of the chimeric protein, the polynucleotide, the vector, the composition, the host cell, or the pharmaceutical composition to a subject in need thereof, wherein the XTEN sequence or sequences extend or increase the half-life of the FVIII protein.

In one embodiment, the chimeric protein is used in the preparation of a medicament for the treatment of a bleeding disorder. In one embodiment, a chimeric protein used in the treatment of hemophilia A is provided.

E1. A recombinant FVIII protein comprising: a first polypeptide comprising Formula I: (A1)-a1-(A2)-a2-[B]; and a second polypeptide comprising Formula II: a3-(A3)-(C1);

wherein the first polypeptide and the second polypeptide are fused or associated as a heterodimer;

wherein, a) A1 is an A1 domain of FVIII; b) A2 is an A2 domain of FVIII; c) [B] is optionally present and is a B domain of FVIII or a fragment thereof; d) A3 is an A3 domain of FVIII; e) C1 is a C1 domain of FVIII; and f) a1, a2, and a3 are acidic spacer regions;

wherein one or more amino acids in a permissive loop-1 region in the A1 domain (A1-1), a permissive loop-2 region in the A1 domain (A1-2), a permissive loop-1 region in the A2 domain (A2-1), a permissive loop-2 region in the A2 domain (A2-2), a permissive loop-1 region in the A3 domain (A3-1), a permissive loop-2 region in the A3 domain (A3-2), the a3 region, or any combinations thereof are substituted or deleted;

wherein the FVIII protein comprises at least one XTEN; and wherein the recombinant FVIII protein exhibits procoagulant activity.

E2. The recombinant FVIII protein of embodiment E1, wherein the one or more amino acids substituted or deleted are in A1-1, A2-1, A3-1, A3-2, or any combinations thereof.

E3. The recombinant FVIII protein of embodiment E1, wherein the one or more amino acids substituted or deleted are in the a3 region.

E4. The recombinant FVIII protein of any one of embodiments E1 to E3, wherein an XTEN is inserted in at least one of A1-1, A1-2, A2-1, A2-2, A3-1, A3-2, or the a3 region.

E5. The recombinant FVIII protein of any one of embodiments E1 to E4, wherein the first polypeptide and the second polypeptide form a single polypeptide chain comprising the formula (A1)-a1-(A2)-a2-[B]-[a3]-(A3)-(C1).

E6. The recombinant FVIII protein of any one of embodiments E1 to E5, wherein the second polypeptide comprises the formula [a3]-(A3)-(C1)-(C2), wherein (C2) is a C2 domain of FVIII.

E7. The recombinant FVIII protein of any one of embodiments E1, E2, or E4 to E6, wherein the permissive loops are contained within surface-exposed, flexible loop structures, and wherein A1-1 is located between beta strand 1 and beta strand 2, A1-2 is located between beta strand 11 and beta strand 12, A2-1 is located between beta strand 22 and beta strand 23, A2-2 is located between beta strand 32 and beta strand 33, A3-1 is located between beta strand 38 and beta strand 39 and A3-2 is located between beta strand 45 and beta strand 46, according to the secondary structure of mature Factor VIII stored as Accession Number 2R7E of the DSSP database.

E8. The recombinant FVIII protein of embodiment E7, wherein the surface-exposed, flexible loop structure comprising A1-1 corresponds to a region in native mature human FVIII from about amino acid 15 to about amino acid 45 of SEQ ID NO: 4.

E9. The recombinant FVIII protein of embodiment E7, wherein A1-1 corresponds to a region in native mature human FVIII from about amino acid 18 to about amino acid 41 of SEQ ID NO: 4.

E10. The recombinant FVIII protein of any one of embodiments E1 to E9, wherein the one or more amino acids substituted or deleted are in A1-1.

E11. The recombinant FVIII protein of embodiment E10, wherein the one or more amino acids substituted or deleted in A1-1 comprise amino acids 19 to 22, amino acids 19 to 26, amino acids 19 to 32, amino acids 19 to 40, amino acids 23 to 26, amino acids 23 to 32, amino acids 23 to 40, amino acids 27 to 32, amino acids 27 to 40, or amino acids 33 to 40 corresponding to native mature human FVIII.

E12. The recombinant FVIII protein of embodiment E10 or E11, wherein an XTEN is inserted in at least one of A1-1, A1-2, A2-1, A2-2, A3-1, A3-2, or the a3 region.

E13. The recombinant FVIII protein of embodiment E10 or E11, wherein an XTEN is inserted immediately downstream of amino acid 18, amino acids 22, amino acids 26, or amino acids 32 corresponding to native human FVIII in A1-1.

E14. The recombinant FVIII protein of embodiment E7, wherein the surface-exposed, flexible loop structure comprising A1-2 corresponds to a region in native mature human FVIII from about amino acid 201 to about amino acid 232 of SEQ ID NO: 4.

E15. The recombinant FVIII protein of embodiment E7, wherein A1-2 corresponds to a region in native mature human FVIII from about amino acid 218 to about amino acid 229 of SEQ ID NO: 4.

E16. The recombinant FVIII protein of any one of embodiments E1 to E15, wherein the one or more amino acids substituted or deleted are in A1-2.

E17. The recombinant FVIII protein of embodiment E16, wherein an XTEN is inserted in at least one of A1-1, A1-2, A2-1, A2-2, A3-1, A3-2, or the a3 region.

E18. The recombinant FVIII protein of embodiment E7, wherein the surface-exposed, flexible loop structure comprising A2-1 corresponds to a region in native mature human FVIII from about amino acid 395 to about amino acid 421 of SEQ ID NO: 4.

E19. The recombinant FVIII protein of embodiment E7, wherein A2-1 corresponds to a region in native mature human FVIII from about amino acid 397 to about amino acid 418 of SEQ ID NO: 4.

E20. The recombinant FVIII protein of any one of embodiments E1 to E19, wherein the one or more amino acids substituted or deleted are in A2-1.

E21. The recombinant FVIII protein of embodiment E20, wherein the one or more amino acids substituted or deleted in A2-1 comprise amino acids 400 to 403 corresponding to native mature human FVIII in A2-1.

E22. The recombinant FVIII protein of embodiment E20 or embodiment E21, wherein an XTEN is inserted in at least one of A1-1, A1-2, A2-1, A2-2, A3-1, A3-2, or the a3 region.

E23. The recombinant FVIII protein of embodiment E20 or embodiment E21, wherein an XTEN is inserted immediately downstream of amino acid 399 corresponding to native human FVIII in A2-1.

E24. The recombinant FVIII protein of embodiment E7, wherein the surface-exposed, flexible loop structure comprising A2-2 corresponds to a region in native mature human FVIII from about amino acid 577 to about amino acid 635 of SEQ ID NO:4.

E25. The recombinant FVIII protein of embodiment E7, wherein A2-2 corresponds to a region in native mature human FVIII from about amino acid 595 to about amino acid 607 of SEQ ID NO: 4.

E26. The recombinant FVIII protein of any one of embodiments E1 to E25, wherein the one or more amino acids substituted or deleted are in A2-2.

E27. The recombinant FVIII protein of embodiment E26, wherein an XTEN is inserted in at least one of A1-1, A1-2, A2-1, A2-2, A3-1, A3-2, or the a3 region.

E28. The recombinant FVIII protein of embodiment E7, wherein the surface-exposed, flexible loop structure comprising A3-1 corresponds to a region in native mature human FVIII from about amino acid 1705 to about amino acid 1732 of SEQ ID NO: 4.

E29. The recombinant FVIII protein of embodiment E7, wherein A3-1 corresponds to a region in native mature human FVIII from about amino acid 1711 to about amino acid 1725 of SEQ ID NO: 4.

E30. The recombinant FVIII protein of any one of embodiments E1 to E29, wherein the one or more amino acids substituted or deleted are in A3-1.

E31. The recombinant FVIII protein of embodiment E30, wherein the one or more amino acids substituted or deleted in A3-1 comprise amino acids 1712 to 1720, amino acids 1712 to 1725, or amino acids 1721 to 1725 corresponding to native mature human FVIII.

E32. The recombinant FVIII protein of embodiment E30 or embodiment E31, wherein an XTEN is inserted in at least one of A1-1, A1-2, A2-1, A2-2, A3-1, A3-2, or the a3 region.

E33. The recombinant FVIII protein of embodiment E30 or embodiment E31, wherein an XTEN is inserted immediately downstream of amino acid 1711 or amino acids 1720 corresponding to native human FVIII in A3-1.

E34. The recombinant FVIII protein of embodiment E7, wherein the surface-exposed, flexible loop structure comprising A3-2 corresponds to a region in native mature human FVIII from about amino acid 1884 to about amino acid 1917 of SEQ ID NO: 4.

E35. The recombinant FVIII protein of embodiment E7, wherein A3-2 corresponds to a region in native mature human FVIII from about amino acid 1899 to about amino acid 1911 of SEQ ID NO: 4.

E36. The recombinant FVIII protein of embodiment E1 to E35, wherein the one or more amino acids substituted or deleted are in A3-2.

E37. The recombinant FVIII protein of embodiment E36, wherein the one or more amino acids substituted or deleted in A3-2 comprise amino acids 1901 to 1905, amino acids 1901 to 1910, amino acids 1906 to 1910, amino acids 1901 to 1905, amino acids 1901 to 1910, or amino acids 1906 to 1910 corresponding to native mature human FVIII.

E38. The recombinant FVIII protein of embodiment E36 or embodiment E37, wherein an XTEN is inserted in at least one of A1-1, A1-2, A2-1, A2-2, A3-1, A3-2, or the a3 region.

E39. The recombinant FVIII protein of embodiment E36 or embodiment E37, wherein an XTEN is inserted immediately downstream of amino acid 1900 or amino acid 1905 corresponding to native human FVIII in A3-2.

E40. The recombinant FVIII protein of any one of embodiments E1 to E39, wherein the one or more amino acids substituted or deleted are in the a3 region.

E41. The recombinant FVIII protein of embodiment E40, wherein the one or more amino acids substituted or deleted in the a3 region comprise amino acids 1649 to 1689 corresponding to native mature human FVIII.

E42. The recombinant FVIII protein of embodiment E40 or embodiment E41, wherein an XTEN is inserted in at least one of A1-1, A1-2, A2-1, A2-2, A3-1, A3-2, or the a3 region.

E43. The recombinant FVIII protein of embodiment E40 or embodiment E41, wherein an XTEN is inserted immediately downstream of amino acid 1645 corresponding to native mature human FVIII.

E44. The recombinant FVIII protein of any one of embodiments E1 to E43, wherein one or more amino acids in at least two, at least three, at least four, at least five, at least six, or seven of the regions of A1-1, A1-2, A2-1, A2-2, A3-1, A3-2, and the a3 region are substituted or deleted.

E45. The recombinant FVIII protein of embodiment E44, wherein an XTEN is inserted into the at least two, at least three, at least four, at least five, at least six, or seven of the regions A1-1, A1-2, A2-1, A2-2, A3-1, A3-2, and the a3 region.

E46. The recombinant FVIII protein of embodiment E45, wherein the XTEN is inserted immediately downstream of an amino acid which corresponds to an amino acid in mature native human FVIII selected from: amino acid 18 of SEQ ID NO: 4, amino acid 22 of SEQ ID NO: 4, amino acid 26 of SEQ ID NO: 4, amino acid 40 of SEQ ID NO: 4, amino acid 216 of SEQ ID NO: 4, amino acid 220 of SEQ ID NO: 4, amino acid 224 of SEQ ID NO: 4, amino acid 336 of SEQ ID NO: 4, amino acids 339 of SEQ ID NO: 4, amino acid 399 of SEQ ID NO: 4, amino acid 403 of SEQ ID NO: 4, amino acid 409 of SEQ ID NO: 4, amino acid 599 of SEQ ID NO: 4, amino acid 603 of SEQ ID NO: 4, amino acid 1711 of SEQ ID NO: 4, amino acid 1720 of SEQ ID NO: 4, amino acid 1725 of SEQ ID NO: 4, amino acid 1900 of SEQ ID NO: 4, amino acid 1905 of SEQ ID NO: 4, amino acid 1910 of SEQ ID NO: 4, or any combination thereof.

E47. The recombinant FVIII protein of any one of embodiments E1 to E46, which comprises at least two, at least three, at least four, at least five, at least six, or at least seven XTENs inserted in the FVIII protein.

E48. The recombinant FVIII protein of embodiment E47, wherein one or more of the at least two, at least three, at least four, at least five, at least six, or at least seven XTENs are inserted into the B domain or a1 region of the FVIII protein or fused to the C-terminus of the FVIII protein, or any combinations thereof.

E49. The recombinant FVIII protein of any one of embodiments E1 to E48, wherein at least two of the XTENs are the same or different.

E50. The recombinant FVIII protein of any one of embodiments E1 to E49, wherein at least one XTEN comprises a sequence of one or more amino acids inserted into the FVIII sequence.

E51. The recombinant FVIII protein of any one of embodiments E1 to E50, which further comprises a spacer between each XTEN and the FVIII polypeptide.

E52. The recombinant FVIII protein of any one of embodiments E1 to E51, wherein the XTEN increases the in vivo half-life of the recombinant FVIII protein.

E53. The recombinant FVIII protein of embodiment E52, wherein the XTEN comprises 36AE, 36AG, 42AE, 42AG, 72AE, 72AG, 144AE, 144AG, 288AE, 288AG, 576AE, 576AG, 864AE.

E54. The recombinant FVIII protein of embodiment E53, wherein the XTEN comprises the sequence selected from the group consisting of SEQ ID NOs: 22-34, 36-44, and 94-108.

E55. The recombinant FVIII protein of any one of embodiments E1 to E54, wherein at least one XTEN comprises an element that which increases the stability of the protein.

E56. The recombinant FVIII protein of any one of embodiments E1 to E55, wherein the recombinant FVIII protein has at least 10%, 20%, 30%, 40%, 50%, 60%, 70%, 80%, 90% or 100% of the procoagulant activity of native FVIII.

E57 The recombinant FVIII protein of any one of embodiments E1 to E56, wherein the procoagulant activity is measured by a chromogenic substrate assay, a one stage clotting assay or both.

E58. A fusion protein comprising the recombinant FVIII protein of any one of embodiments E1 to E57.

E59. A nucleic acid comprising a sequence encoding the recombinant FVIII protein of any one of embodiments E1 to E57.

E60. A set of nucleic acids comprising a set of sequences encoding the recombinant FVIII protein of any one of embodiments E1 to E57 or the fusion protein of embodiment E58.

E61. An expression vector comprising the nucleic acid of embodiment 59 or the set of nucleic acids of embodiment 60.

E62. A set of expression vectors comprising the set of nucleic acids of embodiment E60.

E63. A host cell comprising the nucleic acid of embodiment E59, the set of nucleic acids of embodiment E60, the vector of embodiment E61, or the set of expression vectors of embodiment E62.

E64. The host cell of embodiment E63, wherein the recombinant FVIII protein is expressed in vivo.

E65. The host cell of embodiment E64, wherein the recombinant FVIII protein is expressed in vitro.

E66. A method of producing a recombinant FVIII protein comprising culturing the host cell of any one of embodiments E63 to E65 under conditions in which the recombinant FVIII protein is expressed.

E67. A composition comprising the recombinant FVIII protein of any one of embodiments E1 to E57, the fusion protein of embodiment E58, the nucleic acid of embodiment E59, the set of nucleic acids of embodiment E60, the expression vector of embodiment E61, the set of expression vectors of embodiment E62, or the host cell of any one of embodiment E63 to E65 and a pharmaceutically acceptable excipient.

E68. A method of preventing, treating, ameliorating, or managing a clotting disease or condition in a patient in need thereof by administering an effective amount of the composition of embodiment E67.

E69. A method for diagnosing or imaging a clotting disease or condition in a patient with the composition of embodiment E67.

E70. A method of making a recombinant FVIII protein comprising substituting or deleting one or more amino acids in A1-1, A1-2, A2-1, A2-2, A3-1, A3-2, an a3 region, or any combinations thereof, wherein the recombinant FVIII protein comprises an XTEN and exhibits procoagulant activity.

E71. The method of embodiment E70, wherein the one or more amino acids substituted or deleted are in A1-1, A2-1, A3-1, A3-2, or any combinations thereof.

E72. The method of embodiment E71, wherein an XTEN is inserted into at least two, at least three, at least four, at least five, at least six, or seven of the regions A1-1, A1-2, A2-1, A2-2, A3-1, A3-2, or the a3 region.

E73. The method of any one of embodiments E70 or E71, wherein the XTEN is inserted immediately downstream of an amino acid which corresponds to an amino acid in mature native human FVIII selected from the group consisting of: amino acid 18 of SEQ ID NO: 4, amino acid 22 of SEQ ID NO: 4, amino acid 26 of SEQ ID NO: 4, amino acid 40 of SEQ ID NO: 4, amino acid 216 of SEQ ID NO: 4, amino acid 220 of SEQ ID NO: 4, amino acid 224 of SEQ ID NO: 4, amino acid 336 of SEQ ID NO: 4, amino acid 339 of SEQ ID NO: 4, amino acid 399 of SEQ ID NO: 4, amino acid 403 of SEQ ID NO: 4, amino acid 409 of SEQ ID NO: 4, amino acid 599 of SEQ ID NO: 4, amino acid 603 of SEQ ID NO: 4, amino acids 1645 of SEQ ID NO: 4, amino acid 1711 of SEQ ID NO: 4, amino acid 1720 of SEQ ID NO: 4, amino acid 1725 of SEQ ID NO: 4, amino acid 1900 of SEQ ID NO: 4, amino acid 1905 of SEQ ID NO: 4, amino acid 1910 of SEQ ID NO: 4, and any combination thereof.

E74. The method of any one of embodiments E70 to E73, wherein an additional XTEN is inserted into the B-domain or fused to the C-terminus.

E75. The method of embodiment E74, wherein the additional XTEN is inserted immediately downstream of an amino acid which corresponds to amino acid 745 of SEQ ID NO: 4 or amino acid 2332 of SEQ ID NO: 4.

E76. The method of any one of embodiments E70 to E75, wherein at least one XTEN comprises a sequence of one or more amino acids inserted into the FVIII sequence.

E77. The method of any one of embodiments E70 to E76, wherein at least one XTEN increases the in vivo half-life of the protein.

E78. A method to increase the half-life of a FVIII protein comprising substituting or deleting one or more amino acids in A1-1, A1-2, A2-1, A2-2, A3-1, A3-2, an a3 region, or any combinations thereof and inserting at least one XTEN into the one or more amino acids substituted or deleted, wherein the insertion of at least one XTEN results in increased half-life of the FVIII protein compared to the expression of the corresponding FVIII protein without the at least one XTEN inserted in A1-1, A1-2, A2-1, A2-2, A3-1, A3-2, the a3 region, or any combinations thereof.

E79. The method of embodiment E78, wherein the permissive loops are contained within surface-exposed, flexible loop structures, and wherein A1-1 is located between beta strand 1 and beta strand 2, A1-2 is located between beta strand 11 and beta strand 12, A2-1 is located between beta strand 22 and beta strand 23, A2-2 is located between beta strand 32 and beta strand 33, A3-1 is located between beta strand 38 and beta strand 39 and A3-2 is located between beta strand 45 and beta strand 46, according to the secondary structure of mature Factor VIII stored as Accession Number 2R7E of the DSSP database.

E80. The method of embodiment E79, wherein the surface-exposed, flexible loop structure comprising A1-1 corresponds to a region in native mature human FVIII from about amino acid 15 to about amino acid 45 of SEQ ID NO: 4.

E81. The method of embodiment E79, wherein A1-1 corresponds to a region in native mature human FVIII from about amino acid 18 to about amino acid 41 of SEQ ID NO: 4.

E82. The method of any one of embodiments E79 to E81, wherein the one or more amino acids substituted or deleted are in A1-1.

E83. The method of embodiment E82, wherein the one or more amino acids deleted in A1-1 comprise amino acids 19 to 22, amino acids 19 to 26, amino acids 19 to 32, amino acids 19 to 40, amino acids 23 to 26, amino acids 23 to 32, amino acids 23 to 40, amino acids 27 to 32, amino acids 27 to 40, or amino acids 33 to 40 corresponding to native mature human FVIII.

E84. The method of embodiment E82 or E83, wherein the XTEN is inserted in A1-1, A1-2, A2-1, A2-2, A3-1, A3-2, or the a3 region.

E85. The method of embodiment E82 or E83, wherein the XTEN is inserted immediately downstream of amino acid 18, amino acids 22, amino acids 26, or amino acids 32 corresponding to native human FVIII in A1-1.

E86. The method of embodiment E79, wherein the surface-exposed, flexible loop structure comprising A1-2 corresponds to a region in native mature human FVIII from about amino acid 201 to about amino acid 232 of SEQ ID NO: 4.

E87. The method of embodiment E79, wherein A1-2 corresponds to a region in native mature human FVIII from about amino acid 218 to about amino acid 229 of SEQ ID NO: 4.

E88. The method of any one of embodiments E78 to E87, wherein the one or more amino acids substituted or deleted are in A1-2.

E89. The method of embodiment E88, wherein the XTEN is inserted in A1-1, A1-2, A2-1, A2-2, A3-1, A3-2, or the a3 region.

E90. The method of embodiment E79, wherein the surface-exposed, flexible loop structure comprising A2-1 corresponds to a region in native mature human FVIII from about amino acid 395 to about amino acid 421 of SEQ ID NO: 4.

E91. The method of embodiment E79, wherein A2-1 corresponds to a region in native mature human FVIII from about amino acid 397 to about amino acid 418 of SEQ ID NO: 4.

E92. The method of any one of embodiments E79 to E91, wherein the one or more amino acids substituted or deleted are in A2-1.

E93. The method of embodiment E92, wherein the one or more amino acids deleted in A2-1 comprise amino acids 400 to 403 corresponding to native mature human FVIII.

E94. The method of embodiment E92 or embodiment E93, wherein the XTEN is inserted in A1-1, A1-2, A2-1, A2-2, A3-1, A3-2, or the a3 region.

E95. The method of embodiment 106 or embodiment 107, wherein the XTEN is inserted immediately downstream of amino acid 399 corresponding to native human FVIII.

E96. The method of embodiment E79, wherein the surface-exposed, flexible loop structure comprising A2-2 corresponds to a region in native mature human FVIII from about amino acid 577 to about amino acid 635 of SEQ ID NO: 4.

E97. The method of embodiment E79, wherein A2-2 corresponds to a region in native mature human FVIII from about amino acid 595 to about amino acid 607 of SEQ ID NO: 4.

E98. The method of any one of embodiments E78 to E97, wherein the one or more amino acids substituted or deleted are in A2-2.

E99. The method of embodiment E98, wherein the XTEN is inserted in A1-1, A1-2, A2-1, A2-2, A3-1, A3-2, or the a3 region.

E100. The method of embodiment E79, wherein the surface-exposed, flexible loop structure comprising A3-1 corresponds to a region in native mature human FVIII from about amino acid 1705 to about amino acid 1732 of SEQ ID NO: 4.

E101. The method of embodiment E79, wherein A3-1 corresponds to a region in native mature human FVIII from about amino acid 1711 to about amino acid 1725 of SEQ ID NO: 4.

E102. The method of any one of embodiments E78 to E101, wherein the one or more amino acids substituted or deleted are in A3-1.

E103. The method of embodiment E102, wherein the one or more amino acids substituted or deleted in A3-1 comprise amino acids 1712-1720, amino acids 1712-1725, or amino acids 1721-1725 corresponding to native mature human FVIII.

E104. The method of embodiment E102 or embodiment E103, wherein the XTEN is inserted in A1-1, A1-2, A2-1, A2-2, A3-1, A3-2, or the a3 region.

E105. The method of embodiment E102 or embodiment E103, wherein the XTEN is inserted immediately downstream of amino acid 1711 or amino acids 1720 corresponding to native human FVIII.

E106. The method of embodiment E79, wherein the surface-exposed, flexible loop structure comprising A3-2 corresponds to a region in native mature human FVIII from about amino acid 1884 to about amino acid 1917 of SEQ ID NO: 4.

E107. The method of embodiment E79, wherein A3-2 corresponds to a region in native mature human FVIII from about amino acid 1899 to about amino acid 1911 of SEQ ID NO: 4.

E108. The method of embodiment E78 to E107, wherein the one or more amino acids substituted or deleted are in A3-2.

E109. The method of embodiment E108, wherein the one or more amino acids substituted or deleted in A3-2 comprise amino acids 1901-1905, amino acids 1901-1910, amino acids 1906-1910, amino acids 1901-1905, amino acids 1901-1910, or amino acids 1906-1910 corresponding to native mature human FVIII.

E110. The method of embodiment E108 or embodiment E109, wherein the XTEN is inserted in A1-1, A1-2, A2-1, A2-2, A3-1, A3-2, or the a3 region.

E111. The method of embodiment E108 or embodiment E109, wherein the XTEN is inserted immediately downstream of amino acid 1900 or amino acid 1905 corresponding to native human FVIII.

E112. The method of any one of embodiments E78 to E111, wherein the one or more amino acids substituted or deleted are in the a3 region.

E113. The method of embodiment E112, wherein the one or more amino acids substituted or deleted in the a1 region comprise amino acids 1649 to 1689 corresponding to native mature human FVIII.

E114. The method of embodiment E78 or embodiment E113, wherein the XTEN is inserted in A1-1, A1-2, A2-1, A2-2, A3-1, A3-2, or the a3 region.

E115. The method of embodiment E113 or embodiment E114, wherein an XTEN is inserted immediately downstream of amino acid 1656 corresponding to native mature human FVIII in the a3 region.

BRIEF DESCRIPTION OF THE DRAWINGS/FIGURES

FIG. 1. Half-life of chimeric proteins comprising FVIII polypeptides and XTEN insertions. Chimeric proteins containing XTEN insertions of various sizes and in various locations were administered to DKO mice and HemA mice, and the half-life of the chimeric proteins was measured. Testing VWF-binding FVIII polypeptides (e.g., FVIII polypeptides without a deletion in FVIII amino acids 746-1685) in DKO mice is comparable to testing VWF-binding-deficient FVIII polypeptides (e.g., FVIII polypeptides lacking amino acids 746-1685) in HemA mice.

FIG. 2. Half-life of chimeric proteins comprising FVIII polypeptides with reduced binding to VWF and 4 XTEN insertions. Chimeric proteins pNL0044, pNL0049, pNL0050, and pNL0051, and recombinant Factor VIII were administered to HemA mice, and the half-life of the proteins was measured.

FIG. 3. Effect of XTEN size and insertion site on the half-life of chimeric proteins. Chimeric proteins containing XTEN insertions of various sizes and in various locations were administered to DKO mice and the half-life of the chimeric proteins was measured.

FIG. 4. Example of the method used to replace all or part of loop A1-1.

FIG. 5A-F. Graphs showing half-life effect of XTEN insertions on the chimeric constructs comprising FVIII polypeptides. FIG. 5A shows the FVIII activity of chimeric construct pKY0038 (encoding a FVIII polypeptide with XTEN insertions at amino acid 18 (AE42), amino acid 1720 (AE42), B domain (AE144), C-terminus (AE288), and amino acid 220 (AE42)) compared to the FVIII activity of pNL0051, the base vector. FIG. 5B shows the FVIII activity of chimeric construct pKY0040 (encoding a FVIII polypeptide with XTEN insertions at amino acid 18 (AE42), amino acid 1720 (AE42), B domain (AE144), C-terminus (AE288), and amino acid 333 (AE42)) compared to the FVIII activity of pNL0051, the base vector. FIG. 5C shows the FVIII activity of pKY0044 (encoding a FVIII polypeptide with XTEN insertions at amino acid 18 (AE42), amino acid 1720 (AE42), B domain (AE144), C-terminus (AE288), and amino acid 403 (AE42)) compared to the FVIII activity of pNL0051, the base vector. FIG. 5D shows the FVIII activity of pKY0045 (encoding a FVIII polypeptide with XTEN insertions at amino acid 18 (AE42), amino acid 1720 (AE42), B domain (AE144), C-terminus (AE288), and amino acid 599 (AE42)) compared to the FVIII activity of pNL0051, the base vector. FIG. 5E shows the FVIII activity of pKY0047 (encoding a FVIII polypeptide with XTEN insertions at amino acid 18 (AE42), amino acid 1720 (AE42), B domain (AE144), C-terminus (AE288), and amino acid 1900 (AE42)) compared to the FVIII activity of pNL0051, the base vector. FIG. 5F shows the FVIII activity of pKY0050 (encoding a FVIII polypeptide with XTEN insertions at amino acid 18 (AE42), amino acid 1720 (AE42), B domain (AE144), C-terminus (AE288), and amino acid 2171 (AE42)) compared to the FVIII activity of pNL0051, the base vector. Each graph indicates the region of the chimeric protein wherein the fifth 42aa XTEN is inserted.

DETAILED DESCRIPTION OF THE INVENTION

Definitions

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

The term "polynucleotide" or "nucleotide" is intended to encompass a singular nucleic acid as well as plural nucleic acids, and refers to an isolated nucleic acid molecule or construct, e.g., messenger RNA (mRNA) or plasmid DNA (pDNA). In certain embodiments, a polynucleotide comprises a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a Factor VIII polypeptide contained in a vector is considered isolated for the purposes of the present invention. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can include regulatory elements such as promoters, enhancers, ribosome binding sites, or transcription termination signals.

As used herein, a "coding region" or "coding sequence" is a portion of polynucleotide which consists of codons translatable into amino acids. Although a "stop codon" (TAG, TGA, or TAA) is typically not translated into an amino acid, it may be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions of the present invention can be present in a single polynucleotide construct, e.g., on a single vector, or in separate polynucleotide constructs, e.g., on separate (different) vectors. It follows, then, that a single vector can contain just a single coding region, or comprise two or more coding regions, e.g., a single vector can separately encode a binding domain-A and a binding domain-B as described below. In addition, a vector, polynucleotide, or nucleic acid of the invention can encode heterologous coding regions, either fused or unfused to a nucleic acid encoding a binding domain of the invention. Heterologous coding regions include without limitation specialized elements or motifs, such as a secretory signal peptide or a heterologous functional domain.

Certain proteins secreted by mammalian cells are associated with a secretory signal peptide which is cleaved from the mature protein once export of the growing protein chain across the rough endoplasmic reticulum has been initiated.

Those of ordinary skill in the art are aware that signal peptides are generally fused to the N-terminus of the polypeptide, and are cleaved from the complete or "full-length" polypeptide to produce a secreted or "mature" form of the polypeptide. In certain embodiments, a native signal peptide or a functional derivative of that sequence that retains the ability to direct the secretion of the polypeptide that is operably associated with it. Alternatively, a heterologous mammalian signal peptide, e.g., a human tissue plasminogen activator (TPA) or mouse β-glucuronidase signal peptide, or a functional derivative thereof, can be used.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions may include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

A "vector" refers to any vehicle for the cloning of and/or transfer of a nucleic acid into a host cell. A vector may be a replicon to which another nucleic acid segment may be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

Vectors may be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), -galactosidase (LacZ), -glucuronidase (Gus), and the like. Selectable markers may also be considered to be reporters.

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, and poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment may be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, micro-injection, transduction, cell fusion, DEAE dextran, calcium phosphate precipitation, lipofection (lysosome fusion), use of a gene gun, or a DNA vector transporter.

"Culture," "to culture" and "culturing," as used herein, means to incubate cells under in vitro conditions that allow for cell growth or division or to maintain cells in a living state. "Cultured cells," as used herein, means cells that are propagated in vitro.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced recombinant technology, but is not necessarily translated from a designated nucleic acid sequence. It can be generated in any manner, including by chemical synthesis.

An "isolated" polypeptide or a fragment, variant, or derivative thereof refers to a polypeptide that is not in its natural milieu. No particular level of purification is required. For example, an isolated polypeptide can simply be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

Also included in the present invention are fragments or variants of polypeptides, and any combination thereof. The term "fragment" or "variant" when referring to polypeptide binding domains or binding molecules of the present invention include any polypeptides which retain at least some of the properties (e.g., FcRn binding affinity for an FcRn binding domain or Fc variant, coagulation activity for an FVIII variant, or FVIII binding activity for the VWF fragment) of the reference polypeptide. Fragments of polypeptides include proteolytic fragments, as well as deletion fragments, in addition to specific antibody fragments discussed elsewhere herein, but do not include the naturally occurring full-length polypeptide (or mature polypeptide). Variants of polypeptide binding domains or binding molecules of the present invention include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

A "conservative amino acid substitution" is one in which the amino acid residue is replaced with an amino acid residue having a similar side chain Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acids can be characterized based on their hydrophobicity. A number of scales have been developed. An example is a scale developed by Levitt, M, et al., *J Mol Biol* (1976) 104:59, which is listed in Hopp, T P, et al., *Proc Natl Acad Sci* USA (1981) 78:3824. Examples of "hydrophilic amino acids" are arginine, lysine, threonine, alanine, asparagine, glutamine, aspartate, glutamate, and serine, and glycine. Examples of "hydrophobic amino acids" are tryptophan, tyrosine, phenylalanine, methionine, leucine, isoleucine, and valine. Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

As known in the art, "sequence identity" between two polypeptides is determined by comparing the amino acid sequence of one polypeptide to the sequence of a second polypeptide. When discussed herein, whether any particular polypeptide is at least about 50%, 60%, 70%, 75%, 80%, 85%, 90%, 95%, 99%, or 100% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full-length of the reference polypeptide sequence and that gaps in homology of up to 5% of the total number of amino acids in the reference sequence are allowed.

As used herein, an "amino acid corresponding to" or an "equivalent amino acid" in a FVIII protein sequence is identified by alignment to maximize the identity or similarity between a first FVIII sequence and a second FVIII sequence. The number used to identify an equivalent amino acid in a second FVIII sequence is based on the number used to identify the corresponding amino acid in the first FVIII sequence.

As used herein, the term "insertion site" refers to a position in a FVIII polypeptide, or fragment, variant, or derivative thereof, which is immediately upstream of the position at which a heterologous moiety can be inserted. An "insertion site" is specified as a number, the number being the number of the amino acid in mature native FVIII (SEQ ID NO: 4) to which the insertion site corresponds, which is immediately N-terminal to the position of the insertion. For example, the phrase "a3 comprises an XTEN at an insertion site which corresponds to amino acid 1656 of SEQ ID NO: 4" indicates that the heterologous moiety is located between two amino acids corresponding to amino acid 1656 and amino acid 1657 of SEQ ID NO: 4.

The phrase "immediately downstream of an amino acid" as used herein refers to position right next to the terminal carboxyl group of the amino acid. Similarly, the phrase "immediately upstream of an amino acid" refers to the position right next to the terminal amine group of the amino acid. Therefore, the phrase "between two amino acids of an insertion site" as used herein refers to a position in which an XTEN or any other polypeptide is inserted between two adjacent amino acids. Thus, the phrases "inserted immediately downstream of an amino acid" and "inserted between two amino acids of an insertion site" are used synonymously with "inserted at an insertion site."

The terms "inserted," "is inserted," "inserted into" or grammatically-related terms, as used herein refers to the position of an XTEN in a chimeric polypeptide relative to the analogous position in native mature human FVIII. As used herein the terms refer to the characteristics of the recombinant FVIII polypeptide relative to native mature human FVIII, and do not indicate, imply or infer any methods or process by which the chimeric polypeptide was made. For example, in reference to a chimeric polypeptide provided herein, the phrase "an XTEN is inserted into immediately downstream of residue 745 of the FVIII polypeptide" means that the chimeric polypeptide comprises an XTEN immediately downstream of an amino acid which corresponds to amino acid 745 in native mature human FVIII, e.g., bounded by amino acids corresponding to amino acids 745 and 746 of native mature human FVIII.

As used herein, "internal XTEN" refers to XTEN sequences that have been inserted into the sequence of the FVIII. Internal XTENs can be constructed by insertion of an XTEN sequence into the sequence of FVIII, either by insertion between two adjacent amino acids within a domain ("intradomain") or between two domains ("interdomain") of the FVIII or wherein XTEN replaces a partial, internal sequence of the FVIII.

As used herein, "terminal XTEN" refers to XTEN sequences that have been fused to or in the N- or C-terminus of the FVIII or to a proteolytic cleavage sequence or linker at the N- or C-terminus of the FVIII. Terminal XTENs can be fused to the native termini of the FVIII. Alternatively, terminal XTENs can replace a portion of a terminal sequence of the FVIII.

The term "XTEN release site" refers to a cleavage sequence in chimeric FVIII-XTEN fusion proteins that can be recognized and cleaved by a mammalian protease, effecting release of an XTEN or a portion of an XTEN from the chimeric FVIII-XTEN fusion protein. As used herein, "mammalian protease" means a protease that normally exists in the body fluids, cells or tissues of a mammal XTEN release sites can be engineered to be cleaved by various mammalian proteases (a.k.a. "XTEN release proteases") such as FXIa, FXIIa, kallikrein, FVIIIa, FVIIIa, FXa, FIIa (thrombin), Elastase-2, MMP-12, MMP13, MMP-17, MMP-20, or any protease that is present during a clotting event. Other equivalent proteases (endogenous or exogenous) that are capable of recognizing a defined cleavage site can be utilized. The cleavage sites can be adjusted and tailored to the protease utilized.

A "fusion" or "chimeric" protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a Factor VIII domain of the invention with an Ig Fc domain. A fusion protein is created, for example, by chemical synthesis, or by creating and translating a polynucleotide in which the peptide regions are encoded in the desired relationship. A chimeric protein can further comprises a second amino acid sequence associated with the first amino acid sequence by a covalent, non-peptide bond or a non-covalent bond.

As used herein, the term "half-life" refers to a biological half-life of a particular polypeptide in vivo. Half-life may be represented by the time required for half the quantity administered to a subject to be cleared from the circulation and/or other tissues in the animal. When a clearance curve of a given polypeptide is constructed as a function of time, the curve is usually biphasic with a rapid $\alpha$-phase and longer $\beta$-phase. The $\alpha$-phase typically represents an equilibration of the administered polypeptide between the intra- and extra-vascular space and is, in part, determined by the size of the polypeptide. The $\beta$-phase typically represents the catabolism of the polypeptide in the intravascular space. In some embodiments, FVIII and chimeric proteins comprising FVIII are monophasic, and thus do not have an alpha phase, but just the single beta phase. Therefore, in certain embodiments, the term half-life as used herein refers to the half-life of the polypeptide in the $\beta$-phase. The typical $\beta$ phase half-life of a human antibody in humans is 21 days.

The term "linked" as used herein refers to a first amino acid sequence or nucleotide sequence covalently or non-covalently joined to a second amino acid sequence or nucleotide sequence, respectively. The first amino acid or nucleotide sequence can be directly joined or juxtaposed to the second amino acid or nucleotide sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence can be linked to a second amino acid sequence by a peptide bond or a linker. The first nucleotide sequence can be linked to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucleotide chains) The term "linked" is also indicated by a hyphen (-).

The term "monomer-dimer hybrid" used herein refers to a chimeric protein comprising a first polypeptide chain and a second polypeptide chain, which are associated with each other by a disulfide bond, wherein the first chain comprises a clotting factor, e.g., Factor VIII, and a first Fc region and the second chain comprises, consists essentially of, or consists of a second Fc region without the clotting factor. The monomer-dimer hybrid construct thus is a hybrid comprising a monomer aspect having only one clotting factor and a dimer aspect having two Fc regions.

As used herein, the term "cleavage site" or "enzymatic cleavage site" refers to a site recognized by an enzyme. Certain enzymatic cleavage sites comprise an intracellular processing site. In one embodiment, a polypeptide has an enzymatic cleavage site cleaved by an enzyme that is activated during the clotting cascade, such that cleavage of such sites occurs at the site of clot formation. Exemplary such sites include, e.g., those recognized by thrombin, Factor XIa or Factor Xa. Exemplary FXIa cleavage sites include, e.g., TQSFNDFTR (SEQ ID NO: 45) and SVSQTSKLTR (SEQ ID NO: 46). Exemplary thrombin cleavage sites include, e.g., DFLAEGGGVR (SEQ ID NO: 47), TTKIKPR (SEQ ID NO: 48), LVPRG (SEQ ID NO: 49) and ALRPR (amino acids 1 to 5 of SEQ ID NO: 50). Other enzymatic cleavage sites are known in the art.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency). Other hemostatic disorders include, e.g., Von Willebrand disease, Factor XI deficiency (PTA deficiency), Factor XII deficiency, deficiencies or structural abnormalities in fibrinogen, prothrombin, Factor V, Factor VII, Factor X or factor XIII, Bernard-Soulier syndrome, which is a defect or deficiency in GPIb. GPIb, the receptor for VWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this may increase bleeding risk.

The chimeric molecules of the invention can be used prophylactically. As used herein the term "prophylactic treatment" refers to the administration of a molecule prior to a bleeding episode. In one embodiment, the subject in need of a general hemostatic agent is undergoing, or is about to undergo, surgery. The chimeric protein of the invention can be administered prior to or after surgery as a prophylactic. The chimeric protein of the invention can be administered during or after surgery to control an acute bleeding episode. The surgery can include, but is not limited to, liver transplantation, liver resection, dental procedures, or stem cell transplantation.

The chimeric protein of the invention is also used for on-demand treatment. The term "on-demand treatment" refers to the administration of a chimeric molecule in response to symptoms of a bleeding episode or before an activity that may cause bleeding. In one aspect, the on-demand treatment can be given to a subject when bleeding starts, such as after an injury, or when bleeding is expected, such as before surgery. In another aspect, the on-demand treatment can be given prior to activities that increase the risk of bleeding, such as contact sports.

As used herein the term "acute bleeding" refers to a bleeding episode regardless of the underlying cause. For example, a subject may have trauma, uremia, a hereditary bleeding disorder (e.g., factor VII deficiency) a platelet disorder, or resistance owing to the development of antibodies to clotting factors.

"Treat," "treatment," "treating," as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition, or the prophylaxis of one or more symptoms associated with a disease or condition. In one embodiment, the term treating or treatment means maintaining a FVIII trough level at least about 1 IU/dL, 2 IU/dL, 3 IU/dL, 4 IU/dL, 5 IU/dL, 6 IU/dL, 7 IU/dL, 8 IU/dL, 9 IU/dL, 10 IU/dL, 11 IU/dL, 12 IU/dL, 13 IU/dL, 14 IU/dL, 15 IU/dL, 16 IU/dL, 17 IU/dL, 18 IU/dL, 19 IU/dL, or 20 IU/dL in a subject by administering a chimeric protein or a VWF fragment of the invention. In another embodiment, treating or treatment means maintaining a FVIII trough level between about 1 and about 20 IU/dL, about 2 and about 20 IU/dL, about 3 and about 20 IU/dL, about 4 and about 20 IU/dL, about 5 and about 20 IU/dL, about 6 and about 20 IU/dL, about 7 and about 20 IU/dL, about 8 and about 20 IU/dL, about 9 and about 20 IU/dL, or about 10 and about 20 IU/dL. Treatment or treating of a disease or condition can also include maintaining FVIII activity in a subject at a level comparable to at least about 1%, 2%, 3%, 4%, 5%, 6%, 7%, 8%, 9%, 10%, 11%, 12%, 13%, 14%, 15%, 16%, 17%, 18%, 19%, or 20% of the FVIII activity in a non-hemophiliac subject. The minimum trough level required for treatment can be measured by one or more known methods and can be adjusted (increased or decreased) for each person.

Factor VIII (FVIII) Protein

A "FVIII protein" or a "FVIII polypeptide" as used herein means a functional FVIII polypeptide in its normal role in coagulation, unless otherwise specified. The term a FVIII protein includes a functional fragment, variant, analog, or derivative thereof that retains the function of full-length wild-type Factor VIII in the coagulation pathway. The term FVIII protein is used interchangeably with FVIII polypeptide (or protein) or FVIII. Examples of the FVIII functions include, but not limited to, an ability to activate coagulation, an ability to act as a cofactor for factor IX, or an ability to form a tenase complex with factor IX in the presence of $Ca^{2+}$ and phospholipids, which then converts Factor X to the activated form Xa. The FVIII protein can be the human, porcine, canine, rat, or murine FVIII protein. In addition, comparisons between FVIII from humans and other species have identified conserved residues that are likely to be required for function (Cameron et al., *Thromb. Haemost.* 79:317-22 (1998); U.S. Pat. No. 6,251,632).

In certain aspects, the FVIII polypeptide of the invention has reduced affinity for von Willebrand Factor (VWF).

Exemplary polypeptides with reduced affinity for VWF are described in more detail below.

A number of tests are available to assess the function of the coagulation system: activated partial thromboplastin time (aPTT) test, chromogenic assay, ROTEM assay, prothrombin time (PT) test (also used to determine INR), fibrinogen testing (often by the Clauss method), platelet count, platelet function testing (often by PFA-100), TCT, bleeding time, mixing test (whether an abnormality corrects if the patient's plasma is mixed with normal plasma), coagulation factor assays, antiphospholipid antibodies, D-dimer, genetic tests (e.g., factor V Leiden, prothrombin mutation G20210A), dilute Russell's viper venom time (dRVVT), miscellaneous platelet function tests, thromboelastography (TEG or Sonoclot), thromboelastometry (TEM®, e.g., ROTEM®), or euglobulin lysis time (ELT).

The aPTT test is a performance indicator measuring the efficacy of both the "intrinsic" (also referred to the contact activation pathway) and the common coagulation pathways. This test is commonly used to measure clotting activity of commercially available recombinant clotting factors, e.g., FVIII or FIX. It is used in conjunction with prothrombin time (PT), which measures the extrinsic pathway.

ROTEM analysis provides information on the whole kinetics of haemostasis: clotting time, clot formation, clot stability and lysis. The different parameters in thromboelastometry are dependent on the activity of the plasmatic coagulation system, platelet function, fibrinolysis, or many factors which influence these interactions. This assay can provide a complete view of secondary haemostasis.

FVIII polypeptides and the polynucleotide sequences encoding FVIII polypeptides are known in the art, as are many functional fragments, mutants and modified versions. Examples of FVIII proteins are provided in PCT/US2013/026521, filed Feb. 15, 2013, which is herein incorporated by reference in its entirety. Additional examples of human FVIII sequences (full-length) are shown below.

TABLE 1

| Amino Acid Sequence of Full-length Factor VIII (Full-length FVIII (FVIII signal peptide underlined; FVIII heavy chain is double underlined; B domain is italicized; and FVIII light chain is in plain text) |
|---|
| Signal Peptide (SEQ ID NO: 3) |
| MQIELSTCFFLCLLRFCFS |
| |
| Mature Factor VIII (SEQ ID NO: 4)* |
| ATRRYYLGAVELSWDYMQSDLGELPVDARFPPRVPKSFPFNTSVVYKKTLFVEFTDHLFNIAKPRPPWMGLL |
| GPTIQAEVYDTVVITLKNMASHPVSLHAVGVSYWKASEGAEYDDQTSQREKEDDKVEPGGSHTYVWQVLKEN |
| GPMASDPLCLTYSYLSHVDLVKDLNSGLTGALLVCREGSLAKEKTQTLHKFILLFAVFDEGKSWHSETKNSL |
| MQDRDAASARAWPKMHTVNGYVNRSLPGLIGCHRKSVYWHVIGMGTTPEVHSIFLEGHTELVRNHRQASLEI |
| SPITFLTAQTLLMDLGQFLLFCHISSHQHDGMEAYVKVDSCPEEPQLRMKNNEEAEDYDDDLTDSEMDVVRF |
| DDDNSPSFIQIRSVAKKHPKTWVHYTAAEEEDWDYAPLVLAPDDRSYKSQYLNNGPQRIGRKYKKVRFMAYT |
| DETFKTREAIQHESGILGPLLYGEVGDTLLTTFKKQASRPYNIYPHGITDVRPLYSRRLPKGVKHLKDFPIL |
| PGEIFKYKWTVTVEDGPTKSDPRCLTRYYSSFVNMERDLASGLIGPLLICYKESVDQRGNQIMSDKRNVILF |
| SVFDENRSWYLTENIQRFLPNPAGVQLEDPEFQASNIMHSINGYVFDSLQLSVCLHEVAYWYILSIGAQTDF |
| LSVFFSGYTFKHKMVYEDTLTLFPFSGETVFMSMENPGLWILGCHNSDFRNRGMTALLKVSSCDKNTGDYYE |
| DSYEDISAYLLSKNNAIEPR*SFSQNSRHPSTRQKQFNATTIPENDIEKTDPWRAHRTPMPKIQNVSSSDLLM* |
| *LLRQSPTPHGLSLSDLQEAKYETFSDDPSPGAIDSNNSLSMTHFRPQLHHSGDMTVFTPESGLQLRLNEKLG* |
| *TTAATELKKLDFKVSSTSNNLISTIPSDNLAAGTDNTSSLGPPSMPVHYDSQLDTTLFGKKSSPLTESGGPL* |
| *SLSEENNKSKLLESGLMNSQESSWGKNVSSTESGRLFKGKRAHGPALLTKDNALFKVSISLLKTNKTSNNSA* |
| *TNRKTHIDGPSLLIENSPSVWQNILESDTEFKKVTPLIHDRMLMDKNATALRLNHMSNKTTSSKNMEMVQQK* |
| *KEGPIPPDAQNPDMSFFKMLFLPESARWIQRTHGKNSLNSGQGPSPKQLVSLGPEKSVEGQNFLSEKNKVVV* |
| *GKGEFTKDVGLKEMVFPSSRNLFLTNLDNLHENNTHNQEKKIQEEIEKKETLIQENVVLPQIHTVTGTKNFM* |
| *KNLFLLSTRQNVEGSYDGAYAPVLQDFRSLNDSTNRTKKHTAHFSKKGEEENLEGLGNQTKQIVEKYACTTR* |
| *ISPNTSQQNFVTQRSKRALKQFRLPLEETELEKRIIVDDTSTQWSKNMKHLTPSTLTQIDYNEKEKGAITQS* |
| *PLSDCLTRSHSIPQANRSPLPIAKVSSFPSIRPIYLTRVLFQDNSSHLPAASYRKKDSGVQESSHFLQGAKK* |
| *NNLSLAILTLEMTGDQREVGSLGTSATNSVTYKKVENTVLPKPDLPKYSGKVELLPKVHIYQKDLFPTETSN* |
| *GSPGHLDLVEGSLLQGTEGAIKWNEANRPGKVPFLRVATESSAKTPSKLLDPLAWDNHYGTQIPKEEWKSQE* |
| *KSPEKTAFKKKDTILSLNACESNHAIAAINEGQNKPEIEVTWAKQGRTERLCSQNPPVLKRHQREITRTTLQ* |
| SDQEEIDYDDTISVEMKKEDFDIYDEDENQSPRSFQKKTRHYFIAAVERLWDYGMSSSPHVLRNRAQSGSVP |

TABLE 1-continued

| Amino Acid Sequence of Full-length Factor VIII (Full-length FVIII (FVIII signal peptide underlined; FVIII heavy chain is double underlined; B domain is italicized; and FVIII light chain is in plain text) |
|---|
| QFKKVVFQEFTDGSFTQPLYRGELNEHLGLLGPYIRAEVEDNIMVTFRNQASRPYSFYSSLISYEEDQRQGA |
| EPRKNFVKPNETKTYFWKVQHHMAPTKDEFDCKAWAYFSDVDLEKDVHSGLIGPLLVCHTNTLNPAHGRQVT |
| VQEFALFFTIFDETKSWYFTENMERNCRAPCNIQMEDPTFKENYRFHAINGYIMDTLPGLVMAQDQRIRWYL |
| LSMGSNENIHSIHFSGHVFTVRKKEEYKMALYNLYPGVFETVEMLPSKAGIWRVECLIGEHLHAGMSTLFLV |
| YSNKCQTPLGMASGHIRDFQITASGQYGQWAPKLARLHYSGSINAWSTKEPFSWIKVDLLAPMIIHGIKTQG |
| ARQKFSSLYISQFIIMYSLDGKKWQTYRGNSTGTLMVFFGNVDSSGIKHNIFNPPIIARYIRLHPTHYSIRS |
| TLRMELMGCDLNSCSMPLGMESKAISDAQITASSYFTNMFATWSPSKARLHLQGRSNAWRPQVNNPKEWLQV |
| DFQKTMKVTGVTTQGVKSLLTSMYVKEFLISSSQDGHQWTLFFQNGKVKVFQGNQDSFTPVVNSLDPPLLTR |
| YLRIHPQSWVHQIALRMEVLGCEAQDLY |

TABLE 2

Nucleotide Sequence Encoding Full-Length FVIII (SEQ ID NO: 5)*

| | |
|---|---|
| 661 | ATG CAAATAGAGC TCTCCACCTG |
| 721 | CTTCTTTCTG TGCCTTTTGC GATTCTGCTT TAGTGCCACC AGAAGATACT ACCTGGGTGC |
| 781 | AGTGGAACTG TCATGGGACT ATATGCAAAG TGATCTCGGT GAGCTGCCTG TGGACGCAAG |
| 841 | ATTTCCTCCT AGAGTGCCAA AATCTTTTCC ATTCAACACC TCAGTCGTGT ACAAAAAGAC |
| 901 | TCTGTTTGTA GAATTCACGG ATCACCTTTT CAACATCGCT AAGCCAAGGC CACCCTGGAT |
| 961 | GGGTCTGCTA GGTCCTACCA TCCAGGCTGA GGTTTATGAT ACAGTGGTCA TTACACTTAA |
| 1021 | GAACATGGCT TCCCATCCTG TCAGTCTTCA TGCTGTTGGT GTATCCTACT GGAAAGCTTC |
| 1081 | TGAGGGAGCT GAATATGATG ATCAGACCAG TCAAAGGGAG AAAGAAGATG ATAAAGTCTT |
| 1141 | CCCTGGTGGA AGCCATACAT ATGTCTGGCA GGTCCTGAAA GAGAATGGTC CAATGGCCTC |
| 1201 | TGACCCACTG TGCCTTACCT ACTCATATCT TTCTCATGTG GACCTGGTAA AAGACTTGAA |
| 1261 | TTCAGGCCTC ATTGGAGCCC TACTAGTATG TAGAGAAGGG AGTCTGGCCA AGGAAAAGAC |
| 1321 | ACAGACCTTG CACAAATTTA TACTACTTTT TGCTGTATTT GATGAAGGGA AAAGTTGGCA |
| 1381 | CTCAGAAACA AAGAACTCCT TGATGCAGGA TAGGGATGCT GCATCTGCTC GGGCCTGGCC |
| 1441 | TAAAATGCAC ACAGTCAATG GTTATGTAAA CAGGTCTCTG CCAGGTCTGA TTGGATGCA |
| 1501 | CAGGAAATCA GTCTATTGGC ATGTGATTGG AATGGGCACC ACTCCTGAAG TGCACTCAAT |
| 1561 | ATTCCTCGAA GGTCACACAT TTCTTGTGAG GAACCATCGC CAGGCGTCCT TGGAAATCTC |
| 1621 | GCCAATAACT TTCCTTACTG CTCAAACACT CTTGATGGAC CTTGGACAGT TTCTACTGTT |
| 1681 | TTGTCATATC TCTTCCCACC AACATGATGG CATGGAAGCT TATGTCAAAG TAGACAGCTG |
| 1741 | TCCAGAGGAA CCCCAACTAC GAATGAAAAA TAATGAAGAA GCGGAAGACT ATGATGATGA |
| 1801 | TCTTACTGAT TCTGAAATGG ATGTGGTCAG GTTTGATGAT GACAACTCTC CTTCCTTTAT |
| 1861 | CCAAATTCGC TCAGTTGCCA AGAAGCATCC TAAAACTTGG GTACATTACA TTGCTGCTGA |
| 1921 | AGAGGAGGAC TGGGACTATG CTCCCTTAGT CCTCGCCCCC GATGACAGAA GTTATAAAAG |
| 1981 | TCAATATTTG AACAATGGCC CTCAGCGGAT TGGTAGGAAG TACAAAAAAG TCCGATTTAT |
| 2041 | GGCATACACA GATGAAACCT TTAAGACTCG TGAAGCTATT CAGCATGAAT CAGGAATCTT |
| 2101 | GGGACCTTTA CTTTATGGGG AAGTTGGAGA CACACTGTTG ATTATATTTA AGAATCAAGC |

TABLE 2-continued

```
2161   AAGCAGACCA TATAACATCT ACCCTCACGG AATCACTGAT GTCCGTCCTT TGTATTCAAG
2221   GAGATTACCA AAAGGTGTAA AACATTTGAA GGATTTTCCA ATTCTGCCAG GAGAAATATT
2281   CAAATATAAA TGGACAGTGA CTGTAGAAGA TGGGCCAACT AAATCAGATC CTCGGTGCCT
2341   GACCCGCTAT TACTCTAGTT TCGTTAATAT GGAGAGAGAT CTAGCTTCAG GACTCATTGG
2401   CCCTCTCCTC ATCTGCTACA AAGAATCTGT AGATCAAAGA GGAAACCAGA TAATGTCAGA
2461   CAAGAGGAAT GTCATCCTGT TTTCTGTATT TGATGAGAAC CGAAGCTGGT ACCTCACAGA
2521   GAATATACAA CGCTTTCTCC CCAATCCAGC TGGAGTGCAG CTTGAGGATC CAGAGTTCCA
2581   AGCCTCCAAC ATCATGCACA GCATCAATGG CTATGTTTTT GATAGTTTGC AGTTGTCAGT
2641   TTGTTTGCAT GAGGTGGCAT ACTGGTACAT TCTAAGCATT GGAGCACAGA CTGACTTCCT
2701   TTCTGTCTTC TTCTCTGGAT ATACCTTCAA ACACAAAATG GTCTATGAAG ACACACTCAC
2761   CCTATTCCCA TTCTCAGGAG AAACTGTCTT CATGTCGATG GAAAACCCAG GTCTATGGAT
2821   TCTGGGGTGC CACAACTCAG ACTTTCGGAA CAGAGGCATG AfCGCCTTAC TGAAGGTTTC
2881   TAGTTGTGAC AAGAACACTG GTGATTATTA CGAGGACAGT TATGAAGATA TTTCAGCATA
2941   CTTGCTGAGT AAAAACAATG CCATTGAACC AAGAAGCTTC TCCCAGAATT CAAGACACCC
3001   TAGCACTAGG CAAAAGCAAT TTAATGCCAC CACAATTCCA GAAAATGACA TAGAGAAGAC
3061   TGACCCTTGG TTTGCACACA GAACACCTAT GCCTAAAATA CAAAATGTCT CCTCTAGTGA
3121   TTTGTTGATG CTCTTGCGAC AGAGTCCTAC TCCACATGGG CTATCCTTAT CTGATCTCCA
3181   AGAAGCCAAA TATGAGACTT TTTCTGATGA TCCATCACCT GGAGCAATAG ACAGTAATAA
3241   CAGCCTGTCT GAAATGACAC ACTTCAGGCC ACAGCTCCAT CACAGTGGGG ACATGGTATT
3301   TACCCCTGAG TCAGGCCTCC AATTAAGATT AAATGAGAAA CTGGGGACAA CTGCAGCAAC
3361   AGAGTTGAAG AAACTTGATT TCAAAGTTTC TAGTACATCA AATAATCTGA TTTCAACAAT
3421   TCCATCAGAC AATTTGGCAG CAGGTACTGA TAATACAAGT TCCTTAGGAC CCCCAAGTAT
3481   GCCAGTTCAT TATGATAGTC AATTAGATAC CACTCTATTT GGCAAAAAGT CATCTCCCCT
3541   TACTGAGTCT GGTGGACCTC TGAGCTTGAG TGAAGAAAAT AATGATTCAA AGTTGTTAGA
3601   ATCAGGTTTA ATGAATAGCC AAGAAAGTTC ATGGGGAAAA AATGTATCGT CAACAGAGAG
3661   TGGTAGGTTA TTTAAAGGGA AAAGAGCTCA TGGACCTGCT TTGTTGACTA AAGATAATGC
3721   CTTATTCAAA GTTAGCATCT CTTTGTTAAA GACAAACAAA ACTTCCAATA ATTCAGCAAC
3781   TAATAGAAAG ACTCACATTG ATGGCCCATC ATTATTAATT GAGAATAGTC CATCAGTCTG
3841   GCAAAATATA TTAGAAAGTG ACACTGAGTT TAAAAAAGTG ACACCTTTGA TTCATGACAG
3901   AATGCTTATG GACAAAAATG CTACAGCTTT GAGGCTAAAT CATATGTCAA ATAAAACTAC
3961   TTCATCAAAA AACATGGAAA TGGTCCAACA GAAAAAAGAG GGCCCCATTC CACCAGATGC
4021   ACAAAATCCA GATATGTCGT TCTTTAAGAT GCTATTCTTG CCAGAATCAG CAAGGTGGAT
4081   ACAAAGGACT CATGGAAAGA ACTCTCTGAA CTCTGGGCAA GGCCCCAGTC CAAAGCAATT
4141   AGTATCCTTA GGACCAGAAA AATCTGTGGA AGGTCAGAAT TTCTTGTCTG AGAAAAACAA
4201   AGTGGTAGTA GGAAAGGGTG AATTTACAAA GGACGTAGGA CTCAAAGAGA TGGTTTTTCC
4261   AAGCAGCAGA AACCTATTTC TTACTAACTT GGATAATTTA CATGAAAATA ATACACACAA
4321   TCAAGAAAAA AAAATTCAGG AAGAAATAGA AAAGAAGGAA ACATTAATCC AAGAGAATGT
4381   AGTTTTGCCT CAGATACATA CAGTGACTGG CACTAAGAAT TTCATGAAGA ACCTTTTCTT
4441   ACTGAGCACT AGGCAAAATG TAGAAGGTTC ATATGACGGG GCATATGCTC CAGTACTTCA
4501   AGATTTTAGG TCATTAAATG ATTCAACAAA TAGAACAAAG AAACACACAG CTCATTTCTC
```

TABLE 2-continued

```
4561  AAAAAAAGGG GAGGAAGAAA ACTTGGAAGG CTTGGGAAAT CAAACCAAGC AAATTGTAGA
4621  GAAATATGCA TGCACCACAA GGATATCTCC TAATACAAGC CAGCAGAATT TTGTCACGCA
4681  ACGTAGTAAG AGAGCTTTGA AACAATTCAG ACTCCCACTA GAAGAAACAG AACTTGAAAA
4741  AAGGATAATT GTGGATGACA CCTCAACCCA GTGGTCCAAA AACATGAAAC ATTTGACCCC
4801  GAGCACCCTC ACACAGATAG ACTACAATGA GAAGGAGAAA GGGGCCATTA CTCAGTCTCC
4861  CTTATCAGAT TGCCTTACGA GGAGTCATAG CATCCCTCAA GCAAATAGAT CTCCATTACC
4921  CATTGCAAAG GTATCATCAT TTCCATCTAT TAGACCTATA TATCTGACCA GGGTCCTATT
4981  CCAAGACAAC TCTTCTCATC TTCCAGCAGC ATCTTATAGA AAGAAAGATT CTGGGGTCCA
5041  AGAAAGCAGT CATTTCTTAC AAGGAGCCAA AAAAAATAAC CTTTCTTTAG CCATTCTAAC
5101  CTTGGAGATG ACTGGTGATC AAAGAGAGGT TGGCTCCCTG GGGACAAGTG CCACAAATTC
5161  AGTCACATAC AAGAAAGTTG AGAACACTGT TCTCCCGAAA CCAGACTTGC CCAAAACATC
5221  TGGCAAAGTT GAATTGCTTC CAAAAGTTCA CATTTATCAG AAGGACCTAT TCCCTACGGA
5281  AACTAGCAAT GGGTCTCCTG GCCATCTGGA TCTCGTGGAA GGGAGCCTTC TTCAGGGAAC
5341  AGAGGGAGCG ATTAAGTGGA ATGAAGCAAA CAGACCTGGA AAAGTTCCCT TTCTGAGAGT
5401  AGCAACAGAA AGCTCTGCAA AGACTCCCTC CAAGCTATTG GATCCTCTTG CTTGGGATAA
5461  CCACTATGGT ACTCAGATAC CAAAAGAAGA GTGGAAATCC CAAGAGAAGT CACCAGAAAA
5521  AACAGCTTTT AAGAAAAAGG ATACCATTTT GTCCCTGAAC GCTTGTGAAA GCAATCATGC
5581  AATAGCAGCA ATAAATGAGG GACAAAATAA GCCCGAAATA GAAGTCACCT GGGCAAAGCA
5641  AGGTAGGACT GAAAGGCTGT GCTCTCAAAA CCCACCAGTC TTGAAACGCC ATCAACGGGA
5701  AATAACTCGT ACTACTCTTC AGTCAGATCA AGAGGAAATT GACTATGATG ATACCATATC
5761  AGTTGAAATG AAGAAGGAAG ATTTTGACAT TTATGATGAG GATGAAAATC AGAGCCCCCG
5821  CAGCTTTCAA AAGAAAACAC GACACTATTT TATTGCTGCA GTGGAGAGGC TCTGGGATTA
5881  TGGGATGAGT AGCTCCCCAC ATGTTCTAAG AAACAGGGCT CAGAGTGGCA GTGTCCCTCA
5941  GTTCAAGAAA GTTGTTTTCC AGGAATTTAC TGATGGCTCC TTTACTCAGC CCTTATACCG
6001  TGGAGAACTA AATGAACATT TGGGACTCCT GGGGCCATAT ATAAGAGCAG AAGTTGAAGA
6061  TAATATCATG GTAACTTTCA GAAATCAGGC CTCTCGTCCC TATTCCTTCT ATTCTAGCCT
6121  TATTTCTTAT GAGGAAGATC AGAGGCAAGG AGCAGAACCT AGAAAAAACT TTGTCAAGCC
6181  TAATGAAACC AAAACTTACT TTTGGAAAGT GCAACATCAT ATGGCACCCA CTAAAGATGA
6241  GTTTGACTGC AAAGCCTGGG CTTATTTCTC TGATGTTGAC CTGGAAAAAG ATGTGCACTC
6301  AGGCCTGATT GGACCCCTTC TGGTCTGCCA CACTAACACA CTGAACCCTG CTCATGGGAG
6361  ACAAGTGACA GTACAGGAAT TTGCTCTGTT TTTCACCATC TTTGATGAGA CCAAAAGCTG
6421  GTACTTCACT GAAAATATGG AAAGAAACTG CAGGGCTCCC TGCAATATCC AGATGGAAGA
6481  TCCCACTTTT AAAGAGAATT ATCGCTTCCA TGCAATCAAT GGCTACATAA TGGATACACT
6541  ACCTGGCTTA GTAATGGCTC AGGATCAAAG GATTCGATGG TATCTGCTCA GCATGGGCAG
6601  CAATGAAAAC ATCCATTCTA TTCATTTCAG TGGACATGTG TTCACTGTAC GAAAAAAAGA
6661  GGAGTATAAA ATGGCACTGT ACAATCTCTA TCCAGGTGTT TTTGAGACAG TGGAAATGTT
6721  ACCATCCAAA GCTGGAATTT GGCGGGTGGA ATGCCTTATT GGCGAGCATC TACATGCTGG
6781  GATGAGCACA CTTTTTCTGG TGTACAGCAA TAAGTGTCAG ACTCCCCTGG GAATGGCTTC
6841  TGGACACATT AGAGATTTTC AGATTACAGC TTCAGGACAA TATGGACAGT GGGCCCCAAA
6901  GCTGGCCAGA CTTCATTATT CCGGATCAAT CAATGCCTGG AGCACCAAGG AGCCCTTTTC
```

TABLE 2-continued

| | |
|---|---|
| 6961 | TTGGATCAAG GTGGATCTGT TGGCACCAAT GATTATTCAC GGCATCAAGA CCCAGGGTGC |
| 7021 | CCGTCAGAAG TTCTCCAGCC TCTACATCTC TCAGTTTATC ATaATGTATA GTCTTGATGG |
| 7081 | GAAGAAGTGG CAGACTTATC GAGGAAATTC CACTGGAACC TTAATGGTCT TCTTTGGCAA |
| 7141 | TGTGGATTCA TCTGGGATAA AACACAATAT TTTTAACCCT CCAATTATTG CTCGATACAT |
| 7201 | CCGTTTGCAC CCAACTCATT ATAGCATTCG CAGCACTCTT CGCATGGAGT TGATGGGCTG |
| 7261 | TGATTTAAAT AGTTGCAGCA TGCCATTGGG AATGGAGAGT AAAGCAATAT CAGATGcACA |
| 7321 | GATTACTGCT TCATCCTACT TTACCAATAT GTTTGCCACC TGGTCTCCTT CAAAAGCTCG |
| 7331 | ACTTCACCTC CAAGGGAGGA GTAATGCCTG GAGACCTCAG GTGAATAATC CAAAAGAGTG |
| 7441 | GCTGCAAGTG GACTTCCAGA AGACAATGAA AGTCACAGGA GTAACTACTC AGGGAGTAAA |
| 7501 | ATCTCTGCTT ACCAGCATGT ATGTGAAGGA GTTCCTCATC TCCAGCAGTC AAGATGGCCA |
| 7561 | TCAGTGGACT CTCTTTTTTC AGAATGGCAA AGTAAAGGTT TTTCAGGGAA ATCAAGACTC |
| 7621 | CTTCACACCT GTGGTGAACT CTCTAGACCC ACCGTTACTG ACTCGCTACC TTCGAATTCA |
| 7681 | CCCCCAGAGT TGGGTGCACC AGATTGCCCT GAGGATGGAG GTTCTGGGCT GCGAGGCACA |
| 7741 | GGACCTCTAC |

*The underlined nucleic acids encode a signal peptide.

FVIII polypeptides include full-length FVIII, full-length FVIII minus Met at the N-terminus, mature FVIII (minus the signal sequence), mature FVIII with an additional Met at the N-terminus, and/or FVIII with a full or partial deletion of the B domain. In certain embodiments, FVIII variants include B domain deletions, whether partial or full deletions.

The sequence of native mature human FVIII is presented as SEQ ID NO: 4. A native FVIII protein has the following formula: A1-a1-A2-a2-B-a3-A3-C1-C2, where A1, A2, and A3 are the structurally-related "A domains," B is the "B domain," C1 and C2 are the structurally-related "C domains," and a1, a2 and a3 are acidic spacer regions. Referring to the primary amino acid sequence position in SEQ ID NO:4, the A1 domain of human FVIII extends from Ala1 to about Arg336, the a1 spacer region extends from about Met337 to about Va1374, the A2 domain extends from about Ala375 to about Tyr719, the a2 spacer region extends from about Glu720 to about Arg740, the B domain extends from about Ser741 to about Arg 1648, the a3 spacer region extends from about Glu1649 to about Arg1689, the A3 domain extends from about Ser1690 to about Leu2025, the C1 domain extends from about Gly2026 to about Asn2072, and the C2 domain extends from about Ser2073 to Tyr2332. Other than specific proteolytic cleavage sites, designation of the locations of the boundaries between the domains and regions of FVIII can vary in different literature references. The boundaries noted herein are therefore designated as approximate by use of the term "about."

The human FVIII gene was isolated and expressed in mammalian cells (Toole, J. J., et al., *Nature* 312:342-347 (1984); Gitschier, J., et al., *Nature* 312:326-330 (1984); Wood, W. I., et al., *Nature* 312:330-337 (1984); Vehar, G. A., et al., *Nature* 312:337-342 (1984); WO 87/04187; WO 88/08035; WO 88/03558; and U.S. Pat. No. 4,757,006). The FVIII amino acid sequence was deduced from cDNA as shown in U.S. Pat. No. 4,965,199. In addition, partially or fully B-domain deleted FVIII is shown in U.S. Pat. Nos. 4,994,371 and 4,868,112. In some embodiments, the human FVIII B-domain is replaced with the human Factor V B-domain as shown in U.S. Pat. No. 5,004,803. The cDNA sequence encoding human Factor VIII and amino acid sequence are shown in SEQ ID NOs: 4 and 5, respectively, of US Application Publ. No. 2005/0100990.

The porcine FVIII sequence is published in Toole, J. J., et al., *Proc. Natl. Acad. Sci. USA* 83:5939-5942 (1986). Further, the complete porcine cDNA sequence obtained from PCR amplification of FVIII sequences from a pig spleen cDNA library has been reported in Healey, J. F., et al., *Blood* 88:4209-4214 (1996). Hybrid human/porcine FVIII having substitutions of all domains, all subunits, and specific amino acid sequences were disclosed in U.S. Pat. No. 5,364,771 by Lollar and Runge, and in WO 93/20093. More recently, the nucleotide and corresponding amino acid sequences of the A1 and A2 domains of porcine FVIII and a chimeric FVIII with porcine A1 and/or A2 domains substituted for the corresponding human domains were reported in WO 94/11503. U.S. Pat. No. 5,859,204, Lollar, J. S., also discloses the porcine cDNA and deduced amino acid sequences. U.S. Pat. No. 6,458,563 discloses a B-domain-deleted porcine FVIII.

U.S. Pat. No. 5,859,204 to Lollar, J. S. reports functional mutants of FVIII having reduced antigenicity and reduced immunoreactivity. U.S. Pat. No. 6,376,463 to Lollar, J. S. also reports mutants of FVIII having reduced immunoreactivity. US Appl. Publ. No. 2005/0100990 to Saenko et al. reports functional mutations in the A2 domain of FVIII.

In one embodiment, the FVIII (or FVIII portion of a chimeric protein) may be at least 50%, 60%, 70%, 80%, 90%, 95%, 96%, 97%, 98%, 99%, or 100% identical to a FVIII amino acid sequence of amino acids 1 to 1438 of SEQ ID NO: 6 or amino acids 1 to 2332 of SEQ ID NO: 4 (without a signal sequence) or a FVIII amino acid sequence of amino acids 1 to 19 of SEQ ID NO: 3 and 1 to 1438 of SEQ ID NO: 6 or amino acids 1 to 19 of SEQ ID NO: 3 and amino acids 1 to 2332 of SEQ ID NO: 4 (with a signal sequence), wherein the FVIII has a clotting activity, e.g., activates Factor IX as a cofactor to convert Factor X to activated Factor X. The FVIII (or FVIII portion of a chimeric protein) may be identical to a FVIII amino acid sequence of amino acids 1 to 1438 of SEQ ID NO: 6 or amino acids 1 to 2332 of SEQ ID NO: 4 (without a signal sequence). The FVIII may further comprise a signal sequence.

In some embodiments, the FVIII polypeptide has reduced affinity for VWF. The term "reduced affinity for VWF" encompasses Factor VIII polypeptides, wherein the affinity for VWF is decreased by at least 50%, by at least 60%, by at least 70%, by at least 80%, by at least 90%, or by about 100% compared to wild type FVIII. FVIII binding to VWF may be measured either by an ELISA like assay or as direct binding to immobilized VWF using surface plasmon resonance. Amino acids 1670-1684 in FVIII are important for binding to VWF. Accordingly, FVIII point mutations, deletions, and/or insertions involving this area can modify the ability to bind to vWF.

In one embodiment, a FVIII polypeptide with reduced affinity for vWF lacks amino acids 745-1685. In another embodiment, a FVIII polypeptide with reduced affinity for vWF lacks amino acids 741-1689. In another embodiment, a FVIII polypeptide with reduced affinity for vWF lacks amino acid 1680 or contains a point mutation of amino acid 1680. Examples of point mutations that reduce FVIII affinity for vWF include the following point mutations: Y1680F, Y1680R, Y1680N, Y1680C, and E1682T. Other alternations that reduce FVIII affinity for vWF have been identified, for example, in the C1 and C2 domains of FVIII. In particular, Gln2100, Try2105, Ser2119, Arg2150, and Thr2154 (within the C1 domain) and Pro2300, Arg2304, and Arg2307 (within the C2 domain) have been discussed, for example in D'Oiron et al. *Hemophilia* 14: 138-146 (2008). Additional mutations have been described at Glu2087, Arg2090, Ile2098, Asn2129, and Pro2153. See id.

Non-limited exemplary sequences of FVIII polypeptides with reduced affinity for vWF are shown in Table 3 below. The "mature" form (lacking the signal peptide) of each of these proteins is shown in the table. However, the full-length form of these proteins containing the signal peptide (SEQ ID NO:3) can also be used.

TABLE 3

| Amino Acid Sequences of FVIII Polypeptides with Reduced Affinity for vWF |
|---|
| Mature FVIII Del 745-1656<br>ATRRYYLGAVELSWDYMQSDLGELPVDAREPPRVPKSFPENTSVVYKKTLF<br>VEFTDHLFNIAKPRPPWMGLLGPTIQAEVYDTVVITLKNMASHPVSLHAVG<br>VSYWKASEGAEYDDQTSQREKEDDKVFPGGSHTYVWQVLKENGPMASDPLC<br>LTYSYLSHVDLVKDLNSGLIGALLVCREGSLAKEKTQTLHKFILLFAVEDE<br>GKSWHSETKNSLMQDRDAASARAWPKMHTVNGYVNRSLPGLIGCHRKSVYW<br>FIVIGIVIGTTPEVHSIFLEGHTFLVRNHRQASLEISPITFLTAQTLLMDL<br>GQFLLFCHISSHQHDGMEAYVKVDSCPEEPQLRMKNNEEAEDYDDDLTDSE<br>MDVVRFDDDNSPSFIQIRSVAKKHPKTWVHYIAAEEEDWDYAPLVLAPDDR<br>SYKSQYLNNGPQRIGRKYKKVRFMAYTDETFKTREAIQHESGILGPLLYGE<br>VGDTLLIIFKNQASRPYNIYPHGITDVRPLYSRRLPKGVKHLKDFPILPGE<br>IFKYKWTVTVEDGPTKSDPRCLTRYYSSEVNMERDLASGLIGPLLICYKES<br>VDQRGNQIMSDKRNVILFSVEDENRSWYLTENIQRFLPNPAGVQLEDPEFQ<br>ASNIMHSINGYVFDSLQLSVCLHEVAYWYILSIGAQTDFLSVFFSGYTFKH<br>KMVYEDTLTLFPFSGETVFMSMENPGLWILGCHNSDFRNRGMTALLKVSSC<br>DKNTGDYYEDSYEDISAYLLSKNNAIEPRSFSQNQSPRSFQKKTRHYFIAA<br>VERLWDYGMSSSPHVLRNKAQSGSVPQFKKVVFQEFTDGSFTQFLYRGELN<br>EHLGLLGPYIRAEVEDNIIVIVTFRNQASRPYSFYSSLISYEEDQRQGAEP<br>RKNFVKPNETKTYFWKVQHFFMAPTKDEFDCKAWAYFSDVDLEKDVHSGLI<br>GPLLVCHTNTLNPAHGRQVTVQEFALFFTIFDETKSWYFTENMERNCRAPC<br>NIQMEDPTFKENYRFHAINGYIMDTLPGLVMAQDQRIRWYLLSMGSNENIH<br>SIHFSGHVFTVRKKEEYKMALYNLYPGVFETVEMLPSKAGIWRVECLIGEH<br>LHAGMSTLFLVYSNKCQTPLGMASGHIRDFQITASGQYGQWAPKLARLHYS<br>GSINAWSTKEPFSWIKVDLLAPMIIHGIKTQGARQKFSSLYISQFIIMYSL<br>DGKKWQTYRGNSTGTLMVFFGNVDSSGIKHNIFNPPIIARYIRLHPTHYSI<br>RSTLRMELMGCDLNSCSMPLGMESKAISDAQITASSYFTNMFATWSPSKAR |

TABLE 3-continued

| Amino Acid Sequences of FVIII Polypeptides with Reduced Affinity for vWF |
|---|
| LHLQGRSNAWRPQVNNPKEWLQVDFQKTMKVTGVTTQGVKSLLTSMYVKEF<br>LISSSQDGHQWTLFFQNGKVKVFQGNQDSFTPVVNSLDPPLLTRYLRIHPQ<br>SWVHQIALRMEVLGCEAQDLY (SEQ ID NO: 1) |
| Mature FVIII Del745-1685<br>ATRRYYLGAVELSWDYMQSDLGELPVDARFPPRVPKSFPFNTSVVYKKTLF<br>VEFTDHLFNIAKPRPPWMGLLGPTIQAEVYDTVVITLKNMASHPVSLHAVG<br>VSYWKASEGAEYDDQTSQREKEDDKVFPGGSHTYVWQVLKENGPMASDPLC<br>LTYSYLSHVDLVKDLNSGLIGALLVCREGSLAKEKTQTLHKFILLFAVFDE<br>GKSWHSETKNSLMQDRDAASARAWPKMHTVNGYVNRSLPGLIGCHRKSVYW<br>HVIGMGTTPEVHSIFLEGHTFLVRNHRQASLEISPITFLTAQTLLMDLGQF<br>LLFCHISSHQHDGMEAYVKVDSCPEEPQLRMKNNEEAEDYDDDLTDSEMDV<br>VRFDDDNSPSFIQIRSVAKKHPKTWVHYIAAEEEDWDYAPLVLAPDDRSYK<br>SQYLNNGPQRIGRKYKKVFRMAYTDETFKTREAIQHESGILGPLLYGEVGD<br>TLLIIFKNQASRPYNIYPHGITDVRPLYSRRLPKGVKHLKDFPILPGEIFK<br>YKWTVTVEDGPTKSDPRCLTRYYSSFVNMERDLASGLIGPLLICYKESVDQ<br>RGNQIMSDKRNVILFSVFDENRSWYLTENIQRFLPNPAGVQLEDPEFQASN<br>IMHSINGYVFDSLQLSVCLHEVAYWYILSIGAQTDFLSVFFSGYTFKHKMV<br>YEDTLTLFPFSGETVFMSMENPGLWILGCHNSDFRNRGMTALLKVSSCDKN<br>TGDYYEDSYEDISAYLLSKNNAIEPRSFSQNQSPRSFQKKTRHYFIAAVER<br>LWDYGMSSSPHVLRNRASGSVPQFKKVVFQEFTDGSFTQPLYRGELNEHLG<br>LLGPYIRAEVEDNIMVTFRNQASRPYSFYSSLISYEEDQRQGAEPRKNFVK<br>PNETKTYFWKVQHHMAPTKDEFDCKAWAYFSDVDLEKDVHSGLIGPLLVCH<br>TNTLNPAHGRQVTVQEFALFFTIFDETKSWYFTENMERNCRAPCNIQMEDP<br>TFKENYRFHAINGYIMDTLPLGVMAQDQRIRWYLLSMGSNENIHSIHFSGH<br>VFTVRKKEEYKMALYNLYPGVFETVEMLPSKAGIWRVECLIGEHLHAGMST<br>LFLVYSNKCQTPLGMASGHIRDFQITASGQYGQWAPKLARLHYSGSINAWS<br>TKEPFSWIKVDLLAPMIIHGIKTQGARQKFSSLYISQFIIMYSLDGKKWQT<br>YRGNSTGTLMVFFGNVDSSGIKHNIFNPIIARYIRLHPTHYSIRSTLRMEL<br>MGCDLNSCSMPLGMESKAISDAQITASSYFTNMFATWSPSKARLHLQGRSN<br>AWRPQVNNPKEWLQVDTQKTMKVVTGVTTQGVKSLLTSMYVKEFLISSSQD<br>GHQWTLFFQNGKVKVFQGNQDSFTPVVNSLDPPLLTRYLRIHPQSWVHQIA<br>LRMEVLGCEAQDLY (SEQ ID NO: 2) |
| Mature FVIII Y1680F<br>ATRRYYLGAVELSWDYMQSDLGELPVDARFPPRVPKSFPFNTSVVYKKTLF<br>VEFTDHLFNIAKPRPPWMGLLGPTIQAEVYDTVVITLKNMASHPVSLHAVG<br>VSYWKASEGAEYDDQTSQREKEDDKVFPGGSHTYVWQVLKENGPMASDPLC<br>LTYSYLSHVDLVKDLNSGLIGALLVCREGSLAKEKTQTLHKFILLFAVFDE<br>GKSWHSETKNSLMQDRDAASARAWPKMHTVNGYVNRSLPGLIGCHRKSVYW<br>HVIGMGTTPEVHSIFLEGHTFLVRNHRQASLEISPITFLTAQTLLMOLGQF<br>LLFCHISSHQHDGMEAYVKVDSCPEEPQLRMKNNEEAEDYDDDLTDSEMDV<br>VRFDDDNSPSFIQIRSVAKKHPKTWVHYIAAEEEDWDYAPLVLAPDDRSYK<br>SQYLNNGPQRIGRKYKKVRFMAYTDETFKTREAIQHESGILGPLLYGEVGD<br>TLLIIFKNQASRPYNIYPHGITDVRPLYSRRLPKGVKHLKDFFILPGEIFK<br>YKWTVTVEDGPTICSDPRCLTRYYSSFVNMERDLASGLIGPLLICYKESVD<br>QRGNQIMSDKRNVILFSVFDENRSWYLTENIQRFLPNPAGVQLEDPEFQAS<br>NIMHSINGYVFDSLQLSVCLHEVAYWYILSIGAQTDFLSVFFSGYTFKHKM<br>VYEDTLTLFPFSGETVFMSMENPGLWILGCHNSDFRNRGMTALLKVSSCDK<br>NTGDYYEDSYEDISAYLLSKNNAIEPRSFSQNPPVLKRHQREITRTTLQSD<br>QEEIDYDDTISVEMKKEDFDIFDEDENQSPRSFQKKTRHYFIAAVERLWDY<br>GMSSSPHVLRNRAQSGSVPQFKKVVFQEFTDGSFTQPLYRGELNEHLGLLG<br>PYIRAEVEDNIMVTFRNQASRPYSFYSSLISYEEDQRQGAEPRKNFVKPNE<br>TKTYFWKVQHHMAPTKDEFDCKAWAYFSDVDLEKDVHSGLIGPLLVCHTNT<br>LNPAHGRQVTVQEFALFFTIFDETKSWYFTENMERNCRAPCNIQMEDPTFK<br>ENYRFHAINGYIMDTLPGLVMAQDQRIRWYLLSMGSNENIHSIHFSGHVFT<br>VRKKEEYKMALYNLYPGVFETVEMLPSKAGIWRVECLIGEHLHAGMSTLFL<br>VYSNKCQTPLGMASGHIRDFQITASGQYGQWAPKLARLHYSGSINAWSTKE<br>PFSWKVDLLAPMIIHGKTQGARQKFSSLYISQFIIMYSLDGKKWQTYRGNS<br>TGTLMVFFGNVDSSGIKHNIFNPPIIARYIRLHPTHYSIRSTLRMELMGCD<br>LNSCSMPLGMESKATSDAQITASSYFTNMFATWSPSKARLHLQGRSNAWRP<br>QVNNPKEWLQVDFQKTMKVTGVTTQGVKSLLTSMYVKEFLISSSQDGHQWT<br>LFQNGKVKVFQGNQDSFTPVVNSLDPPLLTRYLRIHPQSWVHQIALRIVIE<br>VLGCEAQDLY (SEQ ID NO: 12) |
| Mature FVIIII R1648A<br>ATRRYYLGAVELSWDYMQSDLGELPVDARFPPRVPKSFPFNTSVVYKKLF<br>VEFTDHLFNIAKPRPPWMGLLGPTIQAEVYDTVVITLKNMASHPVSLHAV<br>GVSYWKASEGAEYDDQTSQREKEDDKVFPGGSHTYVWQVLKENGPMASDP<br>LCLTYSYLSHVDLVKDLNSGLIGALLVCREGSLAKEKTQTLHKFILLFAV<br>FDEGKSWHSETKNSLMQDRDAASARAWPKMHTVNGYVNRSLPGLIGCHRK<br>SVYWHVIGMGTTPEVHSIFLEGHTFLVRNHRQASLEISPITFLTAQTLLM<br>DLGQFLLFCHISSHQHDGMEAYVKVDSCPEEPQLRMKNNEEAEDYDDDLT<br>DSEMDVVRFDDDNSPSFIQIRSVAKKHPKTWVHYIAAEEEDWDYAPLVLA<br>PDDRSYKSQYLNNGPQRIGRKYKKVRFMAYTDETFKTREAIQHESGILGP<br>LLYGEVGDTLLIIFKNQASRPYNIYPHGITDVRITYSRRLPKGVKHLKDF<br>PILPGEIFKYKWFVTVEDGPTKSDPRCLTRYYSSFVNMERDLASGLIGPL |

TABLE 3-continued

Amino Acid Sequences of FVIII Polypeptides with Reduced Affinity for vWF

LICYKESVDQRGNQIMSDKRNVILFSVFDENRSWYLTENIQRFLPNPAGV
QLEDPEFOASNIMHSINGYVFDSLQLSVCLHEVAYWYILSIGAQTDFLSV
FTSGYTFKHKMVYEDTLTLFPFSGETVFIVISMENPGLWILGCENSDFRN
RGMTALLKVSSCDKNIGDYYEDSYEDISAYLLSKNNAIEPRSTSONPPVL
KREQAEITRITLQSDQBEIDYDDTISVEMKKEDFDIYDEDENQSPRSFQK
KTRHYFIAAVERLWDYGMSSSPHVVLRNRAQSGSVPQFKKVVFQEFTDGS
FTQPLYRGELNEHLGLLGPYIRAEVEDNINIVTIRNQASRPYSFYSSLIS
YEEDMGAEPRKNINKPNEIXTYFWKVQFIIIMAPIKDEFDCKAWAYFSDV
DLEKDVEISGLIGPLINCHTNTLNPAHGRQVTVQEFALITTIFDETKSWY
FTENMERNCRAPCNIQMEDPTFKENYRFHAINGYIMDTLIPGINMAQDQR
IRWYLLSMGSNENIHSIHFSGHVFTVRKKEEYKMALYNLYPGVFETVEML
PSKAGIWRVECLIGEIIIHAGMSTLFINYSNKCQTPLGMASGITIIRDFQ
ITASGQYGQWAPKLARLHYSGSINAWSTKEPFSWIKVDLLAPMIIHGIKT
QGAIZQKFSSLYISQFIRAYSLDGKKINQTYRGNSTGIINIVFFGNYDSS
GIKHNIFNPPIIARYIRLHPTIIYSIRSTLRMELMGCDLNSCSMPLGMES
KAISDAQITASSYFTNMFATWSPSKARLHLQGRSNAWRPQVNNPKEWLQV
DFQKTMKVTGVTTQGVKSLLTSMYVKEELISSSQDGHQWILFQNGICSIK
VFQGNODSFTWVNSLDPPLLTRYLRIHPQSWVEQIALRIVIENLGCEAQD
LY (SEQ.ID NO: 13)

Mature FVIII R1648A Y1680F
ATRRYYLGAVELSWDYMQSDLGELPVDARFPPRVPKSFPFNTSVVYKKTL
FVEFTDHLFNIAKPRPPWMGLLGPTIQAEVYDTVVITLKNMASHPVSLHA
VGVSYWKASEGAEYDDQTSQREKEDDKVFPGGSHTYVWQVLKENGPMASD
PLCLTYSYLSHVDLVKDLNSGLIGALLVCREGSLAKEKTQTLHKFILLFA
VFDEGKSWHSETKNSLMQDRDAASARAWPKMHTVNGYVNRSLPGLIGCHR
KSVYWHVIGMGTTPEVHSIFLEGHTFLVRNHRQASLEISFITFLTAQTLL
MDLGQFLLFCHISSHQHDGMEAYVKVDSCPEEPQLRMKNNEEAEDYDDDL
TDSEMDVVRFDDDNSPSFIQIRSVAKKHPKTWVHYIAAEEEDWDYAPLVL
APDDRSYKSQYLNNGPQRIGRKYKKVRFMAYTDETFKTREAIQHESGLGP
LLYGEVGDTLLIIFKNQASRPYNIYPHGITDVRPLYSRRLPKGVKHLKDF
PILPGEIFKYKWTVTVEDGPTKSDPRCLTRYYSSFVNMERDLASGLIGPL
LICYKESVDQRGNQIMSDKRNVILFSVFDENRSWYLTENIQRFLPNPAGV
QLEDPEFQASNIMHSINGYVFDSLQSVCLHEVAYWYILSIGAQTDELSVF
FSGYTFKHKMVYEDTLTLFPFSGETVFMSMENPGLWILGCHNSDFRNRGM
TALLKVSSCDKNTGDYYEDSYEDISAYLLSKNNAIEPRSFSQNPPVLKRH
QAEITRTTLQSDQEEIDYDDTISVEMKKEDFDIFDEDENQSPRSFQKKTR
HYFIAAVERLWDYGMSSSPHVLRNRAQSGSVPQFKKVVFQEFTDGSFTQP
LYRGELNEHLGLLGPYIRAEVEDNIMVTFRNQASRPYSFYSSLISYEEDQ
RQGAEPRKNFVKPNETKTYFWKVQHHMAPTKDEFDCKAWAYFSDVDLEKD
VHSGLIGPLLVCHTNTLNPAHGRQVTVQEFALFFTIFDETKSWYFTENME
RNCRAPCNQMEDPTFKENYRFHAINGYIMDTLPGLVMAQDQRIRWYLLSM
GSNENIHSIHFSGHVFTVRKKEEYKMALYNLYPGVFETVEMLPSKAGIWR
VECLIGEHLHAGMSTLFLVYSNKCQTPLGMASGHIRDMITASGQYGQWAP
KLARLHYSGSINAWSTKEPFSWIKVDLLAPMIIHGIKTQGARQKFSSLYI
SQFIIMYSLDGKKWQTYRGNSTGTLMVFFGNVDSSGIKFINIFNPPIIAR
YIRLHPTHYSIRSTLRMELMGCDLNSCSMPLGMESKAISDAQITASSYFT
NMFATWSPSKARLHLQGRSNAWRPQVNNPKEWLQVDFQKTMKVTGVTTQG
VKSLLTSMYVKEFLISSSQDGHQWTLFFQNGKVKVFQGNQDSFTPVVNSL
DPPLLTRYLRIHPQSWVHQIALRMEVLGCEAQDLY
(SEQ ID NO: 14)

Mature FV111 SVA IQIRSV Insertion
ATRRYYLGAVELSWDYMQSDLGELPVDARFPPRVPKSFPFNTSVVYKKTL
FVEFTDHLFNIAKPRPPWMGLLGPTIQAEVYDTVVITLKNMASHPVSLHA
VGVSYWKASEGAEYDDQTSQREKEDDKVFPGGSHTYVWQVLKENGPMASD
PLCLTYSYLSHVDLVKDLNSGLIGALLVCREGSLAKEKTQTLHKFILLFA
VFDEKSWHSETKNSLMQDRDAASARAWPKMHTVNGYVNRSLPGLIGCHRK
SVYWHVIGMGTTPEVHSIFLEGHTFLVRNHRQASLEISPITFLTAQTLLM
DLGQFLLFCHISSHQHDGMEAYVKVDSCPEEPQLRMKNNEEAEDYDDDLT
DSEMDVVRFDDDNSPSFIQIRSVASVAIQIRSVKKHPKTWVHYIAAEEED
WDYAPLVLAPDDRSYKSQYLNNGPQRIGRKYKKVRFMAYTDETFKTREAI
QHESGILGPLLYGEVGDTLLIIFKNQASRPYNIYPHGITDVRPLYSRRLP
KGVKHLKDFPILPGEIFKYKWTVTVEDGPTKSDPRCLTRYYSSFVNMERD
LASGLIGPLLICYKESVDQRGNQIMSDKRNVILESVFDENRSWYLTENIQ
RFLPNPAGVQLEDPEFQASNIMHSINGYVFDSLQLSVCLHEVAYWYILSI
GAQTDFLSVFFSGYTFKHKMVYEDTLTLFPFSGETVFMSMENPGLWILGC
HNSDFRNRGMTALLKVSSCDKNTGDYYEDSYEDISAYLLSKNNAIEPRSF
SQNPPVLKRHQREITRTTLQSDQEEIDYDDTISVEMKKEDFDIYDEDENQ
SPRSFQKKTRHYFIAAVERLWDYGMSSSPHVLRNRAQSGSVPQFKKVVFQ
EFTDGSFTQPLYRGELNEHLGLLGPYIRAEVEDNIMVTFRNQASRPYSFY
SSLISYEEDQRQGAEPRKNFVKPNETKTYFWKVQHHMAPTKDEFDCKAWA
YFSDVDLEKDVHSGLIGPLLVCHTNTLNPAHGRQVTVQEFALFFTIFDET
KSWYFTENMERNCRAPCNIQMEDPITKENYRFHAINGYIIVIDTLPGLVM
AQDQRIRWYLLSMGSNENIHSIHFSGHVFTVRKKEEYKMALYNLYPGVFE
TVEMLPSKAGIWRVECLIGEHLHAGMSTLFLVYSNKCQTPLGMASGHTRD
FQITASGQYGQWAPKLARLHYSGSINAWSTKEPFSWIKVDLLAPMIIHGI TABLE 3-continued Amino Acid Sequences of FVIII Polypeptides with Reduced Affinity for vWF KTQGARQKFSSLYISQFIIMYSLDGKKWQTYRGNSTGTLMVFFGNVDSSG
IKHNIFNPPIIARYIRLHPTHYSIRSTLRMELMGCDLNSCSMPLGIVIES
KAISDAQITASSYFTNNIFATWSPSKARLHLQGRSNAWRPQVNNPKEWLQ
VDFQKTMKVTGVTTQGVKSLLTSMYVKEFLISSSQDGHQWTLFFQNGKVK
VFQGNQDSFTPVVNSLDPPLLTRYLRIHPQSWVHQIALRMEVLGCEAQDL
Y (SEQ ID NO: 15)

Mature FVIII ATR Insertion
ATRATRRYYLGAVELSWDYMQSDLGELPVDARFPPRVPKSFPFNTSVVYK
KTLFVEFTDHLFNIAKPRPPWMGLLGPTIQAEVYDTVVITLKNIVIASHP
VSLHAVGVSYWKASEGAEYDDQTSQREKEDDKVFPGGSHTYVWQVLKENG
PMASDPLCLTYSYLSHVDLVKDLNSGLIGALLVCREGSLAKEKTQTLFIK
FILLFAVFDEGKSWHSETKNSLMQDRDAASARAWPKMHTVNGYVNRSLPG
LIGCHRKSVYWHVIGMGTTPEVHSIFLEGHTFLVRNHRQASLEISPITFL
TAQTLLMDLGQFLLFCHISSHQHDGMEAYVKVDSCPEEPQLRMKNNEEAE
DYDDDLTDSEMDVVRFDDDNSPSFIQIRSVAKKHPKTWVHYIAAEEEDWD
YAPLVLAPDDRSYKSQYLNNGPQRIGRKYKKVRFMAYTDETFKTREAIQH
ESGILGPLLYGEVGDTLLIIFKNQASRPYNIYPHGITDVRPLYSRRLPKG
VKHLKDFPILPGEIFKYKWTVTVEDGPTKSDPRCLTRYYSSFVNMERDLA
SGLIGPLLICYKESVDQRGNQIMSDKRNVILFSVFDENRSWYLTENIQRF
LPNPAGVQLEDPEFQASNIMHSINGYVFDSLQLSVCLHEVAYWYILSIGA
QTDFLSVFFSGYTFKHKMVYEDTLTLFPFSGETVFMSIVIENLGLWILGC
HNSDFRNRGIVITALLKVSSCDKNTGDYYEDSYEDISAYLLSKNNAIEPR
SFSQNPPVLKRHQREITRTTLQSDQEEIDYDDTISVEMKKEDFDIYDEDE
NQSPRSFQKKTRHYFIAAVERLWDYGMSSSPHVLRNRAQSGSVPQFKKVV
FQEFTDGSFTQPLYRGELNEHLGLLGPYIRAEVEDNIMVTFRNQASRPYS
FYSSLISYEEDQRQGAEPRKNFVKPNETKTYFWKVQIHMAPTKDEFIDCK
AWAYFSDVDLEKDVHSGLIGPLLVCHTNTLNPAHGRQVTVQEFALFFTIF
DETKSWYFTENMERNCRAPCNIQMEDPTFKENYRFHAINGYIMDTLPGLV
MAQDQRIRWYLLSMGSNENIHSTHFSGHVFTVRKKEEYKMALYNLYPGVF
ETVEMLPSKAGIWRVECLIGEHLHAGMSTLFLVYSNKCQTPLGMASGHIR
DFQITASGQYGQWAPKLARLHYSGSINAWSTKEPFSWIKVDLLAPMIIHG
IKTQGARQKFSSLYISQFIIMSLDGKKWQTYRGNSTGTLMVFFGNVDSSG
IKHNIFNPPIIARYIRLHPTFFYSIRSTLRMELMGCDLNSCSMPLGMESK
AISDAQITASSYFTNMFATWSPSKARLHLQGRSNAWRPQVNNPKEWLQVD
FQKTMKVTGVTTQGVKSLLTSMYVKEFLISSSQDGFIQWTLFFQNGKVKV
FQGNQDSFTPVVNSLDPPLLTRYLRIHPQSWVHQIALRMEVLGCEAQDLY
(SEQ ID NO: 16)

Mature FVIII VQL Insertion
ATRRYYLGAVELSWDYMQSDLGELPVDARFPPRVPKSFPFNTSVVYKKTL
FVEFTDFILFNIAKPRPPWMGLLGPTIQAEVYDTVVITLKNMASHPVSLH
AVGVSYWKASEGAEYDDQTSQREKEDDKVFPGGSHTYVWQVLKENGPMAS
DPLCLTYSYLSHVDLVKDLNSGLIGALINCREGSLAKEKTQTLHKFILLF
AVFDEGKSWHSETKNSLMQDRDAASARAWPKMHTVNGYVNRSLPGLIGCH
RKSVYWHVIGMGTTPEVHSIFLEGHTFLVRNFIRQASLEISPIFLTAQTL
LMDLGQFLLFCHISSHQHDGMEAYVKVDSCPEEPVQLQLRMKNNEEAEDY
DDDLTDSEMDVVRFDDDNSPSFIQIRSVAKKHPKTWVHYIAAEEEDWDYA
PLVLAPDDRSYKSQYLNNGPQRIGRKYKKVRFMAYTDETFKTREAIQHES
GILGPLLYGEVGDTLLIIFKNQASRPYNIYPHGITDVRPLYSRRLPKGVK
HLKDFPILPGEIFKYKWTVTVEDGPTKSDPRCLTRYYSSFVNMERDLASG
LIGPLLICYKESVDQRGNQIMSDKRNVILFSVFDENRSWYLTENIQRFLP
NPAGVQLEDPEFQASNIMHSINGYVFDSLQLSVCLHEVAYWYILSIGAQT
DFLSVFFSGYTFKHKMVYEDTLTLFPFSGETVFMSMENPGLWILGCHNSD
FRNRGMTALLKVSSCDKNTGDYYEDSYEDISAYLLSKNNAIEPRSFSQNP
PYLKRHQREITRTTLQSDQEEIDYDDTISVEMKKEDFDIYDEDENQSPRS
FQKKTRHYFIAAVERLWDYGMSSSPHVLRNRAQSGSVPQFKKVVFQEFTD
GSFTQPLYRGELNEHLGLLGPYIRAEVEDNIMVTFRNQASRPYSFYSSLI
SYEEDQRQGAEPRKNFVKPNETKTYFWKVQHFIMAPTKDEFDCKAWAYFS
DVDLEKDVHSGLIGPLLVCHTNTLNPAHGRQVTVQEFALFFTIFDETKSW
YFTENMERNCRAPCNIQMEDPTFKENYRFHAINGYIMDTLPGLVMAQDQR
IRWYLLSMGSNENIHSIHFSGHVFTVRKKEEYKMALYNLYPGVFETVEML
PSKAGIWRVECLIGEHLHAGMSTLFLVYSNKCQTPLGMASGHIRDFQITA
SGQYGQWAPKLARLHYSGSINAWSTKEPFSWIKVDLLAPMIIHGIKTQGA
RQKFSSLYISQFIIMYSLDGKKWQTYRGNSTGTLMVFFGNVDSSGIKHNI
FNPPIIARYIRLHPTHYSIRSTLRIVIELMGCDLNSCSMPLGMESKAISD
AQITASSYFTNMFATWSPSKARLHLQGRSNAWRPQVNNPKEWLQVDFQKT
MKVTGVTTQGVKSLLTSMYVKEFLISSSQDGHQWTLFFQNGKVKVFQGNQ
DSFTPVVNSLDPPLLTRYLRIHPQSWVHQIALRMEVLGCEAQDLY
(SEQ ID NO: 17)

Mature FVIII SVA Insertion
ATRRYYLGAVELSWDYMQSDLGELPVDARFPPRVAKSFPFNTSVVYKKTL
FVEFTDHLFNIAKPRPPWMGLLGPTIQAEVYDTVVITLKNMASHPVSLHA
VGVSYWKASEGAEYDDQTSQREKEDDKVFPGGSHTYVWQVLKENGPMASD
PLCLTYSYLSHVDLVKDLNSGLIGALLVCREGSLAKEKTQTLHKFILLFA
VFDEGKSWHSETKNSLMQDRDAASARAWPKMHTVNGYVNRSLPGLIGCHR TABLE 3-continued Amino Acid Sequences of FVIII Polypeptides with Reduced Affinity for vWF

```
KSVYWHVIGIVIGTTPEVHSIFLEGHTFLYRNHRQASLEISPITFLTAQT
LLMDLGQFLFUESSHQFIDGMEAYVKVDCPEEPQLRMKNNEEAEDYDDDL
TDSEMDVVRFDDDNSPSFIQIRSVASVAKKHPKTWVHYIAAEEEDVMYAP
LVLAPDDRSYKSQYLNNGPQRIGRKYKKVRFMAYTDETFKTREAQHESGI
LGPLLYGEVGDTLLIIFKNQASYNIYPHGITDVRPLYSRRLPKGVKHLKD
FPILPGEIFKYKWTVTVEDGPTKSDPRCLTRYYSSFVNMERDLASGLIGP
LLICYKESVDQRGNQIMSDKRNVILFSVFDENRSWYLTENIQRFLPNPAG
VQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNR
GMTALLKVSSCDKNTGDYYEDSYEDISAYLLSKNNAIEPRSFSQNPPVLK
RHQREITRTTLQSDQEEIDYDDTISVEMKKEDFDIYDEDENQSPRSFQKK
TRHYFLAAVERLWDYGMSSSPHVLRNRAQSGSVPQFKKVVFQEFTDGSFT
QPLYRGELNEHLGLLGPYIRAEVEDNIMVTFRNQASRPYSFYSSLISYEE
DQRQGAEPRKNFVKPNETKTYFWKVQHHIVIAPTKDEFDCKAWAYFSDVD
LEKDVHSGLIGPLLVCHTNTLNPAHGRQVTVQEFALFFTIFDETKSWYFT
ENMERNCRAPCNIQMEDPTFKENYRFHAINGYIMDTLPGLVMAQDQRIRW
YLLSMGSNENIHSIHFSGHVFTVRKKEEYKMALYNLYPGVFETVEMLPSK
AGIWRVECLIGEHLHAGMSTLFLVYSNKCQTPLGMASGHIRDFQITASGQ
YGQWAPKLARLFIYSGSINAWSTKEPFSWIKVDLLAPMIIHGIKTQGARQ
KFSSLYISQFIIMYSLDGKKWQTYRGNSTGTLMVFFGNVDSSGIKHNIFN
PPIIARYIRLHPTHYSIRSTLRMELMGCDLNSCSMPLGMESKAISDAQIT
ASSYFTNMFATWSPSKARLHLQGRSNAWRPQVNNPKEWLQVDFQKTMKVT
GVTTQGVKSLLTSMYVKEFLISSSQDGEIQWTLFFQNGKVKVFQGNQDSF
TPVVNSLDPPLLTRYLRIHPQSWVHQIALRMEVLGCEAQDLY
(SEQ ID NO: 18)
```

Mature FVIII LPK Insertion

```
ATRRYYLGAVELSWDYMQSDLGELPVDAREPPRVPKSFPFNTSVVYKKTL
FVEFTDHLFNIAKPRPPWMGLLGPTIQAEVYDTVVITLKNMASHPVSLHA
VGVSYWKASEGAEYDDQTSQREKEDDKVFPGGSHTYVWQVLKENGPMASD
PLCLTYSYLSITVDLVKDLNSGLIGALLVCREGSLAKEKTQTLHKFILLF
AVFDEGKSWHSETKNSLMQDRDAASARAWPKMHTVNGYVNRSLPGLIGCH
RKSVYWHVIGMGTTPEVHSIFLEGHTFUVRNHRQASLEISPITFLTAQTL
LMDLGQFLLFCHISSHQHDGMEAYVKVDSCPEEPQLRMKNNEEAEDYDDD
LTDSEMDVVREDIDDNSPSFIQIRSVAKKHPKTWVHYIAAEEEDWDYAPL
VLAPDDRSYKSQYLNNGPQRIGRKYKKVRFMAYTDETEKTREAIQHESGI
LGPLLYGEVGDTLLIIFKNQASRPYNIYPHGITDVRPLYSRRLPKLPKGV
KHLKDEPILPGEIFKYKWTVTVEDGPTKSDPRCLTRYYSSFVNMERDLAS
GLIGPLLICYKESVDQRGNQIMSDKRNVILFSVFDENRSWYLTENIQRFL
PNPAGVQLEDPEFQASNIMHSINGYVFDSLQLSVCLHEVAYWYILSIGAQ
TDFLSVFFSGYTFKHKMVYEDTLTLFPFSGETVFMSMENPGLWILGCHNS
DFRNRGMTALLKVSSCDKNTGDYYEDSYEDISAYLLSKNNAIEPRSFSQN
PPVLKRHQREITRTTLQSDQEEIDYDDTISVEMKKEDFDIYDEDENQSPR
SFQKKTRHYFIAAVERLWDYGMSSSPHVLRNRAQSGSVPQFKKVVFQEFT
IDGSFTQPLYRGELNEHLGLLGPYIRAEVEDNEVIVTFRNQASRPYSFYS
SLISYEEDQRQGAEPRKNFVKPNETKTYFWKVQPIHMAPTKDEFDCKAWA
YFSDVDLEKDVHSGLIGPLLVCHTNTLNPAHGRQVTVQEFALFFTIFDET
KSWYFTENMERNCRAPCNIQMEDPTFKENYRFFIAINGYIMDTLPGLVMA
QDQRIRWYLLSMGSNENIHSIHFSGHVFTVRKKFEYKMALYNLYPGVFET
VEMLPSKAGIWRVECLIGEHLHAGMSTLFLVYSNKCQTPLGMASGHIRDF
QVFASGQYGQWAPKLARLHYSGSINAWSTKEPFSWIKVDLLAPMIIFIGI
KTQGARQKFSSLYISQFIIMYSLDGICKWQTYRGNSTGTLMVFFGNVDSS
GIKHNIFNPPIIAKYIRLHPTHYSIRSTLRMELMGCDLNSCSMPLGMESK
AISDAQITASSYFTNMFATWSPSKARLHLQGRSNAWRPQVNNPKEWLQVD
FQKTMKVTGVTTQGVKSLLTSMYVKEFLISSSQDGHQWTLFFQNGKVKVF
QGNQDSFTPVVNSLDPPLLTRYLRIIIPQSWVHQIALRMEVLGCEAQDLY
(SEQ ID NO: 19)
```

Mature FVIII RAQ Insertion

```
ATRRYYLGAVELSWDYMQSDLGELPVDARFPPRVPKSFPFNTSVVYKKTL
FVEFTDHLFNIAKPRPPWMGLLGPTIQAEVYDTVVITLKNMASHPVSLHA
VGVSYVVKASEGAEYDDQTSWKEDDKVFPGGSHTYVWQVLKENGPMASDP
LCLTYSYLSHVDLVKDLNSGLIGALLVCREGSLAKEKTQTLHKFILLFAV
FDEGKSWHSETKNSLMQDRDAASARAWPKMHTVNGYVNRSLPGLIGCHRK
SVYWHVIGMGTTPEVHSIFLEGHTFLVRNHRQASLEISPITFLTAQTLLM
LGQFLLFCHISSHQPIDGMEAYVKVDSCPEEPQLRMKNNEEAEDYDDIDL
TDSEMDVVREDDDNSPSFIQIRSVAKKHPKTWVHYIAAEEEDWDYAPLVL
APDDRSYKSQYLNNGPQRIGRKYKKVRFMAYTDETFKTREAIQPIESGIL
GPLLYGEVGDTLLIIFKNQASRPYNTYPHGITDVRPLYSRRLPKGVKHLK
DFPILPGEIFKYKWTVTVEDGPTKSDPRCLTRYYSSFVNIVIERDLASGL
IGPLLICYKESVDQRGNQIMSDKRNVILFSVDENRSWYLTENIQRFLPNP
AGVQLEDPEFQASNIMHSINGYVFDSLQLSVCLHEVAYWYLSIGAQTDFL
SVFFSGYTFKHKMVYEDTLTLFPFSGETVFMSMENPGLWILGCHNSDFRN
RGMTALLKVSSCDKNTGDYYEDSYEDISAYLLSKNNAIEPRSFSQNPPVL
KRHQREITRTTLQSDQEEIDYDDTISVEMKKEDFDIYDEDENQSPRSFQK
KTRHYFIAAVERLWDYGMSSSPHVLRNRAQRAQSGSVPQFKKVVFQEFTD
GSFTQPLYRGELNEHLGLLGPYIRAEVEDNIMVTFRNQASRPYSFYSSLI
SYEEDQRQGAEPRKNFVKPNETKTYFWKVQHHMAPTKDEFDCKAWAYFSD
VDLEKDVHSGLIGPLLVCHTNTLNPAHGRQVTVQEFALFFTIFDETKSWY
FTENMERNCRAPCNIQMEDPTFKENYRFHAINGYIMDTLPGLVMAQDQRI
RWYLLSMGSNENIPISIHFSGHVFTVRKKEEYKMALYNLYPGVFETVEML
PSKAGIWRVECLIGEHLHAGMSTLFLVYSNKCQTPLGMASGHIRDFQITA
SGQYGQWAPKLARLHYSGSINAWSTKEPFSWIKVDLLAPMIIHGIKTQGA
RQKFSSLYISQFIIMYSLDGKKWQTYRGNSTGTLIVIVFFGNVDSSGIKH
NIFNPPIIARYIRLHPTHYSIRSTLRMELMGCDLNSCSMPLGMESKAISD
AQITASSYFTNMFATWSPSKARLHLQGRSNAWRPQVNNPKEWLQVDFQKT
MKVTGVTTQGVKSLLTSMYVKEFLISSSQDGFIQWTLFFQNGKVKVFQGN
QDSFTPVVNSLDPPLLTRYLRIHTQSWVHQIALRMEVLGCEAQDLY
(SEQ ID NO: 20)
```

Mature FVIH RAQ Insertion R1648A

```
ATRRYYLGAVELSWDYMQSDLGELPVDARFPPRVPKSFPFNTSVVYKKTL
FVEFTDHLFNIAKPRPPWMGLLGPTIQAEVYDTVVITLKNMASHPVSLHA
VGVSYWKASEGAEYDDQTSQREKEDDKVFPGGSHTYVWQVLKENGPMASD
PLCLTYSYLSHVDLVKDLNSGLIGALLVCREGSLAKEKTQTLHKFILLFA
VFDEGKSWHSETKNSLMQDRDAASARAWPKMHTVNGYVNRSLPGLIGCHR
KSVYWHVIGMGTTPEVHSIFLEGHTFLVRNHRQASLEISPITFLTAQTLL
MDLGQFLLFCHISSHQHDGMEAYVKVDSCPEEPQLRMKNNELAEDYDDDL
TDSEMDVVRFDDDNSPSFIQIRSVAKKFIPKTWVHYIAAEEEDWDYAPLV
LAPDDRSYKSQYLNNGPQRIGRKYKKVRFMAYTDETFKTREAIQHESGIL
GPLLYGEVGDTLLIIFKNQASRPYNIYPHGITDVRPLYSRRLPKGVKHLK
DFPILPGEIFKYKWTVTVEDGPTKSDPRCLTRYYSSFVNMERDLASGLIG
PLLICYKESVDQKGNQIMSDKRWILFSVFDENRSWYLTENIQRFLPNPAG
VQLEDPEFQASNIMHSINGYVFDSLQLSVCLHEVAYWYILSIGAQTDFLS
VFFSGYTFKHKWYEDTLTLFPFSGETVFMSMENPGLWILGCHNSDFRNRG
MTALLKVSSCDKNTGDYYEDSYEDISAYLLSKNNAEPRSFSQNPPVLKRH
QAEITRTTLQSDQEEIDYDDTISVEMKKEDFDIYDEDENQSPRSFQKKTR
HYFIAAVERLWDYGMSSSPHVLRNRAQRAQSGSVPQFKKVVFQEFTDGSF
TQPLYRGELNEHLGLLGPYIRAEVEDNIMVTFRNQASRPYSFYSSLISYE
EDQRQGAEPRKNFVKPNETKTYFWKVQRRMAPTKDEFDCKAWAYFSDVDL
EKDVHSGLIGPLLVCHTNTLNPAHGRQVTVQEFALFFTIFDETKSWYFTE
NMERNCRAPCNIQMEDPTFKENYRFHAINGYIMDTLPGLVMAQDQRIRWY
LLSMGSNENIHSIHFSGHVFTVRKKEEYKMALYNLYPGVFETVEMLPSKA
GIWRVECLIGEHLHAGMSTLFINYSNIKCQTPLGMASGIIIRDFQITASG
QYGQWAPKLARLHYSGSINAWSTKEPFSWIKVDLLAPMHHGIKTQGARQK
FSSLYISQFIIMYSLDGKKWQTYRGNSTGTLMVFFGNVDSSGIKHNIFNP
PIIARYIRLHPTHYSIRSTLRMELMGCDLNSCSMPLGMESKAISDAQITA
SSYFTNMFATWSPSKARLIILQGRSNAWRPQVNNPKEWLQVDFQKTMKVT
GVTTQGVKSLLTSMYVKEFLISSSQDGHQWTLFFQNGKVKVFQGNQDSFT
PVVNSLDPPLLTRYLRIIIPQSWVHQIALRMEVLGCEAQDLY
(SEQ ID NO: 21)
```

The "B-domain" of FVIII, as used herein, is the same as the B-domain known in the art that is defined by internal amino acid sequence identity and sites of proteolytic cleavage, e.g., residues Ser741-Arg1648 of full-length human FVIII. The other human FVIII domains are defined by the following amino acid residues: A1, residues Ala1-Arg372; A2, residues Ser373-Arg740; A3, residues Ser1690-Asn2019; C1, residues Lys2020-Asn2172; C2, residues Ser2173-Tyr2332. The A3-C1-C2 sequence includes residues Ser1690-Tyr2332. The remaining sequence, residues Glu1649-Arg1689, is usually referred to as the a3 acidic region. The locations of the boundaries for all of the domains, including the B-domains, for porcine, mouse and canine FVIII are also known in the art. In one embodiment, the B domain of FVIII is deleted ("B-domain-deleted factor VIII" or "BDD FVIII"). An example of a BDD FVIII is REFACTO® (recombinant BDD FVIII), which has the same sequence as the Factor VIII portion of the sequence in Table 4. (BDD FVIII heavy chain is double underlined; B domain is italicized; and BDD FVIII light chain is in plain text). A nucleotide sequence encoding BDD FVIII (SEQ ID NO: 7) is shown in Table 5.

TABLE 4

Amino Acid Sequence of B-domain Deleted Factor VIII (BDD FVIII)

BDD FVIII (SEQ ID NO: 6)

ATRRYYLGAVELSWDYMQSDLGELPVDARFPPRVPKSFPFNTSVVKKTLF

VEFTDHLFNIAKPRPPWMGLLGPTIQAEVYDTVVITLKNMASHPVSLHAV

GVSYWKASEGAEYDDQTSQREKEDDKVFPGGSHTYVWQVLKENGPMASDP

LCLTYSYLSHVDLVKDLNSGLIGALLVCREGSLAKEKTQTLHDFILLFAV

FDEGKSWHSETKNSLMQDRDAASARAWPKMHTVNGYVNRSLPGLLGCHRK

SVYWHVIGMGTTPEVHSIFLEGHTFLVRNHRQASLELSPITFLTAQTLLM

DLGQFLLFCHISSHQHDGMEAYVKVDSCPEEPQLRMKNNEEAEDYDDDLT

DSEMDVVRFDDDNSPSFIQIRSVAKKHPKTWVHYIAAEEEDWDAPLVLAP

DDRSYKSQYLNNGPQRIGRKYKKVRFMAYTDETFKTREAIQHESGILGPL

LGEVGDTLLIIFKNQASRPYNIYPHGITDVRPLYSRRLPKGVKHLKDFPI

LPGEIFKYKWTVTVEDGPTKSDPRCLTRYYSSFVNMERDLASGLIGPLLI

CYKESVDQRGNQIMSDKRNVILFSVFDENRSWYLTENIQRFLPNPAGVQL

EDPEFQASNIMHSINGYVFDSLQLSVCLHEVAYWYILSIGAQTDFLSVFF

SGYTFKHKMVYEDTLTLFPFSGETVFMSMENPGLWILGCHSNDFRNGMTA

LLKVSSCDKNTGDYYEDSYEDISAYLLSKNNAIEPR*SFSQNPPVLKRHQR*

TABLE 4 -continued

Amino Acid Sequence of B-domain Deleted Factor VIII (BDD FVIII)

EITRTTLQSDQEEIDYDDTISVEMKKEDFDIYDEDENQSPRSFQKKTRHY

FIAAVERLWDYGMSSSPHVLRNRAQSGSVPQFKKWFQEFTDGSFTQPLYR

GELNEHLGLLGPYIRAEVEDNIMVTFRNQASRPYSFYSSLISYEEDQRQG

AEPRKNFVKPNETKTYFWKVQHHMAPTKDEFDCXAWAYFSDVDLEKDVHS

GLIGPLLVCHTNTLNPAHGRQVTVQEFALFFTIFDETKSWYFTENMERNC

RAPCNIQMEDPTFKENYRFHAINGYIMDTLPGLVMAQDQRIRWYLLSMGS

NENIHSIHFSGHVFTVRKKEEYKMALYNLYPGVFETVEMLPSKAGIWRVE

CLIGEHLHAGMSTLFLVYSNKCQTPLGMASGHIRDFQITASGQYGQWAPK

LARLHYSGSINAWSTKEPFSWIKVDLLAPMIIHGIKTQGARQKFSSLYIS

QFIIMYSLDGKKWQTYRGNSTGTLMVFFGNVDSSGIKHNIFNPPIIARYI

RLHPTHYSIRSTLRMEIGCDLNSCSMPLGMESKAISDAQITASSYFTNMF

ATWSPSKARLHLQGRSNAWRPQVNNPKEWLQVDFQKTMKVTGVTTQGVKS

LLTSMYVKEFLISSSQDGHQWTLFFQNGKVKVFQGNQDSFTPVVNSLDPP

LLTRYLRIHPQSWVHQIALRMEVLGCEAQDLY

TABLE 5

Nucleotide Sequence Encoding BDD FVIII (SEQ ID NO: 7)*

661 A TGCAAATAGA GCTCTCCACC TGCTTCTTTC

721 TGTGCCTTTT GCGATTCTGC TTTAGTGCCA CCAGAAGATA CTACCTGGGT GCAGTGGAAC

781 TGTCATGGGA CTATATGCAA AGTGATCTCG GTGAGCTGCC TGTGGACGCA AGATTTCCTC

841 CTAGAGTGCC AAAATCTTTT CCATTCAACA CCTCAGTCGT GTACAAAAAG ACTCTGTTTG

901 TAGAATTCAC GGATCACCTT TTCAACATCG CTAAGCCAAG GCCACCCTGG ATGGGTCTGC

961 TAGGTCCTAC CATCCAGGCT GAGGTTTATG ATACAGTGGT CATTACACTT AAGAACATGG

1021 CTTCCCATCC TGTCAGTCTT CATGCTGTTG GTGTATCCTA CTGGAAAGCT TCTGAGGGAG

1081 CTGAATATGA TGATCAGACC AGTCAAAGGG AGAAAGAAGA TGATAAAGTC TTCCCTGGTG

1141 GAAGCCATAC ATATGTCTGG CAGGTCCTGA AAGAGAATGG TCCAATGGCC TCTGACCCAC

1201 TGTGCCTTAC CTACTCATAT CTTTCTCATG TGGACCTGGT AAAAGACTTG AATTCAGGCC

1261 TCATTGGAGC CCTACTAGTA TGTAGAGAAG GGAGTCTGGC CAAGGAAAAG ACACAGACCT

1321 TGCACAAATT TATACTACTT TTTGCTGTAT TTGATGAAGG GAAAAGTTGG CACTCAGAAA

1381 CAAAGAACTC CTTGATGCAG GATAGGGATG CTGCATCTGC TCGGGCCTGG CCTAAAATGC

1441 ACACAGTCAA TGGTTATGTA AACAGGTCTC TGCCAGGTCT GATTGGATGC CACAGGAAAT

1501 CAGTCTATTG GCATGTGATT GGAATGGGCA CCACTCCTGA AGTGCACTCA ATATTCCTCG

1561 AAGGTCACAC ATTTCTTGTG AGGAACCATC GCCAGGCGTC CTTGGAAATC TCGCCAATAA

1621 CTTTCCTTAC TGCTCAAACA CTCTTGATGG ACCTTGGACA GTTTCTACTG TTTTGTCATA

1681 TCTCTTCCCA CCAACATGAT GGCATGGAAG CTTATGTCAA AGTAGACAGC TGTCCAGAGG

1741 AACCCCAACT ACGAATGAAA AATAATGAAG AAGCGGAAGA CTATGATGAT GATCTTACTG

1801 ATTCTGAAAT GGATGTGGTC AGGTTTGATG ATGACAACTC TCCTTCCTTT ATCCAAATTC

TABLE 5-continued

| | | | | | | |
|---|---|---|---|---|---|---|
| 1861 | GCTCAGTTGC | CAAGAAGCAT | CCTAAAACTT | GGGTACATTA | CATTGCTGCT | GAAGAGGAGG |
| 1921 | ACTGGGACTA | TGCTCCCTTA | GTCCTCGCCC | CCGATGACAG | AAGTTATAAA | AGTCAATATT |
| 1981 | TGAACAATGG | CCCTCAGCGG | ATTGGTAGGA | AGTACAAAAA | AGTCCGATTT | ATGGCATACA |
| 2041 | CAGATGAAAC | CTTTAAGACT | CGTGAAGCTA | TTCAGCATGA | ATCAGGAATC | TTGGGACCTT |
| 2101 | TACTTTATGG | GGAAGTTGGA | GACACACTGT | TGATTATATT | TAAGAATCAA | GCAAGCAGAC |
| 2161 | CATATAACAT | CTACCCTCAC | GGAATCACTG | ATGTCCGTCC | TTTGTATTCA | AGGAGATTAC |
| 2221 | CAAAAGGTGT | AAAACATTTG | AAGGATTTTC | CAATTCTGCC | AGGAGAAATA | TTCAAATATA |
| 2281 | AATGGACAGT | GACTGTAGAA | GATGGGCCAA | CTAAATCAGA | TCCTCGGTGC | CTGACCCGCT |
| 2341 | ATTACTCTAG | TTTCGTTAAT | ATGGAGAGAG | ATCTAGCTTC | AGGACTCATT | GGCCCTCTCC |
| 2401 | TCATCTGCTA | CAAAGAATCT | GTAGATCAAA | GAGGAAACCA | GATAATGTCA | GACAAGAGGA |
| 2461 | ATGTCATCCT | GTTTTCTGTA | TTTGATGAGA | ACCGAAGCTG | GTACCTCACA | GAGAATATAC |
| 2521 | AACGCTTTCT | CCCCAATCCA | GCTGGAGTGC | AGCTTGAGGA | TCCAGAGTTC | CAAGCCTCCA |
| 2581 | ACATCATGCA | CAGCATCAAT | GGCTATGTTT | TTGATAGTTT | GCAGTTGTCA | GTTTGTTTGC |
| 9641 | ATGAGGTGGC | ATACTGGTAC | ATTCTAAGCA | TTGGAGCACA | GACTGACTTC | CTTTCTGTCT |
| 2701 | TCTTCTCTGG | ATATACCTTC | AAACACAAAA | TGGTCTATGA | AGACACACTC | ACCCTATTCC |
| 2761 | CATTCTCAGG | AGAAACTGTC | TTCATGTCGA | TGGAAAACCC | AGGTCTATGG | ATTCTGGGGT |
| 2821 | GCCACAACTC | AGACTTTCGG | AACAGAGGCA | TGACCGCCTT | ACTGAAGGTT | TCTAGTTGTG |
| 2881 | ACAAGAACAC | TGGTGATTAT | TACGAGGACA | GTTATGAAGA | TATTTCAGCA | TACTTGCTGA |
| 2941 | GTAAAAACAA | TGCCATTGAA | CCAAGAAGCT | TCTCTCAAAA | CCCACCAGTC | TTGAAACGCC |
| 3001 | ATCAACGGGA | AATAACTCGT | ACTACTCTTC | AGTCAGATCA | AGAGGAAATT | GACTATGATG |
| 3061 | ATACCATATC | AGTTGAAATG | AAGAAGGAAG | ATTTTGACAT | TTATGATGAG | GATGAAAATC |
| 3121 | AGAGCCCCCG | CAGCTTTCAA | AAGAAAACAC | GACACTATTT | TATTGCTGCA | GTGGAGAGGC |
| 3181 | TCTGGGATTA | TGGGATGAGT | AGCTCCCCAC | ATGTTCTAAG | AAACAGGGCT | CAGAGTGGCA |
| 3241 | GTGTCCCTCA | GTTCAAGAAA | GTTGTTTTCC | AGGAATTTAC | TGATGGCTCC | TTTACTCAGC |
| 3301 | CCTTATACCG | TGGAGAACTA | AATGAACATT | TGGGACTCCT | GGGGCCATAT | ATAAGAGCAG |
| 3361 | AAGTTGAAGA | TAATATCATG | GTAACTTTCA | GAAATCAGGC | CTCTCGTCCC | TATTCCTTCT |
| 3421 | ATTCTAGCCT | TATTTCTTAT | GAGGAAGATC | AGAGGCAAGG | AGCAGAACCT | AGAAAAAACT |
| 3481 | TTGTCAAGCC | TAATGAAACC | AAAACTTACT | TTTGGAAAGT | GCAACATCAT | ATGGCACCCA |
| 3541 | CTAAAGATGA | GTTTGACTGC | AAAGCCTGGG | CTTATTTCTC | TGATGTTGAC | CTGGAAAAAG |
| 3601 | ATGTGCACTC | AGGCCTGATT | GGACCCCTTC | TGGTCTGCCA | CACTAACACA | CTGAACCCTG |
| 3661 | CTCATGGGAG | ACAAGTGACA | GTACAGGAAT | TTGCTCTGTT | TTTCACCATC | TTTGATGAGA |
| 3721 | CCAAAAGCTG | GTACTTCACT | GAAAATATGG | AAAGAAACTG | CAGGGCTCCC | TGCAATATCC |
| 3731 | AGATGGAAGA | TCCCACTTTT | AAAGAGAATT | ATCGCTTCCA | TGCAATCAAT | GGCTACATAA |
| 3841 | TGGATACACT | ACCTGGCTTA | GTAATGGCTC | AGGATCAAAG | GATTCGATGG | TATCTGCTCA |
| 3901 | GCATGGGCAG | CAATGAAAAC | ATCCATTCTA | TTCATTTCAG | TGGACATGTG | TTCACTGTAC |
| 3961 | GAAAAAAAGA | GGAGTATAAA | ATGGCACTGT | ACAATCTCTA | TCCAGGTGTT | TTTGAGACAG |
| 4021 | TGGAAATGTT | ACCATCCAAA | GCTGGAATTT | GGCGGGTGGA | ATGCCTTATT | GGCGAGCATC |
| 4081 | TACATGCTGG | GATGAGCACA | CTTTTTCTGG | TGTACAGCAA | TAAGTGTCAG | ACTCCCCTGG |
| 4141 | GAATGGCTTC | TGGACACATT | AGAGATTTTC | AGATTACAGC | TTCAGGACAA | TATGGACAGT |
| 4201 | GGGCCCCAAA | GCTGGCCAGA | CTTCATTATT | CCGGATCAAT | CAATGCCTGG | AGCACCAAGG |

TABLE 5-continued

| | |
|---|---|
| 4261 | AGCCCTTTTC TTGGATCAAG GTGGATCTGT TGGCACCAAT GATTATTCAC GGCATCAAGA |
| 4321 | CCCAGGGTGC CCGTCAGAAG TTCTCCAGCC TCTACATCTC TCAGTTTATC ATCATGTATA |
| 4381 | GTCTTGATGG GAAGAAGTGG CAGACTTATC GAGGAAATTC CACTGGAACC TTAATGGTCT |
| 4441 | TCTTTGGCAA TGTGGATTCA TCTGGGATAA AACACAATAT TTTTAACCCT CCAATTATTG |
| 4501 | CTCGATACAT CCGTTTGCAC CCAACTCATT ATAGCATTCG CAGCACTCTT CGCATGGAGT |
| 4561 | TGATGGGCTG TGATTTAAAT AGTTGCAGCA TGCCATTGGG AATGGAGAGT AAAGCAATAT |
| 4621 | CAGATGCACA GATTACTGCT TCATCCTACT TTACCAATAT GTTTGCCACC TGGTCTCCTT |
| 4681 | CAAAAGCTCG ACTTCACCTC CAAGGGAGGA GTAATGCCTG GAGACCTCAG GTGAATAATC |
| 4741 | CAAAAGAGTG GCTGCAAGTG GACTTCCAGA AGACAATGAA AGTCACAGGA GTAACTACTC |
| 4801 | AGGGAGTAAA ATCTCTGCTT ACCAGCATGT ATGTGAAGGA GTTCCTCATC TCCAGCAGTC |
| 4861 | AAGATGGCCA TCAGTGGACT CTCTTTTTTC AGAATGGCAA AGTAAAGGTT TTTCAGGGAA |
| 4921 | ATCAAGACTC CTTCACACCT GTGGTGAACT CTCTAGACCC ACCGTTACTG ACTCGCTACC |
| 4981 | TTCGAATTCA CCCCCAGAGT TGGGTGCACC AGATTGCCCT GAGGATGGAG GTTCTGGGCT |
| 5041 | GCGAGGCACA GGACCTCTAC |

*The underlined nucleic acids encode a signal peptide.

A "B-domain-deleted FVIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563. In some embodiments, a B-domain-deleted FVIII sequence of the present invention comprises any one of the deletions disclosed at col. 4, line 4 to col. 5, line 28 and Examples 1-5 of U.S. Pat. No. 6,316,226 (also in U.S. Pat. No. 6,346,513). In another embodiment, a B-domain deleted Factor VIII is the S743/Q1638 B-domain deleted Factor VIII (SQ BDD FVIII) (e.g., Factor VIII having a deletion from amino acid 744 to amino acid 1637, e.g., Factor VIII having amino acids 1-743 and amino acids 1638-2332 of SEQ ID NO: 4, i.e., SEQ ID NO: 6). In some embodiments, a B-domain-deleted FVIII of the present invention has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B-domain-deleted Factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and Table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B-domain-deleted FVIII has a deletion of most of the B domain, but still contains amino-terminal sequences of the B domain that are essential for in vivo proteolytic processing of the primary translation product into two polypeptide chain, as disclosed in WO 91/09122. In some embodiments, a B-domain-deleted FVIII is constructed with a deletion of amino acids 747-1638, i.e., virtually a complete deletion of the B domain. Hoeben R. C., et al. *J. Biol. Chem.* 265 (13): 7318-7323 (1990). A B-domain-deleted Factor VIII may also contain a deletion of amino acids 771-1666 or amino acids 868-1562 of FVIII. Meulien P., et al. *Protein Eng.* 2(4): 301-6 (1988). Additional B domain deletions that are part of the invention include: deletion of amino acids 982 through 1562 or 760 through 1639 (Toole et al., *Proc. Natl. Acad. Sci. U.S.A.* (1986) 83, 5939-5942)), 797 through 1562 (Eaton, et al. *Biochemistry* (1986) 25:8343-8347)), 741 through 1646 (Kaufman (PCT published application No. WO 87/04187)), 747-1560 (Sarver, et al., *DNA* (1987) 6:553-564)), 741 through 1648 (Pasek (PCT application No. 88/00831)), or 816 through 1598 or 741 through 1648 (Lagner (Behring Inst. Mitt. (1988) No 82:16-25, EP 295597)). In other embodiments, BDD FVIII includes a FVIII polypeptide containing fragments of the B-domain that retain one or more N-linked glycosylation sites, e.g., residues 757, 784, 828, 900, 963, or optionally 943, which correspond to the amino acid sequence of the full-length FVIII sequence. Examples of the B-domain fragments include 226 amino acids or 163 amino acids of the B-domain as disclosed in Miao, H. Z., et al., *Blood* 103(a): 3412-3419 (2004), Kasuda, A, et al., *J. Thromb. Haemost.* 6: 1352-1359 (2008), and Pipe, S. W., et al., *J. Thromb. Haemost.* 9: 2235-2242 (2011) (i.e., the first 226 amino acids or 163 amino acids of the B domain are retained). In still other embodiments, BDD FVIII further comprises a point mutation at residue 309 (from Phe to Ser) to improve expression of the BDD FVIII protein. See Miao, H. Z., et al., Blood 103(a): 3412-3419 (2004). In still other embodiments, the BDD FVIII includes a FVIII polypeptide containing a portion of the B-domain, but not containing one or more furin cleavage sites (e.g., Arg1313 and Arg 1648). See Pipe, S. W., et al., *J. Thromb. Haemost.* 9: 2235-2242 (2011). Each of the foregoing deletions may be made in any FVIII sequence.

In some embodiments, the FVIII has a partial B-domain. In some embodiments, the FVIII protein with a partial B-domain is FVIII198 (SEQ ID NO: 35).

MQIELSTCFFLCLLRFCFSATRRYYLGAVELSWDYMQSDLGELPVDARFP

PRVPKSFPFNTSVVYKKTLFVEFTDHLFNIAKPRPPWMGLLGPTIQAEVY

-continued

```
DTVVITLKNMASHPVSLHAVGVSYWKASEGAEYDDQTSQREKEDDKVFPG

GSFITYVWQVLKENGPMASDPLCLTYSYLSFIVDLVKDLNSGLIGALLVC

REGSLAKEKTQTLHKFILLFAVFDEGKSWHSETKNSLMQDRDAASARAWP

KMHTVNGYVNRSLPGLIGCHRKSVYWHVIGMGTTPEVHSFLEGHTFLVRN

FIRQASLEISPITFLTAQTLLMDLGQFLLFCHISSHQHDGMEAYVKVDSC

PEEPQLRIVIKNNEEAEDYDDDLTDSEMDVVRFDDDNSPSFIQIRSVAKK

HPKTWVHYIAAEEEDWDYAPLVLAPDDRSYKSQYLNNGPQRIGRKYKKVR

FMAYTDETFKTREAIQHESGILGPLLYGEVGDTLLIIFKNQASRPYNIYP

HGITDVRPLYSRRLFKGVKHLKDFPILPGEIFKYKWTVTVEDGPTKSDPR

CLTRYYSSFVNMERDLASGLIGPLLIYKESVDQRGNQIMSDKRNVILFSV

FDENRSWYLTENIQRFLPNPAGVQLEDPEFQASNIMHSINGYVFDSLQLS

VCLHEVAYWYILSIGAQTDFLSVFFSGYTFKHKMYYEDTLTLFPFSGETV

FMSMENPGLWILGCHNSDFRNRGMTALLKVSSCDKNTGDYYEDSYEDISA

YLLSKNNAIEPRSFSQNSRFIPSTRQKQFNATTIPENDIEKTDPWFAHRT

PMPKIQNVSSSDLLMLLRQSPTPHGLSLSDLQEAKYETFSDDPSPGAIDS

NNSLSEMTHFRPQLHFISGDMVFTPESGLQLRLNEKLGTTAATELKKLDF

KVSSTSNNLISTIPSDNLAAGTDNTSSLGPPSMPVHYDQLDTTLFGKKSS

PLTESGGPLSLSEENNDSKLLESGLMNSQESSWGKNVSSEITRTTLQSDQ

EEIDYDDTISVEMKKEDFDIYDEDENQSPRSFQKKTRHYFIAAVERLWDY

GMSSSPHVLRNRAQSGSVPQFKKVVFQEFTDGSFTQPLYRGELNEHLGLL

GPYIRAEVEDNIMVTFLNQASRPYSFYSSLISYEEDQRQGAEPRKNFVKP

NETKTYFWKVQHFIVIAPTKDEFDCKAWAYFSDVDLEKDVHSGLIGPLLV

CHTNTLNPAHGRQVTVQEFALFFTIFDETKSWYFTENMERNCRAPCNIQM

EDPTFKENYRFHAINGYIMDTLPGLVMAQDQRIRWYLLSMGSNENHIHFS

GHVFTVRKKEEYKMALYNLYPGVFETVEMLPSKAGIWRVECLIGEHLFIA

GMSTLFLVYSNKCQTFLGMASGHIRDFQITASGQYGQWAPKLARLHYSGS

INAWSTKEPFSWIKVIDLLAPMI1HGIKTQGARQKFSSLYISQFIIMYSL

DGKKWQTYRGNSTGTLMVFFGNVIDSSGIKHNIFNPPIIARYIRLIIPTH

YSIRSTLRMELMGCDLNSCSMPLGMESKAISDAQITASSYFTNMFATWSH

PSKARLHLQGRSNAWRPQVNNPKEWLQVDFQKTMKVTGVTTQGVKSLLTS

MYVKEFLISSSQDGQWTLFFQNGKVKVFQGNQDSFTFVVNSLDPPLLTRY

LRIHPQSWVHQIALRMEVLGCEAQDLYDKTHTCPPCPAFELLGGPSVFLF

PPKFKDTLMISRTPEVTCVVVDVSHEDPEVKFNWYVDGVEVHNAKTKPUE

QYNSTYRVVSVLTVLHQDWLNGKEYKCKVSNKALPAPIEKTISKAKGQPL

EPQVYTLPPSRDELTKNQVSLTCLVKGFYPSDIAVEWESNGQPENNYKTT

PPVLDSIDGSFFLYSKLTVDKSRWQQGNVFSCSVMHEALHNHYTQKSLSL

SPGK (SEQ ID NO: 35)
```

FVIII198 is a partial B-domain containing single chain FVIIIFc molecule-226N6. The 226 represents the N-terminus 226 amino acid of the FVIII B-domain, and N6 represents six N-glycosylation sites in the B-domain.

In one embodiment, FVIII is cleaved right after arginine at amino acid 1648 (in full-length Factor VIII or SEQ ID NO: 4), amino acid 754 (in the 5743/Q1638 B-domain deleted Factor VIII or SEQ ID NO: 6), or the corresponding arginine residue (in other variants), thereby resulting in a heavy chain and a light chain. In another embodiment, FVIII comprises a heavy chain and a light chain, which are linked or associated by a metal ion-mediated non-covalent bond.

In other embodiments, FVIII is a single chain FVIII that has not been cleaved right after arginine at amino acid 1648 (in full-length FVIII or SEQ ID NO: 4), amino acid 754 (in the 5743/Q1638 B-domain-deleted FVIII or SEQ ID NO: 6), or the corresponding arginine residue (in other variants). A single chain FVIII may comprise one or more amino acid substitutions. In one embodiment, the amino acid substitution is at a residue corresponding to residue 1648, residue 1645, or both of full-length mature Factor VIII polypeptide (SEQ ID NO: 4) or residue 754, residue 751, or both of SQ BDD Factor VIII (SEQ ID NO: 6). The amino acid substitution can be any amino acids other than arginine, e.g., isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, histidine, ornithine, pyrrolysine, or taurine.

FVIII can further be cleaved by thrombin and then activated as FVIIIa, serving as a cofactor for activated Factor IX (FIXa). And the activated FIX together with activated FVIII forms a Xase complex and converts Factor X to activated Factor X (FXa). For activation, FVIII is cleaved by thrombin after three arginine residues, at amino acids 372, 740, and 1689 (corresponding to amino acids 372, 740, and 795 in the B-domain deleted FVIII sequence), the cleavage generating FVIIIa having the 50 kDa A1, 43 kDa A2, and 73 kDa A3-C1-C2 chains. In one embodiment, the FVIII protein useful for the present invention is non-active FVIII. In another embodiment, the FVIII protein is an activated FVIII.

The protein having FVIII can comprise a sequence at least 50%, 60%, 70%, 80%, 90%, 95%, 96%, 97%, 98%, 99%, or 100% identical to SEQ ID NO: 4 or 6, wherein the sequence has the FVIII clotting activity, e.g., activating Factor IX as a cofactor to convert Factor X to activated Factor X (FXa).

XTEN Sequences

As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a chimeric protein partner, XTENs can serve as a carrier, conferring certain desirable pharmacokinetic, physicochemical and pharmaceutical properties when linked to a FVIII sequence to create a chimeric protein. Such desirable properties include but are not limited to enhanced pharmacokinetic parameters and solubility characteristics. As used herein, "XTEN" specifically excludes antibodies or antibody fragments such as single-chain antibodies or Fc fragments of a light chain or a heavy chain.

Examples of XTENs are provided in PCT/US2013/026521, filed Feb. 15, 2013, which is herein incorporated by reference in its entirety.

In some embodiments, the XTEN sequence is a peptide or a polypeptide having greater than about 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, or 2000 amino acid residues. In certain embodiments, XTEN is a peptide or a polypeptide having greater than about 20 to about 3000 amino acid residues, greater than 30 to about 2500 residues, greater than 40 to about 2000 residues, greater than 50 to about 1500 residues, greater than 60 to about 1000 residues, greater than 70 to about 900 residues, greater than 80 to about 800 residues, greater than 90 to about 700 residues, greater than 100 to about 600 residues, greater than 110 to about 500 residues, or greater than 120 to about 400 residues.

In some embodiments, shorter XTEN sequences improve FVIII half-life and/or activity when inserted in select locations in FVIII, described herein in more detail. Thus, in some embodiments, the inserted XTEN sequence is a peptide or a polypeptide having 36 to 72 residues or 42 to 78 residues. In some embodiments, an inserted XTEN sequence of 36 to 72 residues improves half-life of FVIII more than a longer XTEN sequence (e.g., an XTEN sequence of 288 residues) inserted at the same location. In some embodiments, an XTEN sequence of 42 to 78 residues improves half-life of FVIII more than a longer XTEN sequence (e.g., an XTEN sequence of 294 residues) inserted at the same location. In some embodiments, an XTEN sequence of 36 residues improves half-life of FVIII more than a longer XTEN sequence (e.g., an XTEN sequence of 288 residues) inserted at the same location. In some embodiments, an XTEN sequence of 42 residues improves half-life of FVIII more than a longer XTEN sequence (e.g., an XTEN sequence of 294 residues) inserted at the same location. In some embodiments, an XTEN sequence of 72 residues improves half-life of FVIII more than a longer XTEN sequence (e.g., an XTEN sequence of 288 residues) inserted at the same location. In some embodiments, an XTEN sequence of 78 residues improves half-life of FVIII more than a longer XTEN sequence (e.g., an XTEN sequence of 294 residues) inserted at the same location.

The XTEN sequences of the invention can comprise one or more sequence motifs of 9 to 14 amino acid residues or an amino acid sequence at least 80%, 90%, 91%, 92%, 93%, 94%, 95%, 96%, 97%, 98%, or 99% identical to the sequence motif, wherein the motif comprises, consists essentially of, or consists of 4 to 6 types of amino acids selected from the group consisting of glycine (G), alanine (A), serine (S), threonine (T), glutamate (E) and proline (P). See US 2010-0239554 A1.

In some embodiments, the XTEN comprises non-overlapping sequence motifs in which about 80%, or at least about 85%, or at least about 90%, or about 91%, or about 92%, or about 93%, or about 94%, or about 95%, or about 96%, or about 97%, or about 98%, or about 99% or about 100% of the sequence consists of multiple units of non-overlapping sequences selected from a single motif family selected from Table 6A, resulting in a family sequence. As used herein, "family" means that the XTEN has motifs selected only from a single motif category from Table 6A; i.e., AD, AE, AF, AG, AM, AQ, BC, or BD XTEN, and that any other amino acids in the XTEN not from a family motif are selected to achieve a needed property, such as to permit incorporation of a restriction site by the encoding nucleotides, incorporation of a cleavage sequence, or to achieve a better linkage to FVIII. In some embodiments of XTEN families, an XTEN sequence comprises multiple units of non-overlapping sequence motifs of the AD motif family, or of the AE motif family, or of the AF motif family, or of the AG motif family, or of the AM motif family, or of the AQ motif family, or of the BC family, or of the BD family, with the resulting XTEN exhibiting the range of homology described above. In other embodiments, the XTEN comprises multiple units of motif sequences from two or more of the motif families of Table 6A. These sequences can be selected to achieve desired physical/chemical characteristics, including such properties as net charge, hydrophilicity, lack of secondary structure, or lack of repetitiveness that are conferred by the amino acid composition of the motifs, described more fully below. In the embodiments hereinabove described in this paragraph, the motifs incorporated into the XTEN can be selected and assembled using the methods described herein to achieve an XTEN of about 36 to about 3000 amino acid residues.

TABLE 6A

XTEN Sequence Motifs of 12 Amino Acids and Motif Familes

| Motif Family* | MOTIF SEQUENCE |
|---|---|
| AD | GESPGGSSGSES |
| AD | GSEGSSGPGESS |
| AD | GSSESGSSEGGP |
| AD | SGSSEPSESGSS |
| AE, AM | GSPAGSPTSTEE |
| AE, AM, AQ | GSEPATSGSETP |
| AE, AM, AQ | GTSESATPESGP |
| AE, AM, AQ | GTSTEPSEGSAP |
| AF, AM | GSTSESPSGTAP |
| AF, AM | GTSTPESGSASP |
| AF, AM | GTSPSGESSTAP |
| AF, AM | GSTSSTAESPGP |
| AG, AM | GTPGSGTASSSP |
| AG, AM | GSSTPSGATGSP |
| AG, AM | GSSPSASTGTGP |
| AG, AM | GASPGTSSTGSP |
| AQ | GEPAGSPTSTSE |
| AQ | GTGEPSSTPASE |
| AQ | SGSPSTESAPTE |
| AQ | GSETPSGPSETA |
| AQ | GPSETSTSEPGA |
| AQ | GSPSEPTEGTSA |
| BC | GSGASEPTSTEP |
| BC | GSEPATSGTEPS |
| BC | GTSEPSTSEPGA |
| BC | GTSTEPSEPGSA |
| BD | GSTAGSETSTEA |
| BD | GSETATSGSETA |
| BD | GTSESATSESGA |
| BD | GTSTEASEGSAS |

*Denotes individual motif sequences that, when used together in various permutations, results in a "family sequence"

XTEN can have varying lengths for insertion into or linkage to FVIII. In one embodiment, the length of the XTEN sequence(s) is chosen based on the property or function to be achieved in the fusion protein. Depending on the intended property or function, XTEN can be short or intermediate length sequence or longer sequence that can serve as carriers. In certain embodiments, the XTEN include short segments of about 6 to about 99 amino acid residues, intermediate lengths of about 100 to about 399 amino acid residues, and longer lengths of about 400 to about 1000 and up to about 3000 amino acid residues. Thus, the XTEN inserted into or linked to FVIII can have lengths of about 6, about 12, about 36, about 40, about 42, about 72, about 96, about 144, about 288, about 400, about 500, about 576, about 600, about 700, about 800, about 864, about 900, about 1000, about 1500, about 2000, about 2500, or up to about 3000 amino acid residues in length. In other embodiments, the XTEN sequences is about 6 to about 50, about 50 to about 100, about 100 to 150, about 150 to 250, about 250 to 400, about 400 to about 500, about 500 to about 900, about 900 to 1500, about 1500 to 2000, or about 2000 to about 3000 amino acid residues in length. The precise length of an XTEN inserted into or linked to FVIII can vary without adversely affecting the activity of the FVIII. In one embodiment, one or more of the XTEN used herein has 36 amino acids, 42 amino acids, 72 amino acids, 144 amino acids, 288 amino acids, 576 amino acids, or 864 amino acids in length and can be selected from one or more of the XTEN family sequences; i.e., AD, AE, AF, AG, AM, AQ, BC or BD.

In some embodiments, the XTEN sequence used in the invention is at least 60%, 70%, 80%, 85%, 90%, 91%, 92%, 93%, 94%, 95%, 96%, 97%, 98%, 99%, or 100% identical to a sequence selected from the group consisting of AE36, AG36, AE42, AG42, AE48, AM48, AE72, AG72, AE108, AG108, AE144, AF144, AG144, AE180, AG180, AE216, AG216, AE252, AG252, AE288, AG288, AE324, AG324, AE360, AG360, AE396, AG396, AE432, AG432, AE468, AG468, AE504, AG504, AF504, AE540, AG540, AF540, AD576, AE576, AF576, AG576, AE612, AG612, AE624, AE648, AG648, AG684, AE720, AG720, AE756, AG756, AE792, AG792, AE828, AG828, AD836, AE864, AF864, AG864, AM875, AE912, AM923, AM1318, BC864, BD864, AE948, AE1044, AE1140, AE1236, AE1332, AE1428, AE1524, AE1620, AE1716, AE1812, AE1908, AE2004A, AG948, AG1044, AG1140, AG1236, AG1332, AG1428, AG1524, AG1620, AG1716, AG1812, AG1908, and AG2004. See US 2010-0239554 A1.

In one embodiment, the XTEN sequence is at least 60%, 70%, 80%, 90%, 95%, 96%, 97%, 98%, 99% or 100% identical to an amino acid sequence selected from the group consisting of AE36 (SEQ ID NO: 22), AE42 (SEQ ID NO: 36), AE72 (SEQ ID NO: 23), AE144 (SEQ ID NO: 25), AE144_3B (SEQ ID NO: 26), AE144_4A (SEQ ID NO: 27), AE144_5A (SEQ ID NO: 28), AE144_6B (SEQ ID NO: 29), AG144_A (SEQ ID NO: 30), AG144_B (SEQ ID NO: 31), AG144_C (SEQ ID NO: 32), AG144_F (SEQ ID NO: 33), AE864 (SEQ ID NO: 43), AE576 (SEQ ID NO: 41), AE288 (SEQ IDNO: 39), AE288_2 (SEQ ID NO: 34), AE144 (SEQ ID NO: 37), AG864 (SEQ ID NO: 44), AG576 (SEQ ID NO: 42), AG288 (SEQ ID NO: 40), AG144 (SEQ ID NO: 38), and any combinations thereof. In another embodiment, the XTEN sequence is selected from the group consisting of AE36 (SEQ ID NO: 22), AE42 (SEQ ID NO: 36), AE72 (SEQ ID NO: 23), AE144_2A (SEQ ID NO: 25), AE144_3B (SEQ ID NO: 26), AE144_4A (SEQ ID NO: 27), AE144_5A (SEQ ID NO: 28), AE144_6B (SEQ ID NO: 29), AG144_A (SEQ ID NO: 30), AG144_B (SEQ ID NO: 31), AG144_C (SEQ ID NO: 32), AG144_F (SEQ ID NO: 33), AE864 (SEQ ID NO: 43), AE576 (SEQ ID NO: 41), AE288 (SEQ IDNO: 39), AE288_2 (SEQ ID NO: 34), AE144 (SEQ ID NO: 37), AG864 (SEQ ID NO: 44), AG576 (SEQ ID NO: 42), AG288 (SEQ ID NO: 40), AG144 (SEQ ID NO: 38), and any combinations thereof. The amino acid sequences for certain XTEN sequences of the invention are shown in Table 6B.

TABLE 6B

| XTEN Sequences | |
|---|---|
| XTEN | Amino Acid Sequence |
| AE36<br>SEQ ID NO: 22 | GSPAGSPTSTEEGTSESATPESGPGSEPATSGSETP |
| AE42<br>SEQ ID NO: 36 | GAPGSPAGSPTSTEEGTSESATPESGPGSEPATSGSETPASS |
| AE72<br>SEQ ID NO: 23 | TSESATPESGPGSEPATSGSETPGTSESATPESGPGSEPATSGSETPGTSESATP<br>ESGPGTSTEPSEGSAPG |
| AE78<br>SEQ ID NO: 24 | GAPTSESATPESGPGSEPATSGSETPGTSESATPESGPGSEPATSGSETPGTSES<br>ATPESGPGTSTEPSEGSAPGASS |
| AE144<br>SEQ ID NO: 37 | GSEPATSGSETPGTSESATPESGPGSEPATSGSETPGSPAGSPTSTEEGTSTEPS<br>EGSAPGSEPATSGSETPGSEPATSGSETPGSEPATSGSETPGTSTEPSEGSAPG<br>TSESATPESGPGSEPATSGSETPGTSTEPSEGSAP |
| AE144_2A<br>(SEQ ID NO: 25) | TSTEPSEGSAPGSPAGSFTSTEEGTSTEPSEGSAPGTSTEPSEGSAPGTSESATP<br>ESGPGTSTEPSEGSAPGTSESATPESGPGSEPATSGSETPGTSTEPSEGSAPGTS<br>TEPSEGSAPGTSESATPESGPGTSESATPESGPG |
| AE144_3B<br>(SEQ ID NO: 26) | SPAGSPTSTEEGTSESATPESGPGSEPATSGSETPGTSESATPESGPGTSTEPSE<br>GSAPGTSTEPSEGSAPGTSTEPSEGSAPGTSTEPSEGSAPGTSTEPSEGSAPGT<br>STEPSEGSAPGSPAGSPTSTEEGTSTEPSEGSAPG |
| AE144_4A<br>(SEQ ID NO: 27) | TSESATPESGPGSEPATSGSETPGTSESATPESGPGSEPATSGSETPGTSESATP<br>ESGPGTSTEPSEGSAPGTSESATPESGPGSPAGSPTSTEEGSPAGSPTSTEEGSP<br>AGSPTSTEEGTSESATPESGPGTSTEPSEGSAPG |

TABLE 6B-continued

| XTEN Sequences | |
|---|---|
| XTEN | Amino Acid Sequence |
| AE144_5A (SEQ ID NO: 28) | TSESATPESGPGSEPATSGSETPGTSESATPESGPGSEPATSGSETPGTSESATP ESGPGTSTEPSEGSAPGSPAGSPTSTEEGTSESATPESGPGSEPATSGSETPGTS ESATPESGPGSPAGSPTSTEEGSPAGSPTSTEEG |
| AE144_6B (SEQ ID NO: 29) | TSTEPSEGSAPGTSESATPESGPGTSESATPESGPGTSESATPESGPGSEPATSG SETPGSEPATSGSETPGSPAGSPTSTEEGTSTEPSEGSAPGTSTEPSEGSAPGSE PATSGSETPGTSESATPESGPGTSTEPSEGSAPG |
| AG144 SEQ ID NO: 38 | GTPGSGTASSSPGSSTPSGATGSPGSSPSASTGTGPGSSPSASTGTGPGASPGT SSTGSPGASPGTSSTGSPGSSTPSGATGSPGSSPSASTGTGPGASPGTSSTGSP GSSPSASTGTGPGTPGSGTASSSPGSSTPSGATGSP |
| AG144_A (SEQ ID NO: 30) | GASPGTSSTGSPGSSFSASTGTGPGSSPSASTGTGPGTPGSGTASSSPGSSTPS GATGSPGSSPSASTGTGPGASPGTSSTGSPGTPGSGTASSSPGSSTPSGATGSP GTPGSGTASSSPGASPGTSSTGSPGASPGTSSTGSP |
| AG144_B (SEQ ID NO: 31) | GTPGSGTASSSPGSSTPSGATGSPGASPGTSSTGSPGTPGSGTASSSPGSSTPS GATGSPGSSPSASTGTGPGSSPSASTGTGPGSSTPSGATGSPGSSTPSGATGSP GASPGTSSTGSPGASPGTSSTGSPGASPGTSSTGSP |
| AG144_C (SEQ ID NO: 32) | GTPGSGTASSSPGASPGTSSTGSPGASPGTSSTGSPGASPGTSSTGSPGSSPSA STGTGPGTPGSGTASSSPGASPGTSSTGSPGASPGTSSTGSPGASPGTSSTGSP GSSTPSGATGSPGSSTPSGATGSPGASPGTSSTGSP |
| AG144_F (SEQ ID NO: 33) | GSSPSASTGTGPGSSPSASTGTGPGASPGTSSTGSPGASPGTSSTGSPGSSTPS GATGSPGSSPSASTGTGPGASPGTSSTGSPGSSPSASTGTGPGTPGSGTASSSP GSSTPSGATGSPGSSTPSGATGSPGASPGTSSTGSP |
| AE288 SEQ ID NO: 39 | GTSESATPESGPGSEPATSGSETPGTSESATPESGPGSEPATSGSETPGTSESAT PESGPGTSTEPSEGSAPGSPAGSPTSTEEGTSESATPESGPGSEPATSGSETPGT SESATPESGPGSPAGSPTSTEEGSPAGSPTSTEEGTSTEPSEGSAPGTSESATPE SGPGTSESATPESGPGTSESATPESGPGSEPATSGSETPGSEPATSGSETPGSPA GSPTSTEEGTSTEPSEGSAPGTSTEPSEGSAPGSEPATSGSETPGTSESATPESG PGTSTEPSEGSAP |
| AE288_2 (SEQ ID NO: 34) | GSPAGSPTSTEEGTSESATPESGPGSEPATSGSETPGTSESATPESGPGTSTEPS EGSAPGTSTEPSEGSAPGTSTEPSEGSAPGTSTEPSEGSAPGTSTEPSEGSAPG TSTEPSEGSAPGSPAGSPTSTEEGTSTEPSEGSAPGTSESATPESGPGSEPATSG SETPGTSESATPESGPGSEPATSGSETPGTSESATPESGPGTSTEPSEGSAPGTS ESATPESGPGSPAGSPTSTEEGSPAGSPTSTEEGSPAGSPTSTEEGTSESATPES GPGTSTEPSEGSAP |
| AE288 SEQ ID NO: 40 | PGASPGTSSTGSPGASPGTSSTGSPGTPGSGTASSSPGSSTPSGATGSPGTPGS GTASSSPGSSTPSGATGSPGTPGSGTASSSPGSSTPSGATGSPGSSTPSGATGS PGSSPSASTGTGPGSSPSASTGTGPGASPGTSSTGSPGTPGSGTASSSPGSSTPS GATGSPGSSPSASTGTGPGSSPSASTGTGPGASPTSSTGSPGASPGTSSTGSP GSSTPSGATGSPGSSPSASTGTGPGASPGTSSTGSPGSSPSASTGTGPGTPGSG TASSSPGSSTPSGATGS |
| AR576 SEQ ID NO: 41 | GSPAGSPTSTEEGTSESATPESGPGTSTEPSEGSAPGSPAGSPTSTEEGTSTEPS EGSAPGTSTEPSEGSAPGTSESATPESGPGSEPATSGSETPGSEPATSGSETPG SPAGSPTSTEEGTSESATPESGPGTSTEPSEGSAPGISTEPSEGSAPGSPAGSPT STEEGTSTEPSEGSAPGTSTEPSEGSAPGTSESATPESGPGTSTEPSEGSAPGTS ESATPESGPGSEPATSGSETPGTSTEPSEGSAPGTSTEPSEGSAPGTSESATPES GPGTSESATPESGPGSPAGSPTSTEEGTSESATPESGPGSEPATSGSETPGISES ATPESGPGTSTEPSEGSAPGTSTEPSEGSAPGTSTEPSEGSAPGTSTEPSEGSAP GTSTEPSEGSAPGESPEPSEGSAPGSPAGSPTSTEEGTSTEPSEGSAPGTSESAT PESGPGSEPATSGSETPGTSESATPESGPGSEPATSGSETPGTSESATPESGPGT STEPSEGSAPGTSESATPESGPGSPAGSPTSTEEGSPAGSPTSTEEGSPAGSPTS TEEGTSESATPESGPGTSTEPSEGSAP |
| AG576 SEQ ID NO: 42 | PGTPGSGTASSSPGSSTPSGATGSPGSSPSASTGTGPGSSPSASTGTGPGSSTPS GATGSPGSSTPSGATGSPGASPGTSSTGSPGASPGTSSTGSPGASPGTSSTGSP GTPGSGTASSSPGASPGTSSTGPGASPGTSSTGSPGASPGTSSTGSPGSSPSA STGTGPGTPGSGTASSSPGASPGTSSTGSPGASPGTSSTGSPGASPGTSSTGSP GSSTPSGATGSPGSSTPSGATGSPGASPGTSSTGSPGTPGSGTASSSPGSSTPS GATGSPGSSTPSGATGSPGSSTPSGATGSPGSSPSASTGTGPGASPGTSSTGSP GASPGTSSTGSPGTPGSGTASSSPGASPGTSSTGSPGASPGTSSTGSPGASPGT SSTGSPGASPGTSSTGSPGTPGSGTASSSPGSSTPSGATGSPGTPGSGTSSSP GSSTPSGATGSPGTPGSGTASSSPGSSTPSGATGSPGSSTPSGATGSPGSSPSA STGTGPGSSPSASTGTGPGASPGTSSTGSPGTPGSGTASSSPGSSTPSGATGSP GSSPSASTGTGPGSSPSASTGTGPGASPGTSSTGS |

TABLE 6B-continued

| XTEN Sequences | |
|---|---|
| XTEN | Amino Acid Sequence |
| AE864<br>SEQ ID NO: 43 | GSPAGSPTSTEEGTSESATPESGPGTSTEPSEGSAPGSPAGSPTSTEEGTSTEPS<br>GSAPGTSTEPSEGSAPGTSESATPESGPGSEPATSGSETPGSEPATSGSETPG<br>SPAGSPTSTEEGTSESATPESGPGTSTEPSEGSAPGTSTEPSEGSAPGSPAGSPT<br>STEEGTSTEPSEGSAPGTSTEPSEGSAPGTSESATPESGPGTSTEPSEGSAPGTS<br>ESATPESGPGSEPATSGSETPGTSTEPSEGSAPGTSTEPSEGSAPGTSESATPES<br>GPGTSESATPESGPGSPAGSPTSTEEGTSESATPESGPGSEPATSGSETPGTSES<br>ATPESGPGTSTEPSEGSAPGSTEPSEGSAPGTSTEPSEGSAPGTSTEPSEGSAP<br>GTSTEPSEGSAPGTSTEPSEGSAPGSPAGTSTEEGTSTEPSEGSAPGTSESAT<br>PESGPGSEPATSGSETPGESESATPESGPGSEPATSGSETPGTSESATPESGPGT<br>STEPSEGSAPGTSESATPESGPGSPAGSPTSTEEGSPAGSPTSTEEGSPAGSPTS<br>TEEGTSESDATPESGPGTSTEPSEGSAPGDTSESATPESGPGSEPATSGSETPGTSE<br>SATPESGPGSEPATSGSETPGTSESATPESGPGTSTEPSEGAPGSGSPTSTE<br>EGTSESATPESGPGSATSGSETPGTSESATPESGPGSPAGPTSTEEGSPAG<br>SPTSTEEGTSTEPSEGSAPGTSESATPESGPGTSESATPESGPGTSESATPESGP<br>GSEPATSGSETPGSEPTSGSETPGSPAGSPTSTEEGTSTEPSEGSAPGTSTEPS<br>EGSAPGSEPATSGSETPGTSESATPESGPGTSTEPSEGSAP |
| AE864<br>SEQ ID NO: 44 | GASPGTSSTGSPGSSPSASTGTGPGSSPSASTGTGPGTPGSGTASSSPGSSTPS<br>GATGSPGSSPSASTGTGPGASPGTSSTGSPGTPGSGTASSSPGSSTPSGATGSP<br>GTPGSGTASSSPGASPGTSSTGSPGASPGTSSTGSPGTPGSGTASSSPGSSTPS<br>GATGSPGASPGTSSTGSPGTPGSGTASSSPGSSTPSGATGSPGSSPSASTGTGP<br>GSSPSASTGTGPGSSTPSGATGSPGSSTPSGATGSPGASPGTSSTGSPGASPGT<br>SSTGSPGASPGTSSTGSPGTPGSGTASSSPGASPGTSSTGSPGASPGTSSTGSP<br>GASPGTSSTGSPGSSPSASTGTGPGTPGSGTASSSPGASPGTSSTGSGASPGT<br>SSTGSPGASPGTSSTGSPGSSTPSGATGSPGSSTPSGATGSPGASPGTSSTGSP<br>GTPGSGTASSSPGSSTPSGATGSPGSSTPSGATGSPGSSTPSGATGSPGSSPSA<br>STGTGPGASPGTSSTGSPGASPGTSSTGSPGTPGSGTASSSPGASPGTSSTGSP<br>GASPGTSSTGSPGASPGTSSTGSPGASPGTSSTGSPGTPGSGTASSSPGSSTPS<br>GATGSPGTPGSGTASSSPGSSTPSGATGSPGTPGSGTASSSPGSSTPSGATGSP<br>GSSTPSGATGSPGSSPSASTGTGPGSSPSASTGTGPGASPGTSSTGSPGTPGSG<br>TASSSPGSSTPSGATGSPGSSPSASTGTGPGSSPSASTGTGPGASPGTSSTGSP<br>GASPGTSSTGSPGSSTPSGATGSPGSSPSASTGTGPGASPGTSSTGSPGSSPSA<br>STGTGPGTPGSGTASSSPGSSTPSGATGSPGSSTPSGATGSPGASPGTSSTGSP |
| XTEN_AE72_2A_1<br>(SEQ ID NO: 101) | TSTEPSEGSAPGSPAGSPTSTEEGTSTEPSEGSAPGTSTEPSEGSAPGTSESATP<br>ESGPGTSTEPSEGSAPG |
| XTEN_AE_72_2A_2<br>(SEQ ID NO: 102) | TSESATPESGPGSEPATSGSETPGTSTEPSEGSAPGTSTEPSEGSAPGTSESATP<br>ESGPGTSESATPESGPG |
| XTEN_AE_72_3B_1<br>(SEQ ID NO: 103) | SPAGSPTSTEEGTSESATPESGPGSEPATSGSETPGTSESATPESGPGTSTEPSE<br>GSAPGTSTEPSEGSAPG |
| XTEN_AE_72_3B_2<br>(SEQ ID NO: 104) | TSTEPSEGSAPGTSTEPSEGSAPGTSTEPSEGSAPGTSTEPSEGSAPGSPAGSPT<br>STEEGTSTEPSEGSAPG |
| XTEN_AE_72_4A_2<br>(SEQ ID NO: 105) | TSESATPESGPGSPAGSPTSTEEGSPAGSPTSTEEGSPAGSPTSTEEGTSESATP<br>ESGPGTSTEPSEGSAPG |
| XTEN_AE_72_5A_2<br>(SEQ ID NO: 106) | SPAGSPTSTEEGTSESATPESGPGSEPATSGSETPGTSESATPESGPGSPAGSPT<br>STEEGSPAGSPTSTEEG |
| XTEN_AE_72_6B_1<br>(SEQ ID NO: 107) | TSTEPSEGSAPGTSESATPESGPGTSESATPESGPGTSESATPESGPGSEPATSG<br>SETPGSEPATSGSETPG |
| XTEN_AE_72_6B_2<br>(SEQ ID NO: 102) | SPAGSPTSTEEGTSTEPSEGSAPGTSTEPSEGSAPGSEPATSGSETPGTSESATP<br>ESGPGTSTEPSEGSAPG |
| XTEN_AE_72_1A_1<br>(SEQ ID NO: 96) | SPAGSPTSTEEGTSESATPESGPGTSTEPSEGSAPGSPAGSPTSTEEGTSTEPSE<br>GSAPGTSTEPSEGSAPG |
| XTEN_AE_72_1A_2<br>(SEQ ID NO: 95) | TSESATFESGPGSEPATSGSETPGSEPATSGSETPGSPAGSPTSTEEGTSESATP<br>ESGPGTSTEPSEGSAPG |
| XTEN_AE144_1A<br>(SEQ ID NO: 94) | SPAGSPTSTEEGTSESATPESGPGTSTEPSEGSAPGSPAGSPTSTEEGTSTEPSE<br>GSAPGTSTEPSEGSAPGTSESATPESGPGSEPATSGSETPGSEPATSGSETPGSP<br>AGSPTSTEEGTSESATPESGPGTSTEPSEGSAPG |
| AE150<br>(SEQ ID NO: 98) | GAPGSEPATSGSETPGTSESATPESGPGSEPATSGSETPGSPAGSPTSTEEGTS<br>TEPSEGSAPGSEPATSGSETPGSEPATSGSETPGSEPATSGSETPGTSTEPSEGS<br>APGTSESATPESGPGSEPATSGSETPGTSTEPSEGSAPASS |
| AG150<br>(SEQ ID NO: 99) | GAPGTPGSGTASSSPGSSTPSGATGSPGSSPSASTGTGPGSSPSASTGTGPGAS<br>PGTSSTGSPGASPGTSSTGSPGSSTPSGATGSPGSSPSASTGTGPGASPGTSST<br>GSPGSSPSASTGTGPGTPGSGTASSSPGSSTPSGATGSPASS |

TABLE 6B-continued

| XTEN Sequences | |
|---|---|
| XTEN | Amino Acid Sequence |
| AE294 SEQ ID NO: 100 | GAPGTSESATPESGPGSEPATSGSETPGTSESATPESGPGSEPATSGSETPGTS ESATPESGPGTSTEPSEGSAPGSPAGSPTSTEEGTSESATPESGPGSEPATSGSE TPGTSESATPESGPGSPAGSPTSTEEGSPAGSPTSTEEGTSTEPSEGSAPGTSES ATPESGPGTSESATPESGPGTSESATPESGPGSEPATSGSETPGSEPATSGSETP GSPAGSPTSTEEGTSTEPSEGSAPGTSTEPSEGSAPGSEPATSGSETPGTSESAT PESGPGTSTEPSEGSAPASS |
| AG294 SEQ ID NO: 108 | GAPPGASPGTSSTGSPGASPGTSSTGSPGTPGSGTASSSPGSSTPSGATGSPGT PGSGTASSSPGSSTPSGATGSPGTPGSGTASSSPGSSTPSGATGSPGSSTPSGA TGSPGSSSASTGTGPGSSPSASTGTGPGASPGTSSTGSPGTPGSGTASSSPGS STPSGATGSPGSSPSASTGTGPGSSPSASTGTGPGASPGTSSTGSPGASPGTSS TGSPGSSTPSGATGSPGSSPSASTGTGPGASPGTSSTGSPGSSPSASTGTGPGT PGSGTASSSPGSSTPSGATGSASS |

In some embodiments wherein the XTEN has less than 100% of its amino acids consisting of 4, 5, or 6 types of amino acid selected from glycine (G), alanine (A), serine (S), threonine (T), glutamate (E) and proline (P), or less than 100% of the sequence consisting of the sequence motifs from Table 6A or the XTEN sequences of Table 6B the other amino acid residues of the XTEN are selected from any of the other 14 natural L-amino acids, but are preferentially selected from hydrophilic amino acids such that the XTEN sequence contains at least about 90%, 91%, 92%, 93%, 94%, 95%, 96%, 97%, 98%, or at least about 99% hydrophilic amino acids. An individual amino acid or a short sequence of amino acids other than glycine (G), alanine (A), serine (S), threonine (T), glutamate (E) and proline (P) may be incorporated into the XTEN to achieve a needed property, such as to permit incorporation of a restriction site by the encoding nucleotides, or to facilitate linking to FVIII or an additional half-life extending component, or incorporation of a cleavage sequence.

It is contemplated that the XTEN sequences of the chimeric FVIII-XTEN embodiments are substantially non-repetitive. In general, repetitive amino acid sequences have a tendency to aggregate or form higher order structures, as exemplified by natural repetitive sequences such as collagens and leucine zippers. These repetitive amino acids may also tend to form contacts resulting in crystalline or pseudocrystaline structures. In contrast, the low tendency of non-repetitive sequences to aggregate enables the design of long-sequence XTENs with a relatively low frequency of charged amino acids that would otherwise be likely to aggregate if the sequences were repetitive. The non-repetitiveness of a subject XTEN can be observed by assessing one or more of the following features. In one embodiment, a "substantially non-repetitive" XTEN sequence means that (i) the XTEN contains no three contiguous amino acids that are identical unless the amino acids are serine; (ii) at least about 80% of the XTEN sequence consists of non-overlapping sequence motifs, each of the sequence motifs comprising about 9 to about 14 amino acid residues consisting of four to six amino acids selected from glycine (G), alanine (A), serine (S), threonine (T), glutamate (E) and proline (P), wherein any two contiguous amino acid residues do not occur more than twice in each of the non-overlapping sequence motifs; or (iii) the XTEN sequence has a subsequence score of less than 10. Subsequence score of an XTEN sequence can be calculated according to the formula given by Equation 1:

$$\text{Subsequence score } \frac{\sum_{i=1}^{m} Count_i}{m} \quad \text{I}$$

wherein:

m=(amino acid length of polypeptide)−(amino acid length of subsequence)+1; and $Count_i$=cumulative number of occurrences of each unique subsequence within $sequence_i$.

The choice of the XTEN sequence used in the chimeric FVIII proteins affects the physical or chemical property as the XTEN can exhibit one or more of the following advantageous properties: conformational flexibility, enhanced aqueous solubility, high degree of protease resistance, low immunogenicity, low binding to mammalian receptors, or increased hydrodynamic (or Stokes) radii. In a specific embodiment, the XTEN sequence linked to a FVIII protein in this invention increases pharmacokinetic properties such as longer terminal half-life or increased area under the curve (AUC), so that the chimeric protein described herein stays in vivo for an increased period of time compared to wild type FVIII. In further embodiments, the XTEN sequence used in this invention increases pharmacokinetic properties such as longer terminal half-life or increased area under the curve (AUC), so that FVIII protein stays in vivo for an increased period of time compared to wild type FVIII.

A variety of methods and assays can be employed to determine the physical/chemical properties of proteins comprising the XTEN sequence. Such methods include, but are not limited to analytical centrifugation, EPR, HPLC-ion exchange, HPLC-size exclusion, HPLC-reverse phase, light scattering, capillary electrophoresis, circular dichroism, differential scanning calorimetry, fluorescence, HPLC-ion exchange, HPLC-size exclusion, IR, NMR, Raman spectroscopy, refractometry, and UV/Visible spectroscopy. Additional methods are disclosed in Amau et al., *Prot Expr and Purif* 48, 1-13 (2006).

Additional examples of XTEN sequences that can be used according to the present invention and are disclosed in US Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2.

Chimeric Proteins

Chimeric proteins provided herein comprise a FVIII polypeptide and one or more XTEN sequences. In one embodiment, the chimeric protein comprises a FVIII polypeptide and an inserted XTEN sequence. In another embodiment, the insertions can be multiple insertions, e.g., more than two, three, four, five, six, seven, eight, nine, or ten insertions.

Such XTEN sequences can be fused to the C-terminus or N-terminus of the FVIII protein or inserted between one or more of the two amino acid residues in the FVIII protein while retaining FVIII coagulation activity or FVIII function. In one embodiment, the insertions improve pharmacokinetic properties of the FVIII protein (e.g., half-life).

In some embodiments, a short XTEN (e.g., an XTEN of less than 144 amino acids) is inserted at a particular location in the FVIII polypeptide.

For example, an XTEN of 36 to 78 amino acids can be inserted in an A1, A2, or A3 domain and/or between any of these domains of a FVIII polypeptide. In some embodiments, an XTEN of 36 to 78 amino acids is inserted immediately downstream of an amino acid selected from the group consisting of amino acids 18, 403, 1720, and/or 1900 corresponding to the mature FVIII polypeptide (SEQ ID NO: 4). In some embodiments, an XTEN of 36 to 78 amino acids is inserted immediately downstream of an amino acid selected from the group consisting of amino acids 18, 403, and/or 1720 corresponding to the mature FVIII polypeptide (SEQ ID NO: 4). In some embodiments, an XTEN of 36 to 78 amino acids is inserted immediately downstream of an amino acid selected from the group consisting of amino acids 18 and/or 1720 corresponding to the mature FVIII polypeptide (SEQ ID NO: 4). In some embodiments, the FVIII polypeptide has reduced affinity for vWF (e.g., is lacking amino acids 745-1685).

In some embodiments, a chimeric protein comprises an XTEN of 36 to 78 amino acids inserted immediately downstream of amino acid 18 corresponding to the mature FVIII polypeptide (SEQ ID NO: 4). In some embodiments, the chimeric protein further comprises at three additional XTEN insertions. In some embodiments, the three additional XTEN insertions are immediately downstream of amino acids 403, 745, 1720, 1900 and/or 2332 corresponding to the mature FVIII polypeptide (SEQ ID NO: 4). In some embodiments, the FVIII polypeptide has reduced affinity for vWF (e.g., is lacking amino acids 745-1685).

In some embodiments, a chimeric protein comprises an XTEN of 36 to 78 amino acids inserted immediately downstream of amino acid 403 corresponding to the mature FVIII polypeptide (SEQ ID NO: 4). In some embodiments, the chimeric protein further comprises at three additional XTEN insertions. In some embodiments, the three additional XTEN insertions are immediately downstream of insertion points selected from amino acids 18, 745, 1720, 1900 and/or 2332 corresponding to the mature FVIII polypeptide (SEQ ID NO: 4). In some embodiments, the FVIII polypeptide has reduced affinity for vWF (e.g., is lacking amino acids 745-1685).

In some embodiments, a chimeric protein comprises an XTEN of 36 to 78 amino acids inserted immediately downstream of amino acid 1720 corresponding to the mature FVIII polypeptide (SEQ ID NO: 4). In some embodiments, the chimeric protein further comprises at three additional XTEN insertions. In some embodiments, the three additional XTEN insertions are immediately downstream of insertion points selected from amino acids 18, 403, 745, 1900 and/or 2332 corresponding to the mature FVIII polypeptide (SEQ ID NO: 4). In some embodiments, the FVIII polypeptide has reduced affinity for vWF (e.g., is lacking amino acids 745-1685).

In some embodiments, a chimeric protein comprises an XTEN of 36 to 78 amino acids inserted immediately downstream of amino acids 18 and 1720 corresponding to the mature FVIII polypeptide (SEQ ID NO: 4). In some embodiments, the chimeric protein further comprises at two additional XTEN insertions, e.g., insertions immediately downstream of amino acids 745 and 2332 corresponding to the mature FVIII polypeptide (SEQ ID NO: 4). In some embodiments, the at least two additional XTEN insertions immediately downstream of amino acids 745 and 2332 are 144 and 288 amino acids in length, respectively. In some embodiments, the FVIII polypeptide has reduced affinity for vWF (e.g., is lacking amino acids 745-1685).

In some embodiments, a chimeric protein comprises an XTEN of 36 to 78 amino acids inserted immediately downstream of amino acids 18 and 403 corresponding to the mature FVIII polypeptide (SEQ ID NO: 4). In some embodiments, the chimeric protein further comprises at two additional XTEN insertions, e.g., insertions immediately downstream of amino acids 745 and 2332 corresponding to the mature FVIII polypeptide (SEQ ID NO: 4). In some embodiments, the at least two additional XTEN insertions immediately downstream of amino acids 745 and 2332 are 144 and 288 amino acids in length, respectively. In some embodiments, the FVIII polypeptide has reduced affinity for vWF (e.g., is lacking amino acids 745-1685).

In some embodiments, a chimeric protein comprises an XTEN of 36 to 78 amino acids inserted immediately downstream of amino acids 403 and 1720 corresponding to the mature FVIII polypeptide (SEQ ID NO: 4). In some embodiments, the chimeric protein further comprises at two additional XTEN insertions, e.g., insertions immediately downstream of amino acids 745 and 2332 corresponding to the mature FVIII polypeptide (SEQ ID NO: 4). In some embodiments, the at least two additional XTEN insertions immediately downstream of amino acids 745 and 2332 are 144 and 288 amino acids in length, respectively. In some embodiments, the FVIII polypeptide has reduced affinity for vWF (e.g., is lacking amino acids 745-1685).

In addition, an XTEN of 36 or 42 amino acids can be inserted in an A1, A2, or A3 domain and/or between any of these domains of a FVIII polypeptide. In some embodiments, an XTEN of 36 or 42 amino acids is inserted immediately downstream of insertion points selected from the group consisting of amino acids 18, 403, 1720, and/or 1900 corresponding to the mature FVIII polypeptide (SEQ ID NO: 4). In some embodiments, an XTEN of 36 or 42 amino acids is inserted immediately downstream of insertion points selected from the group consisting of amino acids 18, 403, and/or 1720 corresponding to the mature FVIII polypeptide (SEQ ID NO: 4). In some embodiments, an XTEN of 36 or 42 amino acids is inserted immediately downstream of insertion points selected from the group consisting of amino acids 18 and/or 1720 corresponding to the mature FVIII polypeptide (SEQ ID NO: 4). In some embodiments, the FVIII polypeptide has reduced affinity for vWF (e.g., is lacking amino acids 745-1685).

In some embodiments, a chimeric protein comprises an XTEN of 36 or 42 amino acids inserted immediately downstream of amino acid 18 corresponding to the mature FVIII polypeptide (SEQ ID NO: 4). In some embodiments, the chimeric protein further comprises at three additional XTEN insertions. In some embodiments, the three additional XTEN insertions are immediately downstream of insertion points selected from amino acids 403, 745, 1720, 1900 and/or 2332 corresponding to the mature FVIII polypeptide (SEQ ID NO: 4). In some embodiments, the FVIII polypeptide has reduced affinity for vWF (e.g., is lacking amino acids 745-1685).

In some embodiments, a chimeric protein comprises an XTEN of 36 or 42 amino acids inserted immediately downstream of amino acid 403 corresponding to the mature FVIII polypeptide (SEQ ID NO: 4). In some embodiments, the chimeric protein further comprises at three additional XTEN insertions. In some embodiments, the three additional XTEN insertions are immediately downstream of insertion points selected from amino acids 18, 745, 1720, 1900 and/or 2332 corresponding to the mature FVIII polypeptide (SEQ ID NO: 4). In some embodiments, the FVIII polypeptide has reduced affinity for vWF (e.g., is lacking amino acids 745-1685).

In some embodiments, a chimeric protein comprises an XTEN of 36 or 42 amino acids inserted immediately downstream of amino acid 1720 corresponding to the mature FVIII polypeptide (SEQ ID NO: 4). In some embodiments, the chimeric protein further comprises at three additional XTEN insertions. In some embodiments, the three additional XTEN insertions are immediately downstream of insertion points selected from amino acids 18, 403, 745, 1900 and/or 2332 corresponding to the mature FVIII polypeptide (SEQ ID NO: 4). In some embodiments, the FVIII polypeptide has reduced affinity for vWF (e.g., is lacking amino acids 745-1685).

In some embodiments, a chimeric protein comprises an XTEN of 36 or 42 amino acids inserted immediately downstream of amino acids 18 and 1720 corresponding to the mature FVIII polypeptide (SEQ ID NO: 4). In some embodiments, the chimeric protein further comprises at two additional XTEN insertions, e.g., insertions immediately downstream of amino acids 745 and 2332 corresponding to the mature FVIII polypeptide (SEQ ID NO: 4). In some embodiments, the at least two additional XTEN insertions immediately downstream of amino acids 745 and 2332 are 144 and 288 amino acids in length, respectively. In some embodiments, the FVIII polypeptide has reduced affinity for vWF (e.g., is lacking amino acids 745-1685).

In some embodiments, a chimeric protein comprises an XTEN of 36 or 42 amino acids inserted immediately downstream of amino acids 18 and 403 corresponding to the mature FVIII polypeptide (SEQ ID NO: 4). In some embodiments, the chimeric protein further comprises at two additional XTEN insertions, e.g., insertions immediately downstream of amino acids 745 and 2332 corresponding to the mature FVIII polypeptide (SEQ ID NO: 4). In some embodiments, the at least two additional XTEN insertions immediately downstream of amino acids 745 and 2332 are 144 and 288 amino acids in length, respectively. In some embodiments, the FVIII polypeptide has reduced affinity for vWF (e.g., is lacking amino acids 745-1685).

In some embodiments, a chimeric protein comprises an XTEN of 36 or 42 amino acids inserted immediately downstream of amino acids 403 and 1720 corresponding to the mature FVIII polypeptide (SEQ ID NO: 4). In some embodiments, the chimeric protein further comprises at two additional XTEN insertions, e.g., insertions immediately downstream of amino acids 745 and 2332 corresponding to the mature FVIII polypeptide (SEQ ID NO: 4). In some embodiments, the at least two additional XTEN insertions immediately downstream of amino acids 745 and 2332 are 144 and 288 amino acids in length, respectively. In some embodiments, the FVIII polypeptide has reduced affinity for vWF (e.g., is lacking amino acids 745-1685).

In addition, an XTEN of 72 or 78 amino acids can be inserted in an A1, A2, or A3 domain and/or between any of these domains of a FVIII polypeptide. In some embodiments, an XTEN of 72 or 78 amino acids is inserted immediately downstream of insertion points selected from the group consisting of amino acids 18, 403, 1720, and/or 1900 corresponding to the mature FVIII polypeptide (SEQ ID NO: 4). In some embodiments, an XTEN of 72 or 78 amino acids is inserted immediately downstream of insertion points selected from the group consisting of amino acids 18, 403, and/or 1720 corresponding to the mature FVIII polypeptide (SEQ ID NO: 4). In some embodiments, an XTEN of 72 or 78 amino acids is inserted immediately downstream of an amino acid selected from the group consisting of amino acids 18 and/or 1720 corresponding to the mature FVIII polypeptide (SEQ ID NO: 4). In some embodiments, the FVIII polypeptide has reduced affinity for vWF (e.g., is lacking amino acids 745-1685).

In some embodiments, a chimeric protein comprises an XTEN of 72 or 78 amino acids inserted immediately downstream of amino acid 18 corresponding to the mature FVIII polypeptide (SEQ ID NO: 4). In some embodiments, the chimeric protein further comprises at three additional XTEN insertions. In some embodiments, the three additional XTEN insertions are immediately downstream of insertion points selected from amino acids 403, 745, 1720, 1900 and/or 2332 corresponding to the mature FVIII polypeptide (SEQ ID NO: 4). In some embodiments, the FVIII polypeptide has reduced affinity for vWF (e.g., is lacking amino acids 745-1685).

In some embodiments, a chimeric protein comprises an XTEN of 72 or 78 amino acids inserted immediately downstream of amino acid 403 corresponding to the mature FVIII polypeptide (SEQ ID NO: 4). In some embodiments, the chimeric protein further comprises at three additional XTEN insertions. In some embodiments, the three additional XTEN insertions are immediately downstream of insertion points selected from amino acids 18, 745, 1720, 1900 and/or 2332 corresponding to the mature FVIII polypeptide (SEQ ID NO: 4). In some embodiments, the FVIII polypeptide has reduced affinity for vWF (e.g., is lacking amino acids 745-1685).

In some embodiments, a chimeric protein comprises an XTEN of 72 or 78 amino acids inserted immediately downstream of amino acid 1720 corresponding to the mature FVIII polypeptide (SEQ ID NO: 4). In some embodiments, the chimeric protein further comprises at three additional XTEN insertions. In some embodiments, the three additional XTEN insertions are immediately downstream of insertion points selected from amino acids 18, 403, 745, 1900 and/or 2332 corresponding to the mature FVIII polypeptide (SEQ ID NO: 4). In some embodiments, the FVIII polypeptide has reduced affinity for vWF (e.g., is lacking amino acids 745-1685).

In some embodiments, a chimeric protein comprises an XTEN of 72 or 78 amino acids inserted immediately downstream of amino acids 18 and 1720 corresponding to the mature FVIII polypeptide (SEQ ID NO: 4). In some embodiments, the chimeric protein further comprises at two additional XTEN insertions, e.g., insertions immediately downstream of amino acids 745 and 2332 corresponding to the mature FVIII polypeptide (SEQ ID NO: 4). In some embodiments, the at least two additional XTEN insertions immediately downstream of amino acids 745 and 2332 are 144 and 288 amino acids in length, respectively. In some embodiments, the FVIII polypeptide has reduced affinity for vWF (e.g., is lacking amino acids 745-1685).

In some embodiments, a chimeric protein comprises an XTEN of 72 or 78 amino acids inserted immediately downstream of amino acids 18 and 403 corresponding to the mature FVIII polypeptide (SEQ ID NO: 4). In some embodiments, the chimeric protein further comprises at two additional XTEN insertions, e.g., insertions immediately downstream of amino acids 745 and 2332 corresponding to the mature FVIII polypeptide (SEQ ID NO: 4). In some embodiments, the at least two additional XTEN insertions immediately downstream of amino acids 745 and 2332 are 144 and 288 amino acids in length, respectively. In some embodiments, the FVIII polypeptide has reduced affinity for vWF (e.g., is lacking amino acids 745-1685).

In some embodiments, a chimeric protein comprises an XTEN of 72 or 78 amino acids inserted immediately downstream of amino acids 403 and 1720 corresponding to the mature FVIII polypeptide (SEQ ID NO: 4). In some embodiments, the chimeric protein further comprises at two additional XTEN insertions, e.g., insertions immediately downstream of amino acids 745 and 2332 corresponding to the mature FVIII polypeptide (SEQ ID NO: 4). In some embodiments, the at least two additional XTEN insertions immediately downstream of amino acids 745 and 2332 are 144 and 288 amino acids in length, respectively. In some embodiments, the FVIII polypeptide has reduced affinity for vWF (e.g., is lacking amino acids 745-1685).

Examples of additional insertion sites include, but are not limited to, the sites listed in Tables 7, 8, 9, 10, 11, 12, 13, 14, 15 or any combinations thereof. It will be understood by those of skill in the art that an XTEN inserted within the FVIII sequence at the insertions sites of the foregoing Tables can be selected to be a defined length (e.g., 36, 42, 72, 78, 144 or more amino acids) and/or composition in order to achieve the desired increase in half-life, as described herein.

Examples of XTEN insertions are provided in PCT/US2013/026521, filed Feb. 15, 2013, which is herein incorporated by reference in its entirety.

The FVIII protein linked to one or more XTEN sequences can be represented as $FVIII_{(a \rightarrow b)}$-X-$FVIII_{(c \rightarrow d)}$, wherein $FVIII_{(a \rightarrow b)}$ comprises, consists essentially of, or consists of a first portion of a FVIII protein from amino acid residue "a" to amino acid residue "b"; $FVIII_{(c \rightarrow d)}$ comprises, consists essentially of, or consists of a second portion of a FVIII protein from amino acid residue "c" to amino acid residue "d";

a is the N-terminal amino acid residue of the first portion of the FVIII protein, b is the C-terminal amino acid residue of the first portion of the FVIII protein but is also the N-terminal amino acid residue of the two amino acids of an insertion site in which the XTEN sequence is inserted, c is the N-terminal amino acid residue of the second portion of the FVIII protein but is also the C-terminal amino acid residue of the two amino acids of an insertion site in which the XTEN sequence is inserted, and d is the C-terminal amino acid residue of the FVIII protein, and wherein the first portion of the FVIII protein and the second portion of the FVIII protein are not identical to each other and are of sufficient length together such that the FVIII protein has a FVIII coagulation activity.

In one embodiment, the first portion of the FVIII protein and the second portion of the FVIII protein are fragments of SEQ ID NO: 4 [full length mature FVIII sequence] or SEQ ID NO: 6 [B-domain deleted FVIII] or any of SEQ ID NO:1, 2, and 12-21 [FVIII sequences with reduced affinity for vWF], e.g., N-terminal portion and C-terminal portion, respectively. In certain embodiments, the first portion of the FVIII protein comprises the A1 domain and the A2 domain of the FVIII protein. The second portion of the FVIII protein comprises the A3 domain, the C1 domain, and optionally the C2 domain. In yet other embodiments, the first portion of the FVIII protein comprises the A1 domain and A2 domain, and the second portion of the FVIII protein comprises a portion of the B domain, the A3 domain, the C1 domain, and optionally the C2 domain. In still other embodiments, the first portion of the FVIII protein comprises the A1 domain, A2 domain, and a portion of the B domain of the FVIII protein, and the second portion of the FVIII protein comprises the A3 domain, the C1 domain, and optionally the C2 domain. In still other embodiments, the first portion of the FVIII protein comprises the A1 domain, A2 domain, and a first portion of the B domain of the FVIII protein. The second portion of the FVIII protein comprises a second portion of the B domain, the A3 domain, the C1 domain, and optionally the C2 domain. In some embodiments, the two amino acids ("b" and "c") can be any one or more of the amino acid residues insertion sites shown in Tables 7, 8, 9, 10, 11, 12, 13, 14, and 15. For example, "b" can be the amino acid residue immediately upstream of the site in which one or more XTEN sequences are inserted or linked, and "c" can be the amino acid residue immediately downstream of the site in which the one or more XTEN sequences are inserted or linked. In some embodiments, "a" is the first mature amino acid sequence of a FVIII protein, and "d" is the last amino acid sequence of a FVIII protein. For example, $FVIII_{(a \rightarrow b)}$ can be an amino acid sequence at least 70%, 80%, 90%, 95%, 96%, 97%, 98%, 99%, or 100% identical to amino acids 1 to 745 of SEQ ID NO: 6 [B domain deleted FVIII amino acid sequence] or SEQ ID NO: 4 [full length FVIII] and $FVIII_{(c \rightarrow a)}$ can be amino acids 746 to 1438 of SEQ ID NO: 6 or amino acids 1641 to 2332 of SEQ ID NO: 4, respectively.

In some aspects, the insertion site in the FVIII protein is located in one or more domains of the FVIII protein, which is the N-terminus, the A1 domain, the A2 domain, the A3 domain, the B domain, the C1 domain, the C2 domain, the C-terminus, or two or more combinations thereof or between two domains of the FVIII protein, which are the A1 domain and a1 acidic region, and the a1 acidic region and A2 domain, the A2 domain and a2 acidic region, the a2 acidic region and B domain, the B domain and A3 domain, and the A3 domain and C1 domain, the C1 domain and C2 domain, or any combinations thereof. For example, the insertion sites in which the XTEN sequence can be inserted are selected from the group consisting of the N-terminus and A1 domain, the N-terminus and A2 domain, the N-terminus and A3 domain, the N-terminus and B domain, the N-terminus and C1 domain, the N-terminus and C2 domain, the N-terminus and the C-terminus, the A1 and A2 domains, the A1 and A3 domains, the A1 and B domains, the A1 and C1 domains, the A1 and C2 domains, the A1 domain and the C-terminus, the A2 and A3 domains, the A2 and B domains, the A2 and C1 domains, the A2 and C2 domains, the A2 domain and the C-terminus, the A3 and B domains, the A3 and C1 domains, the A3 and C2 domains, the A3 domain and the C-terminus, the B and C1 domains, the B and C2 domains, the B domain and the C-terminus, the C1 and C2 domains, the C1 and the C-terminus, the C2 domain, and the C-terminus, and two or more combinations thereof. Non-limiting examples of the insertion sites are listed in Tables 7, 8, 9, 10, 11, 12, 13, 14, and 15.

In one embodiment, the FVIII chimeric protein, in which the XTEN sequence is inserted immediately downstream of one or more amino acids (e.g., one or more XTEN insertion sites) in the FVIII protein or linked at the C-terminus or the N-terminus, retains some or all of the activity of wild-type FVIII after linkage to or insertion by the XTEN sequence. The XTEN sequence can be inserted in the FVIII protein once or more than once, twice, three times, four times, five times, or six times such that the insertions do not adversely affect the FVIII activity (i.e., the FVIII protein still retains the coagulation property). In some embodiments, the chimeric protein comprises four XTEN sequences.

The FVIII protein useful in the present invention can be linked to one or more XTEN polypeptides at the N-terminus or C-terminus of the FVIII protein by an optional linker or inserted immediately downstream of one or more amino acids (e.g., one or more XTEN insertion sites) in the FVIII protein by one or more optional linkers. In one embodiment, the two amino acid residues in which the XTEN sequence is inserted or the amino acid residue to which the XTEN sequence is linked correspond to the two or one amino acid residues of SEQ ID NO: 4 [full length mature FVIII] selected from the group consisting of the residues in Table 7, Table 8, Table 9, and Table 10 and any combinations thereof.

In other embodiments, at least one XTEN sequence is inserted in any one or more XTEN insertion sites disclosed herein or any combinations thereof. In one aspect, at least one XTEN sequence is inserted in one or more XTEN insertion sites disclosed in one or more amino acids disclosed in Table 7.

TABLE 7

Exemplary XTEN Insertion Sites

| No. | XTEN Insertion Point* | Insertion Residue | FVIII BDD Downstream Sequence | FVIII Domain |
|---|---|---|---|---|
| 1 | 0 | (N-terminus) | ATR | A1 |
| 2 | 3 | R | RYY | A1 |
| 3 | 17 | M | QSD | A1 |
| 4 | 18 | Q | SDL | A1 |
| 5 | 22 | G | ELP | A1 |
| 6 | 24 | L | PVD | A1 |
| 7 | 26 | V | DAR | A1 |
| 8 | 28 | A | RFP | A1 |
| 9 | 32 | P | RVP | A1 |
| 10 | 38 | F | PFN | A1 |
| 11 | 40 | F | NTS | A1 |
| 12 | 41 | N | TSV | A1 |
| 13 | 60 | N | IAK | A1 |
| 14 | 61 | I | AKP | A1 |
| 15 | 65 | R | PPW | A1 |
| 16 | 81 | Y | DTV | A1 |
| 17 | 111 | G | AEY | A1 |
| 18 | 116 | D | QTS | A1 |
| 19 | 119 | S | QRE | A1 |
| 20 | 120 | Q | REK | A1 |
| 21 | 128 | V | FPG | A1 |
| 22 | 129 | F | PGG | A1 |
| 23 | 130 | P | GGS | A1 |
| 24 | 182 | G | SLA | A1 |
| 25 | 185 | A | KEK | A1 |
| 26 | 188 | K | TQT | A1 |
| 27 | 205 | G | KSW | A1 |
| 28 | 210 | S | ETK | A1 |
| 29 | 211 | E | TKN | A1 |
| 30 | 216 | L | MQD | A1 |
| 31 | 220 | R | DAA | A1 |
| 32 | 222 | A | ASA | A1 |
| 33 | 223 | A | SAR | A1 |
| 34 | 224 | S | ARA | A1 |

TABLE 7-continued

Exemplary XTEN Insertion Sites

| No. | XTEN Insertion Point* | Insertion Residue | FVIII BDD Downstream Sequence | FVIII Domain |
|---|---|---|---|---|
| 35 | 230 | K | MHT | A1 |
| 36 | 243 | P | GLI | A1 |
| 37 | 244 | G | LIG | A1 |
| 38 | 250 | R | KSV | A1 |
| 39 | 318 | D | GME | A1 |
| 40 | 333 | P | QLR | A1 |
| 42 | 334 | Q | LRM | A1 |
| 43 | 336 | R | MKN | a1 |
| 44 | 339 | N | NEE | a1 |
| 45 | 345 | D | YDD | a1 |
| 46 | 357 | V | VRF | a1 |
| 47 | 367 | S | FIQ | a1 |
| 48 | 370 | S | RPY | a1 |
| 49 | 375 | A | KKH | A2 |
| 50 | 376 | K | KHP | A2 |
| 51 | 378 | H | PKT | A2 |
| 52 | 399 | V | LAP | A2 |
| 53 | 403 | D | DRS | A2 |
| 54 | 405 | R | SYK | A2 |
| 55 | 409 | S | QYL | A2 |
| 56 | 416 | P | QRI | A2 |
| 57 | 434 | E | TFK | A2 |
| 58 | 438 | T | REA | A2 |
| 59 | 441 | A | IQH | A2 |
| 60 | 442 | I | QHE | A2 |
| 61 | 463 | I | IFK | A2 |
| 62 | 487 | Y | SRR | A2 |
| 63 | 490 | R | LPK | A2 |
| 64 | 492 | P | KGV | A2 |
| 65 | 493 | K | GVK | A2 |
| 66 | 494 | G | VKH | A2 |
| 67 | 500 | D | FPI | A2 |
| 68 | 506 | G | EIF | A2 |
| 69 | 518 | E | DGP | A2 |
| 70 | 556 | K | ESV | A2 |
| 71 | 565 | Q | IMS | A2 |
| 72 | 566 | I | MSD | A2 |
| 73 | 598 | P | AGV | A2 |
| 74 | 599 | A | GVQ | A2 |
| 75 | 603 | L | EDP | A2 |
| 76 | 616 | S | ING | A2 |
| 77 | 686 | G | LWI | A2 |
| 78 | 713 | K | NTG | A2 |
| 79 | 719 | Y | EDS | A2 |
| 80 | 730 | L | LSK | A2 |
| 81 | 733 | K | NNA | A2 |
| 82 | 745 | N | PPV** | B |
| 83 | 1640 | P | PVL | B |
| 84 | 1652 | R | TTL | B |
| 85 | 1656 | Q | SDQ | A3 |
| 86 | 1685 | N | QSP | A3 |
| 87 | 1711 | M | SSS | A3 |
| 88 | 1713 | S | SPH | A3 |
| 89 | 1720 | N | RAQ | A3 |
| 90 | 1724 | S | GSV | A3 |
| 91 | 1725 | G | SVP | A3 |
| 92 | 1726 | S | VPQ | A3 |
| 93 | 1741 | G | SFT | A3 |
| 94 | 1744 | T | QPL | A3 |
| 95 | 1749 | R | GEL | A3 |
| 96 | 1773 | V | TFR | A3 |
| 97 | 1792 | Y | EED | A3 |
| 98 | 1793 | E | EDQ | A3 |
| 99 | 1796 | Q | RQG | A3 |
| 100 | 1798 | Q | GAE | A3 |
| 101 | 1799 | G | AEP | A3 |
| 102 | 1802 | P | RKN | A3 |
| 103 | 1803 | R | KNF | A3 |
| 104 | 1807 | V | KPN | A3 |
| 105 | 1808 | K | PNE | A3 |
| 106 | 1827 | K | DEF | A3 |
| 107 | 1844 | E | KDV | A3 |
| 108 | 1861 | N | TLN | A3 |
| 109 | 1863 | L | NPA | A3 |

TABLE 7-continued

Exemplary XTEN Insertion Sites

| No. | XTEN Insertion Point* | Insertion Residue | FVIII BDD Downstream Sequence | FVIII Domain |
|---|---|---|---|---|
| 110 | 1896 | E | RNC | A3 |
| 111 | 1900 | R | APC | A3 |
| 112 | 1904 | N | IQM | A3 |
| 113 | 1905 | I | QME | A3 |
| 114 | 1910 | P | TFK | A3 |
| 115 | 1920 | A | ING | A3 |
| 116 | 1937 | D | QRI | A3 |
| 117 | 1981 | G | VFE | A3 |
| 118 | 2019 | N | KCQ | A3 |
| 119 | 2020 | K | CQT | C1 |
| 120 | 2044 | G | QWA | C1 |
| 121 | 2068 | F | SWI | C1 |
| 122 | 2073 | V | DLL | C1 |
| 123 | 2090 | R | QKF | C1 |
| 124 | 2092 | K | FSS | C1 |
| 125 | 2093 | F | SSL | C1 |
| 126 | 2111 | K | WQT | C1 |
| 127 | 2115 | Y | RGN | C1 |
| 128 | 2120 | T | GTL | C1 |
| 129 | 2125 | V | FFG | C1 |
| 130 | 2171 | L | NSC | C1 |
| 131 | 2173 | S | CSM | C2 |
| 132 | 2188 | A | QIT | C2 |
| 133 | 2223 | V | NNP | C2 |
| 134 | 2224 | N | NPK | C2 |
| 135 | 2227 | K | EWL | C2 |
| 136 | 2268 | G | HQW | C2 |
| 137 | 2277 | N | GKV | C2 |
| 138 | 2278 | G | KVK | C2 |
| 139 | 2290 | F | TPV | C2 |
| 140 | 2332 | Y | C terminus of FVIII | CT |

*Indicates an insertion point for XTEN based on the amino acid number of mature full-length human FVIII, wherein the insertion could be either on the N- or C-terminal side of the indicated amino acid.

In some embodiments, one or more XTEN sequences are inserted within about six amino acids up or down from amino acids 32, 220, 224, 336, 339, 399, 416, 603, 1656, 1711, 1725, 1905, or 1910, corresponding to SEQ ID NO: 4 or any combinations thereof.

TABLE 8

Exemplary XTEN Insertion Ranges

| No. | XTEN Insertion Point | Insertion Residue | FVIII BDD Downstream Sequence | FVIII Domain | Distance from insertion residue* |
|---|---|---|---|---|---|
| 9 | 32 | P | RVP | A1 | −3, +6 |
| 31 | 220 | R | DAA | A1 | — |
| 34 | 224 | S | ARA | A1 | +5 |
| 43 | 336 | R | MKN | a1 | −1, +6 |
| 44 | 339 | N | NEE | a1 | −4, +5 |
| 52 | 399 | V | LAP | A2 | −6, +3 |
| 56 | 416 | P | QRI | A2 | +6 |
| 75 | 603 | L | EDP | A2 | _6, +6 |
| 85 | 1656 | Q | SDQ | B | −3, +6 |
| 87 | 1711 | M | SSS | A3 | −6, +1 |
| 91 | 1725 | G | SVP | A3 | +6 |
| 113 | 1905 | I | QME | A3 | +6 |
| 114 | 1910 | P | TFK | A3 | −5, +6 |

*Distance from insertion residue refers to the relative number of amino acids away from the N-terminus (negative numbers) or C-terminus (positive numbers) of the designated insertion residue (residue "0") where an insertion may be made. The designation "−x" refers to an insertion site which is x amino acids away on the N-terminal side of the designated insertion residue. Similarly, the designation "+x" refers to an insertion site which is x amino acids away on the C-terminal side of the designated insertion residue. For example, "−1, +2" indicates that the insertion is made at the N-terminus or C-terminus of amino acid residues denoted −1, 0, +1 or +2.

In other embodiments, one or more XTEN sequences are inserted immediately down stream of one or more amino acids corresponding to the full-length mature human FVIII selected from the group consisting of one or more insertion sites in Table 9.

TABLE 9

Exemplary XTEN Insertion Sites or Ranges

| No. | XTEN Insertion Point Range* | First Insertion Residue | FVIII Domain |
|---|---|---|---|
| 3 | 18-32 | Q | A1 |
| 8 | 40 | F | A1 |
| 18 | 211-224 | E | A1 |
| 27 | 336-403 | R | A1, A2 |
| 43 | 599 | A | A2 |
| 47 | 745-1640 | N | B |
| 50 | 1656-1728 | Q | B, a3, A3 |
| 57 | 1796-1804 | R | A3 |
| 65 | 1900-1912 | R | A3 |
| 81 | 2171-2332 | L | C1, C2 |

*indicates range of insertion sites numbered relative to the amino acid number of mature human FVIII In yet other embodiments, one or more XTENs are inserted in the B domain of FVIII. In one example, an XTEN is inserted between amino acids 740 and 1640 corresponding to SEQ ID NO: 4, wherein the FVIII sequence between amino acids 740 and 1640 is optionally not present. In another example, an XTEN is inserted between amino acids 741 and 1690 corresponding to SEQ ID NO: 4, wherein the FVIII sequence between amino acids 740 and 1690 is optionally not present. In other examples, an XTEN is inserted between amino acids 741 and 1648 corresponding to SEQ ID NO: 4, wherein the FVIII sequence between amino acids 741 and 1648 is optionally not present. In yet other examples, an XTEN is inserted between amino acids 743 and 1638 corresponding to SEQ ID NO: 4, wherein the FVIII sequence between amino acids 743 and 1638 is optionally not present. In still other examples, an XTEN is inserted between amino acids 745 and 1656 corresponding to SEQ ID NO: 4, wherein the FVIII sequence between amino acids 745 and 1656 is optionally not present. In some examples, an XTEN is inserted between amino acids 745 and 1657 corresponding to SEQ ID NO: 4, wherein the FVIII sequence between amino acids 745 and 1657 is optionally not present. In certain examples, an XTEN is inserted between amino acids 745 and 1667 corresponding to SEQ ID NO: 4, wherein the FVIII sequence between amino acids 745 and 1667 is optionally not present. In still other examples, an XTEN is inserted between amino acids 745 and 1686 corresponding to SEQ ID NO: 4, wherein the FVIII sequence between amino acids 745 and 1686 is optionally not present. In some other examples, an XTEN is inserted between amino acids 747 and 1642 corresponding to SEQ ID NO: 4, wherein the FVIII sequence between amino acids 747 and 1642 is optionally not present. In still other examples, an XTEN is inserted between amino acids 751 and 1667 corresponding to SEQ ID NO: 4, wherein the FVIII sequence between amino acids 751 and 1667 is optionally not present.

In some embodiments, one or more XTENs are inserted in one or more amino acids immediately downstream of an amino acid of an insertion site selected from the group consisting of the amino acid residues in Table 10.

TABLE 10

FVIII XTEN insertion sites and construct designations

| Construct Number | Domain | Upstream Residue No.* | Downstream Residue No.* | Upstream Sequence | Downstream Sequence |
|---|---|---|---|---|---|
| F8X-1 | A1 | 3 | 4 | ATR | RYY |
| F8X-2 | A1 | 18 | 19 | YMQ | SDL |
| F8X-3 | A1 | 22 | 23 | DLG | ELP |
| F8X-4 | A1 | 26 | 27 | LPV | DAR |
| F8X-5 | A1 | 40 | 41 | FPF | NTS |
| F8X-6 | A1 | 60 | 61 | LFN | IAK |
| F8X-7 | A1 | 116 | 117 | YDD | QTS |
| F8X-8 | A1 | 130 | 131 | VFP | GGS |
| F8X-9 | A1 | 188 | 189 | KEK | TQT |
| F8X-10 | A1 | 216 | 217 | NSL | MQD |
| F8X-11 | A1 | 230 | 231 | WPK | MHT |
| F8X-12 | A1 | 333 | 334 | EEP | QLR |
| F8X-13 | A2 | 375 | 376 | SVA | KKH |
| F8X-14 | A2 | 403 | 404 | APD | DRS |
| F8X-15 | A2 | 442 | 443 | EAI | QHE |
| F8X-16 | A2 | 490 | 491 | RRL | PKG |
| F8X-17 | A2 | 518 | 519 | TVE | DGP |
| F8X-18 | A2 | 599 | 600 | NPA | GVQ |
| F8X-19 | A2 | 713 | 714 | CDK | NTG |
| F8X-20 | BD | 745 | 746 | SQN | PPV |
| F8X-21 | BD | 745 | 746 | SQN | PPV |
| F8X-22 | BD** | 745 | 746 | SQN | PPV |
| F8X-23 | A3 | 1720 | 1721 | APT | KDE |
| F8X-24 | A3 | 1796 | 1797 | EDQ | RQG |
| F8X-25 | A3 | 1802 | 1803 | AEP | RKN |
| F8X-26 | A3 | 1827 | 1828 | PTK | DEF |
| F8X-27 | A3 | 1861 | 1862 | HTN | TLN |
| F8X-28 | A3 | 1896 | 1897 | NME | RNC |
| F8X-29 | A3 | 1900 | 1901 | NCR | APC |
| F8X-30 | A3 | 1904 | 1905 | PCN | IQM |
| F8X-31 | A3 | 1937 | 1938 | AQD | QRI |
| F8X-32 | C1 | 2019 | 2020 | YSN | KCQ |
| F8X-33 | C1 | 2068 | 2069 | EPF | SWI |
| F8X-34 | C1 | 2111 | 2112 | GKK | WQT |
| F8X-35 | C1 | 2120 | 2121 | NST | GTL |
| F8X-36 | C2 | 2171 | 2172 | CDL | NSC |
| F8X-37 | C2 | 2188 | 2189 | SDA | QIT |
| F8X-38 | C2 | 2227 | 2228 | NPK | EWL |
| F8X-39 | C2 | 2277 | 2278 | FQN | GKV |
| F8X-40 | CT | 2332 | NA | DLY | NA |
| F8X-41 | CT | 2332 | NA | DLY | NA |
| F8X-42 | A1 | 3 | 4 | ATR | ATR |
| pSD0001 | A2 | 403 | 404 | | |
| pSD0002 | A2 | 599 | 600 | | |
| pSD0021 | N-term | 0 | 1 | | |
| pSD0022 | A1 | 32 | 33 | | |
| pSD0023 | A1 | 65 | 66 | | |
| pSD0024 | A1 | 81 | 82 | | |
| pSD0025 | A1 | 119 | 120 | | |
| pSD0026 | A1 | 211 | 212 | | |
| pSD0027 | A1 | 220 | 221 | | |
| pSD0028 | A1 | 224 | 225 | | |
| pSD0029 | A1 | 336 | 337 | | |
| pSD0030 | A1 | 339 | 340 | | |
| pSD0031 | A2 | 378 | 379 | | |
| pSD0032 | A2 | 399 | 400 | | |
| pSD0033 | A2 | 409 | 410 | | |
| pSD0034 | A2 | 416 | 417 | | |
| pSD0035 | A2 | 487 | 488 | | |
| pSD0036 | A2 | 494 | 495 | | |
| pSD0037 | A2 | 500 | 501 | | |
| pSD0038 | A2 | 603 | 604 | | |
| pSD0039 | A3 | 1656 | 1657 | | |
| pSD0040 | A3 | 1711 | 1712 | | |
| pSD0041 | A3 | 1725 | 1726 | | |
| pSD0042 | A3 | 1749 | 1750 | | |
| pSD0043 | A3 | 1905 | 1906 | | |
| pSD0044 | A3 | 1910 | 1911 | | |
| pDS0062 | A3 | 1900 | 1901 | | |

*Indicates the amino acid number of the mature FVIII protein

In one embodiment, the one or more XTEN insertion sites are located within one or more surface-exposed, flexible loop structure of the FVIII protein (e.g., a permissive loop).

For example, at least one XTEN sequence can be inserted in each FVIII "A" domain comprising at least two "permissive loops" into which at least one XTEN polypeptide can be inserted without eliminating procoagulant activity of the recombinant protein, or the ability of the recombinant proteins to be expressed in vivo or in vitro in a host cell. The permissive loops are regions that allow insertion of at least one XTEN sequence with, among other attributes, high surface or solvent exposure and high conformational flexibility. The A1 domain comprises a permissive loop-1 (A1-1) region and a permissive loop-2 (A1-2) region, the A2 domain comprises a permissive loop-1 (A2-1) region and a permissive loop-2 (A2-2) region, the A3 domain comprises a permissive loop-1 (A3-1) region and a permissive loop-2 (A3-2) region.

In one aspect, a first permissive loop in the FVIII A1 domain (A1-1) is located between beta strand 1 and beta strand 2, and a second permissive loop in the FVIII A2 domain (A1-2) is located between beta strand 11 and beta strand 12. A first permissive loop in the FVIII A2 domain (A2-1) is located between beta strand 22 and beta strand 23, and a second permissive loop in the FVIII A2 domain (A2-2) is located between beta strand 32 and beta strand 33. A first permissive loop in the FVIII A3 domain (A3-1) is located between beta strand 38 and beta strand 39, and a second permissive loop in the FVIII A3 (A3-2) is located between beta strand 45 and beta strand 46. In certain aspects, the surface-exposed, flexible loop structure comprising A1-1 corresponds to a region in native mature human FVIII from about amino acid 15 to about amino acid 45 of SEQ IDNO: 4, e.g., from about amino acid 18 to about amino acid 41 of SEQ ID NO: 4. In other aspects, the surface-exposed, flexible loop structure comprising A1-2 corresponds to a region in native mature human FVIII from about amino acid 201 to about amino acid 232 of SEQ ID NO: 4, e.g., from about amino acid 218 to about amino acid 229 of SEQ ID NO: 4. In yet other aspects, the surface-exposed, flexible loop structure comprising A2-1 corresponds to a region in native mature human FVIII from about amino acid 395 to about amino acid 421 of SEQ ID NO: 4, e.g. from about amino acid 397 to about amino acid 418 of SEQ ID NO: 4. In still other embodiments, the surface-exposed, flexible loop structure comprising A2-2 corresponds to a region in native mature human FVIII from about amino acid 577 to about amino acid 635 of SEQ ID NO: 4, e.g., from about amino acid 595 to about amino acid 607 of SEQ ID NO: 4. In certain aspects the surface-exposed, flexible loop structure comprising A3-1 corresponds to a region in native mature human FVIII from about amino acid 1705 to about amino acid 1732 of SEQ ID NO: 4, e.g., from about amino acid 1711 to about amino acid 1725 of SEQ ID NO: 4. In yet other aspects, the surface-exposed, flexible loop structure comprising A3-2 corresponds to a region in native mature human FVIII from about amino acid 1884 to about amino acid 1917 of SEQ ID NO: 4, e.g., from about amino acid 1899 to about amino acid 1911 of SEQ ID NO: 4.

In another embodiment, the one or more amino acids in which at least one XTEN sequence is inserted is located within a3 domain, e g., amino acids 1649 to 1689, corresponding to full-length mature FVIII polypeptide. In a particular embodiment, an XTEN sequence is inserted between amino acids 1656 and 1657 of SEQ ID NO: 4 (full-length mature FVIII). In a specific embodiment, a FVIII protein comprising an XTEN sequence inserted immediately downstream of amino acid 1656 corresponding to SEQ ID NO: 4 further comprises a deletion from amino acid 745 to amino acid 1656 corresponding to SEQ ID NO: 4.

In some embodiments, the one or more insertion sites for one or more XTEN insertions are immediately downstream of one or more amino acids selected from the group consisting of:

(1) amino acid 3,
(2) amino acid 18,
(3) amino acid 22,
(4) amino acid 26,
(5) amino acid 32,
(6) amino acid 40,
(7) amino acid 60,
(8) amino acid 65,
(9) amino acid 81,
(10) amino acid 116,
(11) amino acid 119,
(12) amino acid 130,
(13) amino acid 188,
(14) amino acid 211,
(15) amino acid 216,
(16) amino acid 220,
(17) amino acid 224,
(18) amino acid 230,
(19) amino acid 333,
(20) amino acid 336,
(21) amino acid 339,
(22) amino acid 375,
(23) amino acid 399,
(24) amino acid 403,
(25) amino acid 409,
(26) amino acid 416,
(26) amino acid 442,
(28) amino acid 487,
(29) amino acid 490,
(30) amino acid 494,
(31) amino acid 500,
(32) amino acid 518,
(33) amino acid 599,
(34) amino acid 603,
(35) amino acid 713,
(36) amino acid 745,
(37) amino acid 1656,
(38) amino acid 1711,
(39) amino acid 1720,
(40) amino acid 1725,
(41) amino acid 1749,
(42) amino acid 1796,
(43) amino acid 1802,
(44) amino acid 1827,
(45) amino acid 1861,
(46) amino acid 1896,
(47) amino acid 1900,
(48) amino acid 1904,
(49) amino acid 1905,
(50) amino acid 1910,
(51) amino acid 1937,
(52) amino acid 2019,
(53) amino acid 2068,
(54) amino acid 2111,
(55) amino acid 2120,
(56) amino acid 2171,
(57) amino acid 2188,
(58) amino acid 2227,
(59) amino acid 2277, and
(60) two or more combinations thereof.

In one embodiment, a FVIII protein useful for the invention comprises two XTEN sequences, a first XTEN sequence inserted into a first XTEN insertion site and a second XTEN inserted into a second XTEN insertion site. Non-limiting examples of the first XTEN insertion site and the second XTEN insertion site are listed in Table 11.

TABLE 11

Exemplary Insertion Sites for Two XTENs

| Insertion 1 | | Insertion 2 | |
|---|---|---|---|
| Insertion Site | Domain | Insertion Site | Domain |
| 745 | B | 2332 | CT |
| 26 | A1 | 403 | A2 |
| 40 | A1 | 403 | A2 |
| 18 | A1 | 403 | A2 |
| 26 | A1 | 599 | A2 |
| 40 | A1 | 599 | A2 |
| 18 | A1 | 599 | A2 |
| 1720 | A3 | 1900 | A3 |
| 1725 | A3 | 1900 | A3 |
| 1711 | A3 | 1905 | A3 |
| 1720 | A3 | 1905 | A3 |
| 1725 | A3 | 1905 | A3 |
| 1656 | A3 | 26 | A1 |
| 1656 | A3 | 18 | A1 |
| 1656 | A3 | 40 | A1 |
| 1656 | A3 | 399 | A2 |
| 1656 | A3 | 403 | A2 |
| 1656 | A3 | 1725 | A3 |
| 1656 | A3 | 1720 | A3 |
| 1900 | A3 | 18 | A1 |
| 1900 | A3 | 26 | A1 |
| 1900 | A3 | 40 | A1 |
| 1905 | A3 | 18 | A1 |
| 1905 | A3 | 40 | A1 |
| 1905 | A3 | 26 | A1 |
| 1910 | A3 | 26 | A1 |
| 18 | A1 | 399 | A2 |
| 26 | A1 | 399 | A2 |
| 40 | A1 | 399 | A2 |
| 18 | A1 | 403 | A2 |
| 1656 | A3 | 1900 | A3 |
| 1656 | A3 | 1905 | A3 |
| 1711 | A3 | 40 | A1 |
| 1711 | A3 | 26 | A1 |
| 1720 | A3 | 26 | A1 |
| 1720 | A3 | 40 | A1 |
| 1720 | A3 | 18 | A1 |
| 1725 | A3 | 26 | A1 |
| 1725 | A3 | 40 | A1 |
| 1725 | A3 | 18 | A1 |
| 1720 | A3 | 403 | A2 |
| 1720 | A3 | 399 | A2 |
| 1711 | A3 | 403 | A2 |
| 1720 | A3 | 403 | A2 |
| 1725 | A3 | 403 | A2 |
| 1725 | A3 | 399 | A2 |
| 1711 | A3 | 403 | A2 |
| 1900 | A3 | 399 | A2 |
| 1900 | A3 | 403 | A2 |
| 1905 | A3 | 403 | A2 |
| 1905 | A3 | 399 | A2 |
| 1910 | A3 | 403 | A2 |

The two XTENs inserted or linked to the FVIII protein can be identical or different. In some embodiments, a FVIII protein useful for the invention comprises two XTEN sequences inserted in the FVIII protein, a first XTEN sequence inserted immediately downstream of amino acid 745 corresponding to SEQ ID NO: 4, and a second XTEN sequence inserted immediately downstream of amino acid 2332 corresponding to SEQ ID NO: 4 (the C-terminus). In other embodiments, the first XTEN sequence is inserted immediately downstream of amino acid 18, 26, 40, 1656, or 1720 corresponding to SEQ ID NO: 4, and a second XTEN sequence inserted immediately downstream of amino acid 403 corresponding to SEQ ID NO: 4. In yet other embodiments, the first XTEN sequence is inserted immediately downstream of amino acid 18, 26, or 40 corresponding to SEQ ID NO: 4, and a second XTEN sequence inserted immediately downstream of amino acid 599 corresponding to SEQ ID NO: 4. In still other embodiments, the first XTEN sequence is inserted immediately downstream of amino acid 1656 corresponding to SEQ ID NO: 4, and a second XTEN sequence inserted immediately downstream of amino acid 18, 26, 40, 399, 403, 1725, 1720, 1900, 1905, or 2332 corresponding to SEQ ID NO: 4. In certain embodiments, the first XTEN sequence is inserted immediately downstream of amino acid 1900 corresponding to SEQ ID NO: 4, and a second XTEN sequence inserted immediately downstream of amino acid 18, 26, or 40 corresponding to SEQ ID NO: 4. In some embodiments, the first XTEN sequence is inserted immediately downstream of amino acid 18, 26, or 40 corresponding to SEQ ID NO: 4, and a second XTEN sequence inserted immediately downstream of amino acid 399 corresponding to SEQ ID NO: 4. In other embodiments, the first XTEN sequence is inserted immediately downstream of amino acid 1720 corresponding to SEQ ID NO: 4, and a second XTEN sequence inserted immediately downstream of amino acid 18, 26, or 40 corresponding to SEQ ID NO: 4. In still other embodiments, the first XTEN sequence is inserted immediately downstream of amino acid 1720 corresponding to SEQ ID NO: 4, and a second XTEN sequence inserted immediately downstream of amino acid 18 corresponding to SEQ ID NO: 4. In a particular embodiment, the FVIII protein comprising two XTEN sequences, a first XTEN sequence inserted immediately downstream of amino acid 745 corresponding to SEQ ID NO: 4 and a second XTEN sequence inserted immediately downstream of amino acid 2332 corresponding to SEQ ID NO: 4, wherein the FVIII protein further has a deletion from amino acid 745 corresponding to SEQ ID NO: 4 to amino acid 1685 corresponding to SEQ ID NO: 4, a mutation or substitution at amino acid 1680 corresponding to SEQ ID NO: 4, e.g., Y1680F, a mutation or substitution at amino acid 1648 corresponding to SEQ ID NO: 4, e.g., R1648A, or at least two mutations or substitutions at amino acid 1648 corresponding to SEQ ID NO: 4, e.g., R1648A, and amino acid 1680 corresponding to SEQ ID NO: 4, e.g., Y1680F. In a specific embodiment, the FVIII protein comprises two XTEN sequences, a first XTEN inserted immediately downstream of amino acid 1656 corresponding to SEQ ID NO: 4 and a second XTEN sequence inserted immediately downstream of amino acid 2332 of SEQ ID NO: 4, wherein the FVIII protein further has a deletion from amino acid 745 to amino acid 1656 corresponding to SEQ ID NO: 4.

In certain embodiments, a FVIII protein comprises three XTEN sequences, a first XTEN sequence inserted into a first XTEN insertion site, a second XTEN sequence inserted into a second XTEN sequence, and a third XTEN sequence inserted into a third XTEN insertion site. The first, second, or third XTEN sequences can be identical or different. The first, second, and third insertion sites can be selected from the group of any one of the insertion sites disclosed herein. In some embodiments, the FVIII protein comprising three XTEN sequences can further comprise a mutation or substitution, e g., amino acid 1648 corresponding to SEQ ID NO: 4, e.g., R1648A. For example, non-limiting examples of the first, second, and third XTEN insertion sites are listed in Table 12.

TABLE 12

Exemplary Insertion Sites for Three XTENs

| Insertion 1 | | Insertion 2 | | Insertion 3 | |
|---|---|---|---|---|---|
| Insertion Site | Domain | Insertion Site | Domain | Insertion Site | Domain |
| 26 | A1 | 403 | A2 | 1656 | A3 |
| 26 | A1 | 403 | A2 | 1720 | A3 |
| 26 | A1 | 403 | A2 | 1900 | A3 |
| 26 | A1 | 1656 | A3 | 1720 | A3 |
| 26 | A1 | 1656 | A3 | 1900 | A3 |
| 26 | A1 | 1720 | A3 | 1900 | A3 |
| 403 | A2 | 1656 | A3 | 1720 | A3 |
| 403 | A2 | 1656 | A3 | 1900 | A3 |
| 403 | A2 | 1720 | A3 | 1900 | A3 |
| 1656 | A3 | 1720 | A3 | 1900 | A3 |
| 745 | B | 1900 | | 2332 | |
| 18 | A1 | 745 | B | 2332 | CT |
| 26 | A1 | 745 | B | 2332 | CT |
| 40 | A1 | 745 | B | 2332 | CT |
| 18 | A1 | 745 | B | 2332 | CT |
| 40 | A1 | 745 | B | 2332 | CT |
| 403 | A2 | 745 | B | 2332 | CT |
| 399 | A2 | 745 | B | 2332 | CT |
| 1725 | A3 | 745 | B | 2332 | CT |
| 1720 | A3 | 745 | B | 2332 | CT |
| 1711 | A3 | 745 | B | 2332 | CT |
| 1900 | A3 | 745 | B | 2332 | CT |
| 1905 | A3 | 745 | B | 2332 | CT |
| 1910 | A3 | 745 | B | 2332 | CT |

In some embodiments, a FVIII protein comprises three XTEN sequences, a first XTEN sequence inserted immediately downstream of amino acid 26 corresponding to SEQ ID NO: 4, a second XTEN sequence inserted downstream of amino acid 403 corresponding to SEQ ID NO: 4, and a third XTEN sequence inserted downstream of amino acid 1656, 1720, or 1900 corresponding to SEQ ID NO: 4. In other embodiments, the first XTEN sequence is inserted immediately downstream of amino acid 26 corresponding to SEQ ID NO: 4, a second XTEN sequence is inserted downstream of amino acid 1656 corresponding to SEQ ID NO: 4, and a third XTEN sequence is inserted downstream of amino acid 1720 or 1900 corresponding to SEQ ID NO: 4. In yet other embodiments, the first XTEN sequence is inserted immediately downstream of amino acid 26 corresponding to SEQ ID NO: 4, a second XTEN sequence is inserted downstream of amino acid 1720 corresponding to SEQ ID NO: 4, and a third XTEN sequence is inserted downstream of amino acid 1900 corresponding to SEQ ID NO: 4. In still other embodiments, the first XTEN sequence is inserted immediately downstream of amino acid 403 corresponding to SEQ ID NO: 4, a second XTEN sequence is inserted downstream of amino acid 1656 corresponding to SEQ ID NO: 4, and a third XTEN sequence is inserted downstream of amino acid 1720 or 1900 corresponding to SEQ ID NO: 4. In other embodiments, the first XTEN sequence is inserted immediately downstream of amino acid 403 or 1656 corresponding to SEQ ID NO: 4, a second XTEN sequence is inserted downstream of amino acid 1720 corresponding to SEQ ID NO: 4, and a third XTEN sequence is inserted downstream of amino acid 1900 corresponding to SEQ ID NO: 4. In other embodiments, the first XTEN sequence is inserted immediately downstream of amino acid 18, 26, 40, 399, 403, 1711, 1720, 1725, 1900, 1905, or 1910 corresponding to SEQ ID NO: 4, a second XTEN sequence is inserted downstream of amino acid 745 corresponding to SEQ ID NO: 4, and a third XTEN sequence is inserted downstream of amino acid 2332 corresponding to SEQ ID NO: 4.

In other embodiments, a FVIII protein in the invention comprises four XTEN sequences, a first XTEN sequence inserted into a first insertion site, a second XTEN sequence inserted into a second insertion site, a third XTEN sequence inserted into a third insertion site, and a fourth XTEN sequence inserted into a fourth insertion site. The first, second, third, and fourth XTEN sequences can be identical, different, or combinations thereof. In some embodiments, the FVIII protein comprising four XTEN sequences can further comprise a mutation or substitution, e.g., amino acid 1648 corresponding to SEQ ID NO: 4, e.g., R1648A. Non-limiting examples of the first, second, third, and fourth XTEN insertion sites are listed in Table 13.

TABLE 13

Exemplary Insertion Sites for Four XTENs

| Insertion 1 | | Insertion 2 | | Insertion 3 | | Insertion 4 | |
|---|---|---|---|---|---|---|---|
| Insertion Site | Domain | Insertion Site | Domain | Insertion Site | Domain | Insertion Site | Domain |
| 26 | A1 | 403 | A2 | 1656 | a3 | 1720 | A3 |
| 26 | A1 | 403 | A2 | 1656 | a3 | 1900 | A3 |
| 26 | A1 | 403 | A2 | 1720 | A3 | 1900 | A3 |
| 26 | A1 | 1656 | a3 | 1720 | A3 | 1900 | A3 |
| 403 | A2 | 1656 | a3 | 1720 | A3 | 1900 | A3 |
| 0040 | A1 | 0403 | A2 | 745 | B | 2332 | CT |
| 0040 | A1 | 0403 | A2 | 745 | B | 2332 | CT |
| 0018 | A1 | 0409 | A2 | 745 | B | 2332 | CT |
| 0040 | A1 | 0409 | A2 | 745 | B | 2332 | CT |
| 0040 | A1 | 0409 | A2 | 745 | B | 2332 | CT |
| 0018 | A1 | 0409 | A2 | 745 | B | 2332 | CT |
| 0040 | A1 | 1720 | A3 | 745 | B | 2332 | CT |
| 0026 | A1 | 1720 | A3 | 745 | B | 2332 | CT |
| 0018 | A1 | 1720 | A3 | 745 | B | 2332 | CT |
| 0018 | A1 | 1720 | A3 | 745 | B | 2332 | CT |
| 0018 | A1 | 1720 | A3 | 745 | B | 2332 | CT |
| 0026 | A1 | 1720 | A3 | 745 | B | 2332 | CT |
| 0018 | A1 | 1720 | A3 | 745 | B | 2332 | CT |
| 0018 | A1 | 1900 | A3 | 745 | B | 2332 | CT |
| 0018 | A1 | 1900 | A3 | 745 | B | 2332 | CT |
| 0026 | A1 | 1900 | A3 | 745 | B | 2332 | CT |
| 0040 | A1 | 1900 | A3 | 745 | B | 2332 | CT |
| 0040 | A1 | 1905 | A3 | 745 | B | 2332 | CT |
| 0018 | A1 | 1905 | A3 | 745 | B | 2332 | CT |
| 0040 | A1 | 1905 | A3 | 745 | B | 2332 | CT |
| 0026 | A1 | 1905 | A3 | 745 | B | 2332 | CT |
| 0018 | A1 | 1905 | A3 | 745 | B | 2332 | CT |
| 0018 | A1 | 1905 | A3 | 745 | B | 2332 | CT |
| 0018 | A1 | 1910 | A3 | 745 | B | 2332 | CT |
| 0018 | A1 | 1910 | A3 | 745 | B | 2332 | CT |
| 0040 | A1 | 1910 | A3 | 745 | B | 2332 | CT |
| 0026 | A1 | 1910 | A3 | 745 | B | 2332 | CT |
| 0018 | A1 | 1910 | A3 | 745 | B | 2332 | CT |
| 0026 | A1 | 1910 | A3 | 745 | B | 2332 | CT |
| 0040 | A1 | 1910 | A3 | 745 | B | 2332 | CT |
| 0018 | A1 | 1910 | A3 | 745 | B | 2332 | CT |
| 0409 | A2 | 1720 | A3 | 745 | B | 2332 | CT |
| 0403 | A2 | 1720 | A3 | 745 | B | 2332 | CT |
| 0409 | A2 | 1720 | A3 | 745 | B | 2332 | CT |
| 0403 | A2 | 1720 | A3 | 745 | B | 2332 | CT |
| 0403 | A2 | 1720 | A3 | 745 | B | 2332 | CT |
| 0403 | A2 | 1900 | A3 | 745 | B | 2332 | CT |
| 0403 | A2 | 1900 | A3 | 745 | B | 2332 | CT |
| 0409 | A2 | 1900 | A3 | 745 | B | 2332 | CT |
| 0403 | A2 | 1900 | A3 | 745 | B | 2332 | CT |
| 0403 | A2 | 1900 | A3 | 745 | B | 2332 | CT |
| 0409 | A2 | 1900 | A3 | 745 | B | 2332 | CT |
| 0409 | A2 | 1905 | A3 | 745 | B | 2332 | CT |
| 0403 | A2 | 1905 | A3 | 745 | B | 2332 | CT |
| 0403 | A2 | 1905 | A3 | 745 | B | 2332 | CT |
| 0403 | A2 | 1905 | A3 | 745 | B | 2332 | CT |
| 0409 | A2 | 1905 | A3 | 745 | B | 2332 | CT |
| 0403 | A2 | 1905 | A3 | 745 | B | 2332 | CT |
| 0409 | A2 | 1910 | A3 | 745 | B | 2332 | CT |
| 0403 | A2 | 1910 | A3 | 745 | B | 2332 | CT |
| 0403 | A2 | 1910 | A3 | 745 | B | 2332 | CT |
| 0403 | A2 | 1910 | A3 | 745 | B | 2332 | CT |
| 0403 | A2 | 1910 | A3 | 745 | B | 2332 | CT |
| 1720 | A3 | 1900 | A3 | 745 | B | 2332 | CT |
| 1720 | A3 | 1905 | A3 | 745 | B | 2332 | CT |
| 1720 | A3 | 1910 | A3 | 745 | B | 2332 | CT |
| 1720 | A3 | 1910 | A3 | 745 | B | 2332 | CT |
| 0403 | A2 | 1656 | a3 | 1720 | A3 | 2332 | CT |
| 0403 | A2 | 1656 | a3 | 1900 | A3 | 2332 | CT |

TABLE 13-continued

| Exemplary Insertion Sites for Four XTENs | | | | | | | |
|---|---|---|---|---|---|---|---|
| Insertion 1 | | Insertion 2 | | Insertion 3 | | Insertion 4 | |
| Insertion Site | Domain | Insertion Site | Domain | Insertion Site | Domain | Insertion Site | Domain |
| 0403 | A2 | 1720 | A3 | 1900 | A3 | 2332 | CT |
| 1656 | a3 | 1720 | A3 | 1900 | A3 | 2332 | CT |
| 0018 | A1 | 0403 | A2 | 1656 | a3 | 2332 | CT |
| 0018 | A1 | 0403 | A2 | 1720 | A3 | 2332 | CT |
| 0018 | A1 | 0403 | A2 | 1900 | A3 | 2332 | CT |
| 0018 | A1 | 1656 | a3 | 1720 | A3 | 2332 | CT |
| 0018 | A1 | 1656 | a3 | 1900 | A3 | 2332 | CT |
| 0018 | A1 | 1720 | A3 | 1900 | A3 | 2332 | CT |
| 0018 | A1 | 0403 | A2 | 0745 | B | 2332 | CT |
| 0018 | A1 | 0745 | B | 1720 | A3 | 2332 | CT |
| 0018 | A1 | 0745 | B | 1900 | A3 | 2332 | CT |
| 0403 | A2 | 0745 | B | 1720 | A3 | 2332 | CT |
| 0403 | A2 | 0745 | B | 1900 | A3 | 2332 | CT |
| 0745 | B | 1720 | A3 | 1900 | A3 | 2332 | CT |
| 0188 | A1 | 1900 | A3 | 0745 | B | 2332 | CT |
| 0599 | | 1900 | A3 | 0745 | B | 2332 | CT |
| 2068 | | 1900 | A3 | 0745 | B | 2332 | CT |
| 2171 | | 1900 | A3 | 0745 | B | 2332 | CT |
| 2227 | | 1900 | A3 | 0745 | B | 2332 | CT |
| 2277 | | 1900 | A3 | 0745 | B | 2332 | CT |

In some embodiments, a FVIII protein comprises five XTEN sequences, a first XTEN sequence inserted into a first insertion site, a second XTEN sequence inserted into a second insertion site, a third XTEN sequence inserted into a third XTEN insertion site, a fourth XTEN sequence inserted into a fourth XTEN insertion site, and a fifth XTEN sequence inserted into a fifth XTEN insertion site. The first, second, third, fourth, of fifth XTEN sequences can be identical, different, or combinations thereof. Non-limiting examples of the first, second, third, fourth, and fifth insertion sites are listed in Table 14.

TABLE 14

| Exemplary Insertion Sites for Five XTENs | | | | |
|---|---|---|---|---|
| XTEN Insertion 1 | XTEN insertion 2 | XTEN Insertion 3 | XTEN Insertion 4 | XTEN Insertion 5 |
| 0403 | 1656 | 1720 | 1900 | 2332 |
| 0018 | 0403 | 1656 | 1720 | 2332 |
| 0018 | 0403 | 1656 | 1900 | 2332 |
| 0018 | 0403 | 1720 | 1900 | 2332 |
| 0018 | 1656 | 1720 | 1900 | 2332 |
| 0018 | 0403 | 0745 | 1720 | 2332 |
| 0018 | 0403 | 0745 | 1900 | 2332 |
| 0018 | 0745 | 1720 | 1900 | 2332 |
| 0403 | 0745 | 1720 | 1900 | 2332 |

In certain embodiments, a FVIII protein comprises six XTEN sequences, a first XTEN sequence inserted into a first XTEN insertion site, a second XTEN sequence inserted into a second XTEN insertion site, a third XTEN sequence inserted into a third XTEN insertion site, a fourth XTEN sequence inserted into a fourth XTEN insertion site, a fifth XTEN sequence inserted into a fifth XTEN insertion site, and a sixth XTEN sequence inserted into a sixth XTEN insertion site. The first, second, third, fourth, fifth, or sixth XTEN sequences can be identical, different, or combinations thereof. Examples of the six XTEN insertion sites include, but are not limited to the insertion sites listed in Table 15.

TABLE 15

| Exemplary XTEN Insertion Sites for Six XTENs | | | | | |
|---|---|---|---|---|---|
| XTEN Insertion 1 | XTEN insertion 2 | XTEN Insertion 3 | XTEN Insertion 4 | XTEN Insertion 5 | XTEN Insertion 5 |
| 0018 | 0403 | 1656 | 1720 | 1900 | 2332 |
| 0018 | 0403 | 0745 | 1720 | 1900 | 2332 |

In a particular example, a first XTEN is inserted between amino acids 26 and 27 corresponding to SEQ ID NO: 4, and a second XTEN is inserted between amino acids 1720 and 1721 corresponding to SEQ ID NO: 4 (full-length mature FVIII). In another example, a first XTEN is inserted between amino acids 403 and 404 corresponding to SEQ ID NO: 4, and a second XTEN is inserted between amino acids 1720 and 1721 corresponding to SEQ ID NO: 4. In some examples, a first XTEN is inserted between amino acids 1656 and 1657 corresponding to SEQ ID NO: 4, and a second XTEN is inserted between amino acids 1720 and 1721 corresponding to SEQ ID NO: 4. In other examples, a first XTEN is inserted between amino acids 26 and 27 corresponding to SEQ ID NO: 4, a second XTEN is inserted between amino acids 1656 and 1657 corresponding to SEQ ID NO: 4, and a third XTEN is inserted between amino acids 1720 and 1721 corresponding to SEQ ID NO: 4. In yet other embodiments, a first XTEN is inserted between amino acids 403 and 404 corresponding to SEQ ID NO: 4, a second XTEN is inserted between amino acids 1656 and 1657 corresponding to SEQ ID NO: 4, and a third XTEN is inserted between amino acids 1720 and 1721 corresponding to SEQ ID NO: 4. In still other embodiments, a first XTEN is inserted between amino acids 403 and 404 corresponding to SEQ ID NO: 4, a second XTEN is inserted between amino acids 1656 and 1657 corresponding to SEQ ID NO: 4, and a third XTEN is inserted between amino acids 1720 and 1721 corresponding to SEQ ID NO: 4. In certain embodiments, a first XTEN is inserted between amino acids 26 and 27 corresponding to SEQ ID NO: 4, a second XTEN is inserted between amino acids 1720 and 1721 corresponding to SEQ ID NO: 4, and a third XTEN is inserted between amino acids 1900 and 1901 corresponding to SEQ ID NO: 4. In some embodiments, a first XTEN is inserted between amino acids 26 and 27 corresponding to SEQ ID NO: 4, a second XTEN is inserted between amino acids 1656 and 1657 corresponding to SEQ ID NO: 4, a third XTEN is inserted between amino acids 1720 and 1721 corresponding to SEQ ID NO: 4, and a fourth XTEN is inserted between 1900 and 1901 corresponding to SEQ ID NO: 4.

In a particular embodiment, an XTEN sequence is inserted between amino acids 745 and 746 of a full-length Factor VIII or the corresponding insertion site of the B-domain deleted Factor VIII.

Permissive Loop Replacement with XTEN

The present invention also describes that one or more permissive loops, an a3 region, or a portion thereof can be substituted or deleted in a FVIII protein, which comprises an XTEN, and the FVIII containing the substitution or deletion has procoagulant activity. Substituting or deleting a portion of a permissive loop or an a3 region includes substituting or deleting one or more amino acids in the permissive loop or the a3 region. As previously described, FVIII "A" domain comprise at least two "permissive loops" into which XTENs can be inserted without eliminating procoagulant activity of the recombinant protein, or the ability of the recombinant proteins to be expressed in vivo or in vitro in a host cell. See PCT/US2013/026521, filed Feb. 15, 2013, which is incorporated herein by reference. The permissive loops are regions with, among other attributes, high surface or solvent exposure and high conformational flexibility. Although "permissive sites" tend to cluster in permissive loops, there are other permissive sites outside of the identified permissive loops into which XTENs can be inserted without eliminating procoagulant activity of the recombinant protein, or the ability of the recombinant proteins to be expressed in vivo or in vitro in a host cell. The term "permissive location" refers to both permissive loops and permissive sites. The A1 domain comprises a permissive loop-1 region (A1-1) and a permissive loop-2 region (A1-2), the A2 domain comprises a permissive loop-1 region (A2-1) and a permissive loop-2 region (A2-2), and the A3 domain comprises a permissive loop-1 region (A3-1) and a permissive loop-2 region (A3-2). See PCT/US2013/026521, filed Feb. 15, 2013, which is incorporated herein by reference.

A chimeric FVIII protein of the invention can comprise a substitution or deletion in one or more of the permissive loops in each of the FVIII A domain regions or in an a3 region and can further allow insertion of an XTEN while having procoagulant activity and still being able to be expressed in vivo or in vitro by a host cell. Various crystal structures of FVIII have been determined, of varying degrees of resolution. These structures of FVIII and FVIIIa, determined by X-ray crystallography and molecular dynamic simulation, were used to generate models of accessible surface area and conformational flexibility for FVIII. For example, the crystal structure of human FVIII has been determined by Shen et al. *Blood* 111: 1240-1247 (2008) and Ngo et al. *Structure* 16: 597-606 (2008). The data for these structures is available from the Protein Data Bank (pdb.org) under Accession Numbers 2R7E and 3CDZ, respectively.

In certain embodiments, the permissive loops A1-1, A1-2, A2-1, A2-2, A3-1, and A3-2 are contained within surface-exposed, flexible loop structures in the A domains of FVIII. A1-1 is located between beta strand 1 and beta strand 2, A1-2 is located between beta strand 11 and beta strand 12, A2-1 is located between beta strand 22 and beta strand 23, A2-2 is located between beta strand 32 and beta strand 33, A3-1 is located between beta strand 38 and beta strand 39 and A3-2 is located between beta strand 45 and beta strand 46, according to the secondary structure of mature FVIII stored as Accession Number 2R7E of the PDB database (PDB:2R7E). The secondary structure of PDB Accession Number 2R7E corresponds to the standardized secondary structure assignment according to the DSSP program (Kabsch and Sander, Biopolymers, 22:2577-2637 (1983)). The DSSP secondary structure of the mature FVIII stored as PDB Accession Number 2R7E can be accessed at the DSSP database, available at swift.cmbi.ru.nl/gv/dssp/ (Joosten et al., 39(Suppl. 1): D411-D419 (2010)).

In certain aspects, a surface-exposed, flexible loop structure comprising A1-1 corresponds to a region in native mature human FVIII from about amino acid 15 to about amino acid 45 of SEQ ID NO: 4. In certain aspects, A1-1 corresponds to a region in native mature human FVIII from about amino acid 18 to about amino acid 41 of SEQ ID NO: 4. In certain aspects, the surface-exposed, flexible loop structure comprising A1-2 corresponds to a region in native mature human FVIII from about amino acid 201 to about amino acid 232 of SEQ ID NO: 4. In certain aspects, A1-2 corresponds to a region in native mature human FVIII from about amino acid 218 to about amino acid 229 of SEQ ID NO: 4. In certain aspects, the surface-exposed, flexible loop structure comprising A2-1 corresponds to a region in native mature human FVIII from about amino acid 395 to about amino acid 421 of SEQ ID NO: 4. In certain aspects, A2-1 corresponds to a region in native mature human FVIII from about amino acid 397 to about amino acid 418 of SEQ ID NO: 4. In certain aspects, the surface-exposed, flexible loop structure comprising A2-2 corresponds to a region in native mature human FVIII from about amino acid 577 to about amino acid 635 of SEQ ID NO: 4. In certain aspects, A2-2 corresponds to a region in native mature human FVIII from about amino acid 595 to about amino acid 607 of SEQ ID NO: 4. In certain aspects, the surface-exposed, flexible loop structure comprising A3-1 corresponds to a region in native mature human FVIII from about amino acid 1705 to about amino acid 1732 of SEQ ID NO: 4. In certain aspects, A3-1 corresponds to a region in native mature human FVIII from about amino acid 1711 to about amino acid 1725 of SEQ ID NO: 4. In certain aspects, the surface-exposed, flexible loop structure comprising A3-2 corresponds to a region in native mature human FVIII from about amino acid 1884 to about amino acid 1917 of SEQ ID NO: 4. In certain aspects, A3-2 corresponds to a region in native mature human FVIII from about amino acid 1899 to about amino acid 1911 of SEQ ID NO: 4. In other aspects, the a3 region corresponds to a region in native mature human FVIII from about amino acid 1649 to about amino acid 1689 of SEQ ID NO: 4.

In certain aspects a chimeric FVIII protein comprises one or more XTENs inserted into one or more permissive loops of FVIII, or into the a3 region, or both, wherein one or more amino acids in the one or more permissive loops of FVIII or the a3 region, or both are substituted or deleted and wherein the chimeric FVIII protein has procoagulant activity and can be expressed in vivo or in vitro in a host cell. XTENs to be inserted include, but are not limited to, (i) those that increase the half-life or the in vivo or in vitro stability of FVIII, (ii) a clearance receptor, or (iii) a moiety which aids in visualization or localization of the chimeric FVIII protein. XTENs are discussed in more detail below.

In certain aspects one or more amino acids in the permissive loops A1-1, A1-2, A2-1, A2-2, A3-1, or A3-2 or an a3 region in a chimeric FVIII protein are substituted or deleted, wherein the chimeric FVIII protein has procoagulant activity. In some aspects, the chimeric FVIII protein that contains the substitution or deletion is expressed in vivo or in vitro in a host cell. In other aspects, one or more of the entire permissive loops can be substituted or deleted. In still other aspects, only a portion of the one or more permissive loops is substituted or deleted. In some aspects, any combinations of the substitution or deletion in one or more permissive loops or in the a3 region are possible for the purpose of preparing a chimeric FVIII protein.

In certain aspects, at least one XTEN is inserted in the permissive loops or in the a3 region of the chimeric FVIII protein, e.g., upstream or downstream of the amino acids that are substituted or deleted. In certain aspects a chimeric FVIII protein as described above comprises at least two XTENs inserted into a FVIII protein, wherein at least one of the two XTENs is inserted in the permissive loops A1-1, A1-2, A2-1, A2-2, A3-1, or A3-2 or in the a3 region, or any combinations thereof, in which one or more amino acids are substituted or deleted, and wherein the chimeric FVIII protein has procoagulant activity and can be expressed in vivo or in vitro in a host cell. In one aspect, each of the two XTENs is inserted in the permissive loops of the FVIII protein and/or in the a3 region, e.g., upstream or downstream of the substitution, deletion or a combination thereof. In another aspect, a first XTEN is inserted in a permissive loop of a FVIII protein containing the substitution, deletion, or a combination thereof (e.g., A1-1), e.g., upstream or downstream of a substitution, deletion or a combination thereof, and a second XTEN is inserted in one of the other permissive loops (e.g., A1-2, A2-1, A2-2, A3-1, A3-2) or in the a3 region. In other aspects, the other permissive loops and the a3 region do not contain any substitution or deletion. In some aspects, the first XTEN and the second XTEN can be the same or different. In still other aspects, one or more of the other permissive loops and the a3 region contain substitution, deletion, or a combination thereof. In certain aspects a chimeric FVIII protein as described above comprises at least three XTENs inserted into a FVIII protein, wherein at least one of the three XTENs is inserted into at least one of the permissive loops A1-1, A1-2, A2-1, A2-2, A3-1, or A3-2 or in a3 region, wherein one or more amino acids in the at least one of the permissive loops A1-1, A1-2, A2-1, A2-2, A3-1, or A3-2 or in a3 region are substituted or deleted and wherein the chimeric FVIII protein has procoagulant activity and can be expressed in vivo or in vitro in a host cell. The three XTENs can be the same or different. In certain aspects a chimeric FVIII protein as described above comprises at least four XTENs inserted into a FVIII protein, wherein at least one of the four XTENs is inserted into at least one of the permissive loops A1-1, A1-2, A2-1, A2-2, A3-1, or A3-2 or in a3 region, wherein one or more amino acids in the at least one of the permissive loops A1-1, A1-2, A2-1, A2-2, A3-1, or A3-2 or in a3 region are substituted or deleted, and wherein the chimeric FVIII protein has procoagulant activity and can be expressed in vivo or in vitro in a host cell. The four XTENs can be the same or different. In certain aspects a chimeric FVIII protein as described above comprises at least five XTEN inserted into a FVIII protein, wherein at least one of the five XTENs is inserted into at least one of the permissive loops A1-1, A1-2, A2-1, A2-2, A3-1, or A3-2 or in a3 region, wherein one or more amino acids in the at least one of the permissive loops A1-1, A1-2, A2-1, A2-2, A3-1, or A3-2 or in a3 region are substituted or deleted, and wherein the chimeric FVIII protein has procoagulant activity and can be expressed in vivo or in vitro in a host cell. The five XTENs can be the same or different. In certain aspects a chimeric FVIII protein as described above comprises at least six XTENs inserted into a FVIII protein, wherein at least one of the six XTENs is inserted into at least one of the permissive loops A1-1, A1-2, A2-1, A2-2, A3-1, or A3-2 or in a3 region, one or more amino acids in the at least one of the permissive loops A1-1, A1-2, A2-1, A2-2, A3-1, or A3-2 or in the a3 region are substituted or deleted, and wherein the chimeric FVIII protein has procoagulant activity and can be expressed in vivo or in vitro in a host cell. The six XTENs can be the same or different. In other aspects, at least one XTEN can further be inserted in the a3 region. In still other aspects, at least one XTEN can further be inserted in the B domain, e g., amino acid 745 corresponding to SEQ ID NO: 4 or fused to the C-terminus of the FVIII protein, e g., amino acid 2332 corresponding to SEQ ID NO: 4.

In certain aspects a chimeric FVIII protein as described above comprises at least two XTENs inserted into FVIII, e.g., into two different permissive loops A1-1, A1-2, A2-1, A2-2, A3-1, or A3-2 or in the a3 region, wherein one or more amino acids of each of the two different permissive loops are substituted or deleted and wherein the chimeric FVIII protein has procoagulant activity and can be expressed in vivo or in vitro in a host cell. Alternatively, a chimeric FVIII protein as described above can comprise two or more XTENs inserted into a single permissive loop without XTENs inserted into other permissive loops, wherein one or more amino acids in the single permissive loop are substituted and/or deleted and wherein the chimeric FVIII protein has procoagulant activity and can be expressed in vivo or in vitro in a host cell. In certain aspects a chimeric FVIII protein as described above can comprise at least one XTEN inserted into at least one of the permissive loops as described above, and can further comprise one or more XTENs inserted into a3, wherein the chimeric FVIII protein has procoagulant activity and can be expressed in vivo or in vitro in a host cell. In certain aspects, a chimeric FVIII protein can comprise three, four, five, six or more XTENs inserted into one or more permissive loops or into a3, wherein one or more amino acids in the one or more permissive loops or in the a3 region are substituted or deleted and wherein the chimeric FVIII protein has procoagulant activity and can be expressed in vivo or in vitro in a host cell.

TABLE 17

| | Definition I | Deletion - Definition I | Definition II | Deletion - Definition II |
|---|---|---|---|---|
| A1-1 | 15-45 | 16-44 | 18-41 | 19-40 |
| A1-2 | 201-232 | 202-231 | 218-229 | 219-228 |
| A2-1 | 395-421 | 396-420 | 397-418 | 398-417 |
| A2-2 | 577-635 | 578-634 | 595-607 | 596-606 |
| A3-1 | 1705-1732 | 1706-1731 | 1711-1725 | 1712-1724 |
| A3-2 | 1884-1917 | 1885-1916 | 1899-1911 | 1900-1910 |
| a3 | | | | 1649-1689 |

The permissive loop regions that can be substituted or deleted (Definition I or Definition II) is identified in Table 17. The amino acid residue coordinates of the one or more amino acids that can be substituted or deleted are listed in Table 17 (Deletion-Definition I and Deletion-Definition II). In some aspects, the one or more amino acids substituted or deleted in a chimeric FVIII protein are in amino acids 19 to 40 (A1-1), amino acids 219 to 228 (A1-2), amino acids 398 to 417 (A2-1), amino acids 596 to 606 (A2-2), amino acids 1712 to 1724 (A3-1), amino acids 1900 to 1910 (A3-2), amino acids 1649 to 1689 (a3 region), or any combinations thereof corresponding to native mature human FVIII. In other aspects, the one or more amino acids substituted or deleted are in amino acids 16 to 44 (A1-1), amino acids 202 to 231 (A2-2), amino acids 396 to 420 (A2-1), amino acids 578 to 634 (A2-2), amino acids 1706 to 1731 (A3-1), amino acids 1885 to 1916 (A3-2), or amino acids 1649 to 1689 (a3 region), or any combinations thereof corresponding to native mature human FVIII. In some aspects, the entire permissive loop of A1-1, A1-2, A2-1, A2-2, A3-1, or A3-2 is substituted or deleted. In other aspects, a portion of the permissive loops A1-1, A1-2, A2-1, A2-2, A3-1, or A3-2 is deleted or substituted.

In certain aspects, a chimeric FVIII protein comprises an XTEN inserted anywhere in one or more permissive loops or in the a3 domain, e.g., upstream or downstream of the one or more amino acids substituted or deleted, e.g., immediately downstream of one or more amino acids corresponding to one or more amino acids in mature native human FVIII including, but not limited to: amino acid 18 of SEQ ID NO: 4 with substitution or deletion of amino acids 19 to 40 of SEQ ID NO: 4 or a portion thereof; amino acid 22 of SEQ ID NO: 4 with substitution or deletion of amino acids 23 to 40 of SEQ ID NO: 4 or a portion thereof; amino acid 26 of SEQ ID NO: 4 with substitution or deletion of amino acids 27 to 40 of SEQ ID NO: 4 or a portion thereof, with substitution or deletion of amino acids 19 to 25 of SEQ ID NO: 4 or a portion thereof, or both; amino acid 40 of SEQ ID NO: 4 with substitution or deletion of amino acids 19 to 39 of SEQ ID NO: 4 or a portion thereof; amino acid 216 of SEQ ID NO: 4 with substitution or deletion of amino acids 217 to 228 of SEQ ID NO: 4 or a portion thereof; amino acid 220 of SEQ ID NO: 4 with substitution or deletion of amino acids 221 to 228 of SEQ ID NO: 4 or a portion thereof, with substitution or deletion of amino acid 217 to 219 of SEQ ID NO: 4 or a portion thereof, or both; amino acid 224 of SEQ ID NO: 4 with substitution or deletion of amino acids 225 to 228 of SEQ ID NO: 4 or a portion thereof, with substitution or deletion of amino acids 217 to 223 of SEQ ID NO: 4, or both; amino acid 399 of SEQ ID NO: 4 with substitution or deletion of amino acids 400 to 417 of SEQ ID NO: 4 or a portion thereof, with substitution or deletion of amino acid 398 of SEQ ID NO: 4, or both; amino acid 403 of SEQ ID NO: 4 with substitution or deletion of amino acids 404 to 417 of SEQ ID NO: 4 or a portion thereof, with substitution or deletion of amino acids 398 to 402 of SEQ ID NO: 4, or both; amino acid 409 of SEQ ID NO: 4 with substitution or deletion of amino acids 410 to 417 of SEQ ID NO: 4 or a portion thereof, with substitution or deletion of amino acids 398 to 408 of SEQ ID NO: 4 or a portion thereof, or both; amino acid 599 of SEQ ID NO: 4 with substitution or deletion of amino acids 600 to 606 of SEQ ID NO: 4 or a portion thereof, with substitution or deletion of amino acids 596 to 598 of SEQ ID NO: 4 or a portion thereof, or both; amino acid 603 of SEQ ID NO: 4 with substitution or deletion of amino acids 603 to 606 of SEQ ID NO: 4 or a portion thereof, with substitution or deletion of amino acids 596 to 602 of SEQ ID NO: 4 or a portion thereof, or both; amino acid 1656 of SEQ ID NO: 4 with substitution or deletion of amino acids 1649 to 1655 of SEQ ID NO: 4 or a portion thereof, with substitution or deletion of amino acids 1657 to 1689 of SEQ ID NO: 4 or a portion thereof, or both; amino acid 1711 of SEQ ID NO: 4 with substitution or deletion of amino acids 1712 to 1724 of SEQ ID NO: 4 or a portion thereof; amino acid 1720 of SEQ ID NO: 4 with substitution or deletion of amino acids 1721 to 1724 of SEQ ID NO: 4 or a portion thereof, with substitution or deletion of amino acids 1712 to 1719 of SEQ ID NO: 4 or a portion thereof, or both; amino acid 1725 of SEQ ID NO: 4 with substitution or deletion of amino acids 1712 to 1724 of SEQ ID NO: 4 or a portion thereof; amino acid 1900 of SEQ ID NO: 4 with substitution or deletion of amino acids 1901 to 1910 of SEQ ID NO: 4 or a portion thereof; amino acid 1905 of SEQ ID NO: 4 with substitution or deletion of amino acids 1906 to 1910 of SEQ ID NO: 4 or a portion thereof, with substitution or deletion of amino acids 1901 to 1904 of SEQ ID NO: 4 or a portion thereof, or both; amino acid 1910 of SEQ ID NO: 4 with substitution or deletion of amino acids 1901 to 1909 of SEQ ID NO: 4 or a portion thereof; or any combination thereof. In certain aspects, a chimeric FVIII protein comprises an XTEN inserted in the a3 region, e.g., upstream or downstream of the one or more amino acids substituted, mutated, or deleted, which can be amino acids 1649 to 1689 corresponding to native mature human FVIII, e.g., immediately downstream of amino acid 1656 of SEQ ID NO: 4 with substitution or deletion of amino acids 1649 to 1648 of SEQ ID NO: 4 or a portion thereof, with substitution or deletion of amino acids 1650 to 1689 of SEQ ID NO: 4 or a portion thereof, or the combination thereof.

In some aspects, both of the substitution or deletion of one or more amino acids and the insertion of an XTEN are in the same permissive loop or in the a3 region. In other aspects, the substitution or deletion of one or more amino acids is in one permissive loop, and the insertion of an XTEN is in another permissive loop or in the a3 region. In still other aspects the substitution or deletion of one or more amino acids is in the a3 region, and the insertion of an XTEN is in a permissive loop.

In certain aspects one or more amino acids in A1-1 in a chimeric FVIII protein are substituted or deleted, wherein the chimeric FVIII protein has procoagulant activity. In some aspects, the chimeric FVIII protein that contains the substitution or deletion is expressed in vivo or in vitro in a host cell. In other aspects, the one or more amino acids substituted or deleted are in amino acids 19 to 22, amino acids 19 to 26, amino acids 19 to 32, amino acids 19 to 40, amino acids 23 to 26, amino acids 23 to 32, amino acids 23 to 40, amino acids 27 to 32, amino acids 27 to 40, or amino acids 33 to 40 corresponding to native mature human FVIII. In certain aspects, at least one XTEN is inserted immediately upstream of the one or more amino acids substituted or deleted in A1-1. In some aspects, at least one XTEN is inserted immediately downstream of amino acid 18, amino acids 22, amino acids 26, or amino acids 32 corresponding to native human FVIII in the A1-1 region. In certain aspects a chimeric FVIII protein as described above comprises at least two XTENs inserted into a FVIII protein, wherein at least one of the two XTENs is inserted in A1-1 and wherein the chimeric FVIII protein has procoagulant activity and can be expressed in vivo or in vitro in a host cell. In one aspect, each of the two XTENs is inserted in A1-1, e.g., upstream or downstream of the substitution or deletion in A1-1. In another aspect, a first XTEN is inserted in A1-1, and a second XTEN is inserted in one of the other permissive loops (e.g., A1-2, A2-1, A2-2, A3-1, A3-2) or in an a3 region. In certain aspects, one of the other permissive loops does not contain a substitution or deletion. In other aspects, at least one XTEN can be further inserted in the B domain or fused to the C-terminus of the FVIII protein.

In certain aspects one or more amino acids in A1-2 in a chimeric FVIII protein are substituted or deleted, wherein the chimeric FVIII protein has procoagulant activity. In some aspects, the chimeric FVIII protein that contains the substitution or deletion is expressed in vivo or in vitro in a host cell. In other aspects, the one or more amino acids substituted or deleted are in amino acids 218 to 229 corresponding to native mature human FVIII. In certain aspects, at least one XTEN is inserted in A1-2, e.g., upstream or downstream of the one or more amino acids substituted or deleted. In some aspects, at least one XTEN is inserted immediately downstream of amino acid 216 or 220 corresponding to native human FVIII in the A1-2 region. In certain aspects a chimeric FVIII protein as described above comprises at least two XTENs inserted into a FVIII protein, wherein at least one of the two XTENs is inserted in A1-2 and wherein the chimeric FVIII protein has procoagulant activity and can be expressed in vivo or in vitro in a host cell. In one aspect, each of the two XTENs is inserted in A1-2, e.g., upstream or downstream of the substitution or deletion in A1-2. In another aspect, a first XTEN is inserted in A1-2 and a second XTEN is inserted in one of the other permissive loops (e.g., A1-1, A2-1, A2-2, A3-1, A3-2) or in an a3 region. In certain aspects, one of the other permissive loops does not contain a substitution or deletion. In other aspects, at least one XTEN can further be inserted in the B domain, e.g., amino acid 745 of SEQ ID NO: 4, or fused to the C-terminus of the FVIII protein, e.g., amino acid 2332 of SEQ ID NO: 4.

In certain aspects one or more amino acids in A2-1 in a chimeric FVIII protein are substituted or deleted, wherein the chimeric FVIII protein has procoagulant activity. In some aspects, the chimeric FVIII protein that contains the substitution or deletion is expressed in vivo or in vitro in a host cell. In other aspects, the one or more amino acids substituted or deleted are in amino acids 400 to 403 corresponding to native mature human FVIII. In certain aspects, at least one XTEN is inserted in A2-1, e.g., upstream or downstream of the one or more amino acids substituted or deleted in A2-1. In some aspects at least one XTEN is inserted immediately downstream of amino acid 399 corresponding to native mature human FVIII. In certain aspects a chimeric FVIII protein as described above comprises at least two XTENs inserted into a FVIII protein, wherein at least one of the two XTENs is inserted in A2-1 and wherein the chimeric FVIII protein has procoagulant activity and can be expressed in vivo or in vitro in a host cell. In one aspect, each of the two XTENs is inserted in A2-1, e.g., upstream or downstream of the substitution, deletion or a combination thereof in A2-1. In another aspect, a first XTEN is inserted in A2-1, e.g., upstream or downstream of a substitution, deletion or a combination thereof in A2-1, and a second XTEN is inserted in one of the other permissive loops (e.g., A1-1, A1-2, A2-2, A3-1, A3-2) or in an a3 region. In certain aspects, at least one of the other permissive loops does not contain a substitution or deletion. In other aspects, at least one XTEN can be further inserted in the B domain, e.g., amino acid 745 of SEQ ID NO: 4, or fused to the C-terminus of the FVIII protein, e.g., amino acid 2332 of SEQ ID NO: 4.

In certain aspects one or more amino acids in A2-2 in a chimeric FVIII protein are substituted or deleted, wherein the chimeric FVIII protein has procoagulant activity. In some aspects, the chimeric FVIII protein that contains the substitution or deletion is expressed in vivo or in vitro in a host cell. In other aspects, the one or more amino acids substituted or deleted are in amino acids 595 to 607 corresponding to native mature human FVIII. In certain aspects, at least one XTEN is inserted in A2-2, e.g., upstream or downstream of the one or more amino acids substituted or deleted in A2-2. In some aspects at least one XTEN is inserted immediately downstream of amino acids 599 or 603 corresponding to native mature human FVIII. In certain aspects a chimeric FVIII protein as described above comprises at least two XTENs inserted into a FVIII protein, wherein at least one of the two XTENs is inserted in A2-2 and wherein the chimeric FVIII protein has procoagulant activity and can be expressed in vivo or in vitro in a host cell. In one aspect, each of the two XTENs is inserted in A2-2, e.g., upstream or downstream of the substitution, deletion or a combination thereof in A2-2. In another aspect, a first XTEN is inserted in A2-2, e.g., upstream or downstream of a substitution, deletion or a combination thereof in A2-2, and a second XTEN is inserted in one of the other permissive loops (e.g., A1-1, A1-2, A2-1, A3-1, A3-2) or in an a3 region. In certain aspects, at least one of the other permissive loops does not contain a substitution or deletion. In other aspects, at least one XTEN can be further inserted in the B domain, e.g., amino acid 745 of SEQ ID NO: 4, or fused to the C-terminus of the FVIII protein, e.g., amino acid 2332 of SEQ ID NO: 4.

In certain aspects one or more amino acids in A3-1 in a chimeric FVIII protein are substituted or deleted, wherein the chimeric FVIII protein has procoagulant activity. In some aspects, the chimeric FVIII protein that contains the substitution or deletion is expressed in vivo or in vitro in a host cell. In other aspects, the one or more amino acids substituted or deleted are in amino acids 1712 to 1720, amino acids 1712 to 1725, or amino acids 1721 to 1725 corresponding to native mature human FVIII. In certain aspects, at least one XTEN is inserted in A3-1, e.g., upstream or downstream of the one or more amino acids substituted or deleted in A3-1. In some aspects, at least one XTEN is inserted immediately downstream of amino acid 1711 or amino acids 1720 corresponding to native mature human FVIII. In certain aspects a chimeric FVIII protein as described above comprises at least two XTENs inserted into a FVIII protein, wherein at least one of the two XTENs is inserted in A3-1 and wherein the chimeric FVIII protein has procoagulant activity and can be expressed in vivo or in vitro in a host cell. In one aspect, each of the two XTENs is inserted in A3-1, e.g., upstream or downstream of the substitution, deletion or a combination thereof in A3-1. In another aspect, a first XTEN is inserted in A3-1, e.g., upstream or downstream of a substitution, deletion or a combination thereof in A3-1, and a second XTEN is inserted in one of the other permissive loops (e.g., A1-1, A1-2, A2-1, A2-2, or A3-2) or in an a3 region. In certain aspects, the one of the other permissive loops does not contain a substitution or deletion. In other aspects, at least one XTEN can be further inserted in the B domain, e.g., amino acid 745 of SEQ ID NO: 4, or fused to the C-terminus of the FVIII protein, e.g., amino acid 2332 of SEQ ID NO: 4.

In certain aspects one or more amino acids in A3-2 in a chimeric FVIII protein are substituted or deleted, wherein the chimeric FVIII protein has procoagulant activity. In some aspects, the chimeric FVIII protein that contains the substitution or deletion is expressed in vivo or in vitro in a host cell. In other aspects, the one or more amino acids substituted or deleted are in amino acids 1901 to 1905, amino acids 1901 to 1910, amino acids 1906 to 1910, amino acids 1901 to 1905, amino acids 1901 to 1910, or amino acids 1906 to 1910 corresponding to native mature human FVIII. In certain aspects, at least one XTEN is inserted in A3-2, e.g., upstream or downstream of the one or more amino acids substituted or deleted in A3-2. In some aspects, at least one XTEN is inserted immediately downstream of amino acid 1900 or amino acids 1905 corresponding to native mature human FVIII. In certain aspects a chimeric FVIII protein as described above comprises at least two XTENs inserted into a FVIII protein, wherein at least one of the two XTENs is inserted in A3-2 and wherein the chimeric FVIII protein has procoagulant activity and can be expressed in vivo or in vitro in a host cell. In one aspect, each of the two XTENs is inserted in A3-2, e.g., upstream or downstream of the substitution, deletion or a combination thereof in A3-2. In another aspect, a first XTEN is inserted in A3-2, e.g., upstream or downstream of a substitution, deletion or a combination thereof in A3-2, and a second XTEN is inserted in one of the other permissive loops (e.g., A1-1, A1-2, A2-1, A2-2, or A3-1) or in an a3 region. In certain aspects, the one of the other permissive loops does not contain a substitution or deletion. In other aspects, at least one XTEN can be further inserted in the B domain, e.g., amino acid 745 of SEQ ID NO: 4, or fused to the C-terminus of the FVIII protein, e.g., amino acid 2332 of SEQ ID NO: 4.

In certain aspects one or more amino acids in the a3 region in a chimeric FVIII protein are substituted or deleted, wherein the chimeric FVIII protein has procoagulant activity. In some aspects, the chimeric FVIII protein that contains the substitution or deletion is expressed in vivo or in vitro in a host cell. In other aspects, the one or more amino acids substituted or deleted are in amino acids 1649 to 1689 corresponding to native mature human FVIII. In certain aspects, at least one XTEN is inserted in the a3 region, e.g., upstream or downstream of the one or more amino acids substituted or deleted in the a3 region. In some aspects, at least one XTEN is inserted immediately downstream of amino acid 1656 corresponding to native mature human FVIII. In certain aspects a chimeric FVIII protein as described above comprises at least two XTENs inserted into a FVIII protein, wherein at least one of the two XTENs is inserted in the a3 region and wherein the chimeric FVIII protein has procoagulant activity and can be expressed in vivo or in vitro in a host cell. In one aspect, each of the two XTENs is inserted in the a3 region, e.g., upstream or downstream of the substitution, deletion or a combination thereof in the a3 region. In another aspect, a first XTEN is inserted in the a3 region, e.g., upstream or downstream of a substitution, deletion or a combination thereof in the a3 region, and a second XTEN is inserted in one of the other permissive loops (e.g., A1-1, A1-2, A2-1, A2-2, A3-1, or A3-1) or in an a3 region. In certain aspects, the one of the other permissive loops does not contain a substitution or deletion. In other aspects, at least one XTEN can be further inserted in the B domain, e.g., amino acid 745 of SEQ ID NO: 4, or fused to the C-terminus of the FVIII protein, e.g., amino acid 2332 of SEQ ID NO: 4.

In other aspects, a chimeric FVIII protein comprises a first XTEN inserted into A1-1, A1-2, A2-1, A2-2, A3-1, or A3-2 or a3 region, in which one or more amino acids are substituted or deleted, and a second XTEN inserted into B domain, e.g., immediately downstream of amino acid 745 corresponding to SEQ ID NO: 4.

In some aspects, a chimeric FVIII protein comprises a first XTEN inserted immediately downstream of amino acid 403 of SEQ ID NO: 4 and a second XTEN inserted immediately downstream of amino acid 745 of SEQ ID NO: 4, wherein one or more amino acids of amino acids 404 to 417 corresponding to native mature human FVIII are substituted or deleted. In other aspects, a chimeric FVIII protein comprises a first XTEN inserted immediately downstream of amino acid 1900 corresponding to mature FVIII sequence (i.e., SEQ ID NO: 4) and a second XTEN inserted immediately downstream of amino acid 745 corresponding to SEQ ID NO: 4, wherein one or more amino acids of amino acids 1901 to 1910 corresponding to native mature human FVIII are substituted or deleted. In still other aspects, a chimeric FVIII protein comprises a first XTEN inserted immediately downstream of amino acid 18 corresponding to SEQ ID NO: 4 and a second XTEN inserted immediately downstream of amino acid 745 corresponding to SEQ ID NO: 4, wherein one or more amino acids of amino acids 19 to 22, amino acids 19 to 26, amino acids 19 to 32, amino acids 19 to 40, amino acids 23 to 26, amino acids 23 to 32, amino acids 23 to 40, amino acids 27 to 32, amino acids 27 to 40, or amino acids 33 to 40 corresponding to native mature human FVIII are substituted or deleted.

In yet other aspects, a chimeric FVIII protein comprises a first XTEN inserted immediately downstream of amino acid 1656 corresponding to SEQ ID NO: 4 and a second XTEN inserted immediately downstream of amino acid 1900 corresponding to SEQ ID NO: 4, wherein one or more amino acids in amino acids 1901 to 1910 corresponding to native mature human FVIII are substituted or deleted. In certain aspects, a chimeric FVIII protein comprises a first XTEN inserted immediately downstream of amino acid 26 corresponding to SEQ ID NO: 4, a second XTEN inserted immediately downstream of amino acid 1656 corresponding to SEQ ID NO: 4, and a third XTEN inserted immediately downstream of amino acid 1900 corresponding to SEQ ID NO: 4, wherein one or more amino acids in amino acids 27 to 40 corresponding to native mature human FVIII or amino acids 1901 to 1910 corresponding to native mature human FVIII are substituted or deleted. In some aspects, the first and second XTENs are identical. In other aspects, the first XTENs are different.

In some embodiments, the FVIII protein of the invention can be a dual chain FVIII comprising the FVIII heavy chain (HC) and the FVIII light chain or a single chain FVIII.

In some aspects, the insertion of at least one XTEN into the permissive loops of the A domains (e.g., A1-1, A1-2, A2-1, A2-2, A3-1, or A3-2 as described above) or the a3 region in addition to a substitution or deletion of one or more amino acids in the permissive loops or in the a3 region results in an increase in expression level when compared to the expression level of the chimeric FVIII protein without the at least one XTEN inserted in the permissive loops or in the a3 region. In some aspects, the increase in expression level is determined by an activity assay.

In some aspects, the chimeric FVIII protein comprises two XTENs, the first of the two XTENs inserted into one or more of the permissive loops of the A domains (e.g., A1-1, A1-2, A2-1, A2-2, A3-1, or A3-2 as described above) or into the a3 region, wherein one or more amino acids in the one or more permissive loops and the a3 region are substituted or deleted, and the second of the two XTENs inserted into the a3 region. In some aspects, the chimeric FVIII protein comprises three XTENs, the first and the second of the three XTENs inserted into one or more of the permissive loops of the A domains (e.g., A1-1, A1-2, A2-1, A2-2, A3-1, or A3-2 as described above) or into the a3 region, wherein one or more amino acids in the one or more permissive loops and the a3 region are substituted or deleted, and the third of the three XTENs inserted into the a3 region. In other aspects, the chimeric FVIII protein comprises more than three XTENs, the first of the more than three XTENs inserted into the a3 region and the rest of the more than three XTENs inserted into one or more of the permissive loops of the A domains (e.g., A1-1, A1-2, A2-1, A2-2, A3-1, or A3-2 as described above) or into an a3 region, wherein one or more amino acids in the one or more permissive loops and the a3 region are substituted or deleted.

In some aspects, the increase in expression level caused by the insertion of at least one XTEN into the permissive loops of the A domains (e g., A1-1, A1-2, A2-1, A2-2, A3-1, or A3-2 as described above) or into the a3 region, wherein one or more amino acids in the one or more permissive loops or the a3 region are substituted or deleted, is an increase of at least about 10%, at least about 20%, at least about 30%, at least about 40%, at least about 50%, at least about 60%, at least about 70%, at least about 80%, at least about 90% or at least about 100% when compared to the expression level of the chimeric FVIII protein without the at least one XTEN inserted in the one or more permissive loops or in the a3 region. In some aspects, the increase in expression level caused by the insertion of at least one XTEN inserted into the permissive loops of the A domains (e.g., A1-1, A1-2, A2-1, A2-2, A3-1, or A3-2 as described above) or into the a3 region, wherein one or more amino acids in the one or more permissive loops or the a3 region are substituted or deleted, is an increase of at least about 2-fold, at least about 3-fold, at least about 4-fold, at least about 5-fold, at least about 6-fold, at least about 7-fold, at least about 8-fold, at least about 9-fold, or at least about 10-fold when compared to the expression level of the chimeric FVIII protein without the additional XTEN inserted in the one or more permissive loops or the a3 region.

In some aspects, the chimeric FVIII protein comprises multiple XTEN insertions, e.g., more than two, three, four, five, six, seven, eight, nine, or ten insertions, wherein the insertion sites include, but are not limited to, the sites listed in Tables 18 to 25 or any combinations thereof, and wherein at least one of the insertion sites is located in a permissive loop, e.g., A1-1, A1-2, A2-1, A2-2, A3-1, or A3-2, or in the a3 region, wherein one or more amino acids in the at least one of A1-1, A1-2, A2-1, A2-2, A3-1, or A3-2, or the a3 region are substituted or deleted.

In one aspect, a chimeric FVIII protein comprises two XTENs, wherein at least one of the two XTENs is inserted within a permissive loop or in an a3 region or both of the two XTENs, wherein one or more amino acids in the at least one of A1-1, A1-2, A2-1, A2-2, A3-1, or A3-2, or the a3 region are substituted or deleted. The first and second XTENs can be the same or different. Non-limiting examples of the chimeric FVIII protein comprising two XTENs are listed in Table 19. In one example, the first XTEN is inserted in permissive loop A1-1, and the second XTEN is inserted in loop A2-1, wherein one or more amino acids in A1-1, A2-1, or both are substituted or deleted. In another aspect, the first XTEN is inserted in permissive loop A1-1, and the second XTEN is inserted in permissive loop A2-2, wherein one or more amino acids in A1-1, A2-2, or both are substituted or deleted. In another aspect, the first XTEN is inserted in permissive loop A3-1, and the second XTEN is inserted in permissive loop A3-2, wherein one or more amino acids in A3-1, A3-2, or both are substituted or deleted. In another aspect, the first XTEN is inserted in permissive loop A1-1, and the second XTEN is inserted in the a3 region, wherein one or more amino acids in A1-1 are substituted or deleted. In another aspect, the first XTEN is inserted in permissive loop A2-1, and the second XTEN is inserted in the a3 region, wherein one or more amino acids in A2-1 are substituted or deleted. In another aspect, the first XTEN is inserted in permissive loop A2-2, and the second XTEN is inserted in the a3 region, wherein one or more amino acids in A2-2 are substituted or deleted. In another aspect, the first XTEN is inserted in permissive loop A3-1, and the second XTEN is inserted in the a3 region, wherein one or more amino acids in A3-1 are substituted or deleted. In another aspect, the first XTEN is inserted in permissive loop A1-1, and the second XTEN is inserted in permissive loop A3-2, wherein one or more amino acids in A1-1, A3-2, or both are substituted or deleted. In another aspect, the first XTEN is inserted in permissive loop A2-1, and the second XTEN is inserted in permissive loop A3-2, wherein one or more amino acids in A2-1, A3-2, or both are substituted or deleted. In another aspect, the first XTEN is inserted in permissive loop A3-2, and the second XTEN is inserted in the a3 region, wherein one or more amino acids in A3-2 are substituted or deleted. In another aspect, the first XTEN is inserted in permissive loop A1-1, and the second XTEN is inserted in permissive loop A3-1, wherein one or more amino acids in A1-1, A3-1, or both are substituted or deleted. In another aspect, the first XTEN is inserted in permissive loop A2-1, and the second XTEN is inserted in permissive loop A3-1, wherein one or more amino acids in A2-1, A3-1, or both are substituted or deleted.

In another aspect, a chimeric FVIII protein comprises three XTENs, wherein at least one of the three XTENs is inserted in a permissive loop or in an a3 region, at least two of the three XTENs are inserted in two permissive loops and/or in an a3 region, or any combinations thereof, or the three XTENs are inserted in three permissive loops, in the a3 region, or any combinations thereof, and wherein one or more amino acids in A1-1, A1-2, A2-1, A2-2, A3-1, or A3-2, or in the a3 region are substituted or deleted. The first, second, or third XTENs can be the same or different from each other. The first, second, and third XTENs are the same or different. Non-limiting examples of the chimeric FVIII protein comprising three XTENs are in Table 20 or 21. In one example, the first XTEN is inserted in permissive loop A1-1, the second XTEN is inserted in permissive loop A2-1, and the third XTEN is inserted in the a3 region, wherein one or more amino acids in A1-1, A2-1, or both are substituted or deleted. In another example, the first XTEN is inserted in permissive loop A1-1, the second XTEN is inserted in permissive loop A2-1, and the third XTEN is inserted in permissive loop A3-1, wherein one or more amino acids in A1-1, A2-1, A3-1, or any combinations thereof are substituted or deleted. In another example, the first XTEN is inserted in permissive loop A1-1, the second XTEN is inserted in permissive loop A3-1, and the third XTEN is inserted in permissive loop A3-2, wherein one or more amino acids in A1-1, A3-1, A3-2, or any combinations thereof are substituted or deleted. In another example, the first XTEN is inserted in permissive loop A2-1, the second XTEN is inserted in the a3 region, and the third XTEN is inserted in permissive loop A3-1, wherein one or more amino acids in A2-1, A3-1, or both are substituted or deleted. In another example, the first XTEN is inserted in permissive loop A2-1, the second XTEN is inserted in the a3 region, and the third XTEN is inserted in permissive loop A3-2, wherein one or more amino acids in A2-1, A3-2, or both are substituted or deleted. In another aspect, the first XTEN is inserted in the a3 region, the second XTEN is inserted in permissive loop A3-1, and the third XTEN is inserted in permissive loop A3-2, wherein one or more amino acids in A3-1, A3-2, or both are substituted or deleted. In another aspect, the first XTEN is inserted in permissive loop A1-1, the second XTEN is inserted in the B domain, and the third XTEN is inserted at the carboxy terminus position (CT), wherein one or more amino acids in A1-1 are substituted or deleted. In another aspect, the first XTEN is inserted in permissive loop A2-1, the second XTEN is inserted in the B domain, and the third XTEN is inserted at the CT, wherein one or more amino acids in A2-1 are substituted or deleted. In another aspect, the first XTEN is inserted in permissive loop A3-1, the second XTEN is inserted in the B domain, and the third XTEN is inserted at the CT, wherein one or more amino acids in A3-1 are substituted or deleted. In another aspect, the first XTEN is inserted in permissive loop A3-2, the second XTEN is inserted in the B domain, and the third XTEN is inserted at the CT, wherein one or more amino acids in A3-2 are substituted or deleted. In some embodiments, the FVIII protein comprising three XTENs has reduced affinity for vWF or contains a deletion from amino acid 745 to amino acid 1685 corresponding to SEQ ID NO: 4 or amino acid 745 to amino acid 1656 corresponding to SEQ ID NO: 4 or a mutation or substitution at amino acid 1648 (e.g., R1648A), 1680 (Y1680F), or both, wherein one or more amino acids in A1-1, A1-2, A2-1, A2-2, A3-1, or A3-2 or in the a3 region are substituted or deleted.

In another aspect, a chimeric FVIII protein comprises four XTENs, wherein at least one of the four XTENs is inserted within a permissive loop or in an a3 region, at least two of the four XTENs are inserted within two permissive loop, in an a3 region, or any combinations thereof, at least three of the four XTENs are inserted within three permissive loops, in an a3 region, or any combinations thereof, or all of the four XTENs are inserted within four permissive loops, in an a3 region, or any combinations thereof, wherein one or more amino acids in at least one or more of the permissive loops or the a3 region are substituted or deleted. Non-limiting examples of the chimeric FVIII protein comprising four XTENs are listed in Table 22 or 23. The first, second, third, or fourth XTENs are the same or different. In one example, the first XTEN is inserted in permissive loop A1-1, the second XTEN is inserted in permissive loop A2-1, the third XTEN is inserted in the a3 region, and the fourth XTEN is inserted in permissive loop A3-1, wherein one or more amino acids in A1-1, A2-1, A3-1, or any combinations thereof are substituted or deleted. In another example, the first XTEN is inserted in permissive loop A1-1, the second XTEN is inserted in permissive loop A2-1, the third XTEN is inserted in the a3 region, and the fourth XTEN is inserted in permissive loop A3-2, wherein one or more amino acids in A1-1, A2-1, A3-2, or any combinations thereof are substituted or deleted. In another example, the first XTEN is inserted in permissive loop A1-1, the second XTEN is inserted in permissive loop A2-1, the third XTEN is inserted in permissive loop A3-1, and the fourth XTEN is inserted in permissive loop A3-2, wherein one or more amino acids in A1-1, A2-1, A3-1, A3-2, or any combinations thereof are substituted or deleted. In another aspect, the first XTEN 15 inserted in permissive loop A1-1, the second XTEN is inserted in the a3 region, the third XTEN is inserted in permissive loop A3-1, and the fourth XTEN is inserted in permissive loop A3-2, wherein one or more amino acids in A1-1, A3-1, A3-2, or any combinations thereof are substituted or deleted. In another aspect, the first XTEN is inserted in permissive loop A2-1, the second XTEN is inserted in the a3 region, the third XTEN is inserted in permissive loop A3-1, and the fourth XTEN is inserted in permissive loop A3-2, wherein one or more amino acids in A2-1, A3-1, A3-2, or any combinations thereof are substituted or deleted. In another aspect, the first XTEN is inserted in permissive loop A1-1, the second XTEN is inserted in permissive loop A2-1, the third XTEN is inserted in the B domain, and the fourth XTEN is inserted at the CT, wherein one or more amino acids in A1-1, A2-1, or both are substituted or deleted. In another aspect, the first XTEN is inserted in permissive loop A1-1, the second XTEN is inserted in permissive loop A3-1, the third XTEN is inserted in the B domain, and the fourth XTEN is inserted at the CT, wherein one or more amino acids in A1-1, A3-1, or both are substituted or deleted. In another aspect, the first XTEN is inserted in permissive loop A1-1, the second XTEN is inserted in permissive loop A3-2, the third XTEN is inserted in the B domain, and the fourth XTEN is inserted at the CT, wherein one or more amino acids in A1-1, A3-2, or both are substituted or deleted. In another aspect, the first XTEN is inserted in permissive loop A1-1, the second XTEN is inserted in permissive loop A3-2, the third XTEN is inserted in the B domain, and the fourth XTEN is inserted at the CT, wherein one or more amino acids in A1-1, A3-2, or both are substituted or deleted. In another aspect, the first XTEN is inserted in permissive loop A2-1, the second XTEN is inserted in permissive loop A3-1, the third XTEN is inserted in the B domain, and the fourth XTEN is inserted at the CT, wherein one or more amino acids in A2-1, A3-1, or both are substituted or deleted. In another aspect, the first XTEN is inserted in permissive loop A2-1, the second XTEN is inserted in permissive loop A3-2, the third XTEN is inserted in the B domain, and the fourth XTEN is inserted at the CT, wherein one or more amino acids in A2-1, A3-2, or both are substituted or deleted. In another aspect, the first XTEN is inserted in permissive loop A3-1, the second XTEN is inserted in permissive loop A3-2, the third XTEN is inserted in the B domain, and the fourth XTEN is inserted at the CT, wherein one or more amino acids in A3-1, A3-2, or both are substituted or deleted. In another aspect, the first XTEN is inserted in permissive loop A2-1, the second XTEN is inserted in the a3 region, the third XTEN is inserted in permissive loop A3-1, and the fourth XTEN is inserted at the CT, wherein one or more amino acids in A2-1, A3-1, or both are substituted or deleted. In another aspect, the first XTEN 15 inserted in permissive loop A2-1, the second XTEN is inserted in the a3 region, the third XTEN is inserted in permissive loop A3-2, and the fourth XTEN is inserted at the CT, wherein one or more amino acids in A2-1, A3-2, or both are substituted or deleted. In another aspect, the first XTEN is inserted in the a3 region, the second XTEN is inserted in permissive loop A3-1, the third XTEN is inserted in permissive loop A3-2, and the fourth XTEN is inserted at the CT, wherein one or more amino acids in A3-1, A3-2, or both are substituted or deleted. In another aspect, the first XTEN is inserted in permissive loop A1-1, the second XTEN is inserted in permissive loop A2-1, the third XTEN is inserted in the a3 region, and the fourth XTEN is inserted at the CT, wherein one or more amino acids in A1-1, A2-1, or both are substituted or deleted. In another aspect, the first XTEN is inserted in permissive loop A1-1, the second XTEN is inserted in permissive loop A2-1, the third XTEN is inserted in permissive loop A3-1, and the fourth XTEN is inserted at the CT, wherein one or more amino acids in A1-1, A2-1, A3-1, or any combinations thereof are substituted or deleted. In another aspect, the first XTEN is inserted in permissive loop A1-1, the second XTEN is inserted in permissive loop A2-1, the third XTEN is inserted in permissive loop A3-2, and the fourth XTEN is inserted at the CT, wherein one or more amino acids in A1-1, A2-1, A3-2, or any combinations thereof are substituted or deleted. In another aspect, the first XTEN is inserted in permissive loop A1-1, the second XTEN is inserted in the a3 region, the third XTEN is inserted in permissive loop A3-1, and the fourth XTEN is inserted at the CT, wherein one or more amino acids in A1-1, A3-1, or both are substituted or deleted. In another aspect, the first XTEN is inserted in permissive loop A1-1, the second XTEN is inserted in the a3 region, the third XTEN is inserted in permissive loop A3-2, and the fourth XTEN is inserted at the CT, wherein one or more amino acids in A1-1, A3-2, or both are substituted or deleted. In another aspect, the first XTEN is inserted in permissive loop A1-1, the second XTEN is inserted in permissive loop A3-1, the third XTEN is inserted in permissive loop A3-2, and the fourth XTEN is inserted at the CT, wherein one or more amino acids in A1-1, A3-1, A3-2, or any combinations thereof are substituted or deleted.

In another aspect, a chimeric FVIII protein comprises five XTENs, wherein at least one of the five XTENs is inserted within a permissive loop or in an a3 region, at least two of the five XTENs are inserted within two permissive loops, in an a3 region, or any combinations thereof, at least three of the five XTENs are inserted within three permissive loops, in an a3 region, or any combinations thereof, at least four of the five XTENs are inserted within four permissive loops, in an a3 region, or any combinations thereof, or all of the five XTENs are inserted within five permissive loops, in an a3 region, or any combinations thereof, wherein one or more amino acids in the at least one, at least two, at least three, at least four, or at least five of the permissive loops or the a3 region are substituted or deleted. The first, second, third, fourth, and fifth XTENs are the same or different. Non-limiting examples of the chimeric FVIII protein comprising five XTENs are in TABLE 24. In one example, the first XTEN is inserted in permissive loop A2-1, the second XTEN is inserted in the a3 region, the third XTEN is inserted in permissive loop A3-1, the fourth XTEN is inserted in permissive loop A3-2, and the fifth XTEN is inserted at the CT, wherein one or more amino acids in A2-1, A3-1, A3-2, or any combinations thereof are substituted or deleted. In another aspect, the first XTEN is inserted in permissive loop A1-1, the second XTEN is inserted in permissive loop A2-1, the third XTEN is inserted in the a3 region, the fourth XTEN is inserted in permissive loop A3-1, and the fifth XTEN is inserted at the CT, wherein one or more amino acids in A1-1, A2-1, A3-1, or any combinations thereof are substituted or deleted. In another aspect, the first XTEN is inserted in permissive loop A1-1, the second XTEN is inserted in permissive loop A2-1, the third XTEN is inserted in the a3 region, the fourth XTEN is inserted in permissive loop A3-2, and the fifth XTEN is inserted at the CT, wherein one or more amino acids in A1-1, A2-1, A3-2, or any combinations thereof are substituted or deleted. In another aspect, the first XTEN is inserted in permissive loop A1-1, the second XTEN is inserted in permissive loop A2-1, the third XTEN is inserted in permissive loop A3-1, the fourth XTEN is inserted in permissive loop A3-2, and the fifth XTEN is inserted at the CT, wherein one or more amino acids in A1-1, A2-1, A3-1, A3-2, or any combinations thereof are substituted or deleted. In another aspect, the first XTEN is inserted in permissive loop A1-1, the second XTEN is inserted in the a3 region, the third XTEN is inserted in permissive loop A3-1, the fourth XTEN is inserted in permissive loop A3-2, and the fifth XTEN is inserted at the CT, wherein one or more amino acids in A1-1, A3-1, A3-2, or any combinations thereof are substituted or deleted. In another aspect, the first XTEN is inserted in permissive loop A1-1, the second XTEN is inserted in permissive loop A2-1, the third XTEN is inserted in the B domain, the fourth XTEN is inserted in permissive loop A3-1, and the fifth XTEN is inserted at the CT, wherein one or more amino acids in A1-1, A2-1, A3-1, or any combinations thereof are substituted or deleted. In another aspect, the first XTEN is inserted in permissive loop A1-1, the second XTEN is inserted in permissive loop A2-1, the third XTEN is inserted in the B domain, the fourth XTEN is inserted in permissive loop A3-2, and the fifth XTEN is inserted at the CT, wherein one or more amino acids in A1-1, A2-1, A3-2, or any combinations thereof are substituted or deleted. In another aspect, the first XTEN is inserted in permissive loop A1-1, the second XTEN is inserted in the B domain, the third XTEN is inserted in permissive loop A3-1, the fourth XTEN is inserted in permissive loop A3-2, and the fifth XTEN is inserted at the CT, wherein one or more amino acids in A1-1, A3-1, A3-2, or any combinations thereof are substituted or deleted. In another aspect, the first XTEN is inserted in permissive loop A2-1, the second XTEN is inserted in the B domain, the third XTEN is inserted in permissive loop A3-1, the fourth XTEN is inserted in permissive loop A3-2, and the fifth XTEN is inserted at the CT, wherein one or more amino acids in A2-1, A3-1, A3-2, or any combinations thereof are substituted or deleted.

In another aspect, a chimeric FVIII protein comprises six XTENs, wherein at least one of the six XTENs is inserted within a permissive loop or in an a3 region, at least two of the six XTENs are inserted within two permissive loops, in an a3 region, or any combinations thereof, at least three of the six XTENs are inserted within three permissive loops, in an a3 region, or any combinations thereof, at least four of the six XTENs are inserted within four permissive loops, in an a3 region, or any combinations thereof, at least five of the six XTENs are inserted within five permissive loops, in an a3 region, or any combinations thereof, or all of the six XTENs are inserted within six permissive loops, in an a3 region, or any combinations thereof, wherein one or more amino acids in A1-1, A1-2, A2-1, A2-2, A3-1, or A3-2, or in the a3 region are substituted or deleted. The first, second, third, fourth, fifth, and sixth XTENs are the same or different. Examples of the chimeric FVIII protein comprising six XTENs include, but are not limited to, Table 25. In one example, the first XTEN is inserted in permissive loop A1-1, the second XTEN is inserted in permissive loop A2-1, the third XTEN is inserted in the a3 region, the fourth XTEN is inserted in permissive loop A3-1, the fifth XTEN is inserted in permissive loop A3-2, and the sixth XTEN is inserted at the CT, wherein one or more amino acids in A1-1, A2-1, A3-1, A3-2, or any combinations thereof are substituted or deleted. In another aspect, the first XTEN is inserted in permissive loop A1-1, the second XTEN is inserted in permissive loop A2-1, the third XTEN is inserted in the B domain, the fourth XTEN is inserted in permissive loop A3-1, the fifth XTEN is inserted in permissive loop A3-2, and the sixth XTEN is inserted at the CT, wherein one or more amino acids in A1-1, A2-1, A3-1, A3-2, or any combinations thereof are substituted or deleted.

In certain aspects, a chimeric FVIII protein comprises one XTEN inserted immediately downstream of an amino acid selected from the group consisting of the amino acids in Table 18, wherein one or more amino acids in A1-1, A1-2, A2-1, A2-2, A3-1, or A3-2, or in the a3 region or any combinations thereof are substituted or deleted. In other aspects, a chimeric FVIII protein comprises two XTENs inserted immediately downstream of two amino acids, each of the two amino acids selected from the group consisting of the amino acid in Table 18, wherein one or more amino acids in A1-1, A1-2, A2-1, A2-2, A3-1, or A3-2, or in the a3 region or any combinations thereof are substituted or deleted. In a particular embodiment, the two XTENs are inserted in the two insertion sites selected from the group consisting of the insertion sites in Table 19, wherein one or more amino acids in A1-1, A1-2, A2-1, A2-2, A3-1, or A3-2, or in the a3 region or any combinations thereof are substituted or deleted. In still other aspects, a chimeric FVIII protein comprises three XTENs inserted immediately downstream of three amino acids, each of the three amino acids selected from the group consisting of the amino acid in Table 18, wherein one or more amino acids in A1-1, A1-2, A2-1, A2-2, A3-1, or A3-2, or in the a3 region or any combinations thereof are substituted or deleted. In a specific embodiment, the three XTENs are inserted in the three insertion sites selected from the group consisting of the insertion sites in Tables 20 and 21, wherein one or more amino acids in A1-1, A1-2, A2-1, A2-2, A3-1, or A3-2, or in the a3 region or any combinations thereof are substituted or deleted. In yet other aspects, a chimeric FVIII protein comprises four XTENs inserted immediately downstream of four amino acids, each of the four amino acids selected from the group consisting of the amino acid in Table 18, wherein one or more amino acids in A1-1, A1-2, A2-1, A2-2, A3-1, or A3-2, or in the a3 region or any combinations thereof are substituted or deleted. In a particular embodiment, the four XTENs are inserted in the four insertion sites selected from the group consisting of the insertion sites in Tables 22 and 23, wherein one or more amino acids in A1-1, A1-2, A2-1, A2-2, A3-1, or A3-2, or in the a3 region or any combinations thereof are substituted or deleted. In some aspects, a chimeric FVIII protein comprises five XTENs inserted immediately downstream of five amino acids, each of the five amino acids selected from the group consisting of the amino acid in Table 18, wherein one or more amino acids in A1-1, A1-2, A2-1, A2-2, A3-1, or A3-2, or in the a3 region or any combinations thereof are substituted or deleted. In a particular embodiment, the five XTENs are inserted in the five insertion sites selected from the group consisting of the insertion sites in Table 24, wherein one or more amino acids in A1-1, A1-2, A2-1, A2-2, A3-1, or A3-2, or in the a3 region or any combinations thereof are substituted or deleted. In certain aspects, a chimeric FVIII protein comprises six XTENs inserted immediately downstream of six amino acids, each of the six amino acids selected from the group consisting of the amino acid in Table 18, wherein one or more amino acids in A1-1, A1-2, A2-1, A2-2, A3-1, or A3-2, or in the a3 region or any combinations thereof are substituted or deleted. In a particular embodiment, the six XTENs are inserted in the six insertion sites selected from the group consisting of the insertion sites in Table 25, wherein one or more amino acids in A1-1, A1-2, A2-1, A2-2, A3-1, or A3-2, or in the a3 region or any combinations thereof are substituted or deleted.

In some aspects, a chimeric FVIII protein comprises one XTEN inserted immediately downstream of an amino acid position corresponding to amino acid 26 of SEQ ID NO: 4, amino acid 403 of SEQ ID NO: 4, amino acid 1720 of SEQ ID NO: 4, or amino acid 1900 of SEQ ID NO: 4 in mature native human FVIII, and an additional XTEN inserted immediately downstream of an amino acid corresponding to amino acid 1656 of SEQ ID NO: 4, wherein one or more amino acids of amino acids 27 to 40, amino acids 404 to 417, amino acids 1721 to 1724, or any combinations thereof are substituted or deleted. In some aspects, a chimeric FVIII protein comprises two XTENs inserted immediately downstream of two amino acid positions corresponding to amino acid 26 of SEQ ID NO: 4, amino acid 403 of SEQ ID NO: 4, amino acid 1720 of SEQ ID NO: 4, or amino acid 1900 of SEQ ID NO: 4 in mature native human FVIII, and an additional XTEN inserted immediately downstream of an amino acid corresponding to amino acid 1656 of SEQ ID NO: 4, wherein one or more amino acids of amino acids 27 to 40, amino acids 404 to 417, amino acids 1721 to 1724, amino acids 1901 to 1910, or any combinations thereof are substituted or deleted. In some aspects, a chimeric FVIII protein comprises three XTENs inserted immediately downstream of three amino acid positions corresponding to amino acid 26 of SEQ ID NO: 4, amino acid 403 of SEQ ID NO: 4, amino acid 1720 of SEQ ID NO: 4, or amino acid 1900 of SEQ ID NO: 4 in mature native human FVIII, and an additional XTEN inserted immediately downstream of an amino acid corresponding to amino acid 1656 of SEQ ID NO: 4, wherein one or more amino acids of amino acids 27 to 40, amino acids 404 to 417, amino acids 1721 to 1724, amino acids 1901 to 1910, or any combinations thereof are substituted or deleted.

In certain aspects, a chimeric FVIII protein comprises at least one XTEN inserted into the a3 region of FVIII (e.g., an insertion site which corresponds to amino acid 1656 of SEQ ID NO: 4), either alone or in combination with one or more XTENs inserted into the permissive loops of the A domains (e.g., A1-1, A1-2, A2-1, A2-2, A3-1, or A3-2 as described above) or in the a3 region, wherein one or more amino acids in the permissive loops of the A domains or in the a3 region are substituted or deleted. In some aspects, the FVIII protein comprises two XTENs. In some aspects, the FVIII protein comprises three XTENs. In some aspects, the FVIII protein comprises four XTENs. In some aspects, the FVIII protein comprises five XTENs. In some aspects, the FVIII protein comprises six XTENs.

In some aspects, a chimeric FVIII protein comprises one or more XTEN sequences in an insertion site within a permissive loop, e.g., A1-1, A1-2, A2-1, A2-2, A3-1, A3-2, or a3 region, or any combinations thereof, wherein one or more amino acids in the permissive loop or in the a3 region are substituted or deleted. In one embodiment, the one or more XTEN sequences are inserted within A1-1, wherein one or more amino acids in A1-1 are substituted or deleted. In another embodiment, the one or more XTEN sequences are inserted within A1-2, wherein one or more amino acids in A2-1 are substituted or deleted. In other embodiments, the one or more XTEN sequences are inserted within A2-1, wherein one or more amino acids in A2-1 are substituted or deleted. In still other embodiments, the one or more XTEN sequences are inserted within A2-2, wherein one or more amino acids in A2-2 are substituted or deleted. In yet other embodiments, the one or more XTEN sequences are inserted within A3-1, wherein one or more amino acids in A3-1 are substituted or deleted. In some embodiments, the one or more XTEN sequences are inserted within A3-2, wherein one or more amino acids in A3-1 are substituted or deleted. In certain embodiments, the one or more XTEN sequences are inserted within the a3 region, wherein one or more amino acids in the a3 region are substituted or deleted.

In certain aspects, a chimeric FVIII protein comprises one XTEN sequence inserted at an insertion site listed in Table 18, wherein one or more amino acids in at least one of A1-1, A1-2, A2-1, A2-2, A3-1, A3-2, or the a3 region are substituted or deleted. In other aspects, a chimeric FVIII protein comprises two XTEN sequences inserted in two insertion sites listed in Table 18, wherein one or more amino acids in at least one of A1-1, A1-2, A2-1, A2-2, A3-1, A3-2, or the a3 region are substituted or deleted. In a particular embodiment, the two XTEN sequences are inserted in two insertion sites listed in Table 19, wherein one or more amino acids in at least one of A1-1, A1-2, A2-1, A2-2, A3-1, A3-2, or the a3 region are substituted or deleted. In still other aspects, a chimeric FVIII protein comprises three XTEN sequences inserted in three insertion sites listed in Table 18, wherein one or more amino acids in at least one of A1-1, A1-2, A2-1, A2-2, A3-1, A3-2, or the a3 region are substituted or deleted. In a specific aspect, the three XTEN sequences are inserted in three insertion sites listed in Table 20, Table 21 or both tables, wherein one or more amino acids in at least one of A1-1, A1-2, A2-1, A2-2, A3-1, A3-2, or the a3 region are substituted or deleted. In yet other aspects, a chimeric FVIII protein comprises four XTEN sequences inserted in four insertion sites listed in TABLE 18, wherein one or more amino acids in at least one of A1-1, A1-2, A2-1, A2-2, A3-1, A3-2, or the a3 region are substituted or deleted. In a particular aspect, the four XTEN sequences are inserted in four insertion sites listed in Table 22, Table 23, or both, wherein one or more amino acids in at least one of A1-1, A1-2, A2-1, A2-2, A3-1, A3-2, or the a3 region are substituted or deleted. In some aspects, a chimeric FVIII protein comprises five XTEN sequences inserted in five insertion sites listed in Table 18, wherein one or more amino acids in at least one of A1-1, A1-2, A2-1, A2-2, A3-1, A3-2, or the a3 region are substituted or deleted. In a particular aspect, the five XTEN sequences are inserted in five insertion sites listed in Table 24, wherein one or more amino acids in at least one of A1-1, A1-2, A2-1, A2-2, A3-1, A3-2, or the a3 region are substituted or deleted. In certain aspects, a chimeric FVIII protein comprises six XTEN sequences inserted in six insertion sites listed in Table 18, wherein one or more amino acids in at least one of A1-1, A1-2, A2-1, A2-2, A3-1, A3-2, or the a3 region are substituted or deleted. In a particular embodiment, the six XTEN sequences are inserted in six insertion sites listed in Table 25, wherein one or more amino acids in at least one of A1-1, A1-2, A2-1, A2-2, A3-1, A3-2, or the a3 region are substituted or deleted. In some aspects, all the inserted XTEN sequences are identical. In other aspects, at least one of the inserted XTEN sequences is different from the rest of inserted XTEN sequences.

In some aspects, a chimeric FVIII protein comprises one XTEN sequence inserted immediately downstream of an amino acid position corresponding to amino acid 26 of SEQ ID NO: 4 with a substitution or deletion of amino acids 27 to 40 of SEQ ID NO: 4 or a portion thereof, amino acid 403 of SEQ ID NO: 4 with a substitution or deletion of amino acids 404 to 417 of SEQ ID NO: 4 or a portion thereof, amino acid 1720 of SEQ ID NO: 4 with a substitution or deletion of amino acids 1721 to 1724 of SEQ ID NO: 4 or a portion thereof, or amino acid 1900 of SEQ ID NO: 4 with a substitution or deletion of amino acids 1901 to 1910 of SEQ ID NO: 4 or a portion thereof, and an additional XTEN sequence inserted immediately downstream of an amino acid corresponding to amino acid 1656 of SEQ ID NO: 4. In some aspects, a chimeric FVIII protein comprises two XTEN sequences inserted immediately downstream of two amino acid positions corresponding to amino acid 26 of SEQ ID NO: 4 with a substitution or deletion of amino acids 27 to 40 of SEQ ID NO: 4 or a portion thereof, amino acid 403 of SEQ ID NO: 4 with a substitution or deletion of amino acids 404 to 417 of SEQ ID NO: 4 or a portion thereof, amino acid 1720 of SEQ ID NO: 4 with a substitution or deletion of amino acids 1721 to 1724 of SEQ ID NO: 4 or a portion thereof, or amino acid 1900 of SEQ ID NO: 4 with a substitution or deletion of amino acids 1901 to 1910 of SEQ ID NO: 4 or a portion thereof, and an additional XTEN sequence inserted immediately downstream of an amino acid corresponding to amino acid 1656 of SEQ ID NO: 4. In some aspects, a chimeric FVIII protein comprises three XTEN sequences inserted immediately downstream of three amino acid positions corresponding to amino acid 26 of SEQ ID NO: 4 with a substitution or deletion of amino acids 27 to 40 of SEQ ID NO: 4 or a portion thereof, amino acid 403 of SEQ ID NO: 4 with a substitution or deletion of amino acids 404 to 417 of SEQ ID NO: 4 or a portion thereof, amino acid 1720 of SEQ ID NO: 4 with a substitution or deletion of amino acids 1721 to 1724 of SEQ ID NO: 4 or a portion thereof, or amino acid 1900 of SEQ ID NO: 4 with a substitution or deletion of amino acids 1901 to 1910 of SEQ ID NO: 4 or a portion thereof, and an additional XTEN sequence inserted immediately downstream of an amino acid corresponding to amino acid 1656 of SEQ ID NO: 4.

TABLE 18

FVIII Variants Comprising One XTEN Insertion

| Insertion Site | Domain | Construct | Activity* | Expression ELISA |
|---|---|---|---|---|
| pBC0114 | | | +++ | +++ |
| 3 | A1 | pBC0126 | LLOQ* | LLOQ |
| 3 | A1 | pBC0127 | + | + |
| 18 | A1 | pBC0165 | ++ | ++ |
| 22 | A1 | pBC0183 | +++ | ++ |
| 26 | A1 | pBC0184 | ++ | ++ |
| 40 | A1 | pBC0166 | ++ | ++ |
| 60 | A1 | pBC0185 | LLOQ | LLOQ |
| 116 | A1 | pBC0167 | LLOQ | LLOQ |
| 130 | A1 | pBC0128 | LLOQ | LLOQ |
| 188 | A1 | pBC0168 | ++ | ++ |
| 216 | A1 | pBC0129 | ++ | ++ |
| 230 | A1 | pBC0169 | LLOQ | LLOQ |
| 333 | A1 | pBC0130 | ++ | ++ |
| 375 | A2 | pBC0131 | LLOQ | +++ |
| 403 | A2 | pBC0132 | ++ | ++ |
| 442 | A2 | pBC0170 | ++ | ++ |
| 490 | A2 | pBC0133 | + | ++ |
| 518 | A2 | pBC0171 | LLOQ | + |
| 599 | A2 | pBC0134 | ++ | ++ |
| 713 | A2 | pBC0172 | + | +++ |
| 1720 | A3 | pBC0138 | +++ | +++ |
| 1796 | A3 | pBC0139 | + | ++ |
| 1802 | A3 | pBC0140 | + | ++ |
| 1827 | A3 | pBC0173 | LLOQ | LLOQ |
| 1861 | A3 | pBC0174 | LLOQ | LLOQ |
| 1896 | A3 | pBC0175 | LLOQ | LLOQ |
| 1900 | A3 | pBC0176 | +++ | +++ |
| 1904 | A3 | pBC0177 | + | + |
| 1937 | A3 | pBC0178 | LLOQ | LLOQ |
| 2019 | A3 | pBC0141 | LLOQ | + |
| 403 | A2 | pSD0001 | +++ | +++ |
| 599 | A2 | pSD0002 | + | + |
| 403 | A2 | pSD0003 | +++ | +++ |
| 599 | A2 | pSD0004 | + | + |
| 1720 | A3 | pSD0009 | + | + |
| 1720 | A3 | pSD0010 | ++ | ++ |
| 65 | A1 | pSD0023 | LLOQ | LLOQ |
| 81 | A1 | pSD0024 | LLOQ | LLOQ |
| 119 | A1 | pSD0025 | LLOQ | LLOQ |
| 211 | A1 | pSD0026 | + | + |
| 220 | A1 | pSD0027 | + | + |
| 224 | A1 | pSD0028 | + | + |
| 336 | A1 | pSD0029 | ++ | +++ |
| 339 | A1 | pSD0030 | ++ | +++ |
| 378 | A2 | pSD0031 | LLOQ | ++ |
| 399 | A2 | pSD0032 | ++ | ++ |
| 409 | A2 | pSD0033 | ++ | ++ |
| 416 | A2 | pSD0034 | + | + |
| 487 | A2 | pSD0035 | LLOQ | + |
| 494 | A2 | pSD0036 | LLOQ | + |
| 500 | A2 | pSD0037 | LLOQ | + |
| 603 | A2 | pSD0038 | + | + |
| 1656 | a3 region | pSD0039 | +++ | +++ |
| 1656 | a3 region | pNL009** | ++++ | ND |
| 1711 | A3 | pSD0040 | ++ | + |
| 1725 | A3 | pSD0041 | LLOQ | ++ |
| 1749 | A3 | pSD0042 | LLOQ | LLOQ |
| 1905 | A3 | pSD0043 | ++ | ++ |
| 1910 | A3 | pSD0044 | + | + |
| 1900 | A3 | pSD0062 | ++ | ++ |
| 1900 | A3 | pSD0063 | +++ | ++ |
| 18 | A1 | pSD0045 | +++ | +++ |
| 18 | A1 | pSD0046 | +++ | +++ |
| 22 | A1 | pSD0047 | LLOQ | LLOQ |

TABLE 18-continued

| FVIII Variants Comprising One XTEN Insertion | | | | |
|---|---|---|---|---|
| Insertion Site | Domain | Construct | Activity* | Expression ELISA |
| 22 | A1 | pSD0048 | LLOQ | LLOQ |
| 26 | A1 | pSD0049 | +++ | +++ |
| 26 | A1 | pSD0050 | +++ | +++ |
| 40 | A1 | pSD0051 | +++ | +++ |
| 40 | A1 | pSD0052 | +++ | +++ |
| 216 | A1 | pSD0053 | LLOQ | LLOQ |
| 216 | A1 | pSD0054 | LLOQ | LLOQ |
| 375 | A2 | pSD0055 | LLOQ | + |
| 442 | A2 | pSD0056 | LLOQ | LLOQ |
| 442 | A2 | pSD0057 | LLOQ | LLOQ |
| 1796 | A3 | pSD0058 | LLOQ | LLOQ |
| 1796 | A3 | pSD0059 | + | + |
| 1802 | A3 | pSD0060 | + | + |
| 1802 | A3 | pSD0061 | LLOQ | LLOQ |

*LLOQ: below the limits of quantitation

**pNL009 includes a deletion of 745-1656

TABLE 19

| FVIII Variants Comprising Two XTEN Insertions | | | | | |
|---|---|---|---|---|---|
| Insertion 1 | | Insertion 2 | | | |
| Insertion Site | Domain | Insertion Site | Domain | Construct | Activity |
| 26 | A1 | 403 | A2 | LSD0005.002 | ++ |
| 26 | A1 | 403 | A2 | LSD0005.004 | ++ |
| 40 | A1 | 403 | A2 | LSD0005.005 | ++ |
| 40 | A1 | 403 | A2 | LSD0005.011 | ++ |
| 18 | A1 | 403 | A2 | LSD0005.018 | ++ |
| 26 | A1 | 599 | A2 | LSD0006.002 | + |
| 40 | A1 | 599 | A2 | LSD0006.005 | ++ |
| 40 | A1 | 599 | A2 | LSD0006.007 | ++ |
| 40 | A1 | 599 | A2 | LSD0006.011 | +++ |
| 40 | A1 | 403 | A2 | LSD0007.002 | + |
| 40 | A1 | 403 | A2 | LSD0007.004 | + |
| 26 | A1 | 403 | A2 | LSD0007.013 | ++ |
| 26 | A1 | 599 | A2 | LSD0008.001 | ++ |
| 40 | A1 | 599 | A2 | LSD0008.002 | ++ |
| 26 | A1 | 599 | A2 | LSD0008.006 | + |
| 18 | A1 | 599 | A2 | LSD0008.009 | ++ |
| 40 | A1 | 599 | A2 | LSD0008.017 | + |
| 26 | A1 | 403 | A2 | LSD0007.008 | ++ |
| 1720 | A3 | 1900 | A3 | LSD0044.002 | LLOQ |
| 1725 | A3 | 1900 | A3 | LSD0044.005 | LLOQ |
| 1720 | A3 | 1900 | A3 | LSD0044.039 | LLOQ |
| 1711 | A3 | 1905 | A3 | LSD0044.022 | LLOQ |
| 1720 | A3 | 1905 | A3 | LSD0044.003 | LLOQ |
| 1725 | A3 | 1905 | A3 | LSD0044.001 | LLOQ |
| 1656 | a3 region | 26 | A1 | LSD0038.001 | ++ |
| 1656 | a3 region | 18 | A1 | LSD0038.003 | ++ |
| 1656 | a3 region | 18 | A1 | LSD0038.008 | +++ |
| 1656 | a3 region | 40 | A1 | LSD0038.012 | ++ |
| 1656 | a3 region | 40 | A1 | LSD0038.013 | ++ |
| 1656 | a3 region | 26 | A1 | LSD0038.015 | ++ |
| 1656 | a3 region | 399 | A2 | LSD0039.001 | + |
| 1656 | a3 region | 403 | A2 | LSD0039.003 | ++ |
| 1656 | a3 region | 403 | A2 | LSD0039.010 | ++ |
| 1656 | a3 region | 1725 | A3 | LSD0045.001 | + |
| 1656 | a3 region | 1720 | A3 | LSD0045.002 | ++ |
| 1900 | A3 | 18 | A1 | LSD0042.014 | + |
| 1900 | A3 | 18 | A1 | LSD0042.023 | + |
| 1900 | A3 | 26 | A1 | LSD0042.006 | + |
| 1900 | A3 | 26 | A1 | LSD0042.013 | ++ |
| 1900 | A3 | 40 | A1 | LSD0042.001 | + |
| 1900 | A3 | 40 | A1 | LSD0042.039 | + |
| 1900 | A3 | 26 | A1 | LSD0042.047 | + |
| 1905 | A3 | 18 | A1 | LSD0042.003 | + |

TABLE 19-continued

| FVIII Variants Comprising Two XTEN Insertions | | | | | |
|---|---|---|---|---|---|
| Insertion 1 | | Insertion 2 | | | |
| Insertion Site | Domain | Insertion Site | Domain | Construct | Activity |
| 1905 | A3 | 40 | A1 | LSD0042.004 | LLOQ |
| 1905 | A3 | 26 | A1 | LSD0042.008 | LLOQ |
| 1905 | A3 | 26 | A1 | LSD0042.038 | LLOQ |
| 1905 | A3 | 40 | A1 | LSD0042.082 | LLOQ |
| 1910 | A3 | 26 | A1 | LSD0042.040 | LLOQ |
| 18 | A1 | 399 | A2 | LSD0037.002 | ++ |
| 26 | A1 | 399 | A2 | LSD0037.009 | + |
| 40 | A1 | 399 | A2 | LSD0037.011 | ++ |
| 18 | A1 | 403 | A2 | LSD0047.002 | ++ |
| 18 | A1 | 403 | A2 | LSD0047.005 | + |
| 18 | A1 | 403 | A2 | LSD0048.007 | + |
| 1656 | a3 region | 1900 | A3 | LSD0046.001 | ++ |
| 1656 | a3 region | 1900 | A3 | LSD0046.002 | + |
| 1656 | a3 region | 1905 | A3 | LSD0046.003 | + |
| 1711 | A3 | 40 | A1 | LSD0040.011 | LLOQ |
| 1711 | A3 | 26 | A1 | LSD0040.042 | LLOQ |
| 1720 | A3 | 26 | A1 | LSD0040.002 | + |
| 1720 | A3 | 40 | A1 | LSD0040.008 | + |
| 1720 | A3 | 18 | A1 | LSD0040.021 | + |
| 1720 | A3 | 26 | A1 | LSD0040.037 | LLOQ |
| 1720 | A3 | 18 | A1 | LSD0040.046 | + |
| 1725 | A3 | 26 | A1 | LSD0040.003 | LLOQ |
| 1725 | A3 | 40 | A1 | LSD0040.006 | LLOQ |
| 1725 | A3 | 26 | A1 | LSD0040.007 | LLOQ |
| 1725 | A3 | 18 | A1 | LSD0040.010 | LLOQ |
| 1725 | A3 | 40 | A1 | LSD0040.039 | LLOQ |
| 1725 | A3 | 18 | A1 | LSD0040.052 | + |
| 1720 | A3 | 403 | A2 | LSD0041.001 | + |
| 1720 | A3 | 399 | A2 | LSD0041.004 | LLOQ |
| 1711 | A3 | 403 | A2 | LSD0041.006 | LLOQ |
| 1720 | A3 | 403 | A2 | LSD0041.008 | LLOQ |
| 1725 | A3 | 403 | A2 | LSD0041.010 | LLOQ |
| 1725 | A3 | 403 | A2 | LSD0041.014 | LLOQ |
| 1725 | A3 | 399 | A2 | LSD0041.016 | LLOQ |
| 1711 | A3 | 403 | A2 | LSD0041.035 | LLOQ |
| 1900 | A3 | 399 | A2 | LSD0043.001 | LLOQ |
| 1900 | A3 | 403 | A2 | LSD0043.002 | LLOQ |
| 1905 | A3 | 403 | A2 | LSD0043.005 | LLOQ |
| 1900 | A3 | 399 | A2 | LSD0043.006 | LLOQ |
| 1900 | A3 | 403 | A2 | LSD0043.007 | LLOQ |
| 1900 | A3 | 403 | A2 | LSD0043.008 | LLOQ |
| 1905 | A3 | 399 | A2 | LSD0043.015 | LLOQ |
| 1905 | A3 | 403 | A2 | LSD0043.029 | LLOQ |
| 1910 | A3 | 403 | A2 | LSD0043.043 | LLOQ |

TABLE 20

FVIII Variants Comprising Three XTEN Insertions

| Insertion 1 Insertion Site | Insertion 1 Domain | Insertion 2 Insertion Site | Insertion 2 Domain | Insertion 3 Insertion Site | Insertion 3 Domain | Construct | Activity |
|---|---|---|---|---|---|---|---|
| 26 | A1 | 403 | A2 | 1656 | a3 region | pSD0077 | +++ |
| 26 | A1 | 403 | A2 | 1720 | A3 | pSD0078 | ++ |
| 26 | A1 | 403 | A2 | 1900 | A3 | pSD0079 | ++ |
| 26 | A1 | 1656 | a3 region | 1720 | A3 | pSD0080 | +++ |
| 26 | A1 | 1656 | a3 region | 1900 | A3 | pSD0081 | LLOQ |
| 26 | A1 | 1720 | A3 | 1900 | A3 | pSD0082 | + |
| 403 | A2 | 1656 | a3 region | 1720 | A3 | pSD0083 | +++ |
| 403 | A2 | 1656 | a3 region | 1900 | A3 | pSD0084 | +++ |
| 403 | A2 | 1720 | A3 | 1900 | A3 | pSD0085 | + |
| 1656 | a3 region | 1720 | A3 | 1900 | A3 | pSD0086 | +++ |
| 18 | A1 | 745 | B | 2332 | CT | LSD0049.002 | +++ |
| 26 | A1 | 745 | B | 2332 | CT | LSD0049.008 | +++ |
| 26 | A1 | 745 | B | 2332 | CT | LSD0049.011 | +++ |
| 40 | A1 | 745 | B | 2332 | CT | LSD0049.012 | +++ |
| 40 | A1 | 745 | B | 2332 | CT | LSD0049.020 | +++ |
| 18 | A1 | 745 | B | 2332 | CT | LSD0049.021 | +++ |
| 40 | A1 | 745 | B | 2332 | CT | LSD0050.002 | +++ |
| 18 | A1 | 745 | B | 2332 | CT | LSD0050.003 | +++ |
| 26 | A1 | 745 | B | 2332 | CT | LSD0050.007 | LLOQ |
| 18 | A1 | 745 | B | 2332 | CT | LSD0050.010 | +++ |
| 26 | A1 | 745 | B | 2332 | CT | LSD0050.012 | +++ |
| 40 | A1 | 745 | B | 2332 | CT | LSD0050.014 | +++ |
| 403 | A2 | 745 | B | 2332 | CT | LSD0051.002 | +++ |
| 399 | A2 | 745 | B | 2332 | CT | LSD0051.003 | +++ |
| 403 | A2 | 745 | B | 2332 | CT | LSD0052.001 | +++ |
| 399 | A2 | 745 | B | 2332 | CT | LSD0052.003 | +++ |
| 1725 | A3 | 745 | B | 2332 | CT | LSD0053.021 | LLOQ |
| 1720 | A3 | 745 | B | 2332 | CT | LSD0053.022 | +++ |
| 1711 | A3 | 745 | B | 2332 | CT | LSD0053.024 | +++ |
| 1720 | A3 | 745 | B | 2332 | CT | LSD0054.021 | +++ |
| 1711 | A3 | 745 | B | 2332 | CT | LSD0054.025 | ++ |
| 1725 | A3 | 745 | B | 2332 | CT | LSD0054.026 | +++ |
| 1900 | A3 | 745 | B | 2332 | CT | LSD0055.021 | +++ |
| 1905 | A3 | 745 | B | 2332 | CT | LSD0055.022 | +++ |
| 1900 | A3 | 745 | B | 2332 | CT | LSD0055.026 | +++ |
| 1900 | A3 | 745 | B | 2332 | CT | LSD0056.021 | +++ |
| 1900 | A3 | 745 | B | 2332 | CT | LSD0056.024 | +++ |
| 1910 | A3 | 745 | B | 2332 | CT | LSD0056.025 | +++ |

TABLE 21

FVIII Variants Comprising Three XTEN Insertions

| XTEN insertion1 | XTEN insertion2 | XTEN insertion3 | Additional mutations | Construct ID |
|---|---|---|---|---|
| 0745 | 1900 | 2332 | R1648A | pBC0294 |
| 0745 | 1900 | 2332 | R1648A | pBC0295 |
| 0745 | 1900 | 1232 | R1648A | pBC0296 |
| 0745 | 1900 | 2332 | R1648A | PBC0297 |
| 0745 | 1900 | 2332 | R1648A | pBC0298 |
| 0745 | 1900 | 2332 | R1648A | pBC0299 |
| 0745 | 1900 | 2332 | R1648A | pBC0300 |
| 0745 | 1900 | 2332 | R1648A | pBC0301 |
| 0745 | 1900 | 2332 | R1648A | pBC0302 |
| 0745 | 1900 | 2332 | R1648A | pBC0303 |
| 0745 | 1900 | 2332 | R1648A | pBC0304 |
| 0745 | 1900 | 2332 | R1648A | pBC0305 |
| 0745 | 1900 | 2332 | R1648A | pBC0306 |
| 0745 | 1900 | 2332 | R1648A | pBC0307 |
| 0745 | 1900 | 2332 | R1648A | pBC0308 |
| 0745 | 1900 | 2332 | R1648A | pBC0309 |
| 0745 | 1900 | 2332 | R1648A | pBC0310 |
| 0745 | 1900 | 2332 | R1648A | pBC0311 |

TABLE 21-continued

FVIII Variants Comprising Three XTEN Insertions

| XTEN insertion1 | XTEN insertion2 | XTEN insertion3 | Additional mutations | Construct ID |
|---|---|---|---|---|
| 0745 | 1900 | 2332 | R1648A | pBC0312 |
| 0745 | 1900 | 2332 | R1648A | pBC0313 |
| 0745 | 1900 | 2332 | R1648A | pBC0314 |
| 0745 | 1900 | 2332 | R1648A | pBC0315 |
| 0745 | 1900 | 2332 | R1648A | pBC0316 |
| 0745 | 1900 | 2332 | R1648A | pBC0317 |
| 0745 | 1900 | 2332 | R1648A | pBC0318 |
| 0745 | 1900 | 2332 | R1648A | pBC0319 |
| 0745 | 1900 | 2332 | R1648A | pBC0320 |
| 0018 | 0745 | 2332 | R1648A | pBC0269 |
| 0403 | 0745 | 2332 | R1648A | pBC0270 |
| 1720 | 0745 | 2332 | R1648A | pBC0271 |
| 1900 | 0745 | 2332 | R1648A | pBC0272 |
| 0403 | 0745 | 2332 | R1648A | pBC0273 |
| 1720 | 0745 | 2332 | R1648A | pBC0274 |
| 1900 | 0745 | 2332 | R1648A | pBC0275 |

TABLE 21-continued

| FVIII Variants Comprising Three XTEN Insertions | | | | |
|---|---|---|---|---|
| XTEN insertion1 | XTEN insertion2 | XTEN insertion3 | Additional mutations | Construct ID |
| 0018 | 0745 | 2332 | R1648A | pBC0276 |
| 0403 | 0745 | 2332 | R1648A | pBC0277 |
| 1720 | 0745 | 2332 | R1648A | pBC0278 |
| 1900 | 0745 | 2332 | R1648A | pBC0279 |

TABLE 22

Results of Coagulation Activity Assays for FVIII Variants Comprising Four XTEN Insertions

| Insertion 1 | | Insertion 2 | | Insertion 3 | | Insertion 4 | | | |
|---|---|---|---|---|---|---|---|---|---|
| Insertion Site | Domain | Insertion Site | Domain | Insertion Site | Domain | Insertion Site | Domain | Construct | Activity |
| 26 | A1 | 403 | A2 | 1656 | a3 region | 1720 | A3 | pSD0087 | +++ |
| 26 | A1 | 403 | A2 | 1656 | a3 region | 1900 | A3 | pSD0088 | +++ |
| 26 | A1 | 403 | A2 | 1720 | A3 | 1900 | A3 | pSD0089 | LLOQ |
| 26 | A1 | 1656 | a3 region | 1720 | A3 | 1900 | A3 | pSD0090 | ++ |
| 403 | A2 | 1656 | a3 region | 1720 | A3 | 1900 | A3 | pSD0091 | ++ |

TABLE 23

Results of Coagulation Activity Assays for Additional FVIII Variants Comprising Four XTEN insertions

| XTEN insertion1 | XTEN insertion2 | XTEN insertion3 | XTEN insertion4 | Additional mutations | Construct ID | Activity |
|---|---|---|---|---|---|---|
| 0040 | 0403 | 745 | 2332 | R1648A | LSD0057.001 | ++ |
| 0040 | 0403 | 745 | 2332 | R1648A | LSD0058.006 | ++ |
| 0018 | 0409 | 745 | 2332 | R1648A | LSD0059.002 | + |
| 0040 | 0409 | 745 | 2332 | R1648A | LSD0059.006 | + |
| 0040 | 0409 | 745 | 2332 | R1648A | LSD0060.001 | + |
| 0018 | 0409 | 745 | 2332 | R1648A | LSD0060.003 | + |
| 0040 | 1720 | 745 | 2332 | R1648A | LSD0061.002 | + |
| 0026 | 1720 | 745 | 2332 | R1648A | LSD0061.007 | ++ |
| 0018 | 1720 | 745 | 2332 | R1648A | LSD0061.008 | ++ |
| 0018 | 1720 | 745 | 2332 | R1648A | LSD0061.012 | ++ |
| 0018 | 1720 | 745 | 2332 | R1648A | LSD0062.001 | ++ |
| 0026 | 1720 | 745 | 2332 | R1648A | LSD0062.002 | ++ |
| 0018 | 1720 | 745 | 2332 | R1648A | LSD0062.006 | ++ |
| 0018 | 1900 | 745 | 2332 | R1648A | LSD0063.001 | ++ |
| 0018 | 1900 | 745 | 2332 | R1648A | LSD0064.017 | ++ |
| 0026 | 1900 | 745 | 2332 | R1648A | LSD0064.020 | ++ |
| 0040 | 1900 | 745 | 2332 | R1648A | LSD0064.021 | ++ |
| 0040 | 1905 | 745 | 2332 | R1648A | LSD0065.001 | + |
| 0018 | 1905 | 745 | 2332 | R1648A | LSD0065.014 | + |
| 0040 | 1905 | 745 | 2332 | R1648A | LSD0066.001 | + |
| 0026 | 1905 | 745 | 2332 | R1648A | LSD0066.002 | + |
| 0018 | 1905 | 745 | 2332 | R1648A | LSD0066.009 | ++ |
| 0018 | 1905 | 745 | 2332 | R1648A | LSD0066.011 | ++ |
| 0018 | 1910 | 745 | 2332 | R1648A | LSD0067.004 | ++ |
| 0018 | 1910 | 745 | 2332 | R1648A | LSD0067.005 | + |
| 0040 | 1910 | 745 | 2332 | R1648A | LSD0067.006 | + |
| 0026 | 1910 | 745 | 2332 | R1648A | LSD0067.008 | + |
| 0018 | 1910 | 745 | 2332 | R1648A | LSD0068.001 | + |
| 0026 | 1910 | 745 | 2332 | R1648A | LSD0068.002 | + |
| 0040 | 1910 | 745 | 2332 | R1648A | LSD0068.005 | + |
| 0018 | 1910 | 745 | 2332 | R1648A | LSD0068.010 | ++ |
| 0409 | 1720 | 745 | 2332 | R1648A | LSD0069.004 | + |
| 0403 | 1720 | 745 | 2332 | R1648A | LSD0069.008 | + |
| 0409 | 1720 | 745 | 2332 | R1648A | LSD0070.003 | + |
| 0403 | 1720 | 745 | 2332 | R1648A | LSD0070.004 | ++ |
| 0403 | 1720 | 745 | 2332 | R1648A | LSD0070.005 | ++ |
| 0403 | 1900 | 745 | 2332 | R1648A | LSD0071.001 | ++ |
| 0403 | 1900 | 745 | 2332 | R1648A | LSD0071.002 | + |
| 0409 | 1900 | 745 | 2332 | R1648A | LSD0071.008 | ++ |
| 0403 | 1900 | 745 | 2332 | R1648A | LSD0072.001 | ++ |

TABLE 23-continued

Results of Coagulation Activity Assays for Additional FVIII Variants Comprising Four XTEN insertions

| XTEN insertion1 | XTEN insertion2 | XTEN insertion3 | XTEN insertion4 | Additional mutations | Construct ID | Activity |
|---|---|---|---|---|---|---|
| 0403 | 1900 | 745 | 2332 | R1648A | LSD0072.002 | + |
| 0409 | 1900 | 745 | 2332 | R1648A | LSD0072.003 | + |
| 0409 | 1905 | 745 | 2332 | R1648A | LSD0073.002 | + |
| 0403 | 1905 | 745 | 2332 | R1648A | LSD0073.004 | + |
| 0403 | 1905 | 745 | 2332 | R1648A | LSD0073.006 | + |
| 0403 | 1905 | 745 | 2332 | R1648A | LSD0074.007 | ++ |
| 0409 | 1905 | 745 | 2332 | R1648A | LSD0074.010 | + |
| 0403 | 1905 | 745 | 2332 | R1648A | LSD0074.011 | + |
| 0409 | 1910 | 745 | 2332 | R1648A | LSD0075.004 | + |
| 0403 | 1910 | 745 | 2332 | R1648A | LSD0075.007 | + |
| 0403 | 1910 | 745 | 2332 | R1648A | LSD0076.002 | + |
| 0403 | 1910 | 745 | 2332 | R1648A | LSD0076.003 | + |
| 0403 | 1910 | 745 | 2332 | R1648A | pSD0093 | + |
| 1720 | 1900 | 745 | 2332 | R1648A | pSD0094 | ++ |
| 1720 | 1905 | 745 | 2332 | R1648A | pSD0095 | + |
| 1720 | 1910 | 745 | 2332 | R1648A | pSD0097 | + |
| 1720 | 1910 | 745 | 2332 | R1648A | pSD0098 | + |
| 0403 | 1656 | 1720 | 2332 | | pNL0022 | + |
| 0403 | 1656 | 1900 | 2332 | | pNL0023 | + |
| 0403 | 1720 | 1900 | 2332 | | pNL0024 | LLOQ |
| 1656 | 1720 | 1900 | 2332 | | pNL0025 | + |
| 0018 | 0403 | 1656 | 2332 | | pBC0247 | ++ |
| 0018 | 0403 | 1720 | 2332 | | pBC0248 | + |
| 0018 | 0403 | 1900 | 2332 | | pBC0249 | + |
| 0018 | 1656 | 1720 | 2332 | | pBC0250 | + |
| 0018 | 1656 | 1900 | 2332 | | pBC0251 | ++ |
| 0018 | 1720 | 1900 | 2332 | | pBC0252 | LLOQ |
| 0018 | 0403 | 0745 | 2332 | | LSD57.005 | ++ |
| 0018 | 0745 | 1720 | 2332 | | LSD62.001 | ++ |
| 0018 | 0745 | 1900 | 2332 | | pBC0262 | ++ |
| 0403 | 0745 | 1720 | 2332 | | LSD70.004 | + |
| 0403 | 0745 | 1900 | 2332 | | pBC0266 | + |
| 0745 | 1720 | 1900 | 2332 | | pBC0268 | + |
| 0188 | 1900 | 0745 | 2332 | R1648A | pCS0001 | ND |
| 0599 | 1900 | 0745 | 2332 | R1648A | pCS0002 | ND |
| 2068 | 1900 | 0745 | 2332 | R1648A | pCS0003 | ND |
| 2171 | 1900 | 0745 | 2332 | R1648A | pCS0004 | ND |
| 2227 | 1900 | 0745 | 2332 | R1648A | pCS0005 | ND |
| 2277 | 1900 | 0745 | 2332 | R1648A | pCS0006 | ND |

TABLE 24

FVIII Variants Comprising Five XTEN Insertions

| XTEN Insertion 1 | XTEN insertion 2 | XTEN Insertion 3 | XTEN Insertion 4 | XTEN Insertion 5 | Construct ID | Activity |
|---|---|---|---|---|---|---|
| 0403 | 1656 | 1720 | 1900 | 2332 | pNL0030 | LLOQ |
| 0018 | 0403 | 1656 | 1720 | 2332 | pBC0253 | + |
| 0018 | 0403 | 1656 | 1900 | 2332 | pBC0254 | + |
| 0018 | 0403 | 1720 | 1900 | 2332 | pBC0255 | LLOQ |
| 0018 | 1656 | 1720 | 1900 | 2332 | pBC0256 | + |
| 0018 | 0403 | 0745 | 1720 | 2332 | pBC0259 | + |
| 0018 | 0403 | 0745 | 1900 | 2332 | pBC0260 | + |
| 0018 | 0745 | 1720 | 1900 | 2332 | pBC0263 | + |
| 0403 | 0745 | 1720 | 1900 | 2332 | pBC0267 | LLOQ |

TABLE 25

FVIII Variants Comprising Six XTEN Insertions

| XTEN Insertion 1 | XTEN insertion 2 | XTEN Insertion 3 | XTEN Insertion 4 | XTEN Insertion 5 | XTEN Insertion 6 | Construct ID | Activity |
|---|---|---|---|---|---|---|---|
| 0018 | 0403 | 1656 | 1720 | 1900 | 2332 | pBC0257 | LLOQ |
| 0018 | 0403 | 0745 | 1720 | 1900 | 2332 | pBC0264 | LLOQ |

Chimeric Proteins: Combining Attributes of Reduced Binding to VWF and Select Insertions and Combination of XTEN to Extend Half-Life of FVIII Proteins In one aspect, the present invention is directed to extending a half-life of a Factor VIII protein using select XTEN sequences inserted into a FVIII polypeptide, wherein the Factor VIII polypeptide has reduced binding to VWF. It has been discovered that the half-life of chimeric proteins of FVIII and XTEN can be further enhanced by reducing or eliminating the clearance of the chimeric proteins by VWF receptors while selectively incorporating XTEN of defined lengths in certain insertion sites, thereby combining mutually distinct properties to create FVIII chimeric proteins with enhance pharmacokinetic properties.

Endogenous VWF associates with about 95% to about 98% of endogneous FVIII in non-covalent complexes. While endogenous VWF is a FVIII half-life limiting factor, endogenous VWF bound to a FVIII protein is also known to protect FVIII in various ways. For example, full length VWF (as a multimer having about 250 kDa) can protect FVIII from protease cleavage and FVIII activation, stabilize the FVIII heavy chain and/or light chain, and prevent clearance of FVIII by scavenger receptors. But, at the same time, endogenous VWF limits the FVIII half-life by preventing pinocytosis and by clearing FVIII-VWF complex from the system through the VWF clearance pathway. It is believed, while not bound by a theory, that endogenous VWF is a half-life limiting factor that prevents the half-life of a FVIII protein fused to a half-life extender from being longer than about two-fold of wild-type FVIII. Therefore, the present invention is directed to preventing or inhibiting interaction between endogenous VWF and a FVIII protein using a FVIII protein with reduced affinity for VWF, and then increasing the half-life of this FVIII protein by using an XTEN sequence or two, three, or at least four XTEN sequences, wherein at least one XTEN sequences is less than 144 amino acids in length or no more than 72 or 78 amino acids in length. The resulting FVIII chimeric proteins have the full benefit of half-life extension conferred by the XTEN sequence(s) as compared to wild type FVIII.

In some embodiments, the chimeric proteins provided herein are designed to reduce binding by FVIII binding agents, thereby increasing the terminal half-life of FVIII administered to a subject, while still retaining procoagulant activity. It is believed that the chimeric proteins have comparatively higher and/or sustained activity achieved by reduced active clearance of the molecule by the addition of unstructured XTEN to the FVIII coagulation factor. The clearance mechanisms to remove FVIII from the circulation have yet to be fully elucidated. Uptake, elimination, and inactivation of coagulation proteins can occur in the circulatory system as well as in the extravascular space. Coagulation factors are complex proteins that interact with a large number of other proteins, lipids, and receptors, and many of these interactions can contribute to the elimination of CFs from the circulation. VWF is an example of a FVIII binding agent that binds to FVIII. FVIII and vWF circulate in the blood as a tight, non-covalently linked complex in which VWF serves as a carrier that likely contributes to the protection of FVIII from active cleavage mechanisms, yet nevertheless results in a limitation on the terminal half-life of FVIII. For example: (i) vWF stabilizes the heterodimeric structure of FVIII; (ii) vWF protects FVIII from proteolytic degradation by phospholipid-binding proteases like activated protein C and activated FX (FXa); (iii) VWF interferes with binding of FVIII to negatively charged phospholipid surfaces exposed within activated platelets; (iv) VWF inhibits binding of FVIII to activated FIX (FIXa), thereby denying FVIII access to the FX-activating complex; and (v) VWF prevents the cellular uptake of FVIII (Lenting, P. J., et al., J Thrombosis and Haemostasis (2007) 5(7):1353-1360). While, the VWF-FVIII interaction is of high affinity (<1 nM), the complex is nevertheless in a dynamic equilibrium, such that a small but significant portion of the FVIII molecules (5-8%) circulate as a free protein (Leyte A, et al., Biochem J (1989) 257: 679-683; Noe D A. Haemostasis (1996) 26: 289-303). As such, a portion of native FVIII is unprotected by VWF, allowing active clearance mechanisms to remove the unprotected FVIII from the circulation.

In another aspect, the invention provides FVIII chimeric proteins that associate with VWF but nevertheless but have enhanced protection from active clearance vWF receptors. In one embodiment, the invention provides a FVIII chimeric protein with enhanced protection conferred by the incorporation of four or more XTEN at four or more locations within the FVIII molecule, wherein the XTEN interferes with the interaction of the chimeric protein with those vWF clearance receptors with the result that the pharmacokinetic properties of the chimeric protein are enhanced compared to the corresponding FVIII not linked to XTEN. In another embodiment, the invention provides chimeric proteins that have reduced binding affinity with VWF of at least 5% less, or about 10%, or about 20%, or about 40%, or about 50%, or about 60%, or about 70% less, but are nevertheless configured to have enhanced protection from active clearance receptors conferred by the incorporation of XTEN at one or more locations within the FVIII molecule or at four or more locations within the FVIII molecule, wherein the XTEN interfere with the interaction of factor VIII with those receptors. In the foregoing embodiments, the chimeric proteins have an increased terminal half-life of at least about 12 h, or 24 h, or 48 h, or 72 h, or 96 h, or 120 h, or 144 h, or 7 days, or 10 days, or 14 days, or 21 days compared to the FVIII not linked to XTEN. Also provided herein is a method to create chimeric proteins with reduced clearance wherein the chimeric proteins created with the multiple XTEN insertions are evaluated for inhibition of binding to clearance receptors, compared to FVIII not linked to XTEN, using in vitro binding assays or in vivo pharmacokinetic models described herein or other assays known in the art, and selecting those that demonstrate reduced binding yet retain procoagulant FVIII activity. Provided herein are non-limiting examples of XTEN insertion points within the factor VIII sequence. Using such insertion points, chimeric proteins can have configurations with multiple XTEN inserted with about 100, or about 200, or about 300, or about 400, or about 500 amino acids of the FVIII component of the chimeric protein separating at least four XTEN to further increase the protection against active clearance mechanisms and, hence, increase the terminal half-life of the FVIII. Not to be bound by a particular theory, the XTEN of the chimeric FVIII compositions with high net charge (e.g., chimeric proteins comprising AE family XTEN) are expected to have less non-specific interactions with various negatively-charged surfaces such as blood vessels, tissues, or various receptors, which would further contribute to reduced active clearance. Conversely, the XTEN of the chimeric proteins with a low (or no) net charge (e.g., chimeric proteins comprising AG family XTEN) are expected to have a higher degree of interaction with surfaces that, while contributing to active clearance, can potentiate the activity of the associated coagulation factor, given the known contribution of cell (e.g., platelets) and vascular surfaces to the coagulation process and the intensity of activation of coagulation factors (Zhou, R., et al., Biomaterials (2005) 26(16):2965-2973; London, F., et al. Biochemistry (2000) 39(32):9850-9858). The invention, in part, takes advantage of the fact that certain ligands wherein reduced binding to a clearance receptor, either as a result of a decreased on-rate or an increased off-rate, may be effected by the obstruction of a receptor site by an inserted XTEN forming random coil, resulting in the reduced binding. The choice of the particular configuration of the chimeric protein can be tested by methods disclosed herein to confirm those configurations that reduce the degree of binding to a clearance receptor such that a reduced rate of active clearance is achieved. In one embodiment, the chimeric protein comprises a FVIII-XTEN sequence that has one or more XTEN inserted, wherein the terminal half-life of the chimeric protein is increased at least about two-fold, or at least about three-fold, or at least about four-fold, or at least about five-fold, or at least about six-fold, or at least about eight-fold, or at least about ten-fold, or at least about twenty-fold compared to a FVIII not linked to an XTEN.

Spacers

In some embodiments, the chimeric proteins comprise spacers between the XTEN sequences and the FVIII sequences.

Accordingly, in some embodiments the chimeric protein has the formula:

(XTEN)t-(S)a-(A1)-(S)b-(XTEN)u-(S)b-(A2)-(S)c-(XTEN)v-(S)c-(B)-(S)d-(XTEN)w-(S)d-(A3)-(S)e-(XTEN)x-(S)e-(C1)-(S)f-(XTEN)y-(S)f-(C2)-(S)g-(XTEN)z wherein independently for each occurrence, A1 is an A1 domain of FVIII; A2 is an A2 domain of FVIII; A3 is an A3 domain of FVIII; B is a B domain of FVIII which can be a fragment or a splice variant of the B domain and can be present or absent; C1 is a C1 domain of FVIII; C2 is a C2 domain of FVIII; S is a spacer sequence having between 1 to about 50 amino acid residues that can optionally include a cleavage sequence or amino acids compatible with restrictions sites; a is either 0 or 1; b is either 0 or 1; c is either 0 or 1; d is either 0 or 1; e is either 0 or 1; f is either 0 or 1; g is either 0 or 1; t is either 0 or 1; u is either 0 or 1; v is either 0 or 1; w is 0 or 1, x is either 0 or 1; y is either 0 or 1; z is either 0 or 1 with the proviso that t+u+v+w+x+y+z≥1; and XTEN is an extended recombinant polypeptide as described herein. In some embodiments, the spacer sequence is glycine or a sequence selected from Table 16.

TABLE 16

Spacer Sequences Compatible with Restriction Sites

| Spacer Sequence | Restriction Enzyme |
|---|---|
| GSPG (SEQ ID NO: 89) | BsaI |
| ETET (SEQ ID NO: 90) | BsaI |
| PGSSS (SEQ ID NO 91) | BbsI |
| GAP | AscI |
| GPA | FseI |
| GPSGP (SEQ ID NO: 92) | SfiI |
| AAA | SacII |
| TG | AgeI |
| GT | KpnI |
| GAGSPGAETA (SEQ ID NO: 93) | SfiI |
| ASS | XhoI |

In another aspect, the invention provides chimeric proteins configured with one or more spacer sequences incorporated into or adjacent to the XTEN that are designed to incorporate or enhance a functionality or property to the chimeric proteins, or as an aid in the assembly or manufacture of the fusion protein compositions. Such properties include, but are not limited to, inclusion of cleavage sequence(s) to permit release of components, inclusion of amino acids compatible with nucleotide restrictions sites to permit linkage of XTEN-encoding nucleotides to FVIII-encoding nucleotides or that facilitate construction of expression vectors, and linkers designed to reduce steric hindrance in regions of chimeric fusion proteins.

In a particular embodiment, the chimeric proteins comprises one or more spacer sequences linked at the junction(s) between the FVIII polypeptide and the one or more XTEN incorporated into the chimeric protein, wherein the spacer sequences comprise amino acids that are compatible with nucleotides encoding restriction sites. In another embodiment, the chimeric protein comprises one or more spacer sequences linked at the junction(s) between the FVIII polypeptide and the one more XTEN incorporated into the chimeric protein wherein the spacer sequences comprise amino acids that are compatible with nucleotides encoding restriction sites and the amino acids and the one more spacer sequence amino acids are chosen from glycine (G), alanine (A), serine (S), threonine (T), glutamate (E), and proline (P). In another embodiment, the chimeric protein comprises one or more spacer sequences linked at the junction(s) between the FVIII polypeptide and one more XTEN incorporated into the chimeric protein wherein the spacer sequences comprise amino acids that are compatible with nucleotides encoding restriction sites and the one more spacer sequences are chosen from the sequences of Table 16. The exact sequence of each spacer sequence is chosen to be compatible with cloning sites in expression vectors that are used for a particular chimeric construct. In one embodiment, the spacer sequence has properties compatible with XTEN. In one embodiment, the spacer sequence is GAGSPGAETA (SEQ ID NO: 93). For XTEN sequences that are incorporated internal to the FVIII sequence, each XTEN can be flanked by two spacer sequences comprising amino acids compatible with restriction sites, while XTEN attached to the N- or C-terminus can have only a single spacer sequence at the junction of the two components and another at the opposite end for incorporation into the vector. As would be apparent to one of ordinary skill in the art, the spacer sequences comprising amino acids compatible with restriction sites that are internal to FVIII could be omitted from the construct when an entire chimeric gene is synthetically generated.

Once the gene that encodes the XTEN of desired length and properties is selected, it is genetically fused at the desired location to the nucleotides encoding the FVIII polypeptide by cloning it into the construct adjacent and in frame with the gene coding for FVIII, or alternatively between nucleotides encoding adjacent domains of the FVIII, or alternatively within a sequence encoding a given FVIII domain, or alternatively in frame with nucleotides encoding a spacer/cleavage sequence linked to a terminal XTEN. The spacer polynucleotides can optionally comprise sequences encoding cleavage sequences. As will be apparent to those of skill in the art, multiple permutations of FVIII domains and inserted XTEN are possible.

In some embodiments, the spacer sequences comprise additional XTEN amino acids. For instance, in certain working examples provided herein, a 36 amino acid XTEN sequence (i.e. 36AE; SEQ ID NO:22) is linked to FVIII via one spacer on each end of the XTEN sequence. The amino acid sequence of the spacer on the N-terminus of the XTEN sequence is GAP, and the amino acid sequence of the C-terminus of the XTEN sequence is ASS. These spacer sequences comprise additional XTEN amino acids. Thus, the chimeric protein can be considered to have either a 42 amino acid XTEN sequence (i.e., the 42AE XTEN of SEQ ID NO: 36) or can be considered to have a 36 amino acid XTEN sequence (i.e., the 36 AE XTEN of SEQ ID NO:22) linked to FVIII via a 3-amino acid spacers on each end of the XTEN.

Similarly, a chimeric protein can comprise a 72 amino acid XTEN with a 3 amino acid spacer on the N-terminus of the XTEN and a 3 amino acid spacer on the C-terminus of the XTEN, wherein both spacers comprise additional XTEN amino acids. Such a chimeric protein can be considered to have either a 78 amino acid XTEN sequence (i.e., the 78AE XTEN of SEQ ID NO: 24) or can be considered to have a 72 amino acid XTEN sequence (i.e., the 72 AE XTEN of SEQ ID NO: 23) linked to FVIII via a 3-amino acid spacers on each end of the XTEN.

Ig Constant Region or a Portion Thereof

The chimeric FVIII proteins can further comprise an Ig constant region or a portion thereof. The Ig constant region or a portion thereof can further improve pharmacokinetic or pharmacodynamic properties of the chimeric FVIII proteins. In certain embodiments, the Ig constant region or a portion thereof extends a half-life of a molecule fused to the Ig constant region or a portion thereof.

An Ig constant region is comprised of domains denoted CH (constant heavy) domains (CH1, CH2, etc.). Depending on the isotype, (i.e. IgG, IgM, IgA, IgD, or IgE), the constant region can be comprised of three or four CH domains. Some isotypes (e.g. IgG) constant regions also contain a hinge region. See Janeway et al. 2001, *Immunobiology*, Garland Publishing, N.Y., N.Y.

An Ig constant region or a portion thereof for producing the chimeric FVIII proteins can be obtained from a number of different sources. In some embodiments, an Ig constant region or a portion thereof is derived from a human Ig. It is understood, however, that the Ig constant region or a portion thereof can be derived from an Ig of another mammalian species, including for example, a rodent (e.g. a mouse, rat, rabbit, guinea pig) or non-human primate (e g. chimpanzee, macaque) species. Moreover, the Ig constant region or a portion thereof can be derived from any Ig class, including IgM, IgG, IgD, IgA, and IgE, and any Ig isotype, including IgG1, IgG2, IgG3, and IgG4. In one embodiment, the human isotype IgG1 is used.

A variety of the Ig constant region gene sequences (e.g., human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g., hinge, CH2, and/or CH3 sequences, or portions thereof) can be derived from these sequences using art recognized techniques. The genetic material obtained using any of the foregoing methods may then be altered or synthesized to obtain polypeptides of the present invention. It will further be appreciated that the scope of this invention encompasses alleles, variants and mutations of constant region DNA sequences.

The sequences of the Ig constant region or a portion thereof can be cloned, e.g., using the polymerase chain reaction and primers which are selected to amplify the domain of interest. To clone a sequence of the Ig constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. PCR also can be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

An Ig constant region used herein can include all domains and the hinge region or portions thereof. In one embodiment, the Ig constant region or a portion thereof comprises CH2 domain, CH3 domain, and a hinge region, i.e., an Fc region or an FcRn binding partner.

As used herein, the term "Fc region" is defined as the portion of a polypeptide which corresponds to the Fc region of native Ig, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence).

In one embodiment, the "Fc region" refers to the portion of a single Ig heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an Ig constant region, depending on the Ig isotype can include the CH2, CH3, and CH4 domains, as well as the hinge region. Chimeric FVIII proteins comprising an Fc region of an Ig bestow several desirable properties on a chimeric FVIII protein including increased stability, increased serum half-life (see Capon et al., 1989, *Nature* 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

An Ig constant region or a portion thereof can be an FcRn binding partner. FcRn is active in adult epithelial tissues and expressed in the lumen of the intestines, pulmonary airways, nasal surfaces, vaginal surfaces, colon and rectal surfaces (U.S. Pat. No. 6,485,726). An FcRn binding partner is a portion of an Ig that binds to FcRn.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other Ig classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners useful in the present invention encompass molecules that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of Igs or Ig fragments, or regions, are all based on Kabat et al. 1991, Sequences of Proteins of Immunological Interest, U.S. Department of Public Health, Bethesda, Md.

Fc regions or FcRn binding partners bound to FcRn can be effectively shuttled across epithelial barriers by FcRn, thus providing a non-invasive means to systemically administer a desired therapeutic molecule. Additionally, fusion proteins comprising an Fc region or an FcRn binding partner are endocytosed by cells expressing the FcRn. But instead of being marked for degradation, these fusion proteins are recycled out into circulation again, thus increasing the in vivo half-life of these proteins. In certain embodiments, the portions of Ig constant regions are an Fc region or an FcRn binding partner that typically associates, via disulfide bonds and other non-specific interactions, with another Fc region or another FcRn binding partner to form dimers and higher order multimers.

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the chimeric protein can be administered invasively, e.g., subcutaneously, intravenously.

An FcRn binding partner region is a molecule or a portion thereof that can be specifically bound by the FcRn receptor with consequent active transport by the FcRn receptor of the Fc region. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ $M^{-1}$, or higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

In certain embodiments, a chimeric FVIII protein comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In another embodiment, the "Fc region" includes an amino acid sequence of an Fc domain or derived from an Fc domain. In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain) In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain) In a particular embodiment, an Fc region comprises or consists of amino acids corresponding to EU numbers 221 to 447.

The Fc regions denoted as F, F1, or F2 herein can be obtained from a number of different sources. In one embodiment, an Fc region of the polypeptide is derived from a human Ig. It is understood, however, that an Fc region may be derived from an Ig of another mammalian species, including for example, a rodent (e.g. a mouse, rat, rabbit, or guinea pig) or non-human primate (e.g. chimpanzee, macaque) species. Moreover, the polypeptide of the Fc domains or portions thereof may be derived from any Ig class, including IgM, IgG, IgD, IgA and IgE, and any Ig isotype, including IgG1, IgG2, IgG3 and IgG4. In another embodiment, the human isotype IgG1 is used.

In certain embodiments, the Fc variant confers a change in at least one effector function imparted by an Fc region comprising said wild-type Fc domain (e.g., an improvement or reduction in the ability of the Fc region to bind to Fc receptors (e.g. FcγRI, FcγRII, or FcγRIII) or complement proteins (e.g. C1 q), or to trigger antibody-dependent cytotoxicity (ADCC), phagocytosis, or complement-dependent cytotoxicity (CDCC)). In other embodiments, the Fc variant provides an engineered cysteine residue.

The Fc regions can be art-recognized Fc variants which are known to impart a change (e.g., an enhancement or reduction) in effector function and/or FcR or FcRn binding. Specifically, a binding molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) can be made at one or more of the disclosed amino acid positions. In another embodiment, a different change at one or more of the disclosed amino acid positions (e.g., the different substitution of one or more amino acid position disclosed in the art) may be made.

The Fc region or FcRn binding partner of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc γ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific embodiment incorporates the N297A mutation, removing a highly conserved N-glycosylation site. In addition to alanine other amino acids can be substituted for the wild type amino acids at the positions specified above. Mutations can be introduced singly into Fc giving rise to more than one hundred Fc regions distinct from the native Fc. Additionally, combinations of two, three, or more of these individual mutations can be introduced together, giving rise to hundreds more Fc regions. Moreover, one of the Fc region of a construct of the invention can be mutated and the other Fc region of the construct not mutated at all, or they both can be mutated but with different mutations.

Certain of the above mutations can confer new functionality upon the Fc region or FcRn binding partner. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for FcRn may be increased beyond that of wild type in some instances. This increased affinity can reflect an increased "on" rate, a decreased "off" rate or both an increased "on" rate and a decreased "off" rate. Examples of mutations believed to impart an increased affinity for FcRn include, but not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In one embodiment, the Ig constant region or a portion thereof, e.g, an Fc region, is a polypeptide including the sequence PKNSSMISNTP (SEQ ID NO: 52) and optionally further including a sequence selected from HQSLGTQ (SEQ ID NO: 53), HQNLSDGK (SEQ ID NO: 54), HQNISDGK (SEQ ID NO: 55), or VISSHLGQ (SEQ ID NO: 56) (U.S. Pat. No. 5,739,277).

In another embodiment, the immunoglobulin constant region or a portion thereof comprises an amino acid sequence in the hinge region or a portion thereof that forms one or more disulfide bonds with another immunoglobulin constant region or a portion thereof. The hinge region or a portion thereof can further be linked to one or more domains of CH1, CH2, CH3, a fragment thereof, and any combinations thereof. In a particular embodiment, the immunoglobulin constant region or a portion thereof is a hinge region and CH2.

In certain embodiments, the Ig constant region or a portion thereof is hemi-glycosylated. For example, the chimeric protein comprising two Fc regions or FcRn binding partners may contain a first, glycosylated, Fc region (e.g., a glycosylated CH2 region) or FcRn binding partner and a second, aglycosylated, Fc region (e.g., an aglycosylated CH2 region) or FcRn binding partner. In one embodiment, a linker may be interposed between the glycosylated and aglycosylated Fc regions. In another embodiment, the Fc region or FcRn binding partner is fully glycosylated, i.e., all of the Fc regions are glycosylated. In other embodiments, the Fc region may be aglycosylated, i.e., none of the Fc moieties are glycosylated.

In certain embodiments, a chimeric FVIII protein comprises an amino acid substitution to an Ig constant region or a portion thereof (e.g., Fc variants), which alters the antigen-independent effector functions of the Ig constant region, in particular the circulating half-life of the protein.

Such proteins exhibit either increased or decreased binding to FcRn when compared to proteins lacking these substitutions and, therefore, have an increased or decreased half-life in serum, respectively. Fc variants with improved affinity for FcRn are anticipated to have longer serum half-lives, and such molecules have useful applications in methods of treating mammals where long half-life of the administered polypeptide is desired, e.g., to treat a chronic disease or disorder (see, e.g., U.S. Pat. Nos. 7,348,004, 7,404,956, and 7,862,820). In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the chimeric protein of the invention exhibit reduced transport across the epithelium of kidney glomeruli from the vasculature. In another embodiment, the chimeric protein of the invention exhibit reduced transport across the blood brain barrier (BBB) from the brain, into the vascular space. In one embodiment, a protein with altered FcRn binding comprises at least one Fc region or FcRn binding partner (e.g, one or two Fc regions or FcRn binding partners) having one or more amino acid substitutions within the "FcRn binding loop" of an Ig constant region. The FcRn binding loop is comprised of amino acid residues 280-299 (according to EU numbering) of a wild-type, full-length, Fc region. In other embodiments, an Ig constant region or a portion thereof in a chimeric protein of the invention having altered FcRn binding affinity comprises at least one Fc region or FcRn binding partner having one or more amino acid substitutions within the 15 Å FcRn "contact zone." As used herein, the term 15 Å FcRn "contact zone" includes residues at the following positions of a wild-type, full-length Fc moiety: 243-261, 275-280, 282-293, 302-319, 336-348, 367, 369, 372-389, 391, 393, 408, 424, 425-440 (EU numbering). In other embodiments, a Ig constant region or a portion thereof of the invention having altered FcRn binding affinity comprises at least one Fc region or FcRn binding partner having one or more amino acid substitutions at an amino acid position corresponding to any one of the following EU positions: 256, 277-281, 283-288, 303-309, 313, 338, 342, 376, 381, 384, 385, 387, 434 (e.g., N434A or N434K), and 438. Exemplary amino acid substitutions which altered FcRn binding activity are disclosed in International PCT Publication No. WO05/047327 which is incorporated by reference herein.

An Fc region or FcRn binding partner can also comprise an art recognized amino acid substitution which alters the glycosylation of the chimeric protein. For example, the Fc region or FcRn binding partner of the chimeric FVIII protein can comprise an Fc region having a mutation leading to reduced glycosylation (e.g., N- or O-linked glycosylation) or can comprise an altered glycoform of the wild-type Fc moiety (e.g., a low fucose or fucose-free glycan).

In one embodiment, an unprocessed chimeric FVIII protein can comprise a genetically fused Fc region (i.e., scFc region) having two or more of its constituent Ig constant region or a portion thereof independently selected from the Ig constant region or a portion thereof described herein. In one embodiment, the Fc regions of a dimeric Fc region are the same. In another embodiment, at least two of the Fc regions are different. For example, the Fc regions or FcRn binding partners of the proteins of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc regions or FcRn binding partners of the protein of the invention can differ in sequence at one or more amino acid positions. For example, at least two of the Fc regions or FcRn binding partners may differ at about 5 amino acid positions (e.g., 1, 2, 3, 4, or 5 amino acid positions), about 10 positions, about 15 positions, about 20 positions, about 30 positions, about 40 positions, or about 50 positions).

Linkers

The chimeric FVIII proteins provided here can further comprise one or more linkers. One type of the linkers is a cleavable linker, which can be cleaved by various proteases when administered to a subject in vivo, e.g., at a site of coagulation. In one embodiment, the cleavable linker allows cleavage of moiety, e.g., an XTEN, from the chimeric protein. Another type of the linkers is a processable linker, which contains an intracellular cleavage site and thus can be cleaved by an intracellular processing enzyme in a host cell, allowing convenient expression of a polypeptide and formation of a chimeric protein.

One or more linkers can be present between any two proteins in the chimeric protein. In one embodiment, a chimeric protein comprises (i) an XTEN sequence, and (ii) a FVIII protein, wherein the XTEN sequence is linked to the FVIII protein by a linker, e.g., a cleavable linker.

In certain embodiments, a chimeric protein comprises (i) an XTEN sequence, (ii) a Ig constant region or a portion thereof (e.g., a Fc region), and (iii) a FVIII protein, wherein the XTEN sequence is linked to the FVIII protein and/or the Ig constant region or a portion thereof by an optional linker, e.g., a cleavable linker. The FVIII protein can also be linked to the Ig constant region or a portion thereof by a linker, e.g., a cleavable linker.

The linker useful in the chimeric FVIII proteins provided herein can comprise any organic molecule. In one embodiment, the linker comprises a polymer, e.g., polyethylene glycol (PEG) or hydroxyethyl starch (HES). In another embodiment, the linker comprises an amino acids sequence. The linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Examples of linkers are well known in the art. In one embodiment, the linker comprises the sequence $G_n$. The linker can comprise the sequence $(GA)_n$. The linker can comprise the sequence $(GGS)_n$. In other embodiments, the linker comprises $(GGGS)_n$(SEQ ID NO: 57). In still other embodiments, the linker comprises the sequence $(GGS)_n$ $(GGGGS)_n$ (SEQ ID NO: 58). In these instances, n may be an integer from 1-100. In other instances, n may be an integer from 1-20, i.e., 1, 2, 3, 4, 5, 6, 7, 8, 9, 10, 11, 12, 13, 14, 15, 16, 17, 18, 19, or 20. Examples of linkers include, but are not limited to, GGG, SGGSGGS (SEQ ID NO: 59), GGSGGSGGSGGSGGG (SEQ ID NO: 60), GGSGGSGGGGSGGGGS (SEQ ID NO: 61), GGSGGSGGSGGSGGSGGS (SEQ ID NO: 62), or GGGGSGGGGSGGGGS (SEQ ID NO: 63). The linker does not eliminate or diminish the clotting activity of Factor VIII. Optionally, the linker enhances the activity of Factor VIII protein.

In one embodiment, the linker useful for the chimeric protein is 15-25 amino acids long. In another embodiment, the linker useful for the chimeric protein is 15-20 amino acids long. In some embodiments, the linker for the chimeric protein is 10-25 amino acids long. In other embodiments, the linker for the chimeric protein is 15 amino acids long. In still other embodiments, the linker for the chimeric protein is $(GGGGS)_n$ (SEQ ID NO: 64) where G represents glycine, S represents serine and n is an integer from 1-20.

Cleavage Sites

The linker can also incorporate a moiety capable of being cleaved either chemically (e.g., hydrolysis of an ester bond), enzymatically (i.e., incorporation of a protease cleavage sequence), or photolytically (e.g., a chromophore such as 3-amino-3-(2-nitrophenyl) proprionic acid (ANP)) in order to release one molecule from another.

In one embodiment, the linker is a cleavable linker. The cleavable linkers can comprise one or more cleavage sites at the N-terminus or C-terminus or both. In another embodiment, the cleavable linker consists essentially of or consists of one or more cleavable sites. In other embodiments, the cleavable linker comprises heterologous amino acid linker sequences described herein or polymers and one or more cleavable sites.

In certain embodiments, a cleavable linker comprises one or more cleavage sites that can be cleaved in a host cell (i.e., intracellular processing sites). Non limiting examples of the cleavage site include RRRR (SEQ ID NO: 9), RKRRKR (SEQ ID NO: 10), and RRRRS (SEQ ID NO: 11).

In other embodiments, a cleavable linker comprises one or more cleavage sites that are cleaved by a protease after a chimeric protein comprising the cleavable linker is administered to a subject. In one embodiment, the cleavage site is cleaved by a protease selected from the group consisting of factor XIa, factor XIIa, kallikrein, factor VIIa, factor IXa, factor Xa, factor IIa (thrombin), Elastase-2, MMP-12, MMP-13, MMP-17, and MMP-20. In another embodiment, the cleavage site is selected from the group consisting of a FXIa cleavage site (e.g., KLTR↓AET (SEQ ID NO: 65)), a FXIa cleavage site (e.g, DFTR↓VVG (SEQ ID NO: 66)), a FXIIa cleavage site (e.g., TMTR↓IVGG (SEQ ID NO: 67)), a Kallikrein cleavage site (e.g., SPFR↓STGG (SEQ ID NO: 68)), a FVIIa cleavage site (e.g., LQVR↓IVGG (SEQ ID NO: 69)), a FIXa cleavage site (e.g., PLGR↓IVGG (SEQ ID NO: 70)), a FXa cleavage site (e.g., IEGR↓TVGG (SEQ ID NO: 71)), a FIIa (thrombin) cleavage site (e.g, LTPR↓SLLV (SEQ ID NO: 72)), a Elastase-2 cleavage site (e.g, LGPV↓SGVP (SEQ ID NO: 73)), a Granzyme-B cleavage (e.g, VAGD↓SLEE (SEQ ID NO: 74)), a MMP-12 cleavage site (e.g., GPAG↓LGGA (SEQ ID NO: 75)), a MMP-13 cleavage site (e.g., GPAG↓LRGA (SEQ ID NO: 76)), a MMP-17 cleavage site (e.g., APLG↓LRLR (SEQ ID NO: 77)), a MMP-20 cleavage site (e.g., PALP↓LVAQ (SEQ ID NO: 78)), a TEV cleavage site (e.g., ENLYFQ↓G (SEQ ID NO: 79)), a Enterokinase cleavage site (e.g., DDDK↓IVGG (SEQ ID NO: 80)), a Protease 3C (PRESCISSION™) cleavage site (e.g., LEVLFQ↓GP (SEQ ID NO: 81)), and a Sortase A cleavage site (e.g., LPKT↓GSES) (SEQ ID NO: 82). In certain embodiments, the FXIa cleavage sites include, but are not limited to, e.g., TQSFNDFTR (SEQ ID NO: 83) and SVSQTSKLTR (SEQ ID NO: 84). Non-limiting exemplary thrombin cleavage sites include, e.g., DFLAEGGGVR (SEQ ID NO: 85), TTKIKPR (SEQ ID NO: 86), or LVPRG (SEQ ID NO: 87), and a sequence comprising, consisting essentially of, or consisting of ALRPR (SEQ ID NO: 51) (e.g., ALRPRVVGGA (SEQ ID NO: 88)).

In a specific embodiment, the cleavage site is TLDPRS-FLLRNPNDKYEPFWEDEEK (SEQ ID NO: 8).

Polynucleotides, Vectors, and Host Cells

Also provided in the invention is a polynucleotide encoding (a) a FVIII polypeptide and an XTEN sequence, wherein the FVIII polypeptide has reduced affinity for vWF or (b) a FVIII polypeptide and at least four XTEN sequences.

In some embodiments, a chimeric protein comprising two polypeptide chains or three polypeptide chains can be encoded by a single polynucleotide chain, and then processed into two or three (or more) polypeptide chains. In yet other embodiments, a chimeric protein comprising these polypeptide chains can be encoded by two or three polynucleotide chains.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the invention will include polynucleotides encoding the chimeric protein described herein. In one embodiment, one or more of the coding sequences for the FVIII polypeptide, the XTEN, or both are operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence.

Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired protein or polypeptide.

A gene expression control sequence as used herein is any regulatory nucleotide sequence, such as a promoter sequence or promoter-enhancer combination, which facilitates the efficient transcription and translation of the coding nucleic acid to which it is operably linked. The gene expression control sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression control sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlue Script. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids may be custom designed using standard molecular biology techniques to remove and/or add specific fragments of DNA.

In one insect expression system that may be used to produce the proteins of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example, the polyhedron gene) of the virus and placed under control of an ACNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (see, e.g., Smith et al. (1983) *J Virol* 46:584; U.S. Pat. No. 4,215,051). Further examples of this expression system may be found in Ausubel et al., eds. (1989) Current Protocols in Molecular Biology, Vol. 2, Greene Publish. Assoc. & Wiley Interscience.

Another system which can be used to express the proteins of the invention is the glutamine synthetase gene expression system, also referred to as the "GS expression system" (Lonza Biologics PLC, Berkshire UK). This expression system is described in detail in U.S. Pat. No. 5,981,216.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. See, e.g., Logan & Shenk (1984) *Proc Natl Acad Sci USA* 81:3655). Alternatively, the vaccinia 7.5 K promoter may be used. See, e.g., Mackett et al. (1982) *Proc Natl Acad Sci USA* 79:7415; Mackett et al. (1984) *J Virol* 49:857; Panicali et al. (1982) *Proc Natl Acad Sci USA* 79:4927.

To increase efficiency of production, the polynucleotides can be designed to encode multiple units of the protein of the invention separated by enzymatic cleavage sites. The resulting polypeptide can be cleaved (e.g., by treatment with the appropriate enzyme) in order to recover the polypeptide units. This can increase the yield of polypeptides driven by a single promoter. When used in appropriate viral expression systems, the translation of each polypeptide encoded by the mRNA is directed internally in the transcript; e.g., by an internal ribosome entry site, IRES. Thus, the polycistronic construct directs the transcription of a single, large polycistronic mRNA which, in turn, directs the translation of multiple, individual polypeptides. This approach eliminates the production and enzymatic processing of polyproteins and may significantly increase the yield of polypeptides driven by a single promoter.

Vectors used in transformation will usually contain a selectable marker used to identify transformants. In bacterial systems, this can include an antibiotic resistance gene such as ampicillin or kanamycin. Selectable markers for use in cultured mammalian cells include genes that confer resistance to drugs, such as neomycin, hygromycin, and methotrexate. The selectable marker may be an amplifiable selectable marker. One amplifiable selectable marker is the dihydrofolate reductase (DHFR) gene. Simonsen C C et al. (1983) *Proc Natl Acad Sci USA* 80:2495-9. Selectable markers are reviewed by Thilly (1986) Mammalian Cell Technology, Butterworth Publishers, Stoneham, Mass., and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, U.S. Pat. No. 4,713,339).

The expression vectors can encode for tags that permit easy purification of the recombinantly produced protein. Examples include, but are not limited to, vector pUR278 (Ruther et al. (1983) *EMBO J* 2:1791), in which coding sequences for the protein to be expressed may be ligated into the vector in frame with the lac z coding region so that a tagged fusion protein is produced; pGEX vectors may be used to express proteins of the invention with a glutathione S-transferase (GST) tag. These proteins are usually soluble and can easily be purified from cells by adsorption to glutathione-agarose beads followed by elution in the presence of free glutathione. The vectors include cleavage sites (thrombin or Factor Xa protease or PRESCISSION PROTEASE™ (Pharmacia, Peapack, N.J.)) for easy removal of the tag after purification.

The expression vector or vectors are then transfected or co-transfected into a suitable target cell, which will express the polypeptides. Transfection techniques known in the art include, but are not limited to, calcium phosphate precipitation (Wigler et al. (1978) *Cell* 14:725), electroporation (Neumann et al. (1982) *EMBO J* 1:841), and liposome-based reagents. A variety of host-expression vector systems may be utilized to express the proteins described herein including both prokaryotic and eukaryotic cells. These include, but are not limited to, microorganisms such as bacteria (e.g., *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems, including mammalian cells (e.g., HEK 293, CHO, Cos, HeLa, HKB11, and BHK cells).

In one embodiment, the host cell is a eukaryotic cell. As used herein, a eukaryotic cell refers to any animal or plant cell having a definitive nucleus. Eukaryotic cells of animals include cells of vertebrates, e.g., mammals, and cells of invertebrates, e.g., insects. Eukaryotic cells of plants specifically can include, without limitation, yeast cells. A eukaryotic cell is distinct from a prokaryotic cell, e.g., bacteria.

In certain embodiments, the eukaryotic cell is a mammalian cell. A mammalian cell is any cell derived from a mammal Mammalian cells specifically include, but are not limited to, mammalian cell lines. In one embodiment, the mammalian cell is a human cell. In another embodiment, the mammalian cell is a HEK 293 cell, which is a human embryonic kidney cell line. HEK 293 cells are available as CRL-1533 from American Type Culture Collection, Manassas, Va., and as 293-H cells, Catalog No. 11631-017 or 293-F cells, Catalog No. 11625-019 from Invitrogen (Carlsbad, Calif.). In some embodiments, the mammalian cell is a PER.C6® cell, which is a human cell line derived from retina. PER.C6® cells are available from Crucell (Leiden, The Netherlands). In other embodiments, the mammalian cell is a Chinese hamster ovary (CHO) cell. CHO cells are available from American Type Culture Collection, Manassas, Va. (e.g., CHO-K1; CCL-61). In still other embodiments, the mammalian cell is a baby hamster kidney (BHK) cell. BHK cells are available from American Type Culture Collection, Manassas, Va. (e.g., CRL-1632). In some embodiments, the mammalian cell is a HKB11 cell, which is a hybrid cell line of a HEK293 cell and a human B cell line. Mei et al., *Mol. Biotechnol.* 34(2): 165-78 (2006).

In one embodiment, a plasmid encoding a chimeric protein comprising a FVIII polypeptide and an XTEN and a selectable marker, e.g., zeocin resistance, are transfected into HEK 293 cells, for production of a chimeric protein.

In one embodiment, a plasmid encoding a chimeric protein comprising a FVIII polypeptide with reduced affinity for VWF and an XTEN and a selectable marker, e.g., zeocin resistance, are transfected into HEK 293 cells, for production of a chimeric protein.

In one embodiment, a plasmid encoding a chimeric protein comprising a FVIII polypeptide and at least four XTENs and a selectable marker, e.g., zeocin resistance, are transfected into HEK 293 cells, for production of a chimeric protein.

In still other embodiments, transfected cells are stably transfected. These cells can be selected and maintained as a stable cell line, using conventional techniques known to those of skill in the art.

Host cells containing DNA constructs of the protein are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals, and growth factors. Optionally, the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment, the medium is CD293 (Invitrogen, Carlsbad, Calif.). In another embodiment, the medium is CD17 (Invitrogen, Carlsbad, Calif.). Selection of a medium appropriate for the particular cell line used is within the level of those ordinary skilled in the art.

As used herein, culturing refers to maintaining living cells in vitro for at least a definite time. Maintaining can, but need not include, an increase in population of living cells. For example, cells maintained in culture can be static in population, but still viable and capable of producing a desired product, e.g., a recombinant protein or recombinant fusion protein. Suitable conditions for culturing eukaryotic cells are well known in the art and include appropriate selection of culture media, media supplements, temperature, pH, oxygen saturation, and the like. For commercial purposes, culturing can include the use of any of various types of scale-up systems including shaker flasks, roller bottles, hollow fiber bioreactors, stirred-tank bioreactors, airlift bioreactors, Wave bioreactors, and others.

In one aspect, the present invention is directed to a method of expressing, making, or producing the chimeric protein of the invention comprising a) transfecting a host cell comprising a polynucleotide encoding the chimeric protein and b) culturing the host cell in a culture medium under a condition suitable for expressing the chimeric protein, wherein the chimeric protein is expressed.

In further embodiments, the protein product containing the FVIII protein linked to an XTEN sequence is secreted into the media. Media is separated from the cells, concentrated, filtered, and then passed over two or three affinity columns, e.g., a protein A column and one or two anion exchange columns.

In certain aspects, the present invention relates to the chimeric protein produced by the methods described herein.

In vitro production allows scale-up to give large amounts of the desired altered polypeptides of the invention. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, hydrophobic interaction chromatography (HIC, chromatography over DEAE-cellulose or affinity chromatography.

Pharmaceutical Composition

Compositions containing the chimeric proteins provided herein can contain a suitable pharmaceutically acceptable carrier. For example, they can contain excipients and/or auxiliaries that facilitate processing of the active compounds into preparations designed for delivery to the site of action.

The pharmaceutical composition can be formulated for parenteral administration (i.e. intravenous, subcutaneous, or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

Suitable formulations for parenteral administration also include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances, which increase the viscosity of the suspension, including, for example, sodium carboxymethyl cellulose, sorbitol and dextran. Optionally, the suspension may also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In other embodiments, the compositions comprise pharmaceutically acceptable substances such as wetting agents or minor amounts of auxiliary substances such as wetting or emulsifying agents, preservatives or buffers, which enhance the shelf life or effectiveness of the active ingredients.

Compositions can be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In one embodiment, the chimeric protein of the invention is formulated with another clotting factor, or a variant, fragment, analogue, or derivative thereof. For example, the clotting factor includes, but is not limited to, factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include anti-fibrinolytic drugs, e.g., epsilon-amino-caproic acid, tranexamic acid.

Dosage regimens can be adjusted to provide the optimum desired response. For example, a single bolus can be administered, several divided doses can be administered over time, or the dose can be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form may contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

Non-limiting examples of suitable pharmaceutical carriers are also described in Remington's Pharmaceutical Sciences by E. W. Martin. Some examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition may take the form of tablets or lozenges according to conventional protocols.

For administration by inhalation, the compounds for use according to the present invention are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for rectal administration as a suppository or retention enema, e.g., containing conventional suppository bases such as cocoa butter or other glycerides.

In one embodiment, a pharmaceutical composition comprises a chimeric protein, the polynucleotide encoding the chimeric protein, the vector comprising the polynucleotide, or the host cell comprising the vector, and a pharmaceutically acceptable carrier. The FVIII protein in a chimeric protein has extended half-life compared to wild type FVIII protein or the corresponding FVIII protein without the one or more XTEN sequences. In one embodiment, wherein the half-life of the FVIII protein is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVIII. In another embodiment, the half-life of Factor VIII is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours when administered to a subject. In one embodiment, the subject is a mouse. In another embodiment, the subject is a dog. In another embodiment, the subject is a human.

In some embodiments, the composition is administered by a route selected from the group consisting of topical administration, intraocular administration, parenteral administration, intrathecal administration, subdural administration and oral administration. The parenteral administration can be intravenous or subcutaneous administration.

In other embodiments, the composition is used to treat a bleeding disease or condition in a subject in need thereof. The bleeding disease or condition is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath and any combinations thereof. In still other embodiments, the subject is scheduled to undergo a surgery. In yet other embodiments, the treatment is prophylactic or on-demand.

Gene Therapy

A chimeric protein thereof of the invention can be produced in vivo in a mammal, e g., a human patient, using a gene therapy approach to treatment of a bleeding disease or disorder selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath would be therapeutically beneficial. In one embodiment, the bleeding disease or disorder is hemophilia. In another embodiment, the bleeding disease or disorder is hemophilia A. In one embodiment, the invention provides a method of gene therapy wherein a subject is administered a suitable chimeric protein-encoding nucleic acid operably linked to suitable expression control sequences under conditions effective to express the encoded FVIII chimeric protein in the subject and wherein the FVIII chimeric protein has procoagulant activity sufficient to treat the subject. In certain embodiment, these sequences are incorporated into a viral vector. Suitable viral vectors for such gene therapy include adenoviral vectors, lentiviral vectors, baculoviral vectors, Epstein Barr viral vectors, papovaviral vectors, vaccinia viral vectors, herpes simplex viral vectors, and adeno associated virus (AAV) vectors. The viral vector can be a replication-defective viral vector. In other embodiments, an adenoviral vector has a deletion in its E1 gene or E3 gene. When an adenoviral vector is used, the mammal may not be exposed to a nucleic acid encoding a selectable marker gene. In other embodiments, the sequences are incorporated into a non-viral vector known to those skilled in the art.

Methods of Using Chimeric Protein

The present invention is directed to a method of using a chimeric protein described herein to increase the half-life of a FVIII polypeptide.

In one aspect, the methods provided herein are directed to preventing or inhibiting FVIII interaction with endogenous VWF by mutating the VWF-binding site on the FVIII and at the same time extending half-life of the FVIII protein using an XTEN sequence. In another aspect, the methods provided herein are directed to extending the half-life of a FVIII protein using at least four XTEN sequences wherein at least one of the XTEN sequences is no more than 72 amino acids in length.

In another embodiment, methods provided herein are directed to constructing a FVIII protein having half-life longer than wild-type FVIII. In one embodiment, an XTEN sequence or at least four XTEN sequences extend the half-life of the FVIII polypeptide. The chimeric protein useful in the method provided herein includes any one or more chimeric protein described herein.

Another aspect of the invention includes a method of administering to a subject in need thereof a chimeric protein comprising a FVIII polypeptide and an XTEN sequence or at least four XTEN sequences, wherein the method comprises administering the chimeric protein described herein to the subject.

In one embodiment, the invention is directed to a method of using an XTEN sequence to extend a half-life of a FVIII polypeptide, e.g., a FVIII polypeptide with reduced VWF-binding. In certain embodiments, the FVIII protein linked to an XTEN sequence has reduced clearance or is not cleared by a VWF clearance receptor.

Also provided is a method of increasing the half-life of a FVIII protein comprising administering the chimeric protein described herein to a subject in need thereof.

The half-life of the FVIII protein linked to one or more XTEN sequences can be extended to at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the half-life of the same FVIII protein lacking the XTEN.

The half-life of the FVIII protein linked to at least four XTEN sequences can be extended to at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the half-life of the same FVIII protein lacking the XTEN sequences.

The half-life of a chimeric protein comprising FVIII linked to at least four XTEN sequences, wherein at least one XTEN sequence is no more than 72 amino acids in length can be extended to at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the same chimeric protein except wherein the XTEN sequence no more than 72 amino acids in length is replaced by a longer XTEN sequence, e.g., an XTEN sequence of 288 amino acids.

In other embodiments, the half-life of the chimeric FVIII protein is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours. In still other embodiments, the half-life of the chimeric protein is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life of the chimeric FVIII protein administered to a subject is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days. In one embodiment, the subject is a mouse. In another embodiment, the subject is a dog. In another embodiment, the subject is a human.

In addition, the invention provides a method of treating or preventing a bleeding disease or disorder comprising administering an effective amount of a chimeric protein. In one embodiment, the bleeding disease or disorder is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath. In a specific embodiment, the bleeding disease or disorder is hemophilia A.

The chimeric proteins described herein have many uses as will be recognized by one skilled in the art, including, but not limited to methods of treating a subject having a hemostatic disorder and methods of treating a subject in need of a general hemostatic agent. In one embodiment, the invention relates to a method of treating a subject having a hemostatic disorder comprising administering a therapeutically effective amount of the chimeric protein.

The FVIII protein portion in the chimeric protein treats or prevents a hemostatic disorder by serving as a cofactor to Factor IX on a negatively charged phospholipid surface, thereby forming a Xase complex. The binding of activated coagulation factors to a phospholipid surface localizes this process to sites of vascular damage. On a phospholipid surface, Factor Villa increases the maximum velocity of Factor X activation by Factor IXa, by approximately 200,000-fold, leading to the large second burst of thrombin generation.

The chimeric protein can be used to treat any hemostatic disorder. The hemostatic disorders that can be treated by administration of the chimeric protein of the invention include, but are not limited to, hemophilia A, as well as deficiencies or structural abnormalities relating to Factor VIII. In one embodiment, the hemostatic disorder is hemophilia A.

The chimeric protein can be used prophylactically to treat a subject with a hemostatic disorder. The chimeric protein can be used to treat an acute bleeding episode in a subject with a hemostatic disorder. In another embodiment, the hemostatic disorder can be the result of a defective clotting factor, e.g., von Willebrand's factor. In one embodiment, the hemostatic disorder is an inherited disorder. In another embodiment, the hemostatic disorder is an acquired disorder. The acquired disorder can result from an underlying secondary disease or condition. The unrelated condition can be, as an example, but not as a limitation, cancer, an autoimmune disease, or pregnancy. The acquired disorder can result from old age or from medication to treat an underlying secondary disorder (e.g. cancer chemotherapy).

The invention also relates to methods of treating a subject that does not have a congenital hemostatic disorder, but has a secondary disease or condition resulting in acquisition of a hemostatic disorder, e.g., due to development of an anti-FVIII antibody or a surgery. The invention thus relates to a method of treating a subject in need of a general hemostatic agent comprising administering a therapeutically effective amount of the chimeric protein prepared by the present methods.

The present invention is also related to methods of reducing immunogenicity of FVIII or inducing less immunogenicity against FVIII comprising administering an effective amount of the chimeric proteins described herein, or the polynucleotides encoding the same.

In one embodiment, the subject in need of a general hemostatic agent is undergoing, or is about to undergo, surgery. The chimeric protein of the invention can be administered prior to, during, or after surgery as a prophylactic regimen. The chimeric protein of the invention can be administered prior to, during, or after surgery to control an acute bleeding episode.

The chimeric protein can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding. Non limiting examples of bleeding episodes include a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath, and any combinations thereof.

In prophylactic applications, one or more compositions containing the chimeric protein or a cocktail thereof are administered to a patient not already in the disease state to enhance the patient's resistance or reduce symptoms associated with a disease or disorder. Such an amount is defined to be a "prophylactic effective dose." In therapeutic applications, a relatively high dosage (e.g., from about 1 to 400 mg/kg of polypeptide per dose, with dosages of from 5 to 25 mg being more commonly used for radioimmuno conjugates and higher doses for cytotoxin-drug modified polypeptides) at relatively short intervals is sometimes required until progression of the disease is reduced or terminated, and until the patient shows partial or complete amelioration of symptoms of disease. Thereafter, the patient can be administered a prophylactic regime.

In some embodiments, a chimeric protein or a composition is used for on-demand treatment, which includes treatment for a bleeding episode, hemarthrosis, muscle bleed, oral bleed, hemorrhage, hemorrhage into muscles, oral hemorrhage, trauma, trauma capitis (head trauma), gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. The subject may be in need of surgical prophylaxis, pen-operative management, or treatment for surgery. Such surgeries include, e.g., minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery.

In one embodiment, the chimeric protein is administered intravenously, subcutaneously, intramuscularly, or via any mucosal surface, e.g., orally, sublingually, buccally, nasally, rectally, vaginally or via pulmonary route. The chimeric protein can be implanted within or linked to a biopolymer solid support that allows for the slow release of the chimeric protein to the site of bleeding or implanted into bandage/dressing. The dose of the chimeric protein will vary depending on the subject and upon the particular route of administration used. Dosages can range from 0.1 to 100,000 μg/kg body weight. In one embodiment, the dosing range is 0.1-1,000 μg/kg. In another embodiment, the dosing range is 0.1-500 μg/kg. The protein can be administered continuously or at specific timed intervals. In vitro assays may be employed to determine optimal dose ranges and/or schedules for administration. In vitro assays that measure clotting factor activity are known in the art, e.g., STA-CLOT VIIa-rTF clotting assay or ROTEM clotting assay. Additionally, effective doses may be extrapolated from dose-response curves obtained from animal models, e.g., a hemophiliac dog (Mount et al. 2002, *Blood* 99(8):2670).

Having now described the present invention in detail, the same will be more clearly understood by reference to the following examples, which are included herewith for purposes of illustration only and are not intended to be limiting of the invention. All patents, publications, and articles referred to herein are expressly and specifically incorporated herein by reference.

EXAMPLES

Throughout the examples, the following materials and methods were used unless otherwise stated.

Materials and Methods

In general, the practice of the present invention employs, unless otherwise indicated, conventional techniques of chemistry, biophysics, molecular biology, recombinant DNA technology, immunology (especially, e.g., antibody technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., CS.H.L. Press, Pub. (1999); and Current Protocols in Molecular Biology, eds. Ausubel et al., John Wiley & Sons (1992).

Example 1: Identification of FVIII Molecules with at Least 2-Fold Increase in Half-Life FVIII molecules with reduced VWF binding have been shown to have shorter half lives than wild-type FVIII. XTEN sequences have been shown to increase the half-lives of proteins, but it has also been observed that in some instances, chimeric proteins comprising FVIII molecules and multiple XTEN sequences have half-lives of approximately no more than twice the half-life of wild-type FVIII in HemA mice. In order to determine if this limited half-life could be increased, XTEN sequences of various sizes were inserted into multiple locations of FVIII molecules with reduced VWF binding.

FVIII molecules with reduced binding to VWF were constructed. In particular, amino acids 746-1685 were deleted from FVIII. Tyrosine 1680 in FVIII is essential for VWF binding. FVIII molecules lacking amino acids 746-1685 do not have this critical tyrosine 1680 and are therefore impaired in VWF binding.

Multiple XTENs with varying lengths were inserted at different positions in the FVIII protein lacking amino acids 746-1685 to create chimeric FVIII protein constructs designated PNL049, PNL050 and PNL051. The size and location of the XTEN insertions in these chimeric proteins are summarized in FIG. 1. All of the chimeric proteins tested in this example contained a 144 amino acid XTEN insertion after FVIII residue 745 (symbolized as "B" insertion in FIG. 1) as well as a 288 amino acid XTEN insertion after FVIII residue 2332 (symbolized as "CT" insertion in FIG. 1). The size and location of other XTEN insertions were varied as indicated in FIG. 1.

The resulting chimeric FVIII-XTEN proteins were expressed in HEK293 cells, and FVIII activity in the cell culture medium was monitored by chromogenic assay. Cell culture media was concentrated and used for measuring the half-life of the FVIII-XTEN molecules.

When tested in HemA mice, all three molecules exceeded the 2-fold half-life limit imposed by VWF binding. The half-lives of PNL049, PNL050, and PNL051 were 22, 23, and 22 hours respectively (FIGS. 1 and 2). Each of these constructs contains a 42 amino acid XTEN insertion at amino acid 18 and/or 1720 of Factor VIII. Notably, the half-lives of all three of these proteins were increased as compared to the half-life of PNL044 which contains three XTEN insertions, but no 42 amino acid insertion at amino acid 18 or 1720 of Factor VIII. These results demonstrates that adding an additional 42aa XTEN at either amino acid 18 or 1720 in PNL044 can significantly improve the half-life of FVIII-XTEN chimeric proteins.

Another chimeric protein, LSD62.001, was also tested in FVIII/VWF DKO mice. The location of XTENs in LSD62.001 are the same as the locations of the XTENS in PNL051. However, the XTEN insertion at amino acid 18 of FVIII in LSD62.001 is larger (i.e., 144 amino acids) than the XTEN insertion at the same position in PNL051 (i.e., 42 amino acids). This difference result in a half-life of 14 hours for LSD62.001, while PNL051 had a half-life of 22 hours.

These data indicate that shorter XTEN sequences inserted at locations 18 and 1720 in FVIII in combination with longer B-domain and C-term XTENs can provide better half-life extension than longer XTEN sequences at all of the insertion sites.

Example 2: Impact of XTEN Insertion Length on Half-Life of FVIII-XTEN Chimeric Proteins In order to identify the optimal length of XTEN insertions in FVIII, XTEN insertions ranging in length from 42 amino acids to 288 amino acids were introduced into the FVIII A domains of a FVIII-XTEN chimeric protein that contains (i) a 144 amino acid AE XTEN insertion at amino acid 745 of FVIII and (ii) a 288 amino acid AE XTEN insertion at amino acid 2332 of FVIII.

FVIII-XTEN chimeric proteins were expressed in HEK293 cells, and the activity of the cell culture medium was tested by FVIII chromogenic assay. The half-life of the FVIII-XTEN chimeric proteins was tested in DKO mice using concentrated cell culture medium.

An inverse correlation between FVIII activity and the length of the XTEN insertions in the FVIII A-domain was observed (see FIG. 3).

An inverse correlation between FVIII half-life and the length of XTEN insertions at FVIII amino acids 18 and 1720 was also observed (see FIG. 3). The length of XTEN insertions at FVIII amino acid 403 had a less dramatic effect on the FVIII half-life. The half-life of FVIII-XTEN chimeric proteins increased with XTEN size up to 144 amino acids for XTEN insertions as FVIII amino acid 1900, but the half-life dropped sharply upon further increasing the XTEN length to 288 amino acids at the same insertion site.

When combined with longer B-domain and C-terminus insertions (e.g., insertions after amino acids 745 and 2332 of FVIII), the following XTENs greatly increase half life: (i) a 42 amino acid XTEN inserted after FVIII amino acid 18, (ii), a 42 or 144 amino acid XTEN inserted after FVIII amino acid 403, (iii) a 42 amino acid XTEN inserted after FVIII amino acid 1720, and (iv) a 72 or 144 amino acid XTEN inserted after FVIII amino acid 1900.

These data indicate that the impact that XTEN size has on half-life is dependent on the insertion site.

Example 3: Impact of Multiple Short XTEN Insertion on Half-Life of FVIII-XTEN Chimeric Proteins In order to determine the effect of multiple short XTEN insertions on the half-life of FVIII molecules with reduced affinity for vWF, the chimeric proteins listed in the following table are produced.

TABLE 26

Chimeric Proteins Containing Five XTENs

| Protein | XTEN1 | XTEN2 | XTEN3 | XTEN4 | XTEN5 |
|---|---|---|---|---|---|
| PKY0037 | 216_AE42 | 0018_AE42_1 | 1720_AE42_1 | 0745_AE144_3B | 2332_AE288_1 |
| PKY0038 | 220_AE42 | 0018_AE42_1 | 1720_AE42_1 | 0745_AE144_3B | 2332_AE288_1 |
| PKY0039 | 224_AE42 | 0018_AE42_1 | 1720_AE42_1 | 0745_AE144_3B | 2332_AE288_1 |
| PKY0040 | 333_AE42 | 0018_AE42_1 | 1720_AE42_1 | 0745_AE144_3B | 2332_AE288_1 |
| PKY0041 | 336_AE42 | 0018_AE42_1 | 1720_AE42_1 | 0745_AE144_3B | 2332_AE288_1 |
| PKY0042 | 339_AE42 | 0018_AE42_1 | 1720_AE42_1 | 0745_AE144_3B | 2332_AE288_1 |
| PKY0043 | 399_AE42 | 0018_AE42_1 | 1720_AE42_1 | 0745_AE144_3B | 2332_AE288_1 |
| PKY0044 | 403_AE42 | 0018_AE42_1 | 1720_AE42_1 | 0745_AE144_3B | 2332_AE288_1 |
| PKY0045 | 599_AE42 | 0018_AE42_1 | 1720_AE42_1 | 0745_AE144_3B | 2332_AE288_1 |
| PKY0046 | 603_AE42 | 0018_AE42_1 | 1720_AE42_1 | 0745_AE144_3B | 2332_AE288_1 |
| PKY0047 | 1900_AE42 | 0018_AE42_1 | 1720_AE42_1 | 0745_AE144_3B | 2332_AE288_1 |
| PKY0048 | 1905_AE42 | 0018_AE42_1 | 1720_AE42_1 | 0745_AE144_3B | 2332_AE288_1 |
| PKY0049 | 1910_AE42 | 0018_AE42_1 | 1720_AE42_1 | 0745_AE144_3B | 2332_AE288_1 |
| PKY0050 | 2171_AE42 | 0018_AE42_1 | 1720_AE42_1 | 0745_AE144_3B | 2332_AE288_1 |

Each of these chimeric proteins comprises a FVIII polypeptide lacking amino acids 746-1685. In addition, each contains the following four XTEN insertions: AE42 inserted immediately downstream of residue 18 corresponding to the mature FVIII polypeptide (SEQ ID NO: 4), AE42 inserted immediately downstream of residue 1720 corresponding to the mature FVIII polypeptide (SEQ ID NO: 4), AE144 inserted immediately downstream of residue 0745 corresponding to the mature FVIII polypeptide (SEQ ID NO: 4), and AE288 inserted immediately downstream of residue 2332 corresponding to the mature FVIII polypeptide (SEQ ID NO: 4). Each chimeric protein also contains a fifth XTEN insertion that is AE42, but the location of this insertion varies as indicated in the table.

These proteins are expressed in HEK293 cells, and the activity of the cell culture medium is tested by FVIII chromogenic assay. The half-life of the FVIII-XTEN chimeric proteins is tested in HemA mice using concentrated cell culture medium. Constructs containing the short AE42 XTEN at particularly useful insertion sites have long half-lives and high activity.

Example 4: Complete or Partial Replacement of Permissive Loops with XTEN Sequences of Variable Lengths As illustrated in Table 18, FVIII can accommodate the insertion of XTEN AE42 and XTEN AE144 immediately after positions 18, 22, 26, and 40 without abrogation of its procoagulant activity. This region, spanning residues 18 through 40 in the primary sequence of mature FVIII has been denoted permissive loop A1-1. Since insertion within this loop does not abrogate FVIII activity, it was reasoned that this loop may be dispensable for the function of FVIII and that replacement of part of all of this loop with AE42 XTEN may result in a FVIII variant that retains procoagulant activity. An example of the method used to replace all or part of loop A1-1 is provided in FIG. 4. Here a plasmid encoding FVIII with an AE42 XTEN sequence inserted immediately after residue 18 and a plasmid encoding FVIII with an AE42 XTEN sequence inserted immediately after residue 40 are each digested with the restriction endonuclease AscI, which cleaves at the 5' end of the AE42 XTEN in both plasmids, and with the restriction endonuclease AflII, which cleaves downstream (3') of the AE42 insert at a site that is unique within the each plasmid. The resulting DNA fragments are then ligated such that the AE42 XTEN sequence replaces amino acid residues from position 19 to 40. While this method is used to replace the entire A1-1 loop, it could, by logical extension, be used to replace smaller fragments of the A1-1 loop, such as those spanning residue 19-22, 19-26, 19-32, 23-26, 23-32, 23-40, 27-32, 27-40, and 33-40, as described for constructs pOM001 through pOM010 in Table 28.

This method could be more broadly applied to replace analogous regions of FVIII permissive loop A1-1 with XTEN sequences of a different length. Constructs pOM011 through pOM020 in Table 27 represent FVIII variants in which corresponding segments of the A1-1 loop are replaced with an AE144 XTEN. For replacement of all or part of the A1-1 permissive loop with either AE42 or AE144 XTENs, both the acceptor and donor plasmids are digested with AscI and AflII, the latter being a the unique restriction site that is closest to the A1-1 loop in the 3' direction.

This general method could similarly be applied to replace all or part of permissive loops A2-1, A3-1, and A3-2. As indicated in Table 27, each of these permissive loops differs from one another with regard to the identity of the nearest unique restriction site in the 3' direction from the site of XTEN insertion. Thus, while AscI is used to cleave at the 5' end of the original XTEN insertion, different restriction enzymes are used to cleave at the downstream site, namely, BamHI for permissive loop A2-1, PflMI for permissive loop A3-1, and ApaI for permissive loop A3-2.

TABLE 27

FVIII Constructs in which Part of All of Individual Permissive Loops are Replaced by XTEN Sequences of Various Lengths.

| | Loop Replacement | | | Acceptor (Plasmid) | | | Donor (Insert) | | | Restriction Sites | |
|---|---|---|---|---|---|---|---|---|---|---|---|
| Construct | Loop | Deletion | Insertion | Plasmid | Site | XTEN | Plasmid | Site | XTEN | 5' | 3' |
| pOM001 | A1-1 | 19-22 | AE42 | pBC0165 | 18 | AE42 | pBC0183 | 22 | AE42 | AscI | AflII |
| pOM002 | A1-1 | 19-26 | AE42 | pBC0165 | 18 | AE42 | pBC0184 | 26 | AE42 | AscI | AflII |
| pOM003 | A1-1 | 19-32 | AE42 | pBC0165 | 18 | AE42 | pNL0081.001 | 32 | AE42 | AscI | AflII |
| pOM004 | A1-1 | 19-40 | AE42 | pBC0165 | 18 | AE42 | pBC0166 | 40 | AE42 | AscI | AflII |
| pOM005 | A1-1 | 23-26 | AE42 | pBC0183 | 22 | AE42 | pBC0184 | 26 | AE42 | AscI | AflII |
| pOM006 | A1-1 | 23-32 | AE42 | pBC0183 | 22 | AE42 | pNL0081.001 | 32 | AE42 | AscI | AflII |
| pOM007 | A1 1 | 23-40 | AE42 | pBC0183 | 22 | AE42 | pBC0166 | 40 | AE42 | AscI | AflII |
| pOM008 | A1-1 | 27-32 | AE42 | pBC0184 | 26 | AE42 | pNL0081.001 | 32 | AE42 | AscI | AflII |
| pOM009 | A1-1 | 27-40 | AE42 | pBC0184 | 26 | AE42 | pBC0166 | 40 | AE42 | AscI | AflII |
| pOM010 | A1-1 | 33-40 | AE42 | pNL0081.001 | 32 | AE42 | pBC0166 | 40 | AE42 | AscI | AflII |
| pOM011 | A1-1 | 19-22 | AE144_5A | pBC165 | 18 | AE42 | pSD0047 | 22 | AE144_5A | AscI | AflII |
| pOM012 | A1-1 | 19-26 | AE144_5A | pBC165 | 18 | AE42 | pSD0049 | 26 | AE144_5A | AscI | AflII |
| pOM013 | A1-1 | 19-32 | AE144_5A | pBC165 | 18 | AE42 | pSD0022 | 32 | AE144_5A | AscI | AflII |
| pOM014 | A1-1 | 19-40 | AE144_5A | pBC165 | 18 | AE42 | pSD0051 | 40 | AE144_5A | AscI | AflII |
| pOM015 | A1-1 | 23-26 | AE144_5A | pBC0183 | 22 | AE42 | pSD0049 | 26 | AE144_5A | AscI | AflII |
| pOM016 | A1-1 | 23-32 | AE144_5A | pBC0183 | 22 | AE42 | pSD0022 | 32 | AE144_5A | AscI | AflII |
| pOM017 | A1-1 | 23-40 | AE144_5A | pBC0183 | 22 | AE42 | pSD0051 | 40 | AE144_5A | AscI | AflII |
| pOM018 | A1-1 | 27-32 | AE144_5A | pBC0184 | 26 | AE42 | pSD0022 | 32 | AE144_5A | AscI | AflII |
| pOM019 | A1-1 | 27-40 | AE144_5A | pBC0184 | 26 | AE42 | pSD0051 | 40 | AE144_5A | AscI | AflII |
| pOM020 | A1-1 | 33-40 | AE144_5A | pNL0081.001 | 32 | AE42 | pSD0051 | 40 | AE144_5A | AscI | AflII |
| pOM021 | A2-1 | 400-403 | AE42 | pNL0091.002 | 399 | AE42 | pBC0132 | 403 | AE42 | AscI | BamHI |
| pOM022 | A2-1 | 400-403 | AE144_2A | pNL0091.002 | 399 | AE42 | pSD0001 | 403 | AE144_2A | AscI | BamHI |
| pOM023 | A3-1 | 1712-1720 | AE42 | pNL0097.001 | 1711 | AE42 | pBC0138 | 1720 | AE42 | AscI | PflMI |
| pOM024 | A3-1 | 1712-1725 | AE42 | pNL0097.001 | 1711 | AE42 | pNL0098.001 | 1725 | AE42 | AscI | PflMI |
| pOM025 | A3-1 | 1721-1725 | AE42 | pBC0138 | 1720 | AE42 | pNL0098.001 | 1725 | AE42 | AscI | PflMI |
| pOM026 | A3-1 | 1712-1720 | AE144_4A | pNL0097.001 | 1711 | AE42 | pSD0009 | 1720 | AE144_4A | AscI | PflMI |
| pOM027 | A3-1 | 1712-1725 | AE144_4A | pNL0097.001 | 1711 | AE42 | pSD0041 | 1725 | AE144_4A | AscI | PflMI |

TABLE 27-continued

FVIII Constructs in which Part of All of Individual Permissive Loops are Replaced by XTEN Sequences of Various Lengths.

| | Loop Replacement | | | Acceptor (Plasmid) | | | Donor (Insert) | | | Restriction Sites | |
|---|---|---|---|---|---|---|---|---|---|---|---|
| Construct | Loop | Deletion | Insertion | Plasmid | Site | XTEN | Plasmid | Site | XTEN | 5' | 3' |
| pOM028 | A3-1 | 1721-1725 | AE144_4A | pBC0138 | 1720 | AE42 | pSD0041 | 1725 | AE144_4A | AscI | PflMI |
| pOM029 | A3-2 | 1901-1905 | AE42 | pBC0176 | 1900 | AE42 | pNL0101.001 | 1905 | AE42 | AscI | ApaI |
| pOM030 | A3-2 | 1901-1910 | AE42 | pBC0176 | 1900 | AE42 | pNL0102.001 | 1910 | AE42 | AscI | ApaI |
| pOM031 | A3-2 | 1906-1910 | AE42 | pNL0101.001 | 1905 | AE42 | pNL0102.001 | 1910 | AE42 | AscI | ApaI |
| pOM032 | A3-2 | 1901-1905 | AE144_1A | pBC0176 | 1900 | AE42 | pNL0002 | 1905 | AE144_1A | AscI | ApaI |
| pOM033 | A3-2 | 1901-1910 | AE144_1A | pBC0176 | 1900 | AE42 | pNL0003 | 1910 | AE144_1A | AscI | ApaI |
| pOM034 | A3-2 | 1906-1910 | AE144_1A | pNL0101.001 | 1905 | AE42 | pNL0003 | 1910 | AE144_1A | AscI | ApaI |

Example 5: Complete or Partial Replacement of Permissive Loops with XTEN or Complete or Partial Deletion of Permissive Loops FVIII expression constructs have several restriction endonuclease sites that are unique with respect to the entire FVIII expression plasmid. Thus, any pair of unique restriction sites that flank a particular permissive loop can be used to facilitate the insertion of a synthetic DNA constructs that encodes the intervening FVIII sequence with a complete or partial deletion of that particular permissive loop with replacement of the deleted sequence with XTEN. For example, to replace residues 19-40 in permissive loop A1-1, a DNA fragment would be synthesized that comprises, from its 5' and to its 3' end, the native sequence of the FVIII expression construct from the BsiWI site to the DNA sequence that encodes residue 18, a DNA sequence encoding XTEN, the native sequence of the FVIII expression construct beginning with the DNA sequence that encodes residue 40 up to and including the unique AflII restriction site. This synthetic DNA construct would be excised from its host plasmid with BsiWI and AflII and inserted into the corresponding sites of the FVIII expression construct that had been digested with the same restriction enzymes. Examples of XTEN sequences are disclosed elsewhere herein. These insertions could incorporate unique restriction sites flanking the XTEN insertion for easier subcloning. Alternatively, these synthetic DNA sequences could incorporate amino acid substitutions in the FVIII sequence, including substitutions of non-native amino acid sequences (mutations), in the permissive loops, with XTEN. Alternatively, the XTEN insertions could be either adjacent or nonadjacent to the deletion or substitution within a loop. Examples of partial and complete deletions of FVIII permissive loops A1-1, A1-2, A2-1, A2-2, A3-1, and A3-2 as well as their replacement with XTENs are given in Table 27. Examples of pairs of unique restriction enzymes that are appropriate for generation of these constructs are also given in Table 28. Multiple insertions and replacements could likewise be incorporated into a single FVIII construct, as well as combinations of XTEN insertions/replacements in particular loops with partial or complete deletions in other loops.

TABLE 28

FVIII Constructs in which Part or All of Individual Permissive Loops are Replaced by Different XTEN by Cloning Synthetic DNA Sequences into Unique FVIII Restriction Enzyme Sites

| | Loop Replacement | | Restriction Sites | |
|---|---|---|---|---|
| Construct | Loop | Deletion | 5' | 3' |
| pFW001 | A1-1 | 19-22 | BsiWI | AflII |
| pFW002 | A1-1 | 19-26 | BsiWI | AflII |
| pFW003 | A1-1 | 19-32 | BsiWI | AflII |
| pFW004 | A1-1 | 19-40 | BsiWI | AflII |
| pFW005 | A1-1 | 23-26 | BsiWI | AflII |
| pFW006 | A1-1 | 23-32 | BsiWI | AflII |
| pFW007 | A1-1 | 23-40 | BsiWI | AflII |
| pFW008 | A1-1 | 27-32 | BsiWI | AflII |
| pFW009 | A1-1 | 27-40 | BsiWI | AflII |
| pFW010 | A1-1 | 33-40 | BsiWI | AflII |
| pFW011 | A1-2 | 218-229 | AflII | NheI |
| pFW012 | A2-1 | 400-403 | NheI | BamHI |
| pFW013 | A2-2 | 595-607 | NheI | ClaI |
| pFW014 | A3-1 | 1712-1720 | ClaI | PflMI |
| pFW015 | A3-1 | 1712-1725 | ClaI | PflMI |
| pFW016 | A3-1 | 1721-1725 | ClaI | PflMI |
| pFW017 | A3-2 | 1901-1905 | PflMI | ApaI |
| pFW018 | A3-2 | 1901-1910 | PflMI | ApaI |
| pFW019 | A3-2 | 1906-1910 | PflMI | ApaI |

Example 6: Multiple Intra-Domain 42aa XTEN Insertions were Well Tolerated by FVIII Protein expression of the FVIII-XTEN constructs provided in Table 26 were evaluated by transient-transfection of HEK293 cells. 1 ug of plasmid DNA of each construct was used for a 4 mL culture. Cell culture media were harvested at day 5 post transfection, and the FVIII activity of each sample was measured by FVIII chromogenic assay. Table 29 summarizes the post transfection cell culture FVIII activity of each construct, the observed FVIII activities were all at ++++ level with exception of one construct at +++ level.

TABLE 29

Cell culture FVIII activity of FVIII-XTEN constructs with multiple intra-domain AE42 insertions

| Construct ID | XTEN Insertion Sites_Length ($1^{st}$-$4^{th}$) | $5^{th}$ AE42 XTEN Insertion site | $5^{th}$ AE42 XTEN Insertion Loop | Cell Culture FVIII Activity |
|---|---|---|---|---|
| pNL0051 Base construct | 18_AE42/1720_AE42/ B_AE144/CT_AE288 | non | | ++++ |

TABLE 29-continued

Cell culture FVIII activity of FVIII-XTEN constructs with multiple intra-domain AE42 insertions

| Construct ID | XTEN Insertion Sites_Length ($1^{st}$-$4^{th}$) | $5^{th}$ AE42 XTEN Insertion site | $5^{th}$ AE42 XTEN Insertion Loop | Cell Culture FVIII Activity |
|---|---|---|---|---|
| pKY0037.016 | 18_AE42/1720_AE42/ B_AE144/CT_AE288 | 216 | A1-2 | ++++ |
| pKY0038.006 | 18_AE42/1720_AE42/ B_AE144/CT_AE288 | 220 | A1-2 | ++++ |
| pKY0039.003 | 18_AE42/1720_AE42/ B_AE144/CT_AE288 | 224 | A1-2 | ++++ |
| pKY0040.002 | 18_AE42/1720_AE42/ B_AE144/CT_AE288 | 333 | A1 acidic region | ++++ |
| pKY0041.001 | 18_AE42/1720_AE42/ B_AE144/CT_AE288 | 336 | A1 acidic region | ++++ |
| pKY0042.001 | 18_AE42/1720_AE42/ B_AE144/CT_AE288 | 339 | A1 acidic region | ++++ |
| pKY0043.001 | 18_AE42/1720_AE42/ B_AE144/CT_AE288 | 399 | A2-1 | ++++ |
| pKY0044.001 | 18_AE42/1720_AE42/ B_AE144/CT_AE288 | 403 | A2-1 | ++++ |
| pKY0045.008 | 18_AE42/1720_AE42/ B_AE144/CT_AE288 | 599 | A2-2 | ++++ |
| pKY0046.001 | 18_AE42/1720_AE42/ B_AE144/CT_AE288 | 603 | A2-2 | +++ |
| pKY0047.001 | 18_AE42/1720_AE42/ B_AE144/CT_AE288 | 1900 | A3-2 | ++++ |
| pKY0048.004 | 18_AE42/1720_AE42/ B_AE144/CT_AE288 | 1905 | A3-2 | ++++ |
| pKY0049.003 | 18_AE42/1720_AE42/ B_AE144/CT_AE288 | 1910 | A3-2 | ++++ |
| pKY0050.007 | 18_AE42/1720_AE42/ B_AE144/CT_AE288 | 2171 | C1-C2 junction | ++++ |

There are 6 permissive loops that can tolerate XTEN insertions within FVIII A-domains (A1-1, A1-2, A2-1, A2-2, A3-1, and A3-2; See Example 4, above). The base construct of Table 26, pNL0051, contains representative insertions in loop A1-1 (18), A3-1 (1720), FVIII B domain, and C-terminus (Table 29, second column). The XTEN insertion combination of the base construct was well tolerated by FVIII as demonstrated by the resulting ++++ cell culture FVIII activity. The addition of a fifth intra-domain AE42 XTEN insertion in any one of the other four permissive loops was also well tolerated as indicated by the cell culture FVIII activity of pKY0037.016 (loop A1-2), pKY0043.001 (loop A2-1), pKY0045.008 (loop A2-2), and pKY0047.001 (loop A3-2), as shown in Table 29. In addition to the permissive loops, XTEN insertions around the acidic region of A1 domain (pKY0040.002) and the junction of the C1, C2 domain (PKY0050.007) were also well tolerated by FVIII. Compared to the constructs in Table 23 and Table 24, which contain multiple 144aa intra-domain XTEN insertions, the shorter 42aa XTEN insertions of Table 29 resulted in significantly higher FVIII cell culture activity, indicating that these insertions were better tolerated by FVIII.

Example 7: Combination of 42aa XTEN Intra-Domain Insertions Achieved 3 to 4-Fold Half-Life Extension for FVIII The half-life of select FVIII-XTEN constructs in Table 26 were evaluated in HemA mice using cell culture concentrates. Animals were dosed at 2001U/kg by intravenous injection, and plasma samples were collected at 5 min, 24 hr, 72 hr, and 96 hr post injection. FVIII activity in plasma samples was measured by FVIII chromogenic assay, and the half-life of each molecule was estimated by Phoenix Program.

The half-life of each construct is listed in Table 30. The half-life of the base construct, PNL0051, was measured at 24 hr. Compared to the base construct, various degrees of further improvement were observed when a fifth 42aa XTEN was inserted in A1-2 loop, A2-1 loop, A3-2 loop, or A1 acidic region. The longest half-life achieved by this approach was 30 hrs, which represents a 4-fold improvement over recombinant BDD-FVIII. A fifth XTEN insertion in loop A2-2 or the at the junction of C1-C2 had no additional half-life benefit.

To demonstrate the half-life effect of the fifth XTEN insertion more clearly, the PK curves of the construct with the best half-life from each insertion loop were plotted against the base vector as shown in FIG. 5, where the pNL0051 curve is represented by the solid inverted triangle in each graph. Additional half-life benefits were clearly demonstrated by the upshifting PK curves from constructs with the fifth 42aa XTEN inserted in A1-2 loop, A2-1 loop, A3-2 loop, and acidic region of A1 domain.

TABLE 30

Half-life of FVIII-XTEN constructs in HemA mice

| Construct ID | XTEN Insertion sites_Length (1$^{st}$-4$^{th}$) | 5$^{th}$ 42aa-XTEN Insertion site | 5$^{th}$ AE42 XTEN Insertion Loop | $t_{1/2}$ (hr) |
|---|---|---|---|---|
| pNL0051 base construct | 18_AE42/1720_AE42/ B_AE144/CT_AE288 | non | | 24 |
| pKY0037.016 | 18_AE42/1720_AE42/ B_AE144/CT_AE288 | 216 | A1-2 | 26 |
| pKY0038.006 | 18_AE42/1720_AE42/ B_AE144/CT_AE288 | 220 | A1-2 | 29 |
| PKY0039.003 | 18_AE42/1720_AE42/ B_AE144/CT_AE288 | 224 | A1-2 | 25 |
| PKY0040.002 | 18_AE42/1720_AE42/ B_AE144/CT_AE288 | 333 | A1 acidic region | 30 |
| pKY0042.001 | 18_AE42/1720_AE42/ B_AE144/CT_AE288 | 339 | A1 acidic region | 26 |
| PKY0043.001 | 18_AE42/1720_AE42/ B_AE144/CT_AE288 | 399 | A2-1 | 28 |
| PKY0044.001 | 18_AE42/1720_AE42/ B_AE144/CT_AE288 | 403 | A2-1 | 29 |
| pKY0045.008 | 18_AE42/1720_AE42/ B_AE144/CT_AE288 | 599 | A2-2 | 22 |
| pKY0046.001 | 18_AE42/1720_AE42/ B_AE144/CT_AE288 | 603 | A2-2 | 16 |
| pKY0047.001 | 18_AE42/1720_AE42/ B_AE144/CT_AE288 | 1900 | A3-2 | 27 |
| pKY0049.003 | 18_AE42/1720_AE42/ B_AE144/CT_AE288 | 1910 | A3-2 | 23 |
| pKY0050.007 | 18_AE42/1720_AE42/ B_AE144/CT_AE288 | 2171 | C1-C2 Junction | 18 |
| BDD-FVIII | non | non | | 7.5 |

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are incorporated by reference herein in their entirety.

This application claims the benefit of priority of U.S. Provisional Patent Application No. 61/866,016 filed on Aug. 14, 2013, which is incorporated herein by reference in its entirety.

What is claimed is:

1. A chimeric protein comprising (i) a Factor VIII (FVIII) polypeptide and (ii) four XTENs wherein the FVIII polypeptide has reduced affinity for von Willebrand Factor (VWF), and wherein the FVIII polypeptide lacks amino acids 746-1685 corresponding to the mature human FVIII polypeptide (SEQ ID NO:4).

2. The chimeric protein of claim 1, wherein at least three of the four XTENs are inserted immediately downstream of residues selected from the group consisting of:

(a) residues 18, 745, and 2332 corresponding to the mature FVIII polypeptide (SEQ ID NO: 4);
(b) residues 745, 1720 and 2332 corresponding to the mature FVIII polypeptide (SEQ ID NO: 4); and
(c) residues 745, 1900, and 2332 corresponding to the mature FVIII polypeptide (SEQ ID NO: 4).

3. The chimeric protein of claim 1, wherein at least two of the four XTENs are inserted immediately downstream of residues 745 and 2332 corresponding to the mature FVIII polypeptide (SEQ ID NO: 4).

4. The chimeric protein of claim 1, wherein at least one of the four XTENs is 36 to 72 amino acids in length or 42 to 78 amino acids in length.

5. The chimeric protein of claim 1, wherein at least one of the four XTENs is selected from the group consisting of SEQ ID NO:22 (36AE), SEQ ID NO:36 (42AE), SEQ ID NO: 23 (72AE), and SEQ ID NO: 24 (78AE).

6. The chimeric protein of claim 1, wherein at least one of the four XTENs is selected from the group consisting of SEQ ID NO: 37 (144AE), SEQ ID NO: 38 (144AG), SEQ ID NO: 98 (150AE), SEQ ID NO: 99 (150 AG), and any combination thereof.

7. The chimeric protein of claim 1, wherein:

(a) an XTEN of SEQ ID NO: 22 (36AE) is inserted immediately downstream of residue 18, an XTEN of SEQ ID NO: 37 (144AE) is inserted immediately downstream of residue 745, an XTEN of SEQ ID NO: 37 (144 AE) is inserted immediately downstream of residue 1900, and an XTEN of SEQ ID NO: 39 (288 AE) is inserted immediately downstream of residue 2332;
(b) an XTEN of SEQ ID NO: 36 (42AE) is inserted immediately downstream of residue 18, an XTEN of SEQ ID NO: 98 (150AE) is inserted immediately downstream of residue 745, an XTEN of SEQ ID NO:

98 (150 AE) is inserted immediately downstream of residue 1900, and an XTEN of SEQ ID NO: 100 (294 AE) is inserted immediately downstream of residue 2332;

(c) an XTEN of SEQ ID NO: 37 (144AE) or SEQ ID NO: 39 (288 AE) is inserted immediately downstream of residue 745, an XTEN of SEQ ID NO: 22 (36AE) is inserted immediately downstream of residue 1720, an XTEN of SEQ ID NO: 37 (144 AE) is inserted immediately downstream of residue 1900, and an XTEN of SEQ ID NO: 39 (288 AE) is inserted immediately downstream of residue 2332;

(d) an XTEN of SEQ ID NO: 98 (150AE) is inserted immediately downstream of residue 745, an XTEN of SEQ ID NO: 36 (42AE) is inserted immediately downstream of residue 1720, an XTEN of SEQ ID NO: 98 (150 AE) is inserted immediately downstream of residue 1900, and an XTEN of SEQ ID NO: 100 (294AE) is inserted immediately downstream of residue 2332;

(e) an XTEN of SEQ ID NO: 22 (36AE) is inserted immediately downstream of residue 18, an XTEN of SEQ ID NO: 37 (144AE) is inserted immediately downstream of residue 745, an XTEN of SEQ ID NO: 22 (36 AE) is inserted immediately downstream of residue 1720, and an XTEN of SEQ ID NO: 39 (288 AE) is inserted immediately downstream of residue 2332; or (f) an XTEN of SEQ ID NO: 36 (42AE) is inserted immediately downstream of residue 18, an XTEN of SEQ ID NO: 98 (150AE) is inserted immediately downstream of residue 745, an XTEN of SEQ ID NO: 36 (42 AE) is inserted immediately downstream of residue 1720, and an XTEN of SEQ ID NO: 100 (294 AE) is inserted immediately downstream of residue 2332.

8. A polynucleotide or a set of polynucleotides encoding the chimeric protein of claim 1.

9. A vector or a set of vectors comprising the polynucleotide or the set of polynucleotides of claim 8 and one or more promoter operably linked to the polynucleotide or the set of polynucleotides.

10. A host cell comprising the polynucleotide of claim 8.

11. A pharmaceutical composition comprising the chimeric protein of claim 1 and a pharmaceutically acceptable carrier.

12. A method of treating a bleeding disease or disorder in a subject in need thereof comprising administering an effective amount of the chimeric protein of claim 1.

13. A method of making a chimeric protein, comprising transfecting one or more host cells with the polynucleotide of claim 8 and expressing the chimeric protein in the host cell.

14. A method of extending or increasing the half-life of a FVIII protein, wherein the method comprises administering an effective amount of the chimeric protein of claim 1 to a subject in need thereof, wherein the XTEN sequence or sequences extend or increase the half-life of the FVIII protein.

15. The chimeric protein claim 1, wherein the four XTENs comprise an XTEN of SEQ ID NO: 22 (36AE) is inserted immediately downstream of residue 18, an XTEN of SEQ ID NO: 37 (144AE) is inserted immediately downstream of residue 745, an XTEN of SEQ ID NO: 37 (144 AE) is inserted immediately downstream of residue 1900, and an XTEN of SEQ ID NO: 39 (288 AE) is inserted immediately downstream of residue 2332.

16. The chimeric protein claim 1, wherein the four XTENs comprise an XTEN of SEQ ID NO: 37 (144AE) is inserted immediately downstream of residue 745, an XTEN of SEQ ID NO: 22 (36AE) is inserted immediately downstream of residue 1720, an XTEN of SEQ ID NO: 37 (144 AE) is inserted immediately downstream of residue 1900, and an XTEN of SEQ ID NO: 39 (288 AE) is inserted immediately downstream of residue 2332.

17. The chimeric protein of claim 1, wherein the four XTENs comprise an XTEN of SEQ ID NO: 22 (36AE) is inserted immediately downstream of residue 18, an XTEN of SEQ ID NO: 37 (144AE) is inserted immediately downstream of residue 745, an XTEN of SEQ ID NO: 22 (36 AE) is inserted immediately downstream of residue 1720, and an XTEN of SEQ ID NO: 39 (288 AE) is inserted immediately downstream of residue 2332.

* * * * *